(12) United States Patent
Tremont et al.

(10) Patent No.: US 6,740,663 B2
(45) Date of Patent: May 25, 2004

(54) MONO- AND DI-FLUORINATED BENZOTHIEPINE COMPOUNDS AS INHIBITORS OF APICAL SODIUM CO-DEPENDENT BILE ACID TRANSPORT (ASBT) AND TAUROCHOLATE UPTAKE

(75) Inventors: Samuel Tremont, St. Louis, MO (US); Kevin J. Koeller, Maryland Heights, MO (US)

(73) Assignee: G.D. Searle, LLC, St. Louis, MO (US)

(*) Notice: Subject to any disclaimer, the term of this patent is extended or adjusted under 35 U.S.C. 154(b) by 13 days.

(21) Appl. No.: 10/286,987

(22) Filed: Nov. 4, 2002

(65) Prior Publication Data

US 2004/0067872 A1 Apr. 8, 2004

Related U.S. Application Data

(60) Provisional application No. 60/330,892, filed on Nov. 2, 2001.

(51) Int. Cl.$^7$ .................. A61K 31/44; A61K 31/38; C07D 471/02; C07D 409/00; C07D 337/00
(52) U.S. Cl. .................. 514/300; 514/342; 514/431; 546/122; 546/279.7; 549/9
(58) Field of Search ................ 514/300, 342, 514/431; 549/9; 546/279.7, 122

(56) References Cited

U.S. PATENT DOCUMENTS

| | | |
|---|---|---|
| 3,262,850 A | 7/1966 | Glynne |
| 3,287,370 A | 11/1966 | Mohrbacher |
| 3,389,144 A | 6/1968 | Mohrbacher |
| 3,520,891 A | 7/1970 | Mohrbacher |
| 3,674,836 A | 7/1972 | Creger |
| 3,692,895 A | 9/1972 | Nelson |
| 3,714,190 A | 1/1973 | Boissier |
| 3,781,328 A | 12/1973 | Witte |
| 3,948,973 A | 4/1976 | Phillips |
| 3,962,261 A | 6/1976 | Zinnes |
| 3,972,878 A | 8/1976 | Schirmann |
| 3,983,140 A | 9/1976 | Endo |
| 4,002,750 A | 1/1977 | Ambrogi |
| 4,058,552 A | 11/1977 | Mieville |
| 4,185,109 A | 1/1980 | Rosen |
| 4,231,938 A | 11/1980 | Monaghan |
| 4,251,526 A | 2/1981 | McCall |
| 4,346,227 A | 8/1982 | Terahara |
| 4,410,629 A | 10/1983 | Terahara et al. |
| 4,444,784 A | 4/1984 | Hoffman |
| 4,448,979 A | 5/1984 | Terahara et al. |
| 4,559,332 A | 12/1985 | Grob |
| 5,075,293 A | 12/1991 | Reifschneider |
| 5,153,184 A | 10/1992 | Reifschneider |
| 5,158,943 A | 10/1992 | Sohda |
| 5,244,887 A | 9/1993 | Straub |
| 5,260,316 A | 11/1993 | Van Duzer |
| 5,334,600 A | 8/1994 | Van Duzer |
| 5,350,761 A | 9/1994 | Van Duzer |
| 5,354,772 A | 10/1994 | Kathawala |
| 5,430,116 A | 7/1995 | Kramer |
| 5,502,045 A | 3/1996 | Miettinen |
| 5,512,558 A | 4/1996 | Enhsen |
| 5,519,001 A | 5/1996 | Kushwaha |
| 5,602,152 A | 2/1997 | Berthelon |
| 5,610,151 A | 3/1997 | Glombik |
| 5,663,165 A | 9/1997 | Brieaddy |
| 5,703,188 A | 12/1997 | Mandeville |
| 5,705,524 A | 1/1998 | McGee |
| 5,723,458 A | 3/1998 | Brieaddy |
| 5,767,115 A | 6/1998 | Rosenblum |
| 5,929,062 A | 7/1999 | Haines |
| 5,994,391 A | 11/1999 | Lee |
| 6,020,330 A | 2/2000 | Enhsen |
| 6,034,118 A | 3/2000 | Bischofberger |
| 6,180,659 B1 * | 1/2001 | Yamashita et al. .......... 514/431 |
| 6,235,771 B1 * | 5/2001 | Shiraishi et al. ............ 514/431 |
| 6,346,527 B1 * | 2/2002 | Takenaka et al. ...... 514/213.01 |
| 6,355,671 B1 | 3/2002 | Miyano et al. |
| 6,355,672 B1 | 3/2002 | Yasuma et al. |
| 6,369,220 B1 | 4/2002 | Li et al. |
| 6,387,924 B2 * | 5/2002 | Lee et al. .................... 514/300 |
| 6,441,022 B1 | 8/2002 | Frick et al. |
| 6,479,670 B1 | 11/2002 | Belloni et al. |

FOREIGN PATENT DOCUMENTS

| | | |
|---|---|---|
| AU | A-30209/92 | 12/1992 |
| AU | A-61946/94 | 6/1994 |
| AU | A-61948/94 | 6/1994 |
| AU | A-61949/94 | 6/1994 |
| CA | 2025294 | 3/1991 |
| CA | 2078588 | 3/1993 |
| CA | 2085782 | 6/1993 |
| CA | 2085830 | 6/1993 |
| DE | 1211258 | 2/1968 |
| DE | 3 122 499 A1 | 6/1981 |
| DE | 196 27 430 A1 | 8/1996 |
| EP | 0 022 487 A1 | 6/1980 |
| EP | 0 033 538 B1 | 2/1981 |
| EP | 0 244 364 A2 | 4/1982 |
| EP | 0 067 086 | 10/1982 |
| EP | 0 129 748 | 2/1985 |
| EP | 0 250 265 | 6/1987 |
| EP | 0 338 331 | 6/1989 |

(List continued on next page.)

OTHER PUBLICATIONS

US 3,694,445, 9/1972, Houlihan et al. (withdrawn)

Trayneus, Vincent J. et al, "Seven–Membered Heterocycles.", CA 79:66153, 1973.*

A. Barrett et al., "Total Synthesis and Stereochemical Assignment of the Quinquecyclopropane–Containing Cholesteryl Ester Transfer Protein Inhibitor U–106305", J. Am Chem. Soc., 1996, 118, pp. 7863–7864.

(List continued on next page.)

*Primary Examiner*—Deborah C. Lambkin
(74) *Attorney, Agent, or Firm*—Banner & Witcoff, Ltd.

(57) ABSTRACT

Mono-fluorinated and di-fluorinated benzothiepine apical sodium co-dependent bile acid transport (ASBT) inhibitors are disclosed together with methods of making the same, methods of using the same to treat hyperlipidemic conditions as well as pharmaceutical compositions containing the same compounds.

150 Claims, No Drawings

FOREIGN PATENT DOCUMENTS

| | | |
|---|---|---|
| EP | 0 379 161 | 1/1990 |
| EP | 0 409 281 A1 | 7/1990 |
| EP | 0 531 901 A2 | 2/1992 |
| EP | 0 508 425 A1 | 9/1992 |
| EP | 0 549 967 A1 | 12/1992 |
| EP | 0 526 402 A1 | 2/1993 |
| EP | 0 559 064 A2 | 2/1993 |
| EP | 0 563 731 A1 | 3/1993 |
| EP | 0 568 898 A1 | 4/1993 |
| EP | 0 818 197 A1 | 6/1997 |
| EP | 0 818 448 A1 | 6/1997 |
| EP | 0 796 846 A1 | 7/1997 |
| EP | 0 801 060 A1 | 10/1997 |
| FR | 2 661 676 A1 | 2/1990 |
| GB | 1 211 258 | 2/1968 |
| GB | 2 077 264 A | 6/1981 |
| GB | 2 305 665 | 4/1997 |
| GB | 2 329 334 | 3/1999 |
| JP | 10-287662 | 10/1998 |
| WO | 89/01477 | 2/1989 |
| WO | 91/08205 | 6/1991 |
| WO | 92/17467 | 10/1992 |
| WO | 92/18115 | 10/1992 |
| WO | 92/18462 | 10/1992 |
| WO | 93/16055 | 8/1993 |
| WO | 93/21146 | 10/1993 |
| WO | 94/18183 | 8/1994 |
| WO | 94/18184 | 8/1994 |
| WO | 94/24087 | 10/1994 |
| WO | 95/21843 | 8/1995 |
| WO | 96/05188 | 2/1996 |
| WO | 96/08484 | 3/1996 |
| WO | 96/16051 | 5/1996 |
| WO | 96/40255 | 12/1996 |
| WO | 97/03953 | 2/1997 |
| WO | 97/33882 | 9/1997 |
| WO | 97/49387 | 12/1997 |
| WO | 97/49736 | 12/1997 |
| WO | 98/02432 | 1/1998 |
| WO | 98/06405 | 2/1998 |
| WO | 98/23593 | 6/1998 |
| WO | 98/35937 | 8/1998 |
| WO | 98/38182 | 9/1998 |
| WO | WO 98/38182 | 9/1998 |
| WO | 98/39299 | 9/1998 |
| WO | WO 98/40375 | 9/1998 |
| WO | 98/40375 | 9/1998 |
| WO | 98/56757 | 12/1998 |
| WO | 99/11259 | 3/1999 |
| WO | 99/11260 | 3/1999 |
| WO | 99/11263 | 3/1999 |
| WO | 99/14174 | 3/1999 |
| WO | 99/14204 | 3/1999 |
| WO | 99/14215 | 3/1999 |
| WO | 99/32478 | 7/1999 |
| WO | 99/35135 | 7/1999 |
| WO | 99/64409 | 12/1999 |
| WO | 00/35889 | 6/2000 |

OTHER PUBLICATIONS

P. Barter et al. "High Density Lipoproteins and Coronary Heart Disease", Atherosclerosis, 121 1996, pp. 1–12.

A. Beckwith et al., "Iododediazoniation of Arenediazonium Salts Accompanied by Aryl Radical Ring Closure" J. Org. Chem. 1987, vol. 52, pp. 1922–1930.

D. Bilheimer et al., "Mevinolin and Colestipol Stimulate Receptor–Mediated Clearance of Low Density Lipoprotein From Plasma In Familial Hypercholesterolcmia Heterzygotes", Proc. Natl. Acad. Sci. USA, vol. 80, Jul. 1983, pp. 4124–4128.

C. Bisgaier et al., Cholesteryl Ester Transfer Protein Inhibition By PD 140195, Lipids, vol. 29, No. 12, 1994, pp. 811–818.

D. Blankenhorn et al., "Beneficial Effects of Combined Colestipol–Niacin Therapy On Coronary Atherosclerosis and Coronary Venous Bypass Grafts", JAMA, Jun. 19, 1987, vol. 257, No. 23, pp. 3233–3240.

D. Blankenhorn et al., "Beneficial Effects of Colestipol–Niacin Therapy on the Common Carotid Artery" Circulation vol. 88, Jul. 1, 1993, pp. 20–28.

P. Bonin et al., "A Peptide Inhibitor Of Cholesteryl Ester Transfer Protein Identified By Screening a Bacteriophage Display Library", Journal of Peptide Research, 51, 1998, pp. 216–225.

G. Brown, et al., "Regression of Coronary Artery Disease As A Result of Intensive Lipid–Lowering Therapy in Men With High Levels Of Apolipoprotein B", The New England Journal of Medicine, vol. 323, Nov. 8, 1990, No. 19, pp. 1289–1339.

M. Brown et al., Induction of 3–hydroxy–3Methylglutaryl Coenzyme A Reductase Activity in Human Fibroblasts Incubated with Compactin (ML–236B), A Competitive Inhibitor of the Reductase, The Journal of Biological Chemistry, vol. 253, No. 4, Feb. 22, 1978, pp. 1121 1128.

S. Busch et al., "Cholesteryl Ester Analogs Inhibit Cholesteryl Ester But Not Triglyceride Transfer Catalyzed By The Plasma Cholesteryl Ester–Triglyceride Transfer Protein", Lipids, vol. 25, No. 4 (1990), pp. 216–220.

C. Camoutsis et al., "N–Substituted 4,5–Dihydro–1, 2–Benzothiazepin–3–One 1, 1–Dioxide", J. Heterocyclic Chem. 17, pp. 1135–1136 (1980).

L. Cashin–Hemphill et al., "Beneficial Effects of Colestipol–Niacin on Coronary Atherosclerosis A 4–Year Follow–up", JAMA, Dec. 19, 1990, vol. 264, No. 23, pp. 3013–3017.

P. Catsoulacos et al., "Synthesis of Some N–Substituted 4,5–Dihydro–7,8–dimethoxybenzothiazepin–3–one 1,1–Dioxides", J. Heterocyclic Chem., vol. 13 (1976), pp. 1309–1314.

P. Catsoulacos et al., "Thiazo Compounds. Derivatives of 4, 5–Dihydro–7, 8–Dimethoxybenzothiazepin–3 one I, 1–Dioxides", Journal of Chemical and Engineering Data, vol. 22, No. 3, 1977, pp. 353–354.

K. Cho et al, "A Peptide From Hog Plasma that Inhibits Human Cholesteryl Ester Transfer Protein", Biochimica et Biophysica Acta, 1391, 1998, pp. 133–144.

D. Connolly et al., "Inactivation of Cholesteryl Ester Transfer Protein by Cysteine Modification", Biochemical and Biophysical Research Communications 223, pp. 42–47, 1996.

S. Coval et al., "Wiedendiol–A and–B, Cholesteryl Ester Transfer Protein Inhibitors From The Marine Sponge Xestosponga Wiedenmayeri", Bioorganic & Medicinal Chemistry Letter, vol. 5, No. 6, pp. 605–610, 1995.

J. Davignon et al., "Apolipoprotiein E and Atherosclerosis: Quest for an APO E Receptor Defect Leads to the Discovery of Pseudo Type III Dyslipoproteinemia in a Family", Atherosclerosis IX, pp. 199–203.

J. Davignon et al., "Comparative Efficacy and Safety of Pravastatin, Nicotinic Acid and The Two Combined in Patients with Hypercholesterolemia", The American Journal of Cardiology. Feb. 15, 1994, pp. 339–345.

C. East et al., "Combination Drug Therapy for Familial Combined Hyperlipidemia", Annals of Internal Medicine, Jul. 1, 1988, pp. 25–32.

J. Emmerich et al., "Efficacy and Safety of Simvastatin (Alone or in Association with Cholestyramine) A 1 yr. Study in 66 Patients with Type II Hyperlipoproteinacmia", European Heart Journal (1990), 11, pp. 149–155.

D. Erkelens, "Combination Drug Therapy with HMG Co A Reductase Inhibitors and Bile Acid Sequestrants for Hypercholestcrolmia", Cardiology, 1990, 77, (suppl 4). pp. 33–38.

H. Ginsberg, "Update on the Treatment of Hypercholesterolemia, with a Focus on HMG–CoA Reductase Inhibitors and Combination Regimens", Clinical Cardiology 18, pp. 307–315, (1995).

C. Glucck et al., "Gemfibrozil–Lovastatin Therapy for Primary Hyperlipoproteinemias" The American Journal of Cardiology, Jul. 1, 1992, vol. 70, No. 1, pp. 1–9.

S. Grundy et al., "Influence of Combined Therapy with Mevinolin and Interruption of Bile–Acid Reabsorption on Low Density Lipoproteins in Heterozygous Familial Hypercholesterolemia", Annals of Internal Medicine, 1985, 103: pp. 339–343.

H. Gylling et al., "Effects Of Inhibiting Cholesterol Absorption And Synthesis On Cholesterol And Lipoprotein Metabolism In Hypercholesterolemic Non–Insulin–Dependent Diabetic Men", Journal of Lipid Research, vol. 37, 1996, pp. 1776–1785.

E. Haber, "Molecular Cardiovascular Medicine" Scientific American, pp. 35–40.

V. Hegde et al., "A Depsipeptide Fungal Metabolite Inhibitor Of Cholesteryl Ester Transfer Protein", Bioorganic & Medicinal Chemistry Letters 8, 1998, pp. 1277–1280.

L. Hellberg et al., "5a–Hydroxy–3a–Cholestanecarboxylic" The New Journal for Organic Synthesis, vol. 15, No. 1–2, Feb.–Apr. 1983, pp. 154–156.

J. Heubi et al., "Primary Bile Acid Malabsorption: Defective In Vitro Ileal Active Bile Acid Transport", Gastroenterology 1982, 83: pp. 804–811.

N. Hoogerbrugge et al., "The Additional Effects of Acipimox To Simvastatin In The Treatment of Combined Hyperlipidaemia", Journal of Internal Medicine, 1997, 241: pp. 151–155.

N. Hoogerbrugge et al., "The Effacy and Safety of Pravastatin, Compared To And In Combination With Bile Acid Binding Resins, In Familial Hypercholesterolaemia", Journal of Internal Medicine 1990, 228: pp. 261–266.

A. Hutchesson et al., "Dual Bezafibrate–Simvastatin Therapy For Combined Hyperlipidaemia", Journal of Clinical Pharmacy and Therapeutics 1994, 19, pp. 387–389.

T. Ichibashi, "Mechanism of Hypocholesterolemic Action of S–8921 in Rats: S–8921 Inhibits Ileal Bile Acid Absorption", The Journal Of Pharmacology And Experimental Therapeutics, vol. 284, No. 1, pp. 43–50.

D. Illingworth, et al., "Influence of Lovstatin plus Gemfibrozil on Plasma Lipids and Lipoproteins in Patients With Heterozygous Familial Hypercholesterolemia", Circulation vol. 79, No. 3, Mar. 1989, 590–596.

D. Illingworth, "Mevinolin Plus Colestipol in Therapy for Severe Heterozygous Familial Hypercholesterolemia", Annalos of Internal Medicine, 1984; 101, pp. 598–604.

International Search Report mailed May 23, 2000 based on PCT/US 99/27942.

International Search Report mailed May 23, 2000 based on PCT/US 99/27943.

International Search Report mailed May 23, 2000 based on PCT/US 99/27944.

International Search Report mailed May 23, 2000 based on PCT/US 99/27945.

International Search Report mailed May 18, 2000 based on PCT/US 99/27947.

International Search Report mailed May 15, 2000 based on PCT/US 99/27948.

International Search Report mailed May 17, 2000 based on PCT/US 99/27949.

J. Kane, et al., "Regression of Coronary Atherosclerosis During Treatment of Familial Hypercholesterolemia With Combined Drug Regimens", JAMA, Dec. 19, 1990, Chapter 26, vol. 264, No. 23, pp. 3007–3012.

A. Katritzky et al., "Preparation Of 6–7- And 8–Membered Sultams By Friedel–Crafts Cyclization Of w–Phenylalkanesulfamoyl Chlorides", Organic Preparations and Procedures Int., 24(4), pp. 463–467 (1992).

T. Kazumi et al., "Effects of Niceritrol On Elevated Serum Lipoprotein LP (A) Levels in Diabetic Patients With Or Without Overt Proteinuria", Current Therapeutic Research, vol. 55, No. 5, May 1994, pp. 546–551.

W. Kramer, et al., "Intestinal Bile Acid Absorption", The Journal of Biological Chemistry, vol. 268, No. 24 Issue of Aug. 25, pp. 18035–18046, 1993.

Kuo, M.S. et al., "Discovery, Isolation, Structure Elucidation, and Biosynthesis of U–106305, a Choresteryl Ester Transfer Protein Inhibitor from UC 11136", J. Am. Chem. Soc. 117, pp. 10629–10634 (1995).

Kvis, K. et al., "Benzocycloheptenes and Heterocyclic Analogues as Potential Drugs. VII, 4–Phenyl–,3,4,5–Tetrahydro–1–Benzothiepins and Some Related Compounds", Chem. Commun./Vo.37/(1973) pp. 3808–3816.

Lee, J.C. et al., "A Cholesteryl Ester Transfer Protein Inhibitor from an Insect–associated Fungus", The Journal of Antibiotics 49(7), pp. 693–696.

A.M. Lees et al., "Therapy of Hypercholesterolemia With Mevinolin And Other Lipid–Lowering Drugs", Arteriosclerosis 6, 1986, p. 544a.

T. Leren et al., "Effects of Lovastatin Alone and In Combination with Cholestyramine on Serum Lipids and Apolipoproteins in Heterozygotes for Familial Hypercholesterolemia", International Journal for Research and Investigation on Atherosclerosis and Related Diseases, 73, (1988), pp. 135–141.

M. Lewis, et al., Effects Of 2164U90 on Ileal Bile Acid Absorption and Serum Cholesterol in Rats and Mice, Journal of Lipid Research, vol. 36, 1995,pp. 1098–1105.

R. Lewis, Hawley's Condensed Chemical Dictionary, p. 1238.

W. Ling et al., "Minireview Dietary Phytosterols A Review of Metabolism, Benefits and Side Effects", Life Sciences, vol. 57, No. 3, 1995, pp. 195–206.

H. Mabuchi et al., "Reduction of Serum Cholesterol In Heterozygous Patients with Familial Hypercholesterolemia", The New England Journal of Medicine, vol. 308, Mar. 17, 1983,pp. 609–613.

M. Malloy et al., "Complementarity of Colestipol, Niacin, and Lovastatin in Treatment of Severe Familial Hypercholesterolemia", Annals of Internal Medicine 1987; 107: pp. 616–623.

W. Mandeville et al., Bile Acid Sequestrants: Their Use In Combination With Other Lipid–Lowering Agents, Idrugs 1999 vol. 2., No. 3, pp. 237–242.

G. Marais et al., "Rhabdomyolysis and Acute Renal Failure Induced by Combination Lovastatin and Gemfibrozil Therapy", Annals of Internal Medicine, Feb. 1, 1990, vol. 112, No. 3, pp. 228–230.

P. McCarthy, "New Approaches to Atherosclerosis: An Overview", Medicinal Research Reviews, vol. 13, No. 2, 1993, pp. 139–159.

R. Morton, Regulation of Lipid Transfer Between Lipoproteins By An Endogenous Plasma Protein: Selective Inhibition Among Lipoprotein Classes, Journal of Lipid Research, vol. 35, 1994, pp. 836–847.

F. Nerdel et al., "Quartermay Salts of B–Amino Aldehydes and B–Iodoaldehydes", Chemische Berichte (Ed. H. Zahn), vol. 98 (1965), pp. 728–734.

M. Newman et al., "The Conversion of Phenols to Thiophenols via Dialkylthiocarbamates", The Journal Of Organic Chemistry, vol. 31, Sep.–Dec. 1966, pp. 3980–3984.

A. Orahovats et al., "A Ring Enlargement from Seven–to Ten–Membered–Ring Sulfonamide Derivatives", Helvetica Chimica Acta, vol. 79, (1996), pp. 1121–1128.

H. Pan et al., "Pharmacokinetics and Pharmacodynamics of Pravastatin Alone and With Cholestyramine in Hypercholesterolemia", Clin. Pharmacol Ther. (1980) 9, 313, pp. 201–207.

N. Panagiotopoulos et al., "N(P–Bromophenyl)—4,5—Dihydro—7,8—Dimethoxy Benzothiazepine—ONE 1, 1–Dioxide C17 H16 brNOSS", Cryst. Struct. Comm. (1980) 9, pp. 313–319.

R. Pasternak et al., "Effect of Combination Therapy with Lipid–Reducing Drugs in Patients with Coronary Heart Disease and "Normal" Cholesterol Levels", Annals of Internal Medicine, Oct. 1, 1996, vol. 125, No. 7, pp. 529–538.

R. Patra et al., "Conformational and Steric Requirements Of The Side Chain For Sulphur Participation In Benzthiepin Derivatives", Tetrahedron Letters, vol. 30, No. 32, pp. 4279–4282, 1989.

R. Pierce et al., Myopathy and Rhabdomyolysis Associated With Lovastatin–Gemfibrozil Combination Therapy, JAMA, Jul. 4, 1990, vol. 264, No. 1, pp. 71–75.

W. Pirkle et al., "Trichlorosilane–Induced Cleavage. A Mild Method for Retrieving Carbinols From Carbamates", Journal Organic Chemistry, vol. 42, No. 15, 1977, pp. 2781–2782.

W. Pirkle et al., "Dynamic NMR Studies of Disatereomeric Carbamates: Implications toward the Determination of Relative Configuration by NMR" Journal of Organic Chemistry, vol. 44, No. 26, 1979, pp. 4891–4896.

W. Pirkle et al., "An Example of Automated Liquid Chromatography Synthesis of a Broad–Spectrum Resolving Agent and Resolution of 1–(Naphthyl) 2,2,2–Trifluroethanol", The Journal of Organic Chemistry vol. 39, No. 26, 1974, pp. 3904–3906.

T. Pietzonka et al., "Phosphonate–Containing Analogs Of Cholesteryl Ester As Novel Inhibitors Of Cholesteryl Ester Transfer Protein", Bioorganic & Medicinal Chemistry Letters, vol. 6, No. 16, pp. 1951–1954.

Pravastatin Multicenter Study Group II, "Comparative Efficacy and Safety of Pravastatin and Cholestyramine Alone And Combined in Patients With Hypercholesterolemia", Archives of Internal Medicine, vol. 153, Jun. 14, 1993, pp. 1321–1328.

E. Reihner et al., Regulation of Hepatic Cholesterol Metabolism In Humans: Stimulatory Effects of Cholestyramine on HMG–CoA Reductase Activity and Low Density Lipoprotein Receptor Expression In Gallstone Patients, Journal of Lipid Research, vol. 31, 1990, pp. 2219–2226.

R. Remick et al., "Comparison of Fluoxetine and Desipramine In Depressed Outpatients", Therapeutic Research, vol. 53, No. 5, May 1993, pp. 457–483.

S. Rosenblum et al., Discovery of 1–(4–Fluorophenyl)–(3R)–[3–(4–fluorophenyl)–(3S)–hydroxypropyl]–(4S)–(4–hydroxyphenyl)–2–azetidinone (SCH 58235): A Designed, Potent, Orally Active Inhibitor of Cholesterol Absorption, Journal of Medicinal Chemistry, 1998, vol. 41, No. 6, pp. 973–980.

G. Salem et al., "Benzothiazine and Benzothizepine Derivatives: Structures of N–p–Bromophenyl–6, 7–Dimethoxy–1, 2–Benzothiazin–3(4H)–One 1, 1–Dioxide (BBTZ) and 4, 5–Dihydro–8,9–Dimethoxy–N–(5–Methyl–2–Pyridyl)–1, 2–Benzothiazepin–3–One 1, 1–Dioxide (MPTE)", Acta Cryst. (1986) C42, pp. 1581–1584.

J. Sasaki et al., "Effects of Fluvastatin, A New Inhibitor of HMG–CoA Reductase, and Niceritol on Serum Lipids, Lipoproteins and Cholesterol Ester Transfer Activity in Primary Hypercholesterolemic Patients", International Journal of Clinical Pharmacology and Therapeutics, vol. 33, No. 7, 1995, pp. 420–426.

K. Sindelar et al., Neurotropic and Psychotropic Compounds. XXIX. Derivatives Of 2,3,4,5–Tetrahydro–1–Benzothiepin, Chemical Commun., vol. 33, 1968, pp. 4315–4327.

K. Sindelar et al., Benzocycloheptenes and Hetelrocyclic Analogues As Potential Drugs. III. Further Synthetic Experiments In The Series Of 1–Benzothiepin Derivatives, vol. 37, 1972, 1195–1206.

C. Sirtori, "New Targets For Lipid Lowering And Atherosclerosis Prevention", Pharmac. Ther. vol. 67, No. 3., pp. 433–447, 1995.

Y. Son, "Purification and Characterization of Human Plasma Proteins That Inhibit Lipid Transfer Activities", Biochimica et Biophysica Acta, 795, 1984, pp. 473–480.

D. Sprecher et al., "Low–Dose Combined Therapy with Fluvastin and Cholestyramine in Hyperlipidemic Patients", Ann Intern Med. 1994; 120: pp. 537–543.

C.I. Stassinopoulou, et al., "C NMR Spectra of Benzothiazepinone, Benzothiazinone and Benzosulphonamide N–Substituted Derivatives" Department of Biology, Nuclear Research Center.

E. Stedronsky et al., "Interaction of Bile Acids and Cholesterol with Non–Systemic Agents Having Hypocholesterolemic Properties", Biochimica et Biophysica Acta., 1210, 1994, pp. 255–287.

I. Stein, et al., "Effects of Simvastatin and Cholestyramine in Familial and Nonfamilial Hypercholesterolemia", Arch Intern Med. vol. 150, Feb. 1990, pp. 341–345.

E. Stein, et al., "Lovastatin Alone And In Combination For Treatment Of Primary Hypercholseterolema", Alan R. Liss, Inc. 1988, pp. 281–293.

K. Suckling, et al., Cholesterol Lowering and Bile Acid Excretion in the Hamster with Cholestyramine Treatment, Atherosclerosis, 89, (1991) pp. 183–190.

T. Swenson, "Mechanism of Cholesterly Ester Transfer Protein Inhibition by a Neutralizing Monoclonal Antibody and Mapping of the Monoclonal Antibody Epitope", The Journal of Biological Chemistry, vol. 264, No. 24, Aug. 25, pp. 14318–14326, 1989.

A. Tall, "Plasma Cholesteryl Ester Transfer Protein", Journal of Lipid Research, vol. 34, 1993, pp. 1255–1274.

Y. Tamura et al., Novel Conversions of Benzo [b] thiophen–3 (2–H)–ones into 1,2–Benzisothiazole and Tetrahydro–1, 2–Benzothiazepin–5–One Systems via Sulphimide Intermediates, J.C.S. Perkin I, pp. 2830–2834.

K. Thurmond et al., "Water–Soluble Knedel–like Structures: The Preparation of Shell–Cross–Linked Small Particles", Journal American Chemistry Soc. vol., 118, No. 30, 1996, pp. 7239–7240.

P. Tyle, "Iontophoretic Devices for Drug Delivery", Pharmaceutical Research, vol. 3. No. 6 1986, pp. 318–325.

M. Une et al., Metabolism of 3a, 7a–Dihydroxy–7b–Methyl–5b–Cholanoic Acid and 3a, 7B–Dihydroxy–7a–Methyl–5B–Cholanoic Acid Hamsters, Biochimica et Biophysica Acta, 833 (1985), pp. 196–202.

J. Vacek et al., Comparison of Lavastatin (20 mg) and Nicotinic Acid (1.2g) With Either Drug Alone for Type II Hyperlipoproteinemia, The American Journal Of Cardiology, vol. 76, Jul. 15, 1995, pp. 182–184.

M. Van Heek et al., "In Vivo Metabolism–Based Discovery of a Potent Cholesterol Absorption Inhibitor, SCH58235, in the Rat and Rhesus Monkey Through the Identification of the Active Metabolites of SCH48461", The Journal of Pharmacology and Experimental Therapeutics, vol. 283, No. 1, pp. 157–754.

G. Vega et al., "Treatment of Primary Moderate Hypercholesterolemia With Lovastatin (Mevinolin) and Colestipol", JAMA, Jan. 2, 1987, vol. 257, No. 1, pp. 33–37.

G. Wess et al., "Synthesis and Biological Activity of Bile Acid–Derived HMG–CoA Reductase Inhibitors. The Role of 21–Methyl in Recognition of HMG–CoA Reductase and the Ileal Bile Acid Transport System", Journal Of Medicinal Chemistry 1994, 37, pp. 3240–3246.

J. Wetterau et al., "An MTP Inhibitor that Normalizes Atherogenic Lipoprotein Levels In WHHL Rabbits", Science vol. 282, Oct. 23, 1998, pp. 751–754.

O. Wiklund et al., "Pravastatin and Gemfibrozil Alone and in Combination for the Treatment of Hypercholesterolemia", The American Journal of Medicine vol. 94, Jan. 1993, pp. 13–19.

S. Wirebaugh et al., "A Retrospective Review of the Use of Lipid–Lowering Agents in Combination, Specifically, Gemfibrozil and Lovastatin", Pharmacotherapy vol. 12, No. 6, 1992, pp. 445–450.

J. Witztum, "Drugs Used In The Treatment of Hyperlipoproteinemias", The Pharmacological Basis of Therapeutics, $9^{th}$ Edition, pp. 875–894.

Yan Xia et al., "Substituted 1,3,5–Triazines As Cholesteral Ester Transfer Protein Inhibitors", Bioorganic & Medicinal Chemistry Letters, vol. 6, No. 7, 1996, pp. 919–922.

A. Yamamoto et al., "Effects of Probucol on Xanthomata Regression in Familial Hypercholesterolemia", Am Journal Cardiolgy, 1986, 57: pp. 29H–35H.

K. Ytre–Arne et al., "Simvastatin and Cholestyramine In The Long–Term Treatment of Hypercholesterolaemia", Journal of Internal Medicine (1989): 226, pp. 285–290.

Angelin, B., "Regulation of Hepatic Cholesterol Metabolism in Man," Ann. Med. 23, pp. 10–27 (1991).

Blum, C. B., "Comparison of Properties of Four Inhibitors of 3–Hydroxy–3–Methylglutaryl–Coenzyme A Reductase," Am. J. Cardiol., 73(14), 3D–11D, (1994).

Cayen, M.N., "Disposition, Metabolism and Pharmacokinetics of Anthyperlipidemic Agents in Laboratory Animals and Man," Pharmac. & Ther., 29, pp. 157–204 (1985).

Da Col, et al., "Tolerability and Efficacy of Combination Therapy with Simvastatin Plus Gemfibrosil in Type II Refractory Familial Combined Hyperlipidemia," Curr. Therap. Research, vol. 53, No. 5, pp. 473–483 (1993).

Davignon, et al. "HMG CoA Reductase Inhibitors: A look back and a look ahead," Can. J. Cardiol., 8(8), pp. 843–864 (1992).

Endo, A, "Chemistry, biochemistry and pharmacology of HMG–Co–A reductase Inhibitors," Klin. Wochemschr. 66, pp. 421–427 (1988).

Kramer et al., "Bile acid derived HMG–CoA reductase inhibitors," Biochimica et Biophysica Acta, 1227 pp. 137–154 (1994).

Marcus, A, "Role of the HMG–CoA Reductase Inhibitors in the Treatment of Dyslipidemia: An Evolutionary Review," CVR&R, pp. 13–27 (Jan. 1996).

International Search Report for PCT/US02/35257, 2002.

* cited by examiner

MONO- AND DI-FLUORINATED BENZOTHIEPINE COMPOUNDS AS INHIBITORS OF APICAL SODIUM CO-DEPENDENT BILE ACID TRANSPORT (ASBT) AND TAUROCHOLATE UPTAKE

This is a non-provisional application which claims the benefit of priority of provisional Application No. 60/330,892, filed Nov. 2, 2001, the subject matter of which is incorporated herein by reference.

FIELD OF THE INVENTION

The present invention relates to compounds, pharmaceutical compositions, and methods for treating high blood cholesterol levels in a subject. More particularly, the present invention relates to novel mono-fluorinated or di-fluorinated benzothiepine compounds that are useful as apical sodium co-dependent bile acid transport (ASBT) inhibitors, pharmaceutical compositions containing the same, methods for making the same and methods for treating hyperlipidemic conditions.

DESCRIPTION OF THE RELATED ART

The major metabolic fate of cholesterol in the human body is in the hepatic synthesis of bile acids. Bile acids are both passively and actively reabsorbed from the small intestine and recycled via the enterohepatic circulation to conserve the total pool of bile acids. Dietschy, "Mechanisms for the intestinal absorption of bile acids", *J. Lipid Res.*, 9:297–309 (1968). Bile acids undergo passive absorption in the proximal small intestine and active transport in the terminal ileum. Love et al., "New insights into bile acid transport", *Curr. Opin. Lipidol.*, 9 (3):225–229 (1998). Ileal active transport accounts for the majority of intestinal bile acid uptake and is the exclusive route for taurine-conjugated bile acids. Id. Ileal active transport is mediated by the apical sodium co-dependent bile acid transporter ("ASBT", also known as the ileal bile acid transporter or "IBAT") localized to the distal one-third of the ileum. Craddock et al., "Expression and transport properties of the human ileal and renal sodium-dependent bile acid transporter", *Am. J. Physiol.*, 274 (Gastrointest. Liver Physiol. 37):G157–G169 (1998).

An equilibrium generally exists between hepatic cholesterol and the bile acid pool. Interruption of the enterohepatic recirculation of bile acids (e.g., the binding of intestinal bile acids to a sequestering resin such as cholestyramine; the surgical removal of the ileum to physically eliminate ileal ASBT; or the specific inhibition of ileal ASBT) results in a decrease in the liver bile acid pool and stimulates increased hepatic synthesis of bile acids from cholesterol (i.e., an upregulation of cholesterol-7∀-hydroxylase activity), eventually depleting the liver's pool of esterified cholesterol. In order to maintain liver cholesterol levels necessary to support bile acid synthesis, the de novo synthesis of cholesterol increases in the hepatocytes (i.e., an upregulation of 3-hydroxy-3-methylglutaryl coenzyme-A reductase activity) and also increases the uptake of serum cholesterol by upregulating the number of cell surface low density lipoprotein cholesterol receptors ("LDL receptors"). The number of hepatic LDL receptors directly impacts serum low density lipoprotein ("LDL") cholesterol levels, with an increase in the number of LDL receptors resulting in a decrease in serum cholesterol. The net result, therefore, is that serum LDL cholesterol levels decrease when intestinal bile acid reabsorption is reduced.

A class of antihyperlipidemic agents that operates by inhibiting bile acid reabsorption in the ileum recently has been identified. Examples of this class of agents include the substituted benzothiepines disclosed in U.S. Pat. No. 5,994,391. PCT Patent Application No. WO99/35135 discloses additional substituted benzothiazepine compounds for use as ASBT inhibitors. By way of further example, PCT Patent Application No. WO94/24087 discloses a group of substituted naphthalene compounds for use as ABST inhibitors. The United States Food and Drug Administration, however, has not approved any ASBT inhibitor for use as an antihyperlipidemic agent at this time.

Numerous antihyperlipidemic agents having other modes of action also have been disclosed in the literature as useful for the treatment of hyperlipidemic conditions and disorders. These agents include, for example, commercially available drugs such as nicotinic acid, bile acid sequestrants including cholestyramine and colestipol, 3-hydroxy-3-methylglutaryl coenzyme-A reductase inhibitors ("HMG Co-A reductase inhibitors"), probucol, and fibric acid derivatives including gemfibrozil and clofibrate.

The class of antihyperlipidemic agents known as HMG Co-A reductase inhibitors operates by inhibiting the hepatic enzyme 3-hydroxy-3-methylglutaryl coenzyme-A reductase ("HMG Co-A reductase"). Direct inhibition of HMG Co-A reductase by the monotherapeutic administration of HMG Co-A reductase inhibitors such as pravastatin has been shown to be a clinically effective method of lowering serum LDL cholesterol. Sacks et al., "The Effect of Pravastatin on Coronary Events after Myocardial Infarction in Patients with Average Cholesterol Levels", *New England Journal of Medicine*, 335(14):1001–9 (1996). Monotherapeutic treatment with pravastatin may lead to upregulation of cell surface LDL receptors as a mechanism to provide cholesterol to the liver in support of bile acid synthesis. Fujioka et al., "The Mechanism of Comparable Serum Cholesterol Lowering Effects of Pravastatin Sodium, a 3-Hydroxy-3-Methylglutaryl Coenzyme A Inhibitor, between Once- and Twice-Daily Treatment Regimens in Beagle Dogs and Rabbits", *Jpn. J. Pharmacol.*, Vol. 70, pp. 329–335 (1996).

The administration of an ASBT inhibitor in combination with an HMG Co-A reductase inhibitor is generally disclosed in PCT Application WO98/40375.

The treatment of hypercholesterolemia with an HMG Co-A reductase inhibitor in combination with a bile acid sequestering resin also has been reported in the literature. The administration of the HMG Co-A reductase inhibitor lovastatin in combination with the bile acid sequestering resin colestipol is disclosed in Vega et al., "Treatment of Primary Moderate Hypercholesterolemia With Lovastatin (Mevinolin) and Colestipol", *JAMA*, Vol. 257(1), pp. 33–38 (1987). The administration of the HMG Co-A reductase inhibitor pravastatin in combination with the bile acid sequestering resin cholestyramine is disclosed in Pan et al., "Pharmacokinetics and pharmacodynamics of pravastatin alone and with cholestyramine in hypercholesterolemia", *Clin. Pharmacol. Ther.*, Vol. 48, No. 2, pp. 201–207 (August 1990).

The treatment of hypercholesterolemia with other selected combination regimens also has been reported in the literature. Ginsberg, "Update on the Treatment of Hypercholesterolemia, with a Focus on HMG Co-A Reductase Inhibitors and Combination Regimens", *Clin. Cardiol.*, Vol. 18(6), pp. 307–315 (June 1995), reports that, for resistant cases of hypercholesterolemia, therapy combining an HMG Co-A reductase inhibitor with either a bile acid sequestering resin, niacin or a fibric acid derivative generally is effective and well tolerated. Pasternak et al., "Effect of Combination Therapy with Lipid-Reducing Drugs in Patients with Coronary Heart Disease and 'Normal' Cholesterol Levels", *Annals of Internal Medicine*, Vol. 125, No. 7, pp. 529–540 (Oct. 1, 1996) reports that treatment with either a combination of the HMG Co-A reductase inhibitor pravastatin and nicotinic acid or a combination of pravastatin and the fibric acid derivative gemfibrazol can be effective in lowering LDL cholesterol levels.

It is desirable to provide novel ASBT inhibitors that exhibit improved efficacy, improved potency, and/or reduced dosing requirements for the active compounds relative to the specific combination regimens previously disclosed in the published literature.

SUMMARY OF THE INVENTION

According to one embodiment, the invention comprises novel fluorinated benzothiepine compounds corresponding to Formulas I-1 to I-24 (see the Detailed Description, infra) that are effective agents for the treatment of one or more hyperlipidemic condition(s).

According to another embodiment, the invention comprises pharmaceutical compositions comprising one or more of the novel fluorinated benzothiepine compounds corresponding to Formulas I-1 to I-24 that are suitable for use in treating one or more hyperlipidemic condition(s).

According to yet another embodiment, the invention comprises a method for treating one or more hyperlipidemic condition(s) comprising administering to a subject a therapeutically effective amount of one or more of the novel fluorinated benzothiepine compounds corresponding to Formulas I-1 to I-24.

According to still another embodiment, the invention comprises methods for making the novel benzothiepine compounds corresponding to Formulas I-1 to I-24. Other aspects of the invention will be apparent to those of ordinary skill in view of the present description provided below.

DETAILED DESCRIPTION OF THE PREFERRED EMBODIMENTS

According to one embodiment, the invention comprises novel mono-fluorinated and di-fluorinated benzothiepene compounds defined by Formulas I-1 to I-8:

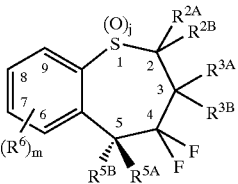
I-1

I-1a

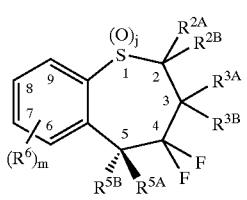
I-1b

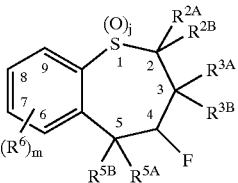
I-2

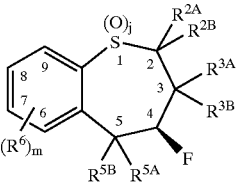
I-3

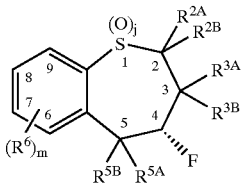
I-4

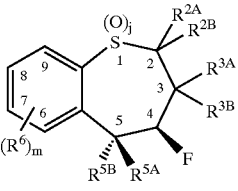
I-5

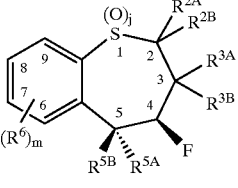
I-6

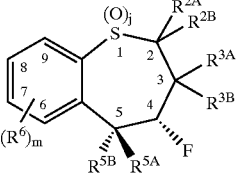
I-7

I-8 or a pharmaceutically acceptable salt, solvate, or prodrug thereof wherein j is 0, 1 or 2; m is 0, 1, 2, 3 or 4;

wherein $R^{2A}$ and $R^{2B}$ are independently selected from the group consisting of hydrogen and hydrocarbyl;

wherein $R^{3A}$, $R^{3B}$, $R^{5A}$, and $R^{5B}$ are independently selected from the group consisting of hydrogen, alkyl; cycloalkyl; alkenyl; alkynyl; aryl; heterocyclyl; quaternary heterocyclyl, oxo; aryl-$R^5$; —$OR^9$; —$NR^9R^{10}$; —$SR^9$; —$S(O)R^9$; —$SO_2R^9$; and —$SO_3R^9$;

wherein $R^9$ and $R^{10}$ are independently selected from the group consisting of hydrogen; hydrocarbyl; amino; and hydrocarbylamino;

wherein $R^5$ is selected from the group consisting of hydrogen; alkyl; cycloalkyl; alkenyl; alkynyl; aryl; heterocyclyl; quaternary heterocyclyl; —$OR^9$; —$SR^9$; —$S(O)R^9$; —$SO_2R^9$; and —$SO_3R^9$;

wherein when $R^5$ is said cycloalkyl, aryl or heterocyclyl, said cycloalkyl, aryl or heterocyclyl are optionally substituted with —NH—X—R or —O—X—R;

wherein X is selected from the group consisting of —(C=O)$_s$-alkyl-; —(C=O)$_s$-alkyl-NH—; —(C=O)$_s$-alkyl-O—; —(C=O)$_s$-alkyl-(C=O)$_t$; and a covalent bond, wherein s and t are independently 0 or 1;

wherein R is selected from the group consisting of monosaccharides, disaccharides, and polysaccharides, wherein said monosaccharides, disaccharides, and polysaccharides are optionally protected with one or more sugar protecting groups;

wherein $R^9$ and $R^{10}$ are as previously defined;

wherein, when $R^5 \neq H$, $R^5$ is optionally substituted with one or more radicals independently selected from the group consisting of halogen; —$NO_2$; —CN; oxo; hydrocarbyl; —$OR^{13}$; —$NR^{13}R^{14}$; —$SR^{13}$; —$S(O)R^{13}$; —$SO_2R^{13}$; —$SO_3R^{13}$; —$NR^{13}OR^{14}$; —$NR^{13}NR^{14}R^{15}$; —$CO_2R^{13}$; —OM; —$SO_2OM$; —$SO_2NR^{13}R^{14}$; —$C(O)NR^{13}R^{14}$; —C(O)OM; —$COR^{13}$; —$NR^{13}C(O)R^{14}$; —$NR^{13}C(O)NR^{14}R^{15}$; —$NR^{13}CO_2R^{14}$; —$OC(O)R^{13}$; —$OC(O)NR^{13}R^{14}$; —$NR^{13}SOR^{14}$; —$NR^{13}SO_2R^{14}$; —$NR^{13}SONR^{14}R^{15}$; —$NR^{13}SO_2NR^{14}R^{15}$; —$PR^{13}R^{14}$; —$P(O)R^{13}R^{14}$; —$P^+R^{13}R^{14}R^{15}A^-$; —$P(OR^{13})OR^{14}$; —$S^+R^{13}R^{14}A^-$; and —$N^+R^{13}R^{14}R^{15}A^-$;

wherein $R^{13}$, $R^{14}$, and $R^{15}$ are independently selected from the group consisting of hydrogen and hydrocarbyl;

wherein $A^-$ is a pharmaceutically acceptable anion;

wherein M is a pharmaceutically acceptable cation;

wherein one or more $R^6$ radicals are independently selected from the group consisting of hydrogen; halogen; —CN; —$NO_2$; hydrocarbyl; —$R^5$; —$OR^{13}$; —$NR^{13}R^{14}$; —$SR^{13}$; —$S(O)R^{13}$; —$S(O)_2R^{13}$; —$SO_3R^{13}$; —$S^+R^{13}R^{14}A^-$; —$NR^{13}OR^{14}$; —$NR^{13}NR^{14}R^{15}$; —OM; —$SO_2OM$; —$SO_2NR^{13}R^{14}$; —$NR^{14}C(O)R^{13}$; —C(O)OM; —$S(O)NR^{13}R^{14}$; —$N^+R^{13}R^{14}R^{15}A^-$; —$PR^{13}R^{14}$; —$P(O)R^{13}R^{14}$; —$P^+R^{13}R^{14}R^{15}A^-$; amino acid residue; peptide residue; polypeptide residue; and carbohydrate residue;

wherein $R^{13}$, $R^{14}$, $R^{15}$, $A^-$, and M are as defined above; and wherein, in each instance, said hydrocarbyl may be optionally substituted with one or more groups comprising one or more heteroatoms, and wherein, in each instance, said hydrocarbyl optionally may have one or more carbon atoms replaced by one or more heteroatoms independently selected from the group consisting of oxygen, nitrogen, sulfur, phosphorus and combinations thereof.

In one embodiment, aryl-$R^5$ is phenyl substituted with —N(H)—X—$R^{33}$ or —O—X—$R^{33}$ wherein X is selected from the group consisting of:
—(C=O)s-alkyl-; —(C=O)s-alkyl-NH—; —(C=O)s-alkyl-O—; —(C=O)s-alkyl-C=O)t; and a covalent bond; wherein $R^{33}$ is selected from selected from the group consisting of monosaccharides, disaccharides, and polysaccharides; and s and t are independently 0 or 1.

In one embodiment, aryl-$R^5$ is phenyl substituted at the para-position with —N(H)—X—$R^{33}$ or —O—X—$R^{33}$ wherein X is selected from the group consisting of:
—(C=O)s-alkyl-; —(C=O)s-alkyl-NH—; —(C=O)s-alkyl-O—; —(C=O)s-alkyl-C=O)t; and a covalent bond; and wherein $R^{33}$ is selected from selected from the group consisting of monosaccharides, disaccharides, and polysaccharides; and s and t are independently 0 or 1.

In another embodiment, aryl-$R^5$ is phenyl substituted at the meta-position with —N(H)—X—$R^{33}$ or —O—X—$R^{33}$ wherein X is selected from the group consisting of:
—(C=O)s-alkyl-; —(C=O)s-alkyl-NH—; —(C=O)s-alkyl-O—; —(C=O)s-alkyl-C=O)t; and a covalent bond; and $R^{33}$ is selected from selected from the group consisting of monosaccharides, disaccharides, and polysaccharides; and s and t are independently 0 or 1.

In another embodiment, aryl-$R^5$ is phenyl substituted with a radical selected from the group consisting of members (1)–(24), (25)–(48), or (49)–(70), of Table 1 below.

Furthermore, the term "hydrocarbyl" includes, but is not limited to moieties such as alkyl, cycloalkyl, alkenyl, cycloalkenyl, alkynyl and moieties optionally substituted with aliphatic or cyclic hydrocarbon groups such as alkaryl, alkenaryl and alkynaryl. Typically, the "hydrocarbyl" moieties comprise 1–20 carbon atoms, 1–18 carbon atoms, 1–12 carbon atoms, 3–12 carbon atoms, 1–6 carbon atoms, or 3–6 carbon atoms.

Also, $R^{5A}$ and $R^{5B}$ may be independently selected from the group consisting of hydrogen, aryl, heterocycle, quaternary heterocycle and quaternary heteroaryl wherein said aryl, heteroaryl, quaternary heterocycle, and quaternary heteroaryl can be substituted with one or more substituent groups independently selected from the group consisting of alkyl, alkenyl, alkynyl, polyalkyl, polyether, aryl, haloalkyl, cycloalkyl, heterocycle, arylalkyl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, C(O)OM, $COR^{13}$, $P(O)R^{13}R^{14}$, $P^+R^{13}R^{14}R^{15}A^-$, $P(OR^{13})OR^{14}$, $S^+R^{13}R^{14}A^-$, and $N^+R^9R^{11}R^{12}A^-$;

wherein said alkyl, alkenyl, alkynyl, polyalkyl, polyether, aryl, haloalkyl, cycloalkyl, and heterocycle can optionally have one or more carbons replaced by O, $NR^7$, $N^+R^7R^8A^-$, S, SO, $SO_2$, $S^+R^7A^-$, $PR^7$, $P(O)R^7$, $P^+P^7R^8A^-$, or phenylene;

wherein said alkyl, alkenyl, alkynyl, polyalkyl, polyether, aryl, haloalkyl, cycloalkyl, and heterocycle can be further substituted with one or more substituent groups selected from the group consisting of $OR^7$, $NR^7R^8$, $SR$, $S(O)R^7$, $SO_2R^7$, $SO_3R^7$, $CO_2R^7$, CN, oxo, $CONR^7R^8$, $N^+R^7R^8R^9A^-$, alkyl, alkenyl, alkynyl, aryl, cycloalkyl, heterocycle, arylalkyl, quaternary heterocycle, quaternary heteroaryl, $P(O)R^7R^8$, $P^+R^7R^8A^-$, and $P(O)(OR^7)OR^8$ wherein $R^7$ and $R^8$ are independently selected from hydrogen and alkyl.

Even further, $R^{5A}$ and $R^{5B}$ may independently have the formula (I):

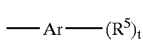
(I)

wherein t is an integer selected from 0, 1, 2, 3, 4 and 5;
wherein Ar is selected from the group consisting of phenyl, thiophenyl, pyridyl, piperazinyl, piperonyl, pyrrolyl, naphthyl, furanyl, anthracenyl, quinolinyl, isoquinolinyl, quinoxalinyl, imidazolyl, pyrazolyl, oxazolyl, isoxazolyl, pyrimidinyl, thiazolyl, triazolyl, isothiazolyl, indolyl, benzoimidazolyl, benzoxazolyl, benzothiazolyl, and benzoisothiazolyl;
wherein one or more $R^5$ are independently selected from the group consisting of alkyl, alkenyl, alkynyl, polyalkyl, polyether, aryl, haloalkyl, cycloalkyl, heterocycle, arylalkyl, halogen, oxo, $OR^{13}$, $NR^{13}R^{14}$, $SR^{13}$, $S(O)R^{13}$, $SO_2R^{13}$, $SO_3R^{13}$, $NR^{13}OR^{14}$, $NR^{13}NR^{14}R^{15}$, $NO_2$, $CO_2R^{13}$, CN, OM, $SO_2OM$, $SO_2NR^{13}R^{14}$, $C(O)NR^{13}R^{14}$, C(O)OM, $CR^{13}$, $P(O)R^{13}R^{14}$, $P^+R^{13}R^{14}R^{15}A^-$, $P(OR^{13})OR^{14}$, $S^+R^{13}R^{14}A^-$, and $N^+R^9R^{11}R^{12}A^-$;
wherein said alkyl, alkenyl, alkynyl, polyalkyl, polyether, aryl, haloalkyl, cycloalkyl, and heterocycle can be further substituted with one or more substituent groups selected from the group consisting of $OR^7$, $NR^7R^8$, $SR^7$, $S(O)R^7$, $SO_2R^7$, $SO_3R^7$, $CO_2R^7$, CN, oxo, $CONR^7R^8$, $N^+R^7R^8R^9A^-$, alkyl, alkenyl, alkynyl, aryl, cycloalkyl, heterocycle, arylalkyl, quaternary heterocycle, quaternary heteroaryl, $P(O)R^7R^8$, $P^+R^7R^8A^-$, and $P(O)(OR^7)OR^8$;
wherein said alkyl, alkenyl, alkynyl, polyalkyl, polyether, aryl, haloalkyl, cycloalkyl, and heterocycle can optionally have one or more carbons replaced by O, $NR^7$, $N^+R^7R^8A^-$, S, SO, $SO_2$, $S^+R^7A^-$, $PR^7$, $P(O)R^7$, $P^+R^7R^8A^-$, or phenylene; and
wherein t and $R^5$ are as previously described.

Yet, even further, $R^{5A}$ and $R^{5B}$ may independently have the formula (II):

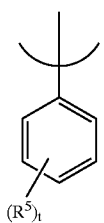
(II)

wherein t and $R^5$ are as previously described.

Furthermore, one or more $R^6$ radicals are in the 6-, 7-, 8- and/or 9-position of the benzo ring of formulas I-1 to I-24 described herein. Preferably, $R^6$ is in the 7-, 8- and/or 9-position of the benzo ring of formulas I-1 to I-24. More preferably, $R^6$ is in the 7- and/or 8-position of the benzo ring of formulas I-1 to I-24. Furthermore, $R^6$ is independently selected from the group consisting of:

(a) alkyl, aryl, cycloalkyl, heterocycle, polyalkyl, acyloxy, polyether, halogen, $OR^{13}$, $NR^{13}R^{14}$, $NR^{13}NR^{14}R^{15}$, $N^+R^9R^{11}R^{12}A^-$; $SR^{13}$, $S^+R^{13}R^{14}$, $CO_2R^{13}$, $NR^{14}C(O)R^{13}$, and $NR^{14}C(O)R^{13}$, wherein alkyl, aryl, cycloalkyl, heterocycle, polyalkyl, acyloxy, and polyether, can be further substituted with $OR^9$, $NR^9R^{10}$, $N^+R^9R^{10}R^{12}A^-$, $SR^9$, $S(O)R^9$, $SO_2R^9$, $SO_3R^9$, oxo, $CO_2R^9$, CN, halogen, $CONR^9R^{10}SO_2OM$, $SO_2NR^9R^{10}$, $PO(OR^{16})OR^{17}$, $P^+R^9R^{11}R^{12}A^-$, $S^+R^9R^{10}A^-$, or C(O)OM;
wherein in $R^6$, one or more carbons are optionally replaced by O, $NR^{13}$, $N^+R^{13}R^{14}A^-$, S, SO, $SO_2$, $S^+R^{13}A^-$, $PR^{13}$, $P(O)R^{13}$, $P^+R^{13}R^{14}A^-$, phenylene, amino acid, peptide, polypeptide, carbohydrate, polyether, or polyalkyl, and
wherein in said polyalkyl, phenylene, amino acid, peptide, polypeptide, and carbohydrate, one or more carbons are optionally replaced by O, $NR^9$, $N^+R^9R^{10}A^-$, S, SO, $SO_2$, $S^+R^9A^-$, $PR^9$, $P^+R^9R^{10}A^-$, or $P(O)R^9$;

(b) alkyl, aryl, cycloalkyl, heterocycle, polyalkyl, acyloxy, polyether, halogen, $OR^{13}$, $NR^{13}R^{14}$, $NR^{13}NR^{14}R^{15}$, $N^+R^9R^{11}R^{12}A^-$, $SR^{13}$, $S^+R^{13}R^{14}$, $CO_2R^{13}$, $NR^{14}C(O)R^{13}$, and $NR^{14}C(O)R^{13}$;
wherein alkyl, aryl, cycloalkyl, heterocycle, polyalkyl, acyloxy, and polyether, can be further substituted with $OR^9$, $NR^9R^{10}$, $N^+R^9R^{11}R^{12}A^-$, $SR^9$, $S(O)R^9$, $SO_2R^9$, $SO_3R^9$, oxo, $CO_2R^9$, CN, halogen, $CONR^9R^{10}SO_2OM$, $SO_2NR^9R^{10}$, $PO(OR^{16})OR^{17}$, $P^+R^9R^{11}R^{12}A^-$, $S^+R^9R^{10}A^-$, or C(O)OM;
wherein $R^7$, $R^8$, $R^9$, $R^{10}$, $R^{11}$, $R^{12}$, $R^{13}$, $R^{14}$, $R^{15}$ and $A^-$ are as previously defined and $R^{16}$ and $R^{17}$ are independently selected from the group consisting of hydrogen and alkyl, and optionally $R^{13}=R^{14}=$ methyl;
wherein in $R^6$, one or more carbons are optionally replaced by O, $NR^{13}$, $N^+R^{13}R^{14}A^-$, S, SO, $SO_2$, $S^+R^{13}A^-$, $PR^{13}$, $P(O)R^{13}$, $P^+R^{13}R^{14}A^-$, phenylene, amino acid, peptide, polypeptide, carbohydrate, polyether, or polyalkyl; and
wherein in said polyalkyl, phenylene, amino acid, peptide, polypeptide, and carbohydrate, one or more carbons are optionally replaced by O, $NR^9$, $N^+R^9R^{10}A^-$, S, SO, $SO_2$, $S^+R^9A^-$, $PR^9$, $P^+R^9R^{10}A^-$, or $P(O)R^9$;

(c) polyether, $OR^{13}$, $NR^{13}R^{14}$ and $N^+R^9R^{11}R^{12}A^-$;

(d) polyether, $OR^{13}$ and $NR^{13}R^{14}$.

According to another embodiment, the class of ASBT inhibitor compounds are as previously defined by Formulas I-1 to I-8 except that:

j is 2;

$R^{2A}$ and $R^{2B}$ are hydrogen;

wherein $R^{3A}$ and $R^{3B}$ are independently selected from the group consisting of hydrogen and alkyl; and wherein $R^{5A}$ and $R^{5B}$ are independently selected from the group consisting of hydrogen and phenyl optionally substituted at the meta or para position with $R^5$ selected from the group consisting of members (1)–(70) denoted in Table 1 below. It is noted that when $R^5$ is a bridging linkage, dimeric or polymeric compounds of the type {-benzothiepene-bridge-benzothiepene-} are formed wherein the benzothiepene is selected from the group consisting of Formulas I-1 to I-24 and exemplary bridging $R^5$ groups include, but are not limited to, (7), (17) and (24) in Table 1 below.

TABLE 1
| | $R^5$ |
|---|---|
| (1) | 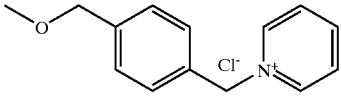 |
| (2) | 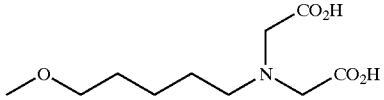 |
| (3) | 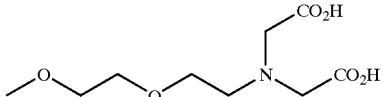 |
| (4) | 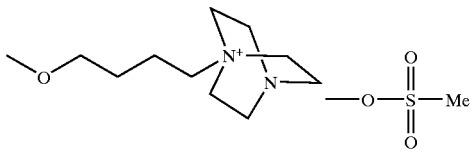 |
| (5) | 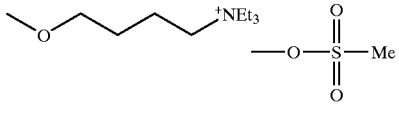 |
| (6) | 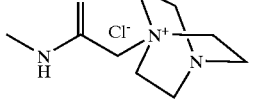 |
| (7) | 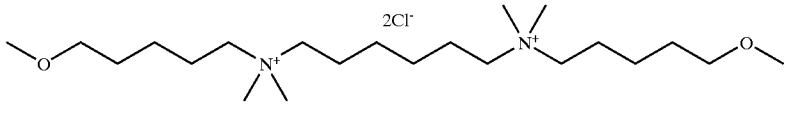 |
| (8) | 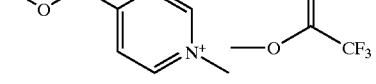 |
| (9) | 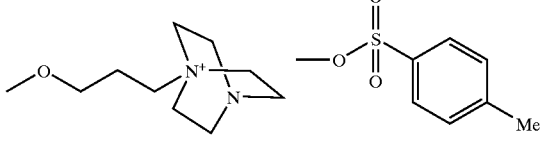 |
| (10) | 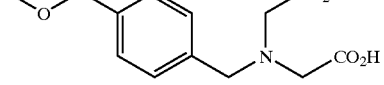 |
| (11) | 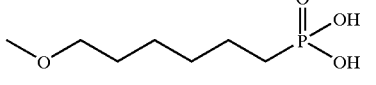 |
| (12) | 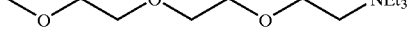 |

TABLE 1-continued

| | R⁵ |
|---|---|
| (13) | [structure: methoxy-butyl chain attached to N⁺-pyridinium with 3-OH; counterion methyl methanesulfonate —O–S(=O)₂–Me] |
| (14) | [structure: 6-(methoxymethyl)pyridin-2-yl-CH₂–N(CH₂CO₂H)₂] |
| (15) | [structure: MeNH–C(=O)–C₆H₄–CH₂–N⁺(quinuclidine) Cl⁻] |
| (15a) | [structure: MeNH–C(=O)–NH–C₆H₄–CH₂–N⁺(quinuclidine) Cl⁻] |
| (16) | [structure: MeO–CH₂–C₆H₄–CH₂–N⁺(quinuclidine) Cl⁻] |
| (17) | [structure: MeO–CH₂–O–R–O–CH₂–OMe]<br>R = 1000 MW PEG |
| (18) | [structure: 4-(methylamino)-1-methylpyridinium; counterion p-toluenesulfonate —O–S(=O)₂–C₆H₄–Me] |
| (19) | [structure: MeNH–S(=O)₂–N(CH₂CO₂H)₂] |
| (20) | [structure: MeO–(CH₂)₄–(1H-tetrazol-5-yl)] |
| (21) | [structure: MeO–(CH₂)₄–S–(tetrazol-5-yl) with N1–CH₂CO₂H] |

TABLE 1-continued

| | R⁵ |
|---|---|
| (22) | methoxyacetyl-glycine (CH₃O-CH₂-C(O)-NH-CH₂-CO₂H) |
| (23) | 4-(methoxymethyl)benzoic acid |
| | [macrocyclic polyamine complex with M, bearing a methyl carbamate substituent] |
| (24) | $M = Co^{II, III}, Mn^{II, III}, Fe^{II, III}, Ni^{II, III}, Cr^{III}, Cu^{II}, Zn^{II}, Cd^{II}, Ga^{III}, In^{III}, V^{IV}, Ru^{II}, Pr^{IV}, Rh^{III}$ or $Ir^{III}$ |
| (25) | N-methyl amide linked to butyl-N(H)-CH₂-[CH(OH)]₄-CH₂OH |
| (26) | N-methyl amide linked to butyl-NH-C(O)-[CH(OH)]₄-CH₂OH |
| (27) | N-methyl gluconamide |
| (28) | N-methyl amide linked to (CH₂)₉-NH-C(O)-[CH(OH)]₄-CH₂OH |
| (29) | N-methyl amide linked to butyl-tetrahydropyran (sugar) |
| (30) | N-methyl amide linked to butyl-tetrahydropyran uronic acid |

TABLE 1-continued

| R⁵ |
|---|
| (31) [chemical structure: N-methylamino pyranose with OH groups and CH2OH] |
| (32) [chemical structure: N-methylamino pyranose with OH groups and COOH] |
| (33) [chemical structure: methylamide-(CH2)9-N-pyranose-COOH with OH groups] |
| (34) [chemical structure: methylamide-(CH2)9-N-pyranose with OH groups and CH2OH] |
| (35) [chemical structure: methylamide-(CH2)3-N-pyranose-COOH with OH groups] |
| (36) [chemical structure: methylamide-(CH2)3-N-pyranose with OH groups and CH2OH] |
| (37) [chemical structure: methyl ester-(CH2)3-NH-CH2-(CHOH)4-CH2OH] |
| (38) [chemical structure: methyl ester-(CH2)3-N(H)-C(O)-(CHOH)4-CH2OH] |
| (39) [chemical structure: methyl ester of gluconic acid, methyl-O-C(O)-(CHOH)4-CH2OH] |

TABLE 1-continued

| | $R^5$ |
|---|---|
| (40) | |
| (41) | |
| (42) | |
| (43) | |
| (44) | |
| (45) | |
| (46) | |
| (47) | |

TABLE 1-continued
| R⁵ |
|---|
| (48) 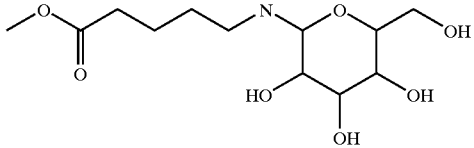 |
| (49) 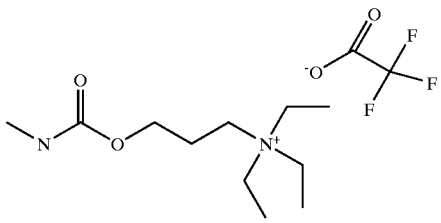 |
| (50) 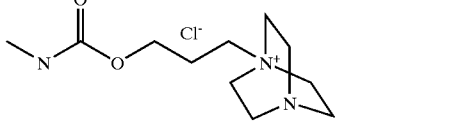 |
| (51) 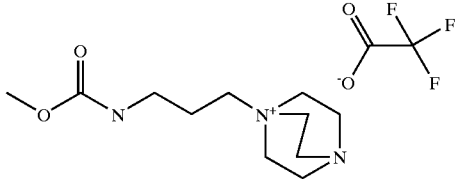 |
| (52) 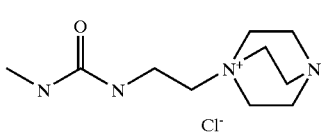 |
| (53) 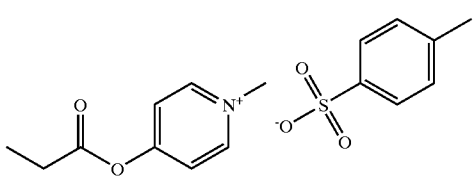 |
| (54) 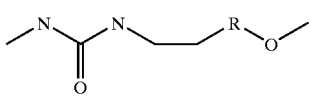 |
| (55) 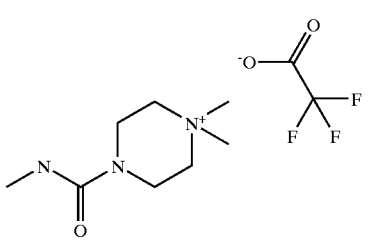 |

TABLE 1-continued

| R⁵ |
| --- |

(56) [structure: N-methylpyridinium with N-methylurea substituent, tosylate counterion]

(57) [structure: N-methyliminodiacetic acid]

(58) [structure: N-methylphthalimide-4,5-dicarboxylic acid]

(59) [structure: 4-(5-methoxypentyloxy)pyridine-2,6-dicarboxylic acid]

(60) [structure: 2-[2-(2-methoxyethoxy)ethyl]malonic acid]

(61) [structure: ethyltrimethylammonium iodide]

(62) [structure: tetraethylammonium bromide]

(63) [structure: ethyltriphenylphosphonium bromide]

TABLE 1-continued

R⁵

(64) 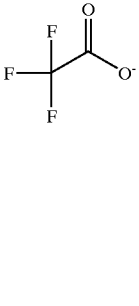

(65) 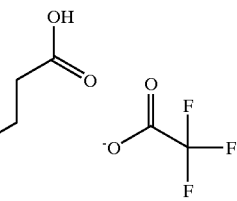

(66) 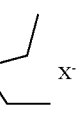

(67) 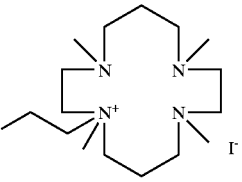

(68) 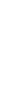

(69) and 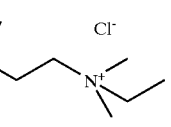

(70) 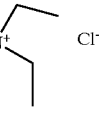

Also, in tails (1)–(70) the specified anion may be replaced by another pharmaceutically acceptable anion (e.g., A⁻ which anion is as previously described). Optionally, R⁵ may be selected from the following: (1)–(24), (25)–(48) or (49)–(70) from Table 1. Further, R⁵ may be acidic or contain a quarternary ammonium nitrogen. Even further, R⁵ may be selected from the following: (1)–(5), (6)–(10), (11)–(15), (16)–(20), (21)–(25), (26)–(30), (31)–(35), (36)–(40), (41)–(45), (46)–(50), (51)–(55), (56)–(60), (61)–(65), (66)–(70), or combinations thereof from Table 1.

Other exemplary embodiments of ASBT inhibitors of the present invention are represented by Formulas I-9 to I-16 below.

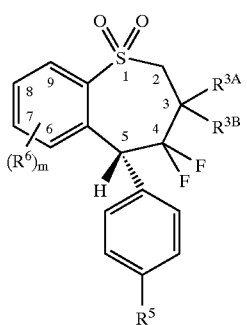

I-9

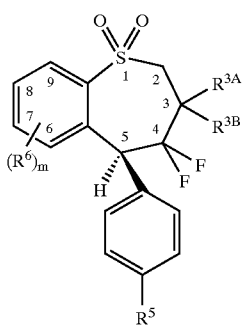

I-10

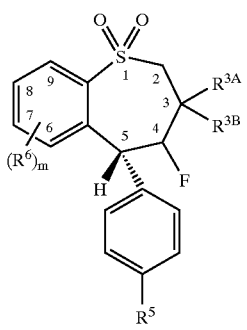

I-11

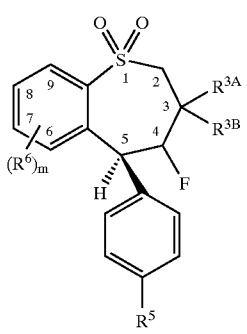

I-12

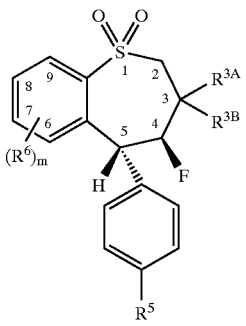

I-13

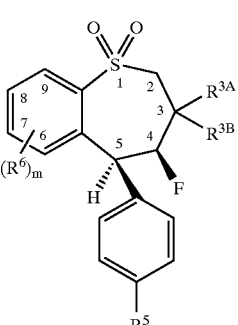

I-14

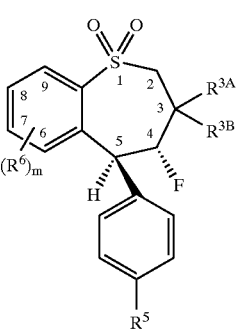

I-15

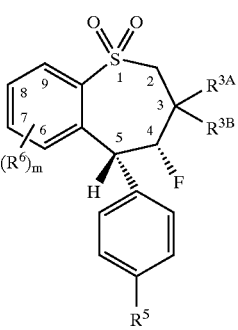

I-16 herein $R^{3A}$ and $R^{3B}$ are independently selected from hydrogen and alkyl, wherein $R^6$ is the same as previously defined, and wherein $R^5$ is selected from the members (1)–(70) of Table 1 above. Note that while $R^5$ is described as being attached to the para-position of the phenyl ring, $R^5$ may be attached to either the ortho or the meta position of the subject phenyl ring described above (e.g., where appropriate, in any of Formulas I-9 to I-16 above and in any of Formulas I-17 to I-24 depicted below.). Preferably, the $R^5$ substituent is at the meta- or the para-position of the $C_5$-phenyl group.

Additional exemplary embodiments of ASBT inhibitors of the present invention are represented by formulas I-17 to I-24 below:

I-17
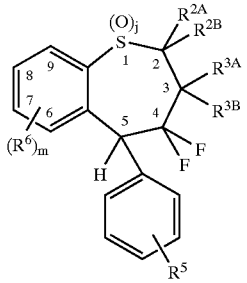

I-18
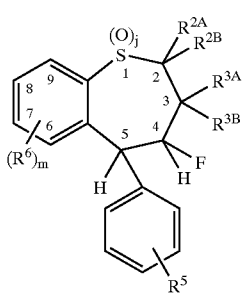

I-19
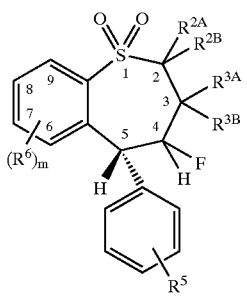

I-20
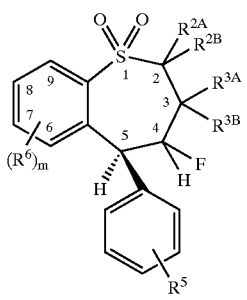

I-21
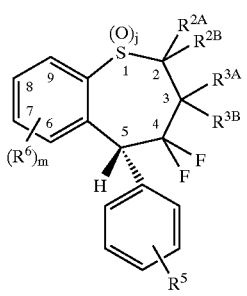

I-22
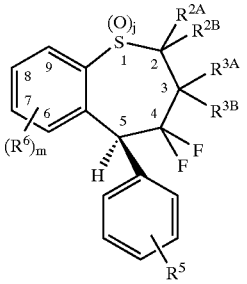

I-23
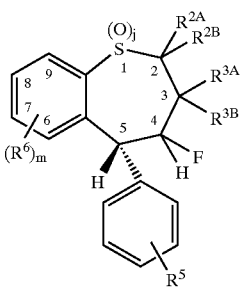

I-24
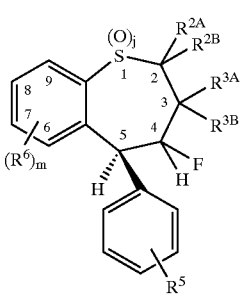

wherein $R^{2A}$, $R^{2B}$, $R^{3A}$, $R^{3B}$, $R^5$, $R^6$, m, and j are as previously described. Optionally, $R^{2A}=R^{2B}=H$ and/or $R^{3A}=R^{3B}$ and/or j=2 and/or m=1.

The novel fluorinated benzothiepine compounds of the present invention are safe and effective anti-hyperlipidemic agents. These compounds generally exhibit at least one desirable characteristic which includes, but is not limited to: (a) improved potency, (b) improved solubility profile, (c) improved compatibility with conventional routes of oral administration, (d) improved safety profile, and (e) elimination of a chiral center at the 4-position ring carbon in the case of the novel di-fluorinated benzothiepenes of the present invention.

The compounds of the present invention are useful for, but not limited to, the treatment of one or more hyperlipidemic condition(s) including the prophylactic treatment of hyperlipidemia in a subject. The methods, compounds, pharmaceutical compositions and kits of the present invention also are useful for the prophylaxis and/or treatment of gallstones. Besides being useful for human treatment, the above-described compounds (e.g., I-1 to I-24) also are useful for veterinary treatment of companion animals (e.g., horses, dogs, cats, etc.), exotic animals and farm animals, including mammals, rodents, and the like. Even though the invention is described in terms of human biology, it will be understood by those of ordinary skill that the present invention is applicable to other mammals, as well.

The above-noted ASBT inhibitors of the present invention may be made according to the exemplary chemical Schemes 1 and 2 below:
SCHEME 1
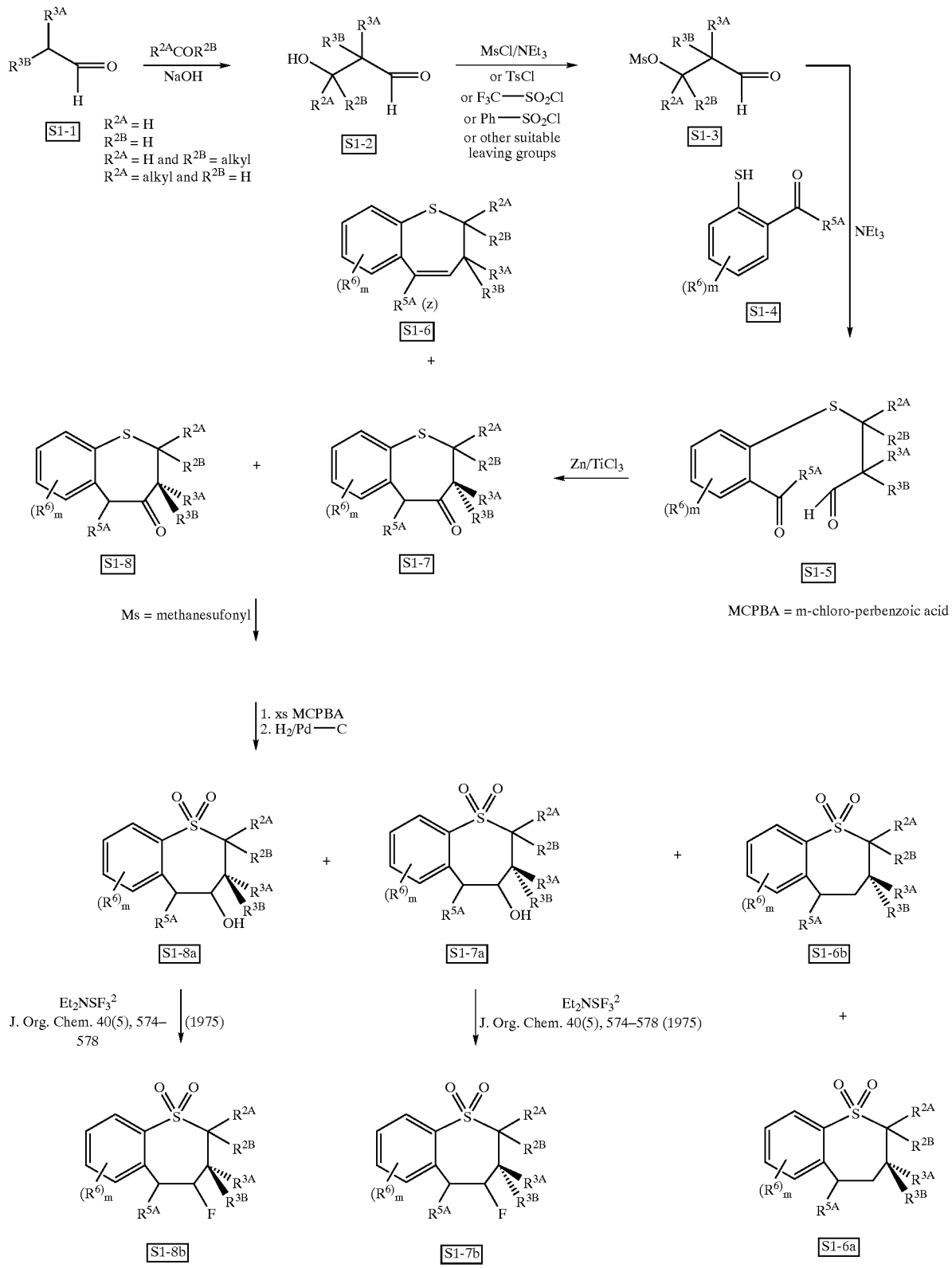

-continued

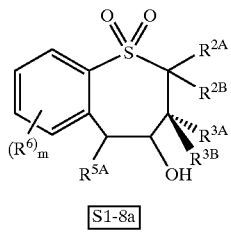

[S1-8a]

Oxalyl chloride, TEA, DMSO, -78 deg. C.
to rt; J Org. Chem. 65 (9), 2711 (2000)

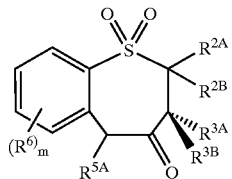

[S1-8c]

Et$_2$NSF$_3^2$
J. Org. Chem., 40(5), 574–578 (1975)

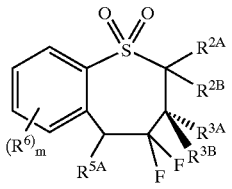

[S1-8d]

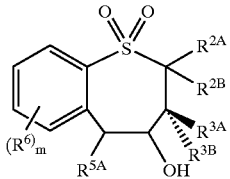

[S1-7a]

Oxalyl chloride, TEA, DMSO, -78 deg. C.
to rt; J Org. Chem. 65 (9), 2711 (2000)
rt = room temperature

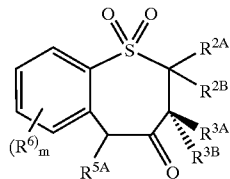

[S1-7c]

Et$_2$NSF$_3^2$
J. Org. Chem., 40(5), 574–578 (1975)

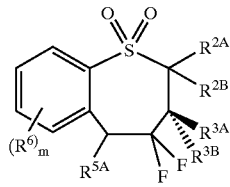

[S1-7d]

As indicated in Scheme 1, the aldehyde S1-1 is reacted with formaldehyde or an aldehyde and sodium hydroxide to yield the compound S1-2 which is converted to the mesylate S1-3 with methanesulfonyl chloride or other suitable leaving group and triethylamine as an exemplary solvent. See, for example, Chem. Ber. 98, 728–734 (1965). Reaction of the mesylate S1-3 with the thiophenol S1-4 in triethylamine yields the keto-aldehyde S1-5, which is prepared according to the procedure indicated in WO 93/16055. The keto-aldehyde S1-5 is then cyclized with a suitable cyclicizing agent such as Zn/TiCl$_3$ in refluxing ethylene glycol dimethyl ether (DME) to yield a racemic mixture of the ketone S1-7 and S1-8 (when $R^{3A} \neq R^{3B}$) together with compound S1-6. Treatment of S1-7 and S1-8 with excess (e.g., 3 equivalents) of m-chloro-perbenzoic acid (MCPBA) yields the a sulfone epoxide (not shown) which, in turn, upon hydrogenation with palladium on carbon (H$_2$/Pd—C) as catalyst yields a racemic mixture of S1-7a and S1-8a (when $R^{3A} \neq R^{3B}$) and another racemic mixture of S1-6a and S1-6b (when $R^{3A} \neq R^{3B}$). It is noted that optically active compounds of the present invention can be prepared by using optically active starting materials of compound S1-2 or by resolution of compounds S1-7a and S1-8a. Resolution of compounds S1-7a and S1-8a can be accomplished with optical resolution agents well known in the art and described in J. Org. Chem., 39 (26), 3904–3906 (1974), J. Org. Chem., 42 (16), 2781–2782 (1977) and J. Org. Chem., 44 (26), 4891–4896 (1979).

Alcohols S1-7a and/or S1-8a can be converted to the mono-fluorinated compounds S1-7b and S1-8b by treatment with dimethylaminosulfur trifluoride (Et$_2$NSF$_3^2$) in accordance with the procedure outlined in J. Org. Chem., 40(5), 574–578 (1975) with retention of stereochemistry. In particular, the alcohol S1-7a and/or S1-8a is/are added to a solution of (Et$_2$NSF$_3^2$) in an inert solvent cooled to −50 to −78° C. The reaction mixture is then warmed to room temperature (or higher). Typically, an initial exothermic reaction may occur during the warm-up period. On occasion, a second exothermic reaction may also occur during the warm-up period. Lower boiling fluorides are distilled out of the reaction mixture at reduced pressure to yield compounds S1-7b and/OR S1-8b. For the higher boiling fluorides, the reaction mixture should be mixed with water, the organic layer separated and dried, and any solvent should be removed from the separated organic layer by distillation. The product fluoride compounds can then be further purified by recyrstallization, or column chromatography.

To obtain the diflourinated compounds 7d and/or 8d, compounds S1-7a and/or S1-8a should first be converted to the ketones S1-7c and/or S1-8c by treatment with oxalyl chloride, triethanolamine (TEA) and dimethyl sulfoxide (DMSO) as indicated in J. Org. Chem., 65 (9), 2711–2715 (2000). Thereafter, ketones S1-7c and/or S1-8c can be converted to the diflourinated compounds S1-7d and/or S1-8d by the same procedure previously described for the conversion of S1-7a and S1-8a to S1-7b and S1-8b outlined in J. Org. Chem. 40(5), 574–578 (1975).

Also, optically active compounds S1-7d and S1-8d can be obtained by using optically active starting materials of compounds S1-2 or S1-3 or by using previously described optical resolving agents to separate optically active compounds S1-7a and S1-8a from each other. Thereafter, separated compounds S1-7a and S1-8a should be converted to S1-7c and S1-8c followed by conversion to S1-7d and S1-8d, respectively, as indicated above.

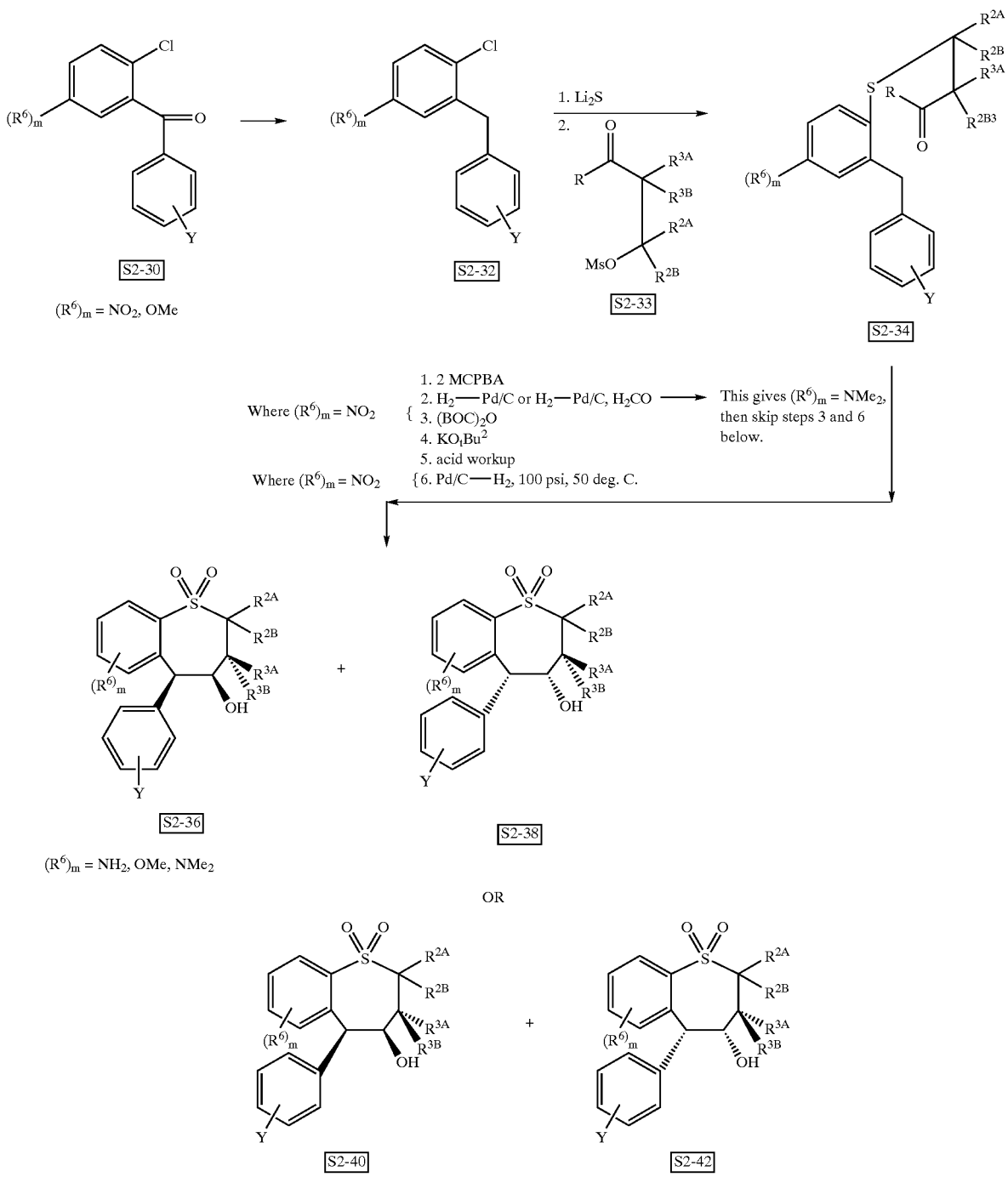

SCHEME 2

-continued

S2-36  S2-38  S2-40  S2-42

(where Y = MeO for each of 36, 38, 40 and 42)

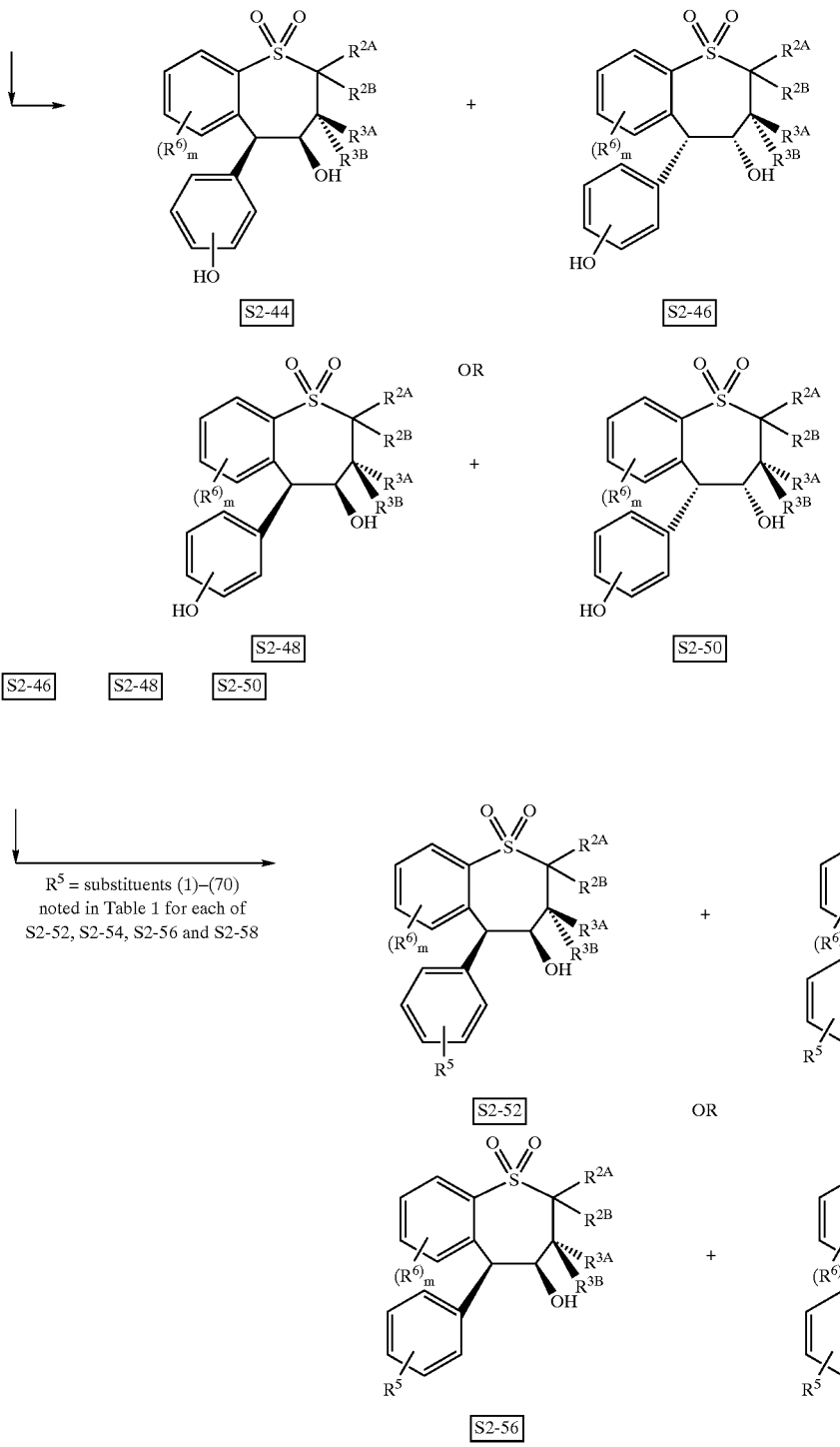

S2-44  S2-46  S2-48  S2-50

$R^5$ = substituents (1)–(70) noted in Table 1 for each of S2-52, S2-54, S2-56 and S2-58

In Scheme 2, compound S2-30 is converted to compound S2-32 with triethylsilane and trifluoromethane sulfonic acid. Reaction of S2-32 with lithium sulfide followed by reacting the resulting sulfide with the mesylate S2-33 gives the sulfide S2-34. Oxidation of S2-34 with 2 equivalents of MCPBA, followed by reduction with $H_2$—Pd/C, protection of the resulting hydroxylamine with di-t-butyldicarbonate, cyclization with potassium t-butoxide, removal of the t-butoxycarbonyl protecting groups (and acid workup) and hydrogenation with Pd/C—$H_2$ at 100 psi and 50° C. yields compounds S2-36, S2-38, S2-40 and S2-42 wherein, for example, $R^6$=—$NH_2$ and m=1 (integer). In Scheme 2, compounds S2-36, S2-38, S2-40 and S2-42 are made using chiral starting materials of compound 33 or by resolving the chiral compounds S2-36, S2-38, S2-40 and S2-42 using the previously noted optical resolution agents. Further, in Scheme 2, Y typically is OMe. However, Y may be another alkoxy, or a halogen (F, Cl, Br, and I).

Exemplary conversion of 36, 38, 40 and 42 (e.g., wherein $R^6$=—$NH_2$ and m=1 and Y=OMe) into 44, 46, 48 and 50 is accomplished according to the procedure outlined in Step 9 of Example 1401, infra. In particular, the methoxy compounds S2-36, S2-38, S2-40 and/or S2-42 (e.g., Y=OMe) and $CH_3Cl$ are placed in a flask purged with $N_2$. The reaction mixture is then cooled to −78° C. and boron tribromide ($BBr_3$) is added. The mixture is allowed to warm to room temperature. After about 4 hours, the reaction mixture is cooled to 0° C. and then quenched with 10% $K_2CO_3$. Thereafter (about 10 min. later), the layers are separated and the aqueous layers extracted twice with ethyl ether. The $CHCl_3$ and ether extracts are combined, washed with saturated aqueous NaCl, dried (MgSO4), filtered and concentrated in vacuo to yield the products S2-44, S2-46, S2-48 and /or S2-50.

Compounds S2-44, S2-46, S2-48 and S2-50 are then converted to compounds S2-52, S2-54, S2-56 and S2-58 (wherein $R^5$ is a moiety selected from members (1)–(70) depicted in Table 1 above) according to the procedures for adding the same groups described and outlined in the Examples, infra.

After formation of compounds S2-52, S2-54, S2-56 and/ or S2-58 (either formed with chiral starting materials or resolved using optical resolving agents), these compounds are subjected to the same mono-fluorinating procedures previously described and outlined in Scheme 1 for the conversion of S1-7a and Si-8a to S1-7b and S1-8b. By carrying out such steps, the corresponding mono-fluorinated compounds of S2-52, S2-54, S2-56 and/or S2-58 are formed, wherein a single C—F bond is formed at the C-4 carbon of the benzothiepine ring, exemplarily depicted in Formulas I-2 to I-8, Formulas I-11 to I-16, Formulas I-19 to I-20, and Formulas I-23 to I-24.

Similarly, the corresponding di-fluorinated compounds of the hydroxy compounds S2-52, S2-54, S2-56 and/or S2-58 are made by subjecting compounds S2-52, S2-54, S2-56 and/or S2-58 to the same di-fluorinating procedures previously described and outlined in Scheme 1 for the conversion of S1-7a and S1-8a to S1-7d and S1-8d. By so doing, the corresponding di-fluorinated compounds of the hydroxy compounds S2-52, S2-54, S2-56 and/or S2-58 are formed. Exemplary difluorinated compounds are depicted in Formulas I-1, I-9, I-10, I-17, and I-22.

Additional Schemes for forming compounds S3-11c and S3-11d analogous to compounds S1-7a and S1-8a are provided in Schemes 3–5 below. Scheme 6 below outlines the procedures for forming other compounds S6-15c and S6-15d analogous to compounds S3-11c and S3-11d, where the stereochemistry at the C-3 carbon is varied when $R^{3A} \ne R^{3B}$. Once formed, compounds S3-11c, S3-11d, S6-15c and S6-15d are subjected to the procedures previously described and outlined in Scheme 2 for the attachment of $R^5$ groups and then subjected to the procedures previously described and outlined in Scheme 1 for formation of the analogous mono-fluorinated and di-fluorinated compounds having the appropriate $R^5$ groups attached off of the phenyl ring attached to the C-5 carbon as depicted or indicated in connection with one or more of Formulas I-1 to I-24. Finally, Scheme 7 below outlines the procedure for forming compound S7-9 utilized in Scheme 3. Schemes 3–7 are as follows:

SCHEME 3

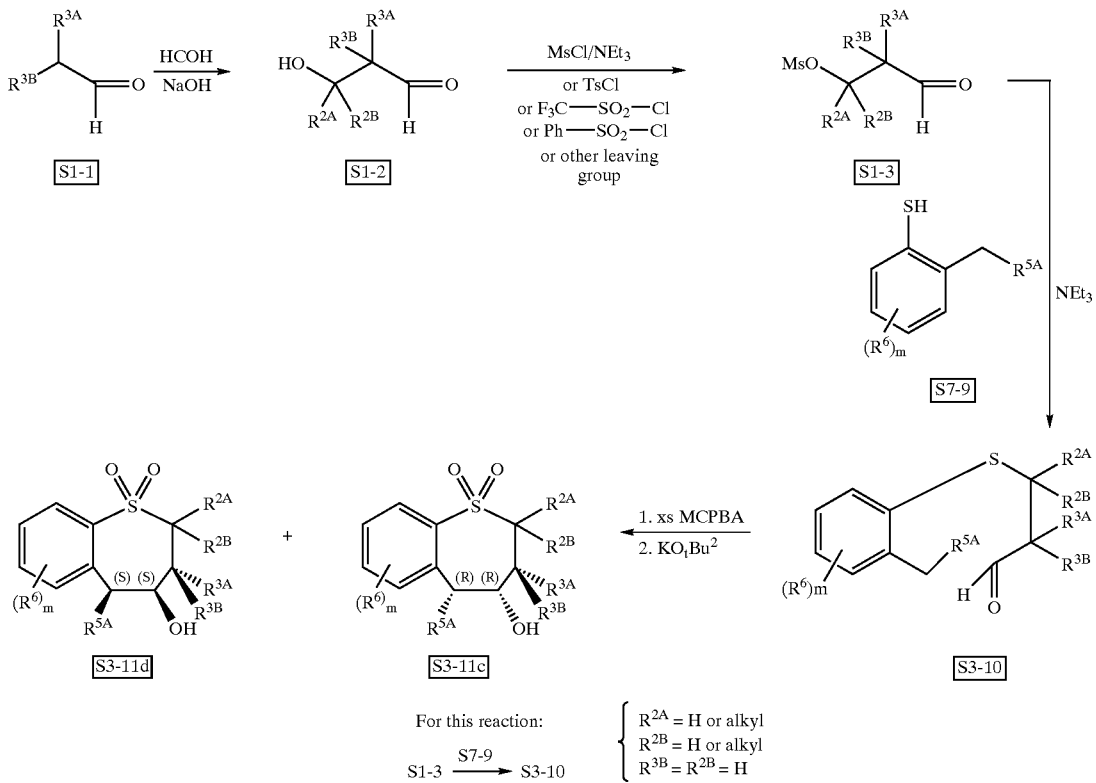

SCHEME 4
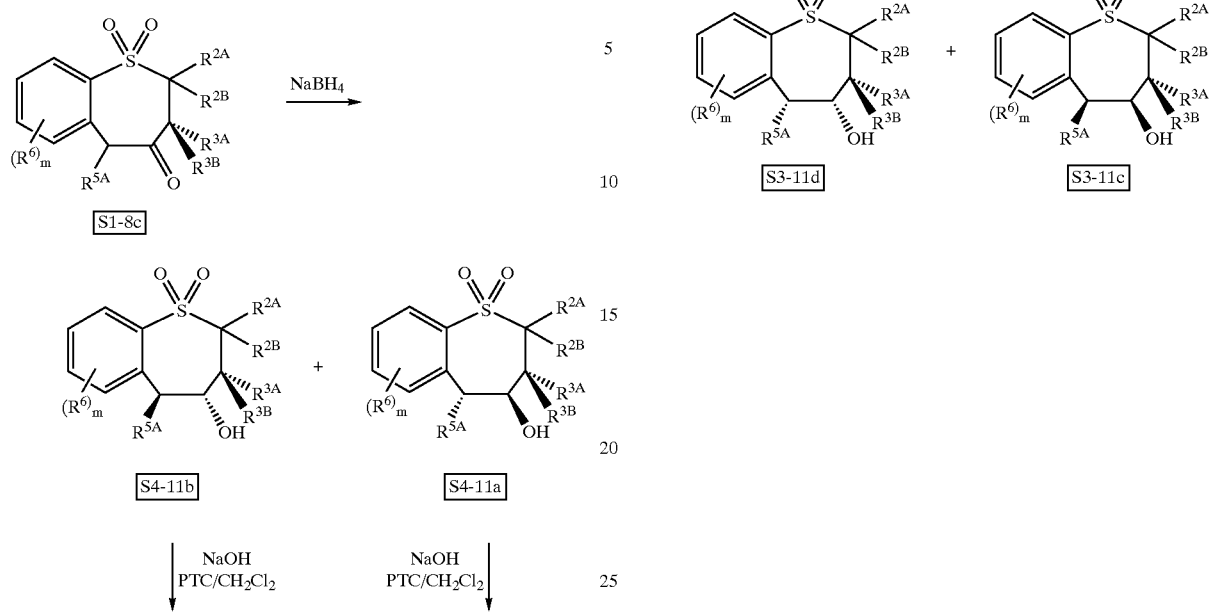
SCHEME 5
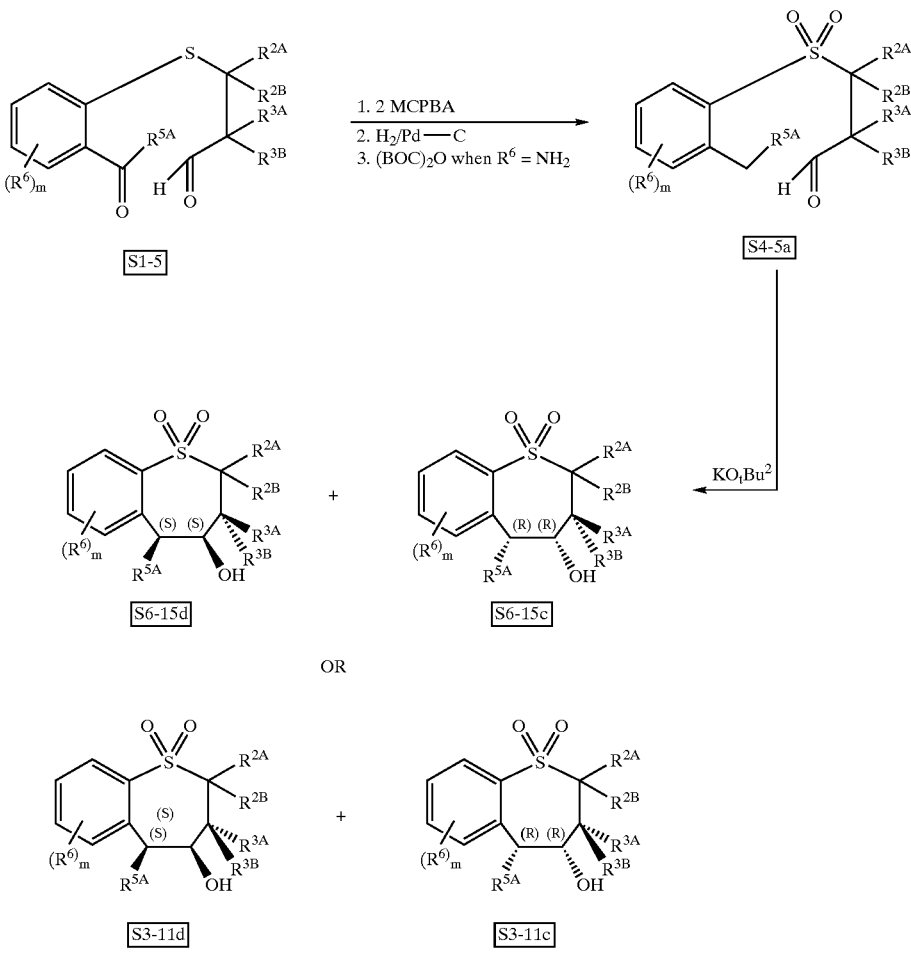

SCHEME 6

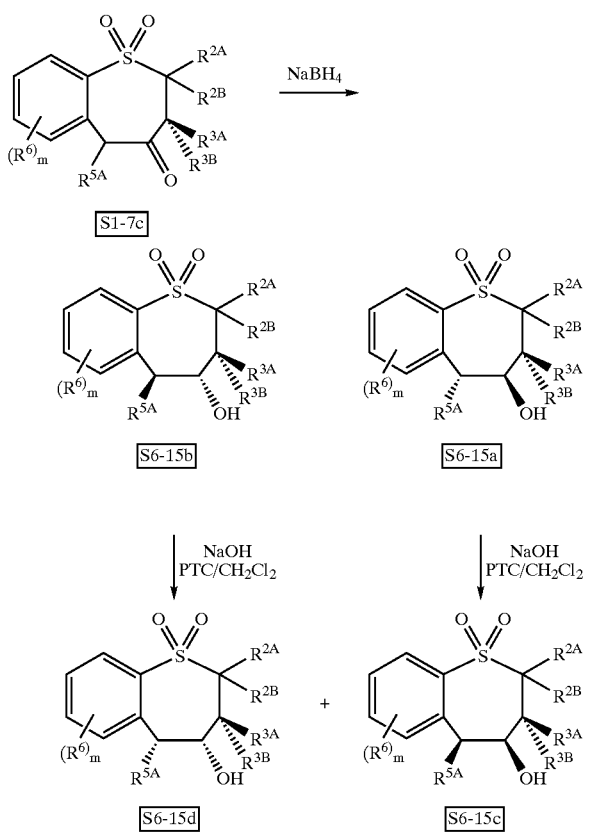

SCHEME 7

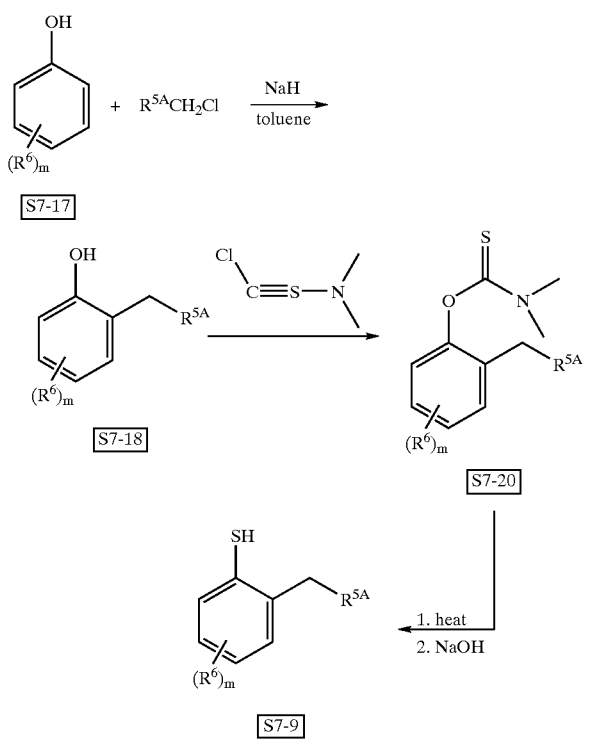

In Scheme 3, compound S1-3 is formed according to the same procedure outlined in Scheme 1. Thereafter, compound S1-3 is reacted with thiophenol S7-9 (e.g., made according to Scheme 7, infra) to yield the sulfide-aldehyde S3-10. Oxidation of S3-10 with 2 equivalents of MCPBA and then cyclization with potassium t-butoxide yields compounds S3-11c and S3-11d. As noted with Scheme 1, either chiral starting materials (such as chiral starting compounds corresponding to those of S1-2) or optical resolving agents may be used to form compounds S3-11c and/or S3-11d.

In Scheme 4, compound 8c is reduced with $NaBH_4$ to yield compounds S4-11a and/or S4-11b (made with chiral starting materials or optical resolving agents). Both S4-11a and S4-11b depict the $R^{5A}$ group and the OH group on opposite sides. Compounds S4-11a and S4-11b can be converted to compounds S3-11c and S3-11d, respectively, by treating the former compounds (S4-11a and/or S4-11b) in methylene chloride with 40–50% sodium hydroxide in the presence of a phase transfer catalyst (PTC). The transformation of S4-11a and S4-11b to S3-11c and S3-11d, respectively, can also be carried out with potassium t-butoxide in tetahydrofuran (THF).

In Scheme 5, compound S1-5 is made according to the procedures described and outlined in Scheme 1. Compound S1-5 is oxidized with 2 equivalents of MCPBA and then treated with $H_2$—Pd/C when $R^6=NO_2$, and protect with $(BOC)_2O$ to yield compound S4-5a. Compound S4-5a, in turn, is cyclized with potassium t-butoxide to yield compounds S3-11c, S3-11d, S6-15c and/or S6-15d (as earlier noted, S3-11c, S3-11d, S6-15c, and/or S6-15d are formed using chiral starting materials or with optical resolving agents).

In Scheme 6, compound S1-7c (formed according to Scheme 1) is reduced with sodium borohydride to give compounds S6-15a and/or S6-15b. Note that compounds S6-15a and S6-15b are formed by utilizing chiral starting materials or by using optical resolving agents. Thereafter, compounds S6-15a and S6-15b can be converted to compounds S6-15c and S6-15d, respectively, by reaction in methylene chloride with 40–50% sodium hydroxide in the presence of a phase transfer agent (PTC) as previously described in connection with Scheme 4.

Scheme 7 outlines an exemplary process for forming compound S7-9 used in Scheme 1. In particular, compound S7-17 is alkylated with an arylmethyl chloride in a nonpolar solvent according to J. Chem. Soc., part 2, 2431–2432 (1958) which gives the ortho-substituted phenol S7-18. Phenol S7-18 is converted to the thiophenol S7-9 via thiocarbamate S7-20 by the procedure described in J. Org. Chem., 31, 3980–3984 (1966). The phenol S7-18 is first reacted with dimethyl thiocarbamoyl chloride and triethylamine to give the thiocarbamate 20 which is chemically rearranged at 200–300° C., and then the rearranged product is hydrolyzed with sodium hydroxide to yield the thiphenol S7-9. Alternatively, thiphenol S7-9 can also be obtained from an analogous 2-acylphenol (i.e., analogous to S7-18 wherein the carbon to which $R^{5A}$ is attached has a carbonyl oxygen attached to it as well—not shown) via the thiocarbamate intermediate S7-20 using $ClC(S)N(CH_3)_2$ as used before to convert S7-18 to S7-20.

Also, see Example 60 (Scheme 8), Example 1396 (Scheme 9), Example 1397 (Schemes 10 and 11). Further, various benzothiepene intermediates can be prepared according to U.S. Pat. No. 5,994,391 and WO 99/32478.

Additional embodiments of the claimed invention include compounds of formulas I-1 to I-24 wherein the substituents are as described below. For example, (a) $R^{2A}$ and $R^{2B}$ are independently selected from the group consisting of hydrogen and alkyl;

(b) $R^{3A}$ and $R^{3B}$ are independently selected from the groups consisting of hydrogen; alkyl; cycloalkyl; alkenyl; cycloalkenyl; alkynyl; aryl; heterocyclyl; arylalkyl; heterocyclylalkyl; alkoxyalkyl; alkoxyalkenyl; alkoxyalkynyl; aryloxyalkyl; aryloxyalkenyl; aryloxyalkynyl; heterocylcyloxyalkyl; heterocycloxyalkenyl; heterocyclyloxyalkynyl; alkylaryl; and (polyalkyl)aryl; or $R^{3A}$ and $R^{3B}$ taken together with the carbon to which they are attached form $C_3$–$C_{10}$ cycloalkyl or $C_3$–$C_{10}$ cycloalkenyl;

wherein the $R^{3A}$ and $R^{3B}$ alkyl; cycloalkyl; alkenyl; cycloalkenyl; alkynyl; aryl; heterocyclyl; arylalkyl; heterocyclylalkyl; alkoxyalkyl; alkoxyalkenyl; alkoxyalkynyl; aryloxyalkyl; aryloxyalkenyl; aryloxyalkynyl; heterocylcyloxyalkyl; heterocycloxyalkenyl; heterocyclyloxyalkynyl; alkylaryl; and (polyalkyl)aryl radicals optionally may be substituted with one or more radicals selected from the group consisting of —CN; halogen; oxo; —$OR^9$; —$NR^9R^{10}$; —$N^+R^9R^{10}R^WA^-$; —$SR^9$; —$S^+R^9R^{10}A^-$; —$PR^9R^{10}$; —$P^+R^9R^{10}R^WA^-$; —$S(O)R^9$; —$SO_2R^9$; —$SO_3R^9$; —$CO_2R^9$; and —$CONR^9R^{10}$; and wherein the $R^{3A}$ and $R^{3B}$ alkyl; cycloalkyl; alkenyl; cycloalkenyl; alkynyl; aryl; heterocyclyl; arylalkyl; heterocyclylalkyl; alkoxyalkyl; alkoxyalkenyl; alkoxyalkynyl; aryloxyalkyl; aryloxyalkenyl; aryloxyalkynyl; heterocylcyloxyalkyl; heterocycloxyalkenyl; heterocyclyloxyalkynyl; alkylaryl; and (polyalkyl)aryl radicals optionally may have one or more carbons replaced by —O—; —$NR^9$—; —$N^+R^9R^{10}A^-$—; —S—; —SO—; —$SO_2$—; —$S^+R^9A^-$—; —$PR^9$—; —$P(O)R^9$—; —$P^+R^9R^{10}A^-$—; or phenylene;

(c) $R^{4A}$ and $R^{4B}$ are independently selected from the group consisting of hydrogen; alkyl; alkenyl; alkynyl; aryl; heterocyclyl; —$OR^9$; —$NR^9R^{10}$; —$SR^9$; —$S(O)R^9$; —$SO_2R^9$; and —$SO_3R^9$; or $R^{4A}$ and $R^{4B}$ together form =O; =$NOR^9$; =S; =$NNR^9R^{10}$; =$NR^9$; or =$CR^{11}R^{12}$;

(d) $R^{5A}$ and $R^5$ are independently selected from the group consisting of alkyl; cycloalkyl; alkenyl; alkynyl; aryl; heterocyclyl; quaternary heterocyclyl; —$OR^9$; —$SR^9$; —$S(O)R^9$; —$SO_2R^9$; and —$SO_3R^9$;

wherein the $R^{5A}$ and $R^5$ alkyl; cycloalkyl; alkenyl; alkynyl; aryl; heterocyclyl; and quaternary heterocyclyl radicals optionally may be substituted with one or more radicals independently selected from the group consisting of halogen; —CN; —$NO_2$; oxo; alkyl; polyalkyl; haloalkyl; hydroxyalkyl; cycloalkyl; alkenyl; alkynyl; aryl; heterocyclyl; quaternary heterocyclyl; arylalkyl; heterocyclylalkyl; polyether; —$OR^{13}$; —$NR^{13}R^{14}$; —$SR^{13}$; —$S(O)R^{13}$; —$SO_2R^{13}$; —$SO_3R^{13}$; —$NR^{13}OR^{14}$; —$NR^{13}NR^{14}R^{15}$; —$CO_2R^{13}$; —OM; —$SO_2OM$; —$SO_2NR^{13}R^{14}$; —$C(O)NR^{13}R^{14}$; —C(O)OM; —$COR^{13}$; —$NR^{13}C(O)R^{14}$; —$NR^{13}C(O)NR^{14}R^{15}$; —$NR^{13}CO_2R^{14}$; —$OC(O)R^{13}$; —$OC(O)NR^{13}R^{14}$; —$NR^{13}SOR^{14}$; —$NR^{13}SO_2R^{14}$; —$NR^{13}SONR^{14}R^{15}$; —$NR^{13}SO_2NR^{14}R^{15}$; —$PR^{13}R^{14}$; —$P(O)R^{13}R^{14}$; —$P^+R^{13}R^{14}R^{15}A^-$; —$P(OR^{13})OR^{14}$; —$P(OR^{13})OR^{14}$; —$S^+R^{13}R^{14}A^-$; and —$N^+R^{13}R^{14}R^{15}A^-$; and wherein the alkyl, polyalkyl, haloalkyl, hydroxyalkyl, cycloalkyl, alkenyl, alkynyl, aryl, heterocyclyl, quaternary heterocyclyl, arylalkyl, heterocyclylalkyl, and polyether substituents of the $R^{5A}$ and $R^5$ radicals optionally may be further substituted with one or more radicals selected from the group consisting of —CN; halogen; hydroxy; oxo; alkyl; cycloalkyl; alkenyl; alkynyl; aryl; heterocyclyl; arylalkyl; heterocyclylalkyl; quaternary heterocyclyl; —$OR^{19}$; —$NR^{19}R^{20}$; —$SR^{19}$; —$S(O)R^{19}$; —$SO_2R^{19}$; —$SO_3R^{19}$; —$CO_2R^{19}$; —$CONR^{19}R^{20}$; —$N^+R^9R^{19}R^{20}A^-$; —$P(O)R^{19}R^{20}$; —$PR^{19}R^{20}$; —$P^+R^9R^{19}R^{20}A^-$; and —$P(O)(OR^{19})OR^{20}$; and wherein the alkyl, polyalkyl, haloalkyl, hydroxyalkyl, cycloalkyl, alkenyl, alkynyl, aryl, heterocyclyl, quaternary heterocyclyl, arylalkyl, heterocyclylalkyl, and polyether substituents of the $R^{5A}$ and $R^5$ radicals optionally may have one or more carbons replaced by —O—; —$NR^{19}$—; —$N^+R^{19}R^{20}A^-$—; —S—; —SO—; —$SO_2$—; —$S^+R^{19}A^-$—; —$PR^{19}$—; —$P(O)R^{19}$—; —$P^+R^{19}R^{20}A^-$—; or phenylene;

(e) $R^{5B}$ is selected from the group consisting of hydrogen; alkyl; cycloalkyl; alkenyl; alkynyl; aryl; heterocyclyl; quaternary heterocyclyl; —$OR^9$; —$SR^9$; —$S(O)R^9$; —$SO_2R^9$; and —$SO_3R^9$;

wherein the $R^{5B}$ alkyl; cycloalkyl; alkenyl; alkynyl; aryl; heterocyclyl; and quaternary heterocyclyl radical optionally may be substituted with one or more radicals independently selected from the group consisting of halogen; —CN; —$NO_2$; oxo; alkyl; polyalkyl; haloalkyl; hydroxyalkyl; cycloalkyl; alkenyl; alkynyl; aryl; heterocyclyl; quaternary heterocyclyl; arylalkyl; heterocyclylalkyl; polyether; —$OR^{13}$; —$NR^{13}R^{14}$; —$SR^{13}$; —$S(O)R^{13}$; —$SO_2R^{13}$; —$SO_3R^{13}$; —$NR^{13}OR^{14}$; —$NR^{13}NR^{14}R^{15}$; —$CO_2R^{13}$; —OM; —$SO_2OM$; —$SO_2NR^{13}R^{14}$; —$C(O)NR^{13}R^{14}$; —C(O)OM; —$COR^{13}$; —$NR^{13}C(O)R^{14}$; —$NR^{13}C(O)NR^{14}R^{15}$; —$NR^{13}CO_2R^{14}$; —$OC(O)R^{13}$; —$OC(O)NR^{13}R^{14}$; —$NR^{13}SOR^{14}$; —$NR^{13}SO_2R^{14}$; —$NR^{13}SONR^{14}R^{15}$; —$NR^{13}SO_2NR^{14}R^{15}$; —$PR^{13}R^{14}$; —$P(O)R^{13}R^{14}$; —$P^+R^{13}R^{14}R^{15}A^-$; —$P(OR^{13})OR^{14}$; —$S^+R^{13}R^{14}A^-$; and —$N^+R^{13}R^{14}R^{15}A^-$; and wherein the alkyl, polyalkyl, haloalkyl, hydroxyalkyl, cycloalkyl, alkenyl, alkynyl, aryl, heterocyclyl, quaternary heterocyclyl, arylalkyl, heterocyclylalkyl, and polyether substituents of the $R^{5B}$ radical optionally may be further substituted with one or more radicals selected from the group consisting of —CN; halogen; hydroxy, oxo; alkyl; cycloalkyl; alkenyl; alkynyl; aryl; heterocyclyl; arylalkyl; heterocyclylalkyl; quaternary heterocyclyl; —$OR^{19}$; —$NR^{19}R^{20}$; —$SR^{19}$; —$S(O)R^{19}$; —$SO_2R^{19}$; —$SO_3R^{19}$; —$CO_2R^{19}$; —$CONR^{19}R^{20}$; —$N^+R^9R^{19}R^{20}A^-$; —$P(O)R^{19}R^{20}$; —$PR^{19}R^{20}$; —$P^+R^9R^{19}R^{20}A^-$; and —$P(O)(OR^{19})R^{20}$; and wherein the alkyl, polyalkyl, haloalkyl, hydroxyalkyl, cycloalkyl, alkenyl, alkynyl, aryl, heterocyclyl, quaternary heterocyclyl, arylalkyl, heterocyclylalkyl, and polyether substituents of the $R^{5B}$ radical optionally may have one or more carbons replaced by —O—; —$NR^{19}$—; —$N^+R^{19}R^{20}A^-$—; —S—; —SO—; —$SO_2$—; —$S^+R^{19}A^-$—; —$PR^{19}$—; —$P(O)R^{19}$—; —$P^+R^{19}R^{20}A^-$—; or phenylene;

(f) one or more $R^6$ (wherein m=1, 2, 3, or 4 in $(R^6)m$) are independently selected from the group consisting of hydrogen; halogen; —CN; —$NO_2$; alkyl; cycloalkyl; polyalkyl; haloalkyl; hydroxyalkyl; alkenyl; alkynyl; aryl; heterocyclyl; quaternary heterocyclyl; arylalkyl;

heterocyclylalkyl; polyether; acyloxy, —$OR^{13}$; —$NR^{13}R^{14}$; —$SR^{13}$; —$S(O)R^{13}$; —$S(O)_2R^{13}$; —$SO_3R^{13}$; —$S^+R^{13}R^{14}A^-$; —$NR^{13}OR^{14}$; —$NR^{13}NR^{14}R^{15}$; —$CO_2R^{13}$; —OM; —$SO_2OM$; —$SO_2NR^{13}R^{14}$; —$NR^{14}C(O)R^{13}$; —$C(O)NR^{13}R^{14}$; —C(O)OM; —$COR^{13}$; —$OR^{18}$; —$S(O)_nNR^{13}R^{14}$; —$NR^{13}R^{18}$; —$NR^{18}OR^{14}$; —$N^+R^{13}R^{14}R^{15}A^-$; —$PR^{13}R^{14}$; —$P(O)R^{13}R^{14}$; —$P^+R^{13}R^{14}R^{15}A^-$; amino acid residue; peptide residue; polypeptide residue; and carbohydrate residue;

wherein the one or more $R^6$ alkyl; cycloalkyl; polyalkyl; haloalkyl; hydroxyalkyl; alkenyl; alkynyl; aryl; heterocyclyl; arylalkyl; heterocyclylalkyl; polyether, acyloxy radicals optionally may be further independently substituted with one or more radicals selected from the group consisting of halogen; —CN; oxo; —$OR^{16}$; —$NR^9R^{10}$; —$N^+R^9R^{10}R^WA^-$; —$SR^{16}$; —$S(O)R^9$; —$SO_2R^9$; —$SO_3R^{16}$; —$CO_2R^{16}$; —$CONR^9R^{10}$; —$SO_2NR^9R^{10}$; —PO$(OR^{16})OR^{17}$; —$P^9R^{10}$; —$P^+R^9R^{11}R^{12}A^-$; —$S^+R^9R^{10}A^-$; and carbohydrate residue;

wherein the one or more $R^6$ quaternary heterocyclyl radical optionally may be independently substituted with one or more radicals selected from the group consisting of halogen; —CN; —$NO_2$; oxo; alkyl; cycloalkyl; polyalkyl; haloalkyl; hydroxyalkyl; alkenyl; alkynyl; aryl; heterocyclyl; arylalkyl; heterocyclylalkyl; polyether; —$OR^{13}$; —$NR^{13}R^{14}$; —$SR^{13}$; —$S(O)R^{13}$; —$SO_2R^{13}$; —$SO_3R^{13}$; —$NR^{13}OR^{14}$; —$NR^{13}NR^{14}R^{15}$; —$CO_2R^{13}$; OM; —$SO_2OM$; —$SO_2NR^{13}R^{14}$; —$C(O)NR^{13}R^{14}$; —C(O)OM; —$COR^{13}$; —$P(O)R^{13}R^{14}$; —$PR^{13}R^{14}$; —$P^+R^{13}R^{14}R^{15}A^-$; —$P(OR^{13})OR^{14}$; —$S^+R^{13}R^{14}A^-$; —$N^+R^{13}R^{14}R^{15}A^-$; and carbohydrate residue;

wherein the one or more $R^6$ radicals comprising carbon optionally may independently have one or more carbons replaced by —O—; —$NR^{13}$—; —$N^+R^{13}R^{14}A^-$—; —S—; —SO—; —$SO_2$—; —$S^+R^{13}A^-$—; —$PR^{13}$—; —$P(O)R^{13}$—; —$PR^{13}R^{14}$; —$P^+R^{13}R^{14}A^-$—; phenylene; amino acid residue; peptide residue; polypeptide residue; carbohydrate residue; polyether, or polyalkyl; wherein said phenylene; amino acid residue; peptide residue; polypeptide residue; carbohydrate residue; and polyalkyl optionally may have one or more carbons replaced by —O—; —$NR^9$—; —$N^+R^9R^{10}A^-$—; —S—; —SO—; —$SO_2$—; —$S^+R^9A^-$—; —$PR^9$—; —$P^+R^9R^{10}A^-$—; or —$P(O)R^9$; or two $R^6$ groups attached to adjacent carbon atoms (e.g., adjacent carbon atoms on the benzo ring) together with the carbon atoms to which they are attached form a $C_4$–$C_{12}$ mono- or bi-cyclic carbocyclic or heterocyclic ring; a mono- or bi-cyclic carbocyclic or heterocyclic ring; or a mono- or bi-cyclic carbocyclic or heterocyclic ring;

wherein the mono- or bi-cyclic carbocyclic or heterocyclic rings optionally may be further substituted with one or more radicals selected from the group consisting of halogen; hydroxy; cyano; nitro; oxo; thioxo; alkyl; haloalkyl; alkoxy; aryl; heterocyclyl; $R^T$; —$OR^{16}$; —$NR^9R^{10}$; —$N^+R^9R^{10}R^WA^-$; —$SR^{16}$; —$S(O)R^9$; —$SO_2R^9$; —$SO_3R^{16}$; —$CO_2R^{16}$; —$CONR^9R^{10}$; —$SO_2NR^9R^{10}$; —$PO(OR^{16})OR^{17}$; —$P^9R^{10}$; —$P^+R^9R^{11}R^{12}A^-$; —$S^+R^9R^{10}A^-$; and carbohydrate residue;

(g) wherein $R^9$, $R^{10}$, and $R^W$ are independently selected from the group consisting of hydrogen; alkyl; cycloalkyl; alkenyl; alkynyl; aryl; heterocyclyl; alkylammoniumalkyl; arylalkyl; heterocyclylalkyl; carboxyalkyl; alkoxyalkyl; carboalkoxyalkyl; carboxyaryl; carboxyheterocyclyl; amino; alkylamino; carboxyalkylamino; alkoxyalkylamino; and acyl;

(h) wherein $R^{11}$ and $R^{12}$ are independently selected from the group consisting of hydrogen; —CN; halogen; oxo; alkyl; alkenyl; alkynyl; aryl; heterocyclyl; arylalkyl; heterocyclylalkyl; carboxyalkyl; alkoxyalkyl; carboalkoxyalkyl; cycloalkyl; cycloalkenyl; haloalkyl; hydroxyalkyl; cyanoalkyl; —$OR^9$; —$NR^9R^{10}$; —$SR^9$; —$S(O)R^9$; —$SO_2R^9$; —$SO_3R^9$; —$CO_2R^9$; and —$CONR^9R^{10}$; or $R^{11}$ and $R^{12}$ together with the carbon atom to which they are attached form a cyclic ring; and (i) wherein $R^{13}$, $R^{14}$, and $R^{15}$ are independently selected from the group consisting of hydrogen; alkyl; haloalkyl; cycloalkyl; polyalkyl; alkenyl; alkynyl; aryl; heterocyclyl; quaternary heterocyclyl; arylalkyl; heterocyclylalkyl; quaternary heterocyclylalkyl; alkylarylalkyl; alkylheterocyclylalkyl; alkylammoniumalkyl; aminoalkyl; aminocarbonylalkyl; alkylaminocarbonylalkyl; carboxyalkylaminocabonylalkyl; and polyether, or $R^{13}$ and $R^{14}$ together with the nitrogen atom to which they are attached form a mono- or polycyclic heterocyclyl that is optionally substituted with one or more radicals selected from the group consisting of oxo, carboxy, and quaternary salts; or wherein $R^{14}$ and $R^{15}$ together with the nitrogen atom to which they are attached form a cyclic ring; and wherein the $R^{13}$, $R^{14}$, and $R^{15}$ alkyl; haloalkyl; cycloalkyl; polyalkyl; alkenyl; alkynyl; aryl; heterocyclyl; quaternary heterocyclyl; arylalkyl; heterocyclylalkyl; quaternary heterocyclylalkyl; alkylarylalkyl; alkylheterocyclylalkyl; alkylammoniunalkyl; aminoalkyl; aminocarbonylalkyl; alkylaminocarbonylalkyl; carboxyalkylaminocarbonylalkyl; and polyether radicals optionally may be substituted with one or more radicals selected from the group consisting of halogen; —CN; sulfo; oxo; alkyl; haloalkyl; hydroxyalkyl; sulfoalkyl; alkenyl; alkynyl; aryl; heterocyclyl; quaternary heterocyclyl; quaternary heterocyclylalkyl; carboxy, carboxyalkyl; guanidinyl; —$OR^{16}$; —$NR^9R^{10}$; —$N^+R^9R^{10}R^WA^-$; —$SR^{16}$; —$S(O)R^9$; —$SO_2R^9$; —$SO_3R^{16}$; —$CO_2R^{16}$; —$CONR^9R^{10}$; —$SO_2NR^9R^{10}$; —$PO(OR^{16})OR^{17}$; —$P^9R^{10}$; —$P^+R^9R^{10}OR^{11}A^-$; —$S^+R^9R^{10}A^-$; and carbohydrate residue; and wherein the $R^{13}$, $R^{14}$, and $R^{15}$ alkyl; haloalkyl; cycloalkyl; polyalkyl; alkenyl; alkynyl; aryl; heterocyclyl; quaternary heterocyclyl; arylalkyl; heterocyclylalkyl; quaternary heterocyclylalkyl; alkylarylalkyl; alkylheterocyclylalkyl; alkylammoniumalkyl; aminoalkyl; aminocarbonylalkyl; alkylaminocarbonylalkyl; carboxyalkylaminocarbonylalkyl; and polyether radicals optionally may have one or more carbons replaced by —O—; —$NR^9$—; —$N^+R^9R^{10}A^-$—; —S—; —SO—; —$SO_2$—; —$S^+R^9A^-$—; —$PR^9$—; —$P^+R^9R^{10}A^-$—; —$P(O)R^9$—; phenylene; carbohydrate residue; amino acid residue; peptide residue; or polypeptide residue; and (j) wherein $R^{16}$ and $R^{17}$ are independently selected from the group consisting of $R^9$ and M; and (k) wherein $R^{18}$ is selected from the group consisting of alkyl; alkenyl; alkynyl; aryl; heterocyclyl; quaternary heterocyclyl; arylalkyl; heterocyclylalkyl; acyl;

alkoxycarbonyl; arylalkoxycarbonyl; and heterocyclylalkoxycarbonyl; and wherein the $R^{18}$ alkyl; alkenyl; alkynyl; aryl; heterocyclyl; quaternary heterocyclyl; arylalkyl; heterocyclylalkyl; acyl; alkoxycarbonyl; arylalkoxycarbonyl; and heterocyclylalkoxycarbonyl radical optionally may be substituted with one or more radicals selected from the group consisting of halogen; —CN; $NO_2$; oxo; —$OR^9$; —$NR^9R^{10}$; —$N^+R^9R^{11}R^{12}A^-$; —$SR^9$; —$S(O)R^9$; —$SO_2R^9$; —$SO_3R^9$; —$CO_2R^9$; —$CONR^9R^{10}$; —$SO_2OM$; —$SO_2NR^9R^{10}$; —$PR^9R^{10}$; —$P(OR^{13})OR^{14}$; —$PO(OR^{16}OR^{17}$; and —$C(O)OM$; and (l) wherein $R^{19}$ and $R^{20}$ are independently selected from the group consisting of hydrogen; alkyl, alkenyl; alkynyl; aryl; and heterocyclyl; and (m) wherein M is a pharmaceutically acceptable cation, wherein $A^-$ is a pharmaceutically acceptable anion; or a pharmaceutically acceptable salt, solvate, or prodrug thereof.

According to another embodiment, the invention includes compounds of formulas I-1 to I-24 having the following substituents:

(a1) $R^{2A}$ and $R^{2B}$ are independently selected from the group consisting of hydrogen and alkyl;

(b1) $R^{3A}$ and $R^{3B}$ are independently selected from the group consisting of hydrogen; alkyl; cycloalkyl; alkenyl; alkynyl; arylalkyl; alkoxyalkyl; alkoxyalkenyl; alkoxyalkynyl; alkylaryl; and (polyalkyl)aryl; or $R^{3A}$ and $R^{3B}$ taken together with the carbon to which they are attached form $C_3$–$C_7$ cycloalkyl or $C_3$–$C_7$ cycloalkenyl;

wherein the $R^{3A}$ and $R^{3B}$ alkyl; cycloalkyl; alkenyl; alkynyl; arylalkyl; alkoxyalkyl; alkoxyalkenyl; alkoxyalkynyl; alkylaryl; and (polyalkyl)aryl radicals optionally may be substituted with one or more radicals selected from the group consisting of —CN; halogen; oxo; —$OR^9$; —$NR^9R^{10}$; —$NR^9R^{10}R^WA^-$; —$SR^9$; —$S^+R^9R^{10}A^-$; —$PR^9R^{10}$; —$P^+R^9R^{10}R^WA^-$; —$S(O)R^9$; —$SO_2R^9$; —$SO_3R^9$; —$CO_2R^9$; and —$CONR^9R^{10}$; and wherein the $R^{3A}$ and $R^{3B}$ alkyl; cycloalkyl; alkenyl; alkynyl; arylalkyl; alkoxyalkyl; alkoxyalkenyl; alkoxyalkynyl; alkylaryl; and (polyalkyl)aryl radicals optionally may have one or more carbons replaced by —O—; —$NR^9$—; —$N^+R^9R^{10}A^-$—, —S—; —SO—; —$SO_2$—; —$S^+R^9A^-$—, —$PR^9$—; —$P(O)R^9$—; —$P^+R^9R^{10}A^-$—, or phenylene;

(c1) $R^{4A}$ and $R^{4B}$ are independently selected from the group consisting of hydrogen; alkyl; alkenyl; alkynyl; aryl; heterocyclyl; —$OR^9$; —$NR^9R^{10}$; —$SR^9$; —$S(O)R^9$; —$SO_2R^9$; and —$SO_3R^9$; or $R^{4A}$ and $R^{4B}$ together form =O; =$NOR^9$; =S; =$NNR^9R^{10}$; =$NR^9$; or =$CR^{11}R^{12}$;

(d1) $R^{5A}$ is selected from the group consisting of alkyl; cycloalkyl; alkenyl; alkynyl; aryl; heterocyclyl; quaternary heterocyclyl; —$OR^9$; —$SR^9$; —$S(O)R^9$; —$SO_2R^9$; and —$SO_3R^9$;

wherein the alkyl, polyalkyl, haloalkyl, hydroxyalkyl, cycloalkyl, alkenyl, alkynyl, aryl, heterocyclyl, quaternary heterocyclyl, arylalkyl, heterocyclylalkyl, and polyether substituents of the $R^{5A}$ radical optionally may be further substituted with one or more radicals selected from the group consisting of —CN; halogen; hydroxy; oxo; alkyl; cycloalkyl; alkenyl; alkynyl; aryl; heterocyclyl; arylalkyl; heterocyclylalkyl; quaternary heterocyclyl; —$OR^{19}$; —$NR^{19}R^{20}$; —$SR^{19}$; —$S(O)R^{19}$; —$SO_2R^{19}$; —$SO_3R^{19}$; —$CO_2R^{19}$; —$CONR^{19}R^{20}$; —$N^+R^9R^{19}R^{20}A^-$—; —$P(O)R^{19}R^{20}$; —$PR^{19}R^{20}$; —$P^+R^9R^{19}R^{20}A^-$; and —$P(O)(OR^{19})OR^{20}$; and wherein the alkyl, polyalkyl, haloalkyl, hydroxyalkyl, cycloalkyl, alkenyl, alkynyl, aryl, heterocyclyl, quaternary heterocyclyl, arylalkyl, heterocyclylalkyl, and polyether substituents of the $R^{5A}$ radical optionally may have one or more carbons replaced by —O—; —$NR^{19}$—; —$N^+R^{19}R^{20}A^-$—; —S—; —SO—; —$SO_2$—; —$S^+R^{19}A^-$—; —$PR^{19}$—; —$P(O)R^{19}$—; —$P^+R^{19}R^{20}A^-$—; or phenylene;

(e1) $R^{5B}$ is selected from the group consisting of hydrogen; alkyl; cycloalkyl; alkenyl; alkynyl; aryl; heterocyclyl; quaternary heterocyclyl; —$OR^9$; —$SR^9$; —$S(O)R^9$; —$SO_2R^9$; and —$SO_3R^9$;

wherein the $R^{5B}$ alkyl; cycloalkyl; alkenyl; alkynyl; aryl; heterocyclyl; and quaternary heterocyclyl radical optionally may be substituted with one or more radicals independently selected from the group consisting of halogen; —CN; —$NO_2$; oxo; alkyl; polyalkyl; haloalkyl; cycloalkyl; alkenyl; alkynyl; aryl; heterocyclyl; quaternary heterocyclyl; arylalkyl; heterocyclylalkyl; polyether,
—$OR^{13}$; —$NR^{13}R^{14}$; —$SR^{13}$; —$S(O)R^{13}$; —$SO_2R^{13}$; —$SO_3R^{13}$; —$NR^{13}OR^{14}$; —$NR^{13}NR^{14}R^{15}$; —$CO_2R^{13}$; —OM; —$SO_2OM$; —$SO_2NR^{13}R^{14}$; —$C(O)NR^{13}R^{14}$;
—$C(O)OM$; —$COR^{13}$; —$NR^{13}C(O)R^{14}$; —$NR^{13}C(O)NR^{14}R^{15}$; —$NR^{13}CO_2R^{14}$;
—$OC(O)R^{13}$; —$OC(O)NR^{13}R^{14}$; —$NR^{13}SOR^{14}$; —$NR^{13}SO_2R^{14}$; —$NR^{13}SONR^{14}R^{15}$;
—$NR^{13}SONR^{14}R^{15}$; —$PR^{13}R^{14}$; —$P(O)R^{13}R^{14}$; —$P^+R^{13}R^{14}R^{15}A^-$; —$P(OR^{13})OR^{14}$; —$S^+R^{13}R^{14}A^-$; and —$N^+R^{13}R^{14}R^{15}A^-$; and wherein the alkyl, polyalkyl, haloalkyl, hydroxyalkyl, cycloalkyl, alkenyl, alkynyl, aryl, heterocyclyl, quaternary heterocyclyl, arylalkyl, heterocyclylalkyl, and polyether substituents of the $R^{5B}$ radical optionally may be further substituted with one or more radicals selected from the group consisting of —CN; halogen; hydroxy; oxo; alkyl; cycloalkyl; alkenyl; alkynyl; aryl; heterocyclyl; arylalkyl; heterocyclylalkyl; quaternary heterocyclyl; —$OR^{19}$; —$NR^{19}R^{20}$; —$SR^{19}$; —$S(O)R^{19}$; —$SO_2R^{19}$; —$SO_3R^{19}$; —$CO_2R^{19}$; —$CONR^{19}R^{20}$; —$N^+R^9R^{19}R^{20}A^-$—; —$P(O)R^{19}R^{20}$; —$PR^{19}R^{20}$; —$P^+R^9R^{19}R^{20}A^-$; and —$P(O)(OR^{19})OR^{20}$; and wherein the alkyl, polyalkyl, haloalkyl, hydroxyalkyl, cycloalkyl, alkenyl, alkynyl, aryl, heterocyclyl, quaternary heterocyclyl, arylalkyl, heterocyclylalkyl, and polyether substituents of the $R^{5B}$ radical optionally may have one or more carbons replaced by —O—; —$NR^{19}$—; —$N^+R^{19}R^{20}A^-$—; —S—; —SO—; —$SO_2$—; —$S^+R^{19}A^-$—; —$PR^{19}$—; —$P(O)R^{19}$—; —$P^+R^{19}R^{20}A^-$—; or phenylene;

(f1) one or more $R^6$ (wherein m=1, 2, 3 or 4 in $(R^6)m$) are independently selected from the group consisting of hydrogen; halogen; —CN; —$NO_2$; alkyl; cycloalkyl; polyalkyl; haloalkyl; alkenyl; alkynyl; aryl; heterocyclyl; quaternary heterocyclyl; arylalkyl; polyether, acyloxy; —$OR^{13}$; —$NR^{13}R^{14}$; —$SR^{13}$; —$S(O)R^{13}$; —$S(O)_2R^{13}$; —$SO_3R^{13}$; —$S^+R^{13}R^{14}A^-$; —$NR^{13}OR^{14}$; —$NR^{13}NR^{14}R^{15}$; —$CO_2R^{13}$; —OM; —$SO_2OM$; —$SO_2NR^{13}R^{14}$; —$NR^{14}C(O)R^{13}$; —$C(O)NR^{13}R^{14}$; —$C(O)OM$;

—$COR^{13}$; —$OR^{18}$; —$S(O)_nNR^{13}R^{14}$; —$NR^{13}R^{18}$; —$NR^{18}OR^{14}$; —$N^+R^{13}R^{14}R^{15}A^-$; —$PR^{13}R^{14}$; —$P(O)R^{13}R^{14}$; —$P^+R^{13}R^{14}R^{15}A^-$; amino acid residue; peptide acid residue; polypeptide acid residue; and carbohydrate acid residue;

wherein the one or more $R^6$ alkyl; cycloalkyl; polyalkyl; haloalkyl; hydroxyalkyl; alkenyl; alkynyl; aryl; heterocyclyl; arylalkyl; heterocyclylalkyl; polyether, and acyloxy radicals optionally may be further independently substituted with one or more radicals selected from the group consisting of halogen; —CN; oxo; —$OR^{16}$; —$NR^9R^{10}$; —$N^+R^9R^{10}R^WA^-$; —$SR^{16}$; —$S(O)R^9$; —$SO_2R^9$; —$SO_3R^{16}$; —$CO_2R^{16}$; —$CONR^9R^{10}$; —$SO_2NR^9R^{10}$; —$PO(OR^{16})OR^{17}$; —$PR^9R^{10}$; —$P^+R^9R^{11}R^{12}A^-$; —$S^+R^9R^{10}A^-$; and carbohydrate residue;

wherein the one or more $R^6$ quaternary heterocyclyl radical optionally may be independently substituted with one or more radicals selected from the group consisting of halogen; —CN; —$NO_2$; oxo; alkyl; cycloalkyl; polyalkyl; haloalkyl; hydroxyalkyl; alkenyl; alkynyl; aryl; heterocyclyl; arylalkyl; heterocyclylallyl; polyether; —$OR^{13}$; —$NR^{13}R^{14}$; —$SR^{13}$; —$S(O)R^{13}$; —$SO_2R^{13}$; —$SO_3R^{13}$; —$NR^{13}OR^{14}$; —$NR^{13}NR^{14}R^{15}$; —$CO_2R^{13}$; OM; —$SO_2OM$; —$SO_2NR^{13}R^{14}$; —$C(O)NR^{13}R^{14}$; —$C(O)OM$; —$COR^{13}$; —$P(O)R^{13}R^{14}$; —$PR^{13}R^{14}$; —$P^+R^{13}R^{14}R^{15}A^-$; —$P(OR^{13})OR^{14}$; —$S^+R^{13}R^{14}A^-$; and —$N^+R^{13}R^{14}R^{15}A^-$; and carbohydrate residue;

wherein the one or more $R^6$ radicals comprising carbon optionally may independently have one or more carbons replaced by —O—; —$NR^{13}$—; —$N^+R^{13}R^{14}A^-$—; —S—; —SO—; —$SO_2$—; —$S^+R^{13}A^-$—; —$PR^{13}$—; —$P(O)R^{13}$—; —$PR^{13}$—; —$P^+R^{13}R^{14}A^-$—; phenylene; amino acid; peptide; polypeptide; carbohydrate; polyether; or polyalkyl; wherein said phenylene; amino acid; peptide; polypeptide; carbohydrate; and polyalkyl optionally may have one or more carbons replaced by —O—; —$NR^9$—; —$N^+R^9R^{10}A^-$—; —S—; —SO—; —$SO_2$—; —$S^+R^9A^-$—; —$PR^9$—; —$P^+R^9R^{10}A^-$—; or —$P(O)R^9$—; or two $R^6$ groups attached to adjacent carbon atoms (e.g., adjacent carbon atoms on the benzo ring) together with the carbon atoms to which they are attached form a $C_4$–$C_{10}$ mono- or bi-cyclic carbocyclic or heterocyclic ring;

wherein the mono- or bi-cyclic carbocyclic or heterocyclic rings optionally may be further substituted with one or more radicals selected from the group consisting of halogen; hydroxy; cyano; nitro; oxo; thioxo; alkyl; haloalkyl; alkoxy; aryl; heterocyclyl; $R^T$; —$OR^{16}$; —$NR^9R^{10}$; —$N^+R^9R^{10}R^WA^-$; —$SR^{16}$; —$S(O)R^9$; —$SO_2R^9$; —$SO_3R^{16}$; —$CO_2R^{16}$; —$CONR^9R^{10}$; —$SO_2NR^9R^{10}$; —$PO(OR^{16})OR^{17}$; —$P^9R^{10}$; —$P^+R^9R^{11}R^{12}A^-$; —$S^+R^9R^{10}A^-$; and carbohydrate residue;

(g1) wherein $R^9$, $R^{10}$, and $R^W$ are independently selected from the group consisting of hydrogen; alkyl; cycloalkyl; alkenyl; alkynyl; aryl; heterocyclyl; alkylammoniumalkyl; arylalkyl; heterocyclylalkyl; carboxyalkyl; alkoxyalkyl; carboalkoxyalkyl; carboxyaryl; carboxyheterocyclyl; amino; alkylamino; carboxyalkylamino; alkoxyalkylamino; and acyl;

(h1) wherein $R^{11}$ and $R^{12}$ are independently selected from the group consisting of hydrogen; —CN; halogen; oxo; alkyl; alkenyl; alkynyl; aryl; heterocyclyl; arylalkyl; heterocyclylalkyl; carboxyalkyl; alkoxyalkyl; carboalkoxyalkyl; cycloalkyl; cycloalkenyl; haloalkyl; hydroxyalkyl; cyanoalkyl; —$OR^9$; —$NR^9R^{10}$; —$SR^9$; —$S(O)R^9$; —$SO_2R^9$; —$SO_3R^9$; —$CO_2R^9$; and —$CONR^9R^{10}$; or $R^{11}$ and $R^{12}$ together with the carbon atom to which they are attached form a cyclic ring; and (i1) wherein $R^{13}$, $R^{14}$, and $R^{15}$ are independently selected from the group consisting of hydrogen; alkyl; haloalkyl; cycloalkyl; polyalkyl; alkenyl; alkynyl; aryl; heterocyclyl; quaternary heterocyclyl; arylalkyl; heterocyclylalkyl; quaternary heterocyclylalkyl; alkylarylalkyl; alkylheterocyclylalkyl; alkylammoniumalkyl; aminoalkyl; aminocarbonylalkyl; alkylaminocarbonylalkyl; carboxyalkylaminocarbonylalkyl; and polyether; or $R^{13}$ and $R^{14}$ together with the nitrogen atom to which they are attached form a mono- or polycyclic heterocyclyl that is optionally substituted with one or more radicals selected from the group consisting of oxo, carboxy, and quaternary salts; or wherein $R^{14}$ and $R^{15}$ together with the nitrogen atom to which they are attached form a cyclic ring; and wherein the $R^{13}$, $R^{14}$, and $R^{15}$ alkyl; haloalkyl; cycloalkyl; polyalkyl; alkenyl; alkynyl; aryl; heterocyclyl; quaternary heterocyclyl; arylalkyl; heterocyclylalkyl; quaternary heterocyclylalkyl; alkylarylalkyl; alkylheterocyclylalkyl; alkylammoniumalkyl; aminoalkyl; aminocarbonylalkyl; alkylaminocarbonylalkyl; carboxyalkylaminocarbonylalkyl; and polyether radicals optionally may be substituted with one or more radicals selected from the group consisting of halogen; —CN; sulfo; oxo; alkyl; haloalkyl; hydroxyalkyl; sulfoalkyl; alkenyl; alkynyl; aryl; heterocyclyl; quaternary heterocyclyl; quaternary heterocyclylalkyl; carboxy, carboxyalkyl; guanidinyl; —$OR^{16}$; —$NR^9R^{10}$; —$N^+R^9R^{10}R^WA^-$; —$SR^{16}$; —$S(O)R^9$; —$SO_2R^9$; —$SO_3R^{16}$; —$CO_2R^{16}$; —$CONR^9R^{10}$; —$SO_2NR^9R^{10}$; —$PO(OR^{16})OR^{17}$; —$P^9R^{10}$; —$P^+R^9R^{10}R^{11}A^-$; —$S^+R^9R^{10}A^-$; and carbohydrate residue; and wherein the $R^{13}$, $R^{14}$, and $R^{15}$ alkyl; haloalkyl; cycloalkyl; polyalkyl; alkenyl; alkynyl; aryl; heterocyclyl; quaternary heterocyclyl; arylalkyl; heterocyclylalkyl; quaternary heterocyclylalkyl; alkylarylalkyl; alkylheterocyclylalkyl; alkylammoniumalkyl; aminoalkyl; aminocarbonylalkyl; alkylaminocarbonylalkyl; carboxyalkylaminocarbonylalkyl; and polyether radicals optionally may have one or more carbons replaced by —O—; —$NR^9$—; —$N^+R^9R^{10}A^-$—; —S—; —SO—; —$SO_2$—; —$S^+R^9A^-$—; —$PR^9$—; —$P^+R^9R^{10}A^-$—; —$P(O)R^9$—; phenylene; carbohydrate residue; amino acid residue; peptide residue; or polypeptide residue; and (j1) wherein $R^{16}$ and $R^{17}$ are independently selected from the group consisting of $R^9$ and M; and (k1) wherein $R^{18}$ is selected from the group consisting of alkyl; alkenyl; alkynyl; aryl; heterocyclyl; quaternary heterocyclyl; arylalkyl; heterocyclylalkyl; acyl; alkoxycarbonyl; arylalkoxycarbonyl; and heterocyclylalkoxycarbonyl; and wherein the $R^{18}$ alkyl; alkenyl; alkynyl; aryl; heterocyclyl; quaternary heterocyclyl; arylalkyl; heterocyclylalkyl; acyl; alkoxycarbonyl; arylalkoxycarbonyl; and heterocyclylalkoxycarbonyl radical optionally may be substituted with one or more radicals selected from the group consisting of halogen;

—CN; NO$_2$; oxo; —OR$^9$; —NR$^9$R$^{10}$; —N$^+$R$^9$R$^{11}$R$^{12}$A$^-$; —SR$^9$; —S(O)R$^9$; —SO$_2$R$^9$; —SO$_3$R$^9$; —CO$_2$R$^9$; —CONR$^9$R$^{10}$; —SO$_2$OM; —SO$_2$NR$^9$R$^{10}$; —PR$^9$R$^{10}$; —P(OR$^{13}$)OR$^{14}$; —PO(OR$^{16}$)OR$^{17}$; and —C(O)OM; and (l1) wherein R$^{19}$ and R$^{20}$ are independently selected from the group consisting of hydrogen; alkyl, alkenyl; alkynyl; aryl; and heterocyclyl; and (m1) same as (m) above.

According to another embodiment the compounds of formulas I-1 to I-24 have the following substituents:

(a2) R$^{2A}$ and R$^{2B}$ are independently selected from the group consisting of hydrogen and (C$_1$–C$_7$)alkyl;

(b2) R$^{3A}$ and R$^{3B}$ taken together with the carbon to which they are attached form (C$_3$–C$_7$)cycloalkyl;

wherein the R$^{3A}$ and R$^{3B}$ (C$_1$–C$_{10}$)alkyl; (C$_3$–C$_{10}$)cycloalkyl; (C$_2$–C$_{10}$)alkenyl; (C$_2$–C$_{10}$)alkynyl; aryl (C$_1$–C$_{10}$)alkyl; (C$_1$–C$_{10}$)alkoxy(C$_1$–C$_{10}$)alkyl; (C$_1$–C$_{10}$)alkoxy(C$_2$–C$_{10}$)alkenyl; (C$_1$–C$_{10}$)alkoxy(C$_2$–C$_{10}$)alkynyl; (C$_1$–C$_{10}$)alkylaryl; and (polyalkyl)aryl radicals optionally may be independently substituted with one or more radicals selected from the group consisting of —CN; halogen; oxo; —OR$^9$; —NR$^9$R$^{10}$; —N$^+$R$^9$R$^{10}$R$^W$A$^-$; —SR$^9$; —S$^+$R$^9$R$^{10}$A$^-$; —PR$^9$R$^{10}$; —P$^+$R$^9$R$^{10}$R$^W$A$^-$; —S(O)R$^9$; —SO$_2$R$^9$; —SO$_3$R$^9$; —CO$_2$R$^9$; and —CONR$^9$R$^{10}$;

wherein the R$^{3A}$ and R$^{3B}$ (C$_1$–C$_{10}$)alkyl; (C$_3$–C$_{10}$)cycloalkyl; (C$_2$–C$_{10}$)alkenyl; (C$_2$–C$_{10}$)alkynyl; aryl (C$_1$–C$_{10}$)alkyl; (C$_1$–C$_{10}$)alkoxy(C$_1$–C$_{10}$)alkyl; C$_1$–C$_{10}$)alkoxy(C$_2$–C$_{10}$)alkenyl; (C$_1$–C$_{10}$)alkoxy(C$_2$–C$_{10}$)alkynyl; (C$_1$–C$_{10}$)alkylaryl; and (polyalkyl)aryl radicals optionally may have one or more carbons independently replaced by —O—; —NR$^9$—; —N$^+$R$^9$R$^{10}$A$^-$—; —S—; —SO—; —SO$_2$—; —S$^+$R$^9$A$^-$—; —PR$^9$; —P(O)R$^9$—; —P$^+$R$^9$R$^{10}$A$^-$—; or phenylene;

(c2) R$^{4A}$ and R$^{4B}$ are independently selected from the group consisting of hydrogen; (C$_1$–C$_{10}$)alkyl; (C$_2$–C$_{10}$)alkenyl; (C$_2$–C$_{10}$)alkynyl; aryl; heterocyclyl; —OR$^9$; —NR$^9$R$^{10}$; —SR$^9$; —S(O)R$^9$; —SO$_2$R$^9$; and —SO$_3$R$^9$; or R$^{4A}$ and R$^{4B}$ together form =O; =NOR$^9$; =S; =NNR$^9$R$^{10}$; =NR$^9$; or =CR$^{11}$R$^{12}$; or (d2) R$^{5A}$ is selected from the group consisting of (C$_1$–C$_{10}$)alkyl; (C$_3$–C$_{10}$)cycloalkyl; (C$_2$–C$_{10}$)alkenyl; (C$_2$–C$_{10}$)alkynyl; aryl; heterocyclyl; quaternary heterocyclyl; —OR$^9$; —SR$^9$; —S(O)R$^9$; —SO$_2$R$^9$; and —SO$_3$R$^9$;

wherein the R$^{5A}$ C$_1$–C$_{10}$)alkyl; (C$_3$–C$_{10}$)cycloalkyl; (C$_2$–C$_{10}$)alkenyl; (C$_2$–C$_{10}$)alkynyl; aryl; heterocyclyl; and quaternary heterocyclyl radical optionally may be substituted with one or more radicals independently selected from the group consisting of halogen; —CN; —NO$_2$; oxo; (C$_1$–C$_{10}$)alkyl; polyalkyl; halo(C$_1$–C$_{10}$)alkyl; (C$_3$–C$_{10}$)cycloalkyl; (C$_2$–C$_{10}$)alkenyl; (C$_2$–C$_{10}$)alkynyl; aryl; heterocyclyl; quaternary heterocyclyl; aryl(C$_1$–C$_{10}$)alkyl; heterocyclyl(C$_1$–C$_{10}$)alkyl; polyether; —OR$^{13}$; —NR$^{13}$R$^{14}$; —SR$^{13}$; —S(O)R$^{13}$; —SO$_2$R$^{13}$; —SO$_3$R$^{13}$; —NR$^{13}$OR$^{14}$; —NR$^{13}$NR$^{14}$R$^{15}$; —CO$_2$R$^{13}$; —OM; —SO$_2$OM; —SO$_2$NR$^{13}$R$^{14}$; —C(O)NR$^{13}$R$^{14}$; —C(O)OM; —COR$^{13}$; —NR$^{13}$C(O)R$^{14}$; —NR$^{13}$C(O)NR$^{14}$R$^{15}$; —NR$^{13}$CO$_2$R$^{14}$; —OC(O)R$^{13}$; —OC(O)NR$^{13}$R$^{14}$; —NR$^{13}$SOR$^{14}$; —NR$^{13}$SO$_2$R$^{14}$; —NR$^{13}$SONR$^{14}$R$^{15}$; —NR$^{13}$SO$_2$NR$^{14}$R$^{15}$; —P(O)R$^{13}$R$^{14}$; —PR$^{13}$R$^{14}$; —P$^+$R$^{13}$R$^{14}$R$^{15}$A$^-$; —P(OR$^{13}$)OR$^{14}$; —S$^+$R$^{13}$R$^{14}$A$^-$; and —N$^+$R$^{13}$R$^{14}$R$^{15}$A$^-$; and wherein the (C$_1$–C$_{10}$)alkyl, polyalkyl, halo(C$_1$–C$_{10}$)alkyl, hydroxy(C$_1$–C$_{10}$)alkyl, (C$_3$–C$_{10}$)Cycloalkyl, (C$_2$–C$_{10}$)alkenyl, (C$_2$–C$_{10}$)alkynyl, aryl, heterocyclyl, quaternary heterocyclyl, aryl(C$_1$–C$_{10}$)alkyl, heterocyclyl(C$_1$–C$_{10}$)alkyl, and polyether substituents of the R$^{5A}$ radical optionally may be further substituted with one or more radicals selected from the group consisting of —CN; halogen; hydroxy; oxo; (C$_1$–C$_{10}$)alkyl; (C$_3$–C$_{10}$)cycloalkyl; (C$_2$–C$_{10}$)alkenyl; (C$_2$–C$_{10}$)alkynyl; aryl; heterocyclyl; aryl (C$_1$–C$_{10}$)alkyl; heterocyclyl(C$_1$–C$_{10}$)alkyl; quaternary heterocyclyl; —OR$^{19}$; —NR$^{19}$R$^{20}$; —SR$^{19}$; —S(O)R$^{19}$; —SO$_2$R$^{19}$; —SO$_3$R$^{19}$; —CO$_2$R$^{19}$; —CONR$^{19}$R$^{20}$; —N$^+$R$^9$R$^{19}$R$^{20}$A—; —P(O)R$^{19}$R$^{20}$; —PR$^{19}$R$^{20}$; —P$^+$R$^9$R$^{19}$R$^{20}$A$^-$; and —P(O)(OR$^{19}$)OR$^{20}$; and wherein the (C$_1$–C$_{10}$)alkyl, polyalkyl, halo(C$_1$–C$_{10}$)alkyl, hydroxy(C$_1$–C$_{10}$)alkyl, (C$_3$–C$_{10}$)cycloalkyl, (C$_2$–C$_{10}$)alkenyl, (C$_2$–C$_{10}$)alkynyl, aryl, heterocyclyl, quaternary heterocyclyl, aryl(C$_1$–C$_{10}$)alkyl, heterocyclyl(C$_1$–C$_{10}$)alkyl, and polyether substituents of the R$^{5A}$ radical optionally may have one or more carbons replaced by —O—; —NR$^{19}$—; —N$^+$R$^{19}$R$^{20}$A$^-$—; —S—; —SO—; —SO$_2$—; —SO$_2$—; —S$^+$R$^{19}$A$^-$—; —PR$^{19}$—; —P(O)R$^{19}$—; —P$^+$R$^{19}$R$^{20}$A$^-$—; or phenylene;

(e2) R$^{5B}$ is selected from the group consisting of hydrogen; (C$_1$–C$_{10}$)alkyl; (C$_3$–C$_{10}$)cycloalkyl; (C$_2$–C$_{10}$)alkenyl; (C$_2$–C$_{10}$)alkynyl; aryl; heterocyclyl; quaternary heterocyclyl; —OR$^9$; —SR$^9$; —S(O)R$^9$; —SO$_2$R$^9$; and —SO$_3$R$^9$;

wherein the R$^{5B}$ (C$_1$–C$_{10}$)alkyl; (C$_3$–C$_{10}$)cycloalkyl; (C$_2$–C$_{10}$)alkenyl; (C$_2$–C$_{10}$)alkynyl; aryl; heterocyclyl; and quaternary heterocyclyl radical optionally may be substituted with one or more radicals independently selected from the group consisting of halogen; —CN; —NO$_2$; oxo; (C$_1$–C$_{10}$)alkyl; polyalkyl; halo(C$_1$–C$_{10}$)alkyl; (C$_3$–C$_{10}$)cycloalkyl; (C$_2$–C$_{10}$)alkenyl; (C$_2$–C$_{10}$)alkynyl; aryl; heterocyclyl; quaternary heterocyclyl; aryl(C$_1$–C$_{10}$)alkyl; heterocyclyl(C$_1$–C$_{10}$)alkyl; polyether; —OR$^{13}$; —NR$^{13}$R$^{14}$; —SR$^{13}$; —S(O)R$^{13}$; —SO$_2$R$^{13}$; —SO$_3$R$^{13}$; —NR$^{13}$OR$^{14}$; —NR$^{13}$NR$^{14}$R$^5$; —CO$_2$R$^{13}$; —OM; —SO$_2$OM; —SO$_2$NR$^{13}$R$^{14}$; —C(O)NR$^{13}$R$^{14}$; —C(O)OM; —COR$^{13}$; —NR$^{13}$C(O)R$^{14}$; —NR$^{13}$C(O)NR$^{14}$R$^{15}$; —NR$^{13}$CO$_2$R$^{14}$; —OC(O)R$^{13}$; —OC(O)NR$^{13}$R$^{14}$; —NR$^{13}$SOR$^{14}$; —NR$^{13}$SO$_2$R$^{14}$; —NR$^{13}$SONR$^{14}$R$^{15}$; —NR$^{13}$SO$_2$NR$^{14}$R$^{15}$; —P(O)R$^{13}$R$^{14}$; —PR$^{13}$R$^{14}$; —P$^+$R$^{13}$R$^{14}$R$^{15}$A$^-$; —P(OR$^{13}$)OR$^{14}$; —S$^+$R$^{13}$R$^{14}$A$^-$; and —N$^+$R$^{13}$R$^{14}$R$^{15}$A$^-$;

wherein the (C$_1$–C$_{10}$)alkyl, polyalkyl, halo(C$_1$–C$_{10}$)alkyl, hydroxy(C$_1$–C$_{10}$)alkyl, (C$_3$–C$_{10}$)cycloalkyl, (C$_2$–C$_{10}$)alkenyl, (C$_2$–C$_{10}$)alkynyl, aryl, heterocyclyl, quaternary heterocyclyl, aryl(C$_1$–C$_{10}$)alkyl, heterocyclyl(C$_1$–C$_{10}$)alkyl, and polyether substituents of the R$^{5B}$ radical optionally may be further substituted with one or more radicals selected from the group consisting of —CN; halogen; hydroxy; oxo; (C$_1$–C$_{10}$)alkyl; (C$_3$–C$_{10}$)cycloalkyl; (C$_2$–C$_{10}$)alkenyl; (C$_2$–C$_{10}$)alkynyl; aryl; heterocyclyl; aryl (C$_1$–C$_{10}$)alkyl; heterocyclyl(C$_1$–C$_{10}$)alkyl; quaternary heterocyclyl; —OR$^{19}$; —NR$^{19}$R$^{20}$; —SR$^{19}$; —S(O)R$^{19}$; —SO$_2$R$^{19}$; —SO$_3$R$^{19}$; —CO$_2$R$^{19}$; —CONR$^{19}$R$^{20}$; —N$^+$R$^9$R$^{19}$R$^{20}$A—; —P(O)R$^{19}$R$^{20}$; —PR$^{19}$R$^{20}$; —P$^+$R$^9$R$^{19}$R$^{20}$A$^-$; and —P(O)(OR$^{19}$)R$^{20}$;

wherein the $(C_1-C_{10})$alkyl, polyalkyl, halo$(C_1-C_{10})$alkyl, hydroxy$(C_1-C_{10})$alkyl, $(C_3-C_{10})$cycloalkyl, $(C_2-C_{10})$alkenyl, $(C_2-C_{10})$alkynyl, aryl, heterocyclyl, quaternary heterocyclyl, aryl$(C_1-C_{10})$alkyl, heterocyclyl$(C_1-C_{10})$alkyl, and polyether substituents of the $R^{5B}$ radical optionally may have one or more carbons replaced by —O—; —NR$^{19}$—; —N$^+$R$^{19}$R$^{20}$A$^-$—; —S—; —SO—; —SO$_2$—; —S$^+$R$^{19}$A$^-$—; —PR$^{19}$—; —P(O)R$^{19}$—; —P$^+$R$^{19}$R$^{20}$A$^-$—; or phenylene;

(f2) one or more R$^6$ (wherein m=1, 2, 3 or 4 in (R$^6$)m) radicals are independently selected from the group consisting of hydrogen; halogen; —CN; —NO$_2$; $(C_1-C_{10})$alkyl; $(C_3-C_{10})$cycloalkyl; polyalkyl; halo$(C_1-C_{10})$alkyl; $(C_2-C_{10})$alkenyl; $(C_2-C_{10})$alkynyl; aryl; heterocyclyl; quaternary heterocyclyl; aryl$(C_1-C_{10})$alkyl; polyether, acyloxy; —OR$^{13}$; —NR$^{13}$R$^{14}$; —SR$^{13}$; —S(O)R$^{13}$; —S(O)$_2$R$^3$; —SO$_3$R$^{13}$; —S$^+$R$^{13}$R$^{14}$A$^-$; —NR$^{13}$OR$^{14}$; —NR$^{13}$NR$^{14}$R$^{15}$; —CO$_2$R$^{13}$; —OM; —SO$_2$OM; —SO$_2$NR$^{13}$R$^{14}$; —NR$^{14}$C(O)R$^{13}$; —C(O)NR$^{13}$R$^{14}$; —C(O)OM; —COR$^{13}$; —OR$^{18}$; —S(O)$_n$NR$^{13}$R$^{14}$; —NR$^{13}$R$^{18}$; —NR$^{18}$OR$^{14}$; —N$^+$R$^{13}$R$^{14}$R$^{15}$A$^-$; —PR$^{13}$R$^{14}$; —P(O)R$^{13}$R$^{14}$; —P$^+$R$^{13}$R$^{14}$R$^{15}$A$^-$; amino acid residue; peptide acid residue; polypeptide acid residue; and carbohydrate acid residue;

wherein one or more of the R$^6$ $(C_1-C_{10})$alkyl; $(C_3-C_{10})$cycloalkyl; polyalkyl; halo$(C_1-C_{10})$alkyl; hydroxy$(C_1-C_{10})$alkyl; $(C_2-C_{10})$alkenyl; $(C_2-C_{10})$alkynyl; aryl; heterocyclyl; aryl$(C_1-C_{10})$alkyl; heterocyclyl$(C_1-C_{10})$alkyl; polyether; and acyloxy radicals optionally may be further independently substituted with halogen; —CN; oxo; —OR$^{16}$; —NR$^9$R$^{10}$; —N$^+$R$^9$R$^{11}$R$^{12}$A$^-$; —SR$^{16}$; —S(O)R$^9$; —SO$_2$R$^9$; —SO$_3$R$^{16}$; —CO$_2$R$^{16}$; —CONR$^9$R$^{10}$; —SO$_2$NR$^9$R$^{10}$; —PO(OR$^{16}$)OR$^{17}$; —PR$^9$R$^{10}$; —P$^+$R$^9$R$^{11}$R$^{12}$A$^-$; or —S$^+$R$^9$R$^{10}$A$^-$;

wherein one or more of the R$^6$ quaternary heterocyclyl radical optionally may be independently substituted with one or more radicals selected from the group consisting of halogen; —CN; —NO$_2$; oxo; $(C_1-C_{10})$alkyl; $(C_3-C_{10})$cycloalkyl; polyalkyl; halo$(C_1-C_{10})$alkyl; hydroxy$(C_1-C_{10})$alkyl; $(C_2-C_{10})$alkenyl; $(C_2-C_{10})$alkyl; aryl; heterocyclyl; aryl$(C_1-C_{10})$alkyl; heterocyclyl$(C_1-C_{10})$alkyl; polyether, —OR$^{13}$; —NR$^{13}$R$^{14}$; —SR$^{13}$; —S(O)R$^{13}$; —SO$_2$R$^{13}$; —SO$_3$R$^{13}$; —NR$^{13}$OR$^{14}$; NR$^{13}$NR$^{14}$R$^{15}$; —CO$_2$R$^{13}$; —OM; —SO$_2$OM; —SO$_2$NR$^{13}$R$^{14}$; —C(O)NR$^{13}$R$^{14}$; —C(O)OM; —COR$^{13}$; —P(O)R$^{13}$R$^{14}$; —PR$^{13}$R$^{14}$; —P$^+$R$^{13}$R$^{14}$R$^{15}$A$^-$; —P(OR$^{13}$)OR$^{14}$; —S$^+$R$^{13}$R$^{14}$A$^-$; and —N$^+$R$^{13}$R$^{14}$R$^{15}$A$^-$; and wherein one or more of the R$^6$ radicals comprising carbon optionally may independently have one or more carbons replaced by —O—; —NR$^{13}$—; —N$^+$R$^{13}$R$^{14}$A$^-$—; —S—; —SO—; —SO$_2$—; —S$^+$R$^{13}$A$^-$—; —PR$^{13}$—; —P(O)R$^{13}$—; —PR$^{13}$—; —P$^+$R$^{13}$R$^{14}$A$^-$—; phenylene; amino acid residue; peptide residue; polypeptide residue; carbohydrate residue; polyether; or polyalkyl; wherein said phenylene; amino acid residue; peptide residue; polypeptide residue; carbohydrate residue; and polyalkyl optionally may have one or more carbons replaced by —O—; —NR$^9$—; —N$^+$R$^9$R$^{10}$A$^-$—; —S—; —SO—; —SO$_2$—; —S$^+$R$^9$A$^-$—; —PR$^9$—; —P$^+$R$^9$R$^{10}$A$^-$—; or —P(O)R$^9$—; or two R$^6$ groups attached to adjacent carbon atoms (e.g., adjacent carbon atoms on the benzo ring) together with the carbon atoms to which they are attached form a $C_4-C_{10}$ mono or bi-cyclic carbocyclic or heterocyclic ring;

wherein the mono- or bi-cyclic carbocyclic or heterocyclic rings optionally may be further substituted with one or more radicals selected from the group consisting of halogen; hydroxy; cyano; nitro; oxo; thioxo; $(C_1-C_0)$alkyl; halo$(C_1-C_{10})$alkyl; $(C_1-C_{10})$alkoxy; aryl; —OR$^{16}$; —NR$^9$R$^{10}$; —N$^+$R$^9$R$^{10}$R$^W$A$^-$; —SR$^{16}$; —S(O)R$^9$; —SO$_2$R$^9$; —SO$_3$R$^{16}$; —CO$_2$R$^{16}$; —CONR$^9$R$^{10}$; —SO$_2$NR$^9$R$^{10}$; —PO(OR$^{16}$)OR$^{17}$; —P$^9$R$^{10}$; —P$^+$R$^9$R$^{11}$R$^{12}$A$^-$; —S$^+$R$^9$R$^{10}$A$^-$; and carbohydrate residue;

(g2) wherein R$^9$, R$^{10}$, and R$^W$ are independently selected from the group consisting of hydrogen; $(C_1-C_{10})$alkyl; $(C_3-C_{10})$cycloalkyl; $(C_2-C_{10})$alkenyl; $(C_2-C_{10})$alkynyl; aryl; heterocyclyl; ammonium$(C_1-C_{10})$alkyl; $(C_1-C_{10})$alkylammonium$(C_1-C_{10})$alkyl; aryl$(C_1-C_{10})$alkyl; heterocyclyl$(C_1-C_{10})$alkyl; carboxy$(C_1-C_{10})$alkyl; carbo$(C_1-C_{10})$alkoxy$(C_1-C_{10})$alkyl; carboxyheterocyclyl; carboxy$(C_1-C_{10})$alkylamino; and acyl; and (h2) wherein R$^{11}$ and R$^{12}$ are independently selected from the group consisting of hydrogen; —CN; halogen; oxo; $(C_1-C_{10})$alkyl; $(C_2-C_{10})$alkenyl; $(C_2-C_{10})$alkynyl; aryl; heterocyclyl; aryl$(C_1-C_{10})$alkyl; carboxy$(C_1-C_{10})$alkyl; carbo$(C_1-C_{10})$alkoxy$(C_1-C_{10})$alkyl; $(C_3-C_{10})$cycloalkyl; cyano$(C_1-C_{10})$alkyl; —OR$^9$; —NR$^9$R$^{10}$; —SR$^9$; —S(O)R$^9$; —SO$_2$R$^9$; —SO$_3$R$^9$; —CO$_2$R$^9$; and —CONR$^9$R$^{10}$; or R$^{11}$ and R$^{12}$ together with the carbon atom to which they are attached form a cyclic ring;

(i2) wherein R$^{13}$, R$^{14}$, and R$^{15}$ are independently selected from the group consisting of hydrogen; $(C_1-C_{10})$alkyl; halo$(C_1-C_{10})$alkyl; $(C_3-C_{10})$cycloalkyl; polyalkyl; $(C_2-C_{10})$alkenyl; $(C_2-C_{10})$alkynyl; aryl; heterocyclyl; quaternary heterocyclyl; aryl$(C_1-C_{10})$alkyl; heterocyclyl$(C_1-C_{10})$alkyl; quaternary heterocyclyl $(C_1-C_{10})$alkyl; $(C_1-C_{10})$alkylaryl$(C_1-C_{10})$alkyl; $(C_1-C_{10})$alkylheterocyclyl$(C_1-C_{10})$alkyl; $(C_1-C_{10})$alkylammonium$(C_1-C_{10})$alkyl; carboxy$(C_1-C_{10})$alkylaminocarbonyl$(C_1-C_{10})$alkyl; and polyether; or wherein R$^{13}$ and R$^{14}$ together with the nitrogen atom to which they are attached form a mono- or polycyclic heterocyclyl that is optionally substituted with one or more radicals selected from the group consisting of oxo, carboxy, and quaternary salts; or wherein R$^{14}$ and R$^{15}$ together with the nitrogen atom to which they are attached form a cyclic ring; and wherein the R$^{13}$, R$^{14}$ and R$^{15}$ $(C_1-C_{10})$alkyl; halo$(C_1-C_{10})$alkyl; $(C_3-C_{10})$cycloalkyl; polyalkyl; $(C_2-C_{10})$alkenyl; $(C_2-C_{10})$alkynyl; aryl; heterocyclyl; quaternary heterocyclyl; aryl$(C_1-C_{10})$alkyl; heterocyclyl$(C_1-C_{10})$alkyl; quaternary heterocyclyl $(C_1-C_{10})$alkyl; $(C_1-C_{10})$alkylaryl $(C_1-C_{10})$alkyl; $(C_1-C_{10})$alkylheterocyclyl$(C_1-C_{10})$alkyl; $(C_1-C_{10})$alkylammonium$(C_1-C_{10})$alkyl; aminocarbonyl $(C_1-C_{10})$alkyl; $(C_1-C_{10})$alkylaminocarbonyl $(C_1-C_{10})$alkyl; carboxy$(C_1-C_{10})$alkylaminocarbonyl $(C_1-C_{10})$alkyl; and polyether radicals optionally may be substituted with one or more radicals selected from the group consisting of halogen; —CN; sulfo; oxo; $(C_1-C_{10})$alkyl; sulfo $(C_1-C_{10})$alkyl; heterocyclyl; quaternary heterocyclyl; quaternary heterocyclyl$(C_1-C_{10})$alkyl; carboxy; carboxy$(C_1-C_{10})$alkyl; guanidinyl; —OR$^{16}$; —NR$^9$R$^{10}$; N$^+$R$^9$R$^{10}$R$^W$A$^-$; —SR$^{16}$;

—S(O)R$^9$; —SO$_2$R$^9$; —SO$_3$R$^{16}$; —CO$_2$R$^{16}$; —CONR$^9$R$^{10}$; —SO$_2$NR$^9$R$^{10}$; —PO(OR$^{16}$)OR$^{17}$; —PR$^9$R$^{10}$; —P$^+$R$^9$R$^{10}$R$^{11}$A$^-$; —S$^+$R$^9$R$^{10}$A$^-$; and carbohydrate residue;

wherein the R$^{13}$, R$^{14}$ and R$^{15}$ (C$_1$–C$_{10}$)alkyl; halo (C$_1$–C$_{10}$)alkyl; (C$_3$–C$_{10}$)cycloalkyl; polyalkyl; (C$_2$–C$_{10}$)alkenyl; (C$_2$–C$_{10}$)alkynyl; aryl; heterocyclyl; quaternary heterocyclyl; aryl(C$_1$–C$_{10}$)alkyl; heterocyclyl(C$_1$–C$_{10}$)alkyl; quaternary heterocyclyl (C$_1$–C$_{10}$)alkyl; (C$_1$–C$_{10}$)alkylaryl(C$_1$–C$_{10}$)alkyl; (C$_1$–C$_{10}$)alkylheterocyclyl(C$_1$–C$_{10}$)alkyl; (C$_1$–C$_{10}$) alkylammonium(C$_1$–C$_{10}$)alkyl; aminocarbonyl (C$_1$–C$_{10}$)alkyl; (C$_1$–C$_{10}$)alkylaminocarbonyl (C$_1$–C$_{10}$)alkyl; carboxy(C$_1$–C$_{10}$)alkylaminocarbonyl(C$_1$–C$_{10}$)alkyl; and polyether radicals optionally may have one or more carbons replaced by —O—; —NR$^9$—; —N$^+$R$^9$R$^{10}$A$^-$—; —S—; —SO—; —SO$_2$—; —S$^+$R$^9$A$^-$—; —PR$^9$—; —P$^+$R$^9$R$^{10}$A$^-$—; —P(O)R$^9$—; phenylene; carbohydrate residue; amino acid residue; peptide residue; or polypeptide residue;

(j2) wherein R$^{16}$ and R$^{17}$ are independently selected from the group consisting of R$^9$ and M;

(k2) wherein R$^{18}$ is selected from the group consisting of (C$_1$–C$_{10}$)alkyl; heterocyclyl; quaternary heterocyclyl; aryl(C$_1$–C$_{10}$)alkyl; acyl; and aryl(C$_1$–C$_{10}$)alkoxycarbonyl;

wherein the R$^{18}$ (C$_1$–C$_{10}$)alkyl; heterocyclyl; quaternary heterocyclyl; aryl(C$_1$–C$_{10}$)alkyl; acyl; and aryl (C$_1$–C$_{10}$)alkoxycarbonyl radical optionally may be substituted with one or more radicals selected from the group consisting of halogen; —CN ; oxo; —OR$^9$; —NR$^9$R$^{10}$; —N$^+$R$^9$R$^{11}$R$^{12}$A$^-$; —SR$^9$; —S(O)R$^9$; —SO$_2$R$^9$; —SO$_3$R$^9$; —CO$_2$R$^9$; —CONR$^9$R$^{10}$; —SO$_2$OM; —SO$_2$NR$^9$R$^{10}$; —PR$^9$R$^{10}$; —P(OR$^{13}$) OR$^{14}$; —PO(OR$^{16}$OR$^{17}$; and —C(O)OM;

(l2) wherein R$^{19}$ and R$^{20}$ are independently selected from the group consisting of hydrogen and (C$_1$–C$_{10}$)alkyl; and (m2) same as (m1) above;

(n2) provided that aryl is selected from the group consisting of optionally substituted phenyl, biphenyl and naphthyl;

(o2) provided that heterocyclyl is selected from the group consisting of optionally substituted heterocyclyl comprising a 4 to 10 membered ring and comprising one or more ring atoms that are heteroatoms selected from the group consisting of oxygen, nitrogen, sulfur and phosphorus.

According to another embodiment, the substituents on the compounds of formulas I-1 to I-24 are as follows:

(a3) R$^{2A}$ and R$^{2B}$ are independently selected from the group consisting of hydrogen and (C$_1$–C$_{10}$)alkyl;

(b3) R$^{3A}$ and R$^{3B}$ are independently selected from the group consisting of hydrogen and (C$_1$–C$_{10}$)alkyl; or R$^{3A}$ and R$^{3B}$ taken together with the carbon to which they are attached form (C$_3$–C$_7$)cycloalkyl;

(c3) R$^{4A}$ and R$^{4B}$ are independently selected from the group consisting of hydrogen and —OR$^9$;

(d3) R$^{5A}$ is selected from phenyl, wherein said phenyl is optionally substituted with one or more radicals independently selected from the group consisting of R5 halogen; hydroxy, —NO$_2$; (C$_1$–C$_{10}$)alkyl; halo (C$_1$–C$_{10}$)alkyl; aryl(C$_1$–C$_{10}$)alkyl; heterocyclyl(C$_1$–C$_{10}$)alkyl; polyether; —OR$^{13}$; —NR$^{13}$R$^{14}$; and —NR$^{13}$C(O)R$^{14}$;

(e3) R$^{5B}$ is hydrogen;

(f3) one or more R$^6$ (wherein m=1, 2, 3 or 4 in (R$^6$)m) radicals are independently selected from the group consisting of hydrogen; —NO$_2$; (C$_1$–C$_{10}$)alkyl; halo (C$_1$–C$_{10}$)alkyl; —OR$^{13}$; —NR$^{13}$R$^{14}$; or two R$^6$ groups attached to adjacent carbon atoms (e.g., adjacent carbon atoms on the benzo ring) together with the carbon atoms to which they are attached form a C$_5$–C$_8$ mono-cyclic carbocyclic or heterocyclic ring;

wherein the mono-cyclic carbocyclic or heterocyclic rings optionally may be further substituted with one or more radicals selected from the group consisting of halogen; hydroxy; cyano; nitro; oxo; thioxo; (C$_1$–C$_{10}$)alkyl; halo(C$_1$–C$_{10}$)alkyl; (C$_1$–C$_{10}$)alkoxy; aryl; —OR$^{16}$; —NR$^9$R$^{10}$; —N$^+$R$^9$R$^{10}$R$^W$A$^-$; —SR$^{16}$; —S(O)R$^9$; —SO$_2$R$^9$; —SO$_3$R$^{16}$; —CO$_2$R$^{16}$; —CONR$^9$R$^{10}$; —SO$_2$NR$^9$R$^{10}$; —PO(OR$^{16}$)OR$^{17}$; —PR$^9$R$^{10}$; —P$^+$R$^9$R$^{11}$R$^{12}$A$^-$; —S$^+$R$^9$R$^{10}$A$^-$; and carbohydrate residue;

(g3) wherein R$^9$, R$^{10}$ and R$^W$ are independently selected from the group consisting of hydrogen; (C$_1$–C$_{10}$)alkyl; heterocyclyl; ammonium(C$_1$–C$_{10}$)alkyl; (C$_1$–C$_{10}$)alkylammonium(C$_1$–C$_{10}$)alkyl; aryl(C$_1$–C$_{10}$)alkyl; heterocyclyl(C$_1$–C$_{10}$)alkyl; carboxy(C$_1$–C$_{10}$)alkyl; carbo(C$_1$–C$_{10}$)alkoxy(C$_1$–C$_{10}$)alkyl; carboxyheterocyclyl; carboxy(C$_1$–C$_{10}$)alkylamino; and acyl;

(h3) wherein R$^{11}$ and R$^{12}$ are independently selected from the group consisting of hydrogen; (C$_1$–C$_{10}$)alkyl; heterocyclyl; aryl(C$_1$–C$_{10}$)alkyl; carboxy(C$_1$–C$_{10}$)alkyl; and carbo(C$_1$–C$_{10}$)alkoxy(C$_1$–C$_{10}$)alkyl; or R$^{11}$ and R$^{12}$ together with the carbon atom to which they are attached form a cyclic ring;

(i3) wherein R$^{13}$, R$^{14}$, and R$^{15}$ are independently selected from the group consisting of hydrogen; (C$_1$–C$_{10}$)alkyl; halo(C$_1$–C$_{10}$)alkyl; heterocyclyl; quaternary heterocyclyl; aryl(C$_1$–C$_{10}$)alkyl; heterocyclyl(C$_1$–C$_{10}$)alkyl; quaternary heterocyclyl(C$_1$–C$_{10}$)alkyl; (C$_1$–C$_{10}$) alkylheterocyclyl(C$_1$–C$_{10}$)alkyl; (C$_1$–C$_{10}$) alkylamnmonium(C$_1$–C$_{10}$)alkyl; and polyether; or wherein the R$^{13}$, R$^{14}$, and R$^{15}$ (C$_1$–C$_{10}$)alkyl; halo (C$_1$–C$_{10}$)alkyl; heterocyclyl; quaternary heterocyclyl; aryl(C$_1$–C$_{10}$)alkyl; heterocyclyl(C$_1$–C$_{10}$)alkyl; quaternary heterocyclyl(C$_1$–C$_{10}$)alkyl; (C$_1$–C$_{10}$) alkylheterocyclyl(C$_1$–C$_{10}$)alkyl; (C$_1$–C$_{10}$) alkylammonium(C$_1$–C$_{10}$)alkyl; and polyether radicals optionally may be substituted with one or more radicals selected from the group consisting of halogen; (C$_1$–C$_{10}$)alkyl; heterocyclyl; quaternary heterocyclyl; quaternary heterocyclyl(C$_1$–C$_{10}$)alkyl; carboxy; carboxy(C$_1$–C$_{10}$)alkyl; —OR$^{16}$; —NR$^9$R$^{10}$; —N$^+$R$^9$R$^{10}$R$^W$A$^-$; and —CONR$^9$R$^{10}$;

(j3) wherein R$^{16}$ is selected from the group consisting of R$^9$ and M;

(k3) same as (k2) above;

(l3) same as (l2) above;

(m3) same as (m2) above;

(n3) provided that aryl is selected from the group consisting of optionally substituted phenyl, biphenyl and naphthyl;

(o3) provided that heterocyclyl is selected from the group consisting of optionally substituted heterocyclyl comprising a 5 to 8 membered ring and comprising one or more ring atoms that are heteroatoms selected from the group consisting of oxygen, nitrogen, sulfur and phosphorus.

According to another embodiment, the substituents of formulas I-1 to I-24 are as follows:

(a4) $R^{2A}$ and $R^{2B}$ are independently selected from the group consisting of hydrogen, methyl, ethyl, n-propyl, isopropyl, n-butyl, isobutyl, sec-butyl, tert-butyl, pentyl and hexyl; and (b4) $R^{3A}$ and $R^{3B}$ are independently selected from the group consisting of hydrogen, methyl, ethyl, n-propyl, isopropyl, n-butyl, isobutyl, sec-butyl, tert-butyl, pentyl, hexyl, phenoxymethylene, phenoxyethylene, phenoxypropylene, pyridinyloxymethylene, pyridinyloxyethylene; methylpyridinyloxymethylene, methylpyridinyloxyethylene, pyrimidinyloxymethylene, and pyrimidinyloxyethylene; or $R^{3A}$ and $R^{3B}$ taken together with the carbon to which they are attached form cyclopropyl, cyclobutyl, cyclopentyl, or cyclohexyl;

(c4) $R^{4A}$ and $R^{4B}$ are independently selected from the group consisting of hydrogen, hydroxy, methyl, ethyl, phenyl, pyridinyl, amino, methylamino, dimethylamino, ethylamino and diethylamino;

(d4) same as (d3) above;

(e4) $R^{5B}$ is hydrogen;

(f4) one or more $R^6$ (wherein m=1, 2, 3 or 4 in $(R^6)m$) radicals are independently selected from the group consisting of hydrogen, hydroxy, methyl, ethyl, n-propyl, isopropyl, n-butyl, isobutyl, tert-butyl, sec-butyl, methoxy, ethoxy, n-propoxy, isopropoxy, methylthio, methylsulfinyl, methylsulfonyl, ethylthio, ethylsulfinyl, ethylsulfonyl, amino, hydroxyamino, methylamino, dimethylamino, ethylamino, diethylamino, trimethylammonium, triethylammonium, N-methyl—N-carboxymethyl-amino, N,N-dimethyl-N-carboxymethyl-ammonium, methylcarbonylamino, chloromethylcarbonylamino, fluoromethylcarbonylamino, bromomethylcarbonylamino, iodomethylcarbonylamino, ethylcarbonylamino, n-propylcarbonylamino, n-butylcarbonylamino, n-pentylcarbonylamino, n-hexylcarbonylamino, benzyloxycarbonylamino, aminoimidocarbonylamino, morpholinyl, N-methyl-morpholinium, azetidinyl, N-methyl-azetidinium, pyrrolidine, N-methyl-pyrrolidinium, piperazinyl, N-methylpiperazinyl, N,N'-dimethyl-piperazinium, piperidinyl, methylpiperidinyl, N-methyl-piperidinium, and thienyl; or two $R^6$ groups attached to adjacent carbon atoms (e.g., adjacent carbon atoms on the benzo ring) together with the carbon atoms to which they are attached form a $C_4$–$C_{10}$ mono- or bi-cyclic carbocyclic or heterocyclic ring;

wherein said mono- or bi-cyclic carbocyclic or heterocyclic ring is selected from the group consisting of cyclobutyl, cyclopentyl, cyclohexyl, cyclopentenyl, cyclohexenyl, phenyl, naphthyl, tetrahydronaphthyl, indenyl, indanyl, biphenyl, pyrrolyl, imidazolyl, pyrazolyl, pyridyl, pyrazinyl, pyrimidyl, pyridazinyl, triazolyl, tetrazolyl, indolizinyl, indolyl, isoindolyl, purinyl, quinolyl, isoquinolyl, phthalazinyl, naphthyridinyl, quinoxalinyl, quinazolinyl, cinnolinyl, pteridinyl, furanyl, pyranyl, thiophenyl, dithiolyl, oxazolyl, isoxazolyl, oxadiazolyl, oxatriazolyl, dioxazolyl, oxazinyl, isooxazinyl, oxathiolyl, thiazolyl, isothiazolyl, thiodiazolyl, oxathiazolyl, oxathiazinyl, chromanyl, thiochromanyl, pyrrolidinyl, imidazolidinyl, dihydrothiophenyl, dihydropyranyl, dihydrofuranyl, dihydrothiazolyl, dihydroindolyl, pyrrolinyl, piperidinyl, piperazinyl, morpholinyl, benzoxazolyl, benzodioxolyl, benzodioxanyl, benzoxadiazolyl, dihydrobenzofuryl, benzothienyl, benzothiazolyl, benzothiadiazolyl, benzopyran, benzothiopyran, benzimidazolyl, benzotriazolyl, tetrazolopyridazinyl cyclohexofuryl, and cyclohexenofuryl wherein the mono- or bi-cyclic carbocyclic or heterocyclic rings optionally may be further substituted with one or more radicals selected from the group consisting of halogen; hydroxy; cyano; nitro; oxo; thioxo; methyl; ethyl; propyl; butyl; pentyl; hexyl; methoxy; ethoxy, propoxy, butoxy, pentoxy, hexyloxy, amino; methylamino; dimethylamino; ethylamino; and diethylamino; or a pharmaceutically acceptable salt, solvate, or prodrug thereof;

(g4) same as (g3) above;

(h4) same as (h3) above;

(i4) same as (i3) above;

(j4) same as (j3) above;

(k4) same as (k3) above;

(l4) same as (l3) above;

(m4) same as (m3) above;

(n4) same as (n3) above;

(o4) same as (o3) above).

According to another embodiment, the substituents on compounds of formulas I-1 to I-24 are as follows:

(a5) $R^{2A}$ and $R^{2B}$ are hydrogen; or (b5) $R^{3A}$ and $R^{3B}$ are independently selected from the group consisting of hydrogen, methyl, ethyl, n-propyl, isopropyl, n-butyl, isobutyl, sec-butyl, tert-butyl, pentyl, and hexyl;

(c5) $R^{4A}$ and $R^{4B}$ are independently selected from the group consisting of hydrogen, and hydroxy;

(d5) same as (d4) above;

(e5) $R^{5B}$ is hydrogen;

(f5) one or more $R^6$ (wherein m=1, 2, 3 or 4 in $(R^6)m$) radicals are independently selected from the group consisting of hydrogen, hydroxy, methyl, ethyl, n-propyl, isopropyl, n-butyl, isobutyl, tert-butyl, sec-butyl, methoxy, ethoxy, n-propoxy, isopropoxy, methylthio, methylsulfinyl, methylsulfonyl, ethylthio, ethylsulfinyl, ethylsulfonyl, amino, hydroxyamino, methylamino, dimethylamino, ethylamino, and diethylamino; or two $R^6$ groups attached to adjacent carbon atoms (e.g., adjacent carbon atoms on the benzo ring) together with the carbon atoms to which they are attached form a $C_5$–$C_{10}$ mono- or bi-cyclic carbocyclic or heterocyclic ring;

wherein said mono- or bi-cyclic carbocyclic or heterocyclic ring is selected from the group consisting of cyclopentyl, cyclohexyl, cyclopentenyl, cyclohexenyl, phenyl, naphthyl, tetrahydronaphthyl, indenyl, indanyl, biphenyl, pyrrolyl, imidazolyl, pyrazolyl, pyridyl, pyrazinyl, pyrimidyl, pyridazinyl, triazolyl, tetrazolyl, indolizinyl, indolyl, isoindolyl, purinyl, quinolyl, isoquinolyl, phthalazinyl, naphthyridinyl, quinoxalinyl, quinazolinyl, cinnolinyl, pteridinyl, furanyl, pyranyl, thiophenyl, dithiolyl, oxazolyl, isoxazolyl, oxadiazolyl, oxatriazolyl, dioxazolyl, oxazinyl, isooxazinyl, oxathiolyl, thiazolyl, isothiazolyl, thiodiazolyl, oxathiazolyl, oxathiazinyl, chromanyl, thiochromanyl, pyrrolidinyl, imidazolidinyl, dihydrothiophenyl, dihydropyranyl, dihydrofuranyl, dihydrothiazolyl, dihydroindolyl, pyrrolinyl, piperidinyl, piperazinyl, morpholinyl, benzoxazolyl, benzodioxolyl, benzodioxanyl, benzoxadiazolyl, dihydrobenzofuryl, benzothienyl, benzothiazolyl, benzothiadiazolyl, benzopyran, benzothiopyran, benzimidazolyl, benzotriazolyl, tetrazolopyridazinyl cyclohexofuryl, and cyclohexenofuryl.

wherein the mono- or bi-cyclic carbocyclic or heterocyclic rings optionally may be further substituted with one or more radicals selected from the group consisting of halogen; hydroxy, cyano; nitro; oxo; thioxo; methyl; ethyl; propyl; butyl; pentyl; hexyl; methoxy; ethoxy; propoxy; butoxy; pentoxy; hexyloxy; amino; methylamino; dimethylamino; ethylamino; and diethylamino;

(g5) same as (g4) above;
(h5) same as (h4) above;
(i5) same as (i4) above;
(j5) same as (j4) above;
(k5) same as (k4) above;
(l5) same as (l4) above; or
(m5) wherein $A^-$ is a pharmaceutically acceptable anion; or a pharmaceutically acceptable salt, solvate, or prodrug thereof;
(n5) same as (n4) above;
(o5) same as (o4) above.

According to another embodiment, the substituents on compounds I-1 to I-24 are as follows:

(a6) same as (a1) above;
(b6) same as (b1) above;
(c6) same as (c1) above;
(d6) $R^{5A}$ is selected from the group consisting of aryl; heterocyclyl; and quaternary heterocyclyl;

wherein the $R^{5A}$ aryl; heterocyclyl; and quaternary heterocyclyl radical optionally may be substituted with one or more radicals independently selected from the group consisting of halogen; —CN; —NO$_2$; oxo; alkyl; polyalkyl; haloalkyl; cycloalkyl; alkenyl; alkynyl; aryl; heterocyclyl; quaternary heterocyclyl; arylalkyl; heterocyclylalkyl; polyether; —OR$^{13}$; —NR$^{13}$R$^{14}$; —SR$^{13}$; —S(O)R$^{13}$; —SO$_2$R$^{13}$; —SO$_3$R$^{13}$; —NR$^{13}$OR$^{14}$; —NR$^{13}$NR$^{14}$R$^{15}$; —CO$_2$R$^{13}$; —OM; —SO$_2$OM; —SO$_2$NR$^{13}$R$^{14}$; —C(O)NR$^{13}$R$^{14}$; —C(O)OM; —COR$^{13}$; —NR$^{13}$C(O)R$^{14}$; —NR$^{13}$C(O)NR$^{14}$R$^{15}$; —NR$^{13}$CO$_2$R$^{14}$; —OC(O)R$^{13}$; OC(O)NR$^{13}$R$^{14}$; —NR$^{13}$SOR$^{14}$; —NR$^{13}$SO$_2$R$^{14}$; —NR$^{13}$SONR$^{14}$R$^{15}$; —NR$^{13}$SO$_2$NR$^{14}$R$^{15}$; —PR$^{13}$R$^{14}$; —P(O)R$^{13}$R$^{14}$; —P$^+$R$^{13}$R$^{14}$R$^{15}$A$^-$; —P(OR$^{13}$)OR$^{14}$; —S$^+$R$^{13}$R$^{14}$A$^-$; and —N$^+$R$^{13}$R$^{14}$R$^{15}$A$^-$;

wherein the alkyl, polyalkyl, haloalkyl, hydroxyalkyl, cycloalkyl, alkenyl, alkynyl, aryl, heterocyclyl, quaternary heterocyclyl, arylalkyl, heterocyclylalkyl, and polyether substituents of the $R^{5A}$ radical optionally may be further substituted with one or more radicals selected from the group of —CN; halogen; hydroxy, oxo; alkyl; cycloalkyl; alkenyl; alkynyl; aryl; heterocyclyl; arylalkyl; heterocyclylalkyl; quaternary heterocyclyl; —OR$^{19}$; —NR$^{19}$R$^{20}$; —SR$^{19}$; —S(O)R$^{19}$; —SO$_2$R$^{19}$; —SO$_3$R$^{19}$; —CO$_2$R$^{19}$; —CONR$^{19}$R$^{20}$; —N$^+$R$^9$R$^{19}$R$^{20}$A$^-$; —P(O)R$^{19}$R$^{20}$; —PR$^{19}$R$^{20}$; —P$^+$R$^9$R$^{19}$R$^{20}$A$^-$; and —P(O)(OR$^{19}$)OR$^{20}$;

wherein the alkyl, polyalkyl, haloalkyl, hydroxyalkyl, cycloalkyl, alkenyl, alkynyl, aryl, heterocyclyl, quaternary heterocyclyl, arylalkyl, heterocyclylalkyl, and polyether substituents of the $R^{5A}$ radical optionally may have one or more carbons replaced by —O—; —NR$^{19}$—; —N$^+$R$^{19}$R$^{20}$A$^-$—; —S—; —SO—; —SO$_2$—; —S$^+$R$^{19}$A$^-$—; —PR$^{19}$—; —P(O)R$^{19}$—; —P$^+$R$^{19}$R$^{20}$A$^-$—; or phenylene;

(e6) same as (e1) above;
(f6) wherein $R^9$, $R^{10}$, and $R^W$ are independently selected from the group consisting of hydrogen; alkyl; cycloalkyl; alkenyl; alkynyl; aryl; heterocyclyl; alkylammoniumalkyl; arylalkyl; heterocyclylalkyl; carboxyalkyl; carboalkoxyalkyl; carboxyheterocyclyl; carboxyalkylamino; and acyl;
(g6) wherein $R^{11}$ and $R^{12}$ are independently selected from the group consisting of hydrogen; —CN; halogen; oxo; alkyl; alkenyl; alkynyl; aryl; heterocyclyl; arylalkyl; carboxyalkyl; carboalkoxyalkyl; cycloalkyl; cyanoalkyl; —OR$^9$; —NR$^9$R$^{10}$; —SR$^9$; —S(O)R$^9$; —SO$_2$R$^9$; —SO$_3$R$^9$; —CO$_2$R$^9$; and —CONR$^9$R$^{10}$; or $R^{11}$ and $R^{12}$ together with the carbon atom to which they are attached form a cyclic ring;
(h6) wherein $R^{13}$, $R^{14}$, and $R^{15}$ are independently selected from the group consisting of hydrogen; alkyl; haloalkyl; cycloalkyl; polyalkyl; alkenyl; alkynyl; aryl; heterocyclyl; quaternary heterocyclyl; arylalkyl; heterocyclylalkyl; quaternary heterocyclylalkyl; alkylarylalkyl; alkylheterocyclylalkyl; alkylammoniumalkyl; carboxyalkylaminocarbonylalkyl; and polyether, or wherein $R^{13}$ and $R^{14}$ together with the nitrogen atom to which they are attached form a mono- or polycyclic heterocyclyl that is optionally substituted with one or more radicals selected from the group consisting of oxo, carboxy, and quaternary salts; or wherein $R^{14}$ and $R^{15}$ together with the nitrogen atom to which they are attached form a cyclic ring; and wherein the $R^{13}$, $R^{14}$, and $R^{15}$ alkyl; haloalkyl; cycloalkyl; polyalkyl; alkenyl; alkynyl; aryl; heterocyclyl; quaternary heterocyclyl; arylalkyl; heterocyclylalkyl; quaternary heterocyclylalkyl; alkylarylalkyl; alkylheterocyclylalkyl; alkylammoniumalkyl; aminocarbonylalkyl; alkylaminocarbonylalkyl; carboxyalkylaminocarbonylalkyl; and polyether radicals optionally may be substituted with one or more radicals selected from the group consisting of halogen; —CN; sulfo; oxo; alkyl; sulfoalkyl; heterocyclyl; quaternary heterocyclyl; quaternary heterocyclylalkyl; carboxy; carboxyalkyl; guanidinyl; —OR$^{16}$; —NR$^9$R$^{10}$; —N$^+$R$^9$R$^{10}$R$^W$A$^-$; —SR$^{16}$; —S(O)R$^9$; —SO$_2$R$^9$; —SO$_3$R$^{16}$; —CO$_2$R$^{16}$; —CONR$^9$R$^{10}$; —SO$_2$NR$^9$R$^{10}$; —PO(OR$^{16}$)OR$^{17}$; —PR$^9$R$^{10}$; —P$^+$R$^9$R$^{10}$R$^{11}$A$^-$; —S$^+$R$^9$R$^{10}$A$^-$; and carbohydrate residue;

wherein the $R^{13}$, $R^{14}$, and $R^{15}$ alkyl; haloalkyl; cycloalkyl; polyalkyl; alkenyl; alkynyl; aryl; heterocyclyl; quaternary heterocyclyl; arylalkyl; heterocyclylalkyl; quaternary heterocyclylalkyl; alkylarylalkyl; alkylheterocyclylalkyl; alkylammoniumalkyl; aminocarbonylalkyl; alkylaminocarbonylalkyl; carboxyalkylaminocarbonylalkyl; and polyether radicals optionally may have one or more carbons replaced by —O—; —NR$^9$—; —N$^+$R$^9$R$^{10}$A$^-$—; —S—; —SO—; —SO$_2$—; —S$^+$R$^9$A$^-$—; —PR$^9$—;

—$P^+R^9R^{10}A^-$—; —$P(O)R^9$—; phenylene; carbohydrate residue; amino acid residue; peptide residue; or polypeptide residue;

(i6) wherein $R^{16}$ and $R^{17}$ are independently selected from the group consisting of $R^9$ and M; and (j6) wherein $R^{18}$ is selected from the group consisting of alkyl; alkenyl; alkynyl; aryl; heterocyclyl; quaternary heterocyclyl; arylalkyl; heterocyclylalkyl; acyl; alkoxycarbonyl; arylalkoxycarbonyl; and heterocyclylalkoxycarbonyl;

wherein the $R^{18}$ alkyl; alkenyl; alkynyl; aryl; heterocyclyl; quaternary heterocyclyl; arylalkyl; heterocyclylalkyl; acyl; alkoxycarbonyl; arylalkoxycarbonyl; and heterocyclylalkoxycarbonyl radical optionally may be substituted with one or more radicals selected from the group consisting of halogen; —CN; oxo; —$OR^9$; —$NR^9R^{10}$; —$N^+R^9R^{11}R^{12}A^-$; —$SR^9$; —$S(O)R^9$; —$SO_2R^9$; —$SO_3R^9$; —$CO_2R^9$; —$CONR^9R^{10}$; —$SO_2OM$; —$SO_2NR^9R^{10}$; —$PR^9R^{10}$; —$P(OR^{13})OR^{14}$; —$PO(OR^{16})OR^{17}$; and —$C(O)OM$;

(k6) wherein $R^{19}$ and $R^{20}$ are independently selected from the group consisting of hydrogen and alkyl; and (l6) same as (l1) above;

(m6) same as (m1) above.

According to another embodiment, the substituents of compounds of formulas I-1 to I-24 are as follows:

(a7) same as (a1) above;

(b7) same as (b1) above;

(c7) $R^{5A}$ has the formula

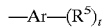

wherein t is an integer from 0 to 5; Ar is selected from the group consisting of phenyl; thiophenyl; pyridyl; piperazinyl; piperonyl; pyrrolyl; naphthyl; furanyl; anthracenyl; quinolinyl; isoquinolinyl; quinoxalinyl; imidazolyl; pyrazolyl; oxazolyl; isoxazolyl; pyrimidinyl; thiazolyl; triazolyl; isothiazolyl; indolyl; benzoimidazolyl; benzoxazolyl; benzothiazolyl; and benzoisothiazolyl;

one or more $R^5$ are independently selected from the group consisting of halogen; —CN; —$NO_2$; oxo; alkyl; polyalkyl; haloalkyl; cycloalkyl; alkenyl; alkynyl; aryl; heterocyclyl; quaternary heterocyclyl; arylalkyl; heterocyclylalkyl; polyether, —$OR^{13}$; —$NR^{13}R^{14}$; —$SR^{13}$; —$S(O)R^{13}$; —$SO_2R^{13}$; —$SO_3R^{13}$; —$NR^{13}OR^{14}$; —$NR^{13}NR^{14}R^{15}$; —$CO_2R^{13}$; —OM; —$SO_2OM$; —$SO_2NR^{13}R^{14}$; —$C(O)NR^{13}R^{14}$; —$C(O)OM$; —$COR^{13}$; —$NR^{13}C(O)R^{14}$; —$NR^{13}C(O)NR^{14}R^{15}$; —$NR^{13}CO_2R^{14}$; —$OC(O)R^{13}$; —$OC(O)NR^{13}R^{14}$; —$NR^{13}SOR^{14}$; —$NR^{13}SO_2R^{14}$; —$NR^{13}SONR^{14}R^{15}$; —$NR^{13}SO_2NR^{14}R^{15}$; —$PR^{13}R^{14}$; —$P(O)R^{13}R^{14}$; —$P^+R^{13}R^{14}R^{15}A^-$; —$P(OR^{13})OR^{14}$; —$S^+R^{13}R^{14}A^-$; and —$N^+R^{13}R^{14}R^{15}A^-$; and wherein the alkyl, polyalkyl, haloalkyl, hydroxyalkyl, cycloalkyl, alkenyl, alkynyl, aryl, heterocyclyl, quaternary heterocyclyl, arylalkyl, heterocyclylalkyl, and polyether substituents of the $R^5$ radical optionally may be further substituted with one or more radicals selected from the group consisting of —CN; halogen; hydroxy, oxo; alkyl; cycloalkyl; alkenyl; alkynyl; aryl; heterocyclyl; arylalkyl; heterocyclylalkyl; quaternary heterocyclyl; —$OR^{19}$; —$NR^{19}R^{20}$; —$SR^{19}$; —$S(O)R^{19}$; —$SO_2R^{19}$; —$SO_3R^{19}$; —$CO_2R^{19}$; —$CONR^{19}R^{20}$; —$N^+R^9R^{19}R^{20}A^-$; $P(O)R^{19}R^{20}$; —$PR^{19}R^{20}$; —$P^+R^9R^{19}R^{20}A^-$; and —$P(O)(OR^{19})OR^{20}$;

wherein the alkyl, polyalkyl, haloalkyl, hydroxyalkyl, cycloalkyl, alkenyl, alkynyl, aryl, heterocyclyl, quaternary heterocyclyl, arylalkyl, heterocyclylalkyl, and polyether substituents of the $R^5$ radical optionally may have one or more carbons replaced by —O—; —$NR^{19}$—; —$N^+R^{19}R^{20}A^-$—; —S—; —SO—; —$SO_2$—; —$S^+R^{19}A^-$—; —$PR^{19}$—; —$P(O)R^9$—; —$P^+R^{19}R^{20}A^-$—; or phenylene;

(d7) same as (d1) above;

(e7) same as (e1) above;

(f7) wherein $R^9$, $R^{10}$, and $R^W$ are independently selected from the group consisting of hydrogen; alkyl; cycloalkyl; alkenyl; alkynyl; aryl; heterocyclyl; alkylammoniumalkyl; arylalkyl; heterocyclylalkyl; carboxyalkyl; carboalkoxyalkyl; carboxyheterocyclyl; carboxyalkylamino; and acyl;

(g7) wherein $R^{11}$ and $R^{12}$ are independently selected from the group consisting of hydrogen; —CN; halogen; oxo; alkyl; alkenyl; alkynyl; aryl; heterocyclyl; arylalkyl; carboxyalkyl; carboalkoxyalkyl; cycloalkyl; cyanoalkyl; —$OR^9$; —$NR^9R^{10}$; —$SR^9$; —$S(O)R^9$; —$SO_2R^9$; —$SO_3R^9$; —$CO_2R^9$; and —$CONR^9R^{10}$; or $R^{11}$ and $R^{12}$ together with the carbon atom to which they are attached form a cyclic ring; and (h7) wherein $R^{13}$, $R^{14}$, and $R^{15}$ are independently selected from the group consisting of hydrogen; alkyl; haloalkyl; cycloalkyl; polyalkyl; alkenyl; alkynyl; aryl; heterocyclyl; quaternary heterocyclyl; arylalkyl; heterocyclylalkyl; quaternary heterocyclylalkyl; alkylarylalkyl; alkylheterocyclylalkyl; alkylammoniumalkyl; carboxyalkylaminocarbonylalkyl; and polyether, or wherein $R^{13}$ and $R^{14}$ together with the nitrogen atom to which they are attached form a mono- or polycyclic heterocyclyl that is optionally substituted with one or more radicals selected from the group consisting of oxo, carboxy, and quaternary salts; or wherein $R^{14}$ and $R^{15}$ together with the nitrogen atom to which they are attached form a cyclic ring; and wherein the $R^{13}$, $R^{14}$, and $R^{15}$ alkyl; haloalkyl; cycloalkyl; polyalkyl; alkenyl; alkynyl; aryl; heterocyclyl; quaternary heterocyclyl; arylalkyl; heterocyclylalkyl; quaternary heterocyclylalkyl; alkylarylalkyl; alkylheterocyclylalkyl; alkylammoniumalkyl; aminocarbonylalkyl; alkylaminocarbonylalkyl; carboxyalkylaminocarbonylalkyl; and polyether radicals optionally may be substituted with one or more radicals selected from the group consisting of halogen; —CN; sulfo; oxo; alkyl; sulfoalkyl; heterocyclyl; quaternary heterocyclyl; quaternary heterocyclylalkyl; carboxy; carboxyalkyl; guanidinyl; —$OR^{16}$; —$NR^9R^{10}$; —$N^+R^9R^{10}R^WA^-$; —$SR^{16}$; —$S(O)R^9$; —$SO_2R^9$; —$SO_3R^{16}$; —$CO_2R^{16}$; —$CONR^9R^{10}$; —$SO_2NR^9R^{10}$; —$PO(OR^{16})OR^{17}$; —$PR^9R^{10}$; —$P^+R^9R^{10}R^{11}A^-$; —$S^+R^9R^{10}A^-$; and carbohydrate residue; and wherein the $R^{13}$, $R^{14}$, and $R^{15}$ alkyl; haloalkyl; cycloalkyl; polyalkyl; alkenyl; alkynyl; aryl; heterocyclyl; quaternary heterocyclyl; arylalkyl; heterocyclylalkyl; quaternary heterocyclylalkyl; alkylarylalkyl; alkylheterocyclylalkyl; alkylammoniumalkyl; aminocarbonylalkyl; alkylaminocarbonylalkyl; carboxyalkylaminocarbonylalkyl; and polyether radicals optionally may have one or more carbons replaced by —O—; —NR⁹—; —N⁺R⁹R¹⁰A⁻—; —S—; —SO—; —SO₂—; —S⁺R⁹A⁻—; —PR⁹—; —P⁺R⁹R¹⁰A⁻—; —P(O)R⁹—; phenylene; carbohydrate residue; amino acid residue; peptide residue; or polypeptide residue;

(i7) wherein R¹⁶ and R¹⁷ are independently selected from the group consisting of R⁹ and M;

(j7) wherein R¹⁸ is selected from the group consisting of alkyl; alkenyl; alkynyl; aryl; heterocyclyl; quaternary heterocyclyl; arylalkyl; heterocyclylalkyl; acyl; alkoxycarbonyl; arylalkoxycarbonyl; and heterocyclylalkoxycarbonyl;

wherein the R¹⁸ alkyl; alkenyl; alkynyl; aryl; heterocyclyl; quaternary heterocyclyl; arylalkyl; heterocyclylalkyl; acyl; alkoxycarbonyl; arylalkoxycarbonyl; and heterocyclylalkoxycarbonyl radical optionally may be substituted with one or more radicals selected from the group consisting of halogen; —CN; oxo; —OR⁹; —NR⁹R¹⁰; —N⁺R⁹R¹¹R¹²A⁻; —SR⁹; —S(O)R⁹; —SO₂R⁹; —SO₃R⁹; —CO₂R⁹; —CONR⁹R¹⁰; —SO₂OM; —SO₂NR⁹R¹⁰; —PR⁹R¹⁰; —P(OR¹³)OR¹⁴; —PO(OR¹⁶)OR¹⁷; and —C(O)OM;

(k7) wherein R¹⁹ and R²⁰ are independently selected from the group consisting of hydrogen and alkyl;

(l7) same as (l1) above;

(m7) same as (m1) above.

According to another embodiment, the substituents of compounds of formulas I-1 to I-24 are as follows:

(a8) same as (a7) above;

(b8) same as (b7) above;

(c8) wherein R⁵ᴬ is:

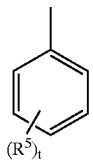

II wherein R⁵ is as defined in (c7) above and t is 1, 2, 3, 4 or 5;

(d8) same as (d7) above;

(e8) same as (e7) above;

(f8) same as (f7) above;

(g8) same as (g7) above;

(h8) same as (h7) above;

(i8) same as (i7) above;

(j8) same as (j7) above;

(k8) same as (k7) above;

(l8) same as (l7) above;

(m8) same as (m7) above.

According to another embodiment, the substituents of compounds of formulas I-1 to I-24 are as follows:

(a9) same as (a8) above;

(b9) same as (b8) above;

(c9) wherein R⁵ᴬ is:

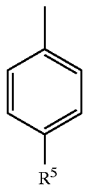

IIA wherein R⁵ is as defined in (c8) above;

(d9) same as (d8) above;

(e9) same as (e8) above;

(f9) same as (f8) above;

(g9) same as (g8) above;

(h9) same as (h8) above;

(i9) same as (i8) above;

(j9) same as (j8) above;

(k9) same as (k8) above;

(l9) same as (l8) above;

(m9) same as (m8) above.

According to another embodiment, the substituents of compounds of formulas I-1 to I-24 are as follows:

(a10) same as (a8) above;

(b10) same as (b8) above;

(c10) wherein R⁵ᴬ is:

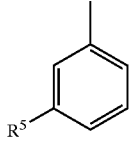

IIB wherein R⁵ is as defined in (c8) above;

(d10) same as (d9) above;

(e10) same as (e9) above;

(f10) same as (f9) above;

(g10) same as (g9) above;

(h10) same as (h9) above;

(i10) same as (i9) above;

(j10) same as (j9) above;

(k10) same as (k9) above;

(l10) same as (l9) above;

(m10) same as (m9) above.

Preferably, in each of the various embodiments of the invention described above, in each of Formulas I-1 to I-24 and in each of the benzothiepine intermediates and products (containing a benzothiepene 7 membered ring described in Schemes 1–7), at least one or more of the following conditions are satisfied:

(1) j is 1 or 2. Preferably, j is 2; and/or (2) The substituents at the 2-position of the benzothiepine are independently selected from the group consisting of hydrogen and alkyl. Preferably, these substituents are hydrogen; and/or (3) The substituents at the 3-position of the benzothiepine are independently selected from the group consisting of hydrogen and alkyl. Preferably, these substituents are independently selected from the group consisting of $C_{1-6}$ alkyls. More preferably, these substituents are selected from the group consisting of ethyl, propyl and butyl. Still more preferably, either (a) one of these 3-position substituents is ethyl and the other is n-butyl, or (b) both of these 3-position substituents are n-butyl; and/or (4) The substituents at the 5-position of the benzothiepene is aryl or substituted aryl. Preferably, the aryl is phenyl that is optionally substituted at the meta and/or the para position. More preferably, the substitution at the meta and/or the para position of the phenyl is glucuronidated or monosubstituted with a radical selected from the group consisting of $-R^5$, $-OR^{13}$, $-NR^{13}C(O)R^{14}$, $-NR^{13}C(O)NR^{14}R^{15}$, $-NR^{13}CO_2R^{14}$, $-OC(O)R^{13}$, $-OC(O)NR^{13}R^{14}$, $-NR^{13}SOR^{14}$, $-NR^{13}SO_2R^{14}$, $-NR^{13}SONR^{14}R^{15}$, and $-NR^{13}SO_2NR^{14}R^{15}$ wherein $R^5$, $R^{13}$, $R^{14}$ and $R^{15}$ are as previously defined; and/or (6) Only one of $R^{5A}$ or $R^{5B}$ is hydrogen; and/or (7) One or more substituents $R^6$ of the benzo ring of the benzothiepine are independently selected from the group consisting of halogen, $-OR^{13}$ and $-NR^{13}R^{14}$, wherein $R^{13}$ and $R^{14}$ are as previously defined. Preferably, the substituents of the benzo ring are independently selected from the group consisting of halogen, hydroxy, alkoxy, amino, alkylamino and dialkylamino. Still more preferably, the substituents are independently selected from the group consisting of chloro, methoxy and dimethylamino.

Alternative Forms Of Novel Compounds

Also included in the family of compounds of Formulas I-1 to I-24 are (a) the stereoisomers thereof, (b) the pharmaceutically-acceptable salts thereof (c) the tautomers thereof, (d) the protected acids and the conjugate acids thereof, and (e) the prodrugs thereof.

(a) The Stereoisomers

The stereoisomers of these compounds may include, but are not limited to, enantiomers, diastereomers, racemic mixtures and combinations thereof. Such stereoisomers can be prepared and separated using conventional techniques, either by reacting enantiomeric starting materials, or by separating isomers of compounds of the present invention. Isomers may include geometric isomers. Examples of geometric isomers includes, but are not limited to, cis isomers or trans isomers across a double bond. Other isomers are contemplated among the compounds of the present invention. The isomers may be used either in pure form or in admixture with other isomers of the inhibitors described above.

(b) The Pharmaceutically-Acceptable Salts

Pharmaceutically-acceptable salts of the compounds of the present invention (Formulas I-1 to I-24) include salts commonly used to form alkali metal salts or form addition salts of free acids or free bases. The nature of the salt is not critical, provided that it is pharmaceutically-acceptable. Suitable pharmaceutically-acceptable acid addition salts of compounds of Formulas I-1 to I-24 may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids. Examples of organic and sulfonic classes of organic acids includes, but are not limited to, formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicyclic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, N-hydroxybutyric, salicyclic, galactaric and galacturonic acid and combinations thereof.

Suitable pharmaceutically-acceptable base addition salts of compounds of Formulas I-1 to I-24 include metallic salts, such as salts made from aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, histidine, glucamine, isopropylamine, lysine, morpholine, N-ethyl morpholine, piperazine, piperidine, triethylamine, and trimethylamine. The above salts may be prepared by conventional means from the corresponding compounds of the invention by reacting, for example, the appropriate acid or base with the compounds of Formulas I-1 to I-24.

(c) The Tautomers

Tautomers of the aforementioned compounds (Formulas I-1 to I-24) are encompassed by the present invention. Thus, for example, (even though not shown) a carbonyl includes its hydroxy tautomer.

(d) The Protected Acids and the Conjugate Acids

The protected acids of these compounds (Formulas I-1 to I-24) include, but are not limited to, protected acids such as esters, hydroxyamino derivatives, amides and sulfonamides. Thus, for example, primary and secondary amines can be reacted with carboxylic acid substituted forms of the compounds of Formulas I-1 to I-24 to form amides which can be useful as prodrugs. Preferred amines are heterocyclicamines, including optionally substituted aminothiazoles, optionally substituted amino-isoxazoles, optionally substituted aminopyridines, optionally substituted aniline derivatives, optionally substituted sulfonamides, optionally substituted aminocarboxylic acids, and the like. The esters, hydroxyamino derivatives and sulfonamides can be prepared from the acids by methods known to one skilled in the art.

(e) The Prodrugs

The present invention includes the prodrugs of the compounds of Formulas I-1 to I-24.

Dosages And Treatment Regimen

Dosage levels of the compounds of Formulae I-1 to I-24 typically are from about 0.001 mg to about 10,000 mg daily, preferably from about 0.005 mg to about 1,000 mg daily, more preferably from about 0.008 mg to about 100 mg daily, and even more preferably from about 0.05 mg to about 50 mg daily. On the basis of mg/kg daily dose, either given in a single or divided doses, dosages typically range from about 0.001/75 mg/kg to about 10,000/75 mg/kg, preferably from about 0.005/75 mg/kg to about 1,000/75 mg/kg, more preferably from about 0.008/75 to about 100/75 mg/kg, and even more preferably from about 0.05/75 mg/kg to about 50/75 mg/kg.

The total daily dose of each drug can be administered to the patient in a single dose, or in multiple subdoses. Typically, subdoses can be administered two to six times per day, preferably two to four times per day, and even more preferably two to three times per day. Doses can be in immediate release form or sustained release form sufficiently effective to obtain the desired control over the hyperlipidemic condition.

The dosage regimen to prevent, treat, give relief from, or ameliorate a hyperlipidemic condition or disorder, or to otherwise protect against or treat high cholesterol blood (or plasma) levels with the combinations and compositions of the present invention is selected in accordance with a variety of factors. These factors include, but are not limited to, the type, age, weight, sex, diet, and medical condition of the subject, the severity of the disease, the route of administration, pharmacological considerations such as the activity, efficacy, pharmacokinetics and toxicology profiles of the particular inhibitors employed, whether a drug delivery system is utilized, and whether the inhibitors are administered with other active ingredients. Thus, the dosage regimen actually employed may vary widely and therefore deviate from the preferred dosage regimen set forth above.

Initial treatment of a patient suffering from a hyperlipidemic condition or disorder can begin with the dosages indicated above. Treatment generally should be continued as necessary over a period of several weeks to several months or years until the hyperlipidemic condition or disorder has been controlled or eliminated. Patients undergoing treatment with the combinations of the compounds disclosed herein can be routinely monitored, for example, by measuring serum LDL and total cholesterol levels by any of the methods well-known in the art to determine the effectiveness of the combination therapy. Continuous and intermittent analysis of such data permits modification of the treatment regimen during therapy so that optimal therapeutically effective amounts of each type of inhibitor are administered at any time for an appropriate duration of time. In this way, the treatment regimen/dosing schedule can be rationally modified over the course of therapy so that the lowest amount of inhibitor that exhibits satisfactory therapeutic effectiveness is administered, and so that administration is continued only so long as is necessary to successfully treat or otherwise ameliorate the hyperlipidemic condition. Of course, maintenance dosing to keep the hyperlipidemic condition under the desired control may be instituted as necessary.

Pharmaceutical Compositions

For the prophylaxis or treatment of the conditions and disorders referred to above, the compounds of this invention (Formulas I-1 to I-24) can be administered as the compound per se. Alternatively, pharmaceutically-acceptable salts are particularly suitable for medical applications because of their greater aqueous solubility relative to that of the parent compound.

The compounds of the present invention also can be administered with an acceptable carrier in the form of a pharmaceutical composition. The carrier must be acceptable in the sense of being compatible with the other ingredients of the composition and must not be intolerably deleterious to the recipient. The carrier can be a solid or a liquid, or both, and preferably is formulated with the compound as a unit-dose composition, for example, a tablet, which can contain from about 0.05% to about 95% by weight of the active compound(s) based on a total weight of the dosage form. Other pharmacologically active substances can also be present, including other compounds useful in the treatment of a hyperlipidemic condition.

The active compounds of the present invention may be administered by any suitable route, preferably in the form of a pharmaceutical composition adapted to such a route, and in a therapeutically effective dose for the treatment intended. The active compounds and compositions, for example, may be administered orally, sublingually, nasally, pulmonarily, mucosally, parenterally, intravascularly, intraperitoneally, subcutaneously, intramuscularly or topically. Unit dose formulations, particularly orally administrable unit dose formulations such as tablets or capsules, generally contain, for example, from about 0.001 to about 500 mg, preferably from about 0.005 mg to about 100 mg, and more preferably from about 0.01 to about 50 mg, of the active ingredient. In the case of pharmaceutically acceptable salts, the weights indicated above for the active ingredient refer to the weight of the pharmaceutically active ion derived from the salt.

For oral administration, the pharmaceutical composition may be in the form of, for example, a tablet, a capsule, a suspension, an emulsion, a paste, a solution, a syrup or other liquid form. The pharmaceutical composition is preferably made in the form of a dosage unit containing a particular amount of the active ingredient. If administered by mouth, the compounds may be admixed with, for example, lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration.

Oral delivery of the compounds of the present invention can include formulations, as are well known in the art, to provide immediate delivery or prolonged or sustained delivery of the drug to the gastrointestinal tract by any number of mechanisms. Immediate delivery formulations include, but are not limited to, oral solutions, oral suspensions, fast-dissolving tablets or capsules, sublingual tablets, disintegrating tablets and the like. Prolonged or sustained delivery formulations include, but are not limited to, pH sensitive release of the active ingredient from the dosage form based on the changing pH of the small intestine, slow erosion of a tablet or capsule, retention in the stomach based on the physical properties of the formulation, bioadhesion of the dosage form to the mucosal lining of the intestinal tract, or enzymatic release of the active drug from the dosage form. The intended effect is to extend the time period over which the active drug molecule is delivered to the site of action (for example, the ileum for ASBT inhibitors) by manipulation of the dosage form. Thus, enteric-coated and enteric-coated controlled release formulations are within the scope of the present invention. Suitable enteric coatings include cellulose acetate phthalate, polyvinylacetate phthalate, hydroxypropylmethyl-cellulose phthalate and anionic polymers of methacrylic acid and methacrylic acid methyl ester. Such prolonged or sustained delivery formulations preferably are in a dispersed form at the time they reach the ileum. Other examples of suitable coatings include products known as Eudragit S provided in a thickness sufficient to release the active ingredient in the desired location of the GI tract. Preferably, in the case of an Eudragit S coating, the coating has a thickness from about 10 to about 50 microns, more preferably from about 20 to 45 microns, even more preferably from about 25 to about 43 microns and most preferably from about 30 to about 40 microns. The coating of Eudragit S may be combined with other coating materials known as Eudragit L. Formulations of ASBT inhibitor(s), such as tablets coated with Eudragit S and/or Eudragit L, can be readily formed by those of ordinary skill.

Pharmaceutical compositions suitable for oral administration can be presented in discrete units, such as capsules, cachets, lozenges, or tablets, each containing a predetermined amount of at least one compound of the present invention; as a powder or granules; as a solution or a suspension in an aqueous or non-aqueous liquid; or as an oil-in-water or water-in-oil emulsion. As indicated, such compositions can be prepared by any suitable method of pharmacy which includes the step of bringing into association the inhibitor(s) and the carrier (which can constitute one or more accessory ingredients). In general, the compositions are prepared by uniformly and intimately admixing the inhibitor(s) with a liquid or finely divided solid carrier, or both, and then, if necessary, shaping the product. For example, a tablet can be prepared by compressing or molding a powder or granules of the inhibitors, optionally with one or more accessory ingredients. Compressed tablets can be prepared by compressing, in a suitable machine, the compound in a free-flowing form, such as a powder or granules optionally mixed with a binder, lubricant, inert diluent and/or surface active/dispersing agent(s). Molded tablets can be made, for example, by molding the powdered compound in a suitable machine.

Liquid dosage forms for oral administration can include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, and sweetening, flavoring, and perfuming agents.

Pharmaceutical compositions suitable for buccal (sub-lingual) administration include lozenges comprising a compound of the present invention in a flavored base, usually sucrose, and acacia or tragacanth, and pastilles comprising the inhibitors in an inert base such as gelatin and glycerin or sucrose and acacia.

Formulations for parenteral administration, for example, may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, cone oil, cottonseed oil, peanut oil, sesame oil, benzyl alcohol, sodium chloride, and/or various buffers. Other adjuvants and modes of administration are well and widely known in the pharmaceutical art.

Pharmaceutically acceptable carriers encompass all the foregoing and the like. The pharmaceutical compositions of the invention can be prepared by any of the well-known techniques of pharmacy, such as admixing the components. The above considerations in regard to effective formulations and administration procedures are well known in the art and are described in standard textbooks. Formulation of drugs is discussed in, for example, Hoover, John E., *Remington's Pharmaceutical Sciences*, Mack Publishing Co., Easton, Pa. (1975); Liberman, et al., Eds., *Pharmaceutical Dosage Forms*, Marcel Decker, New York, N.Y. (1980); and Kibbe, et al., Eds., *Handbook of Pharmaceutical Excipients* (3$^{rd}$ Ed.), American Pharmaceutical Association, Washington (1999); *U.S. Pharamacopeia* (Twenty-First Revision—USP XXI) National Formulary (Sixteenth Edition—XVI), United States Pharmacopeial Convention, Inc., Rockville, Md. (1985) and its later editions; and *Remington's Pharmaceutical Sciences*. 16$^{th}$ Edition, Arthur Osol, Editor and Chairman of the Editorial Board, Mack Publishing Co., Easton, Pa. (1980) and its later editions.

Methods Of Use

The present invention also includes methods for the treatment of one or more hyperlipidemic condition(s) in a subject. One such method comprises the step of administering to a subject in need thereof, a therapeutically effective amount of one or more compounds of Formulas I-1 to I-24.

The present invention further includes methods for the treatment of gallstones in a subject. An exemplary method for the treatment of gallstones comprises the step of administering to a subject in need thereof, a therapeutically effective amount of one or more compound(s) of Formulas I-1 to I-24.

The methods and compounds of the present invention may be used alone or in conjunction with additional therapies and/or compounds known to those skilled in the art in the prevention or treatment of hyperlipidemia Alternatively, the methods and compounds described herein may be used, partially or completely, in conjunctive therapy. By way of example, the compounds may be administered alone or in conjunction with other anti-hyperlipidemic agents, such as together with HMG-CO-A reductase inhibitors, bile acid sequestering agents, fibric acid derivatives, nicotinic acid, and/or probucol. The above-noted combination therapeutic agents may be provided in a kit.

Terms

As used herein, various terms are defined below.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

The term "subject" as used herein includes mammals (eg., humans and animals).

The term "treatment" includes any process, action, application, therapy, or the like, for improving the subject's medical condition, directly or indirectly, including, but not limited to, hyperlipidemia or conditions associated with hyperlipidemia.

The terms "prophylaxis" and "prevention" include either preventing the onset of a clinically evident hyperlipidemic condition or disorder altogether or preventing the onset of a preclinically evident stage of a hyperlipidemic condition or disorder in an individual. These terms encompass the prophylactic treatment of a subject at risk of developing a hyperlipidemic condition or disorder such as, but not limited to, atherosclerosis and hypercholesterolemia.

The term "combination therapy" or "co-therapy" means the administration of two or more therapeutic agents to treat a hyperlipidemic condition and/or disorder, for example atherosclerosis and hypercholesterolemia. Such administration encompasses co-administration of two or more therapeutic agents in a substantially simultaneous manner, such as in a single capsule having a fixed ratio of active ingredients or in multiple, separate capsules for each inhibitor agent. In addition, such administration encompasses use of each type of therapeutic agent in a sequential manner. In either case, the treatment regimen will provide beneficial effects of the drug combination in treating the hyperlipidemic condition.

The phrase "therapeutically-effective" means the amount of each agent administered that will achieve the goal of improvement in hyperlipidemic condition or disorder severity, while avoiding or minimizing adverse side effects associated with the given therapeutic treatment.

The term "pharmaceutically acceptable" means that the subject item is appropriate for use in a pharmaceutical product.

The term "prodrug" includes a compound that is a drug precursor that, following administration to a subject and subsequent absorption, is converted to an active species in vivo. Conversion to the active, species in vivo is typically via some process, such as metabolic conversion. An example of a prodrug is an acylated form of the active compound.

The term "ASBT inhibitor" includes a compound capable of inhibiting absorption of bile acids from the intestine into the circulatory system of a mammal, indicating that of a human. This includes increasing the fecal excretion of bile acids, as well as reducing the blood plasma or serum concentrations of cholesterol and cholesterol ester, and more specifically, reducing LDL and VLDL cholesterol.

Where the term "alkyl" is used, either alone or within other terms such as "haloalkyl", and "hydroxyalkyl", it includes linear or branched radicals having one to about twenty carbon atoms, preferably, one to about twelve carbon atoms, more preferably, "lower alkyl" radicals having one to about six carbon atoms and, even more preferably, lower alkyl radicals having one to three carbon atoms. Examples of such radicals include, but are not limited to, methyl, ethyl, n-propyl, isopropyl, n-butyl, isobutyl, sec-butyl, tert-butyl, pentyl, iso-amyl, hexyl and the like.

Where the term "alkenyl" is used, either alone or within other terms such as "arylalkenyl", it includes linear or branched radicals having at least one carbon-carbon double bond in a radical having from two to about twenty carbon atoms, preferably, from two to about twelve carbon atoms, and more preferably "lower alkenyl" radicals having from two to about six carbon atoms. Examples of alkenyl radicals include, but are not limited to, ethenyl, propenyl, allyl, propenyl, butenyl and 4-methylbutenyl.

The terms "alkenyl" and "lower alkenyl", include radicals having "cis" and "trans" orientations, or alternatively, "E" and "Z" orientations.

The term "alkynyl" includes, but is not limited to, linear or branched radicals having from two to about twenty carbon atoms or, preferably, from two to about twelve carbon atoms, more preferably "lower alkynyl" radicals having from two to about ten carbon atoms, most preferably lower alkynyl radicals having from two to about six carbon atoms. Examples of such radicals include propargyl, butynyl, and the like.

The term "cycloalkyl" includes, but is not limited to, saturated carbocyclic radicals having from three to about twelve carbon atoms, more preferably "lower cycloalkyl" radicals having from three to about ten carbon atoms. Examples of such radicals include cyclopropyl, cyclobutyl, cyclopentyl and cyclohexyl. The term "cycloalkyl" additionally encompasses spiro systems wherein the cycloalkyl ring has a carbon ring atom in common with the seven-membered heterocyclic ring of the benzothiepene.

The term "cycloalkenyl" includes, but is not limited to, unsaturated carbocyclic radicals having at least one double bond and having from three to twelve carbon atoms and more preferably "lower cycloalkenyl" radicals having from four to about ten carbon atoms. Cycloalkenyl radicals that are partially unsaturated carbocyclic radicals that contain two double bonds (that may or may not be conjugated) can be called "cycloalkyldienyl". Examples of cycloalkenyl radicals includes, but is not limited to, cyclobutenyl, cyclopentenyl and cyclohexenyl.

The terms "halo" and "halogen" include, but are not limited to, halogen atoms such as fluorine, chlorine, bromine or iodine. The term "haloalkyl" includes radicals wherein any one or more of the alkyl carbon atoms is substituted with a halogen atom. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same or different halogen atoms. "Lower haloalkyl" includes radicals having one to six carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl" includes alkyl radicals having all hydrogen atoms replaced with fluoro atoms. Examples include trifluoromethyl and pentafluoroethyl.

The term "hydroxyalkyl" includes, but is not limited to, linear or branched alkyl radicals preferably having from one to about ten carbon atoms, more preferably "lower hydroxyalkyl" radicals having from one to six carbon atoms and even more preferably lower hydroxyalkyl radicals having from one to three carbon atoms wherein one or more of the carbon atoms are substituted with one or more hydroxyl radicals. Examples of such radicals include hydroxymethyl, hydroxyethyl, hydroxypropyl, hydroxybutyl and hydroxyhexyl.

The term "aryl" includes, but is not limited to, a carbocyclic aromatic system containing one or more rings wherein such rings may be attached together in a pendent manner or may be fused. The term "aryl" includes aromatic radicals such as cyclopentodienyl phenyl, naphthyl, tetrahydronaphthyl, indanyl, biphenyl, and anthracenyl. Further, "aryl" group may optionally have from one to three substituents such as lower alkyl, hydroxy, halo, haloalkyl, nitro, cyano, alkoxy and lower alkylamino.

The term "heterocyclyl" includes, but is not limited to, saturated, partially saturated and unsaturated heteroatom-containing ring-shaped radicals, where the heteroatoms may be nitrogen, sulfur, oxygen or combinations thereof. Preferred heterocyclyls include, but are not limited to, 3–10 membered ring heterocyclyl, particularly 5–8 membered ring heterocyclyl. Examples of saturated heterocyclic radicals include saturated 3 to 6-membered heteromonocyclic groups containing 1 to 4 nitrogen atoms (e.g., pyrrolidinyl, imidazolidinyl, piperidino, piperazinyl); saturated 3 to 6-membered heteromonocyclic groups containing from 1 to 2 oxygen atoms and from 1 to 3 nitrogen atoms (e.g., morpholinyl); saturated 3 to 6-membered heteromonocyclic groups containing 1 to 2 sulfur atoms and 1 to 3 nitrogen atoms (e.g., thiazolidinyl). Examples of partially saturated heterocyclyl radicals include dihydrothiophene, dihydropyran, dihydrofuran and dihydrothiazole. Examples of unsaturated heterocyclic radicals, also termed "heteroaryl" radicals, include unsaturated 5 to 6 membered heteromonocyclyl groups containing 1 to 4 nitrogen atoms, for example, pyrrolinyl, imidazolyl, pyrazolyl, 2-pyridyl, 3-pyridyl, 4-pyridyl, pyrimidyl, pyrazinyl, pyridazinyl, triazolyl (e.g., 4H-1,2,4-triazolyl, 1H-1,2,3-triazolyl, 2H-1,2,3-triazolyl); unsaturated condensed heterocyclic groups containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo [1,5-b]pyridazinyl); unsaturated 3 to 6-membered heteromonocyclic groups containing an oxygen atom, for example, pyranyl, 2-furyl, 3-furyl, etc.; unsaturated 5 to 6-membered heteromonocyclic groups containing a sulfur atom, for example, 2-thienyl, 3-thienyl, etc.; unsaturated 5- to 6-membered heteromonocyclic groups containing 1 to 2 oxygen atoms and 1 to 3 nitrogen atoms, for example, isoxazolyl, oxadiazolyl (e.g., 1,2,4-oxadiazolyl, 1,3,4-oxadiazolyl, 1,2,5-oxadiazolyl); unsaturated condensed heterocyclic groups containing 1 to 2 oxygen atoms and 1 to 3 nitrogen atoms (e.g., benzoxazolyl, benzoxadiazolyl); unsaturated 5 to 6-membered heteromonocyclic groups containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl); unsaturated condensed heterocyclic groups containing 1 to 2 sulfur atoms and 1 to 3 nitrogen atoms (e.g., benzothiazolyl, benzothiadiazolyl) and the like. The term also includes radicals where heterocyclic radicals are fused with aryl radicals. Examples of such fused bicyclic radicals include benzofuran, benzothiophene, and the like. The "heterocyclyl" group may optionally have 1 to 3 substituents such as lower alkyl, hydroxy, oxo, amino and lower alkylamino. The term "heterocyclyl" includes all positioned isomers.

"Heteroaryl" radicals can include, but are not limited to, fused or unfused radicals, particularly 3–10 membered fused or unfused radicals. Preferred examples of heteroaryl radicals include benzofuryl, 2,3-dihydrobenzofuryl, benzothienyl, indolyl, dihydroindolyl, chromanyl, benzopyran, thiochromanyl, benzothiopyran, benzodioxolyl, benzodioxanyl, pyridyl, thienyl, thiazolyl, furyl, and pyrazinyl. More preferred heteroaryl radicals are 5- or 6-membered heteroaryl, containing one or two heteroatoms selected from sulfur, nitrogen and oxygen such as thienyl, furanyl, thiazolyl, imidazolyl, pyrazolyl, isoxazolyl, isothiazolyl, pyridyl, piperidinyl or pyrazinyl. The term "heteroaryl" includes, but is not limited to, a fully unsaturated heterocyclyl. The term "heteroaryl" includes all positional isomers.

In either the "heterocyclyl" or the "heteroaryl" radical, the point of attachment to the molecule of interest can be at the heteroatom or elsewhere within the ring.

The term "triazolyl" includes, but is not limited to, all positional isomers. In all other heterocyclyl and heteroaryl which contain more than one ring heteroatom and for which isomers are possible, such isomers are included in the definition of said heterocyclyl and heteroaryl.

The term "quaternary heterocyclyl" includes, but is not limited to, a heterocyclyl in which one or more of the heteroatoms, for example, nitrogen, sulfur, phosphorus or oxygen, has such a number of bonds that it is positively charged (and therefore the term is intended to encompass both ternary and quaternary positively charged structures). The point of attachment of the quaternary heterocyclyl to the molecule of interest can be at a heteroatom or elsewhere.

The term "quaternary heteroaryl" includes, but is not limited to, a heteroaryl in which one or more of the heteroatoms, for example, nitrogen, sulfur, phosphorus or oxygen, has such a number of bonds that it is positively charged (and therefore the term is intended to encompass both ternary and quaternary positively charged structures). The point of attachment of the quaternary heteroaryl to the molecule of interest can be at a heteroatom or elsewhere.

The term "oxo" includes, but is not limited to, an oxygen with two bonds.

The term "polyalkyl" includes, but is not limited to, a branched or straight hydrocarbon chain having a molecular weight up to about 20,000 gms, more preferably up to about 10,000 gms, and most preferably up to about 5,000 gms.

The term "polyether" includes, but is not limited to, a polyalkyl wherein one or more carbons are replaced by oxygen, wherein the polyether has a molecular weight up to about 20,000 gms, more preferably up to about 10,000 gms, and most preferably up to about 5,000 gms.

The term "polyalkoxy" includes, but is not limited to, a polymer of alkylene oxides, wherein the polyalkoxy has a molecular weight up to about 20,000 gms, more preferably up to about 10,000 gms, and most preferably up to about 5,000 gms.

The term "carbohydrate residue" includes, but is not limited to, residues derived from carbohydrates, but is not limited to, mono-, di-, tri-, tetra- and polysaccharides wherein the polysaccharides can have a molecular weight of up to about 20,000 gms, for example, hydroxypropyl-methylcellulose or chitosan residue; compounds derived from aldoses and ketoses with from 3 to 7 carbon atoms and which belong to the D- or L-series; aminosugars; sugar alcohols; and saccharic acids. Nonlimiting specific examples of such carbohydrates include glucose, mannose, fructose, galactose, ribose, erythrose, glycerinaldehyde, sedoheptulose, glucosamine, galactosamine, glucoronic acid, galacturonic acid, gluconic acid, galactonic acid, mannoic acid, glucamine, 3-amino-1,2-propanediol, glucaric acid and galactaric acid.

The term "peptide residue" includes, but is not limited to, polyamino acid residue containing up to about 100 amino acid units.

The term "polypeptide residue" includes, but is not limited to, a polyamino acid residue containing from about 100 amino acid units to about 1000 amino acid units, more preferably from about 100 amino acid units to about 750 amino acid units, and even more preferably from about 100 amino acid units to about 500 amino acid units.

The term "alkylammoniumalkyl" includes, but is not limited to, an $—NH_2$ group or a mono-, di- or tri-substituted amino group, any of which is bonded to an alkyl wherein said alkyl is bonded to the molecule of interest.

The term "sulfo" includes, but is not limited to, a $—SO_2—$ group, a $—SO_3H$ group, and its salts.

The term "sulfoalkyl" includes, but is not limited to, an alkyl group to which a sulfonate group is bonded, wherein said alkyl is bonded to the molecule of interest.

The term "aralkyl" includes, but is not limited to, aryl-substituted alkyl radicals, preferably "lower aralkyl" radicals having aryl radicals attached to alkyl radicals having from one to six carbon atoms, and even more preferably lower aralkyl radicals having phenyl attached to alkyl portions having from one to three carbon atoms. Examples of such radicals include benzyl, diphenylmethyl and phenylethyl. The aryl in said aralkyl may be optionally substituted with halo, alkyl, alkoxy, halkoalkyl and haloalkoxy. The term "arylalkenyl" includes aryl-substituted alkenyl radicals. Preferable arylalkenyl radicals are "lower arylalkenyl" radicals having aryl radicals attached to alkenyl radicals having from one to ten carbon atoms.

The term "heterocyclylalkyl" includes, but is not limited to, an alkyl radical that is substituted with one or more heterocyclyl groups. Preferable heterocyclylalkyl radicals are "lower heterocyclylalkyl" radicals having from one or more heterocyclyl groups attached to an alkyl radical having from one to ten carbon atoms.

The term "heteroarylalkyl" includes, but is not limited to, an alkyl radical that is substituted with one or more heteroaryl groups. Preferable heteroarylalkyl radicals are "lower heteroarylalkyl" radicals having from one or more heteroaryl groups attached to an alkyl radical having from one to ten carbon atoms.

The term "quaternary heterocyclylalkyl" includes, but is not limited to, an alkyl radical that is substituted with one or more quaternary heterocyclyl groups. Preferable quaternary heterocyclylalkyl radicals are "lower quaternary heterocyclylalkyl" radicals having from one or more quaternary heterocyclyl groups attached to an alkyl radical having from one to ten carbon atoms.

The term "quaternary heteroarylalkyl" includes, but is not limited to, an alkyl radical that is substituted with one or more quaternary heteroaryl groups. Preferable quaternary heteroarylalkyl radicals are "lower quaternary heteroarylalkyl" radicals having from one or more quaternary heteroaryl groups attached to an alkyl radical having from one to ten carbon atoms.

The term "alkylheteroarylalkyl" includes, but is not limited to, a heteroarylalkyl radical that is substituted with one or more alkyl groups. Preferable alkylheteroarylalkyl radicals are "lower alkylheteroarylalkyl" radicals with alkyl portions having from one to ten carbon atoms.

The term "alkoxy" includes, but is not limited to, an alkyl radical which is attached to the molecule of interest by oxygen, such as a methoxy radical. More preferred alkoxy radicals are "lower alkoxy" radicals having from one to six carbon atoms. Examples of such radicals include methoxy, ethoxy, propoxy, iso-propoxy, butoxy and tert-butoxy.

The term "carboxy" includes, but is not limited to, the carboxy group, —CO2H, and its salts.

The term "carboxyalkyl" includes, but is not limited to, an alkyl radical that is substituted with one or more carboxy groups. Preferable carboxyalkyl radicals are "lower carboxyalkyl" radicals having one or more carboxy groups attached to an alkyl radical having from one to six carbon atoms.

The term "carboxyheterocyclyl" includes, but is not limited to, a heterocyclyl radical that is substituted with one or more carboxy groups.

The term "carboxyheteroaryl" includes, but is not limited to, a heteroaryl radical that is substituted with one or more carboxy groups.

The term "carboalkoxyalkyl" includes, but is not limited to, an alkyl radical that is substituted with one or more alkoxycarbonyl groups. Preferable carboalkoxyalkyl radicals are "lower carboalkoxyalkyl" radicals having one or more alkoxycarbonyl groups attached to an alkyl radical having from one to six carbon atoms.

The term "carboxyalkylamino" includes, but is not limited to, an amino radical that is mono- or di-substituted. When used in combination, for example "alkylaryl" or "arylalkyl," the individual terms "alkyl" and "aryl" listed above have the meaning indicated above.

The term "acyl" includes, but is not limited to, an organic acid group in which the hydroxy of the carboxy group has been removed. Examples of acyl groups include, but are not limited to, acetyl and benzoyl.

The term "hydrocarbyl" refers to radicals consisting exclusively of the elements carbon and hydrogen. These radicals include, for example, alkyl, cycloalkyl, alkenyl, cycloalkenyl, alkynyl, and aryl moieties. These radicals also include alkyl, cycloalkyl, alkenyl, cycloalkenyl, alkynyl, and aryl moieties substituted with other aliphatic or cyclic hydrocarbon groups, such as alkaryl, alkenaryl and alkynaryl. Preferably, these moieties comprise 1 to 20 carbon atoms, 1–10 carbons or 1–6 carbons.

The term "a substituted hydrocarbyl" refers to a hydrocarbyl radical that is substituted with a group comprising at least one atom other than carbon, such as but not limited to, halogen, oxygen, nitrogen, sulfur and phosphorus. Examples of such substituted hydrocarbyl include hydrocarbyl radicals substituted with groups such as, but not limited to, lower alkoxy such as methoxy, ethoxy, and butoxy, halogen such as chloro and fluoro; ethers; acetals; ketals; esters; heterocyclyl such as furyl and thienyl; alkanoxy; hydroxy, protected hydroxy, acyl; acyloxy; nitro; cyano; amino; and amido. Substituted hydrocarbyl also includes hydrocarbyl radicals in which a carbon chain atom is replaced with a heteroatom such as nitrogen, oxygen, sulfur, or a halogen.

The term "sugar protecting group" means a protecting group on one or more hydroxy groups of a given sugar. Examples of such "sugar protecting groups" include, but are not limited to, acetyl, trialkylsilyl, alkyl (e.g, methyl), alkoxy (e.g., methoxy, ethoxy), tetrahydropyranyl (THP), etc.

Abbreviations used herein have the following meanings:

| TERM | DEFINITION |
| --- | --- |
| THF | tetrahydrofuran |
| PTC | phase transfer catalyst |
| Aliquart 336 | methyltricaprylylammonium chloride |
| MCPBA | m-chloroperbenzoic acid |
| Celite | a brand of diatomaceous earth filtering aid |
| DMF | Dimethylformamide |
| DME | -ethylene glycol dimethyl ether |
| BOC | t-butoxycarbonyl group |
| Me | Methyl |
| Et | Ethyl |
| Bu | Butyl |
| EtOAc | Ethyl acetate |
| $Et_2O$ | diethyl ether |
| $CH_2Cl_2$ | methylene chloride |
| $MgSO_4$ | magnesium sulfate |
| NaOH | sodium hydroxide |
| $CH_3OH$ | Methanol |
| HCl | hydrochloric acid |
| NaCl | sodium chloride |
| NaH | sodium hydride |
| LAH | lithium aluminum hydride |
| LiOH | lithium hydroxide |
| $Na_2SO_3$ | sodium sulfite |
| $NaHCO_3$ | sodium bicarbonate |
| DMSO | Dimethylsulfoxide |
| $KOSiMe_3$ | potassium trimethylsilanolate |
| PEG | polyethylene glycol |
| MS | Mass spectrometry |
| HRMS | high resolution mass spectrometry |
| ES | Electrospray |
| NMR | nuclear magnetic resonance spectroscopy |
| GC | gas chromatography |
| MPLC | medium pressure liquid chromatography |
| HPLC | high pressure liquid chromatography |
| RPHPLC | reverse phase high pressure liquid chromatography |
| RT | Room temperature |
| h or hr | hour(s) |
| Min | minute(s) |

Biological Evaluation

The inhibitor concentration of the compounds of the present invention is to be determined by the following assays. These assays are to be performed in vitro and in animal models.

In Vitro Assay of Compounds that Inhibit ASBT-Mediated Uptake of [14C]-Taurocholate (TC) in H14 Cells Seed baby hamster kidney cells (BHK) transfected with the cDNA of human ASBT (H14 cells) in 96 well Top-Count tissue culture plates at 60,000 cells/well (run assays within 24 hours of seeding), 30,000 cells/well (run assays within 48 hours of seeding), and 10,000 cells/well (run assays within 72 hours of seeding).

On the day of assay, gently wash the cell monolayer once with 100 mL assay buffer (Dulbecco's Modified Eagle's medium with 4.5 g/L glucose plus 0.2% (w/v) fatty acid free bovine serum albumin ((FAF) BSA). To each well, add 50 mL of a two-fold concentrate of test compound in assay buffer along with 50 mL of 6 mM [$^{14}$C]-taurocholate in assay buffer (final concentration of 3 mM [$^{14}$C]-taurocholate). Incubate the cell culture plates for 2 hours at 37° C. prior to gently washing each well twice with 100 mL 4° C. Dulbecco's phosphate-buffered saline (PBS) containing 0.2% (w/v) (FAF)BSA. Then gently wash wells once with 100 mL 4° C. PBS without (FAF)BSA. To each 200 mL of liquid, add scintillation counting fluid. Heat seal the plates and shake for 30 minutes at room temperature prior to measuring the amount of radioactivity in each well on a Packard Top-Count instrument.

In Vitro Assay of Compounds that Inhibit Uptake of [$^{14}$C]-Alanine

The alanine uptake assay is performed in an identical fashion to the taurocholate assay, except that labeled alanine is substituted for the labeled taurocholate.

In Vivo Assay of Compounds that Inhibit Rat Ileal Uptake of [$^{14}$C]-Taurocholate into Bile (See Une et al. "Metabolism of 3α,7β-Dihydroxy-7β-methyl-5β-cholanoic Acid and 3α,7β-Dihydroxy-7α-methyl-5β-cholanoic Acid in Hamsters", *Biochimica et Biophysica Acta*, Vol. 833, pp. 196–202 (1985)).

Anesthetize male wistar rats (200–300 g) with inactin @100 mg/kg. Cannulate bile ducts with a 10" length of PE10 tubing. Expose the small intestine and lay out on a gauze pad. Insert a canulae (⅛" luer lock, tapered female adapter) at 12 cm from the junction of the small intestine and the cecum. Cut a slit at 4 cm from this same junction (utilizing a 8 cm length of ileum). Use 20 mL of warm Dulbecco's phosphate buffered saline, pH 6.5 ("PBS") to flush out the intestine segment. Cannulate the distal opening with a 20 cm length of silicone tubing (0.02" I.D.×0.037" O.D.). Hook up the proximal cannulae to a peristaltic pump and wash the intestine for 20 minutes with warm PBS at 0.25 ml/minute. Continuously monitor the temperature of the gut segment.

At the start of the experiment, load 2.0 mL of control sample ([$^{14}$C]-taurocholate @0.05 mi/mL with 5 mM cold taurocholate) into the gut segment with a 3 mL syringe and begin bile sample collection. Infuse control sample at a rate of 0.25 ml/minute for 21 minutes. Collect bile sample fractions every 3 minutes for the first 27 minutes of the procedure. After the 21 minutes of sample infusion, wash out the ileal loop with 20 mL of warm PBS (using a 30 mL syringe), and then wash out the loop for 21 minutes with warm PBS at 0.25 ml/minutes. Initiate a second perfusion as described above but with test compound being administered as well (21 minutes administration followed by 21 minutes of wash out) and sample bile every 3 minutes for the first 27 minutes. If necessary, conduct a third perfusion as above that containing the control sample.

Measurement of Hepatic Cholesterol Concentration (HEPATIC CHOL)

Weigh liver tissue and homogenize in chloroform:methanol (2:1). After homogenization and centrifugation, separate the supernatant and dry under nitrogen. Dissolve the residue in isopropanol and measure the cholesterol content enzymatically, using a combination of cholesterol oxidase and peroxidase, as described by Allain, C. A., et al., *Clin. Chem.* 20, 470 (1974).

Measurement of Hepatic HMG CoA-Reductase Activity (HMG COA)

Prepare Hepatic microsomes by homogenizing liver samples in a phosphate/sucrose buffer, followed by centrifugal separation. Resuspend the final pelleted material in buffer and assay an aliquot for HMG CoA reductase activity by incubating for 60 minutes at 37° C. in the presence of $^{14}$C-HMG-CoA (Dupont-NEN). Stop the reaction by adding 6N HCl followed by centrifugation. Separate an aliquot of the supernatant by thin-layer chromatography, and scrape off the plate the spot corresponding to the enzyme product. Extract and determine radioactivity by scintillation counting. (See Akerlund, J. and Bjorkhem, I., *J. Lipid Res.* 31, 2159(1990)).

Determination of Serum Cholesterol (SER.CHOL, HDL-CHOL, TGI and VLDL+LDL)

Measure total serum cholesterol (SER.CHOL) enzymatically using a commercial kit from Wako Fine Chemicals (Richmond, Va.); Cholesterol C11, Catalog No. 276-64909. Assay HDL cholesterol (HDL-CHOL) using this same kit after precipitation of VLDL and LDL with Sigma Chemical Co. HDL Cholesterol reagent, Catalog No. 352-3 (dextran sulfate method). Enzymatically assay total serum triglycerides (blanked) (TGI) with Sigma Chemical Co. GPO-Trinder, Catalog No. 337-B. Calculate VLDL and LDL (VLDL+LDL) cholesterol concentrations as the difference between total and HDL cholesterol.

Measurement of Hepatic Cholesterol 7α-Hydroxylase Activity (7α-OHase)

Prepare hepatic microsomes by homogenizing liver samples in a phosphate/sucrose buffer, followed by centrifugal separation. Resuspend the final pelleted material in buffer and assay an aliquot for cholesterol 7α-hydroxylase activity by incubating for 5 minutes at 37° C. in the presence of NADPH. Following extraction into petroleum ether, evaporate the organic solvent and dissolve the residue in acetonitrile/methanol. Separate the enzymatic product by injecting an aliquot of the extract onto a $C_{18}$ reversed phase HPLC column and quantitate the eluted material using UV detection at 240 nm. (See Horton, J. D., et al., *J. Clin. Invest.* 93, 2084(1994).)

Rat Gavage Assay

Administer ASBT inhibitors to male Wister rats (275–300 g) using an oral gavage procedure. Administer drug or vehicle (0.2% Tween 80 in water) once a day (9:00–10:00 am.) for 4 days at varying dosages in a final volume of 2 mL per kilogram of body weight. Collect total fecal samples during the final 48 hours of the treatment period and analyze for bile acid content using an enzymatic assay as described below. Determine compound efficacy by comparison of the increase in fecal bile acid (FBA) concentration in treated rats to the mean FBA concentration of rats in the vehicle group.

Measurement of Fecal Bile Acid Concentration (FBA)

Collect total fecal output from individually housed hamsters is collected for 24 or 48 hours, dried under a stream of nitrogen, pulverized and weighed. Approximately 0.1 gram is weighed out and extracted into an organic solvent (butanol/water). Following separation and drying, the residue is dissolved in methanol and the amount of bile acid present is measured enzymatically using the 3α-hydroxysteroid steroid dehydrogenase reaction with bile acids to reduce NAD. (See Mashige, F., et al., *Clin. Chem.* 27, 1352 (1981)).

[$^3$H]Taurocholate Uptake in Rabbit Brush Border Membrane Vesicles (BBMV)

Prepare rabbit Ileal brush border membranes from frozen ileal mucosa by the calcium precipitation method describe by Malathi et al. (See *Biochimica Biophysica Acta*, 554, 259 (1979)). The method for measuring taurocholate is essentially as described by Kramer et al. (Reference: (1992) *Biochimica Biophysica Acta*, 1111, 93) except the assay volume is 200 µL instead of 100 µL. Briefly, incubate at room temperature a 190 µL solution containing 2µM [$^3$H]-taurocholate (0.75 µCi), 20 mM tris, 100 mM sodium chloride, 100 mM mannitol pH 7.4 for 5 seconds with 10 µL of brush border membrane vesicles (60–120 µg protein). Initiate the incubation by the addition of BBMV while vortexing and stop the reaction by the addition of 5 mL of ice cold buffer (20 mM Hepes-tris, 150 mM KCl) followed immediately by filtration through a nylon filter (0.2 µm pore) and an additional 5 mL wash with stop buffer.

Acyl-CoA: Cholesterol Acyl Transferase (ACAT)

Prepare hamster liver and rat intestinal microsomes from tissue as described previously (See *J. Biol. Chem.* 255, 9098 (1980)) and use as a source of ACAT enzyme. The assay consists of a 2.0 mL incubation containing 24 µM Oleoyl-CoA (0.05 µCi) in a 50 mM sodium phosphate, 2 mM DTT pH 7.4 buffer containing 0.25 % BSA and 200 µg of microsomal protein. Initiate the assay by the addition of oleoyl-CoA. Allow the reaction to proceed for 5 minutes at 37° C. and terminate it by the addition of 8.0 mL of chloroform/methanol (2:1). To the extraction, add 125 µg of cholesterol oleate in chloroform methanol to act as a carrier and the organic and separate the aqueous phases of the extraction by centrifugation after thorough vortexing. Take the chloroform phase to dryness and then spot on a silica gel 60 thin layer chromatography plate and develop in hexane/ethyl ether (9:1). Determine the amount of cholesterol ester formed by measuring the amount of radioactivity incorporated into the cholesterol oleate spot on the thin layer chromatography plate with a Packard instaimager.

As various changes could be made in the above methods and apparatus without departing from the scope of the invention, it is intended that all matter contained in the above description be interpreted as illustrative and not in a limiting sense. All documents, books, patents, references and publications mentioned in this application are expressly incorporated by reference in their entirety as if fully set forth at length.

Dog Model for the Evaluation of Lipid-Lowering Drugs

Obtain male beagle dogs weighing 6–12 kg from a vendor, such as Marshall farms. Feed each dog once a day for two hours and give water ad libitum. Randomly assign dogs to dosing groups consisting of 6 to 12 dogs each, corresponding to: vehicle, i.g.; 1 mg/kg, i.g.; 2 mg/kg, i.g.; 4 mg/kg, i.g.; 2 mg/kg, p.o. (powder in capsule). Perform intra-gastric dosing of a therapeutic compound dissolved in aqueous solution (for example, 0.2% Tween 80 solution (polyoxyethylene mono-oleate, Sigma Chemical Co., St. Louis, Mo.)) using a gavage tube. Prior to initiating dosing, draw blood samples from the cephalic vein before the morning feeding in order to evaluate serum cholesterol (total and HDL) and triglycerides. For several consecutive days, dose animals in the morning prior to feeding. Thereafter, allow animals to eat for two hours before remaining food is removed. Collect feces over a 2-day period at the end of the study and analyze for bile acid or lipid content. Collect blood samples at the end of the treatment period for comparison with pre-study serum lipid levels. Determine statistical significance using the standard Student's T-test, with $p<0.05$.

Dog Serum Lipid Measurement

Collect blood from the cephalic veins of fasted dogs using serum separator tubes (Vacutainer SST, Becton Dickinson and Co., Franklin Lakes, N.J.). Centrifuge the blood at 2000 rpm for 20 minutes and decant the serum.

Measure total cholesterol in a 96-well format using a Wako enzymatic diagnostic kit (Cholesterol CII) (Wako Chemicals, Richmond, Va.), utilizing the cholesterol oxidase reaction to produce hydrogen peroxide, which is measured calorimetrically. Prepare a standard curve from 0.5 to 10 mg cholesterol in the first two columns of the plate. Add the serum samples (20–40 mL, depending on the expected lipid concentration) or known serum control samples to individual wells in duplicate. Add water to bring the volume to 100 mL in each well. Add a 100-ml aliquot of color reagent to each well, and read the plates at 500 nm after a 15-minute incubation at 37° C.

HDL cholesterol was assayed using Sigma kit No. 352-3 (Sigma Chemical Co., St. Louis, Mo.), which utilizes dextran sulfate and $Mg^{2+}$ to selectively precipitate LDL and VLDL. Add a volume of 150 mL of each serum sample to individual microfuge tubes, followed by 15 mL of HDL cholesterol reagent (Sigma 352-3). Mix samples and centrifuge at 5000 rpm for 5 minutes. Then mix a 50 mL aliquot of the supernatant with 200 mL of saline and assay using the same procedure as for total cholesterol measurement.

Measure triglycerides using Sigma kit No. 337 in a 96-well plate format. This procedure will measure the release glycerol from triglycerides with lipoprotein lipase. Use standard solutions of glycerol (Sigma 339-11) ranging from 1 to 24 mg to generate the standard curve. Add serum samples (20–40 mL, depending on the expected lipid concentration) to wells in duplicate. Add water to bring the volume to 100 mL in each well and then add 100 mL of color reagent to each well. After mixing and a 15-minutes of incubation, read the plates at 540 nm and calculate the triglyceride values from the standard curve. Run a replicate plate using a blank enzyme reagent to correct for any endogenous glycerol in the serum samples.

Dog Fecal Bile Acid Measurement

Collect fecal samples to determine the fecal bile acid (FBA) concentration for each animal. Obtain fecal collections during the final 48 hours of the study, for two consecutive 24-hour periods between 9:00 am. and 10:00 a.m. each day, prior to dosing and feeding. Weigh the separate two-day collections from each animal, combine and homogenize with distilled water in a processor (Cuisinart) to generate a homogeneous slurry. Extract a sample of 1.4 g of the homogenate in a final concentration of 50% tertiary butanol/distilled water (2:0.6) for 45 minutes in a 37° C. water bath and centrifuge for 13 minutes at 2000×G.

Determine the concentration of bile acids (mmoles/day) using a 96-well enzymatic assay system. Add a 20-mL aliquot of the fecal extract to two sets each of triplicate wells in a 96-well assay plate. Analyze a standardized sodium taurocholate solution and a standardized fecal extract solution (previously made from pooled samples and characterized for its bile acid concentration) for assay quality control. Similarly add aliquots of sodium taurocholate (20 mL), serially diluted to generate a standard curve, to two sets of triplicate wells. Add a 230-mL reaction mixture containing 1M hydrazine hydrate, 0.1 M pyrophosphate and 0.46 mg/ml NAD to each well. Then add a 50-mL aliquot of 3α-hydroxysteroid dehydrogenase enzyme (HSD; 0.8 units/ml) or assay buffer (0.1 M sodium pyrophosphate) to one of the two sets of triplicates. Obtain all reagents from Sigma Chemical Co., St. Louis, Mo. Following 60 minutes of incubation at room temperature, measure the optical density at 340 nm and calculate the mean of each set of triplicate samples. Use the difference in optical density±HSD enzyme to determine the bile acid concentration (mM) of each sample, based on the sodium taurocholate standard curve. Use the bile acid concentration of the extract, the weight of the fecal homogenate (grams) and the body weight of the animal to calculate the corresponding FBA concentration in mmoles/kg/day for each animal. Substrate the mean FBA concentration (mmoles/kg/day) of the vehicle group from the FBA concentration of each treatment group to determine the increase (delta value) in FBA concentration as a result of the treatment.

Below are various illustrative examples for making various compounds in connection with the invention. The following examples and specific embodiments are provided for illustrative purposes and not intended to limit the scope of the invention.

SPECIFIC EMBODIMENTS

1. A compound comprising a benzothiepene of Formula I-1 or I-2:


I-1 or

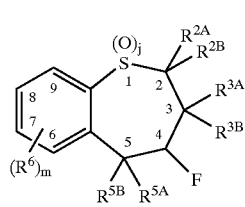

I-2 or a pharmaceutically acceptable salt, solvate, or prodrug thereof wherein j is 0, 1 or 2;

wherein m is 0, 1, 2, 3 or 4;

wherein $R^{2A}$ and $R^{2B}$ are independently selected from the group consisting of hydrogen and hydrocarbyl;

wherein $R^{3A}$, $R^{3B}$, $R^{5A}$, and $R^{5B}$ are independently selected from the group consisting of hydrogen, alkyl; cycloalkyl; alkenyl; alkynyl; heterocyclyl; quaternary heterocyclyl, oxo; aryl-$R^5$; —$OR^9$; —$NR^9R^{10}$; —$SR^9$; —$S(O)R^9$; —$SO_2R^9$; and —$SO_3R^9$;

wherein $R^9$ and $R^{10}$ are independently selected from the group consisting of hydrogen; hydrocarbyl; amino; and hydrocarbylamino;

wherein $R^5$ is selected from the group consisting of hydrogen; hydrocarbyl, heterocyclyl; quaternary heterocyclyl; —$OR^9$; —$SR^9$; —$S(O)R^9$; —$SO_2R^9$; and —$SO_3R^9$;

wherein when $R^5$ is said cycloalkyl, aryl or heterocyclyl, said cycloalkyl, aryl or heterocyclyl are optionally substituted with —NH—X—R or —O—X—R;

wherein X is selected from the group consisting of —(C=O)$_s$-alkyl-; —(C=O)$_s$-alkyl-NH—; —(C=O)$_s$-alkyl-O—; —(C=O)$_s$-alkyl-(C=O)$_t$; and a covalent bond, wherein s and t are independently 0 or 1;

wherein R is selected from the group consisting of monosaccharides, disaccharides, and polysaccharides, wherein said monosaccharides, disaccharides, and polysaccharides are optionally protected with one or more sugar protecting groups;

wherein $R^9$ and $R^{10}$ are as previously defined;

wherein, when $R^5 \neq H$, $R^5$ is optionally substituted with one or more radicals independently selected from the group consisting of halogen; —$NO_2$; —CN; oxo; hydrocarbyl; —$OR^{13}$; —$NR^{13}R^{14}$; —$SR^{13}$; —$S(O)R^{13}$; —$SO_2R^{13}$; —$SO_3R^{13}$; —$NR^{13}OR^{14}$; —$NR^{13}NR^{14}R^{15}$; —$CO_2R^{13}$; —OM; —$SO_2OM$; —$SO_2NR^{13}R^{14}$; —C(O)$NR^{13}R^{14}$; —C(O)OM; —$COR^3$; —$NR^{13}C(O)R^{14}$; —$NR^{13}C(O)NR^{14}R^{15}$; —$NR^{13}CO_2R^{14}$; —$OC(O)R^{13}$; —$OC(O)NR^{13}R^{14}$; —$NR^{13}SOR^{14}$; —$NR^{13}SO_2R^{14}$; —$NR^{13}SONR^{14}R^{15}$; —$NR^{13}SO_2NR^{14}R^{15}$; —$PR^{13}R^{14}$; —$P(O)R^{13}R^{14}$; —$P^+R^{13}R^{14}R^{15}A^-$; —$P(OR^{13})OR^{14}$; —$S^+R^{13}R^{14}A^-$; and —$N^+R^{13}R^{14}R^{15}A^-$;

wherein $R^{13}$, $R^{14}$, and $R^{15}$ are independently selected from the group consisting of hydrogen and hydrocarbyl;

wherein $A^-$ is a pharmaceutically acceptable anion;

wherein M is a pharmaceutically acceptable cation;

wherein one or more $R^6$ radicals are independently selected from the group consisting of hydrogen; halogen; —CN; —$NO_2$; hydrocarbyl; —$R^5$; —$OR^{13}$; —$NR^{13}R^{14}$; —$SR^{13}$; —$S(O)R^{13}$; —$S(O)_2R^{13}$; —$SO_3R^{13}$; —$S^+R^{13}R^{14}A^-$; —$NR^{13}OR^{14}$; —$NR^{13}NR^{14}R^{15}$; —OM; —$SO_2OM$; —$SO_2NR^{13}R^{14}$; —$NR^{14}C(O)R^{13}$; —C(O)OM; —$S(O)NR^{13}R^{14}$; —$N^+R^{13}R^{14}R^5A^-$; —$PR^{13}R^{14}$; —$P(O)R^{13}R^{14}$; —$P^+R^{13}R^{14}R^{15}A^-$; amino acid residue; peptide residue; polypeptide residue; and carbohydrate residue;

wherein $R^{13}$, $R^{14}$, $R^{15}$, $A^-$, and M are as defined above; and wherein, in each instance, said hydrocarbyl may be optionally substituted with one or more groups comprising one or more heteroatoms, and wherein, in each instance, said hydrocarbyl optionally may have one or more carbon atoms replaced by one or more heteroatoms independently selected from the group consisting of oxygen, nitrogen, sulfur, phosphorus and combinations thereof.

2. The compound of embodiment 1 or a pharmaceutically acceptable salt, solvate or prodrug thereof, wherein $R^{2A}$ and $R^{2B}$ are independently selected from the group consisting of hydrogen and alkyl, $R^{3A}$ and $R^{3B}$ are independently selected from the group consisting of hydrogen, alkyl, alkenyl, alkynyl, cycloalkyl, cycloalkylalkyl, aryl and arakyl and $R^5$ is selected from the group consisting of alkyl, cycloalkyl, alkenyl, alkynyl and aryl.

3. The compound of embodiment 1 or a pharmaceutically acceptable salt, solvate or prodrug thereof, wherein $R^{5A}$ is aryl optionally substituted with said radical $R^5$ selected from the group consisting of (1)–(69) and (70):
(1) 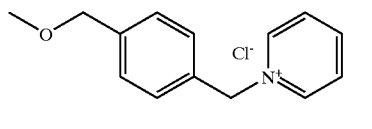
(2) 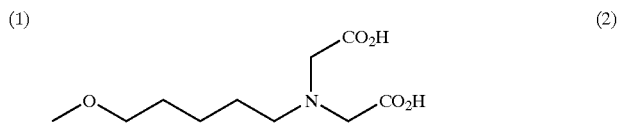
(3) 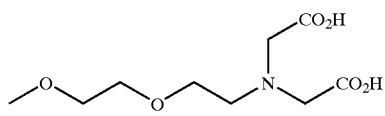
(4)
(5) 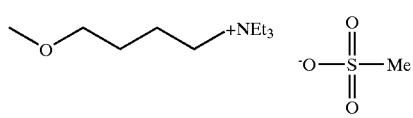
(6)
(7) 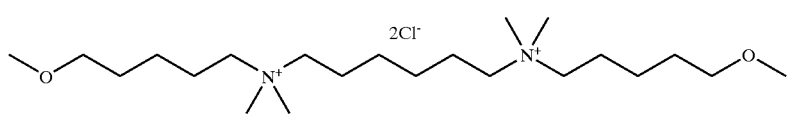
(8) 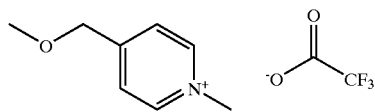
(9)
(10) 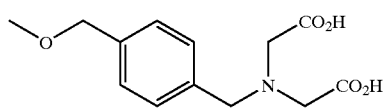
(11)
(12) 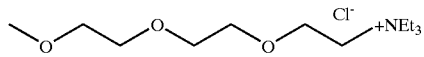
(13)
(14) 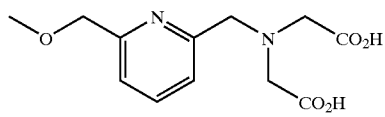
(15)
(15a) 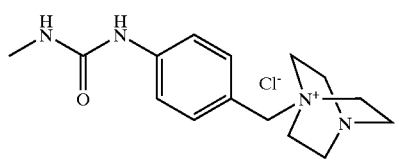
(16)
(17) 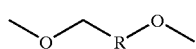
R = 1000 MW PEG
(18)

-continued
(19) 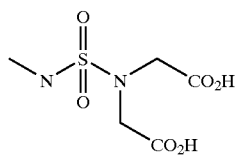
(20) 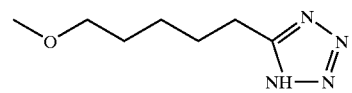
(21) 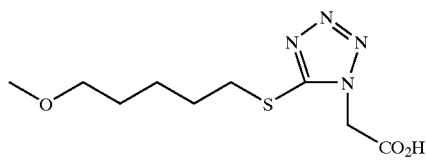
(22) 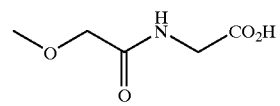
(23) 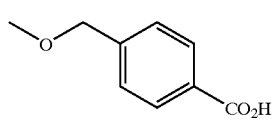
(24) 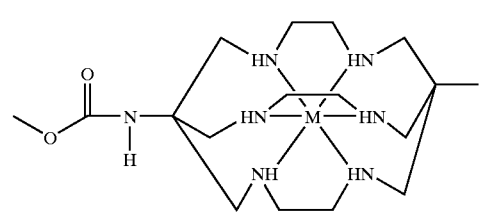
M = $Co^{II, III}$, $Mn^{II, III}$, $Fe^{II, III}$, $Ni^{II, III}$, $Cr^{III}$, $Cu^{II}$, $Zn^{II}$, $Cd^{II}$, $Ga^{III}$, $In^{III}$, $V^{IV}$, $Ru^{II}$, $Pr^{IV}$, $Rh^{III}$ or $Ir^{III}$
(25) 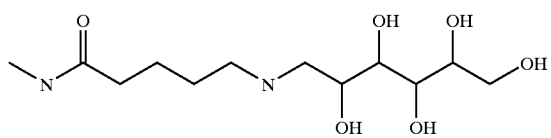
(26) 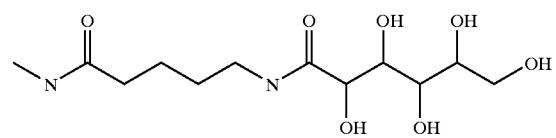
(27) 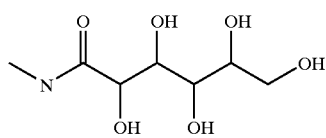
(28) 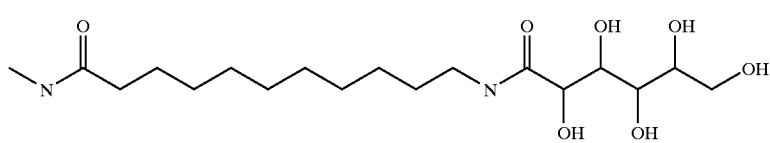
(29) 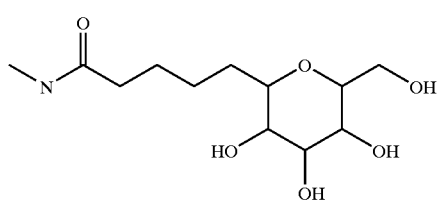
(30) 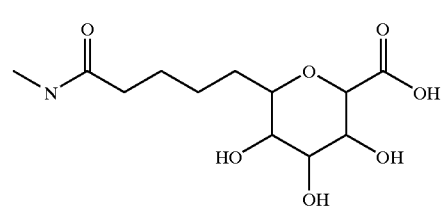
(31) 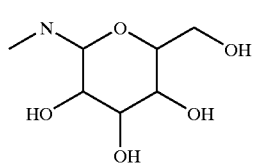
(32) 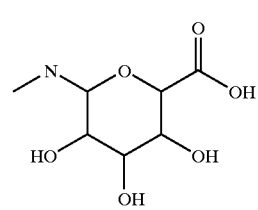

-continued
(33)
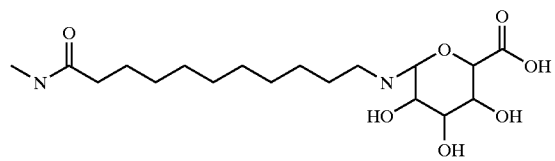
(34)
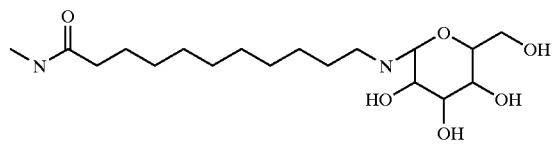
(35)
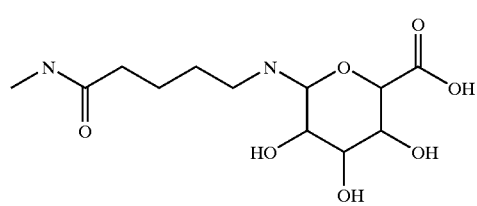
(36)
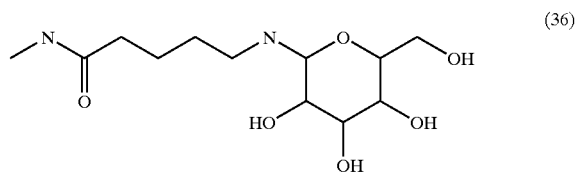
(37)
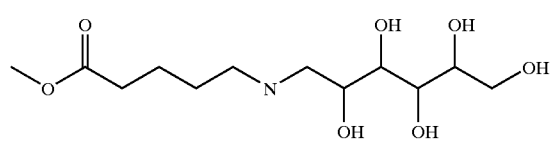
(38)
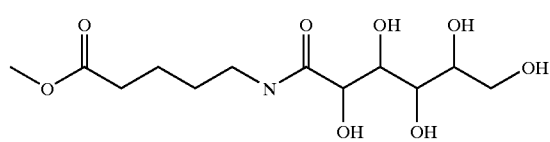
(39)
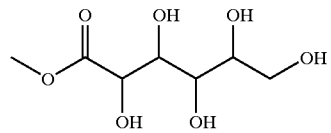
(40)
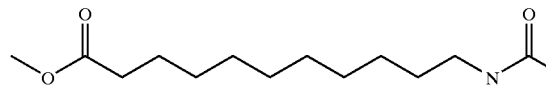
(41)
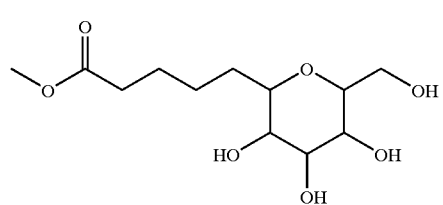
(42)
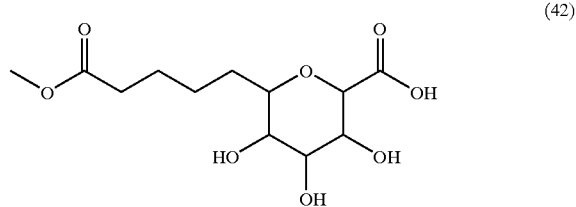
(43)
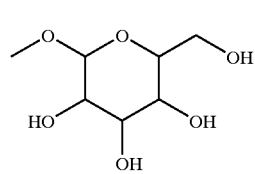
(44)
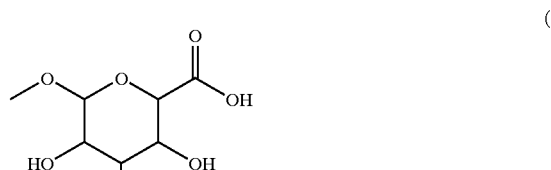
(45)
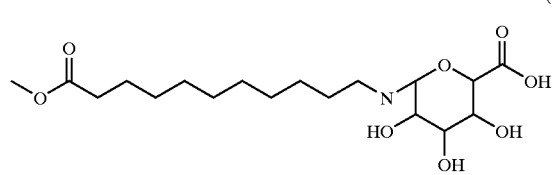
(46)
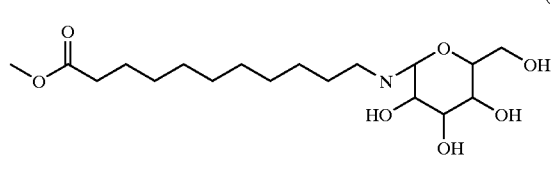
(47)
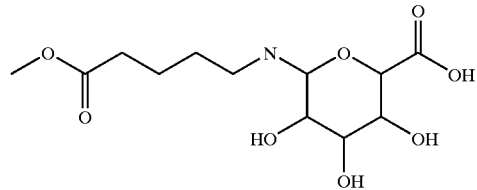
(48)
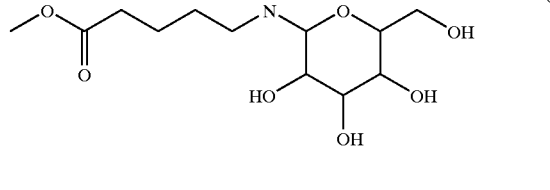

-continued
(49) 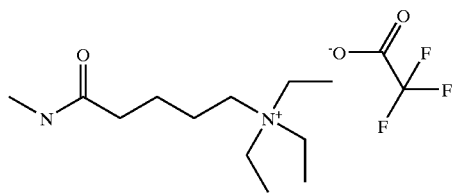
(50) 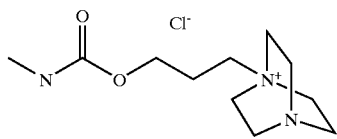
(51) 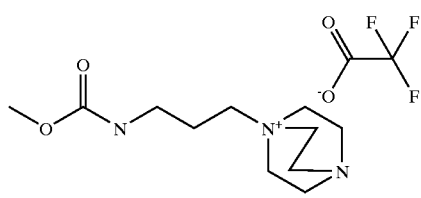
(52) 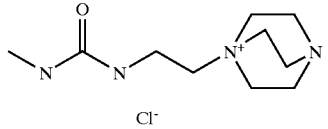
(53) 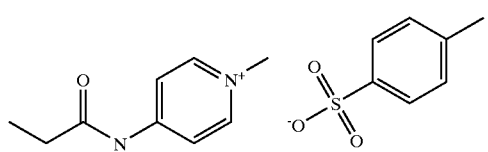
(54) 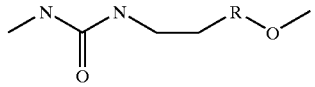
(55) 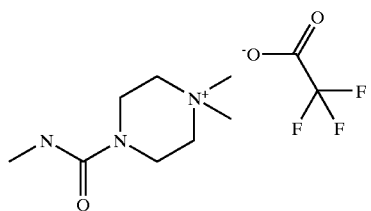
(56) 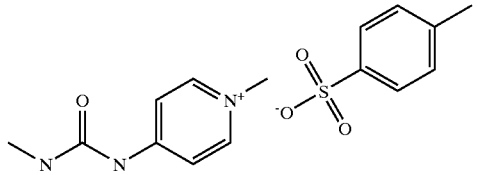
(57) 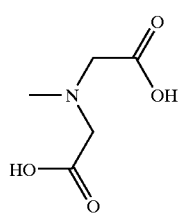
(58) 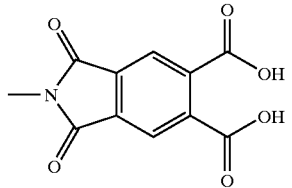
(59) 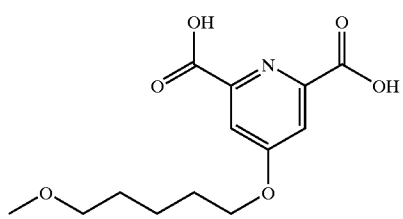
(60) 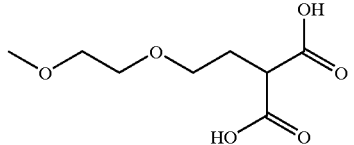
(61) 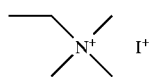
(62) 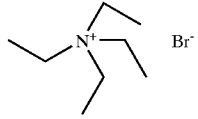
(63) 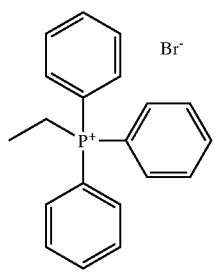
(64) 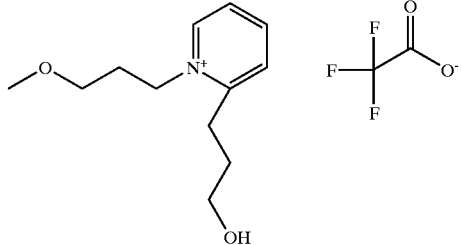

-continued

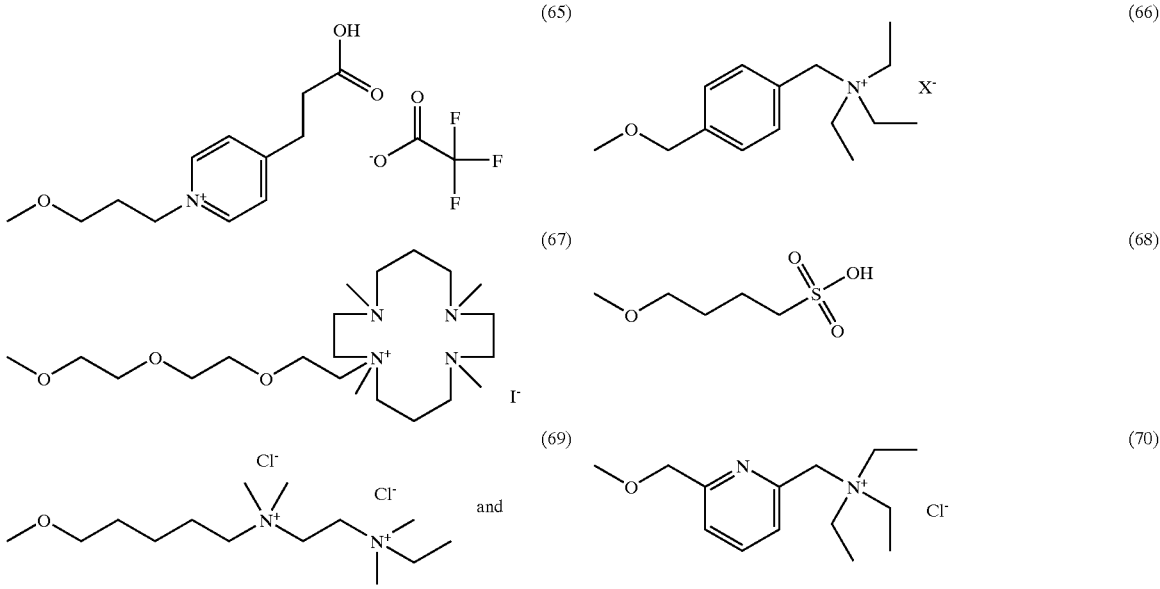

provided that when said $R^5$ is (7), (17) or (24), then said $R^{5A}$ is a left end of said $R^5$ and $R^{5B}$ is a right end of said $R^5$ or vice versa.

4. The compound of embodiment 3 or a pharmaceutically acceptable salt, solvate or prodrug thereof, wherein $R^{5A}$ is phenyl optionally substituted at least at either a para position or a meta position of said phenyl with said radical $R^5$.

5. The compound of embodiment 1 or a pharmaceutically acceptable salt, solvate or prodrug thereof, wherein j=2, $R^{2A}$ and $R^{2B}$ are independently selected from the group consisting of hydrogen and alkyl, and $R^{3A}$ and $R^{3B}$ are independently selected from the group consisting of hydrogen and alkyl.

6. The compound of embodiment 1 or a pharmaceutically acceptable salt, solvate or prodrug thereof, wherein j=2, at least one of $R^{2A}$ and $R^{2B}$ is hydrogen, and $R^{3A}$ and $R^{3B}$ each are alkyl.

7. The compound of embodiment 6 or a pharmaceutically acceptable salt, solvate or prodrug thereof, wherein $R^{2A}$=$R^{2B}$=H and $R^{3A}$ and $R^{3B}$ are independently selected from the group consisting of ethyl, propyl and butyl.

8. The compound of embodiment 1 or a pharmaceutically acceptable salt, solvate or prodrug thereof, wherein $R^{2A}$ and $R^{2B}$ are independently selected from the group consisting of hydrogen and $C_{1-10}$ alkyl, $R^{3A}$ and $R^{3B}$ are independently selected from the group consisting of hydrogen and $C_{1-10}$ alkyl.

9. The compound of embodiment 1 or a pharmaceutically acceptable salt, solvate or prodrug thereof, wherein $R^{2A}$ and $R^{2B}$ are independently selected from the group consisting of hydrogen and $C_{1-6}$ alkyl, and $R^{3A}$ and $R^{3B}$ are independently selected from the group consisting of hydrogen and $C_{1-6}$ alkyl.

10. The compound of embodiment 1 or a pharmaceutically acceptable salt, solvate or prodrug thereof, wherein $R^{2A}$ and $R^{2B}$ are the same radical.

11. The compound of embodiment 10 or a pharmaceutically acceptable salt, solvate or prodrug thereof, wherein $R^{2A}$ and $R^{2B}$ are the same alkyl radical.

12. The compound of embodiment 10 or a pharmaceutically acceptable salt, solvate or prodrug thereof wherein $R^{2A}$ and $R^{2B}$ are the same radical selected from the group consisting of hydrogen, $C_{1-10}$ alkyl, $C_{1-10}$ alkenyl and $C_{1-10}$ alkynyl.

13. The compound of embodiment 10 or a pharmaceutically acceptable salt, solvate or prodrug thereof, wherein $R^{3A}$ and $R^{3B}$ are the same radical.

14. The compound of embodiment 11 or a pharmaceutically acceptable salt, solvate or prodrug thereof, wherein $R^{3A}$ and $R^{3B}$ are the same alkyl radical.

15. The compound of embodiment 12 or a pharmaceutically acceptable salt, solvate or prodrug thereof, wherein $R^{3A}$ and $R^{3B}$ are the same radical selected from the group consisting of hydrogen, $C_{1-10}$ alkyl, $C_{1-10}$ alkenyl and $C_{1-10}$ alkynyl.

16. The compound of embodiment 1 or a pharmaceutically acceptable salt, solvate or prodrug thereof, wherein $R^{3A}$ and $R^{3B}$ are the same radical.

17. The compound of embodiment 16 or a pharmaceutically acceptable salt, solvate or prodrug thereof, wherein $R^{3A}$ and $R^{3B}$ are the same alkyl radical.

18. The compound of embodiment 16 or a pharmaceutically acceptable salt, solvate or prodrug thereof, wherein $R^{3A}$ and $R^{3B}$ are the same radical selected from the group consisting of hydrogen, $C_{1-10}$ alkyl, $C_{1-10}$ alkenyl and $C_{1-10}$ alkynyl.

19. The compound of embodiment 1 or a pharmaceutically acceptable salt, solvate or prodrug thereof, wherein $R^{2A}$ and $R^{2B}$ are the same $C_{1-20}$ hydrocarbyl radical.

20. The compound of embodiment 19 or a pharmaceutically acceptable salt, solvate or prodrug thereof, wherein $R^{2A}$ and $R^{2B}$ are the same $C_{1-10}$ hydrocarbyl radical.

21. The compound of embodiment 20 or a pharmaceutically acceptable salt, solvate or prodrug thereof, wherein $R^{2A}$ and $R^{2B}$ are the same $C_{1-6}$ hydrocarbyl radical.

22. The compound of embodiment 1 or a pharmaceutically acceptable salt, solvate or prodrug thereof, wherein $R^{3A}$ and $R^{3B}$ are the same $C_{1-20}$ hydrocarbyl radical.

23. The compound of embodiment 22 or a pharmaceutically acceptable salt, solvate or prodrug thereof, wherein $R^{3A}$ and $R^{3B}$ are the same $C_{1-10}$ hydrocarbyl radical.

24. The compound of embodiment 23 or a pharmaceutically acceptable salt, solvate or prodrug thereof, wherein $R^{3A}$ and $R^{3B}$ are the same $C_{1-6}$ hydrocarbyl radical.

25. The compound of embodiment 11 or a pharmaceutically acceptable salt, solvate or prodrug thereof, wherein $R^{2A}$ and $R^{2B}$ are each n-butyl.

26. The compound of embodiment 10 or a pharmaceutically acceptable salt, solvate or prodrug thereof, wherein $R^{2A}$ and $R^{2B}$ are each H.

27. The compound of embodiment 13 or a pharmaceutically acceptable salt, solvate or prodrug thereof, wherein $R^{3A}$ and $R^{3B}$ are each H or n-butyl.

28. The compound of embodiment 1 or a pharmaceutically acceptable salt, solvate or prodrug thereof, wherein one or more radicals $R^6$ are selected from the group consisting of hydrogen, halogen, hydroxy, alkoxy, amino, alkylamino and dialkylamino.

29. The compound of embodiment 28 or a pharmaceutically acceptable salt, solvate or prodrug thereof, wherein one or more radicals $R^6$ are selected from the group consisting of methoxy, ethoxy and dimethylamino.

30. The compound of embodiment 1 or a pharmaceutically acceptable salt, solvate or prodrug thereof, wherein j=2, m=1, one of $R^{5A}$ and $R^{5B}$ is hydrogen and the other of $R^{5A}$ and $R^{5B}$ is a phenyl radical optionally substituted at a para position of said phenyl radical with said radical $R^5$ selected from the group consisting of (1)–(69) and (70):

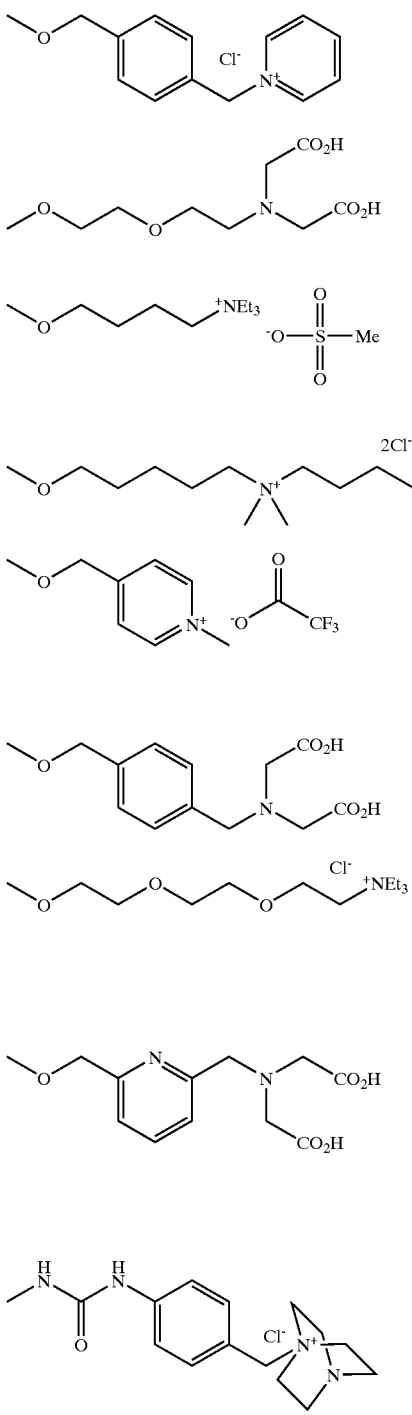
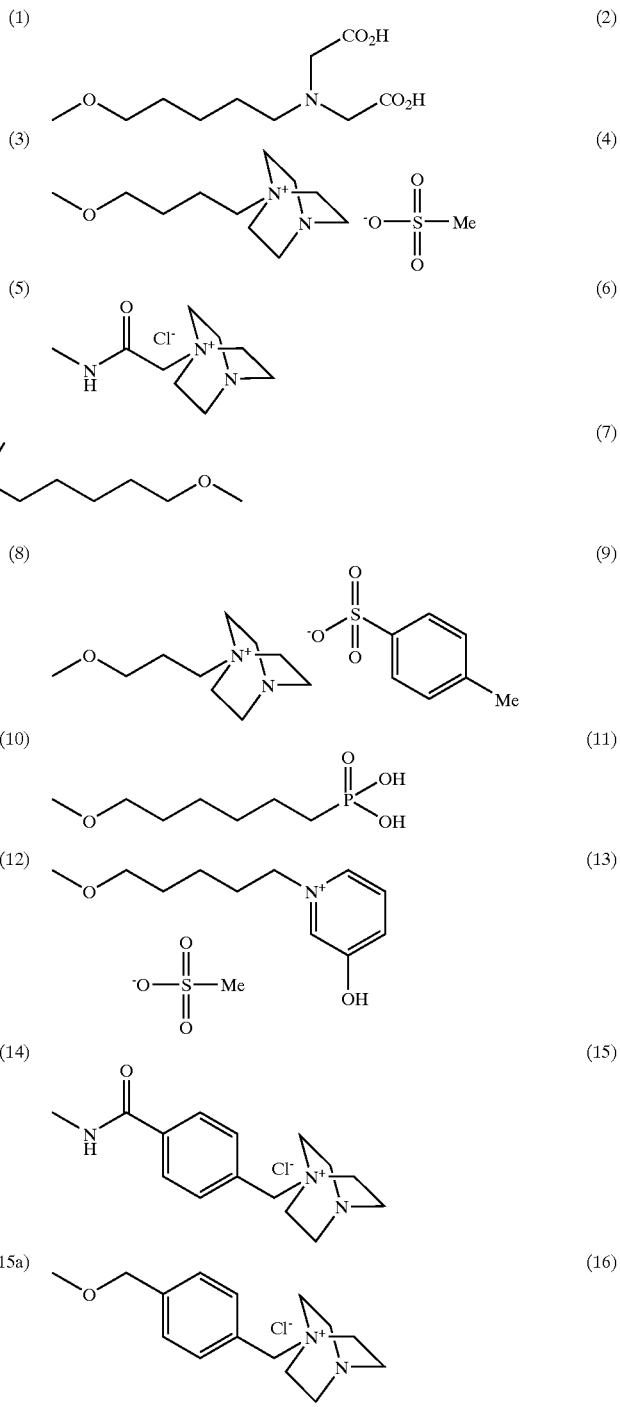

-continued
(17) 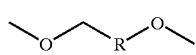
R = 1000 MW PEG
(18) 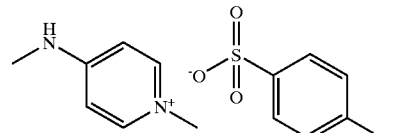
(19) 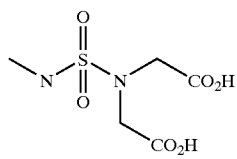
(20) 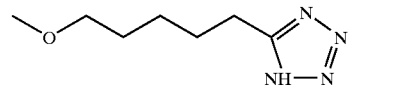
(21) 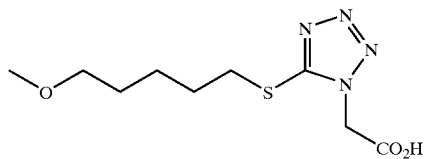
(22) 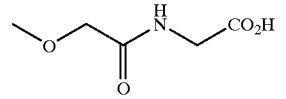
(23) 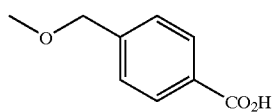
(24) 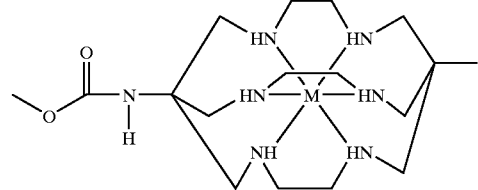
M = $Co^{II, III}$, $Mn^{II, III}$, $Fe^{II, III}$, $Ni^{II, III}$, $Cr^{III}$, $Cu^{II}$, $Zn^{II}$, $Cd^{II}$, $Ga^{III}$, $In^{III}$, $V^{IV}$, $Ru^{II}$, $Pr^{IV}$, $Rh^{III}$ or $Ir^{III}$
(25) 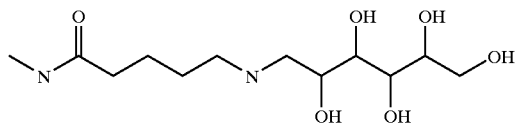
(26) 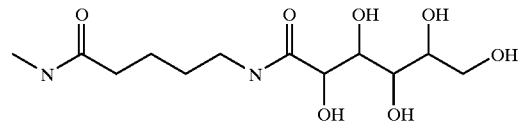
(27) 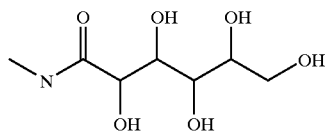
(28) 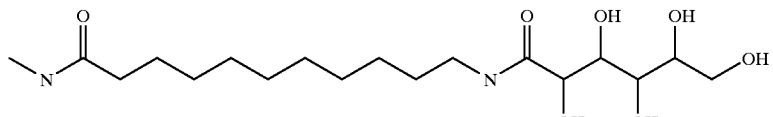
(29) 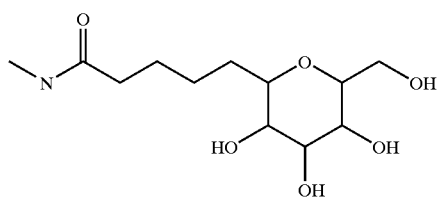
(30) 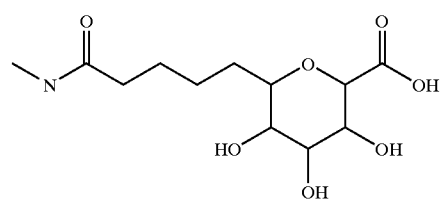
(31) 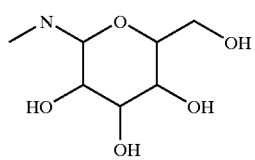
(32) 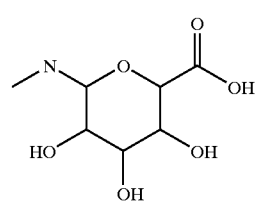

-continued
(33) 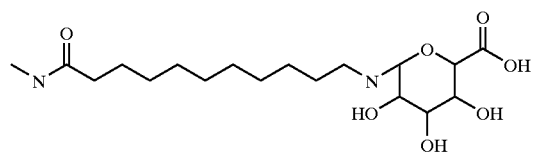
(34) 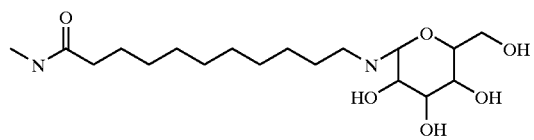
(35) 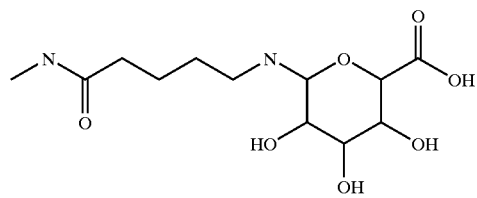
(36) 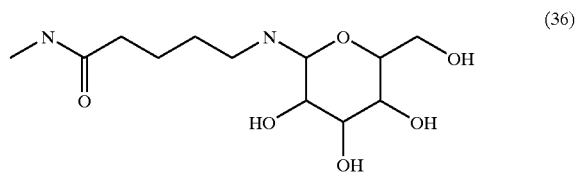
(37) 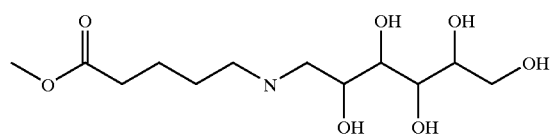
(38) 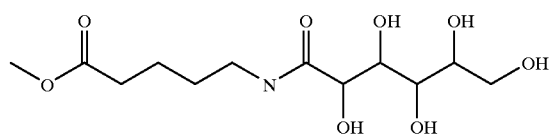
(39) 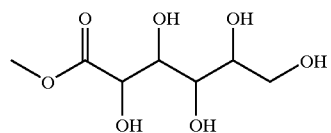
(40) 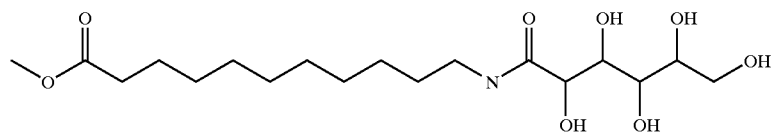
(41) 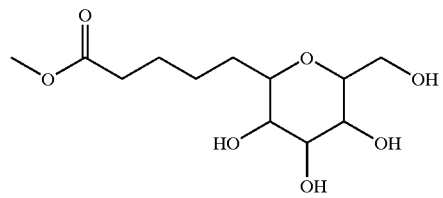
(42) 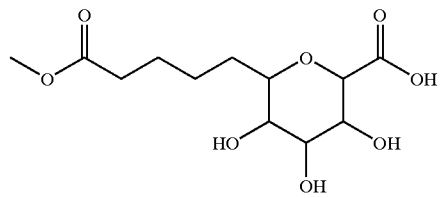
(43) 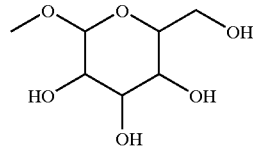
(44) 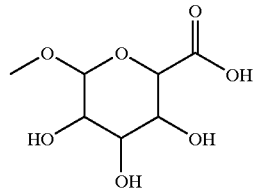
(45) 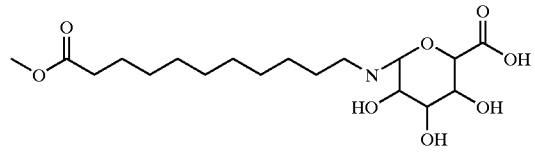
(46) 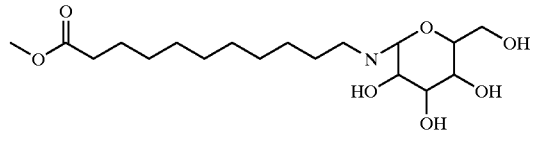
(47) 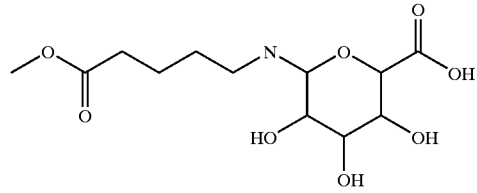
(48) 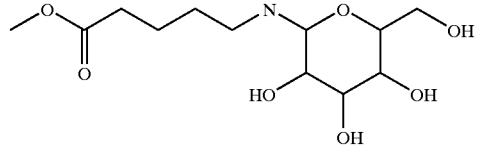

-continued
(49) 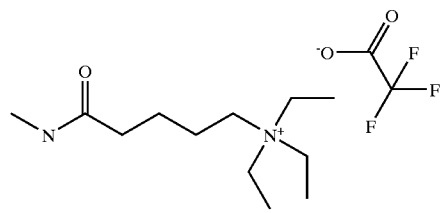
(50) 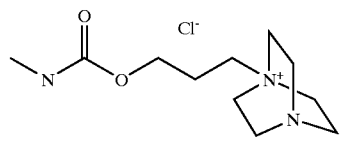
(51) 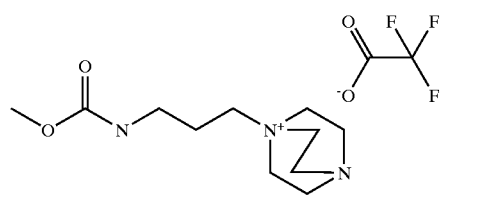
(52) 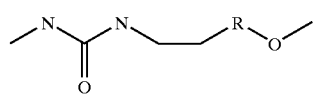
(53) 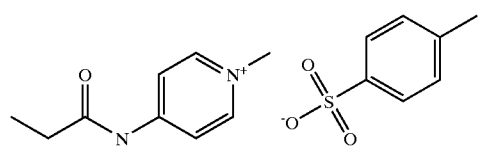
(54) 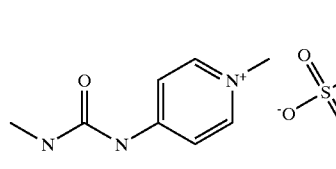
(55) 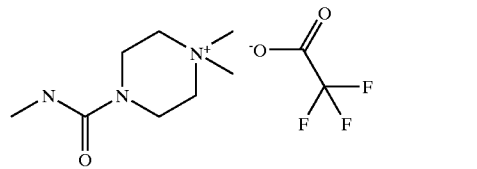
(56) 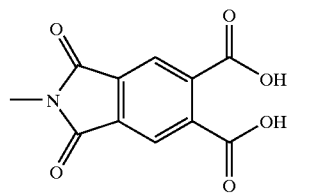
(57) 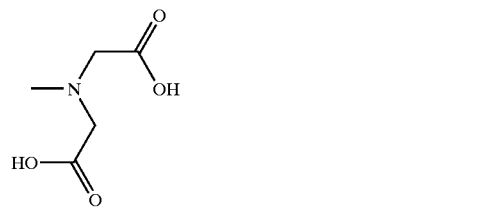
(58) 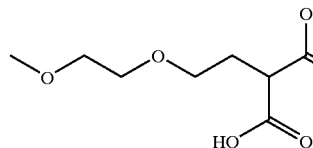
(59) 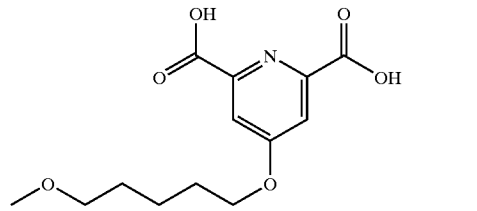
(60) 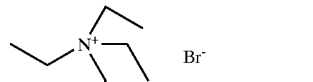
(61) 
(62) 
(63) 
(64) 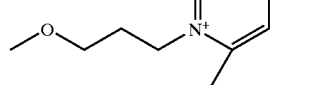

-continued

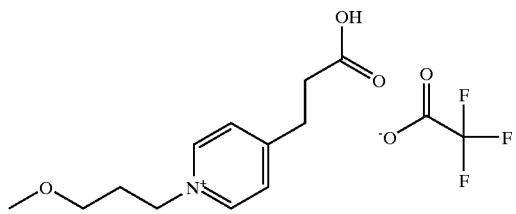 (65)

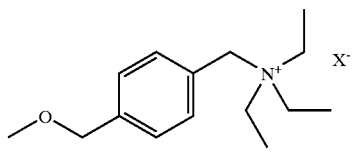 (66)

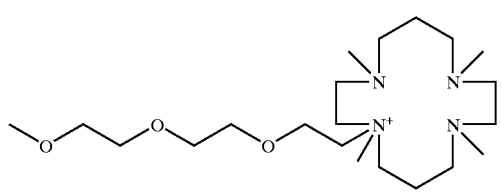 (67)

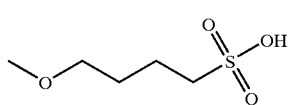 (68)

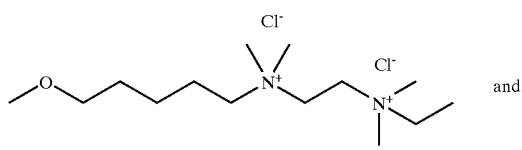 (69)

and

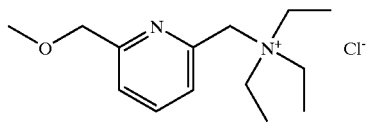 (70)

provided that when said $R^5$ is (7), (17) or (24), then said $R^{5A}$ is a left end of said $R^5$ and $R^{5B}$ is a right end of said $R^5$ or vice versa.

31. The compound of embodiment 1 wherein said benzothiepene comprises the compound of Formula I-17 or I-18:

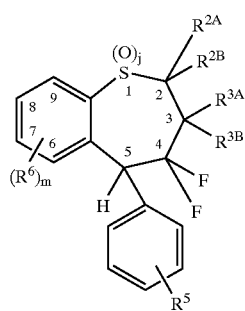 I-17

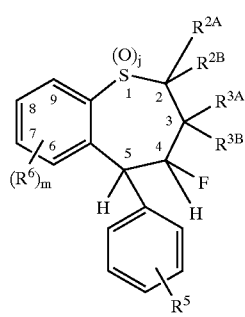 I-18.

32. The compound of embodiment 31 wherein said $R^5$ is attached to either a para-position or a meta-position on said phenyl ring attached to the 5-position ring carbon of said benzothiepene compound of said Formulas I-17 or I-18.

33. The compound of embodiment 31 wherein said benzothiepene of said Formula I-17 comprises a member selected from the group consisting

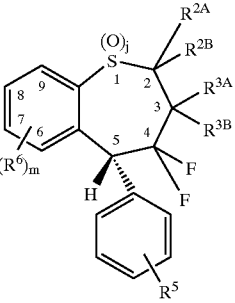 I-21

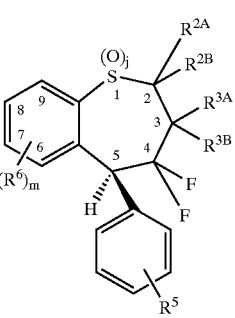 I-22.

of Formulas I-21 and I-22:-

34. The compound of embodiment 33 wherein said benzothiepene of said Formulas I-21 and I-22 comprise Formulas I-9 and I-10, respectively, represented by:

I-9
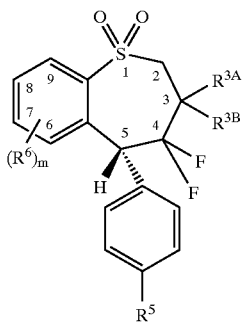

I-10.
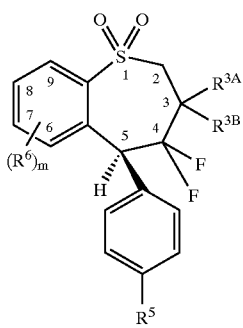

35. The compound of embodiment 31 wherein said benzothiepene of said Formula I-18 comprises a member selected from the group consisting of Formulas I-23, and I-24:

I-23
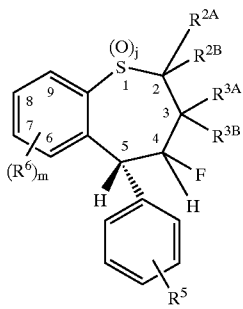

I-24.
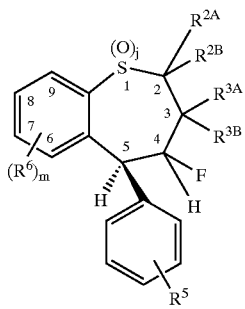

36. The compound of embodiment 35 wherein said benzothiepene of said Formulas I-23 and I-24 comprise Formulas I-19 and I-20, respectively, represented by:

I-19
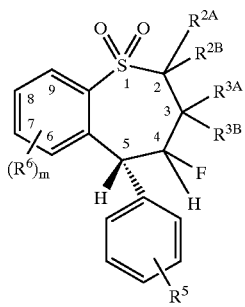

I-20.
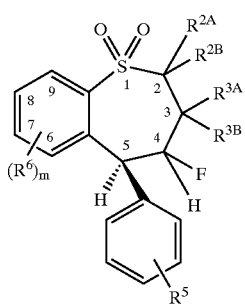

37. The compound of embodiment 35 wherein said $R^5$ is attached to either a meta-position or a para-position on said phenyl ring attached to said 5-position carbon ring of said benzothiepenes of said Formulas I-23 and I-24.

38. The compound of embodiments 31–37 wherein said $R^5$ is selected from the group consisting of (1)–(69) and (70):

(1)
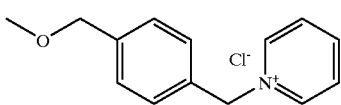

(2)
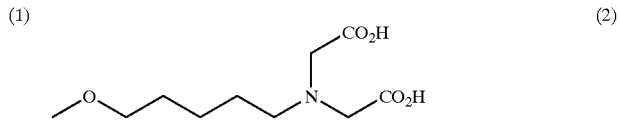

(3)
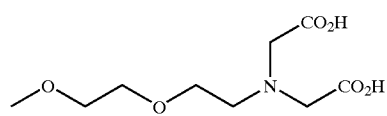

(4)
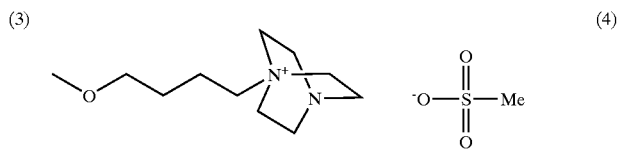

-continued
(5) 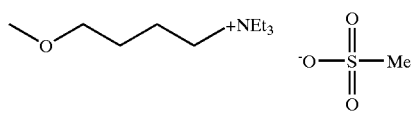 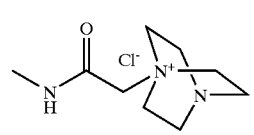 (6)
(7) 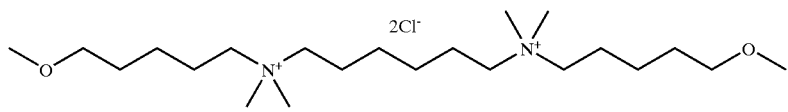
(8) 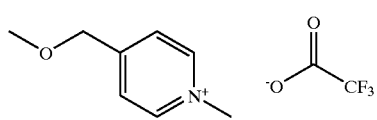 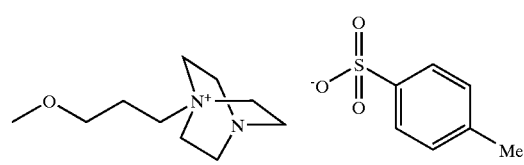 (9)
(10) 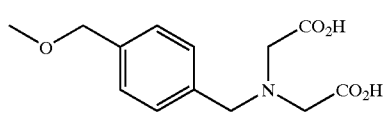 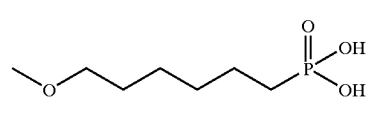 (11)
(12) 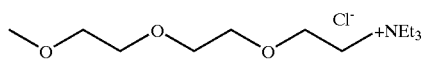 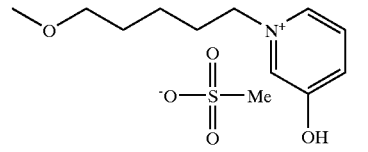 (13)
(14) 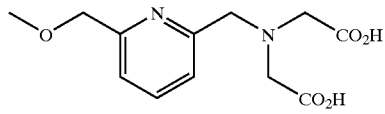 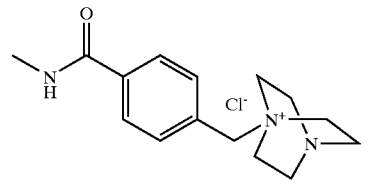 (15)
(15a) 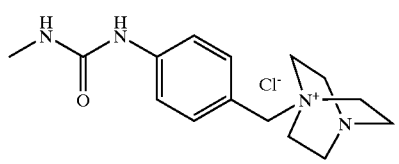 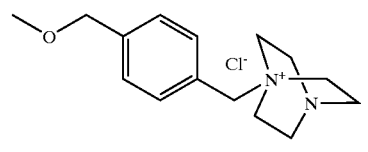 (16)
(17) 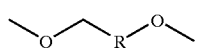
R = 1000 MW PEG
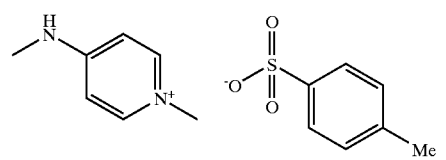 (18)
(19) 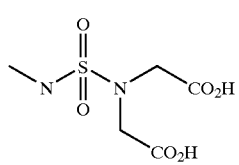 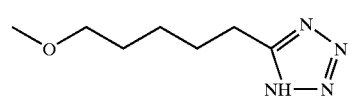 (20)
(21) 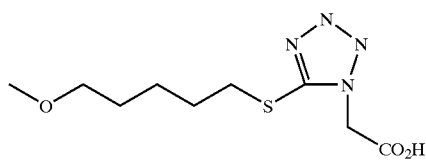 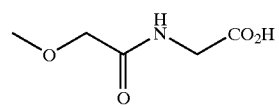 (22)

-continued
(23)
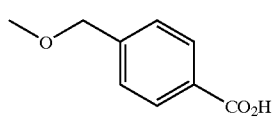
(24)
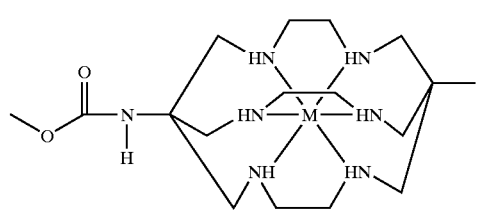
M = Co^{II, III}, Mn^{II, III}, Fe^{II, III}, Ni^{II, III}, Cr^{III}, Cu^{II}, Zn^{II}, Cd^{II}, Ga^{III}, In^{III}, V^{IV}, Ru^{II}, Pr^{IV}, Rh^{III} or Ir^{III}
(25)
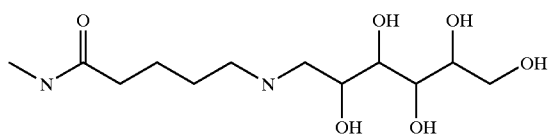
(26)
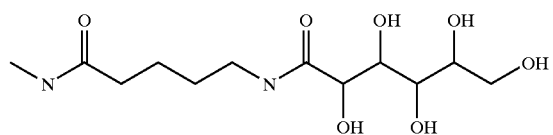
(27)
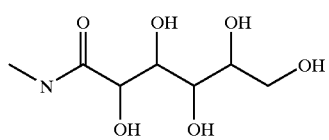
(28)
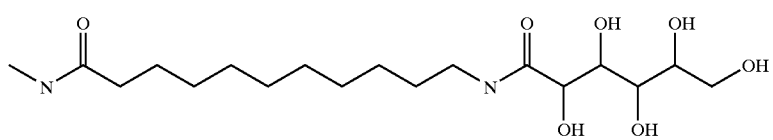
(29)
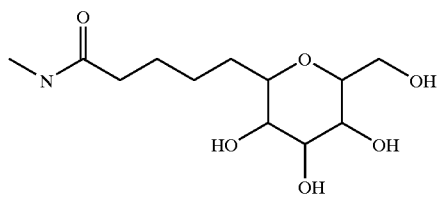
(30)
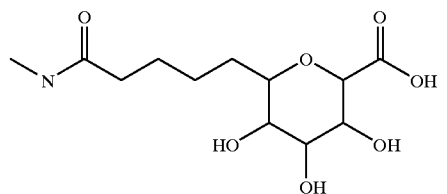
(31)
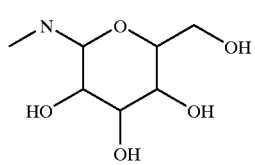
(32)
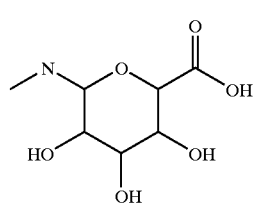
(33)
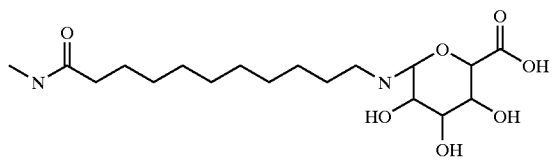
(34)
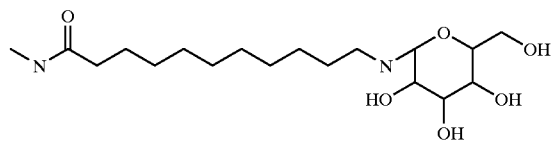
(35)
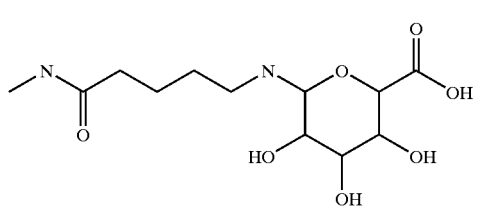
(36)
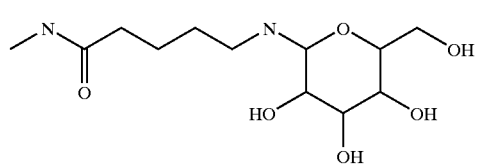

-continued

-continued
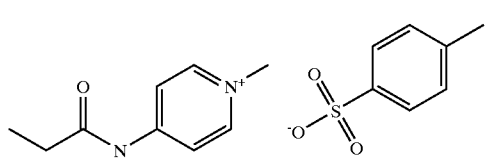(53)
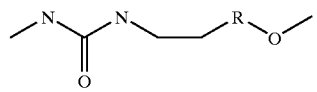(54)
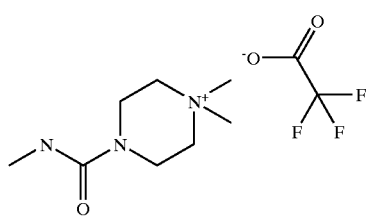(55)
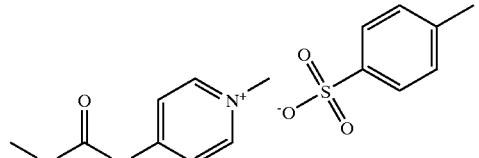(56)
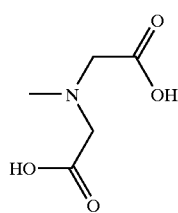(57)
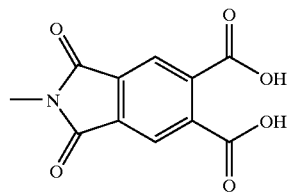(58)
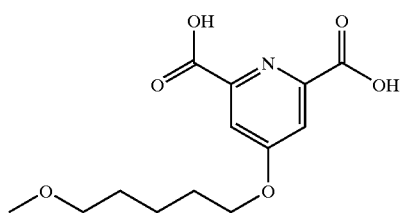(59)
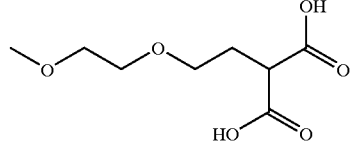(60)
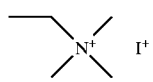(61)
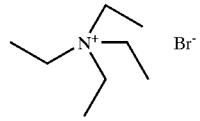(62)
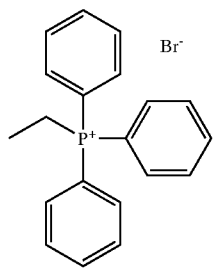(63)
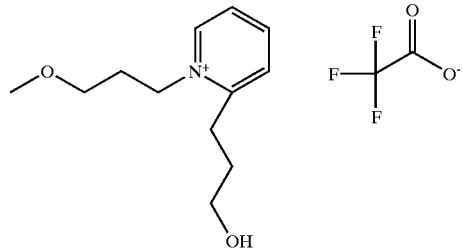(64)
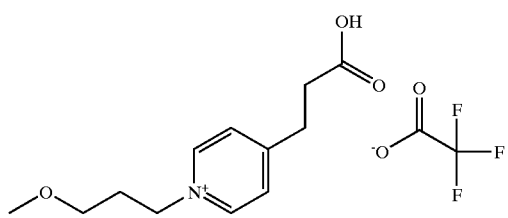(65)
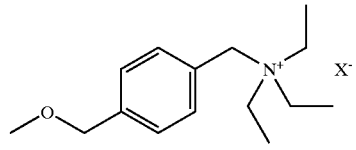(66)
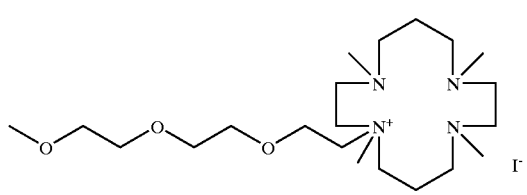(67)
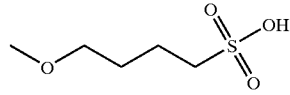(68)

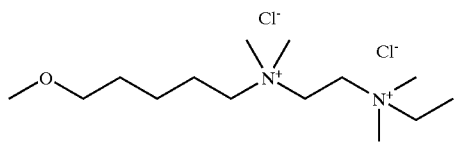

(69)

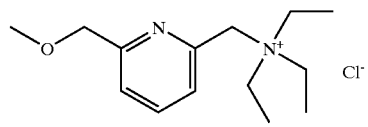

(70)

wherein when said $R^5$ is said (7), said (17) or said (24), then said $R^{5A}$ represents a left-end of said $R^5$ and said $R^{5B}$ represents a right end of said $R^5$ or vice versa.

39. A method for treating a hyprelipidemic condition in a subject comprising administering to said subject in need thereof a therapeutically effective amount of a compound of Formulas I-1 or I-2, wherein said Formulas I-1 and I-2 are represented by:

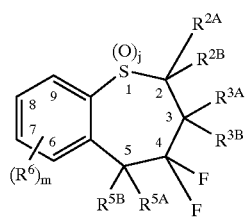

I-1

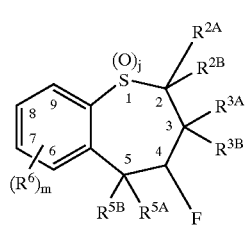

I-2 or a pharmaceutically acceptable salt, solvate, or prodrug thereof wherein j is 0, 1 or 2;

wherein m is 0, 1, 2, 3 or 4;

wherein $R^{2A}$ and $R^{2B}$ are independently selected from the group consisting of hydrogen and hydrocarbyl;

wherein $R^3A$, $R^3B$, $R^5A$, and $R^{5B}$ are independently selected from the group consisting of hydrogen, alkyl; cycloalkyl; alkenyl; alkynyl; heterocyclyl; quaternary heterocyclyl, oxo; aryl-$R^5$; —$OR^9$; —$NR^9R^{10}$; —$SR^9$; —$S(O)R^9$; —$SO_2R^9$; and —$SO_3R^9$;

wherein $R^9$ and $R^{10}$ are independently selected from the group consisting of hydrogen; hydrocarbyl; amino; and hydrocarbylamino;

wherein $R^5$ is selected from the group consisting of hydrogen; hydrocarbyl, heterocyclyl; quaternary heterocyclyl; —$OR^9$; —$SR^9$; —$S(O)R^9$; —$SO_2R^9$; and —$SO_3R^9$;

wherein when $R^5$ is said cycloalkyl, aryl or heterocyclyl, said cycloalkyl, aryl or heterocyclyl are optionally substituted with —NH—X—R or —O—X—R;

wherein X is selected from the group consisting of —$(C=O)_s$-alkyl-; —$(C=O)_s$-alkyl-NH—; —$(C=O)_s$-alkyl-O—; —$(C=O)_s$-alkyl-$(C=O)_t$; and a covalent bond, wherein s and t are independently 0 or 1;

wherein R is selected from the group consisting of monosaccharides, disaccharides, and polysaccharides, wherein said monosaccharides, disaccharides, and polysaccharides are optionally protected with one or more sugar protecting groups;

wherein $R^9$ and $R^{10}$ are as previously defined;

wherein, when $R^5 \neq H$, $R^5$ is optionally substituted with one or more radicals independently selected from the group consisting of halogen; —$NO_2$; —CN; oxo; hydrocarbyl; —$OR^{13}$; —$NR^{13}R^{14}$; —$SR^{13}$; —$S(O)R^{13}$; —$SO_2R^{13}$; —$SO_3R^{13}$; —$NR^{13}OR^{14}$; —$NR^{13}NR^{14}R^{15}$; —$CO_2R^{13}$; —OM; —$SO_2OM$; —$SO_2NR^{13}R^{14}$; —$C(O)NR^{13}R^{14}$; —C(O)OM; —$COR^{13}$; —$NR^{13}C(O)R^{14}$; —$NR^{13}C(O)NR^{14}R^{15}$; —$NR^{13}CO_2R^{14}$; —$OC(O)R^{13}$; —$OC(O)NR^{13}R^{14}$; —$NR^{13}SOR^{14}$; —$NR^{13}SO_2R^{14}$; —$NR^{13}SONR^{14}R^{15}$; —$NR^{13}SO_2NR^{14}R^{15}$; —$PR^{13}R^{14}$; —$P(O)R^{13}R^{14}$; —$P^+R^{13}R^{14}R^{15}A^-$; —$P(OR^{13})OR^{14}$; —$S^+R^{13}R^{14}A^-$; and —$N^+R^{13}R^{14}R^{15}A^-$;

wherein $R^{13}$, $R^{14}$, and $R^{15}$ are independently selected from the group consisting of hydrogen and hydrocarbyl;

wherein $A^-$ is a pharmaceutically acceptable anion;

wherein M is a pharmaceutically acceptable cation;

wherein one or more $R^6$ radicals are independently selected from the group consisting of hydrogen; halogen; —CN; —$NO_2$; hydrocarbyl; —$R^5$; —$OR^{13}$; —$NR^{13}R^{14}$; —$SR^{13}$; —$S(O)R^{13}$; —$S(O)_2R^{13}$; —$SO_3R^{13}$; —$S^+R^{13}R^{14}A^-$; —$NR^{13}OR^{14}$; —$NR^{13}NR^{14}R^{15}$; —OM; —$SO_2OM$; —$SO_2NR^{13}R^{14}$; —$NR^{14}C(O)R^{13}$; —C(O)OM; —$S(O)NR^{13}R^{14}$; —$N^+R^{13}R^{14}R^{15}A$—; —$PR^{13}R^{14}$; —$P(O)R^{13}R^{14}$; —$P^+R^{13}R^{14}R^{15}A^-$; amino acid residue; peptide residue; polypeptide residue; and carbohydrate residue;

wherein $R^{13}$, $R^{14}$, $R^{15}$, $A^-$, and M are as defined above; and wherein, in each instance, said hydrocarbyl may be optionally substituted with one or more groups comprising one or more heteroatoms, and wherein, in each instance, said hydrocarbyl optionally may have one or more carbon atoms replaced by one or more heteroatoms independently selected from the group consisting of oxygen, nitrogen, sulfur, phosphorus and combinations thereof.

40. A method of treating gallstones or a condition associated therewith in a subject comprising administering to said subject in need thereof a therapeutically effective amount of a compound of Formulas I-1 or I-2 represented by:

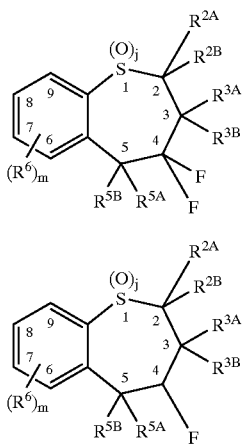

or a pharmaceutically acceptable salt, solvate, or prodrug thereof wherein j is 0, 1 or 2;

wherein m is 0, 1, 2, 3 or 4;

wherein $R^{2A}$ and $R^{2B}$ are independently selected from the group consisting of hydrogen and hydrocarbyl;

wherein $R^{3A}$, $R^{3B}$, $R^{5A}$, and $R^{5B}$ are independently selected from the group consisting of hydrogen, alkyl; cycloalkyl; alkenyl; alkynyl; heterocyclyl; quaternary heterocyclyl, oxo; aryl-$R^5$; —$OR^9$; —$NR^9R^{10}$; —$SR^9$; —$S(O)R^9$; —$SO_2R^9$; and —$SO_3R^9$;

wherein $R^9$ and $R^{10}$ are independently selected from the group consisting of hydrogen; hydrocarbyl; amino; and hydrocarbylamino;

wherein $R^5$ is selected from the group consisting of hydrogen; hydrocarbyl, heterocyclyl; quaternary heterocyclyl; —$OR^9$; —$SR^9$; —$S(O)R^9$; —$SO_2R^9$; and —$SO_3R^9$;

wherein when $R^5$ is said cycloalkyl, aryl or heterocyclyl, said cycloalkyl, aryl or heterocyclyl are optionally substituted with —NH—X—R or —OX—R;

wherein X is selected from the group consisting of —(C=O)$_s$-alkyl-; —(C=O)$_s$-alkyl-NH—; —(C=O)$_s$-alkyl-O—; —(C=O)$_s$-alkyl-(C=O)$_t$; and a covalent bond, wherein s and t are independently 0 or 1;

wherein R is selected from the group consisting of monosaccharides, disaccharides, and polysaccharides, wherein said monosaccharides, disaccharides, and polysaccharides are optionally protected with one or more sugar protecting groups;

wherein $R^9$ and $R^{10}$ are as previously defined;

wherein, when $R^5 \ne H$, $R^5$ is optionally substituted with one or more radicals independently selected from the group consisting of halogen; —$NO_2$; —CN; oxo; hydrocarbyl; —$OR^{13}$; —$NR^{13}R^{14}$; —$SR^{13}$; —$S(O)R^{13}$; —$SO_2R^{13}$; —$SO_3R^{13}$; —$NR^{13}OR^{14}$; —$NR^{13}NR^{14}R^{15}$; —$CO_2R^{13}$; —OM; —$SO_2OM$; —$SO_2NR^{13}R^{14}$; —$C(O)NR^{13}R^{14}$; —C(O)OM; —$COR^{13}$; —$NR^{13}C(O)R^{14}$; —$NR^{13}C(O)NR^{14}R^{15}$; —$NR^{13}CO_2R^{14}$; —$OC(O)R^{13}$; —$OC(o)NR^{13}R^{14}$; —$NR^{13}SOR^{14}$; —$NR^{13}SO_2R^{14}$; —$NR^{13}SONR^{14}R^{15}$; —$NR^{13}SO_2NR^{14}R^{15}$; —$PR^{13}R^{14}$; —$P(O)R^{13}R^{14}$; —$P^+R^{13}R^{14}R^{15}A^-$; —$P(OR^{13})OR^{14}$; —$S^+R^{13}R^{14}A^-$; and —$N^+R^{13}R^{14}R^{15}A^-$;

wherein $R^{13}$, $R^{14}$, and $R^{15}$ are independently selected from the group consisting of hydrogen and hydrocarbyl;

wherein $A^-$ is a pharmaceutically acceptable anion;

wherein M is a pharmaceutically acceptable cation;

wherein one or more $R^6$ radicals are independently selected from the group consisting of hydrogen; halogen; —CN; —$NO_2$; hydrocarbyl; —$R^5$; —$OR^{13}$; —$NR^{13}R^{14}$; —$SR^{13}$; —$S(O)R^{13}$; —$S(O)_2R^{13}$; —$SO_3R^{13}$; —$S^+R^{13}R^{14}A^-$; —$NR^{13}OR^{14}$; —$NR^{13}NR^{14}R^{15}$; —OM; —$SO_2OM$; —$SO_2NR^{13}R^{14}$; —$NR^{14}C(O)R^{13}$; —C(O)OM; —$S(O)NR^{13}R^{14}$; —$N^+R^{13}R^{14}R^{15}A^-$; —$PR^{13}R^{14}$; —$P(O)R^{13}R^{14}$; —$P^+R^{13}R^{14}R^{15}A^-$; amino acid residue; peptide residue; polypeptide residue; and carbohydrate residue;

wherein $R^{13}$, $R^{14}$, $R^{15}$, $A^-$, and M are as defined above; and wherein, in each instance, said hydrocarbyl may be optionally substituted with one or more groups comprising one or more heteroatoms, and wherein, in each instance, said hydrocarbyl optionally may have one or more carbon atoms replaced by one or more heteroatoms independently selected from the group consisting of oxygen, nitrogen, sulfur, phosphorus and combinations thereof.

41. The method of embodiment 39, wherein said subject is a mammal.

42. The method of embodiment 41, wherein said subject is a human.

43. The method of embodiment 40 wherein said subject is a mammal.

44. The method of embodiment 43, wherein said mammal is a human.

45. The method of embodiment 39, wherein said therapeutically effective amount is administered in a single dose or in multiple divided doses.

46. The method of embodiment 40, wherein said therapeutically effective amount is administered in a single dose or in multiple divided doses.

47. A method for treating a hyperlipidemic condition in a subject comprising administering to said subject in need thereof a therapeutically effective amount of a compound of Formulas I-17 or I-18 represented by:

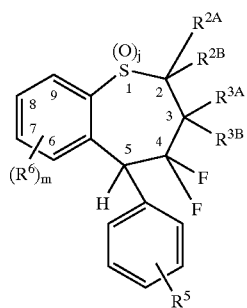

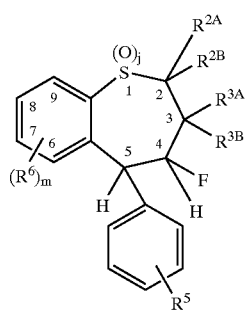

or a pharmaceutically acceptable salt, solvate, or prodrug thereof wherein j is 0, 1 or 2;

wherein m is 0, 1, 2, 3 or 4;

wherein $R^{2A}$ and $R^{2B}$ are independently selected from the group consisting of hydrogen and hydrocarbyl;

wherein $R^{3A}$, $R^{3B}$, $R^{5A}$, and $R^{5B}$ are independently selected from the group consisting of hydrogen, alkyl; cycloalkyl; alkenyl; alkynyl; heterocyclyl; quaternary heterocyclyl, oxo; aryl-$R^5$; —$OR^9$; —$NR^9R^{10}$; —$SR^9$; —$S(O)R^9$; —$SO_2R^9$; and —$SO_3R^9$;

wherein $R^9$ and $R^{10}$ are independently selected from the group consisting of hydrogen; hydrocarbyl; amino; and hydrocarbylamino;

wherein $R^5$ is selected from the group consisting of hydrogen; hydrocarbyl, heterocyclyl; quaternary heterocyclyl; —$OR^9$; —$SR^9$; —$S(O)R^9$; —$SO_2R^9$; and —$SO_3R^9$;

wherein when $R^5$ is said cycloalkyl, aryl or heterocyclyl, said cycloalkyl, aryl or heterocyclyl are optionally substituted with —NH—X—R or —O—X—R;

wherein X is selected from the group consisting of —(C=O)$_s$-alkyl-; —(C=O)$_s$-alkyl-NH—; —(C=O)$_s$-alkyl-O—; —(C=O)$_s$-alkyl-(C=O)$_t$; and a covalent bond, wherein s and t are independently 0 or 1;

wherein R is selected from the group consisting of monosaccharides, disaccharides, and polysaccharides, wherein said monosaccharides, disaccharides, and polysaccharides are optionally protected with one or more sugar protecting groups;

wherein $R^9$ and $R^{10}$ are as previously defined;

wherein, when $R^5 \neq H$, $R^5$ is optionally substituted with one or more radicals independently selected from the group consisting of halogen; —$NO_2$; —CN; oxo; hydrocarbyl; —$OR^{13}$; —$NR^{13}R^{14}$; —$SR^{13}$; —$S(O)R^{13}$; —$SO_2R^{13}$; —$SO_3R^{13}$; —$NR^{13}OR^{14}$; —$NR^{13}NR^{14}R^{15}$; —$CO_2R^{13}$; —OM; —$SO_2OM$; —$SO_2NR^{13}R^{14}$; —$C(O)NR^{13}R^{14}$; —C(O)OM; —$COR^{13}$; —$NR^{13}C(O)R^{14}$; —$NR^{13}C(O)NR^{14}R^{15}$; —$NR^{13}CO_2R^{14}$; —$OC(O)R^{13}$; —$OC(O)NR^{13}R^{14}$; —$NR^{13}SOR^{14}$; —$NR^{13}SO_2R^{14}$; —$NR^{13}SONR^{14}R^{15}$; —$NR^{13}SO_2NR^{14}R^{15}$; —$PR^{13}R^{14}$; —$P(O)R^{13}R^{14}$; —$P^+R^{13}R^{14}R^{15}A^-$; —$P(OR^{13})OR^{14}$; —$S^+R^{13}R^{14}A^-$; and —$N^+R^{13}R^{14}R^{15}A^-$;

wherein $R^{13}$, $R^{14}$, and $R^{15}$ are independently selected from the group consisting of hydrogen and hydrocarbyl;

wherein $A^-$ is a pharmaceutically acceptable anion;

wherein M is a pharmaceutically acceptable cation;

wherein one or more $R^6$ radicals are independently selected from the group consisting of hydrogen; halogen; —CN; —$NO_2$; hydrocarbyl; —$R^5$; —$OR^{13}$; —$NR^{13}R^{14}$; —$SR^{13}$; —$S(O)R^{13}$; —$S(O)_2R^{13}$; —$SO_3R^{13}$; —$S^+R^{13}R^{14}A^-$; —$NR^{13}OR^{14}$; —$NR^{13}NR^{14}R^{15}$; —OM; —$SO_2OM$; —$SO_2NR^{13}R^{14}$; —$NR^{14}C(O)R^{13}$; —C(O)OM; —$S(O)NR^{13}R^{14}$; —$N^+R^{13}R^{14}R^{15}A^-$; —$PR^{13}R^{14}$; —$P(O)R^{13}R^{14}$; —$P^+R^{13}R^{14}R^{15}A^-$; amino acid residue; peptide residue; polypeptide residue; and carbohydrate residue;

wherein $R^{13}$, $R^{14}$, $R^{15}$, $A^-$, and M are as defined above; and wherein, in each instance, said hydrocarbyl may be optionally substituted with one or more groups comprising one or more heteroatoms, and wherein, in each instance, said hydrocarbyl optionally may have one or more carbon atoms replaced by one or more heteroatoms independently selected from the group consisting of oxygen, nitrogen, sulfur, phosphorus and combinations thereof.

48. The method of embodiment 47 wherein said Formula I-17 comprises a member selected from the group consisting of I-21 and I-22 represented by:

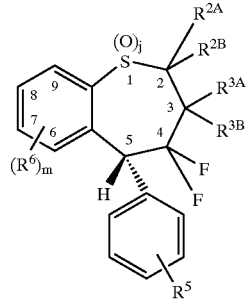

I-21

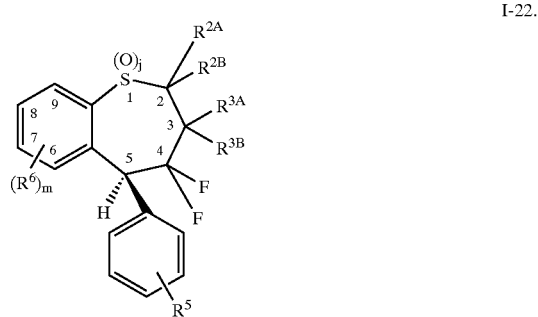

I-22.

49. The method of embodiment 48 wherein said Formulas I-21 and I-22 comprise Formulas I-9 and I-10, respectively, represented by:

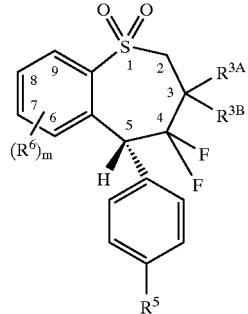

I-9

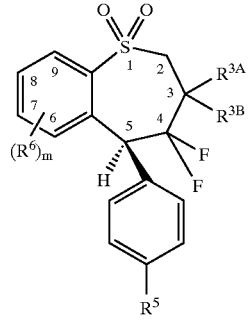

I-10.

50. The method of embodiment 47 wherein said Formula I-18 comprises a member selected from the group consisting of I-19 and I-20 represented by:

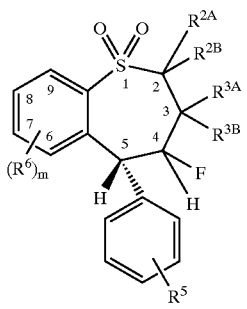

I-19

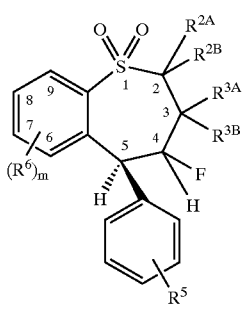

I-20.

51. The method of embodiment 50 wherein said Formulas I-19 and I-20 comprise Formulas I-11 and I-12, respectively, represented by:

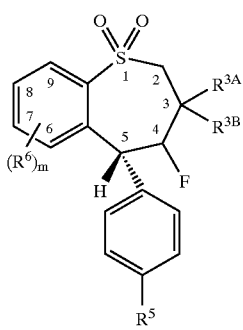

I-11

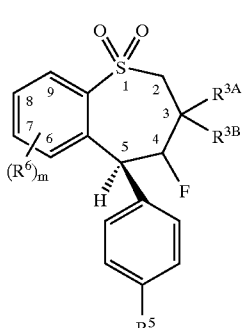

I-12.

52. The method of embodiment 51 where said Formula I-11 comprises a member selected from the group consisting of Formulas I-13 and I-16 represented by:

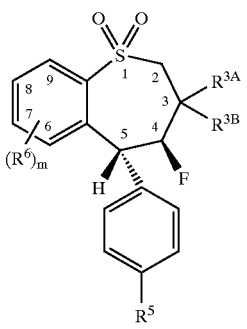

I-13

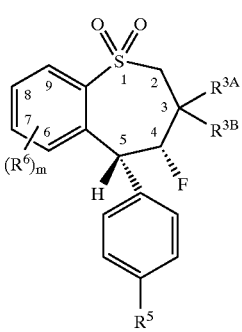

I-16.

53. The method of embodiment 51 wherein said Formula I-12 comprises a member selected from the group consisting of Formulas I-14 and I-15 represented by:

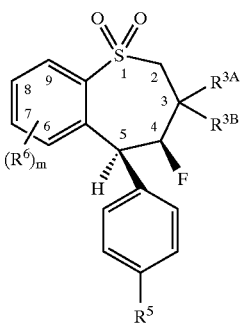

I-14

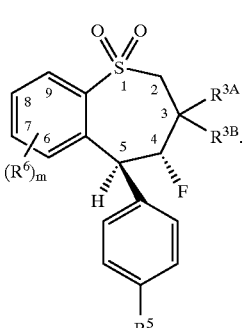

I-15

54. The method of embodiments 47–53 wherein said $R^5$ is a member selected from the group consisting of (1)–(69) and (70):
(1)
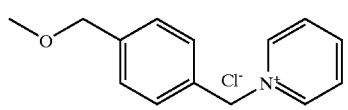
(2)
(3)
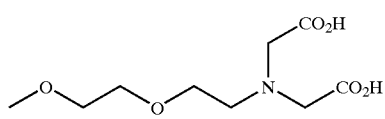
(4)
(5)
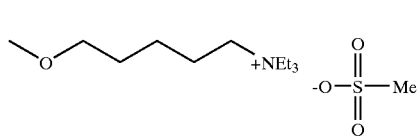
(6)
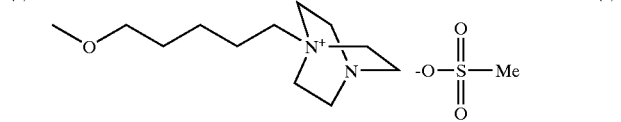
(7)
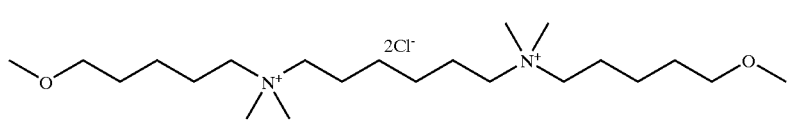
(8)
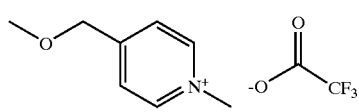
(9)
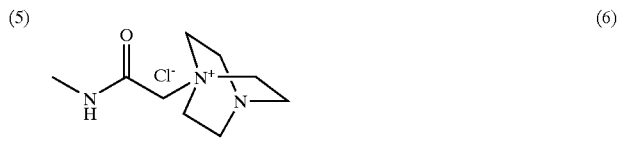
(10)
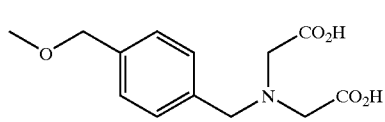
(11)
(12)
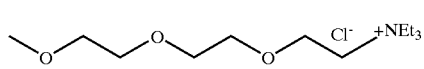
(13)
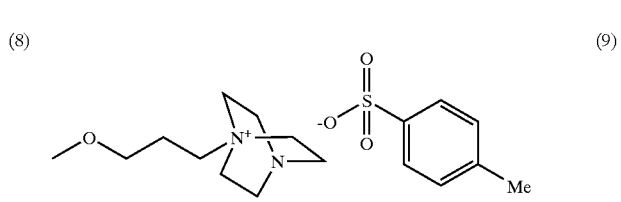
(14)
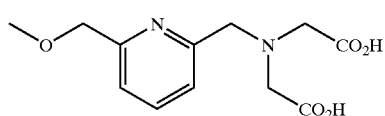
(15)
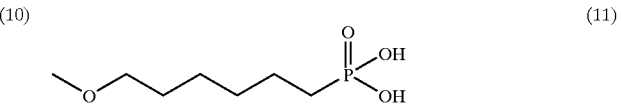
(15a)
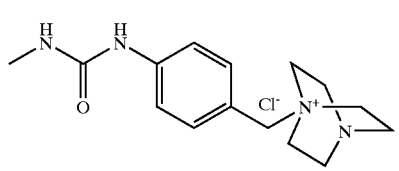
(16)
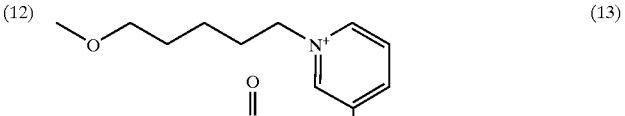
(17)
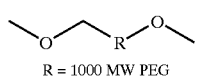
R = 1000 MW PEG
(18)
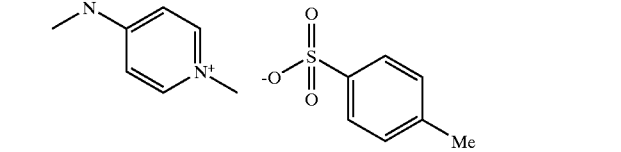

-continued
(19)
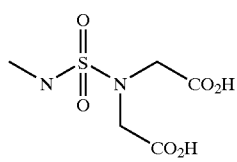
(20)
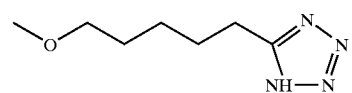
(21)
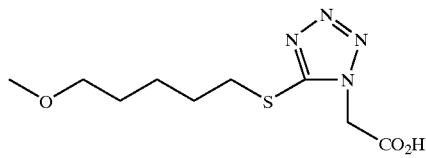
(22)
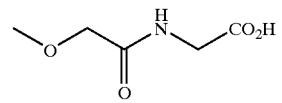
(23)
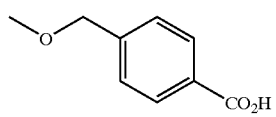
(24)
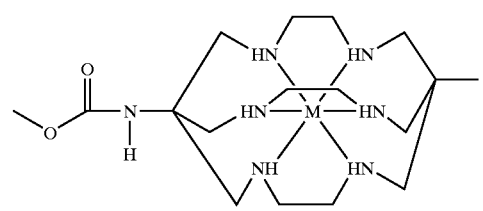
M = $Co^{II,III}$, $Mn^{II,III}$, $Fe^{II,III}$, $Ni^{II,III}$, $Cr^{III}$, $Cu^{II}$, $Zn^{II}$, $Cd^{II}$, $Ga^{III}$, $In^{III}$, $V^{IV}$, $Ru^{II}$, $Pr^{IV}$, $Rh^{III}$ or $Ir^{III}$
(25)
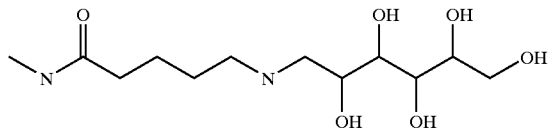
(26)
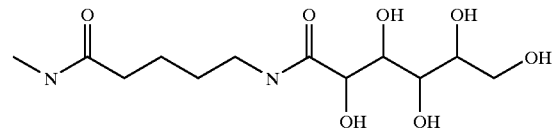
(27)
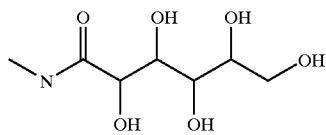
(28)
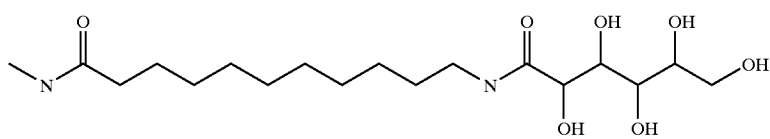
(29)
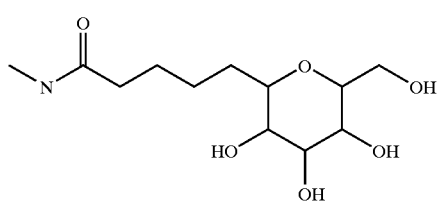
(30)
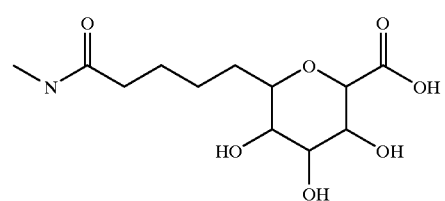
(31)
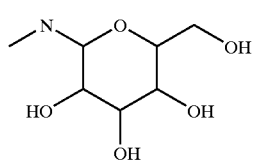
(32)
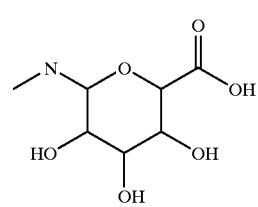

-continued
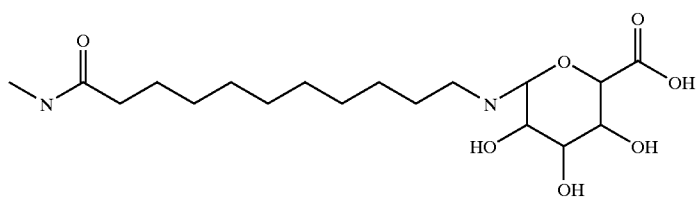
(33)
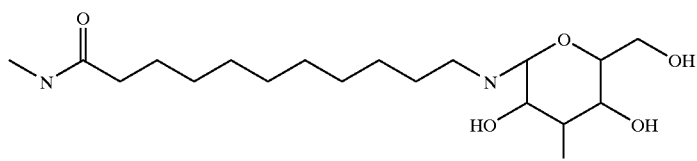
(34)
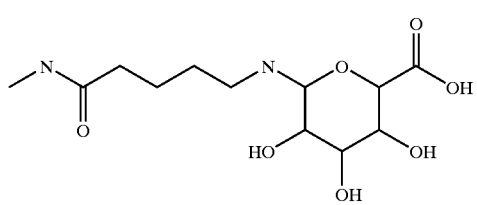
(35)
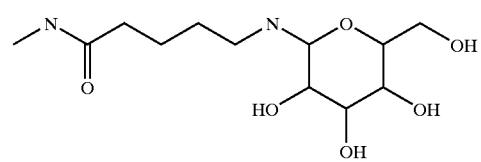
(36)
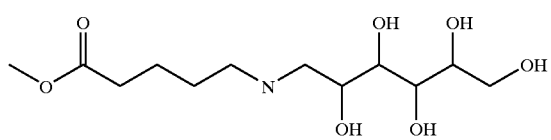
(37)
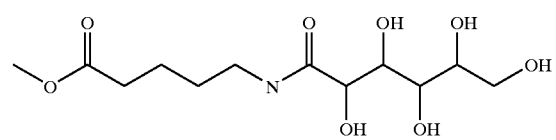
(38)
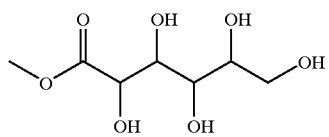
(39)
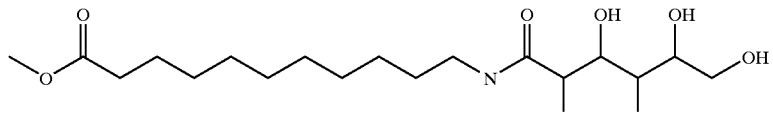
(40)
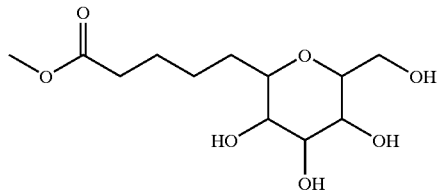
(41)
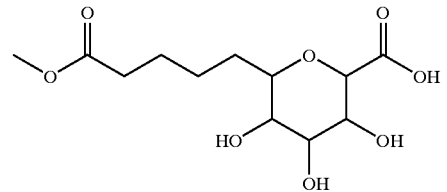
(42)
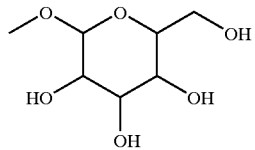
(43)
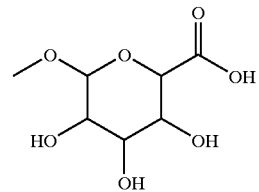
(44)
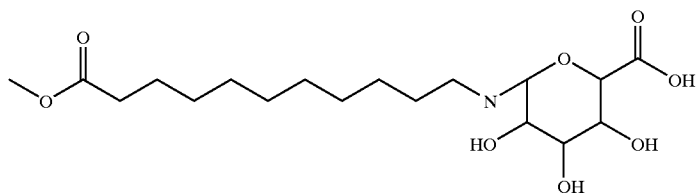
(45)

-continued
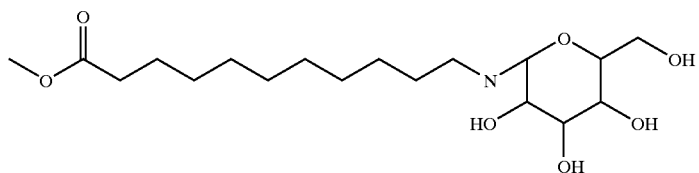
(46)
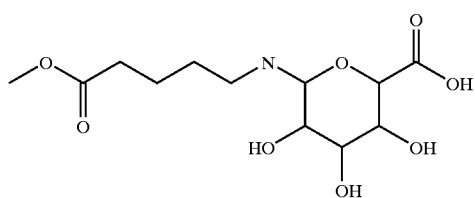
(47)
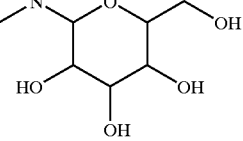
(48)
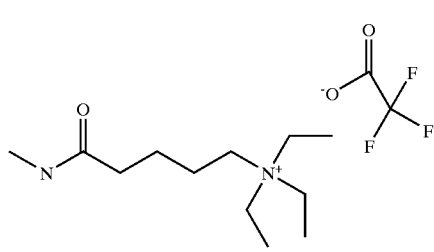
(49)
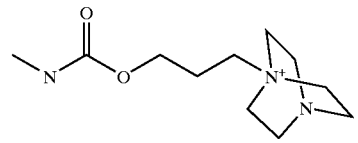
(50)
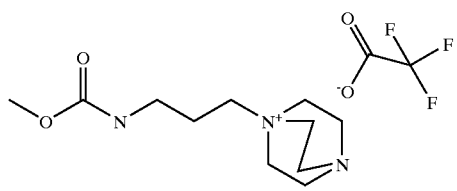
(51)
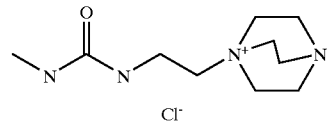
(52)
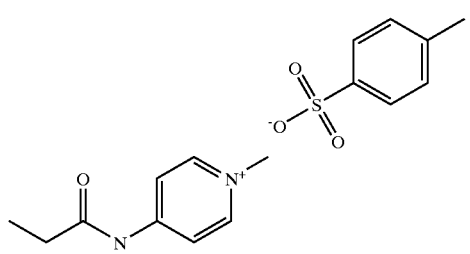
(53)
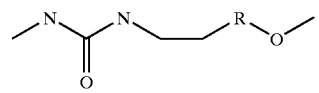
(54)
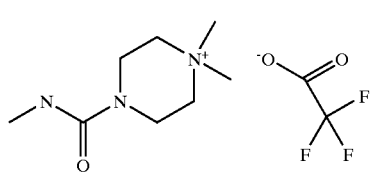
(55)
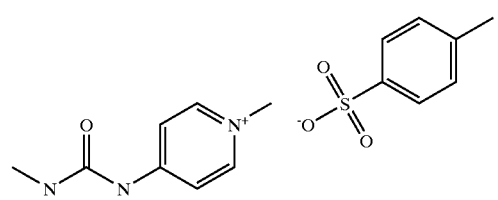
(56)

(57) 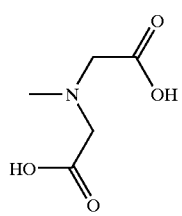
(58) 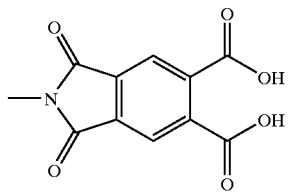
(59) 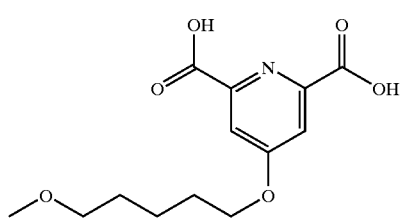
(60) 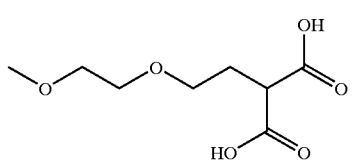
(61) 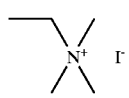
(62) 
(63) 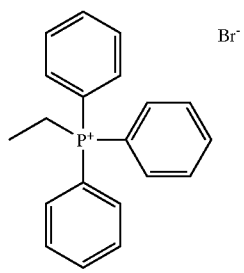
(64) 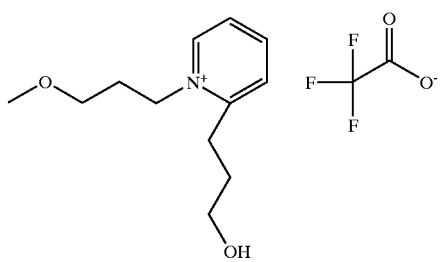
(65) 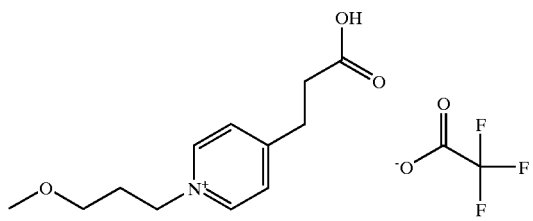
(66) 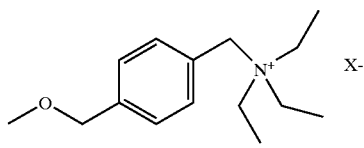
(67) 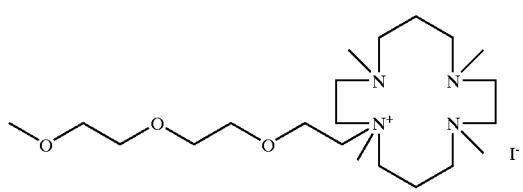
(68) 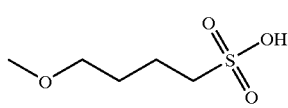
(69) 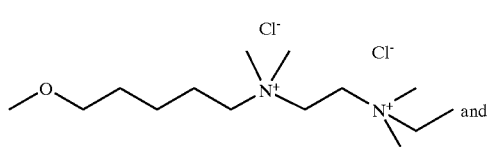 and
(70) 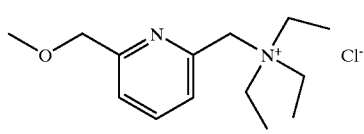

provided that when said R⁵ is (7), (17) or (24), then said R⁵ᴬ is a left end of said R⁵ and said R⁵ᴮ is a right end of said R⁵ or vice versa.

55. A method for treating gallstones or a condition associated therewith in a subject in need thereof, said method comprising administering a therapeutically effective amount of a compound of Formulas I-17 or I-18 represented by:

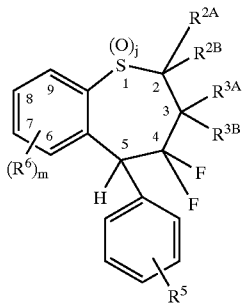

I-17

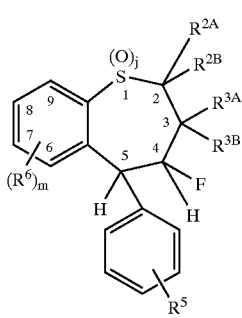

I-18 or a pharmaceutically acceptable salt, solvate, or prodrug thereof wherein j is 0, 1 or 2;

wherein m is 0, 1, 2, 3 or 4;

wherein $R^{2A}$ and $R^{2B}$ are independently selected from the group consisting of hydrogen and hydrocarbyl; wherein $R^{3A}$, $R^{3B}$, $R^{5A}$, and $R^{5B}$ are independently selected from the group consisting of hydrogen, alkyl; cycloalkyl; alkenyl; alkynyl; heterocyclyl; quaternary heterocyclyl, oxo; aryl-$R^5$; —$OR^9$; —$NR^9R^{10}$; —$SR^9$; —$S(O)R^9$; —$SO_2R^9$; and —$SO_3R^9$;

wherein $R^9$ and $R^{10}$ are independently selected from the group consisting of hydrogen; hydrocarbyl; amino; and hydrocarbylamino;

wherein $R^5$ is selected from the group consisting of hydrogen; hydrocarbyl, heterocyclyl; quaternary heterocyclyl; —$OR^9$; —$SR^9$; —$S(O)R^9$; —$SO_2R^9$; and —$SO_3R^9$;

wherein when $R^5$ is said cycloalkyl, aryl or heterocyclyl, said cycloalkyl, aryl or heterocyclyl are optionally substituted with —NH—X—R or —O—X—R;

wherein X is selected from the group consisting of —(C=O)ₛ-alkyl-; —(C=O)ₛ-alkyl-NH—; —(C=O)ₛ-alkyl-O—; —(C=O)ₛ-alkyl-(C=O)ₜ; and a covalent bond, wherein s and t are independently 0 or 1;

wherein R is selected from the group consisting of monosaccharides, disaccharides, and polysaccharides, wherein said monosaccharides, disaccharides, and polysaccharides are optionally protected with one or more sugar protecting groups;

wherein $R^9$ and $R^{10}$ are as previously defined;

wherein, when $R^5 \neq H$, $R^5$ is optionally substituted with one or more radicals independently selected from the group consisting of halogen; —$NO_2$; —CN; oxo; hydrocarbyl; —$OR^{13}$; —$NR^{13}R^{14}$; —$SR^{13}$; —$S(O)R^{13}$; —$SO_2R^{13}$; —$SO_3R^{13}$; —$NR^{13}OR^{14}$; —$NR^{13}NR^{14}R^5$; —$CO_2R^{13}$; —OM; —$SO_2OM$; —$SO_2NR^{13}R^{14}$; —$C(O)NR^{13}R^{14}$; —C(O)OM; —$COR^{13}$; —$NR^{13}C(O)R^{14}$; —$NR^{13}C(O)NR^{14}R^{15}$; —$NR^{13}CO_2R^{14}$; —$OC(O)R^{13}$; —$OC(O)NR^{13}R^{14}$; —$NR^{13}SOR^{14}$; —$NR^{13}SO_2R^{14}$; —$NR^{13}SONR^{14}R^{15}$; —$NR^{13}SO_2NR^{14}R^{15}$; —$PR^{13}R^{14}$; —$P(O)R^{13}R^{14}$; —$P^+R^{13}R^{14}R^{15}A^-$; —$P(OR^{13})OR^{14}$; —$S^+R^{13}R^{14}A^-$; and —$N^+R^{13}R^{14}R^{15}A^-$;

wherein $R^{13}$, $R^{14}$, and $R^{15}$ are independently selected from the group consisting of hydrogen and hydrocarbyl;

wherein $A^-$ is a pharmaceutically acceptable anion;

wherein M is a pharmaceutically acceptable cation;

wherein one or more $R^6$ radicals are independently selected from the group consisting of hydrogen; halogen; —CN; —$NO_2$; hydrocarbyl; —$R^5$; —$OR^{13}$; —$NR^{13}R^{14}$; —$SR^{13}$; —$S(O)R^{13}$; —$S(O)_2R^{13}$; —$SO_3R^{13}$; —$S^+R^{13}R^{14}A^-$; —$NR^{13}OR^{14}$; —$NR^{13}NR^{14}R^{15}$; —OM; —$SO_2OM$; —$SO_2NR^{13}R^{14}$; —$NR^{14}C(O)R^{13}$; —C(O)OM; —$S(O)NR^{13}R^{14}$; —$N^+R^{13}R^{14}R^{15}A^-$; —$PR^{13}R^{14}$; —$P(O)R^{13}R^{14}$; —$P^+R^{13}R^{14}R^{15}A^-$; amino acid residue; peptide residue; polypeptide residue; and carbohydrate residue;

wherein $R^{13}$, $R^{14}$, $R^{15}$, $A^-$, and M are as defined above; and wherein, in each instance, said hydrocarbyl may be optionally substituted with one or more groups comprising one or more heteroatoms, and wherein, in each instance, said hydrocarbyl optionally may have one or more carbon atoms replaced by one or more heteroatoms independently selected from the group consisting of oxygen, nitrogen, sulfur, phosphorus and combinations thereof.

56. The method of embodiment 55 wherein said Formula I-17 comprises a member selected from the group consisting of I-21 and I-22 represented by:

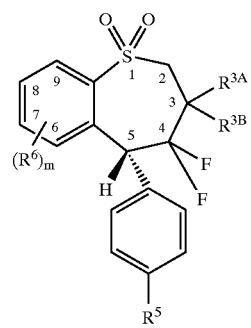

I-9

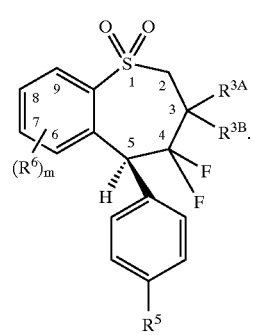

I-10

57. The method of embodiment 56 wherein said Formulas I-21 and I-22 comprise Formulas I-9 and I-10, respectively, represented by:

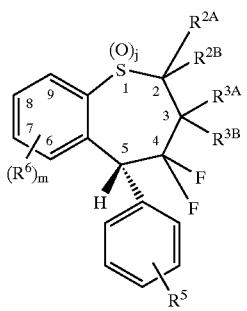

I-21

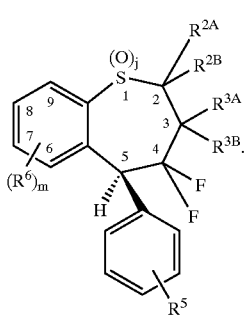

I-22

58. The method of embodiment 57 wherein said Formula I-18 comprises a member selected from the group consisting of I-19 and I-20 represented by:

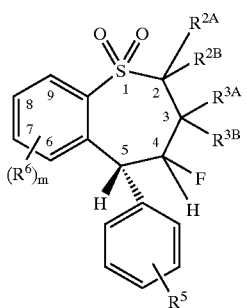

I-19

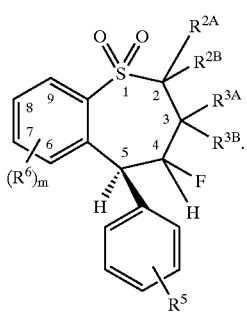

I-20

59. The method of embodiment 58 wherein said Formulas I-19 and I-20 comprise Formulas I-11 and I-12, respectively, represented by:

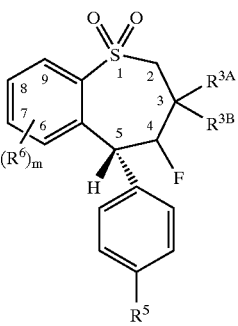

I-11

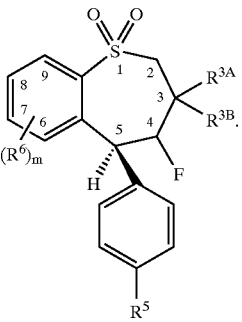

I-12

60. The method of embodiment 59 wherein said Formula I-11 comprises a member selected from the group consisting of Formulas I-13 and I-16 represented by:

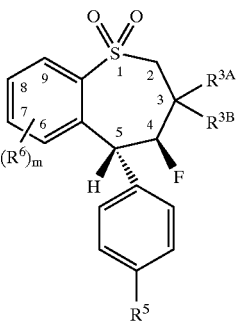

I-13

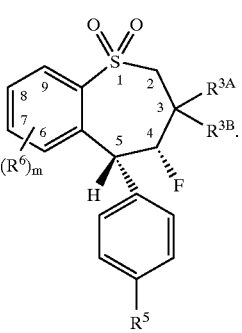

I-16

61. The method of embodiment 59 wherein said Formula I-12 comprises a member selected from the group consisting of Formulas I-14 and I-15 represented by:
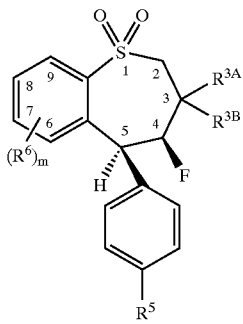
I-14
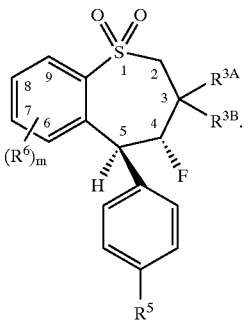
I-15
62. The method of embodiments 55–61 wherein said $R^5$ is a member selected from the group consisting of (1)–(69) and (70):
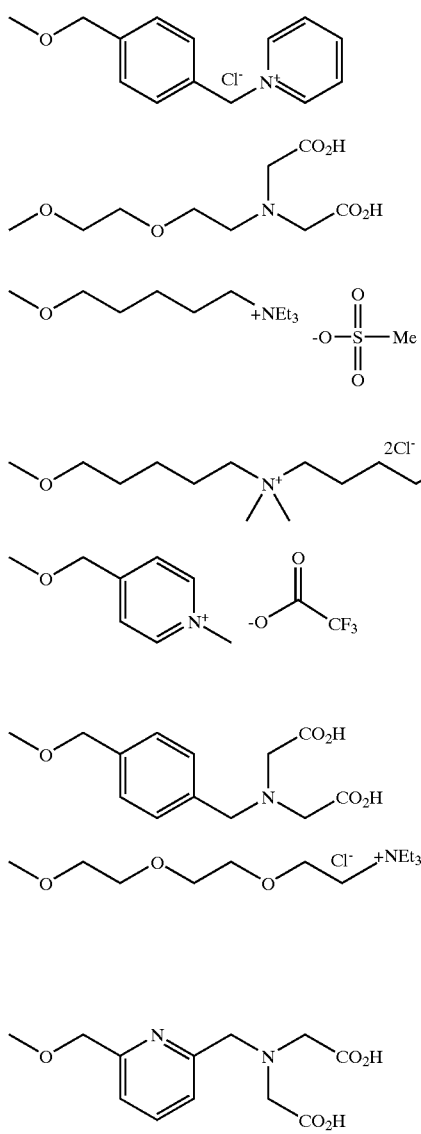
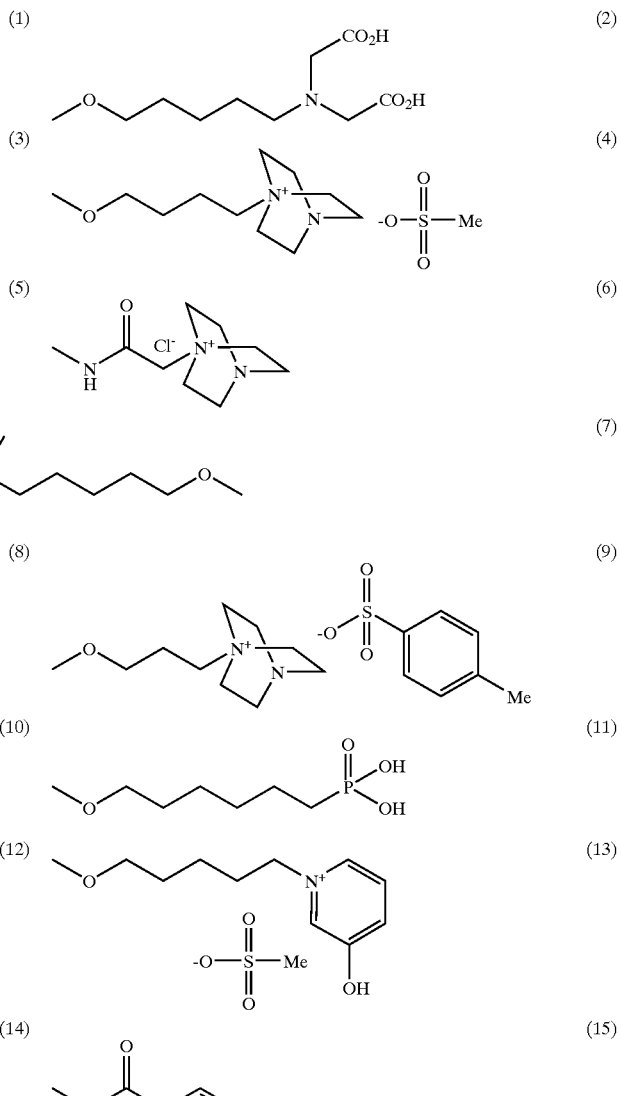

-continued
(15a) 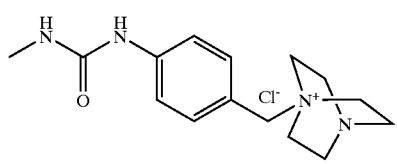
(16) 
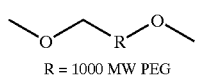
R = 1000 MW PEG
(17) (18) 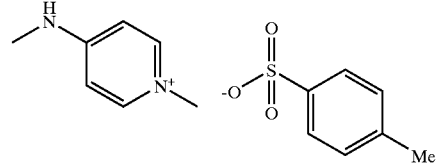
(19) 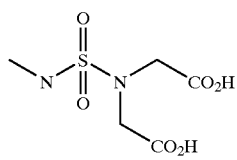
(20) 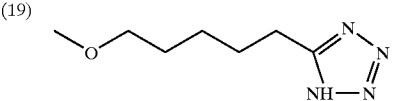
(21) 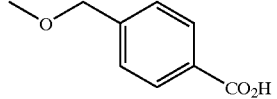
(22) 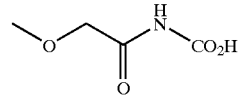
(23) 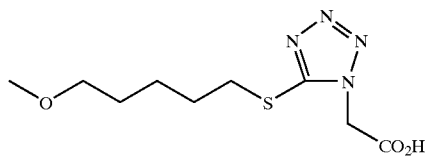
(24) 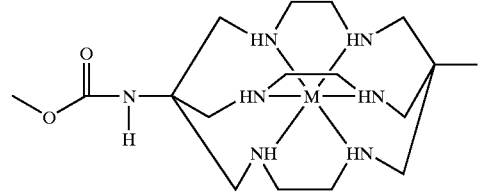
M = $Co^{II,III}$, $Mn^{II,III}$, $Fe^{II,III}$, $Ni^{II,III}$, $Cr^{III}$, $Cu^{II}$, $Zn^{II}$, $Cd^{II}$, $Ga^{III}$, $In^{III}$, $V^{IV}$, $Ru^{II}$, $Pr^{IV}$, $Rh^{III}$ or $Ir^{III}$
(25) 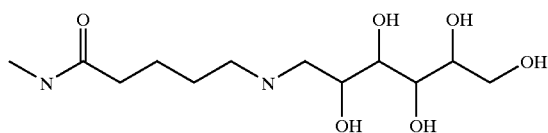
(26) 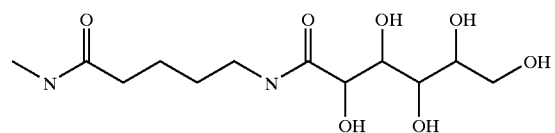
(27) 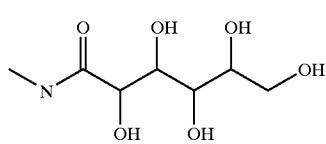

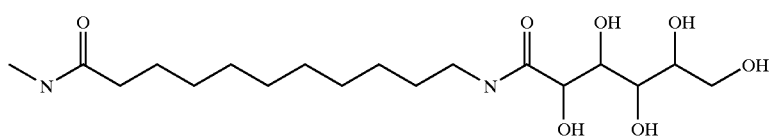
(28)
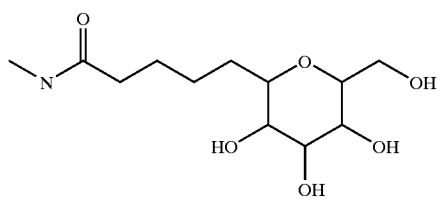
(29)
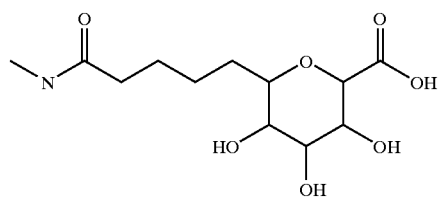
(30)
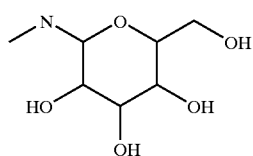
(31)
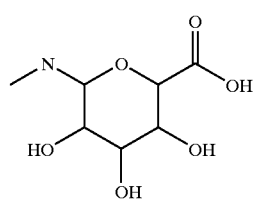
(32)
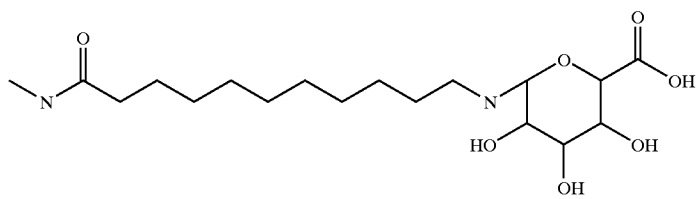
(33)
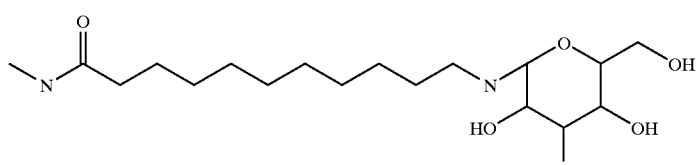
(34)
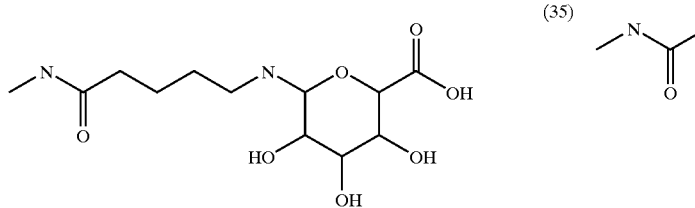
(35)
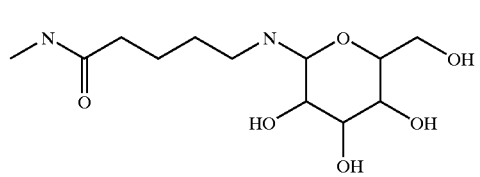
(36)
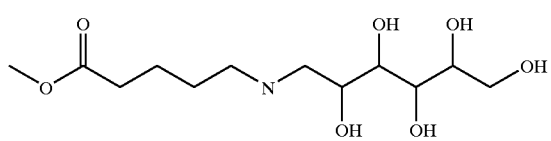
(37)
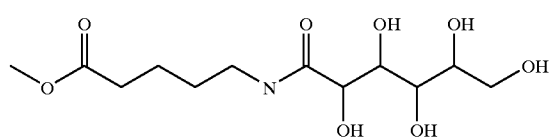
(38)

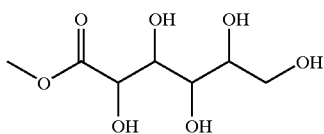
(39)
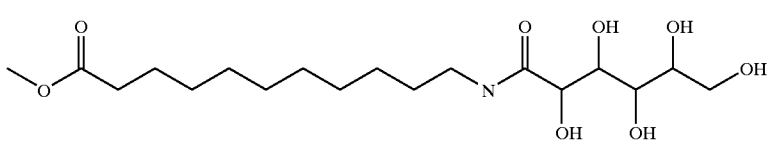
(40)
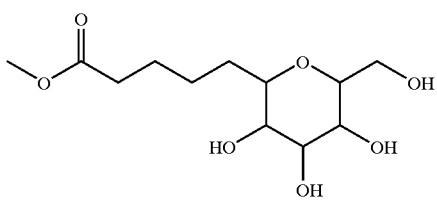
(41)
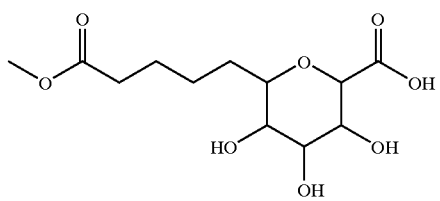
(42)
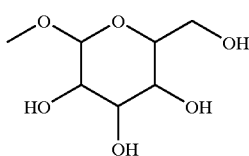
(43)
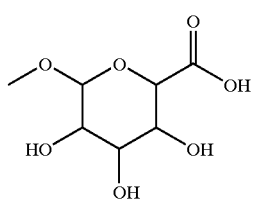
(44)
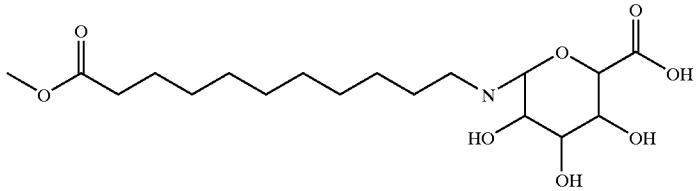
(45)
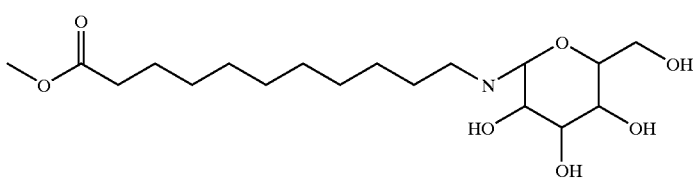
(46)
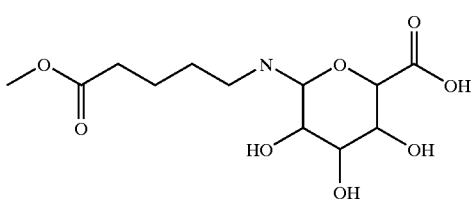
(47)
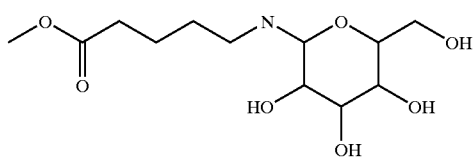
(48)
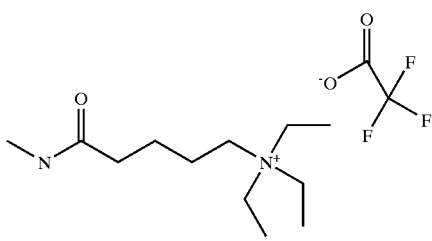
(49)
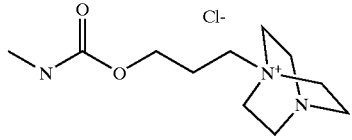
(50)

-continued
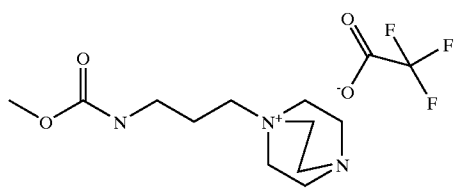
(51)
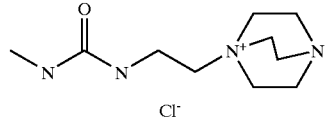
(52)
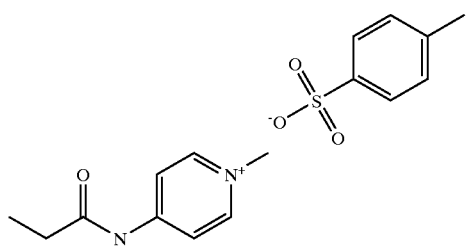
(53)
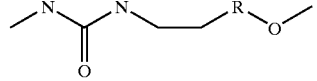
(54)
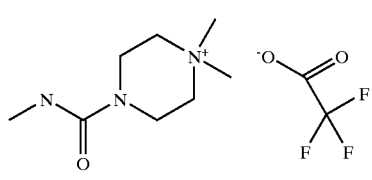
(55)
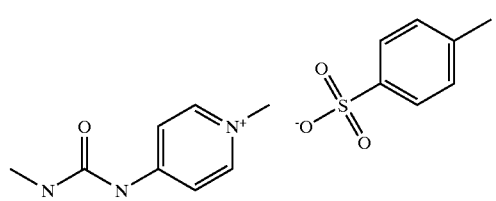
(56)
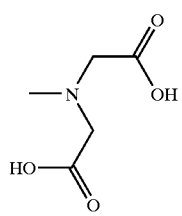
(57)
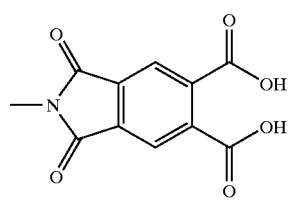
(58)
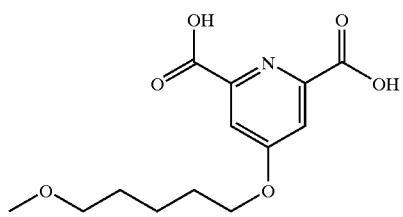
(59)
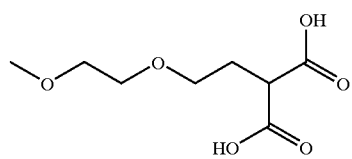
(60)
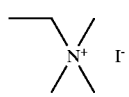
(61)
(62)
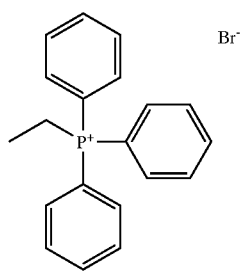
(63)
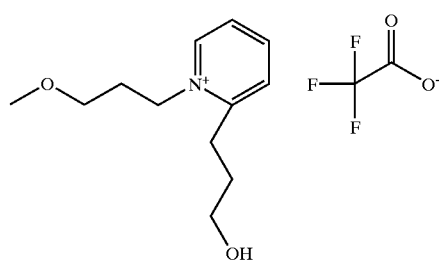
(64)

-continued

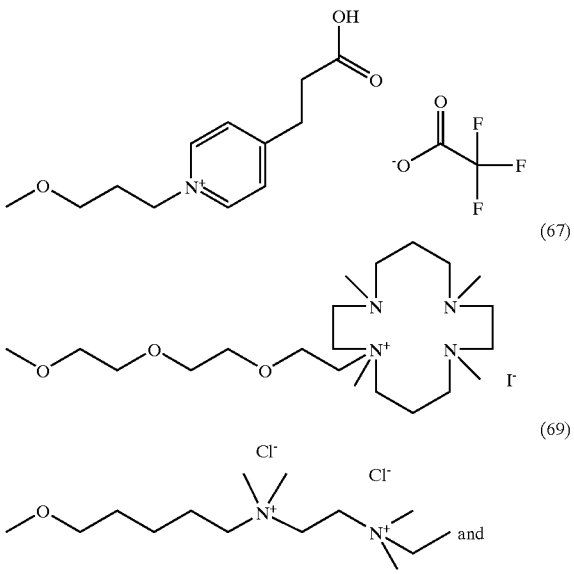

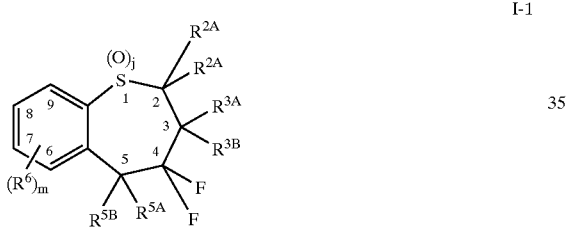

provided that when said $R^5$ is (7), (17) or (24), then said $R^{5A}$ is a left end of said $R^5$ and said $R^{5B}$ is a right end of said $R^5$ or vice versa.

63. A method of forming a compound of the Formula I-1:

I-1 or a pharmaceutically acceptable salt, solvate, or prodrug thereof wherein j is 0, 1 or 2;

wherein m is 0, 1, 2, 3 or 4;

wherein $R^{2A}$ and $R^{2B}$ are independently selected from the group consisting of hydrogen and hydrocarbyl;

wherein $R^{3A}$, $R^{3B}$, $R^{5A}$, and $R^{5B}$ are independently selected from the group consisting of hydrogen, alkyl; cycloalkyl; alkenyl; alkynyl; heterocyclyl; quaternary heterocyclyl, oxo; aryl-$R^5$; —$OR^9$; —$NR^9R^{10}$; —$SR^9$; —$S(O)R^9$; —$SO_2R^9$; and —$SO_3R^9$;

wherein $R^9$ and $R^{10}$ are independently selected from the group consisting of hydrogen; hydrocarbyl; amino; and hydrocarbylamino;

wherein $R^5$ is selected from the group consisting of hydrogen; hydrocarbyl; heterocyclyl; quaternary heterocyclyl; —$OR^9$; —$SR^9$; —$S(O)R^9$; —$SO_2R^9$; and —$SO_3R^9$;

wherein when $R^5$ is said cycloalkyl, aryl or heterocyclyl, said cycloalkyl, aryl or heterocyclyl are optionally substituted with —NH—X—R or —O—X—R;

wherein X is selected from the group consisting of —(C=O)$_s$-alkyl-; —(C=O)$_s$-alkyl-NH—; —(C=O)$_s$-alkyl-O—; (C=O)$_s$-alkyl-(C=O)$_t$; and a covalent bond, wherein s and t are independently 0 or 1;

wherein R is selected from the group consisting of monosaccharides, disaccharides, and polysaccharides, wherein said monosaccharides, disaccharides, and polysaccharides are optionally protected with one or more sugar protecting groups;

wherein $R^9$ and $R^{10}$ are as previously defined;

wherein, when $R^5 \ne H$, $R^5$ is optionally substituted with one or more radicals independently selected from the group consisting of halogen; —$NO_2$; —CN; oxo; hydrocarbyl; —$OR^{13}$; —$NR^{13}R^{14}$; —$SR^{13}$; —$S(O)R^{13}$; —$SO_2R^{13}$; —$SO_3R^{13}$; —$NR^{13}OR^{14}$; —$NR^{13}NR^{14}R^{15}$; —$CO_2R^{13}$; —OM; —$SO_2O$ M; —$SO_2NR^{13}R^{14}$; —$C(O)NR^{13}R^{14}$; —$C(O)OM$; —$COR^{13}$; —$NR^{13}C(O)R^{14}$; —$NR^{13}C(O)NR^{14}R^{15}$; —$NR^{13}CO_2R^{14}$; —$OC(O)R^{13}$; —$OC(O)NR^{13}R^{14}$; —$NR^{13}SOR^{14}$; —$NR^{13}SO_2R^{14}$; —$NR^{13}SONR^{14}R^{15}$; —$NR^{13}SO_2NR^{14}R^{15}$; —$PR^{13}R^{14}$; —$P(O)R^{13}R^{14}$; —$P^+R^{13}R^{14}R^{15}A^-$; —$P(OR^{13})OR^{14}$; —$S^+R^{13}R^{14}A^-$; and —$N^{30}R^{13}R^{14}R^{15}A^-$;

wherein $R^{13}$, $R^{14}$, and $R^{15}$ are independently selected from the group consisting of hydrogen and hydrocarbyl;

wherein $A^-$ is a pharmaceutically acceptable anion;

wherein M is a pharmaceutically acceptable cation;

wherein one or more $R^6$ radicals are independently selected from the group consisting of hydrogen; halogen; —CN; —$NO_2$; hydrocarbyl; —$R^5$; —$OR^{13}$; —$NR^{13}R^{14}$; —$SR^{13}$; —$S(O)R^{13}$; —$S(O)_2R^{13}$; —$SO_3R^{13}$; —$S^+R^{13}R^{14}A^-$; —$NR^{13}OR^{14}$; —$NR^{13}NR^{14}R^{15}$; —OM; —$SO_2OM$; —$SO_2NR^{13}R^{14}$; —$NR^{14}C(O)R^{13}$; —$C(O)OM$; —$S(O)NR^{13}R^{14}$; —$N^{30}R^{13}R^{14}R^{15}A^-$; —$PR^{13}R^{14}$; —$P(O)R^{13}R^{14}$; —$P^+R^{13}R^{14}R^{15}A$—; amino acid residue; peptide residue; polypeptide residue; and carbohydrate residue;

wherein $R^{13}$, $R^{14}$, $R^{15}$, $A^-$, and M are as defined above; and wherein, in each instance, said hydrocarbyl may be optionally substituted with one or more groups comprising one or more heteroatoms, and wherein, in each instance, said hydrocarbyl optionally may have one or more carbon atoms replaced by one or more heteroatoms independently selected from the group consisting of oxygen, nitrogen, sulfur, phosphorus and combinations thereof, said method comprising the steps of:

(a) forming a compound of Formula S1-78c:

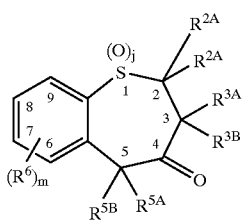

S1-78c wherein $R^{2A}$, $R^{2B}$, $R^{3A}$, $R^{3B}$, $R^{5A}$, $R^{5B}$, $R^6$, m and j are as previously defined; and (b) treating said compound of Formula S1-78c with diethylaminosulfur trifluoride to form said compound of Formula I-1.

64. The method of embodiment 63 wherein said treating step (b) is carried out in an inert solvent.

65. The method of embodiment 64 wherein said treating step (b) is carried out in said inert solvent cooled to from about −50° C. to about −78° C.

66. A method of forming a compound of Formula I-2:

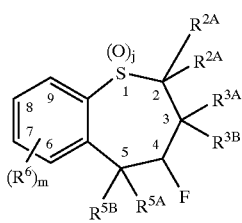

I-2 or a pharmaceutically acceptable salt, solvate, or prodrug thereof wherein j is 0, 1 or 2;

wherein m is 0, 1, 2, 3 or 4;

wherein $R^{2A}$ and $R^{2B}$ are independently selected from the group consisting of hydrogen and hydrocarbyl;

wherein $R^{3A}$, $R^{3B}$, $R^{5A}$, and $R^{5B}$ are independently selected from the group consisting of hydrogen, alkyl; cycloalkyl; alkenyl; alkynyl; heterocyclyl; quaternary heterocyclyl, oxo; aryl-$R^5$; —$OR^9$; —$NR^9R^{10}$; —$SR^9$; —$S(O)R^9$; —$SO_2R^9$; and —$SO_3R^9$;

wherein $R^9$ and $R^{10}$ are independently selected from the group consisting of hydrogen; hydrocarbyl; amino; and hydrocarbylamino;

wherein $R^5$ is selected from the group consisting of hydrogen; hydrocarbyl; heterocyclyl; quaternary heterocyclyl; —$OR^9$; —$SR^9$; —$S(O)R^9$; —$SO_2R^9$; and —$SO_3R^9$;

wherein when $R^5$ is said cycloalkyl, aryl or heterocyclyl, said cycloalkyl, aryl or heterocyclyl are optionally substituted with —NH—X—R or —O—X—R;

wherein X is selected from the group consisting of —(C=O)$_s$-alkyl-; —(C=O)$_s$-alkyl-NH—; —(C=O)$_s$-alkyl-O—; —(C=O)$_s$-alkyl-(C=O)$_t$; and a covalent bond, wherein s and t are independently 0 or 1;

wherein R is selected from the group consisting of monosaccharides, disaccharides, and polysaccharides, wherein said monosaccharides, disaccharides, and polysaccharides are optionally protected with one or more sugar protecting groups;

wherein $R^9$ and $R^{10}$ are as previously defined;

wherein, when $R^5 \neq H$, $R^5$ is optionally substituted with one or more radicals independently selected from the group consisting of halogen; —$NO_2$; —CN; oxo; hydrocarbyl; —$OR^{13}$; —$NR^{13}R^{14}$; —$SR^{13}$; —$S(O)R^{13}$; —$SO_2R^{13}$; —$SO_3R^{13}$; —$NR^{13}OR^{14}$; —$NR^{13}NR^{14}R^{15}$; —$CO_2R^{13}$; —OM; —$SO_2OM$; —$SO_2NR^{13}R^{14}$; —$C(O)NR^{13}R^{14}$; —$C(O)OM$; —$COR^{13}$; —$NR^{13}C(O)R^{14}$; —$NR^{13}C(O)NR^{14}R^{15}$; —$NR^{13}CO_2R^{14}$; —$OC(O)R^{13}$; —$OC(O)NR^{13}R^{14}$; —$NR^{13}SOR^{14}$; —$NR^{13}SO_2R^{14}$; —$NR^{13}SONR^{14}R^{15}$; —$NR^{13}SO_2NR^{14}R^{15}$; —$PR^{13}R^{14}$; —$P(O)R^{13}R^{14}$; —$P^+R^{13}R^{14}R^{15}A^-$; —$P(OR^{13})OR^{14}$; —$S^+R^{13}R^{14}A^-$; and —$N^{30}R^{13}R^{14}R^{15}A^-$;

wherein $R^{13}$, $R^{14}$, and $R^{15}$ are independently selected from the group consisting of hydrogen and hydrocarbyl;

wherein $A^-$ is a pharmaceutically acceptable anion;

wherein M is a pharmaceutically acceptable cation;

wherein one or more $R^6$ radicals are independently selected from the group consisting of hydrogen; halogen; —CN; —$NO_2$; hydrocarbyl; —$R^5$; —$OR^{13}$; —$NR^{13}R^{14}$; —$SR^{13}$; —$S(O)R^{13}$; —$S(O)_2R^{13}$; —$SO_3R^{13}$; —$S^+R^{13}R^{14}A^-$; —$NR^{13}OR^{14}$; —$NR^{13}NR^{14}R^{15}$; —OM; —$SO_2OM$; —$SO_2NR^{13}R^{14}$; —$NR^{14}C(O)R^{13}$; —$C(O)OM$; —$S(O)NR^{13}R^{14}$; —$N^{30}R^{13}R^{14}R^{15}A^-$; —$PR^{13}R^{14}$; —$P(O)R^{13}R^{14}$; —$P^+R^{13}R^{14}R^{15}A^-$; amino acid residue; peptide residue; polypeptide residue; and carbohydrate residue;

wherein $R^{13}$, $R^{14}$, $R^{15}$, $A^-$, and M are as defined above; and wherein, in each instance, said hydrocarbyl may be optionally substituted with one or more groups comprising one or more heteroatoms, and wherein, in each instance, said hydrocarbyl optionally may have one or more carbon atoms replaced by one or more heteroatoms independently selected from the group consisting of oxygen, nitrogen, sulfur, phosphorus and combinations thereof, said method comprising the steps of:

(a) forming a compound of Formula S1-78a:

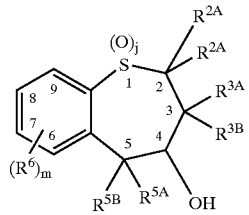

S1-78a wherein $R^{2A}$, $R^{2B}$, $R^{3A}$, $R^{3B}$, $R^{5A}$, $R^{5B}$, $R^6$, m and j are as previously defined; and (b) treating said compound of Formula S1-78a with diethylaminosulfur trifluoride to form said compound of Formula I-2.

67. The method of embodiment 66 wherein said treating step (b) is carried out in an inert solvent.

68. The method of embodiment 67 wherein said treating step (b) is carried out in said inert solvent cooled to from about −50° C. to about −78° C.

69. The method of embodiment 63 wherein said compound of Formula I-1 comprises Formula I-17 represented by:

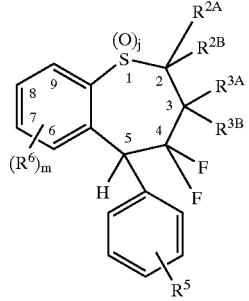

I-17 wherein $R^{2A}$, $R^{2B}$, $R^{3A}$, $R^{3B}$, $R^{5A}$, $R^{5B}$, $R^6$, m and j are as previously defined and $R^5$ is selected from the group consisting of (1)–(69) and (70):
(1) 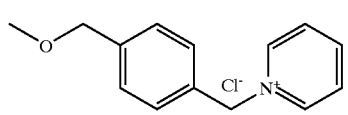
(2) 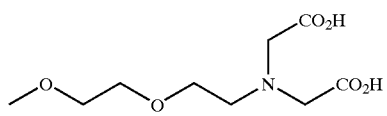
(3) 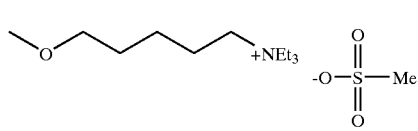
(4)
(5)
(6)
(7)
(8)
(9)
(10) 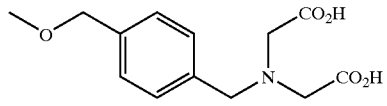
(11)
(12) 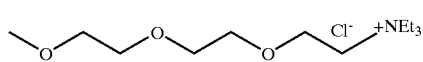
(13)
(14) 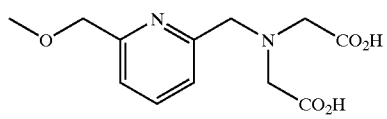
(15)
(15a) 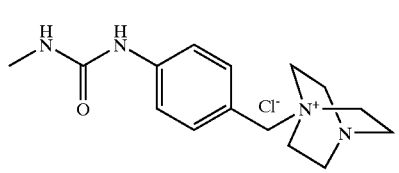
(16)
(17) 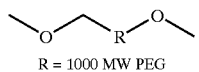
R = 1000 MW PEG
(18)

-continued
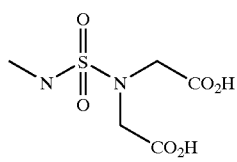 (19)
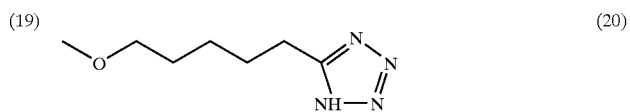 (20)
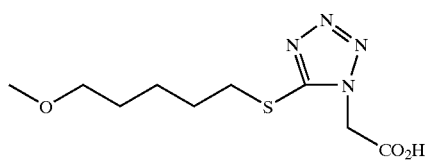 (21)
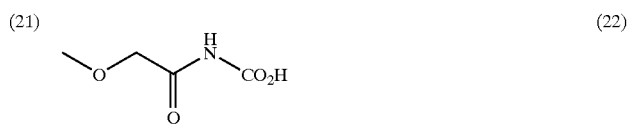 (22)
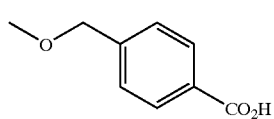 (23)
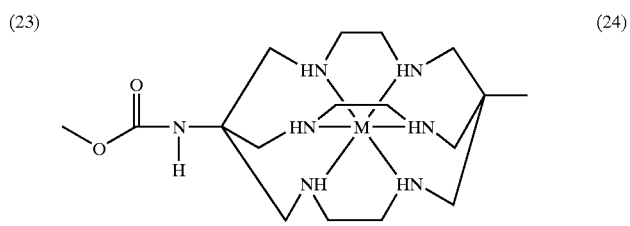 (24)
M = $Co^{II,III}$, $Mn^{II,III}$, $Fe^{II,III}$, $Ni^{II,III}$, $Cr^{III}$, $Cu^{II}$, $Zn^{II}$, $Cd^{II}$, $Ga^{III}$, $In^{III}$, $V^{IV}$, $Ru^{II}$, $Pr^{IV}$, $Rh^{III}$ or $Ir^{III}$
 (25)
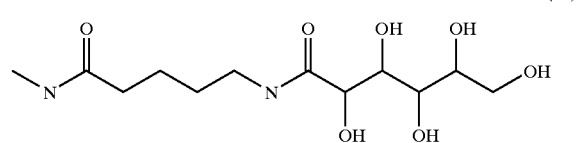 (26)
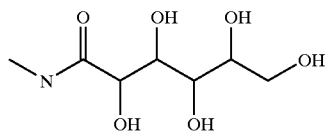 (27)
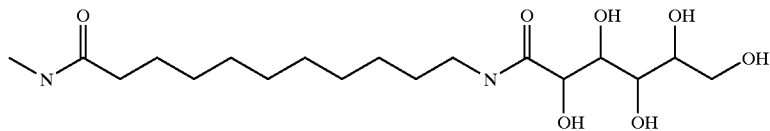 (28)
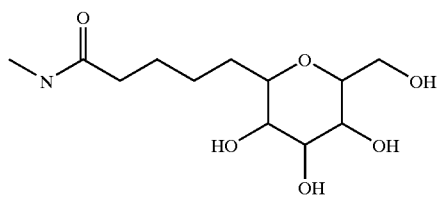 (29)
 (30)

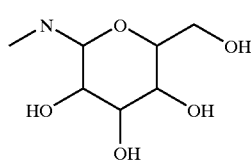
(31)
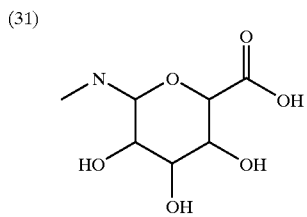
(32)
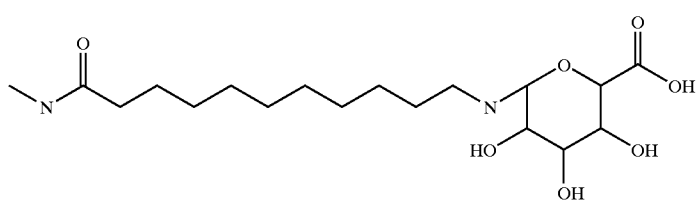
(33)
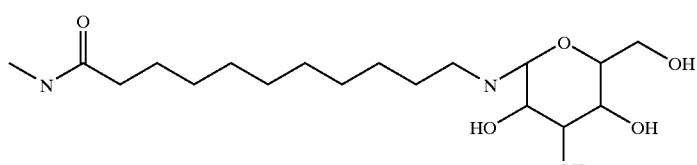
(34)
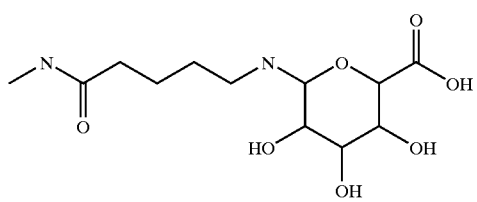
(35)
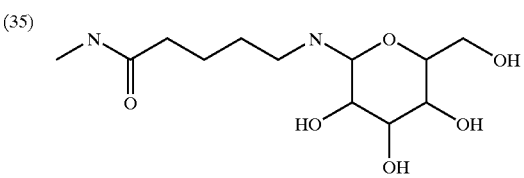
(36)
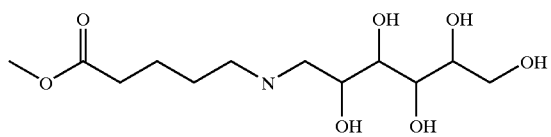
(37)
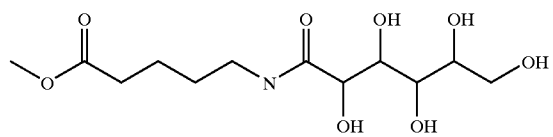
(38)
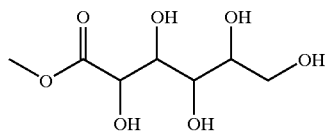
(39)
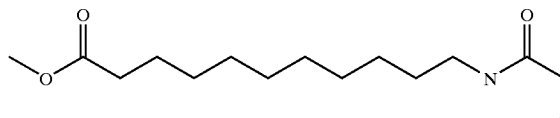
(40)
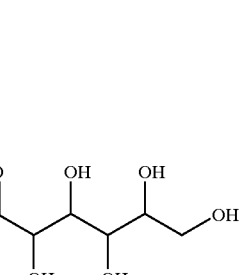
(41)
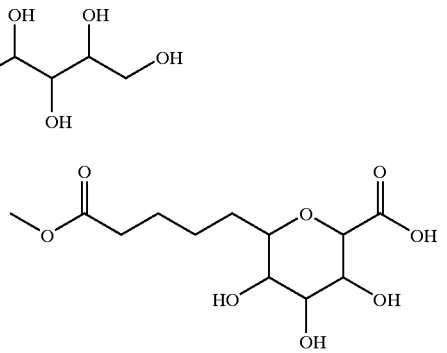
(42)

-continued
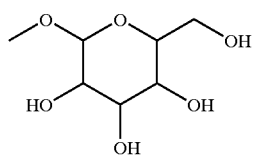 (43)
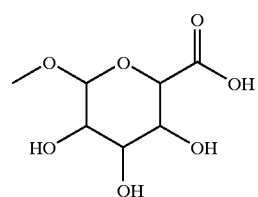 (44)
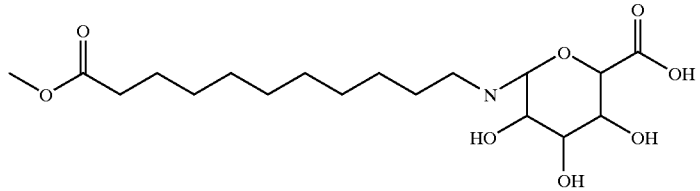 (45)
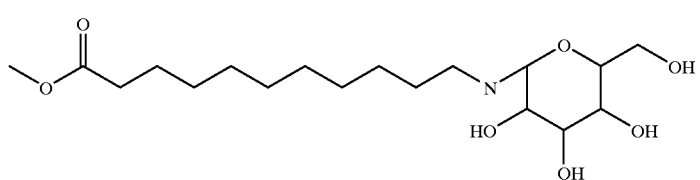 (46)
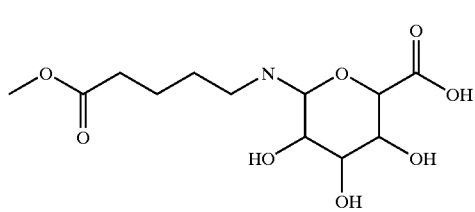 (47)
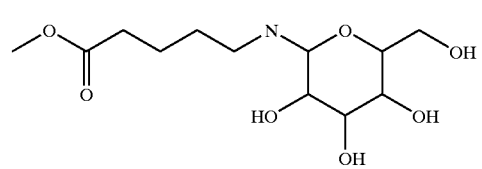 (48)
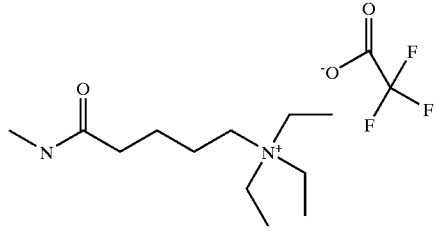 (49)
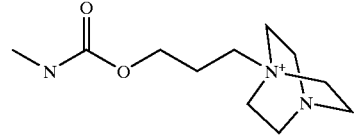 (50)
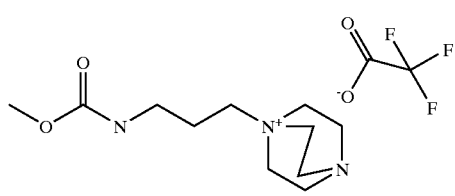 (51)
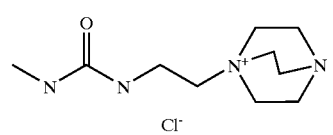 (52)

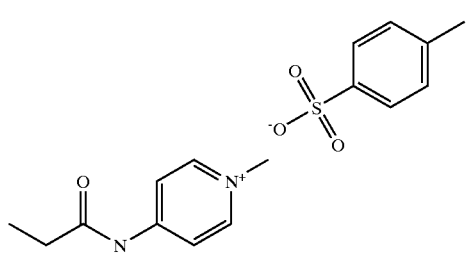
(53)
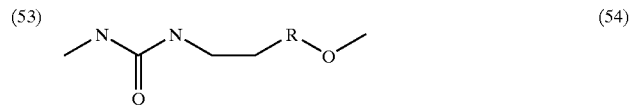
(54)
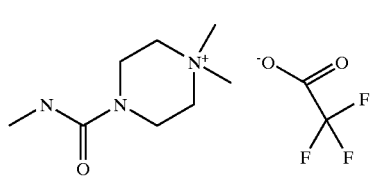
(55)
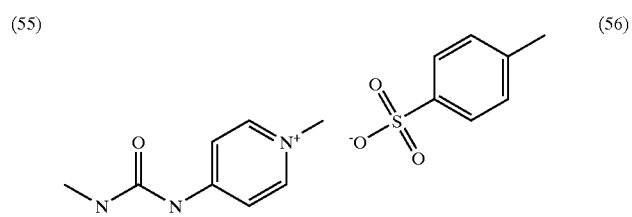
(56)
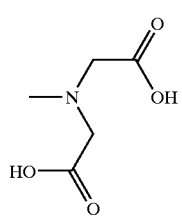
(57)
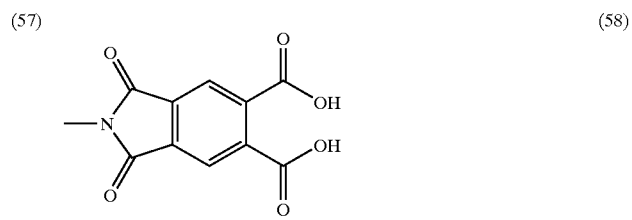
(58)
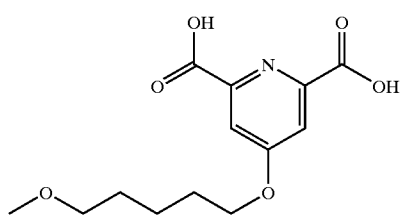
(59)
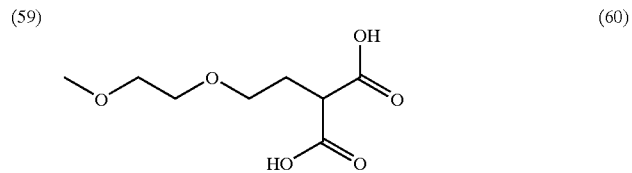
(60)
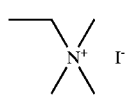
(61)
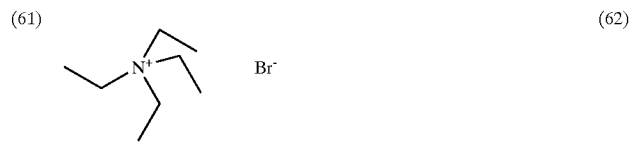
(62)
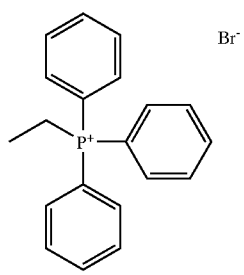
(63)
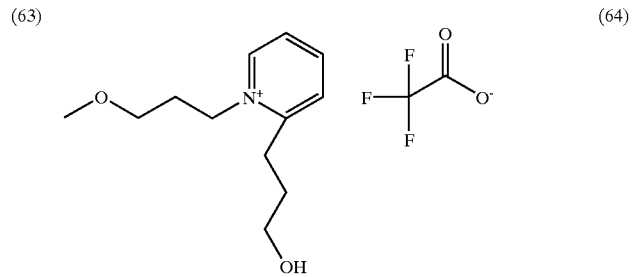
(64)

-continued

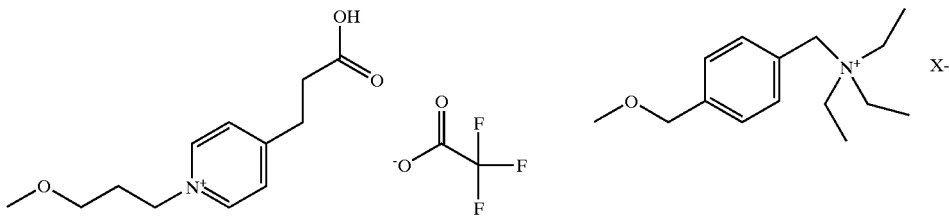

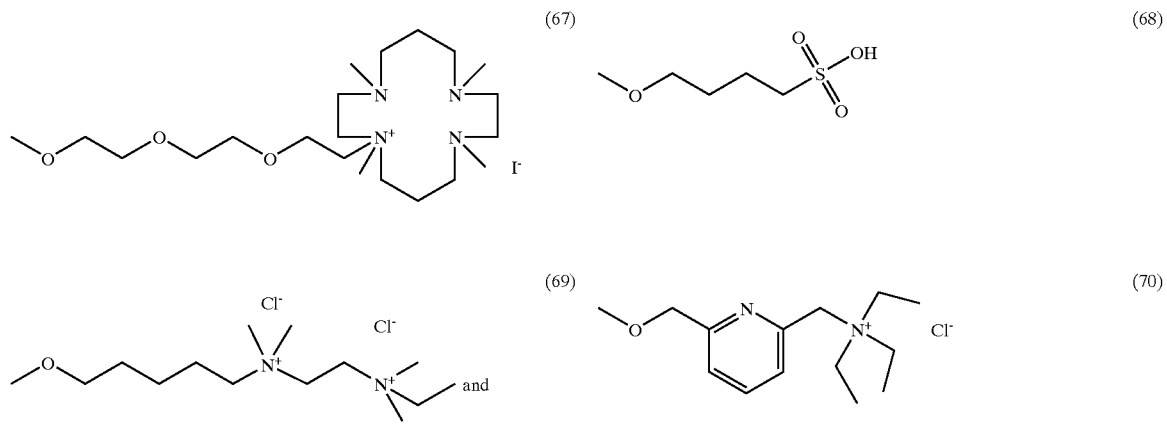

provied that when said $R^5$ is (7), (17) or (24), then said $R^{5A}$ is a left end of said $R^5$ and said $R^{5B}$ is a right end of said $R^5$ or vice versa.

70. The method of embodiment 69 wherein said Formula I-17 comprises Formulas I-21 or I-22 represented by:

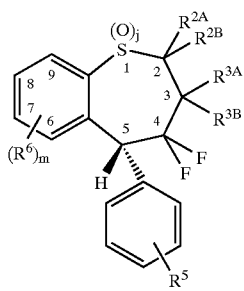

I-21

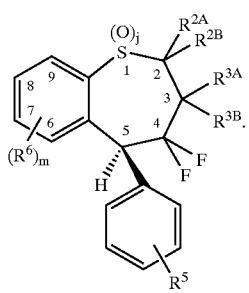

I-22

71. The method of embodiment 70 wherein said Formulas I-21 and I-22 comprise Formulas I-9 and I-10, respectively, represented by:

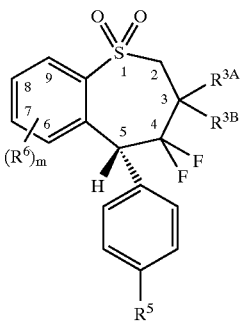

I-9

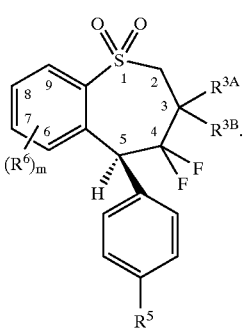

I-10

72. The method of embodiment 70 wherein said $R^5$ group is attached at least either at a meta position or at a para position of said phenyl ring attached to said 5-carbon on position of said benzothiepene of said Formulas I-21 or I-22.-

73. The method of embodiment 66 wherein said compound of Formula I-2 is selected from the group consisting of Formulas I-3 and I-4 represented by:
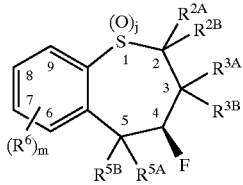
I-3
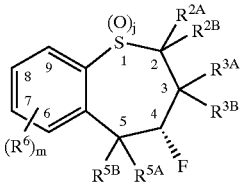
I-4
wherein $R^{2A}$, $R^{2B}$, $R^{3A}$, $R^{3B}$, $R^{5A}$, $R^{5B}$, $R^6$, m and j are as previously defined and said $R^5$ is selected from the group consisting of (1)–(69) and (70):
(1)
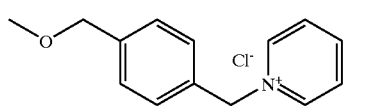
(2)
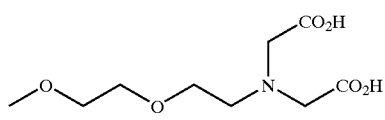
(3)
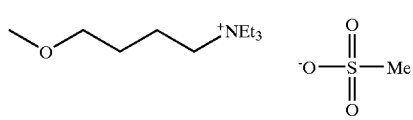
(4)
(5)
(6)
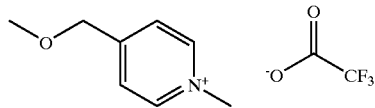
(7)
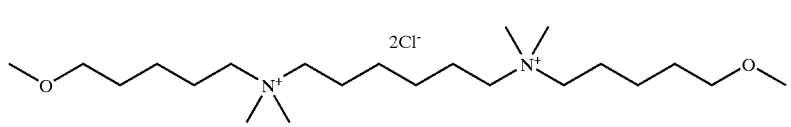
(8)
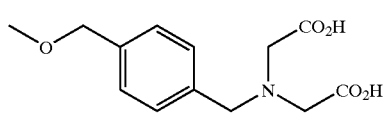
(9)
(10)
(11)
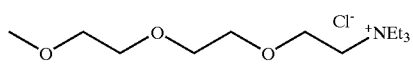
(12)
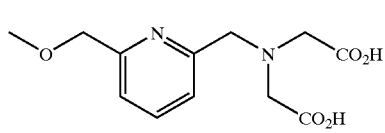
(13)
(14)
(15)
(15a)
(16)
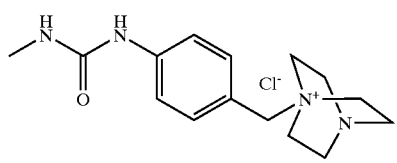

-continued
(17) 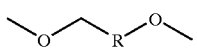
R = 1000 MW PEG
(18) 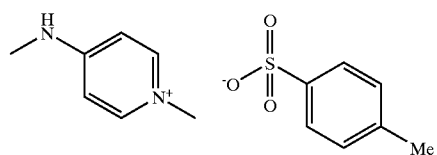
(19) 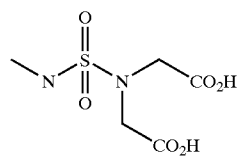
(20) 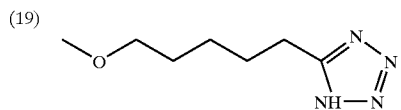
(21) 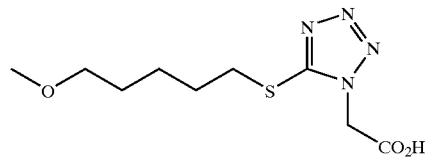
(22) 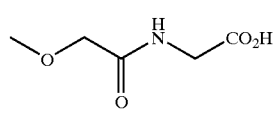
(23) 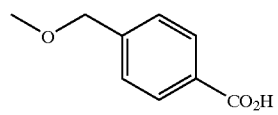
(24) 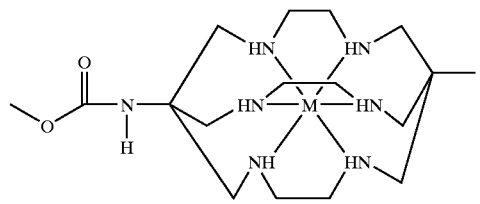
M = $Co^{II, III}$, $Mn^{II, III}$, $Fe^{II, III}$, $Ni^{II, III}$, $Cr^{III}$, $Cu^{II}$, $Zn^{II}$, $Cd^{II}$, $Ga^{III}$, $In^{III}$, $V^{IV}$, $Ru^{II}$, $Pr^{IV}$, $Rh^{III}$ or $Ir^{III}$
(25) 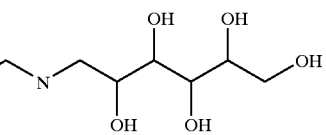
(26) 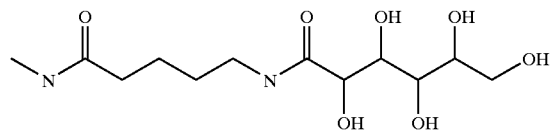
(27) 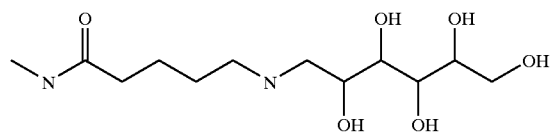
(28) 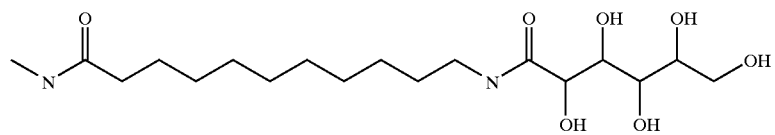
(29) 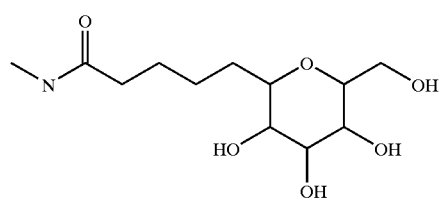
(30) 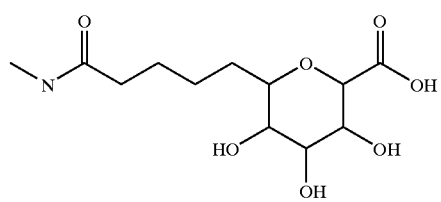

-continued

-continued
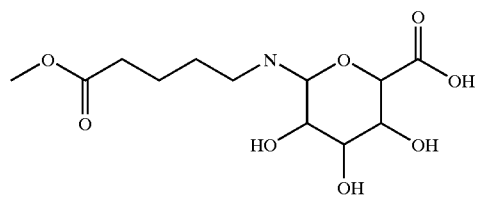 (47)
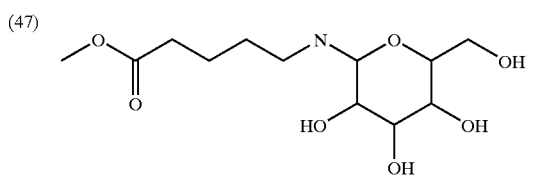 (48)
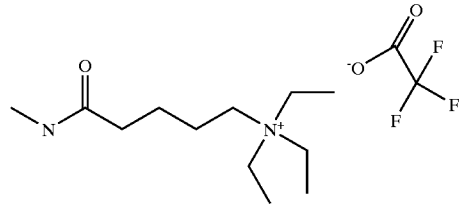 (49)
(50)
(51)
(52)
 (53)
(54)
 (55)
(56)
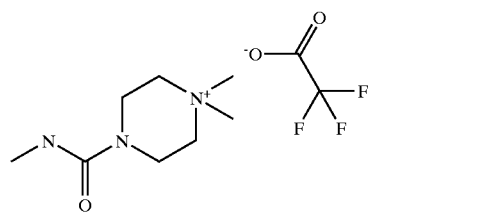 (57)
(58)
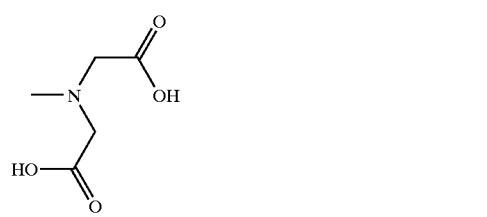 (59)
(60)
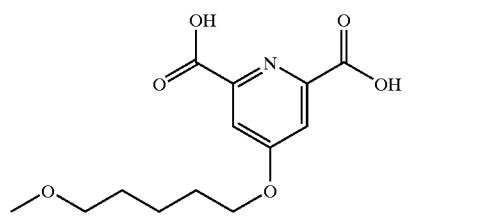 (61)
(62)

(63) 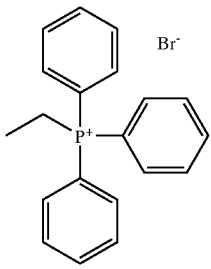

(64) 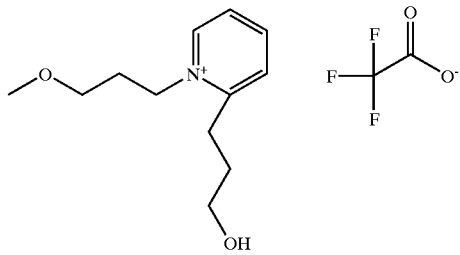

(65) 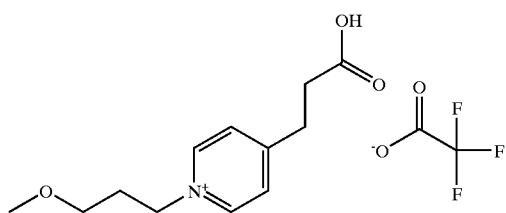

(66) 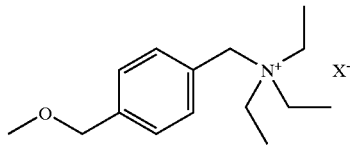

(67) 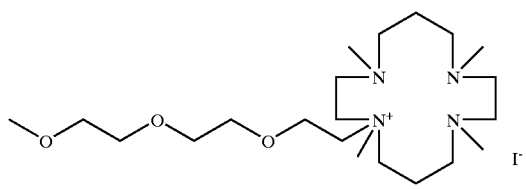

(68) 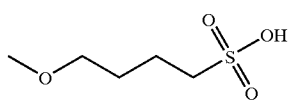

(69) 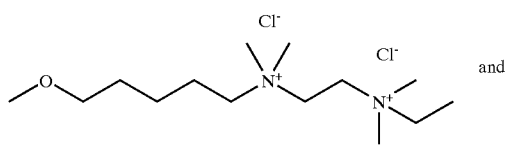  and

(70) 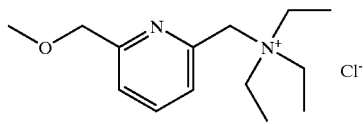

provided that when said $R^5$ is (7), (17) or (24), then said $R^{5A}$ is a left end of said $R^5$ and said $R^{5B}$ is a right end of said $R^5$ or vice versa.

74. The method of embodiment 73 wherein said Formula I-3 comprises a member selected from the group consisting of Formulas I-5 and I-6 represented by:

I-5
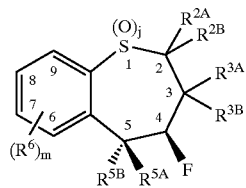

I-6
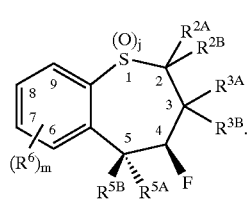

75. The method of embodiment 73 wherein said Formula I-4 comprises a member selected from the group consisting of Formulas I-7 and I-8 represented by:

I-7
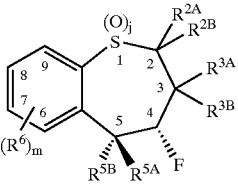

I-8
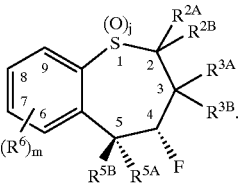

76. The method of embodiment 74 wherein said compounds of Formulas I-6 and I-5 comprise Formulas I-13 and I-14, respectively, represented by:

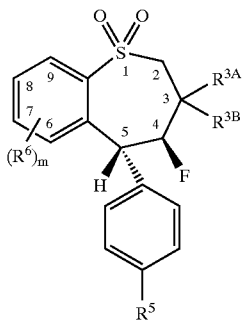

I-13

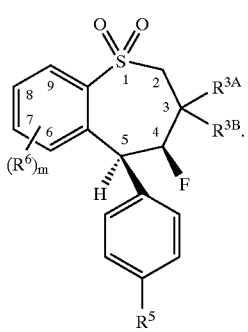

I-14

77. The method of embodiment 75 wherein said Formulas I-7 and I-8 comprise Formulas I-15 and I-16, respectively, represented by:

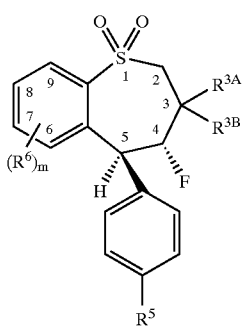

I-15

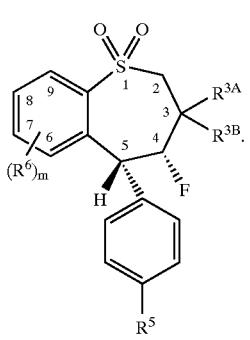

I-16

78. The method of embodiment 66 wherein said compound of Formula I-2 comprise a compound of Formula I-18 represented by:

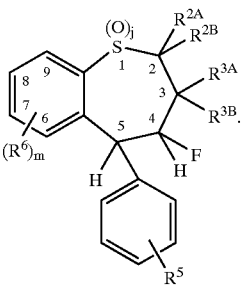

I-18

79. The method of embodiment 78 wherein said compound of Formula I-18 comprises a member selected from the group consisting of Formnulas I-23 and I-24 represented by:

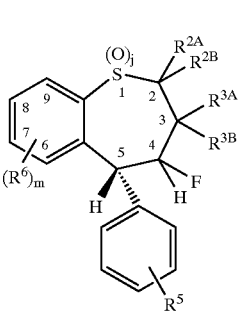

I-23

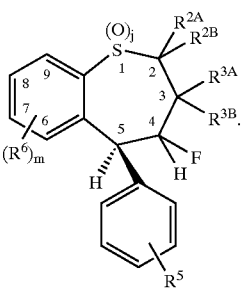

I-24

80. The method of embodiment 79 wherein said compounds of Formulas I-23 and I-24 comprises Formulas I-19 and I-20, respectively, represented by:

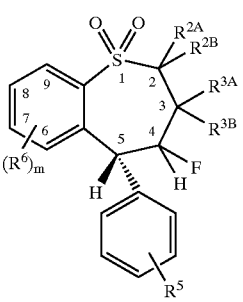

I-19

-continued

I-20

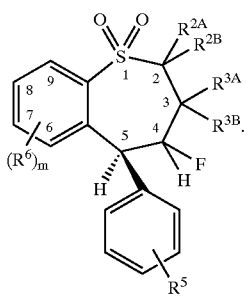

81. The method of embodiment 66 wherein said compound of Formula I-2 is selected from the group consisting of Formulas I-11 and I-12, respectively, represented by:

I-11

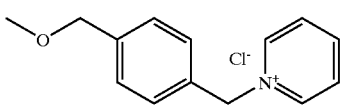

-continued

I-12

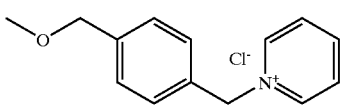

82. The compound of embodiment 1 wherein said compound of Formula I-1 comprises Formula I-17 represented by:

I-17

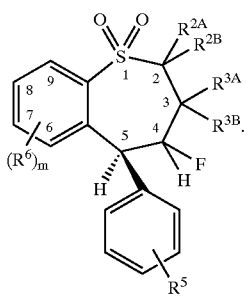

wherein $R^{2A}$, $R^{2B}$, $R^{3A}$, $R^{3B}$, $R^{5A}$, $R^{5B}$, $R^6$, m and j are as previously defined and said $R^5$ is selected from the group consisting of (1)–(69) and (70):

(1)

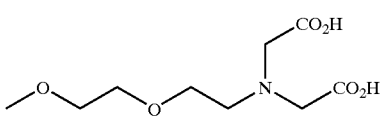

(2)

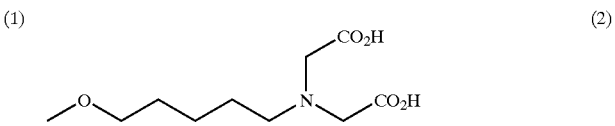

(3)

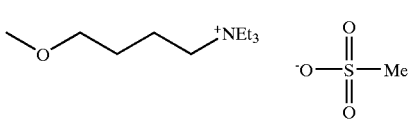

(4)

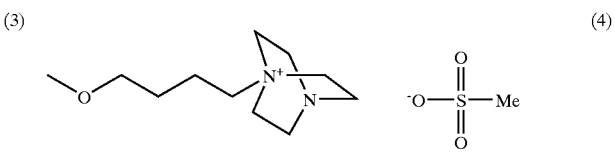

(5)

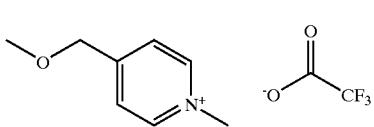

(6)

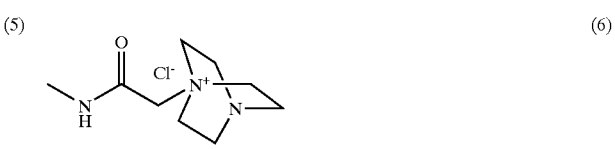

(7)

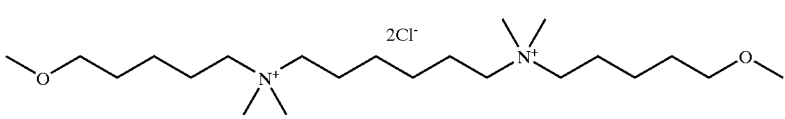

(8)

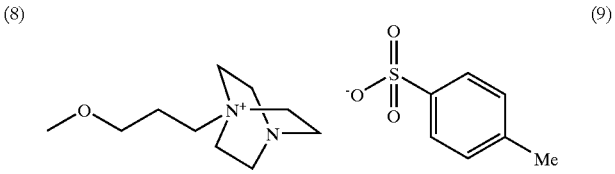

(9)

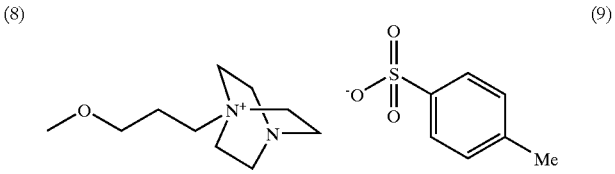

-continued
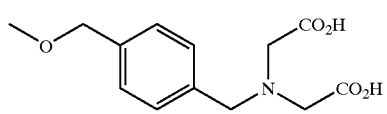 (10)
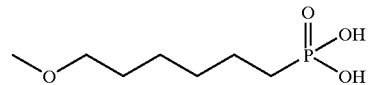 (11)
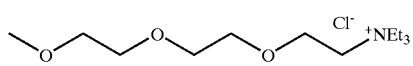 (12)
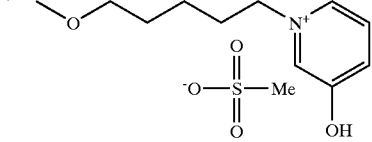 (13)
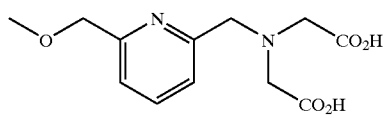 (14)
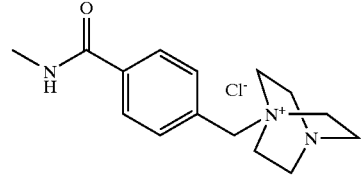 (15)
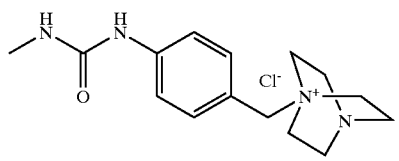 (15a)
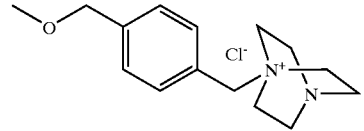 (16)
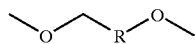 
R = 1000 MW PEG
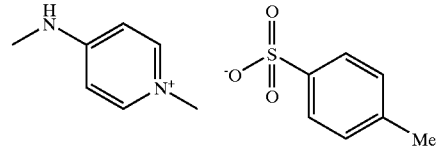 (17)
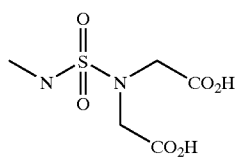 (18)
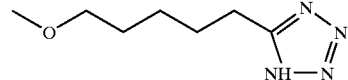 (19)
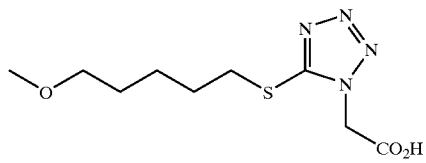 (20)
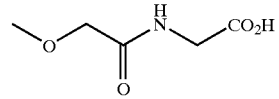 (21)
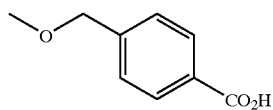 (22)
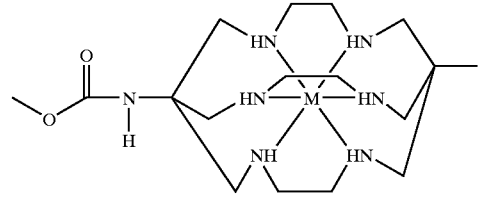 (23)
M = $Co^{II, III}$, $Mn^{II, III}$, $Fe^{II, III}$, $Ni^{II, III}$, $Cr^{III}$, $Cu^{II}$, $Zn^{II}$, $Cd^{II}$, $Ga^{III}$, $In^{III}$, $V^{IV}$, $Ru^{II}$, $Pr^{IV}$, $Rh^{III}$ or $Ir^{III}$
(24)
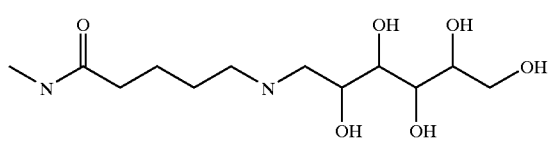 (25)

(26)
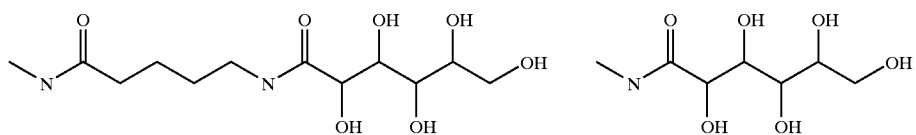
(27)
(28)
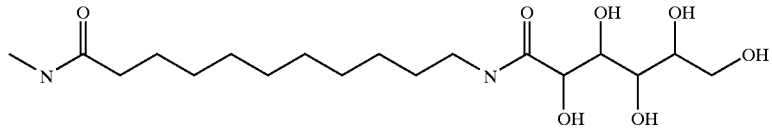
(29)
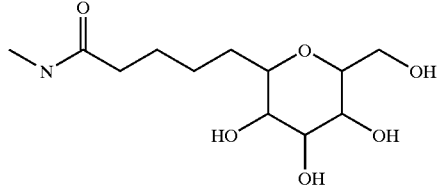
(30)
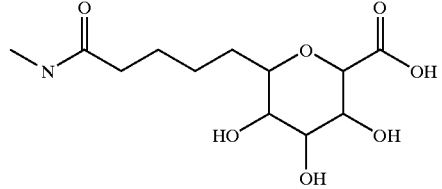
(31)
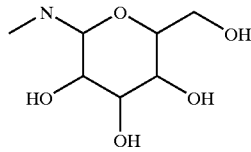
(32)
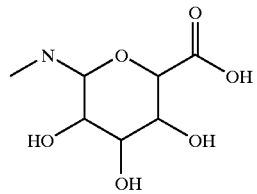
(33)
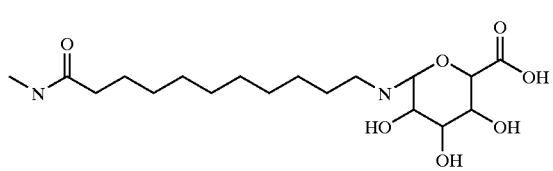
(34)
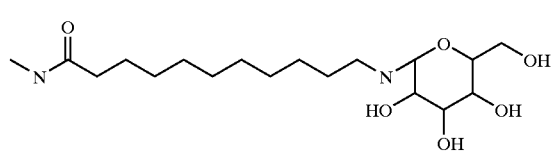
(35)
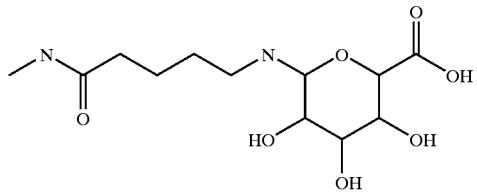
(36)
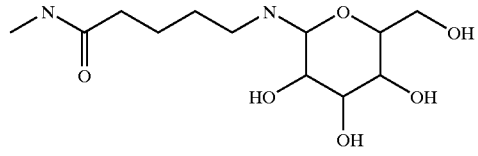
(37)
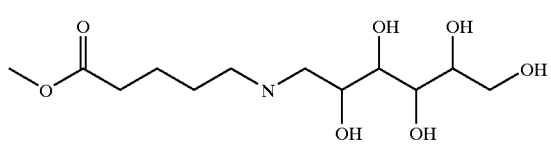
(38)
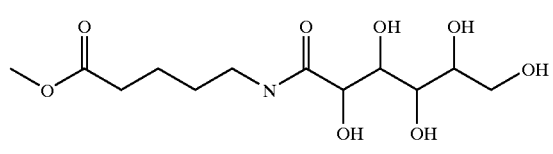
(39)
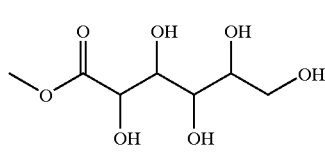
(40)
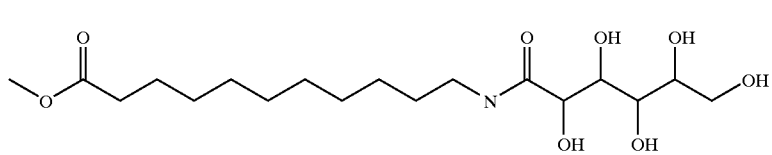

-continued
(41) 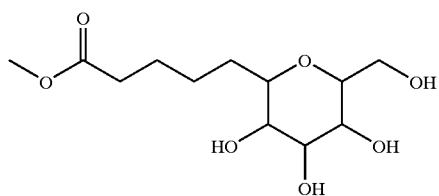
(42) 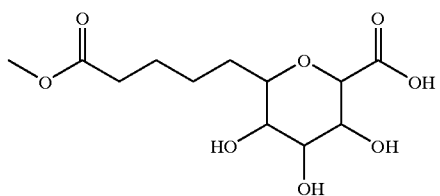
(43) 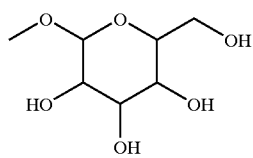
(44) 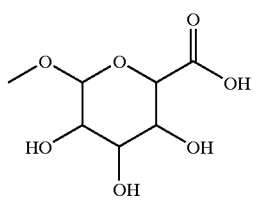
(45) 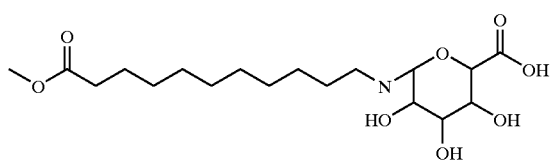
(46) 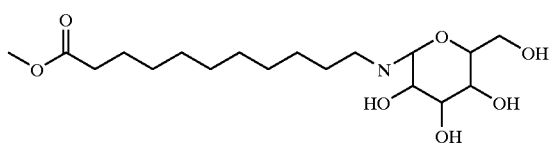
(47) 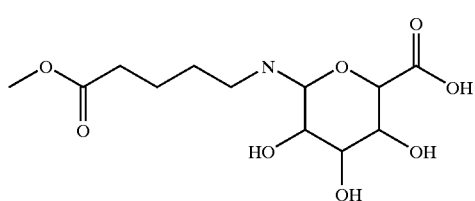
(48) 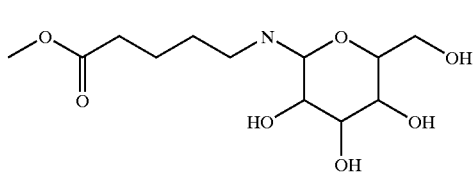
(49) 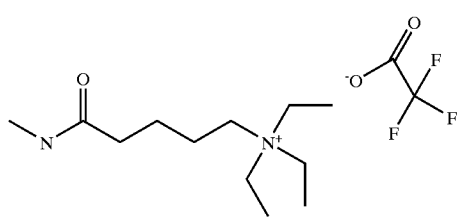
(50) 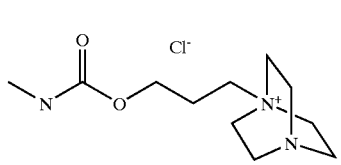
(51) 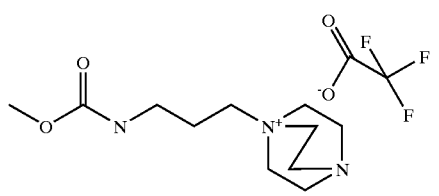
(52) 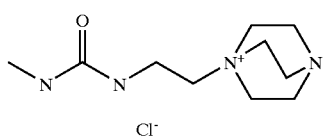
(53) 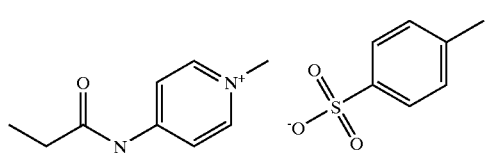
(54) 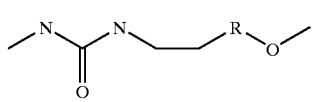
(55) 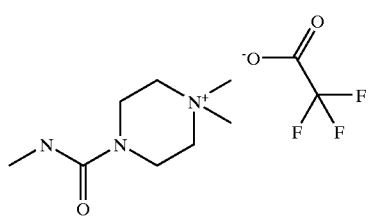
(56) 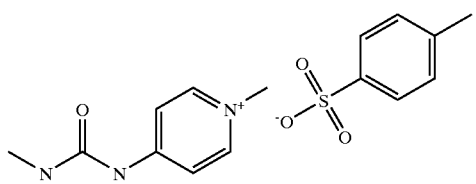

-continued
(57) 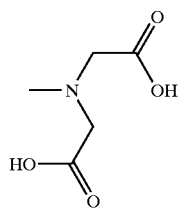
(58) 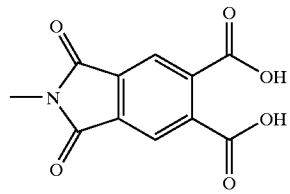
(59) 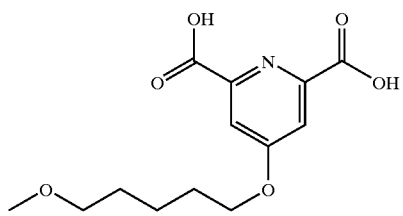
(60) 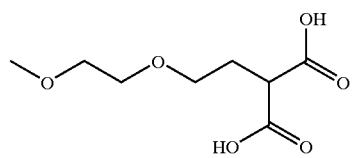
(61) 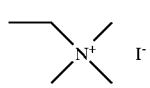
(62) 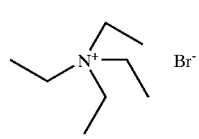
(63) 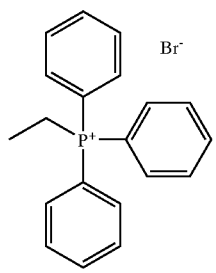
(64) 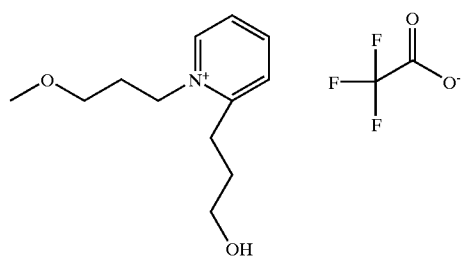
(65) 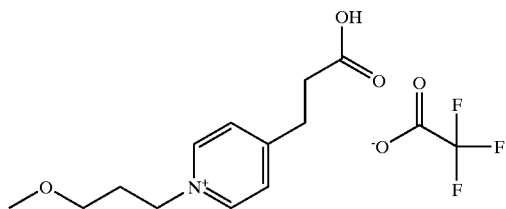
(66) 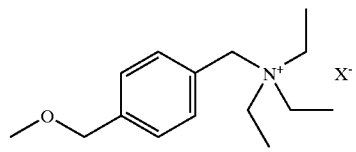
(67) 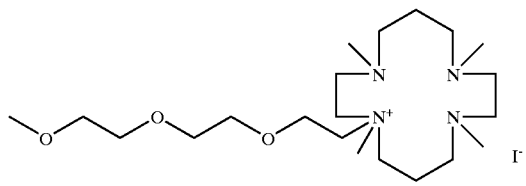
(68) 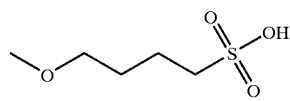
(69) 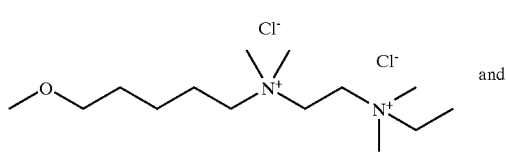 and
(70) 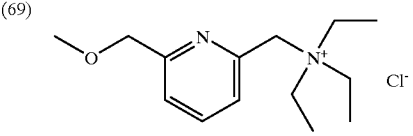
provided that when said $R^5$ is (7), (17) or (24), then said $R^{5A}$ is a left end of said $R^5$ and said $R^{5B}$ is a right end of said $R^5$ or vice versa.

83. The compound of embodiment 82 wherein said compound of Formula 17 comprises a member selected from the group consisting of Formulas I-21 and I-22 represented by:

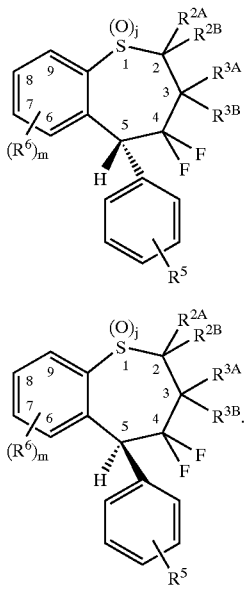

I-21

I-22

84. The method of embodiment 83 wherein said compounds of Formulas I-21 and I-22 comprise Formulas I-9 and I-10, respectively, represented by:

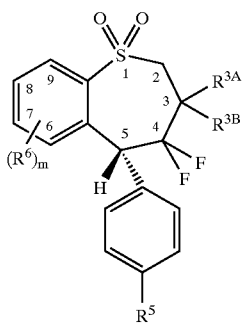

I-9

I-10

85. The compound of embodiment 1 wherein said compound of Formula I-2 is selected from the group consisting of Formulas I-3 and I-4 represented by:

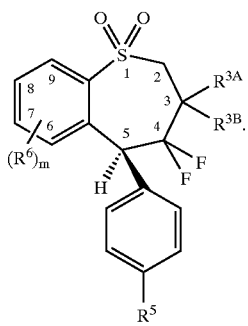

I-3

I-4 wherein $R^{2A}$, $R^{2B}$, $R^{3A}$, $R^{3B}$, $R^{5A}$, $R^{5B}$, $R^6$, m and j are as previously defined and said $R^5$ is selected from the group consisting of (1)–(69) and (70):

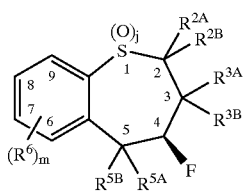

(1)

(2)

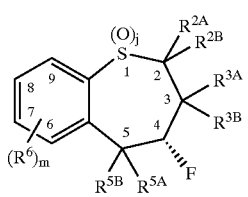

(3)

(4)

(5)

(6)

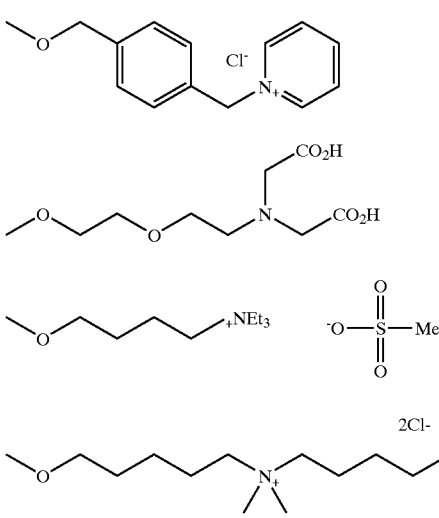

(7)

-continued
(8)
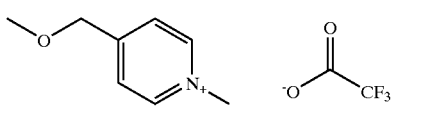
(9)
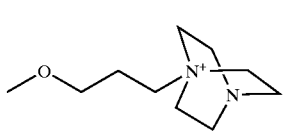
(10)
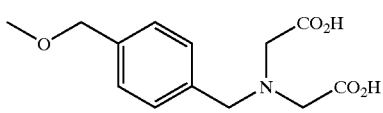
(11)
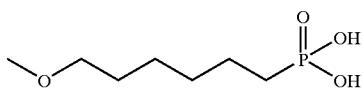
(12)
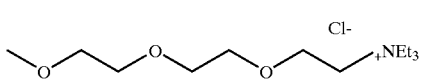
(13)
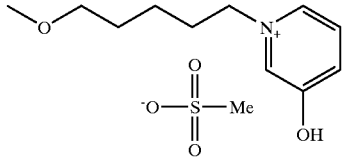
(14)
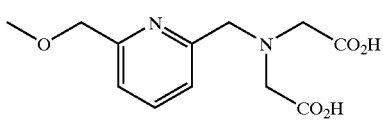
(15)
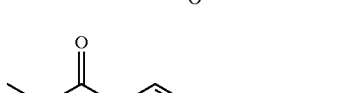
(15a)
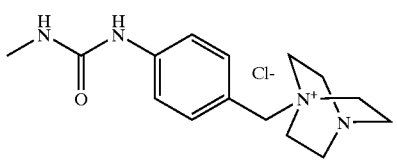
(16)
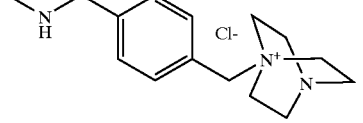
R = 1000 MW PEG
(17)

(18)
(19)
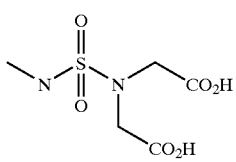
(20)
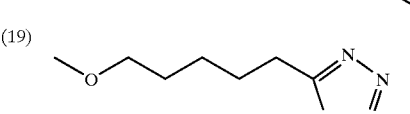
(21)
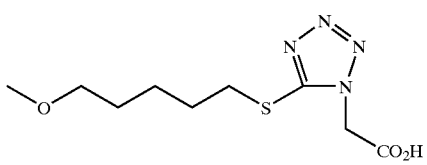
(22)

(23)
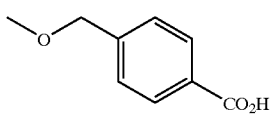
(24)
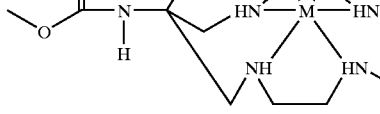
M = $Co^{II, III}$, $Mn^{II, III}$, $Fe^{II, III}$, $Ni^{II, III}$, $Cr^{III}$, $Cu^{II}$, $Zn^{II}$, $Cd^{II}$, $Ga^{III}$, $In^{III}$, $V^{IV}$, $Ru^{II}$, $Pr^{IV}$, $Rh^{III}$ or $Ir^{III}$ -continued
(25) 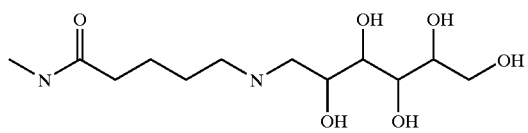
(26) 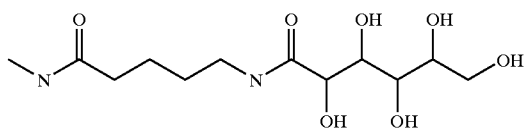
(27) 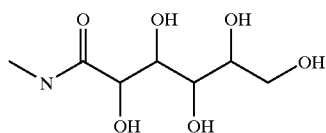
(28) 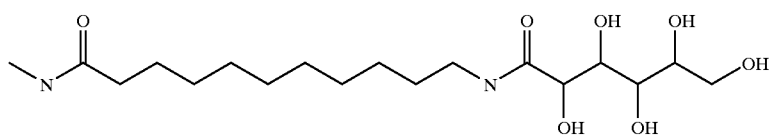
(29) 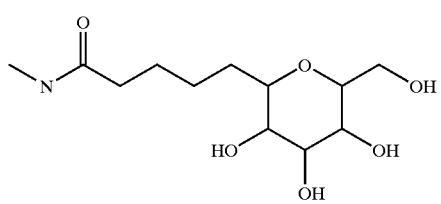
(30) 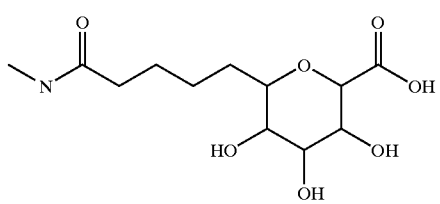
(31) 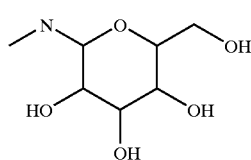
(32) 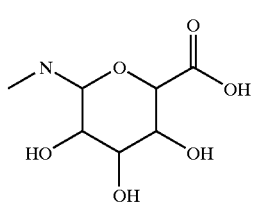
(33) 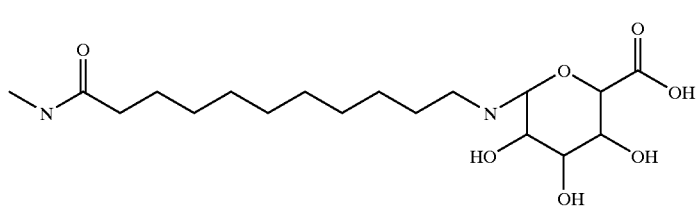
(34) 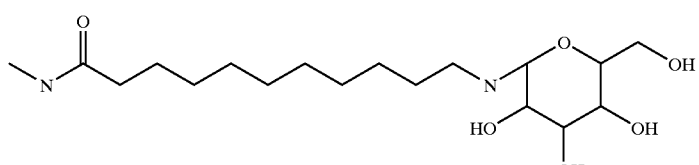
(35) 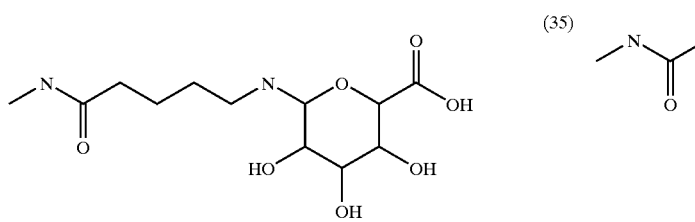
(36) 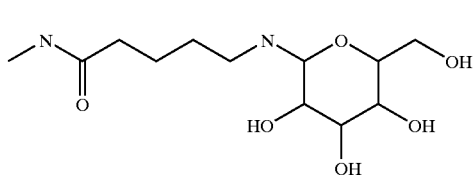
(37) 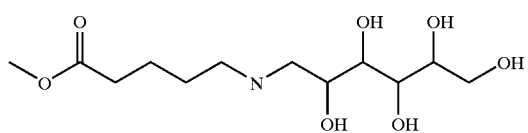
(38) 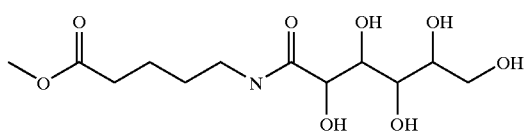

-continued
(39)
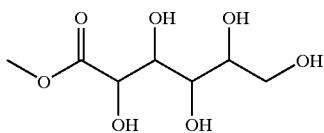
(40)
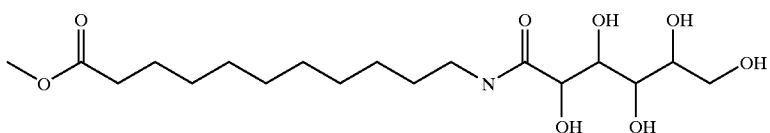
(41)
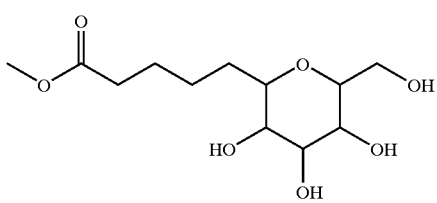
(42)
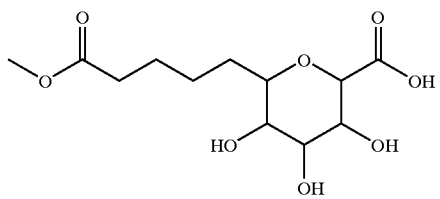
(43)
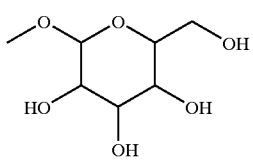
(44)
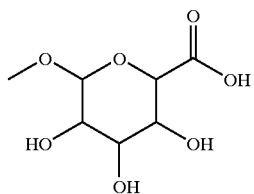
(45)
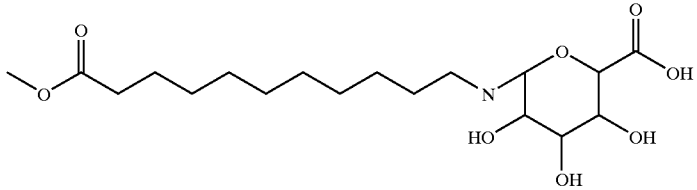
(46)
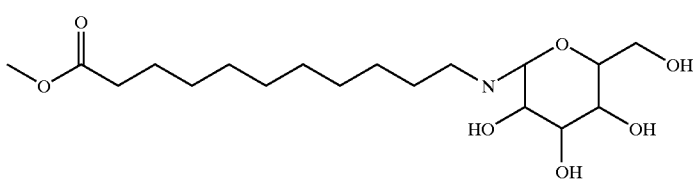
(47)
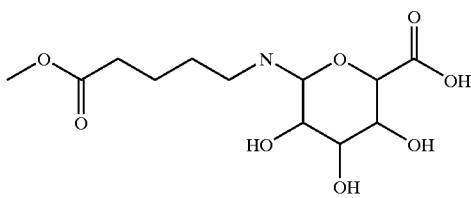
(48)
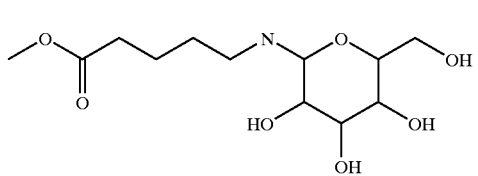
(49)
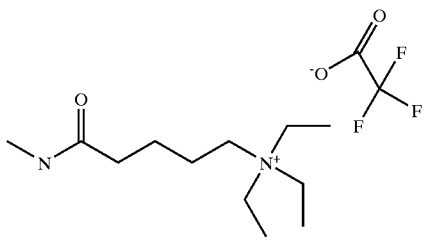
(50)
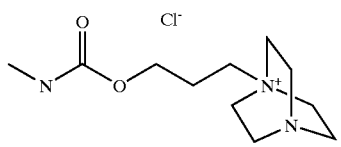

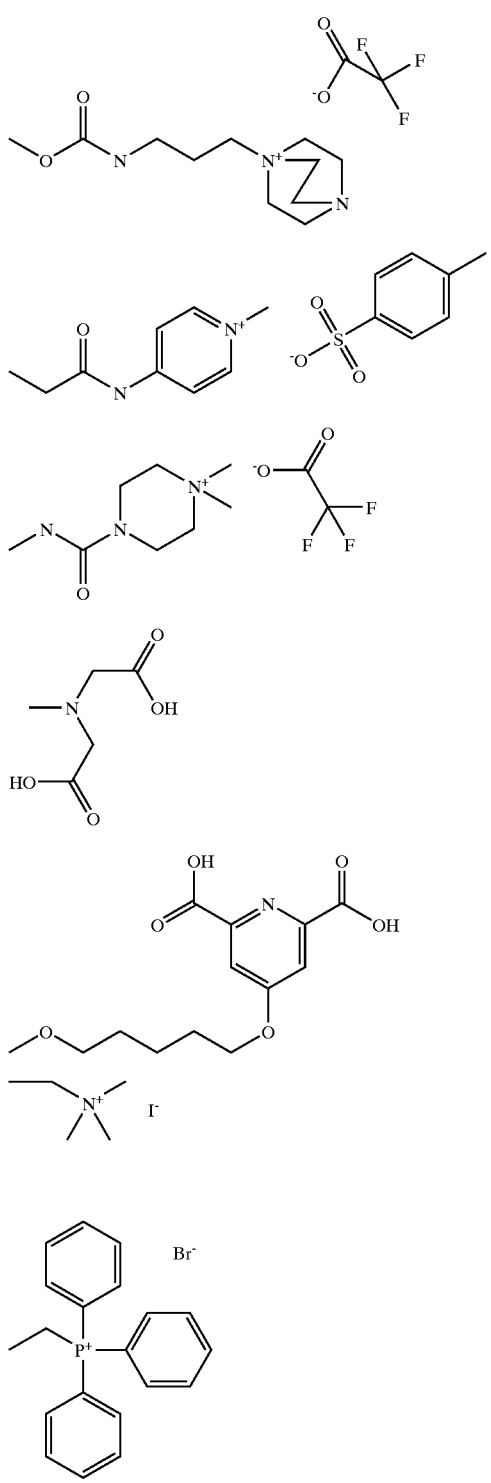
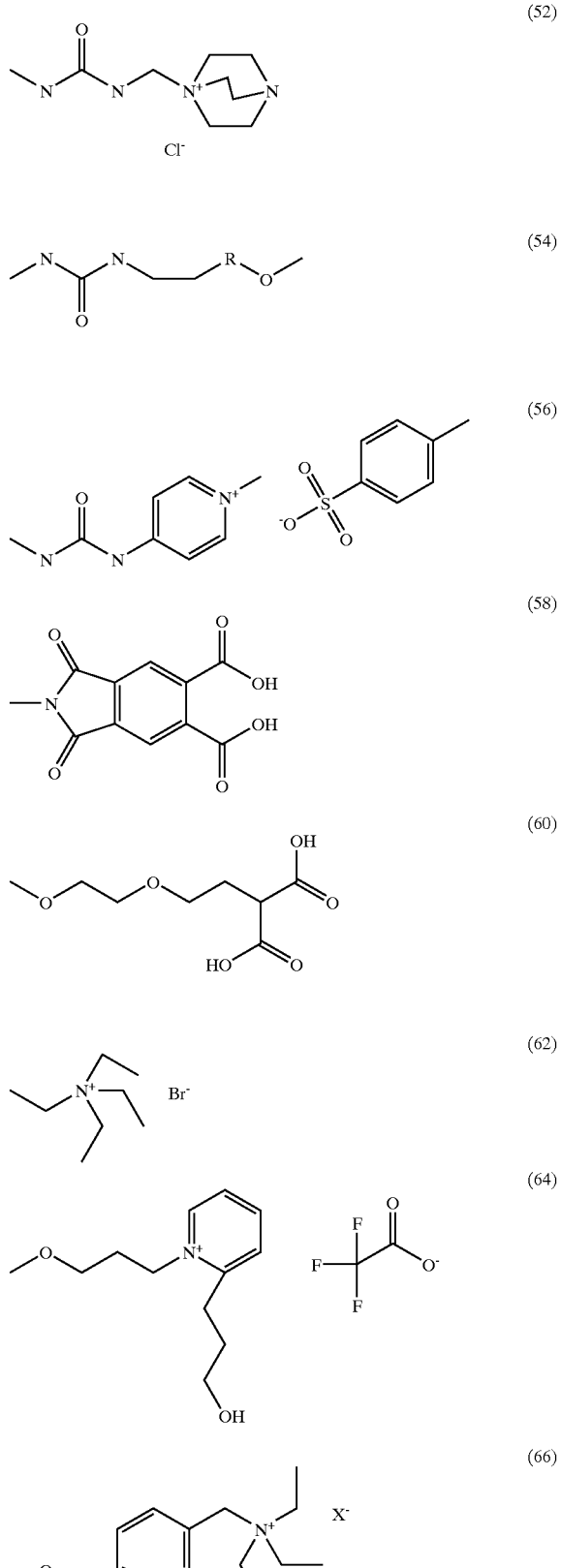

-continued (67)

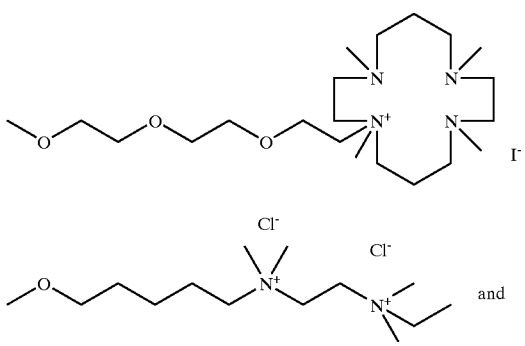

(68)

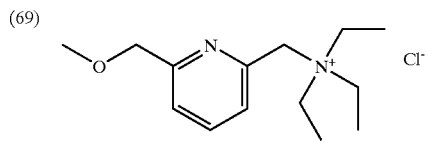

(69)

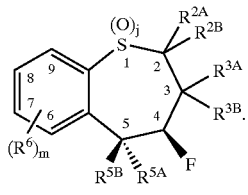 and (70)

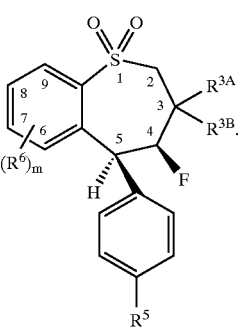

provided that when said $R^5$ is (7), (17) or (24), then said $R^{5A}$ is a left end of said $R^5$ and said $R^{5B}$ is a right end of said $R^5$ or vice versa.

86. The compound of embodiment 85 wherein said Formula I-3 comprises a member selected from the group consisting of Formulas I-5 and I-6 represented by:

I-5

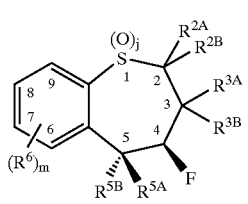

I-6

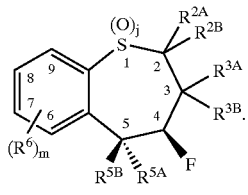

87. The compound of embodiment 85 wherein said Formula I-4 comprises a member selected from the group consisting of Formulas I-7 and I-8 represented by:

I-7

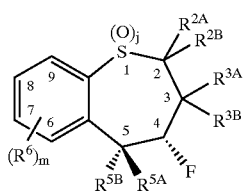

I-8

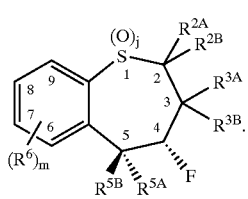

88. The compound of embodiment 86 wherein said compounds of Formulas I-6 and I-5 comprise Formulas I-13 and I-14, respectively, represented by:

I-13

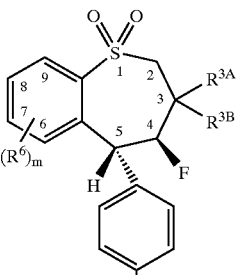

I-14

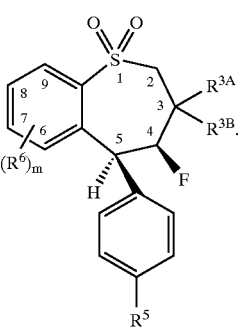

89. The compound of embodiment 87 wherein said compounds of Formulas I-7 and I-8 comprise Formulas I-15 and I-16, respectively, represented by:

I-15

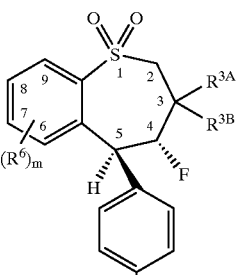

-continued
I-16
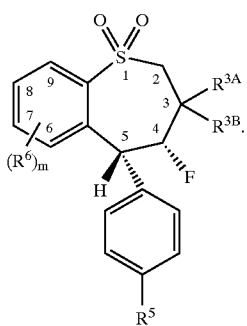
I-18
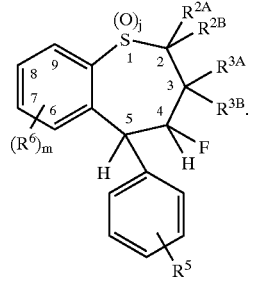
90. The compound of embodiment 1 wherein said compound of Formula I-2 comprises a compound of Formula I-18 represented by:
wherein $R^{2A}$, $R^{2B}$, $R^{3A}$, $R^{3B}$, $R^{5A}$, $R^{5B}$, $R^6$, m and j are as previously defined and said $R^5$ is selected from the group consisting of (1)–(69) and (70):
(1)
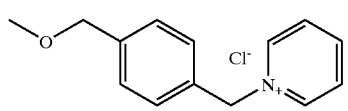
(2)
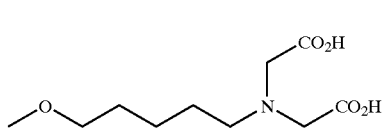
(3)
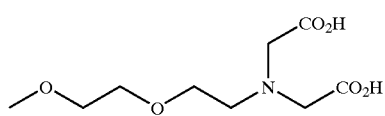
(4)
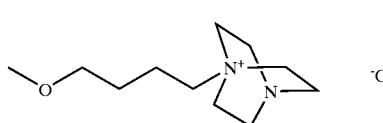
(5)
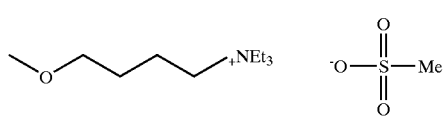
(6)
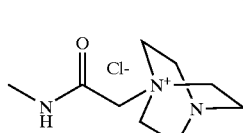
(7)
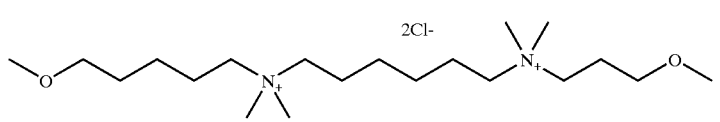
(8)
(9)
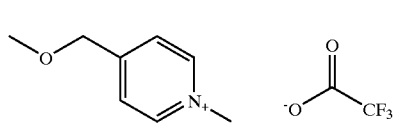
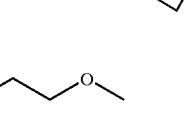
(10)
(11)
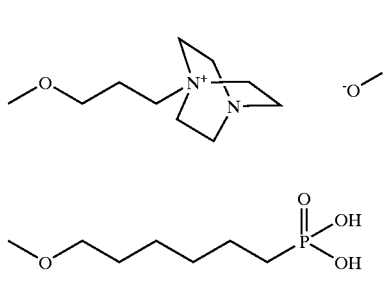
(12)
(13)
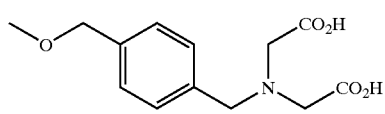
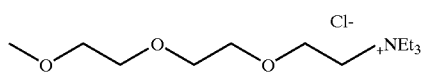
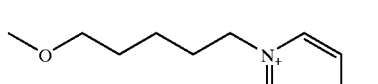
(14)
(15)
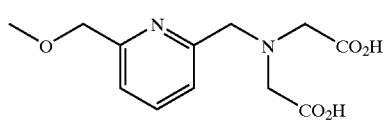
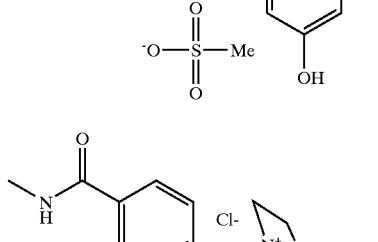

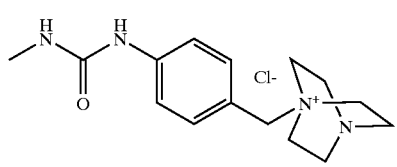
(15a)
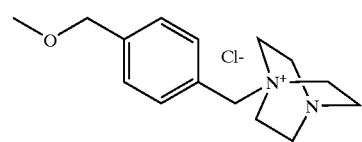
(16)
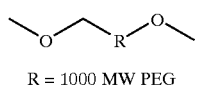
R = 1000 MW PEG
(17)
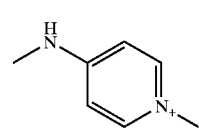
(18)
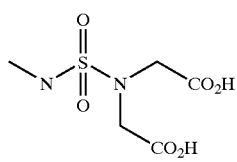
(19)
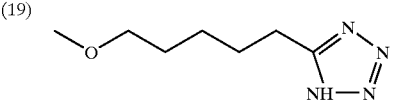
(20)
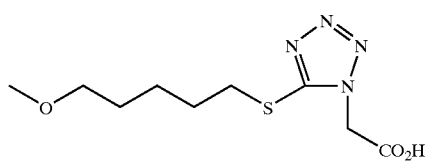
(21)
(22)
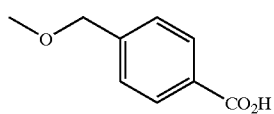
(23)
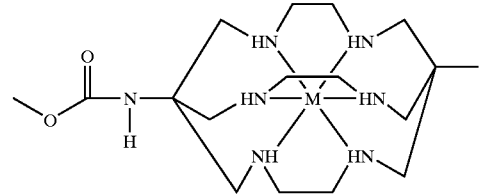
M = $Co^{II, III}$, $Mn^{II, III}$, $Fe^{II, III}$, $Ni^{II, III}$, $Cr^{III}$, $Cu^{II}$, $Zn^{II}$, $Cd^{II}$, $Ga^{III}$, $In^{III}$, $V^{IV}$, $Ru^{II}$, $Pr^{IV}$, $Rh^{III}$ or $Ir^{III}$
(24)
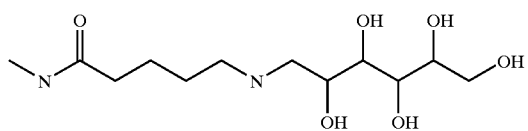
(25)
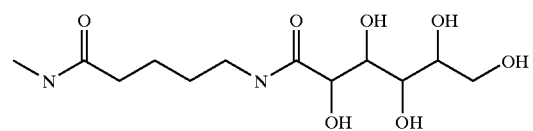
(26)
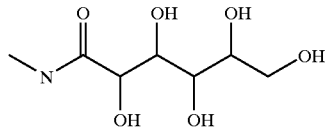
(27)
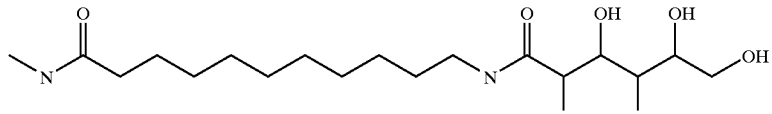
(28)
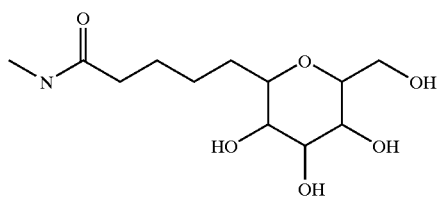
(29)
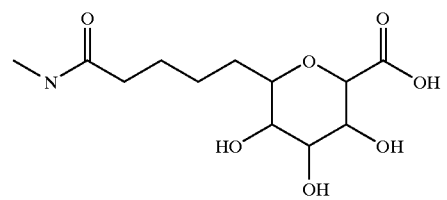
(30)

-continued
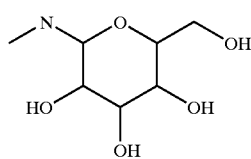 (31)
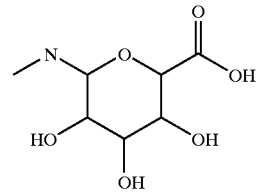 (32)
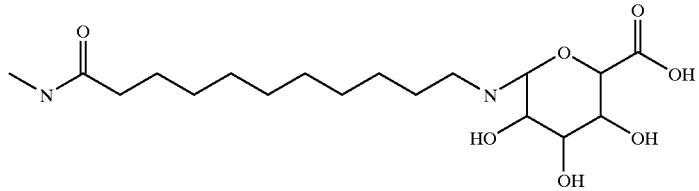 (33)
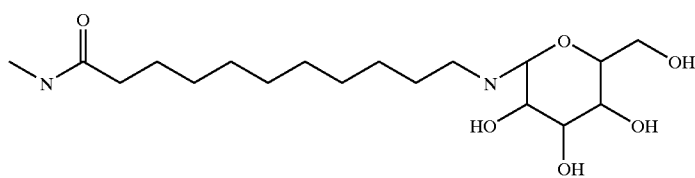 (34)
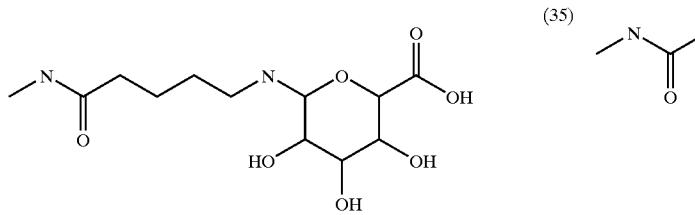 (35)
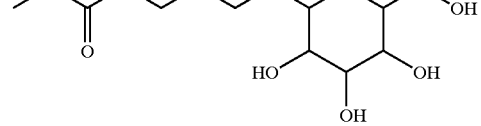 (36)
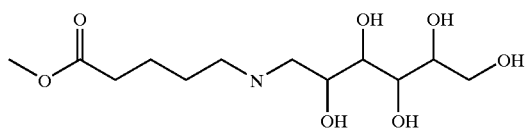 (37)
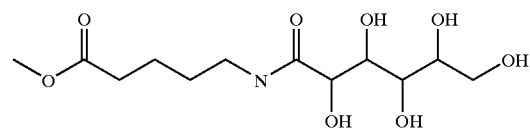 (38)
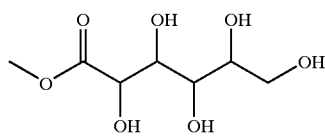 (39)
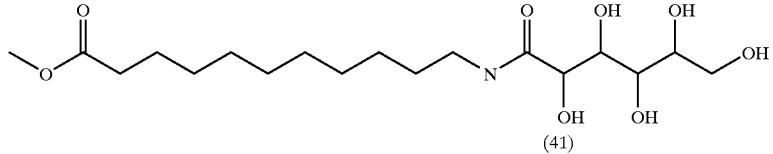 (40)
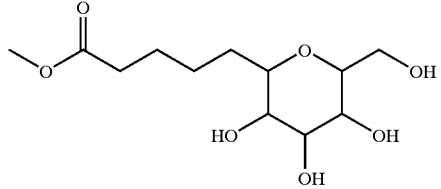 (41)
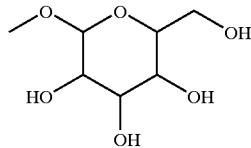 (42)
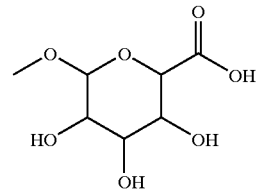 (43)
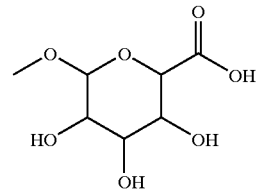 (44)

-continued
(45)
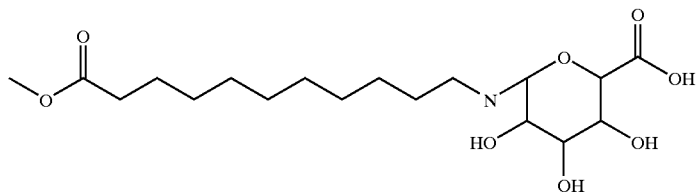
(46)
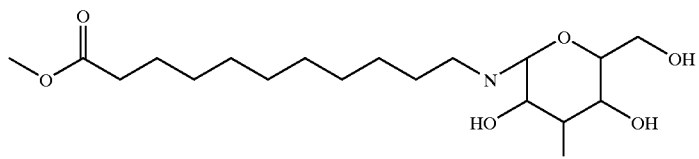
(47)
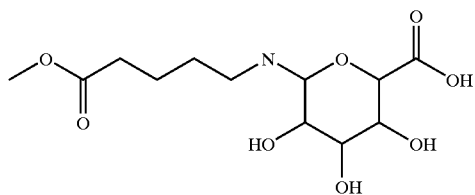
(48)
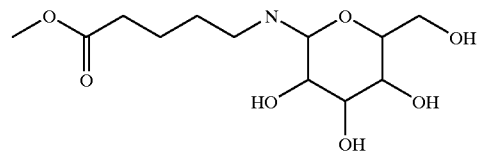
(49)
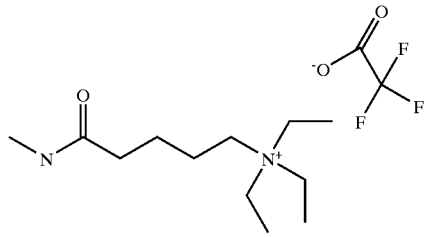
(50)
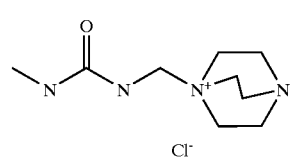
(51)
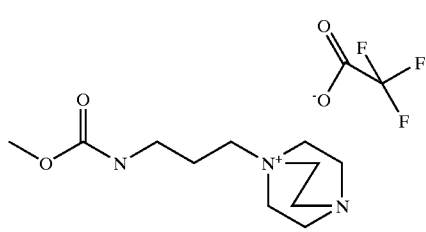
(52)
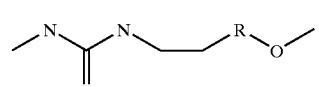
(53)
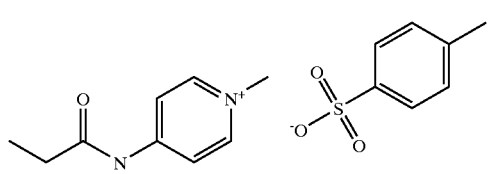
(54)
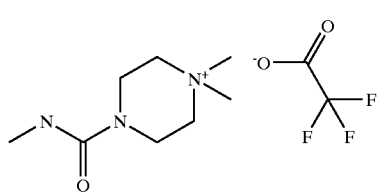
(55)
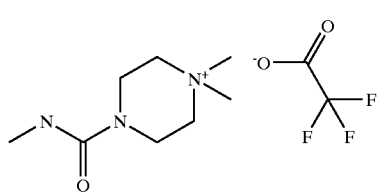
(56)
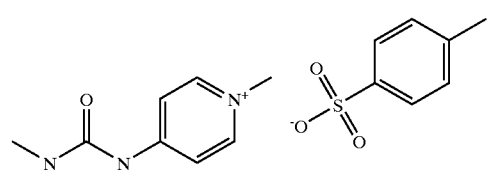
(57)
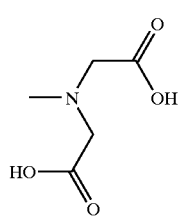
(58)
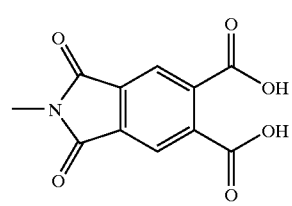

-continued
(59) 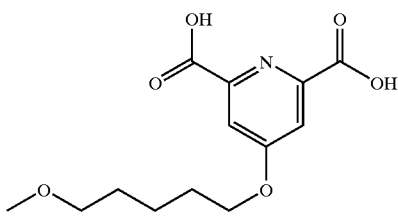
(60) 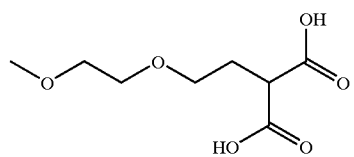
(61) 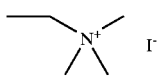
(62) 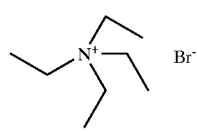
(63) 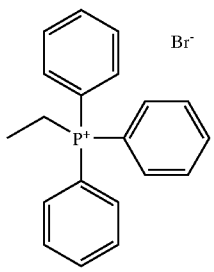
(64) 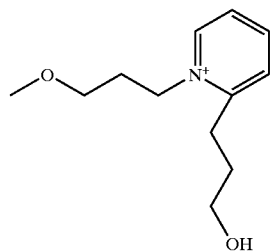
(65) 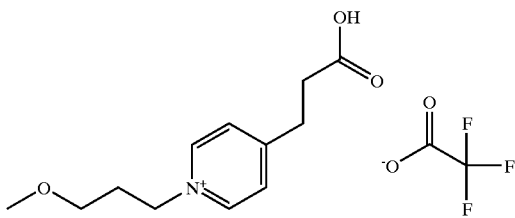
(66) 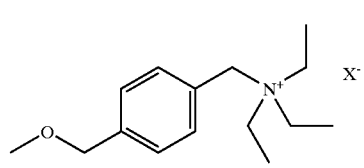
(67) 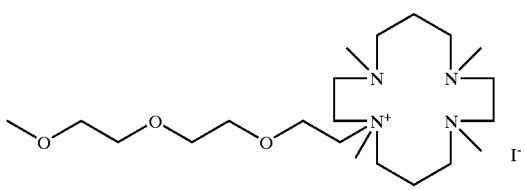
(68) 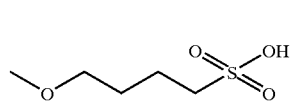
(69) 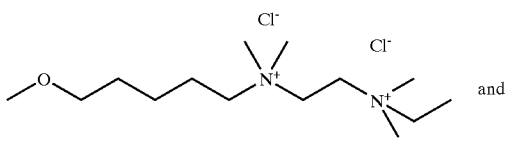
(70) 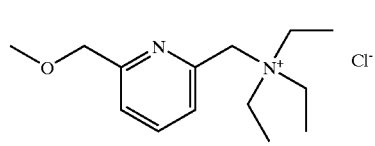
provided that when said $R^5$ is (7), (17) or (24), then said $R^{5A}$ is a left end of said $R^5$ and said $R^{5B}$ is a right end of said $R^5$ or vice versa.
91. The compound of embodiment 90 wherein said compound of Formula I-18 comprises a member selected from the group consisting of I-23 and I-24 represented by:
I-23
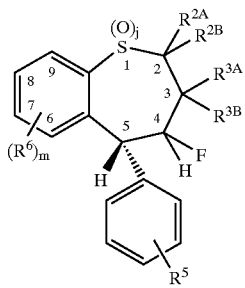

-continued

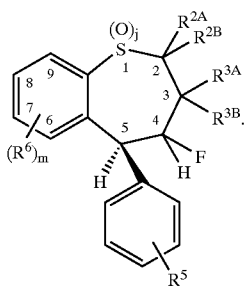
I-24

92. The compound of embodiment 91 wherein said compounds of Formulas I-23 and I-24 comprise compounds of Formulas I-19 and I-20, respectively, represented by:

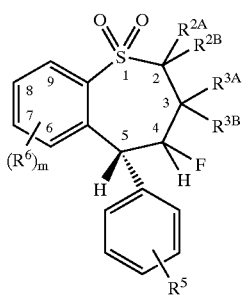
I-19

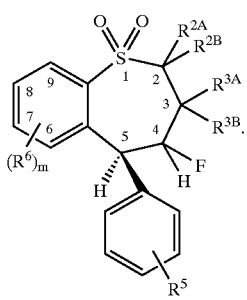
I-20

93. The compound of embodiment 1 wherein said compound of Formula I-2 is selected from the group consisting of Formulas I-11 and I-12 represented by:

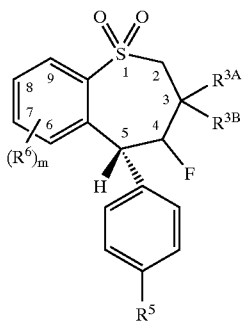
I-11

-continued

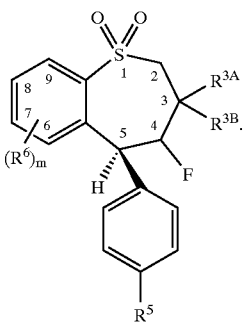
I-12

94. The method of embodiment 39 wherein said hyperlipidemic condition is hypercholesterolemia.

95. The method of embodiment 94 wherein said therapeutically effective amount is a daily dose from about 0.001 mg to about 10,000 mg.

96. The method of embodiment 95 wherein said daily dose is from about 0.005 mg to about 1,000 mg.

97. The method of embodiment 96 wherein said daily dose is from about 0.008 to about 100 mg.

98. The method of embodiment 97 wherein said daily dose is from about 0.05 mg to about 50 mg.

99. The method of embodiments 95–98 wherein said daily dose is administered as a single dose or in multiple divided doses.

100. The method of embodiment 40 wherein said therapeutically effective amount is a daily dose from about 0.001 mg to about 10,000 mg 101. The method of embodiment 100 wherein said daily dose is from about 0.005 mg to about 1,000 mg.

102. The method of embodiment 101 wherein said daily dose is from about 0.008 to about 100 mg.

103. The method of embodiment 102 wherein said daily dose is from about 0.05 mg to about 50 mg.

104. The method of embodiments 100–103 wherein said daily dose is administered as a single dose or in multiple divided doses.

105. The method of embodiment 95 wherein said daily dose is administered orally.

106. The method of embodiment 95 wherein said daily dose is administered parenterally.

107. The method of embodiment 95 wherein said daily dose is administered rectally.

108. The method of embodiment 107 wherein said daily dose is administered as a rectal dosage form comprising a suppository.

109. The method of embodiment 94 wherein said therapeutically effective amount is administered as a slow release dosage form.

110. The method of embodiment 109 wherein said slow release dosage form comprises an implant.

111. The method of embodiment 105 wherein said daily dose is administered in the form of an oral dosage form selected from the group consisting of a tablet, a capsule, a powder, a solution, a suspension, an emulsion, and a syrup.

112. The method of embodiment 111 wherein said solution comprises a syrup.

113. The method of embodiment 111 wherein said oral dosage form comprises a sublingual tablet, an effervescent tablet, or a slow release tablet.

114. The method of embodiment 106 wherein said parenteral dosage form is selected from the group consisting of an intramuscular injection, an intravenous injection, and a subcutaneous injection.

115. The method of embodiment 95 wherein said daily dose is administered topically.

116. The method of embodiment 100 wherein said daily dose is administered parenterally.

117. The method of embodiment 100 wherein said daily dose is administered rectally or vaginally.

118. The method of embodiment 117 wherein said daily dose is administered as a rectal dosage form or a vaginal dosage form comprising a suppository.

119. The method of embodiment 100 wherein said daily dose is administered as a slow release dosage form.

120. The method of embodiment 119 wherein said slow release dosage form comprises an implant.

121. The method of embodiment 100 wherein said daily dose is administered in the form of an oral dosage form selected from the group consisting of a tablet, a capsule, a powder, a solution, a suspension, and an emulsion.

122. The method of embodiment 121 wherein said solution comprises a syrup.

123. The method of embodiment 121 wherein said tablet comprises a sublingual tablet, an effervescent tablet, or a slow release tablet.

124. The method of embodiment 116 wherein said parenteral dosage form is selected from the group consisting of an intramuscular injection, an intravenous injection, and a subcutaneous injection.

125. The method of embodiment 100 wherein said daily dose is administered topically.

126. The method of embodiment 125 wherein said daily dose is administered in the form of a topical dosage form selected from the group consisting of a lotion, a cream, a suspension, an emulsion, a paste, and a solution.

127. The method of embodiment 115 wherein said daily dose is administered in the form of a topical dosage form selected from the group consisting of a lotion, a cream, a suspension, an emulsion, a paste, and a solution.

128. A pharmaceutical composition comprising a compound of Formula I-1 or I-2 of embodiment 1 and a pharmaceutically acceptable carrier.

129. The pharmaceutical composition of embodiment 128 wherein said compound of Formula I-1 comprises Formula I-17 represented by:

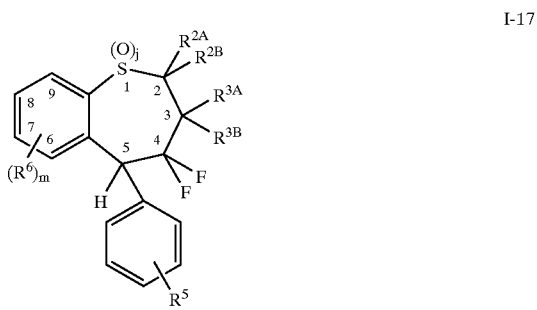

wherein $R^{2A}$, $R^{2B}$, $R^{3A}$, $R^{3B}$, $R^{5A}$, $R^{5B}$, $R^6$, m and j are as previously defined and said $R^5$ is selected from the group consisting of (1)–(69) and (70):

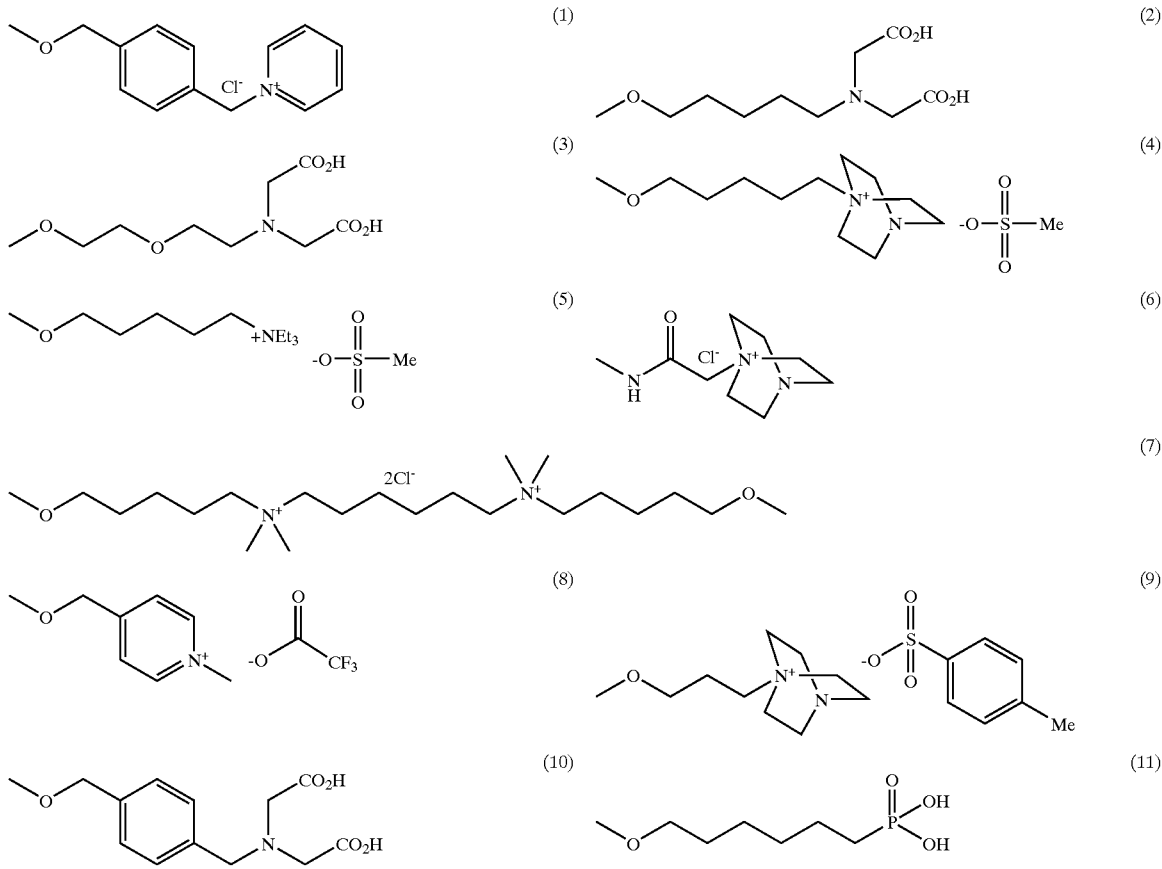

-continued
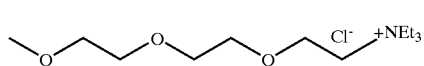 (12)
 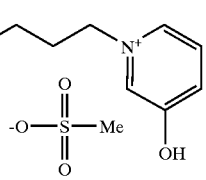 (13)
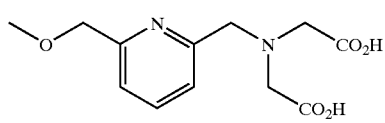 (14)
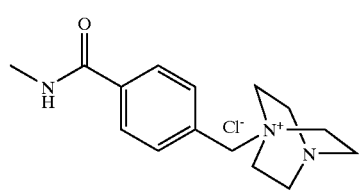 (15)
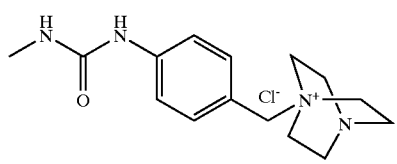 (15a)
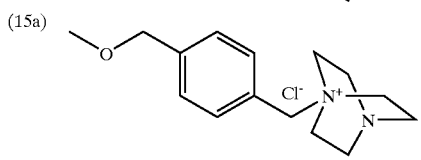 (16)
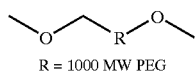
R = 1000 MW PEG
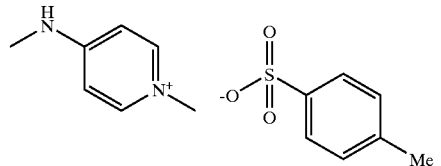 (17)
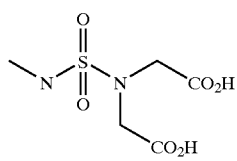 (18)
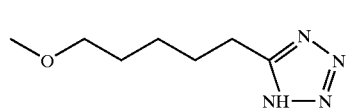 (19)
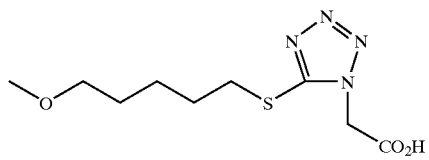 (20)
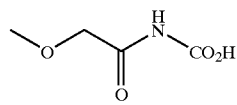 (21)
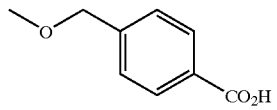 (22)
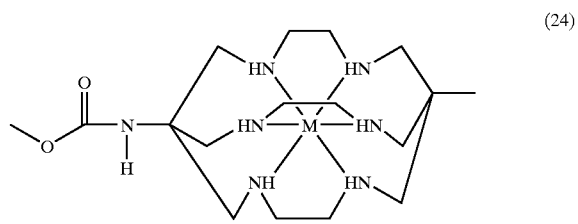 (23)
M = Co^{II,III}, Mn^{II,III}, Fe^{II,III}, Ni^{II,III}, Cr^{III}, Cu^{II}, Zn^{II}, Cd^{II}, Ga^{III}, In^{III}, V^{IV}, Ru^{II}, Pr^{IV}, Rh^{III} or Ir^{III}
(24)
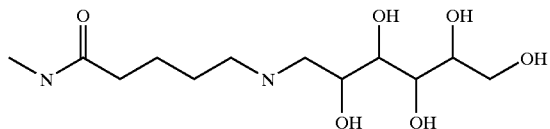 (25)
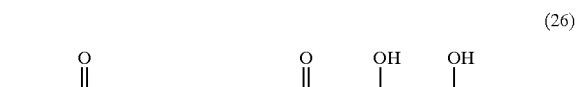 (26)
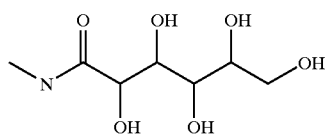 (27)
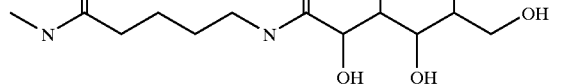

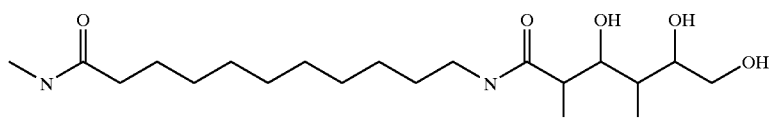
(28)
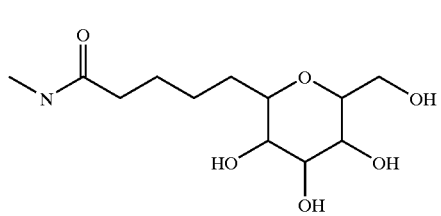
(29)
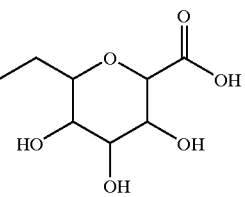
(30)
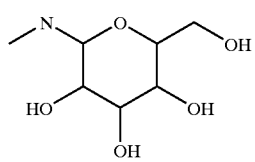
(31)
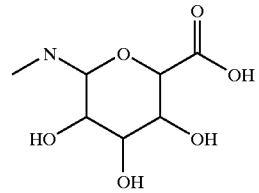
(32)
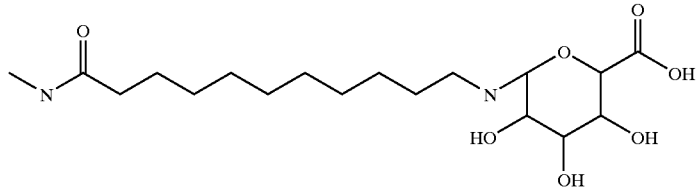
(33)
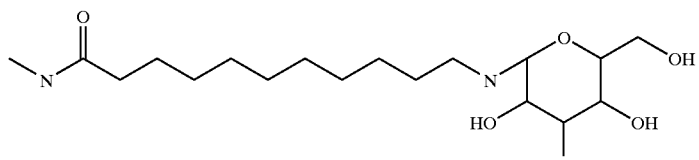
(34)
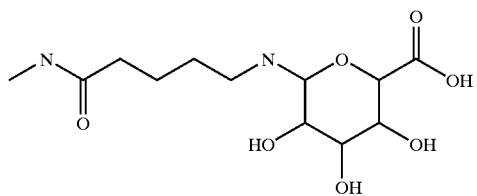
(35)
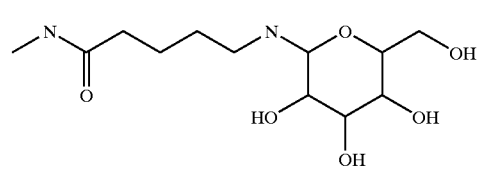
(36)
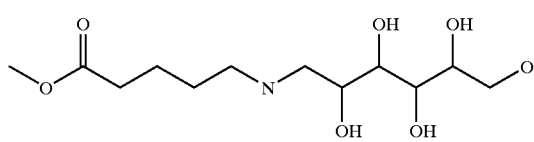
(37)
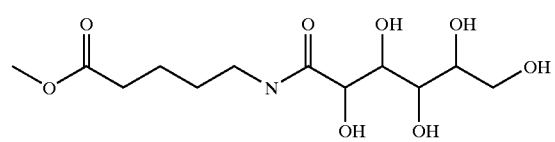
(38)
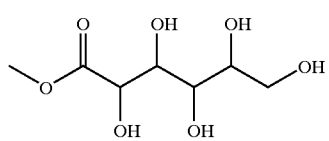
(39)
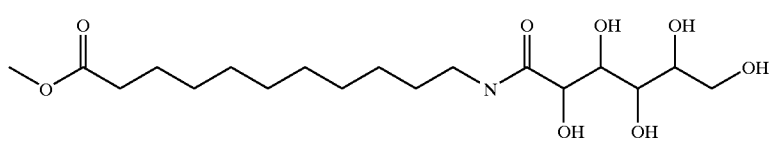
(40)

-continued
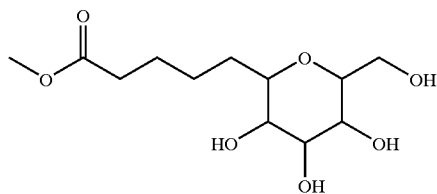 (41)
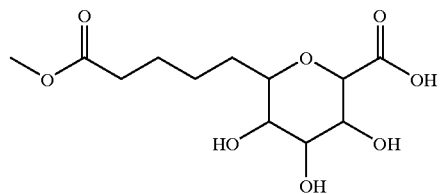 (42)
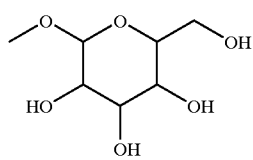 (43)
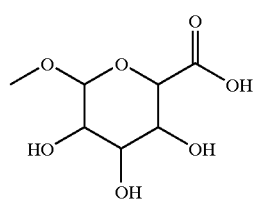 (44)
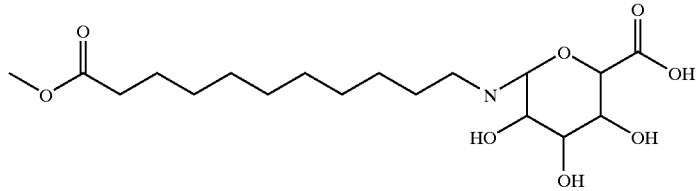 (45)
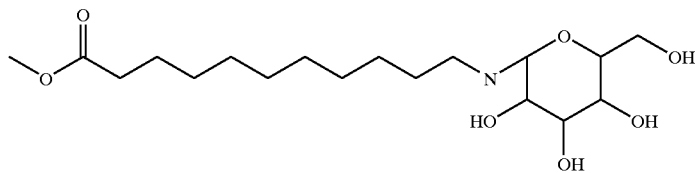 (46)
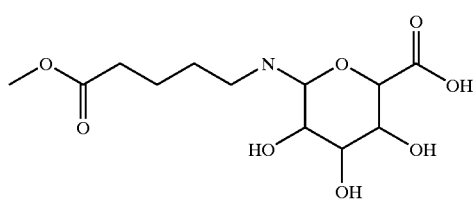 (47)
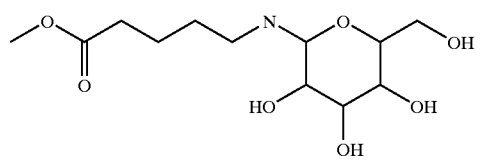 (48)
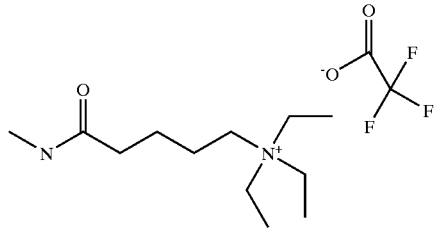 (49)
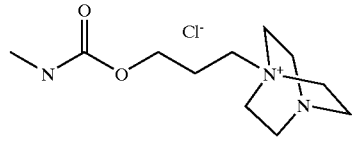 (50)
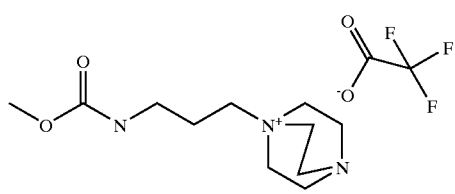 (51)
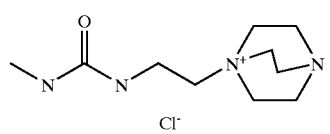 (52)

-continued
(53) 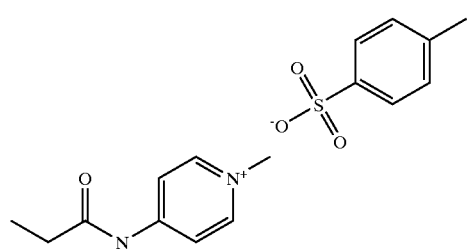
(54) 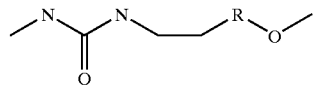
(55) 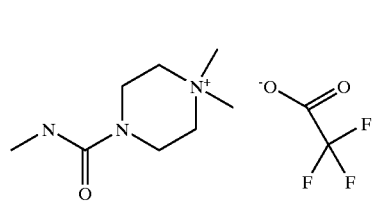
(56) 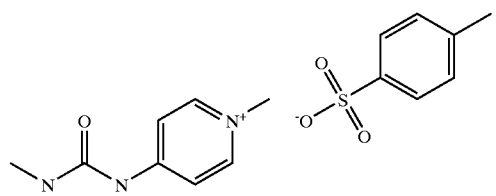
(57) 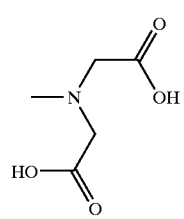
(58) 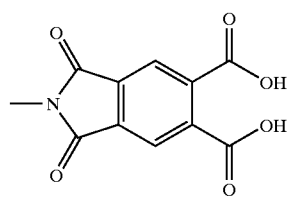
(59) 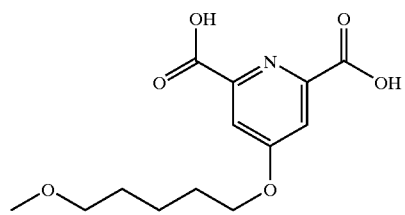
(60) 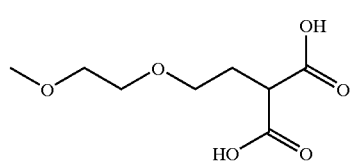
(61) 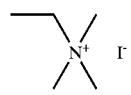
(62) 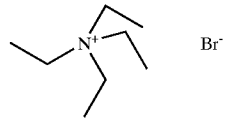
(63) 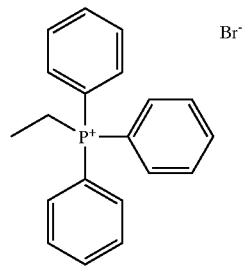
(64) 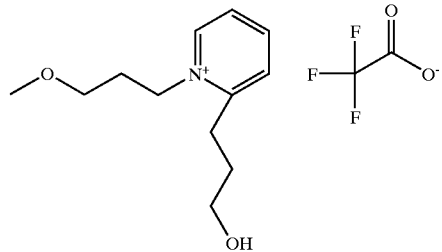
(65) 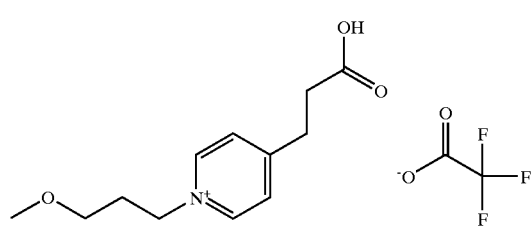
(66) 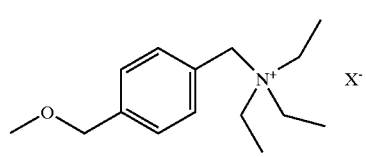

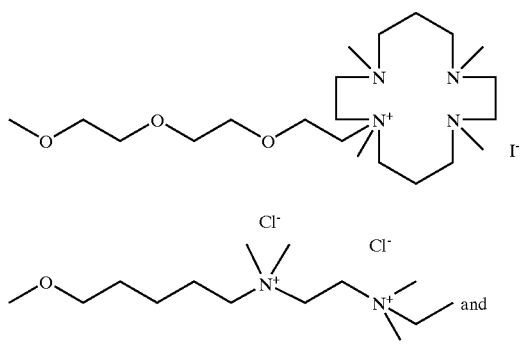
(67)

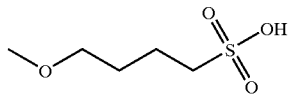
(68)

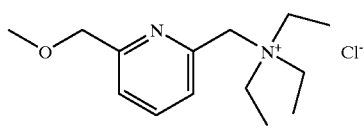
(70)

provided that when said $R^5$ is (7), (17) or (24), then said $R^{5A}$ is a left end of said $R^5$ and $R^{5B}$ is a right end of said $R^5$ or vice versa.

130. The pharmaceutical composition of embodiment 129 wherein said compound of Formula I-17 comprises a member selected from the group consisting of Formulas I-21 and I-22 represented by:

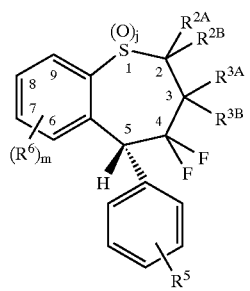

I-21

I-22

131. The pharmaceutical composition of embodiment 130 wherein said compounds of Formulas I-21 and I-22 comprise Formulas I-9 and I-10, respectively, represented by:

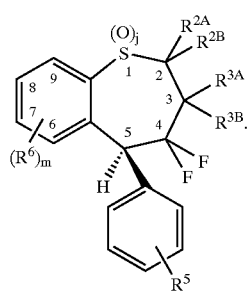

I-9

I-10

132. The pharmaceutical composition of embodiment 128 wherein said compound of Formula I-2 is selected from the group consisting of Formulas I-3 and I-4 represented by:

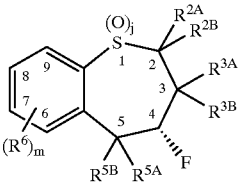

I-3

I-4 wherein $R^{2A}$, $R^{2B}$, $R^{3A}$, $R^{3B}$, $R^{5A}$, $R^{5B}$, $R^6$, m and j are as previously defined and said $R^5$ is selected from the group consisting of (1)–(69) and (70):

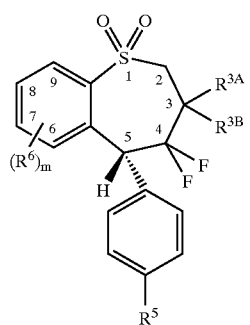

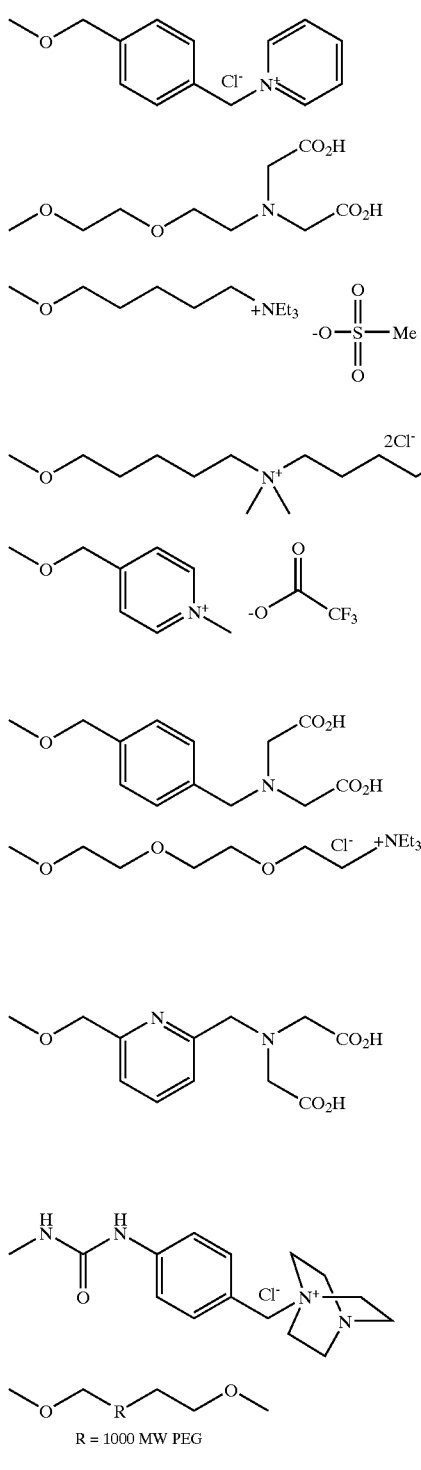
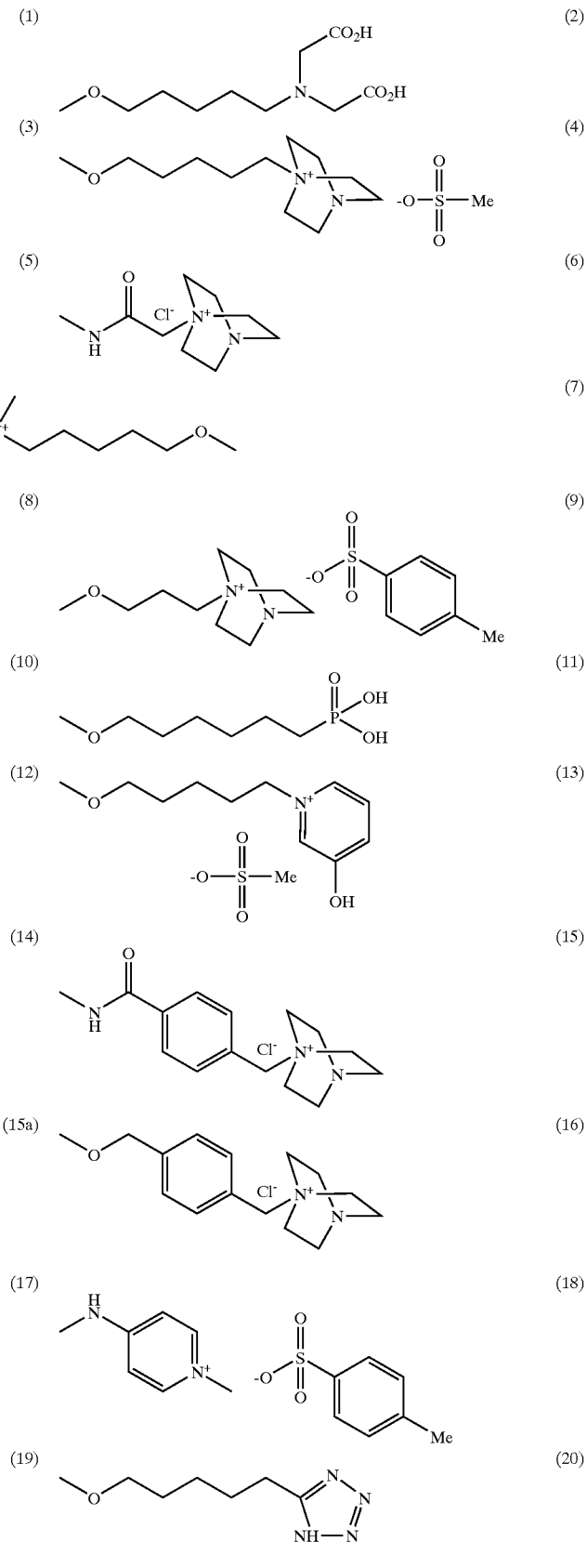

-continued
(21)
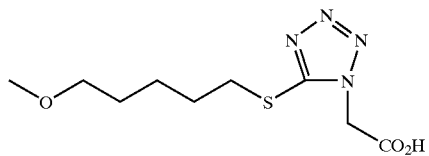
(22)
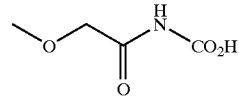
(23)
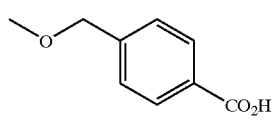
(24)
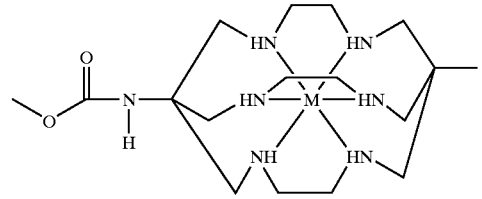
$M = Co^{II,III}, Mn^{II,III}, Fe^{II,III}, Ni^{II,III},$
$Cr^{III}, Cu^{II}, Zn^{II}, Cd^{II}, Ga^{III}, In^{III}, V^{IV},$
$Ru^{II}, Pr^{IV}, Rh^{III}$ or $Ir^{III}$
(25)
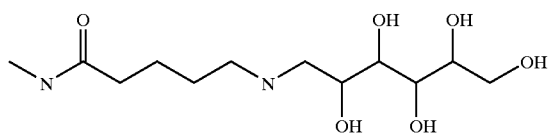
(26)
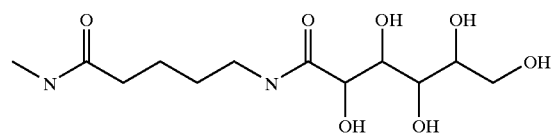
(27)
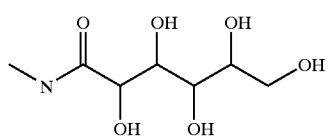
(28)
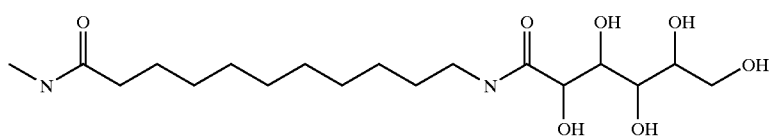
(29)
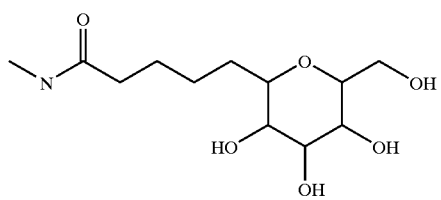
(30)
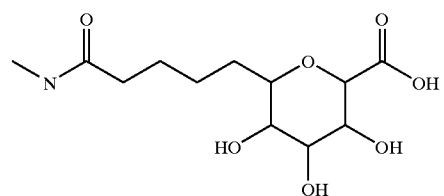
(31)
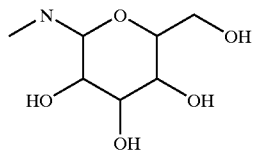
(32)
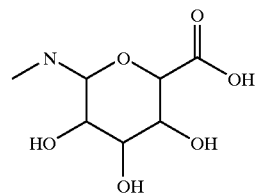
(33)
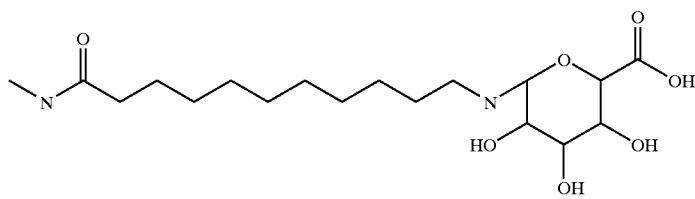

-continued
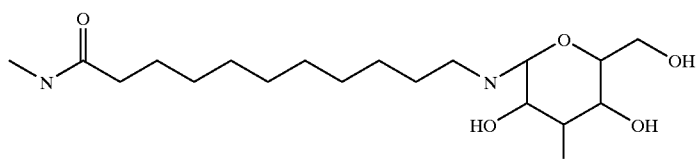
(34)
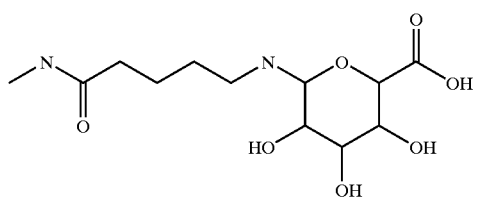
(35)
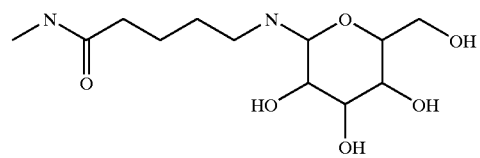
(36)
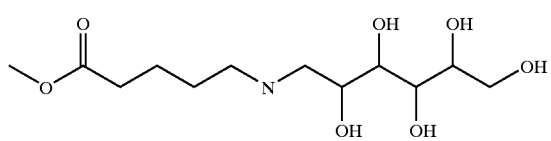
(37)
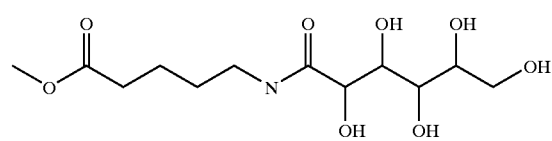
(38)
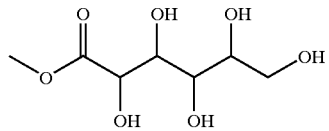
(39)
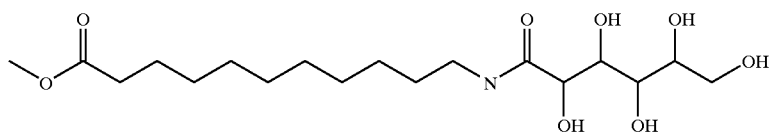
(40)
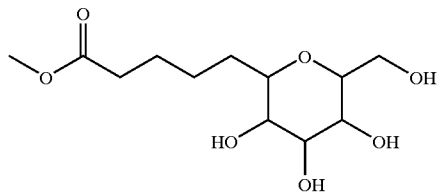
(41)
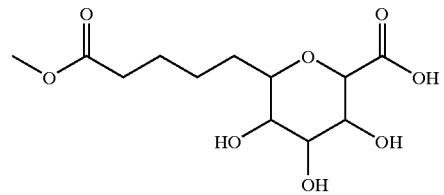
(42)
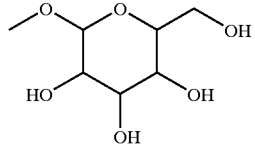
(43)
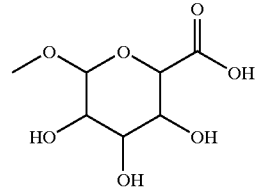
(44)
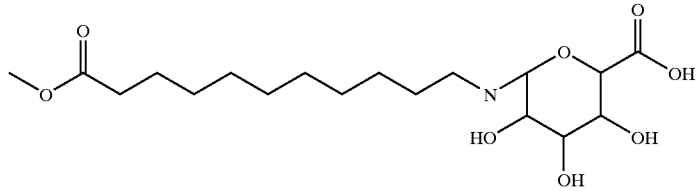
(45)
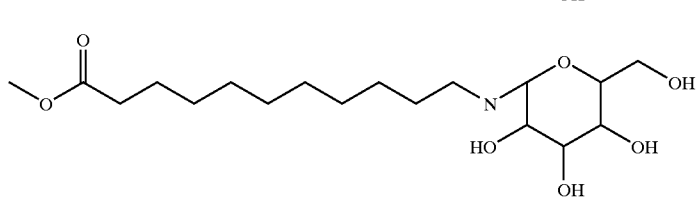
(46)

-continued
(47) 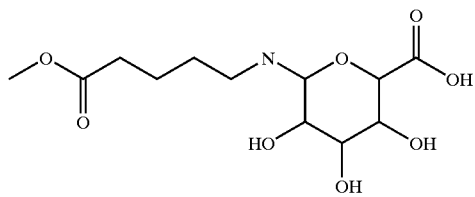
(48) 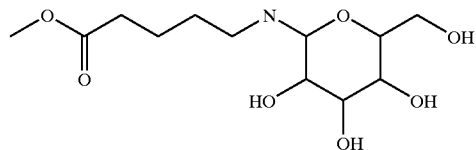
(49) 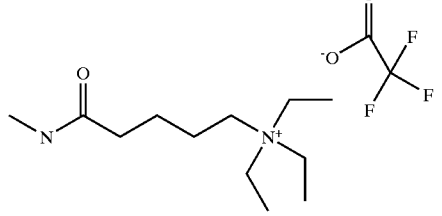
(50) 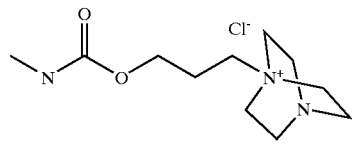
(51) 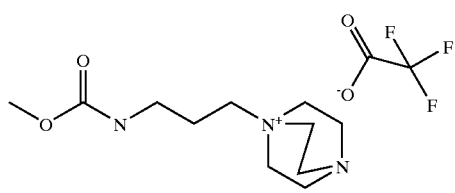
(52) 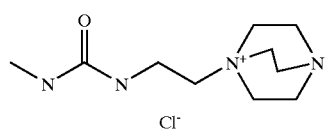
(53) 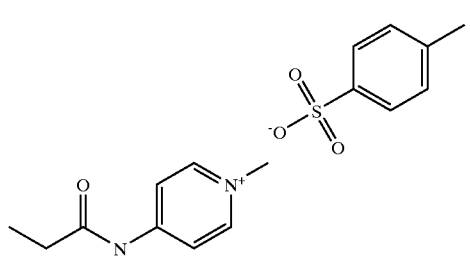
(54) 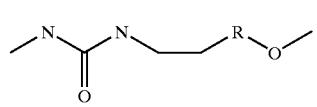
(55) 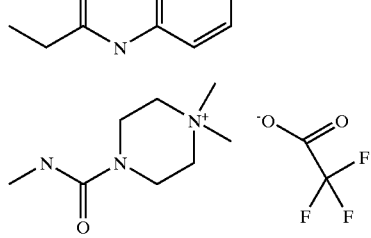
(56) 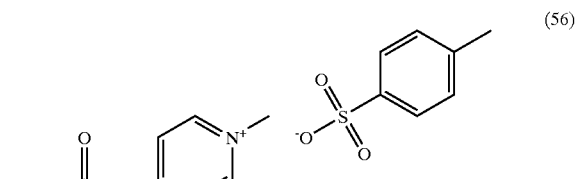
(57) 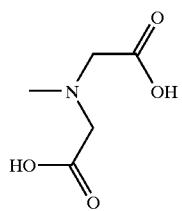
(58) 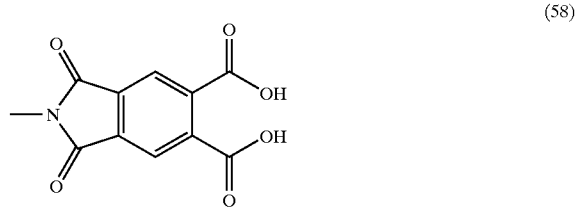
(59) 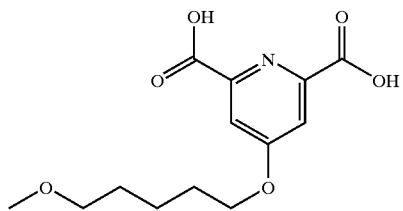
(60) 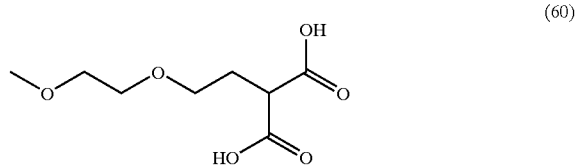
(61) 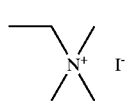
(62) 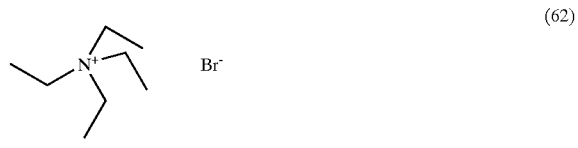

-continued

(63)
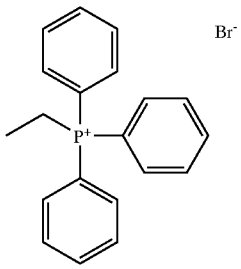

(64)
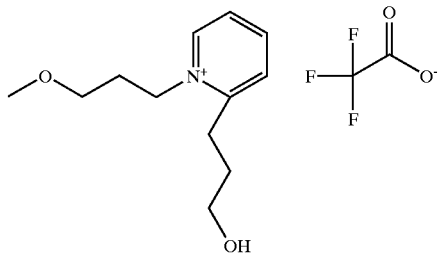

(65)
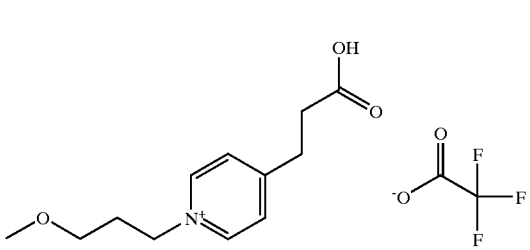

(66)
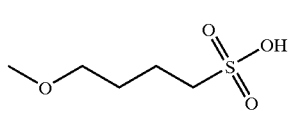

(67)
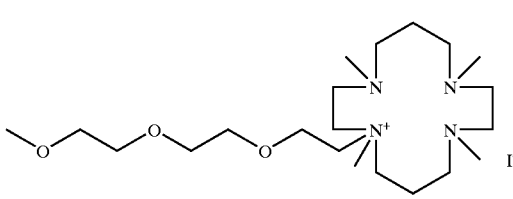

(68)

(69)
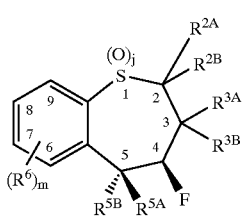 and

(70)

provided that when said $R^5$ is (7), (17) or (24), then said $R^{5A}$ is a left end of said $R^5$ and said $R^{5B}$ is a right end of said $R^5$ or vice versa.

133. The pharmaceutical composition of embodiment 132 wherein said Formula I-3 comprises a member selected from the group consisting of Formulas I-5 and I-6 represented by:

I-5
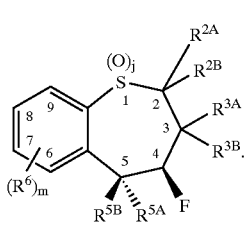

I-6
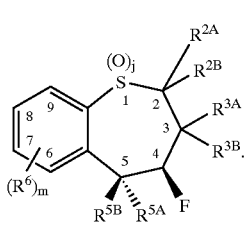

134. The pharmaceutical composition of embodiment 132 wherein said Formula I-4 comprises a member selected from the group consisting of Formulas I-7 and I-8 represented by.

I-7

I-8

135. The pharmaceutical composition of embodiment 133 wherein said compounds of Formulas I-6 and I-5 comprise Formulas I-13 and I-14, respectively, represented by:

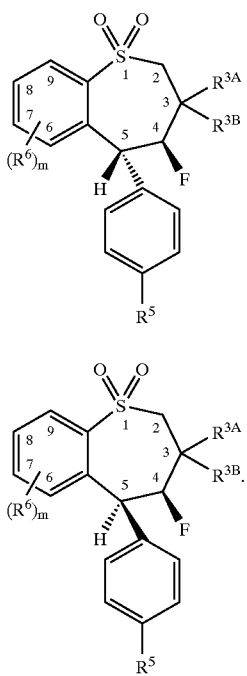

I-13

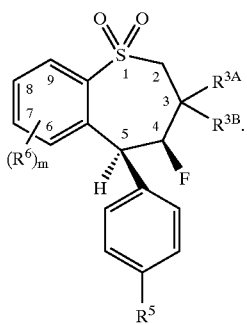

I-14

136. The pharmaceutical composition of embodiment 134 wherein said compounds of Formulas I-7 and I-8 comprise Formulas I-15 and I-16, respectively, represented by:

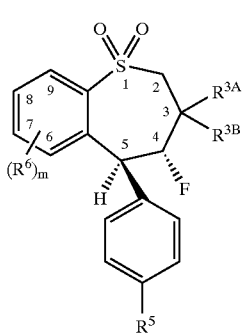

I-15

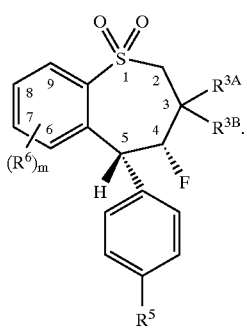

I-16

137. The pharmaceutical composition of embodiment 128 wherein said compound of Formula I-2 comprises a compound of Formula I-18 represented by:

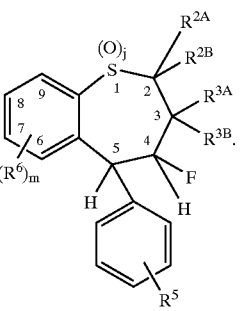

I-18

138. The pharmaceutical composition of embodiment 137 wherein said compound of Formula I-18 comprises a member selected from the group I-23 and I-24 represented by:

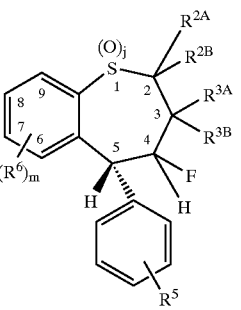

I-23

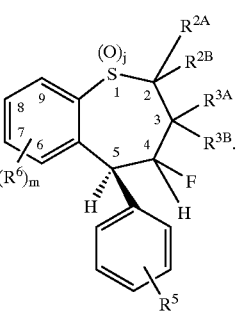

I-24

139. The pharmaceutical composition of embodiment 138 wherein said compound of Formulas I-23 and I-24 comprise compounds of Formulas I-19 and I-20, respectively, represented by:

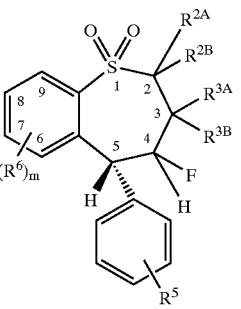

I-19

-continued

I-20

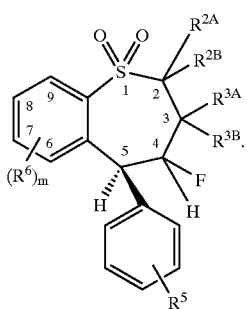

140. The pharmaceutical composition of embodiment 128 wherein said compound of Formula I-2 is selected from the group consisting of Formulas I-11 and I-12 represented by:

I-11

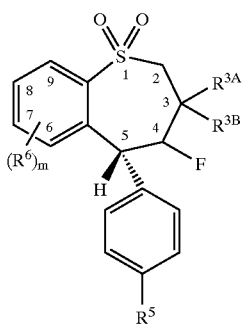

I-12

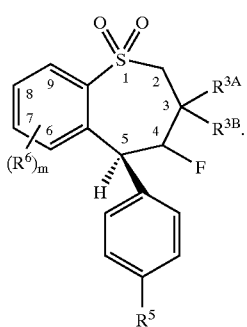

141. The pharmaceutical composition of embodiment 128 provided in a coated dosage form, said coated dosage form having a coating of cellulose acetate phthalate, polyvinylacetate pththalate, hydroxypropylmethyl cellulose phthalate, or an anionic polymer of methacrylic acid and methacrylic acid methyl ester.

142. The compound of embodiment 1 provided in a coated dosage form, said coated dosage form having a coating of cellulose acetate phthalate, polyvinylacetate pththalate, hydroxypropylmethyl cellulose phthalate, or an anionic polymer of methacrylic acid and methacrylic acid methyl ester.

143. The pharmaceutical composition of embodiment 128 provided in a dosage form selected from the group consisting of a tablet, a capsule, a suspension, an emulsion, a solution, a cream, a paste, a lotion, a suppository, or a powder.

144. The pharmaceutical composition of embodiment 128 in a dosage form selected from the group consisting of a sublingual tablet, an effervescent tablet, and a coated tablet.

145. The pharmaceutical composition of embodiment 128 provided in a dosage form comprising a slow release dosage form.

146. The pharmaceutical composition of embodiment 145 wherein said slow release dosage form is selected from the group consisting of an implant or a coated tablet.

147. The pharmaceutical composition of embodiment 146 wherein said solution, said suspension or said emulsion are suitable for parenteral administration to said subject.

148. The pharmaceutical composition of embodiment 143 wherein said solution comprises a syrup.

149. The pharmaceutical composition of embodiment 128 provided in a dosage form comprising a dispersion.

150. The compound of embodiment 1 provided in a dosage form selected from the group consisting of a tablet, a capsule, a suspension, an emulsion, a solution, a cream, a paste, a lotion, a suppository, and a powder.

EXAMPLES OF SYNTHETIC PROCEDURES

The following examples use a numbering scheme for referring to the various compounds depicted below that may be different from the numbering scheme that is used in the earlier part of this patent application.

Preparation 1

2-Ethyl-2-(mesyloxymethyl)hexanal (1)

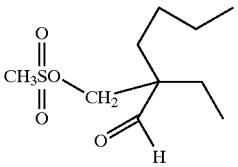

To a cold (10° C.) solution of 12.6 g (0.11 mole) of methanesulfonyl chloride and 10.3 g (0.13 mole) of triethylamine was added dropwise 15.8 g of 2-ethyl-2-(hydroxymethyl)hexanal, prepared according to the procedure described in Chem. Ber. 98, 728–734 (1965), while maintaining the reaction temperature below 30° C. The reaction mixture was stirred at room temperature for 18 h, quenched with dilute HCl and extracted with methylene chloride. The methylene chloride extract was dried over $MgSO_4$ and concentrated in vacuo to give 24.4 g of brown oil.

Preparation 2

2-((2-Benzoylphenylthio)methyl-2-ethylhexanal (2)

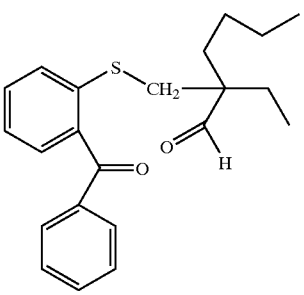

A mixture of 31 g (0.144 mol) of 2-mercaptobenzophenone, prepared according to the procedure described in WO 93/16055, 24.4 g (0.1 mole) of 2-ethyl-2-(mesyloxymethyl)-hexanal 1, 14.8 g (0.146 mole)

of triethylamine, and 80 mL of 2-methoxyethyl ether was held at reflux for 24 h. The reaction mixture was poured into 3N HCl and extracted with 300 mL of methylene chloride. The methylene chloride layer was washed with 300 mL of 10% NaOH, dried over MgSO$_4$ and concentrated in vacuo to remove 2-methoxyethyl ether. The residue was purified by HPLC (10% EtOAc-hexane) to give 20.5 g (58%) of 2 as an oil.

Example 1

3-Butyl-3-ethyl-5-phenyl-2,3-dihydrobenzothiepine (3), cis-3-Butyl-3-ethyl-5-phenyl-2,3-dihydrobenzothiepin-(5H)4-one (4a) and trans-3-Butyl-3-ethyl-5-phenyl-2,3-dihydro-benzothiepin-(5H)4-one (4b)

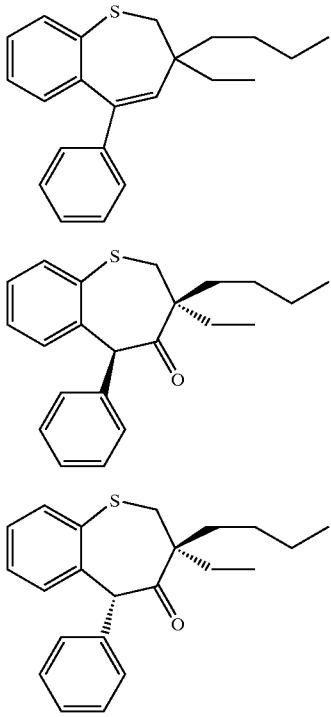

A mixture of 2.6 g (0.04 mole) of zinc dust, 7.2 g (0.047 mole) of TiCl$_3$ and 80 mL of anhydrous ethylene glycol dimethyl ether (DME) was held at reflux for 2 h. The reaction mixture was cooled to 5° C. To the reaction mixture was added dropwise a solution of 3.54 g (0.01 mole) of 2 in 30 mL of DME in 40 min. The reaction mnixture was stirred at room temperature for 16 h and then was held at reflux for 2 h and cooled before being poured into brine. The organic was extract into methylene chloride. The methylene chloride extract was dried over MgSO$_4$ and concentrated in vacuo. The residue was purified by HPLC (hexane) to give 1.7 g (43%) of 3 as an oil in the first fraction. The second fraction was discarded and the third fraction was further purified by HPLC (hexane) to give 0.07 g (2%) of 4a in the earlier fraction and 0.1 g (3%) of 4b in the later fraction.

Example 2 cis-3-Butyl-3-ethyl-5-phenyl-2,3-dihydrobenzothiepin-(5)4-one-1,1-dioxide (5a) and trans-3-Butyl-3-ethyl-5-phenyl-2,3-dihydro-benzothiepin-(5H)4-one-1,1-dioxide (5b)

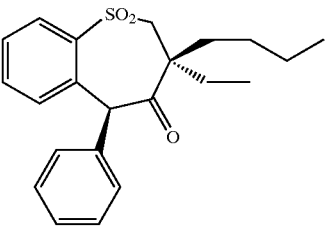

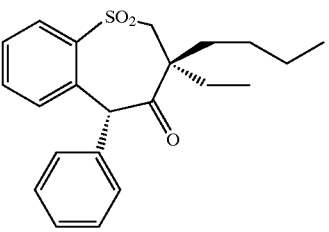

To a solution of 1.2 g (3.5 mmole) of 50–60% MCPBA in 20 mL of methylene chloride was added 0.59 g (1.75 mmole) of a mixture of 4a and 4b in 10 mL of methylene chloride. The reaction mixture was stirred for 20 h. An additional 1.2 g (1.75 mmole) of 50–60% MAPBA was added and the reaction mixture was stirred for an additional 3 h then was triturated with 50 mL of 10% NaOH. The insoluble solid was filtered. The methylene chloride layer of the filtrate was washed with brine, dried over MgSO$_4$, and concentrated in vacuo. The residual syrup was purified by HPLC (5% EtOAc-hexane) to give 0.2 g (30%) of 5a as an oil in the first fraction and 0.17 g (26%) of 5b as an oil in the second fraction.

Example 3

(3α,4α,5β)3-Butyl-3-ethyl-4-hydroxy-5-pheny-2,3,4,5-tetrahydrobenzothiepine-1,1-dioxide (6a), (3α,4β,5α)3-Butyl-3-ethyl-4-hydroxy-5-phenyl-2,3,4,5-tetrahydro-benzothiepine-1,1-dioxide (6b), (3α,4α,5α)3-Butyl-3-ethyl-4-hydroxy-5-phenyl-2,3,4,5-tetrahydrobenzothiepine-1,1-dioxide (6c), and (3α,4β,5β) 3-Butyl-3-ethyl-4-hydroxy-phenyl-2,3,4,5-tetrahydrobenzothiepine-1,1-dioxide (6d)

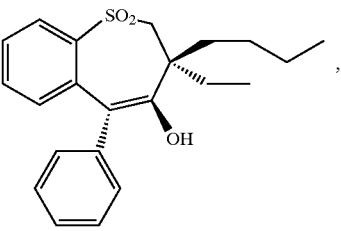

-continued

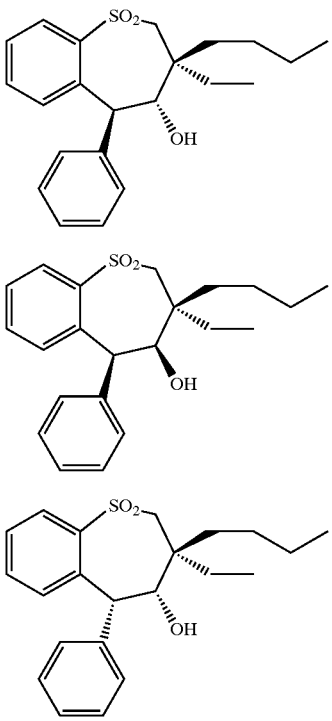

6b

6c

6d

A. Reduction of 5a and 5b with Sodium Borohydride

To a solution of 0.22 g (0.59 mmole) of 5b in 10 mL of ethanol was added 0.24 g (6.4 mmole) of sodium borohydride. The reaction mixture was stirred at room temperature for 18 h and concentrated in vacuo to remove ethanol. The residue was triturated with water and extracted with methylene chloride. The methylene chloride extract was dried over MgSO$_4$ and concentrated in vacuo to give 0.2 g of syrup. In a separate experiment, 0.45 g of 5a was treated with 0.44 g of sodium borohydride in 10 mL of ethanol and was worked up as described above to give 0.5 g of syrup which was identical to the 0.2 g of syrup obtained above. These two materials were combined and purified by HPLC using 10% EtOAc-hexane as eluant. The first fraction was 0.18 g (27%) of 6a as a syrup. The second fraction was 0.2 g (30%) of 6b also as a syrup. The column was then eluted with 20% EtOAc-hexane to give 0.077 g (11%) of 6c in the third fraction as a solid. Recrystallization from hexane gave a solid, mp 179–181° C. Finally, the column was eluted with 30% EtOAc-hexane to give 0.08 g (12%) of 6d in the fourth fraction as a solid. Recrystallization from hexane gave a solid, mp 160–161° C.

B. Conversion of 6a to 6c and 6d With NaOH and PTC

To a solution of 0.29 g (0.78 mmole) of 6a in 10 mL CH$_2$Cl$_2$, was added 9 g of 40% NaOH. The reaction mixture was stirred for 0.5 h at room temperature and was added one drop of Aliquat-336 (methyltricaprylylammonium chloride) phase transfer catalyst (PTC). The mixture was stirred for 0.5 h at room temperature before being treated with 25 mL of ice-crystals then was extracted with CH$_2$Cl$_2$ (3×10 ml), dried over MgSO$_4$ and concentrated in vacuo to recover 0.17 g of a colorless film. The components of this mixture were separated using an HPLC and eluted with EtOAc-hexane to give 12.8 mg (4%) of 2-(2-benzylphenylsulfonylmethyl)-2-ethylhexenal in the first fraction, 30.9 mg (11%) of 6c in the second fraction and 90.0 mg (31%) of 6d in the third fraction.

Oxidation of 6a to 5b

To a solution of 0.20 g (0.52 mmole) of 6a in 5 mL of CH$_2$Cl$_2$ was added 0.23 g (1.0 mmole) of pyridinium chlorochromate. The reaction mixture was stirred for 2 h then was treated with additional 0.23 g of pyridinium chlorochromate and stirred overnight. The dark reaction mixture was poured into a ceramic filterfrit containing silica gel and was eluted with CH$_2$Cl$_2$. The filtrate was concentrated in vacuo to recover 167 mg (87%) of 5b as a colorless oil.

Example 4

3-Butyl-3-ethyl-5-phenyl-2,3-dihydrobenzothiepine-1,1-dioxide (7)

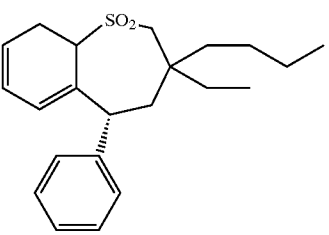

7

To a solution of 5.13 g (15.9 mmole) of 3 in 50 mL of CH$_2$Cl$_2$ was added 10 g (31.9 mmole)of 50–60% MCPBA (m-chloroperoxybenzoic acid) portionwise causing a mild reflux and formation of a white solid. The reaction mixture was allowed to stir overnight under N$_2$ and was triturated with 25 mL of water followed by 50 mL of 10% NaOH solution. The organic was extracted into CH$_2$Cl$_2$ (4×20 mL). The CH$_2$Cl$_2$ extract was dried over MgSO$_4$ and evaporated to dryness to recover 4.9 g (87%) of an opaque viscous oil.

Example 5

(1aα,2β,8bα)2-Butyl-2-ethyl-8b-phenyl-1α,2,3,8b-tetrahydro-benzothiepino[4,5-b]oxirene-4,4-dioxide (8a) (1aα2α,8bα)2-Butyl-2-ethyl-8b-phenyl-1a,2,3,8b-tetrahydro-benzothiepino[4,5-b]oxirene-4,4-dioxide (8b)

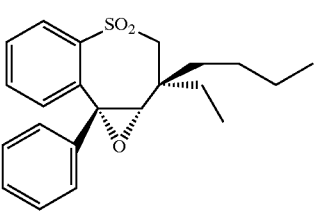

8a

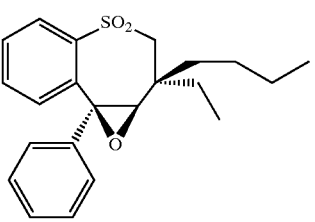

8b

To 1.3 g (4.03 mole) of 3 in 25 mL of CHCl$_3$ was added portionwise 5 g (14.1 mmole) of 50–60% MCPBA causing a mild exotherm. The reaction mixture was stirred under N$_2$ overnight and was then held at reflux for 3 h. The insoluble white slurry was filtered. The filtrate was extracted with 10% potassium carbonate (3×50 mL), once with brine, dried over MgSO$_4$, and concentrated in vacuo to give 1.37 g of a light yellow oil. Purification by HPLC gave 0.65 g of crystalline product. This product is a mixture of two isomers. Trituration of this crystalline product in hexane recovered 141.7 mg (10%) of a white crystalline product. This isomer was characterized by NMR and mass spectra to be the (1aα,2β, 8bα) isomer 8a. The hexane filtrate was concentrated in vacuo to give 206 mg of white film which is a mixture of 30% 8a and 70% 8b by $^1$H NMR.

Example 6 cis-3-Butyl-3-ethyl-5-phenyl-2,3,4,5-tetrahydrobenzothiepine-1,1-dioxide (9a), trans-3-Butyl-3-ethyl-5-phenyl-2,3,4,5-tetrahydrobenzothiepine-1,1-dioxide (9b), and 3-Butyl-3-ethyl-4-hydroxy-5-cyclohexylidine-2,3,4,5-tetrahydrobenzothiepine-1,1-dioxide (10)

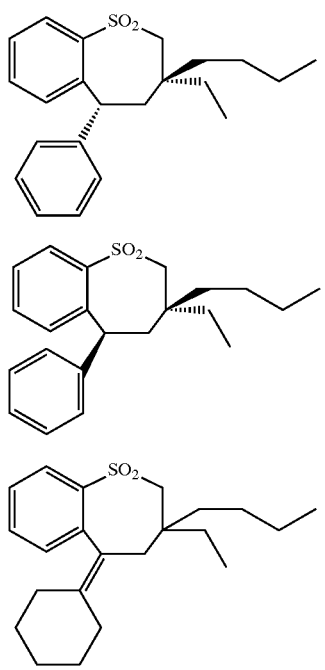

9b

9a

10

A mixture of 0.15 g (0.4 mmole) of a 3:7 mixture of 8a and 8b was dissolved in 15 ml MeOH in a 3 oz. Fisher/Porter vessel, then was added 0.1 g of 10% Pd/C catalyst. This mixture was hydrogenated at 70 psi H$_2$ for 5 h and filtered. The filtrate was evaporated to dryness in vacuo to recover 0.117 g of a colorless oil. This material was purified by HPLC eluting with EtOAc-hexane. The first fraction was 4.2 mg (3%) of 9b. The second fraction, 5.0 mg (4%), was a 50/50 mixture of 9a and 9b. The third fraction was 8.8 mg (6%) of 6a. The fourth fraction was 25.5 mg (18%) of 6b. The fifth fraction was 9.6 mg (7%) of a mixture of 6b and a product believed to be 3-butyl-3-ethyl-4,5-dihydroxy-5-phenyl-2,3,4,5-tetrahydrobenzothiepine-1,1-dioxide based on mass spectrum. The sixth fraction was 7.5 mg (5%) of a mixture of 6d and one of the isomers of 10, 10a Example 7

In another experiment, a product (3.7 g) from epoxidation of 3 with excess MCPBA in refluxing CHCl$_3$ under air was hydrogenated in 100 mL of methanol using 1 g of 10% Pd/C catalyst and 70 psi hydrogen. The product was purified by HPLC to give 0.9 g (25%) of 9b, 0.45 g (13%) of 9a, 0.27 g (7%) of 6a, 0.51 g (14%) of 6b, 0.02 g (1%) of 6c, 0.06 g (2%) of one isomer of 10, 10a and 0.03 g (1%) of another isomer of 10, 10b.

Example 8

2-((2-Benzoylphenylthio)methyl)butyraldehyde (11)

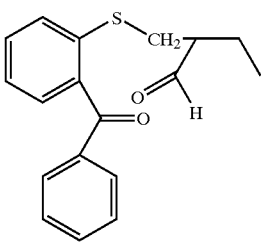

11

To an ice bath cooled solution of 9.76 g (0.116 mole) of 2-ethylacrolein in 40 mL of dry THF was added 24.6 g (0.116 mole) of 2-mercaptobenzophenone in 40 mL of THF followed by 13 g (0.128 mole) of triethylamine. The reaction mixture was stirred at room temperature for 3 days, diluted with ether, and was washed successively with dilute HCl, brine, and 1 M potassium carbonate. The ether layer was dried over MgSO$_4$ and concentrated in vacuo. The residue was purified by HPLC (10% EtOAc-hexane) to give 22 g (64%) of 11 in the second fraction. An attempt to further purify this material by kugelrohr distillation at 0.5 torr (160–190° C.) gave a fraction (12.2 g) which contained starting material indicating a reversed reaction during distillation. This material was dissolved in ether (100 mL) and was washed with 50 mL of 1 M potassium carbonate three times to give 6.0 g of a syrup which was purified by HPLC (10% EtOAc-hexane) to give 5.6 g of pure 11.

Example 9

3-Ethyl-5-phenyl-2,3-dihydrobenzothiepine (12)

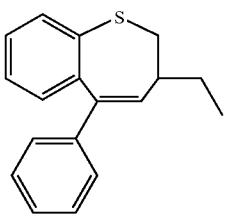

12

To a mixture of 2.61 g (0.04 mole) of zinc dust and 60 mL of DME was added 7.5 g (0.048 mole) of TiCl$_3$. The reaction mixture was held at reflux for 2 h. A solution of 2.98 g (0.01 mole) of 11 was added dropwise in 1 h. The reaction mixture was held at reflux for 18 h, cooled and poured into water. The organic was extracted into ether. The ether layer was washed with brine and filtered through Celite. The filtrate was dried over MgSO$_4$ and concentrated. The residual oil (2.5 g) was purified by HPLC to give 2.06 g (77%) of 12 as an oil in the second fraction.

Example 10

(1aα,2α,8bα)2-Ethyl-8b-phenyl-1a,2,3,8b-tetrahydro-benzothiepino-[4,5-b]oxirene-4,4-dioxide (13)

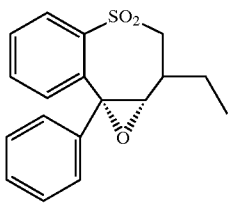

To a solution of 1.5 g (5.64 mmole) of 12 in 25 ml of CHCl₃ was added 6.8 g (19.4 mmole) of 50–60% MCPB portionwise causing an exotherm and formation of a white solid. The mixture was stirred at room temperature overnight diluted with 100 ml methylene chloride and washed successively with 10% K₂CO₃ (4×50 ml), water (twice with 25 ml) and brine. The organic layer was then dried over MgSO₄ and evaporated to dryness to recover 1.47 g of an off white solid. ¹H NMR indicated that only one isomer is present. This solid was slurried in 200 ml of warm Et₂O and filtered to give 0.82 g (46%) of 13 as a white solid, mp 185–186.5° C.

Example 11

(3α,4β,5α)3-Ethyl-4-hydroxy-5-phenyl-2,3,4,5-tetrahydro-benzothiepine-1,1-dioxide (14a), (3α,4β,5β)3-Ethyl-4-hydroxy-5-phenyl-2,3,4,5-tetrahydrobenzothiepine-1,1-dioxide (14b), and cis-3-Ethyl-5-phenyl-2,3,4,5-tetrahydro-benzothiepine-1,1-dioxide (15)

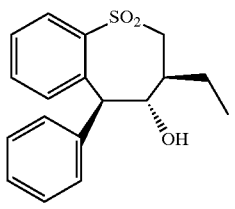

14a

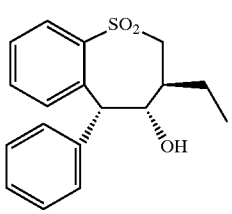

14b

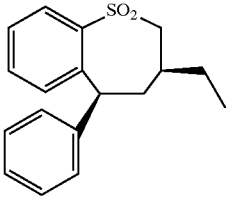

15

A mixture of 0.5 g (1.6 mole) of 13, 50 ml of acetic acid and 0.5 g of 10% Pd/C catalyst was hydrogenated with 70 psi hydrogen for 4 h. The crude reaction slurry was filtered and the filtrate was stirred with 150 ml of a saturated NaHCO₃ solution followed by 89 g of NaHCO₃ powder portionwise to neutralize the rest of acetic acid. The mixture was extracted with methylene chloride (4×25 ml), then the organic layer was dried over MgSO₄ and concentrated in vacuo to give 0.44 g (87%) of a voluminous white solid which was purified by HPLC (EtOAc-Hexane) to give 26.8 mg (6%) of 15 in the first fraction, 272 mg (54%) of 14a as a solid, mp 142–143.5° C., in the second fraction, and 35 mg (7%) of impure 14b in the third fraction.

Example 12

2-Ethyl-2-((2-hydroxymethylphenyl)thiomethyl)hexenal (16)

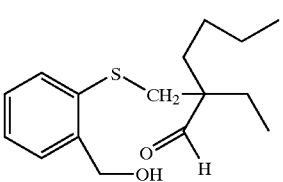

16

A mixture of 5.0 g (0.036 mole) of 2-mercaptobenzyl alcohol, 6.4 g (0.032 mole) of 1, 3.6 g (0.036 mole) of triethylamine and 25 mL of 2-methoxyethyl ether was held at reflux for 7 h. Additional 1.1 g of mercaptobenzyl alcohol and 0.72 g of triethylamine was added to the reaction mixture and the mixture was held at reflux for additional 16 h. The reaction mixture was cooled and poured into 6N HCl and extracted with methylene chloride. The methylene chloride extract was washed twice with 10% NaOH, dried over MgSO₄ and concentrated in vacuo to give 9.6 g of residue. Purification by HPLC (20% EtOAc-hexane) gave 3.7 g (41%) of 16 as an oil.

Example 13

2-Ethyl-2-((2-formylphenyl)thiomethyl)hexenal (17)

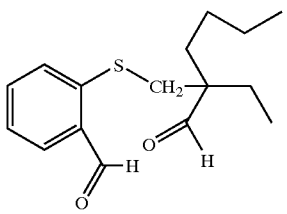

A mixture of 3.7 g of 16, 5.6 g (0.026 mole) of pyridinium chlorochromate, 2 g of Celite and 30 mL of methylene chloride was stirred for 18 h and filtered through a bed of silica gel. The silica gel was eluted with methylene chloride. The combined methylene chloride eluant was purified by HPLC (20% ETOAc-hexane) to give 2.4 g (66%) of an oil.

Example 14

3-Butyl-3-ethyl-2,3-dihydrobenzothiepine (18)

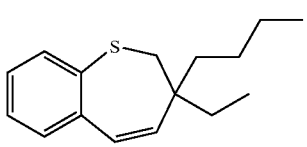

A mixture of 2.6 g (0.04 mole) of zinc dust, 7.2 g (0.047 mole) of $TiCl_3$, and 50 mL of DME was held at reflux for 2 h and cooled to room temperature. To this mixture was added 2.4 g (8.6 mmole) of 17 in 20 mL of DME in 10 min. The reaction mixture was stirred at room temperature for 2 h and held at reflux for 1 h then was let standing at room temperature over weekend. The reaction mixture was poured into dilute HCl and was stirred with methylene chloride. The methylene chloride-water mixture was filtered through Celite. The methylene chloride layer was washed with brine, dried over $MgSO_4$, and concentrated in vacuo to give 3.0 g of a residue. Purification by HPLC gave 0.41 g (20%) of 18 as an oil in the early fraction.

Example 15

(1aα,2α8bα)2-Butyl-2-ethyl-1a,2,3,8b-tetrahydro-benzothiepino[4,5-b]oxirene-4,4-dioxide (19a) and (1aα,2β,8bα)2-Butyl-2-ethyl-8b-phenyl-1a,2,3,8b-tetrahydro-benzothiepino[4,5-b]oxirene-4,4-dioxide (19b)

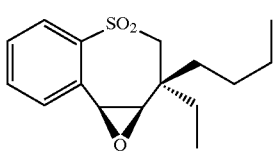

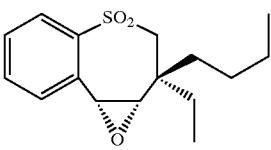

To a solution of 0.4 g of 0.4 g (1.6 mmole) of 18 in 30 mL of methylene chloride was added 2.2 g (3.2 mmole) of 50–60% MCPBA. The reaction mixture was stirred for 2 h and concentrated in vacuo. The residue was dissolved in 30 mL of $CHCl_3$ and was held at reflux for 18 h under $N_2$. The reaction mixture was stirred with 100 mL of 10% NaOH and 5 g of sodium sulfite. The methylene chloride layer was washed with brine, dried over $MgSO_4$ and concentrated in vacuo. The residue was purified by HPLC (20% EtOAc-hexane) to give a third fraction which was further purified by HPLC (10% EtOAc-hexane) to give 0.12 g of syrup in the first fraction. Recrystallization from hexane gave 0.08 g (17%) of 19a, mp 89.5–105.5° C. The mother liquor from the first fraction was combined with the second fraction and was further purified by HPLC to give additional 19a in the first fraction and 60 mg of 19b in the second fraction. Crystallization from hexane gave 56 mg of a white solid.

Example 16

3-Butyl-3-ethyl-4,5-dihydroxy-5-phenyl-2,3,4,5-tetrahydro-benzothiepine-1,1-dioxide (20)

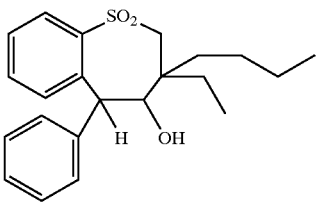

This product was isolated along with 6b from hydrogenation of a mixture of 8a and 8b.

Example 17

3-Butyl-3-ethyl-4-hydroxy-5-phenylthio-2,3,4,5-tetrahydro-benzothiepine-1,1-dioxide (21)

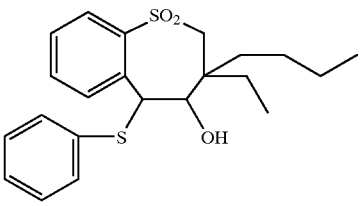

A mixture of 25 mg (0.085 mmole) of 19b, 0.27 g (2.7 mmole) of thiophenol, 0.37 g (2.7 mmole) of potassium carbonate, and 4 mL of DMF was stirred at room temperature under $N_2$ for 19 h. The reaction mixture was poured into water and extracted with methylene chloride. The methylene chloride layer was washed successively with 10% NaOH and brine, dried over $MgSO_4$, and concentrated in vacuo to give 0.19 g of semisolid which contain substantial amounts of diphenyl disulfide. This material was purified by HPLC (5% EtOAc-hexane) to remove diphenyl disulfide in the first fraction. The column was then eluted with 20% EtOAc-hexane to give 17 mg of a first fraction, 4 mg of a second fraction and 11 mg of a third fraction which were three different isomers of 21, i.e. 21a, 21b, and 21c, respectively, by $^1$H NMR and mass spectra.

Example 18

Alternative Synthesis of 6c and 6d

A. Preparation from 2-((2-Benzoylphenylthio)methyl)-2-ethylhexanal (2)

Step 1. 2-((2-Benzoylphenylsulfonyl)methyl)-2-ethylhexanal (44)

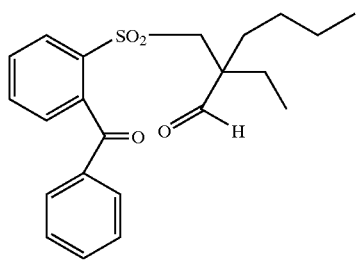

44

To a solution of 9.0 g (0.025 mole) of compound 2 in 100 ml of methylene chloride was added 14.6 g (0.025 mol) of 50–60% MCPBA portionwise. The reaction mixture was stirred at room temperature for 64 h then was stirred with 200 ml of 1 M potassium carbonate and filtered through Celite. The methylene chloride layer was washed twice with 300 ml of 1 M potassium carbonate, once with 10% sodium hydroxide and once with brine. The insoluble solid formed during washing was removed by filtration through Celite. The methylene chloride solution was dried and concentrated in vacuo to give 9.2 g (95%) of semisolid. A portion (2.6 g) of this solid was purified by HPLC(10% ethyl acetate-hexane) to give 1.9 g of crystals, mp 135–136° C.

Step 2. 2-((2-Benzylphenylsulfonyl)methyl)-2-ethylhexanal (45)

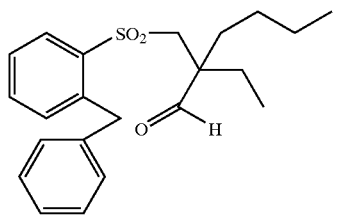

45

A solution of 50 g (0.13 mole) of crude 44 in 250 ml of methylene chloride was divided in two portions and charged to two Fisher-Porter bottles. To each bottle was charged 125 ml of methanol and 5 g of 10% Pd/C. The bottles were pressurized with 70 psi of hydrogen and the reaction mixture was stirred at room temperature for 7 h before being charged with an additional 5 g of 10% Pd/C. The reaction mixture was again hydrogenated with 70 psi of hydrogen for 7 h. This procedure was repeated one more time but only 1 g of Pd/C was charged to the reaction mixture. The combined reaction mixture was filtered and concentrated in vacuo to give 46.8 g of 45 as brown oil.

Step 3. (3α,4α,5α)3-Butyl-3-ethyl-4-hydroxy-5-phenyl-2,3,4,5-tetrahydrobenzothiepine-1,1-dioxide (6c), and (3α,4β,5β)3-Butyl-3-ethyl-4-hydroxy-5-phenyl-2,3,4,5-tetrahydrobenzothiepine-1,1-dioxide (6d)

To a solution of 27.3 g (73.4 mmole) of 45 in 300 ml of anhydrous THF cooled to 2° C. with an ice bath was added 9.7 g (73.4 mmole) of 95% potassium t-butoxide. The reaction mixture was stirred for 20 min, quenched with 300 ml of 10% HCl and extracted with methylene chloride. The methylene chloride layer was dried over magnesium sulfate and concentrated in vacuo to give 24.7 g of yellow oil. Purification by HPLC (ethyl acetate-hexane) yielded 9.4 g of recovered 45 in the first fraction, 5.5 g (20%) of 6c in the second fraction and 6.5 g (24%) of 6d in the third fraction.

B. Preparation from 2-Hydroxydiphenylmethane

Step 1. 2-Mercaptodiphenylmethane (46)

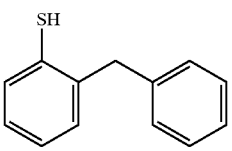

46

To a 500 ml flask was charged 16 g (0.33 mol) of 60% sodium hydride oil dispersion. The sodium hydride was washed twice with 50 ml of hexane. To the reaction flask was charged 100 ml of DMF. To this mixture was added a solution of 55.2 g (0.3 mol) of 2-hydroxydiphenylmethane in 200 ml of DMF in 1 h while temperature was maintained below 30° C. by an ice-water bath. After complete addition of the reagent, the mixture was stirred at room temperature for 30 min then cooled with an ice bath. To the reaction mixture was added 49.4 g (0.4 mole) of dimethyl thiocarbamoyl chloride at once. The ice bath was removed and the reaction mixture was stirred at room temperature for 18 h before being poured into 300 ml of water. The organic was extracted into 500 ml of toluene. The toluene layer was washed successively with 10% sodium hydroxide and brine and was concentrated in vacuo to give 78.6 g of a yellow oil which was 95% pure dimethyl O-2-benzylphenyl thiocarbamate. This oil was heated at 280–300° C. in a kugelrohr pot under house vacuum for 30 min. The residue was kugelrohr distilled at 1 torr (180–280° C.). The distillate (56.3 g) was crystallized from methanol to give 37.3 g (46%) of the rearranged product dimethyl S-2-benzylphenyl thiocarbamate as a yellow solid. A mixture of 57 g (0.21 mole) of this yellow solid, 30 g of potassium hydroxide and 150 ml of methanol was stirred overnight then was concentrated in vacuo. The residue was diluted with 200 ml of water and extracted with ether. The aqueous layer was made acidic with concentrate HCl, The oily suspension was extracted into ether. The ether extract was dried over magnesium sulfate and concentrated in vacuo. The residue was crystallized from hexane to give 37.1 g (88%) of 2-mercapto-diphenylmethane as a yellow solid.

Step 2. 2-((2-Benzylphenylthio)methyl)-2-ethylhexanal (47)

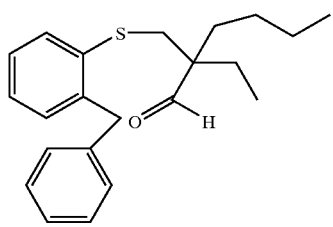

47

A mixture of 60 g (03 mole) of yellow solid from step 1, 70 g (0.3 mole) of compound 1 from preparation 1, 32.4 g (0.32 mole) of triethylarnine, 120 ml of 2-methoxyethyl ether was held at reflux for 6 hr and concentrated in vacuo. The residue was triturated with 500 ml of water and 30 ml of concentrate HCl. The organic was extracted into 400 ml of ether. The ether layer was washed successively with brine, 10% sodium hydroxide and brine and was dried over magnesium sulfate and concentrated in vacuo. The residue (98.3 g) was purified by HPLC with 2–5% ethyl acetate-hexane as eluent to give 2-((2-benzylphenylthio)methyl)-2-ethylhexanal 47 as a yellow syrup.

Step 3. 2-((2-Benzylphenylsulfonyl)methyl)-2-ethyl-hexanal (45)

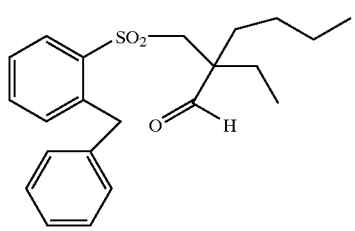

45

To a solution of 72.8 g (0.21 mole) of yellow syrup from step 2 in 1 liter of methylene chloride cooled to 10° C. was added 132 g of 50–60% MCPBA in 40 min. The reaction mixture was stirred for 2 h. An additional 13 g of 50–60% MCPBA was added to the reaction mixture. The reaction mixture was stirred for 2 h and filtered through Celite. The methylene chloride solution was washed twice with 1 liter of 1 M potassium carbonate then with 1 liter of brine. The methylene chloride layer was dried over magnesium sulfate and concentrated to 76g of 2-((2-benzylphenylsulfonyl)methyl)-2-ethylhexanal 45 as a syrup.

Step 4. (3α,4α,5α)3-Butyl-3-ethyl-4-hydroxy-5-phenyl-2,3,4,5-tetrahydrobenzothiepine-1,1-dioxide (6c), and (3α,4β,5β)3-Butyl-3-ethyl-4-hydroxy-5-phenyl-2,3,4,5-tetrahydrobenzothiepine-1,1-dioxide (6d)

Reaction of 45 with potassium t-butoxide according to the procedure in step 3 of procedure A gave pure 6c and 6d after HPLC.

Example 19

(3α,4β,5β)3-Butyl-3-ethyl-4-hydroxymethoy-phenyl-2,3,4,5-tetrahydrobenzothiepine-1,1-dioxide (25) and (3α,4α,5α)3-Butyl-3-ethyl-4-hydroxy-8-methoxy-5-phenyl-2,3,4,5-tetrahydrobenzothiepine-1,1-dioxide (26)

Step 1. Preparation of 2-((2-benzoyl-4-methoxy Phenylthio) methyl)-2-ethylhexanal (22)

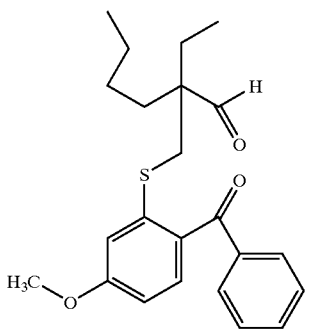

22

2-Hydroxy-4-methoxybenzophenone was converted to the dimethyl O-2-benzoyphenyl thiocarbamate by methods previously described in example 18. The product can be isolated by recrystallization from ethanol. Using this improved isolation procedure no chromatography was needed. The thermal rearrangement was performed by reacting the thiocarbamate(5 g) in diphenyl ether at 260° C. as previously described. The improved isolation procedure which avoided a chromatography step was described below.

The crude pyrolysis product was then heated at 65° C. in 100 ml of methanol and 100 ml of THF in the presence of 3.5 g of KOH for 4 h. After removing THF and methanol by rotary evaporation the solution was extracted with 5% NaOH and ether. The base layer was acidified and extracted with ether to obtain a 2.9 g of crude thiophenol product. The product was further purified by titrating the desired mercaptan into base with limited KOH. After acidification and extraction with ether pure 2-mercapto-4-methoxybenzophenone (2.3 g) was isolated.

2-mercapto-4-methoxybenzophenone can readily be converted to the 2-(2-benzoyl-4-methoxyphenylthio)methyl)-2-ethylhexanal (22) by reaction with 2-ethyl-2-(mesyloxymethyl)hexanal (1) as previously described.

Step 2. 2-((2-Benzoyl-5-methoxyphenylsulfonyl)methyl)-2-ethylhexanal (23)

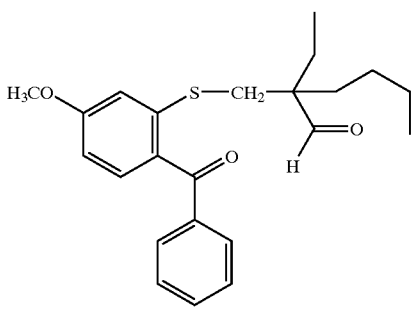

23

Substrate 22 was readily oxidized to 2-((2-benzoyl-5-methoxyphenyl-sulfonyl)methyl)-2-ethylhexanal (23) as described in example 18.

Step 3. 2-((2-Benzyl-5-methoxyphenylsulfonyl)methyl)-2-ethylhexanal (24)

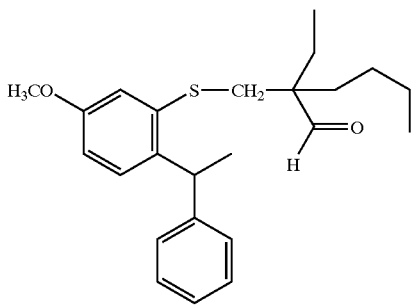

24

Sulfone 23 was then reduced to 2-((2-benzyl-5-methoxyphenyl-sulfonyl)methyl)-2-ethylhexanal (24) as described in example 18.

Step 4. (3α,4β,5β)3-Butyl-3-ethyl-4-hydroxy-8-methoxy-5-phenyl-2,3,4,5-tetrahydrobenzothiepine-1,1-dioxide (25) and (3α,4α,5α)3-Butyl-3-ethyl-4-hydroxy-8-methoxy-5-phenyl-2,3,4,5-tetrahydrobenzothiepine-1,1-dioxide (26)

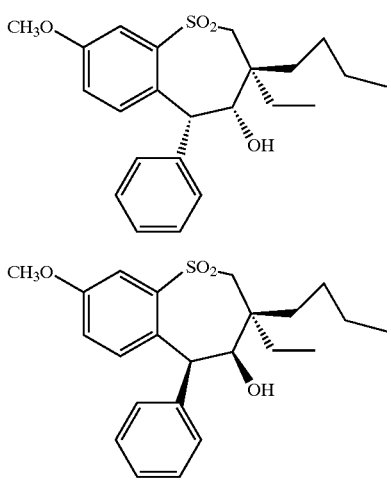

25

26

A 3-neck flask equipped with a powder addition funnel, thermocouple and nitrogen bubbler was charged with 19.8 g (0.05 mole) of sulfone 24 in 100 ml dry THF. The reaction was cooled to −1.6° C. internal temperature by means of ice/salt bath. Slowly add 5.61 g (0.05 mole) of potassium t-butoxide by means of the powder addition funnel. The resulting light yellow solution was maintained at −1.6° C. After 30 min reaction 400 ml of cold ether was added and this solution was extracted with cold 10% HCl. The acid layer was extracted with 300 ml of methylene chloride. The organic layers were combined and dried over magnesium sulfate and after filtration stripped to dryness to obtain 19.9 g of product. $^1$H nmr and glpc indicated a 96% conversion to a 50/50 mixture of 25 and 26. The only other observable compound was 4% starting sulfone 24.

The product was then dissolved in 250 ml of 90/10 hexane/ethyl acetate by warming to 50° C. The solution was allowed to cool to room temperature and in this way pure 26 can be isolated. The crystallization can be enhanced by addition of a seed crystal of 26. After 2 crystallizations the mother liquor which was now 85.4% 25 and has a dry weight of 8.7 g. This material was dissolved in 100 ml of 90/10 hexane/ethyl acetate and 10 ml of pure ethyl acetate at 40° C. Pure 25 can be isolated by seeding this solution with a seed crystal of 25 after storing it overnight at 0° C.

Example 20

(3α,4α,5α)3-Butyl-3-ethyl-4,8-dihydroxy-5-phenyl-2,3,4,5-tetrahydrobenzothiepine-1,1-dioxide (27)

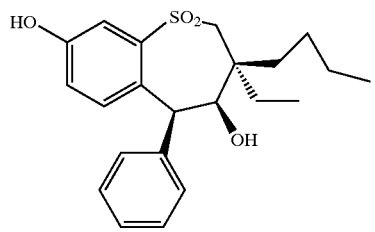

27

In a 25 ml round bottomed flask, 1 g of 26(2.5 mmoles) and 10 ml methylene chloride were cooled to −78° C. with stirring. Next 0.7 ml of boron tribromide(7.5 mmole) was added via syringe. The reaction was allowed to slowly warm to room temperature and stirred for 6 h. The reaction was then diluted with 50 ml methylene chloride and washed with saturated NaCl and then water. The organic layer was dried over magnesium sulfate. The product (0.88 g)27 was characterized by NMR and mass spectra.

Example 21

General Alkylation of Phenol 27

A 25 ml flask was charged with 0.15 g of 27(0.38 mmole), 5 ml anhydrous DMF, 54 mg of potassium carbonate(0.38 mmole) and 140 mg ethyl iodide (0.9 mmole). The reaction was stirred at room temperature overnight. The reaction was diluted with 50 ml ethyl ether and washed with water (25 ml) then 5% NaOH (20 ml) and then sat. NaCl. After stripping off the solvent the ethoxylated product 28 was obtained in high yield. The product was characterized by NMR and mass spectra.

This same procedure was used to prepare products listed in table 1 from the corresponding iodides or bromides. For higher boiling alkyl iodides and bromides only one equivalent of the alkyl halide was used.

Table 2

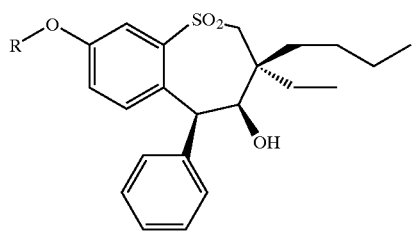

Formula for Table 2

| Compound No. | R |
|---|---|
| 27 | H |
| 26 | Me |
| 28 | Et |
| 29 | Hexyl |
| 30 | Ac |
| 31 | $(CH_2)_6$-N-pthalimide |

Example 22

(3α,4α,5α)3-Butyl-3-ethyl-4-hydroxy-7-hydroxyamino-5-phenyl-2,3,4,5-tetrahydrobenzothiepine-1,1-dioxide (37) and (3α,4β,5β)3-Butyl-3-ethyl-4-hydroxy-7-hydroxyamino-5-phenyl-2,3,4,5-tetrahydrobenzothiepine-1,1-dioxide (38)

Step 1. Preparation of 2-Chloro-5-nitrodiphenylmethane (32)

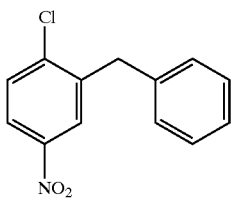

32

Procedure adapted from reference :Synthesis-Stuttgart 9, 770–772 (1986) Olah G. et al.

Under nitrogen, a 3 neck flask was charged with 45 g (0.172 mole) of 2-chloro-5-nitrobenzophenone in 345 ml methylene chloride and the solution was cooled to ice/water temperature. By means of an additional funnel, 150 g ( 0.172 mole) of trifluoromethane sulfonic acid in 345 ml methylene chloride was added slowly. Next 30 g of triethylsilane (0.172 mole) in 345 ml methylene chloride was added dropwise to the chilled solution. Both addition steps(trifluoromethane sulfonic acid and triethylsilane)were repeated. After the additions were completed the reaction was allowed to slowly warm up to room temperature and stirred for 12 h under nitrogen. The reaction mixture was then poured into a chilled stirred solution of 1600 ml of saturated sodium bicarbonate. Gas evolution occurred. Poured into a 4 liter separatory funnel and separated layers. The methylene chloride layer was isolated and combined with two 500 ml methylene chloride extractions of the aqueous layer. The methylene chloride solution was dried over magnesium sulfate and concentrated in vacuo. The residue was recrystallized from hexane to give 39 g product. Structure 32 was confirmed by mass spectra and proton and carbon NMR.

Step 2. Preparation of 2-((2-Benzyl-4-nitrophenylthio)methyl)-2-ethylhexanal (33)

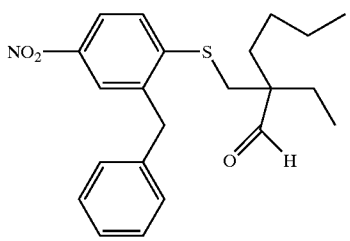

33

The 2-chloro-5-nitrodiphenylmethane product 32 (40 g, 0.156 mole) from above was placed in a 2 liter 2 neck flask with water condenser. Next 150 ml DMSO and 7.18 g (0.156 mole) of lithium sulfide was added and the solution was stirred at 75° C. for 12 h. The reaction was cooled to room temperature and then 51.7 g of mesylate IV was added in 90 ml DMSO. The reaction mixture was heated to 80° C. under nitrogen. After 12 h monitored by TLC and added more mysylate if necessary. Continued the reaction until the reaction was completed. Next the reaction mixture was slowly poured into a 1900 ml of 5% acetic aqueous solution with stirring, extracted with 4×700 ml of ether, and dried over MgSO$_4$. After removal of ether, 82.7 g of product was isolated. The material can be further purified by silica gel chromatography using 95% hexane and 5% ethyl acetate. If pure mysylate was used in this step there was no need for further purification. The product 33 was characterized by mass spectra and NMR.

Step 3. Oxidation of the Nitro Product 33 to the Sulfone 2-((2-Benzyl-4-nitrophenylsulfonyl)methyl)-2-ethylhexanal (34)

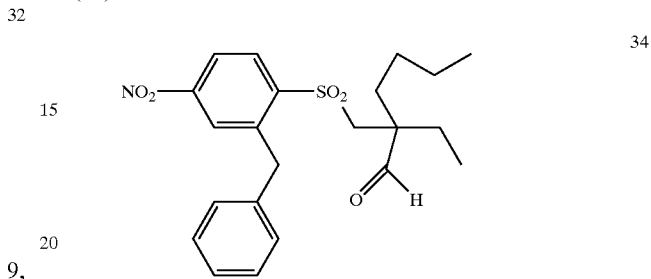

34

The procedure used to oxidize the sulfide 33 to the sulfone 34 has been previously described.

Step 4. Reduction of 34 to 2-((2-Benzyl-4-hydroxyaminophenylsulfonyl)methyl-2-ethylhexanal (35)

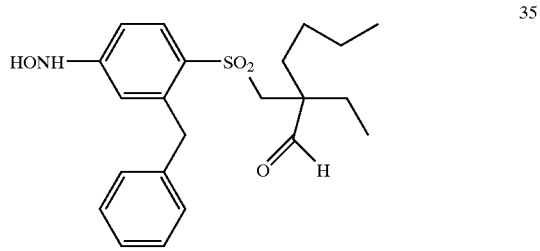

35

A 15 g sample of 34 was dissolved in 230 ml of ethanol and placed in a 500 ml rb flask under nitrogen. Next 1.5 g of 10 wt. % Pd/C was added and hydrogen gas was bubbled through the solution at room temperature until the nitro substrate 34 was consumed. The reaction could be readily monitored by silica gel TLC using 80/20 hexane/EtOAc. Product 35 was isolated by filtering off the Pd/C and then stripping off the EtOH solvent. The product was characterized by NMR and mass spectra.

Step 5. Preparation of the 2-((2-Benzyl-4-N,O-di-(t-butoxycarbonyl)hydroxyaminophenylsulfonyl)methyl)-2-ethylhexanal (36).

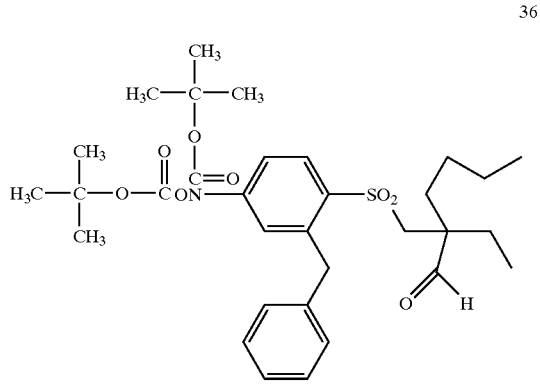

36

A 13.35 g sample of 35 (0.0344 mole) in 40 ml of dry THF was stirred in a 250 ml round bottomed flask. Next added 7.52 g (0.0344 mole) of di-t-butyl dicarbonate in 7 ml THF. Heated at 60° C. overnight. Stripped off THF and redissolved in methylene chloride. Extracted with 1% HCl; and then 5% sodium bicarbonate.

The product was further purified by column chromatography using 90/10 hexanelethyl acetate and then 70/30 hexane/ethyl acetate. The product 36 was obtained (4.12 g) which appeared to be mainly the di-t-butoxycarbonyl) derivatives by proton NMR.

Step 6. (3α,4α,5α)3-Butyl-3-ethyl-4-hydroxy-7-hydroxyamino-5-phenyl-2,3,4,5-tetrahydrobenzothiepine-1,1-dioxide (37) and (3α,4β,5β)3-Butyl-3-ethyl-4-hydroxy-7-hydroxyamino-5-phenyl-2,3,4,5-tetrahydrobenzothiepine-1,1-dioxide (38)

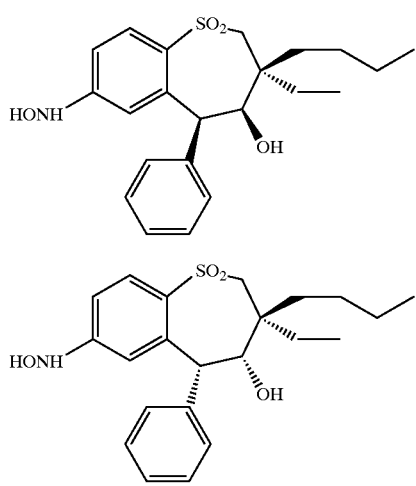

A 250ml 3-neck round bottomed flask was charged with 4 g of 36 (6.8 mmoles), and 100 ml of anhydrous THF and cooled to −78° C. under a nitrogen atmosphere. Slowly add 2.29 g potassium tert-butoxide(20.4 mmoles) with stirring and maintaining a −78° C. reaction temperature. After 1 h at −78° C. the addition of base was completed and the temperature was brought to −10° C. by means of a ice/salt bath. After 3 h at −10° C., only trace 36 remained by TLC. Next add 35 ml of deionized water to the reaction mixture at −10° C. and stirred for 5 min. Stripped off most of the THF and added to separatory funnel and extracted with ether until all of the organic was removed from the water phase. The combined ether phases were washed with saturated NaCl and then dried over sodium sulfate. The only products by TLC and NMR were the two BOC protected isomers of 37 and 38. The isomers were separated by silica gel chromatography using 85% hexane and 15% ethyl acetate; BOC-37 (0.71 g) and BOC-38 (0.78 g).

Next the BOC protecting group was removed by reacting 0.87 g of BOC-38 (1.78 mmoles) with 8.7 ml of 4 M HCl (34.8 mmoles)in dioxane for 30 min. Next added 4.74 g of sodium acetate (34.8 mmoles) to the reaction mixture and 16.5 ml ether and stirred until clear. After transferring to a separatory funnel extracted with ether and water and then dried the ether layer with sodium sulfate. After removing the ether, 0.665 g of 38 was isolated. Isomer 37 could be obtained in a similar procedure.

Example 23

(3α,4α,5α)3-Butyl-3-ethyl-7-(n-hexylamino)-4-hydroxy-5-phenyl-2,3,4,5-tetrahydrobenzothiepine-1,1-dioxide (40) and (3α,4β,5β)3-Butyl-3-ethyl-7-(n-hexylamino)-4-hydroxy-5-phenyl-2,3,4,5-tetrahydrobenzothiepine-1,1-(dioxide (41)

Step 1. 2-((2-Benzyl-4-(n-hexylamino)phenylsulfonyl)methyl)-2-ethylhexanal (39)

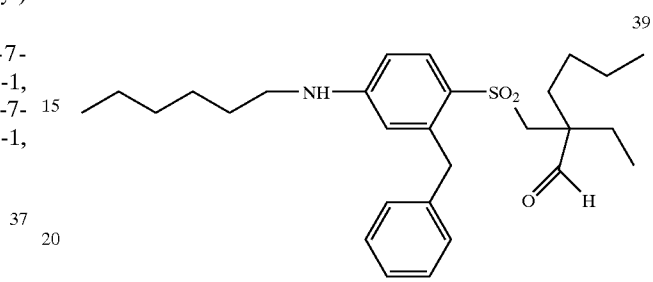

In a Fischer porter bottle weighed out 0.5 g of 34 (1.2 mmoles) and dissolved in 3.8 ml of ethanol under nitrogen. Next added 0.1 g of Pd/C and 3.8 ml of hexanal. Seal and pressure to 50 psi of hydrogen gas. Stirred for 48 h. After filtering off the catalyst and removing the solvent by rotary evaporation 39 was isolated by column chromatography (0.16 g) using 90/10 hexane ethyl acetate and gradually increasing the mobile phase to 70/30 hexane/ethyl acetate. The product was characterized by NMR and mass spectra.

Step 2. (3α,4α,5α)3-Butyl-3-ethyl-7-(n-hexylamino)-4-hydroxy-5-phenyl-2,3,4,5-tetrahydrobenzothiepine-1,1-dioxide (40) and (3α,4β,5β)3-Butyl-3-ethyl-7-(n-hexylamino)-4-hydroxy-5-phenyl-2,3,4,5-tetrahydrobenzothiepine-1,1-dioxide (41)

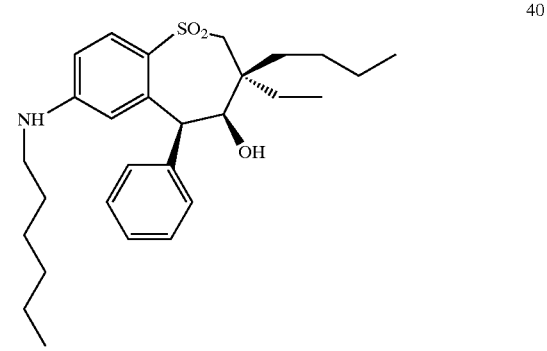

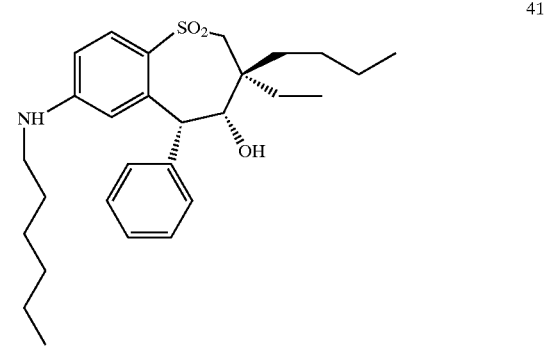

A 2-neck, 25 ml round bottomed flask with stir bar was charged with 0.158 g 39 (0.335 mmole) and 5 ml anhydrous THF under nitrogen. Cool to −10° C. by means of a salt/water bath. Slowly add 0.113 g of potassium tert butoxide (0.335 mmole). After 15 min at −10° C. all of the starting material was consumed by TLC and only the two isomers 40 and 41 were observed. Next added 5 ml of chilled 10% HCl and stirred at −10° C. for 5 min. Transferred to a separatory fiunel and extract with ether. Dried over sodium sulfate. Proton NMR of the dried product (0.143 g) indicated only the presence of the two isomers 40 and 41. The two isomers were separated by silica gel chromatography using 90/10 hexane ethyl acetate and gradually increasing the mobile phase to 70/30 hexanelethyl acetate. 40 (53.2 mg); 41(58.9 mg).

Example 24

Quaternization of Amine Substrates 40 and 41

Amine products such as 40 and 41 can be readily alkylated to quaternary salts by reaction with alkyl halides. For example 40 in DMF with 5 equivalents of methyl iodide in the presence of 2,6 dimethyl lutidine produces the dimethylhexylamino quaternary salt.

Example 25

(3α,4β,5β)3-Butyl-3-ethyl-4-hydroxy-5-(4-iodophenyl)-2,3,4,5-tetrahydrobenzothiepine-1,1-doxide (42)

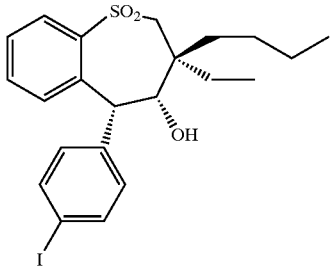

42

In a 25 ml round bottomed flask 0.5 g (1.3 mmole) of 6d, 0.67 g of mercuric triflate were dissolved in 20 ml of dry methylene chloride with stirring. Next 0.34 g of Iodine was added and the solution was stirred at room temperature for 30 h.

The reaction was then diluted with 50 ml methylene chloride and washed with 10 ml of 1 M sodium thiosulfate; 10 ml of saturated KI; and dried over sodium sulfate. See Tetrahedron, Vol.50, No. 17, pp 5139–5146 (1994) Bachki, F. Et al. Mass spectrum indicated a mixture of 6d, mono iodide 42 and a diiodide adduct. The mixture was separated by column chromatography and 42 was characterized bt NMR and mass spectra.

Example 26

(3α,4β,5β)3-Butyl-5-(4-carbomethoxyphenyl)-3-ethyl-4-hydroxy-2,3,4,5-tetrahydrobenzothiepine-1,1-dioxide (43)

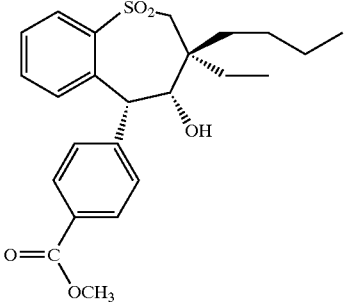

43

A 0.1 g sample of 42 (0.212 mmole), 2.5 ml dry methanol, 38 μl triethylamine (0.275 mmole), 0.3 ml toluene and 37 mg of palladium chloride (0.21 mmole) was charged to a glass lined mini reactor at 300 psi carbon monoxide. The reaction was heated at 100° C. overnight. The catalyst was filtered and a high yield of product was isolated.

The product was characterized by NMR and mass spectra.

Note the ester functionalized product 43 can be converted to the free acid by hydrolysis.

Example 27

(3α,4α,5α)3-Butyl-3-ethyl-4-hydroxy-7-methoxy-5-phenyl-2,3,4,5-tetrahydrobenzothiepine-1,1-dioxide (48), and (3α,4β,5β)3-Butyl-3-ethyl-4-hydroxy-7-methoxy-5-phenyl-2,3,4,5-tetrahydrobenzothiepine-1,1-dioxide (49)

Step 1. 2-Mercapto-5-methoxybenzophenone (50)

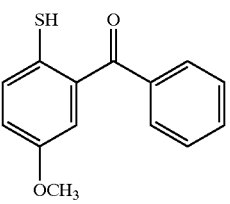

50

Reaction of 66.2 g of 4-methoxythiophenol with 360 ml of 2.5 N n-butyllithium, 105 g of tetramethylethylenediamine and 66.7 g of benzonitrile in 600 ml cyclohexane according to the procedure in WO 93/16055 gave 73.2 g of brown oil which was kugelrohr distilled to remove 4-methoxythiophenol and gave 43.86 g of crude 50 in the pot residue.

Step 2. 2-((2-Benzoyl-4-methoxyphenylthio)methyl-2-ethylhexanal (51)

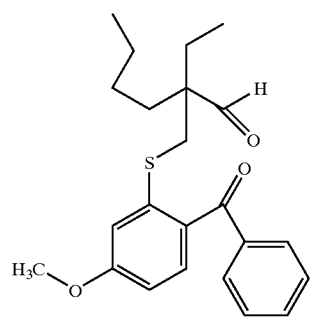

51

Reaction of 10 g (0.04 mole) of crude 50 with 4.8 g (0.02 mole) of mesylate 1 and 3.2 ml (0.23 mole) of triethylamine in 50 ml of diglyme according to the procedure for the preparation of 2 gave 10.5 g of crude product which was purified by HPLC (5% ethyl acetate-hexane) to give 1.7 g (22%) of 51.

Step 3. 2-((2-Benzoyl-4-methoxyphenylsulfonyl)methyl)-2-ethyl-hexanal (52)

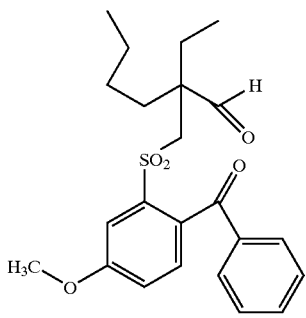

A solution of 1.2 g (3.1 mmoles) of 51 in 25 ml of methylene chloride was reacted with 2.0 g (6.2 mmoles) of 50–60% MCPBA according to the procedure of step 2 of procedure A in example 18 gave 1.16 g (90%) of 52 as a yellow oil.

Step 4. 2-((2-Benzyl-4-methoxyphenylsulfonyl)methyl)-2-ethylhexanal (53)

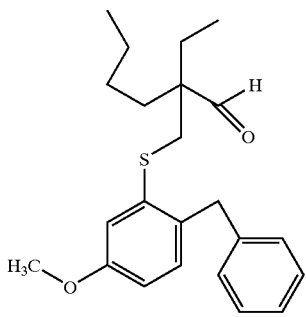

Hydrogenation of 1.1 g of 52 according to the procedure of step 3 of procedure A of example 18 gave 53 as a yellow oil (1.1 g).

Step 5. (3α,4α,5α)3-Butyl-3-ethyl-4-hydroxy-7-methoxy-5-phenyl-2,3,4,5-tetrahydrobenzothiepine-1,1-dioxide (48), and (3α,4β,5β)3-Butyl-3-ethyl-4-hydroxy-7-methoxy-5-phenyl-2,3,4,5-tetrahydrobenzothiepine-1,1-dioxide (49)

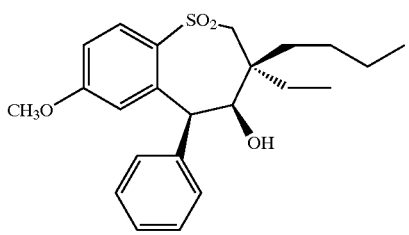

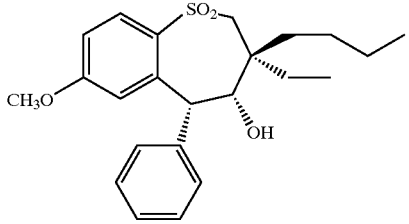

A solution of 1.1 g of 53, 0.36 g of potassium t-butoxide and 25 ml of anhydrous THF was held at reflux for 2 h and worked up as in step 4 of procedure A of example 18 to give 1.07 g of a crude product which was purified by HPLC to give 40 mg (4%) of 48 as crystals, mp 153–154° C. and 90 mg (8%) of 49 as solid, mp 136–140° C.

Example 28

5-Phenyl-2,3-dihydrospirobenzothiepine-3,1'-cyclohexane (57)

Step 1. 1-(Hydroxymethyl)-cyxclohexanecarboxaldehyde (54)

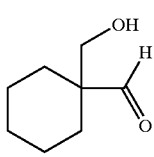

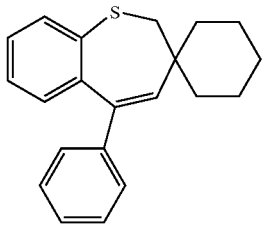

To a cold (0° C.) mixture of 100 g (0.891 mole) of cyclohexanecarboxaldehyde, 76.5 g of 37% of formaldehyde in 225 ml of methanol was added dropwise 90 ml of 1 N Sodium hydroxide in 1 h. The reaction mixture was stirred at room temperature over 48 then was evaporated to remove methanol. The reaction mixture was diluted with water and extracted with methylene chloride. The organic layer was washed with water, brine, and dried over sodium sulfate and concentrated under vacuum to give 75 g (59.7%) of thick oil. Proton NMR and mass spectra were consistent with the product.

Step 2. 1-(Mesyloxymethyl)cyclohexanecarboxaldehyde (55)

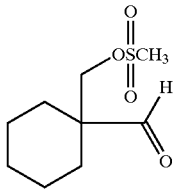

To a cold (0° C.) mixture of alcohol 54(75 g, 0.54 mole) and 65.29 g (0.57 mole) of methanesulfonyl chloride in 80 ml of methylene chloride was added a solution of pyridine (47.96 g, 0.57 mole) in 40 ml of methylene chloride. The reaction mixture was stirred at room temperature for 18 h then quenched with water, acidified with conc. HCl and extracted with methylene chloride. The organic layer was washed with water, brine, and dried over sodium sulfate and concentrated under vacuum to give 91.63 g (77.8%) of thick oil. Proton NMR and mass spectra were consistent with the product.

Step 3. 1-((2-Benzoylphenylthio)methyl)cyclohexanecarboxaldehyde (56)

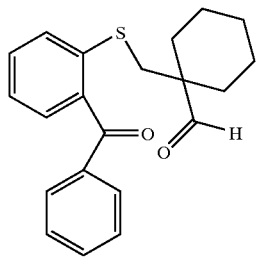

56

A mixture of 69 g (0.303 mole) of 2-mercaptobenzophenone, 82 g (0.303 mole) of mesylate 55, 32 g of triethylamine, and 150 ml of diglyme was stirred and held at reflux for 24 h. The mixture was cooled, poured into dil. HCl and extracted with methylene chloride. The organic layer was washed with 10% NaOH, water, brine, and dried over sodium sulfate and concentrated under vacuum to remove excess diglyme. This was purified by silica gel flush column (5% EtOAc: Hexane) and gave 18.6 g (75.9%) of yellow oil. Proton NMR and mass spectra were consistent with the product.

Step 4. 5-Phenyl-2,3-dihydrospirobenzothiepine-3,1'-cyclohexane (57)

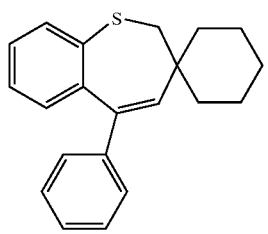

57

To a mixture of 6.19 g of zinc dust and 100 ml of dry DME was added TiCl$_3$(16.8 g, 0.108 mole). The reaction mixture was heated to reflux for 2 h. A solution of compound 56 (8.3 g, 0.023 mole) in 50 ml of DME was added dropwise to the reaction mixture in 1 h and the mixture was held at reflux for 18 h. The mixture was cooled, poured into water and extracted with ether. The organic layer was washed with water, brine, and dried over sodium sulfate, filtered through celite and concentrated under vacuum. The residue was purified by HPLC (10% EtOAc: Hexane) to give 4.6 g (64%) of white solid, mp 90–91° C. Proton and carbon NMR and mass spectra were consistent with the product.

Example 29

8b-Phenyl-1a,2,3,8b-tetrahydrospiro(benzothiepino [4,5-b]oxirene-2,1'-cyclohexane)-4,4-dioxide (58)

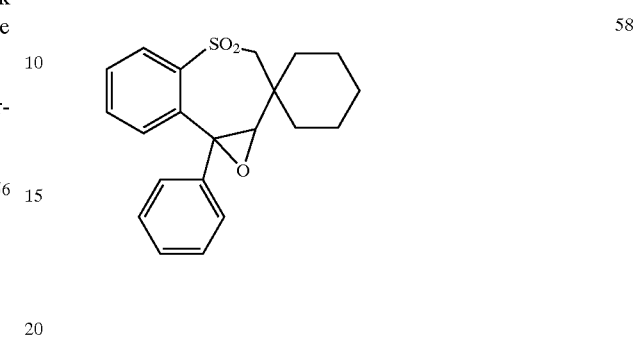

58

To a solution of 57 (4.6 g, 15 mmole) in 50 ml chloroform under nitrogen was added 55% MCPBA (16.5 g, 52.6 mmole) portionwise with spatula. The reaction was held at reflux for 18 h and washed with 10% NaOH(3×), water, brine, and dried over sodium sulfate and concentrated under vacuum to give 5 g of crude product. This was recrystallized from Hexane/EtOAc to give 4.31 g (81%) of yellow solid, mp 154–155° C. Proton and carbon NMR and mass spectra were consistent with the product Example 30 trans-4-Hydroxy-5-phenyl-2,3,4,5-tetrahydrospiro (benzothiepine-3,1'-cyclohexane)-1,1-dioxide (59)

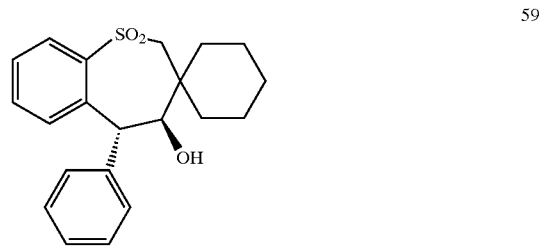

59

A mixture of 0.5 g (1.4 mmoles) of 58, 20 ml of ethanol, 10 ml of methylene chloride and 0.4 g of 10% Pd/C catalyst was hydrogenated with 70 psi hydrogen for 3 h at room temperature. The crude reaction slurry was filtered through Celite and evaporated to dryness. The residue was purified by HPLC (10% EtOAc-Hexane, 25% EtOAc-Hexane). The first fraction was 300 mg (60%) as a white solid, mp 99–100° C. Proton NMR showed this was a trans isomer. The second fraction gave 200 mg of solid which was impure cis isomer.

Example 31 cis-4-Hydroxy-5-phenyl-2,3,4,5-tetrahydrospiro(benzothiepine-3,1'-cyclohexane)-1,1-dioxide (60)

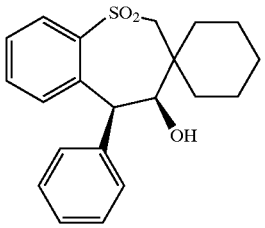

60

To a solution of 0.2 g (0.56 mmole) of 59 in 20 ml of CH$_2$Cl$_2$, was added 8 g of 50% NaOH and one drop of Aliquat-336 (methyltricaprylylammonium chloride) phase transfer catalyst. The reaction mixture was stirred for 10 h at room temperature. Twenty g of ice was added to the mixture and the mixture was extracted with CH$_2$Cl$_2$ (3×10 ml) washed with water, brine and dried over MgSO$_4$ and concentrated in vacuo to recover 0.15 g of crude product. This was recrystallized from Hexane/EtOAc to give 125 mg of white crystal, mp 209–210° C. Proton and carbon NMR and mass spectra were consistent with the product.

Example 32

(3α,4α,5α)3-Butyl-3-ethyl-4-hydroxy-5-phenyl-2,3,4,5-tetrahydrobenzothiepine (61), and (3α,4β,5β)3-Butyl-3-ethyl-4-hydroxy-5-phenyl-2,3,4,5-tetrahydrobenzothiepine (62)

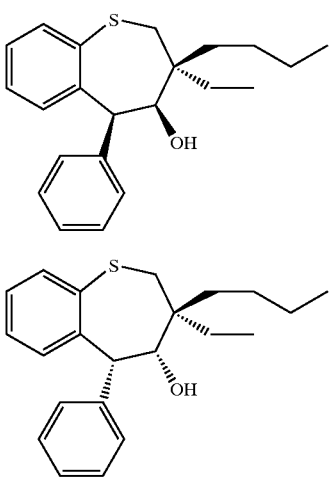

To a solution of 0.5 g (1.47 mmole) of compound 47 in 5 ml of anhydrous THF was added 0.17 g (1.47 mmole) of 95% potassium t-butoxide. The reaction mixture was stirred at room temperature for 18 h and quenched with 10 ml of 10% HCl. The organic was extracted into methylene chloride. The methylene chloride extract was dried over magnesium sulfate and concentrated in vacuo. The residue was purified by HPLC (2% EtOAc-hexane) to give 47 mg of 61 in the second fraction and 38 mg of 62 in the third fraction. Proton NMR and mass spectra were consistent with the assigned structures.

Example 33

(3α,4α,5α)3-Butyl-3ethyl-hydroxy-7-amino-5-phenyl-2,3,4,5-tetrahydrobenzothiepine-1,1-dioxide (63) and (3α,4β,5β)3-Butyl-3-ethyl-4-hydroxy-7-amino-5-phenyl-2,3,4,5-tetrahydrobenzothiepine-1,1-dioxide (64)

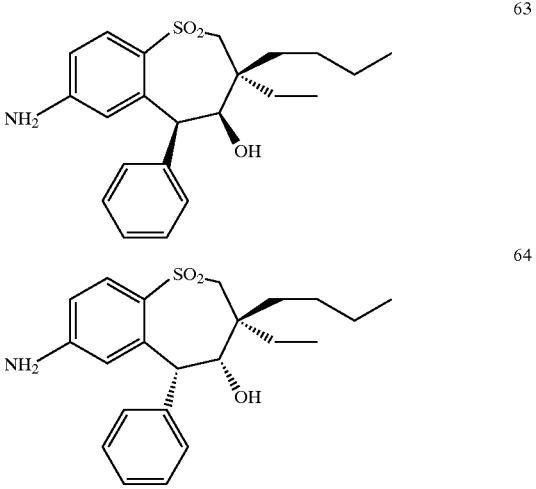

An autoclave was charged with 200 mg of 37 in 40 cc ethanol and 0.02 g 10% Pd/C. After purging with nitrogen the clave was charged with 100 psi hydrogen and heated to 55° C. The reaction was monitored by TLC and mass spec and allowed to proceed until all of 37 was consumed. After the reaction was complete the catalyst was filtered and the solvent was removed in vacuo and the only observable product was amine 63. This same procedure was used to produce 64 from 38.

Example 34

(3α,4α,5α)3-Butyl-3-ethyl-4-hydroxy-7-methoxy-5-(3'-methoxyphenyl)-2,3,4,5-tetrahydrobenzothiepine-1,1-dioxide (65), and (3α,4β,5β)3-Butyl-3-ethyl-4-hydroxy-7-methoxy-5-(3'-methoxyphenyl)-2,3,4,5-tetrahydrobenzothiepine-1,1-dioxide (66)

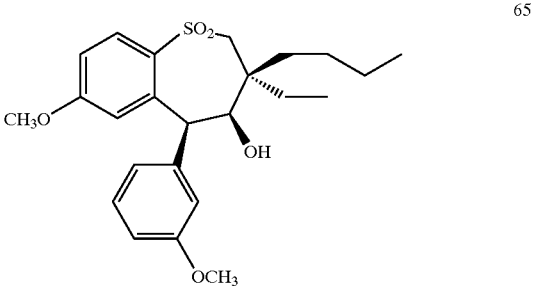

261
-continued

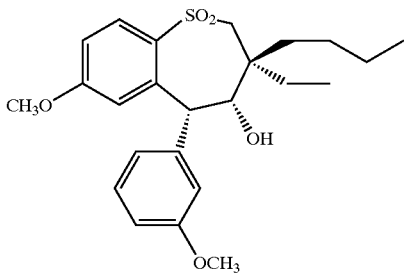
66

Alklation of e-methoxyphenol with 3-methoxybenzyl chloride according to the procedure described in J. Chem. Soc, 2431 (1958) gave 4-methoxy-2-(3'-methoxybenzyl)phenol in 35% yield. This material was converted to compound 65, mp 138.5–141.5° C., and compound 66, mp 115.5–117.5° C., by the procedure similar to that in Example 18 method B.

Example 35

(3α,4α,5α)3-Butyl-3-ethyl-4-hydroxy-7-methoxy-5-(3'-(trifluoromethyl)phenyl-2,3,4,5-tetrahydrobenzothiepine-1,1-dioxide (67), and (3α,4β,5β)3-Butyl-3-ethyl-4-hydroxy-7-methoxy-5-(3'-(trifluoromethyl)phenyl)-2,3,4,5-tetrahydrobenzothiepine-1,1-dioxide (68)

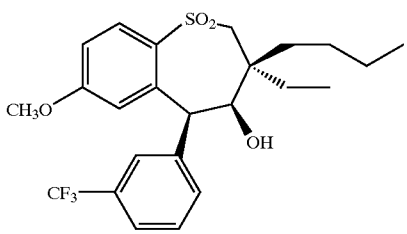
67

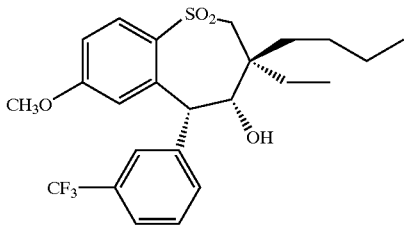
68

Alkylation of 4-methoxyphenol with 3-(trifluoromethyl)benzyl chloride according o the procedure described in J. Chem. Soc. 2431 (1958) gave 4-methoxy-2-(3'-trifluoromethyl)benzyl)phenol. This material was converted to compound 67, mp 226.5–228° C., and compound 68, mp 188–190° C., byu the procedure similar to that in Example 18 method B.

262

Example 36

(3α,4α,5α)3-Butyl-3-ethyl-5-(4'-fluorophenyl)-4-hydroxy-7-methoxy-2,3,4,5-tetrahydrobenzothiepine-1,1-dioxide (69), and (3α,4β,5β)3-Butyl-3-ethyl-5-(4-'-fluorophenyl)-4-hydroxy-7-methoxy-2,3,4,5-tetrahydrobenzothiepine-1,1-dioxide (70)

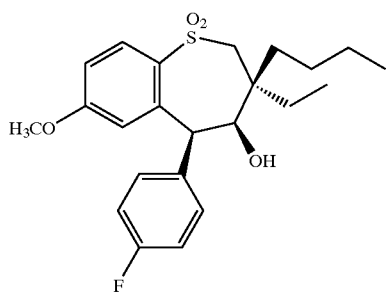
69

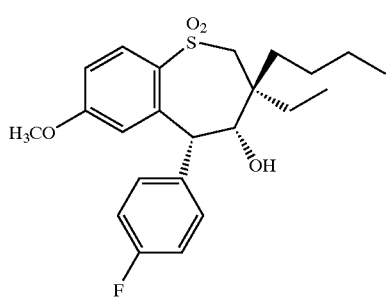
70

Alkylation of 4-methoxyphenol with 4-fluorobenzyl chloride according to the procedure described in J. Chem. Soc, 2431 (1958) gave 4-methoxy-2-(4'-fluorobenzyl)phenol. This material was converted to compound 69 and compound 70 by the procedure similar to that in Example 18 method B.

Example 37

(3α,4α,5α)3-Butyl-3-ethyl-5-(3'-fluorophenyl)-4-hydroxy-7-methoxy-2,3,4,5-tetrahydrobenzothiepine-1,1-dioxide (71), and (3α,4β,5β)3-Butyl-3-ethyl-5-(3'-fluorophenyl)-4-hydroxy-7-methoxy-2,3,4,5-tetrahydrobenzothiepine-1,1-dioxide (72)

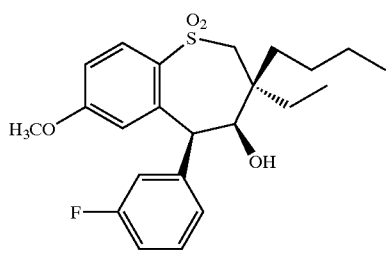
71

263
-continued

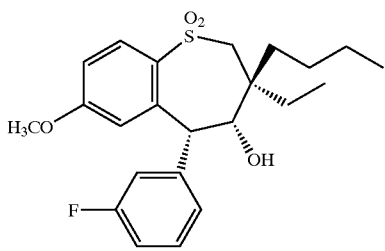
72

Alkylation of 4-methoxyphenol with 3-fluorobenzyl chloride according to the procedure described in J. Chem. Soc, 2431 (1958) gave 4-methoxy-2-(3'-fluorobenzyl)phenol. This material was converted to compound 71 and compound 72 by the procedure similar to that in Example 18 method B.

Example 38

(3α,4α,5α)3-Butyl-3-ethyl-5-(2'-fluorophenyl)-4-hydroxy-7-methoxy-2,3,4,5-tetrahydrobenzothiepine-1,1-dioxide (73), and (3α,4β,5β)3-Butyl-3-ethyl-5-(2'-fluorophenyl)-4-hydroxy-7-methoxy-2,3,4,5-tetrahydrobenzothiepine-1,1-dioxide (74)

73
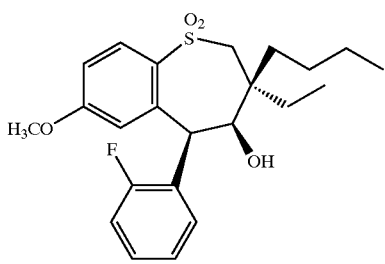

74
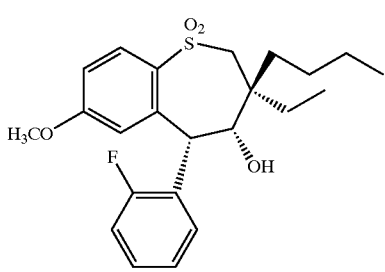

Alkylation of 4-methoxyphenol with 2-fluorobenzyl chloride according to the procedure described in J. Chem. Soc, 2431 (1958) gave 4-methoxy-2-(2'-fluorobenzyl)phenol. This material was converted to compound 73 and compound 74 by the procedure similar to that in Example 18 method B.

264
Example 39

(3α,4α,5α)3-Butyl-7-bromo-3-ethyl-4-hydroxy-5-(3'-methoxyphenyl)-2,3,4,5-tetrahydrobenzothiepine-1,1-dioxide (75), and (3α,4β,5β)3-Butyl-7-bromo-3-ethyl-4-hydroxy-5-(3'-methoxyphenyl)-2,3,4,5-tetrahydrobenzothiepine-1,1-dioxide (76)

75
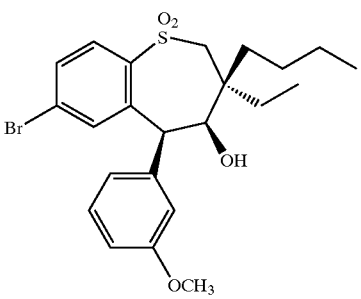

76
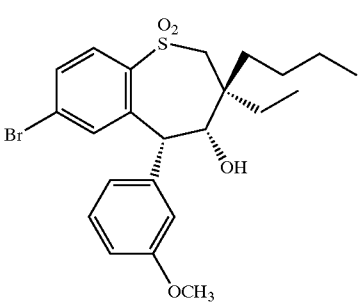

Alklation of 4-bromophenol with 3-methoxybenzyl chloride according to the procedure described in J. Chem. Soc, 2431 (1958) gave 4-bromo-2-(3'-methoxybenzy)phenol. This material was converted to compound 75, mp 97–101.5° C., and compound 76, mp 102–106° C., by the procedure similar to that in Example 18 to method B.

Example 40

(3α,4α,5α)3-Butyl-3-ethyl-7-fluoro-5-(4'-fluorophenyl)-4-hydroxy-2,3,4,5-tetydrobenzothiepine-1,1-dioxide (77), and (3α,4β,5β)3-Butyl-3-ethyl-7-fluro-5-(4'-fluorophenyl)-4-hydroxy-2,3,4,5-tetydrobenzothiepine-1,1-dioxide (78)

77
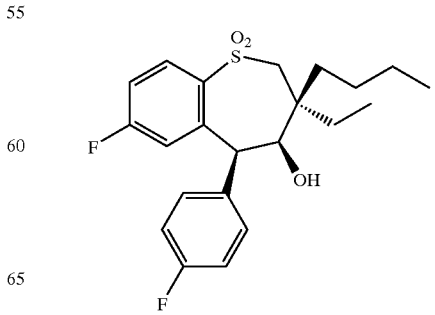

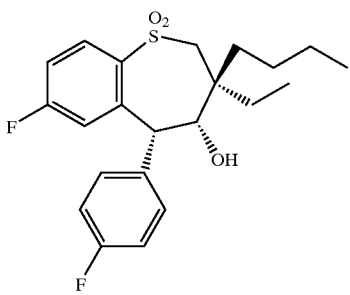

78

Alklation of 4-fluorophenol with 4-fluorobenzyl chloride according to the procedure described in J. Chem. Soc, 2431 (1958) gave 4-fluoro-2-(4'fluorobenzl)phenol. This material was converted to compound 77, mp 228–230° C., and compound 78, mp 134.5–139° C., by the procedure similar to that in Example 18 method B.

Example 41

(3α,4α,5α)3-Butyl-3-ethyl-7-fluoro-4-hydroxy-5-(3'-methoxyphenyl)-2,3,4,5-tetrahydrobenzothiepine-1,1-dioxide (79), and (3α,4β,5β)3-Butyl-3-ethyl-7-fluoro-4-hydroxy-5-(3'-methoxyphenyl)-2,3,4,5-tetrahydrobenzothiepine-1,1-dioxide (80)

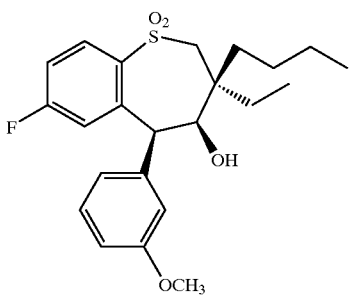

79

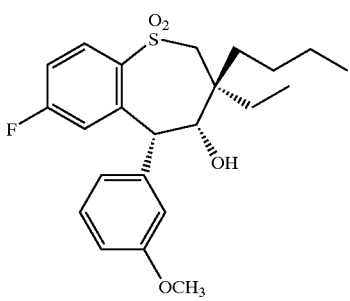

80

Alkylation of 4-fluorophenol with 3-methoxybenzyl chloride according to the procedure described in J. Chem. Soc, 2431 (1958) gave 4-fluoro-2-(3'-methoxybenzyl)phenol. This material was converted to compound 79, as a solid and compound 80, mp 153–155° C., by the procedure similar to that in Example 18 method B.

Example 42

(3α,4β,5β)3-Butyl-3-ethyl-5-(4'-fluorophenyl)-4-hydroxy-7-methylthio-2,3,4,5-tetrahydrobenzothiepine-1,1-dioxide (81)

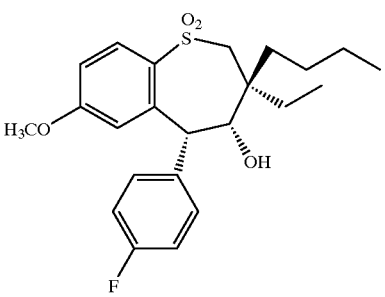

81

A mixture of 0.68 (1.66 mmol) of compound 77, 0.2 g (5 mmol) of sodium methanethiolate and 15 ml of anhydrous DMF was stirred at room temperature for 16 days. The reaction mixture was dilute with ether and washed with water and brine and dried over MgSO$_4$. The ether solution was concentrated in vacuo. The residue was purified by HPLC (20% ethyl acetate in hexanes). The first fraction was impure (3α,4α,5α)3-butyl-3-ethyl-4-hydroxy-7-methylthio-5-(4'-fluorophenyl)-2,3,4,5-tetrahydrobenzothiepine-1,1-dioxide. The second fraction was compound 81, mp 185–186.5° C.

Example 43

(3α,4β,5β)3-Butyl-3-ethyl-5-(4'-fluoropheny)-4-hydroxy-7-(1-pyrrolidinyl)-2,3,4,5-tetrahydrobenzothiepine-1,1-dioxide (82)

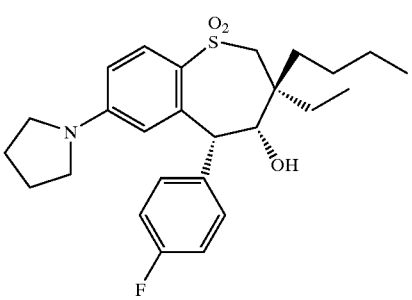

82

A mixture of 0.53 g (1.30 mmol) of compound 78 and 5 ml of pyrrolidine was held at reflux for 1 h. The reaction mixture was diluted with ether and washed with water and brine and dried over MgSO$_4$. The ether solution was concentrated in vacuo. The residue was crystallized from ether-hexanes to give compound 82, mp 174.5–177° C.

Example 44

(3α,4β,5β)3-Butyl-3-ethyl-5-(4'-fluorophenyl)-4-hydroxy-7-(1-morpholinyl)-2,3,4,5-tetrahydrobenzothiepine-1,1-dioxide (83)

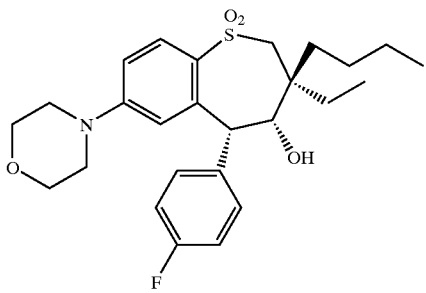

A mixture of 0.4 g (0.98 mmol) of compound 78 and 5.0 g (56 mmol) of morpholine was held at reflux for 2 h and concentrated in vacuo. The residue was diluted with ether (30 ml) and washed with water and brine and dried over MgSO$_4$.

The ether solution was concentrated in vacuo. The residue was recrystallized from ether-hexanes to give compound 83, mp 176.5–187.5° C.

Example 45

(3α,4α,5α)3-Butyl-3-ethyl-5-(4'-fluorophenyl)-4-hydroxy-7-methyl-2,3,4,5-tetrahydrobenzothiepine-1,1-dioxide (84), and (3α,4β,5β)3-Butyl-3-ethyl-5-(4'-fluorophenyl)-4-hydroxy-7-methyl-2,3,4,5-tetrahydrobenzothiepine-1,1-dioxide (85)

84

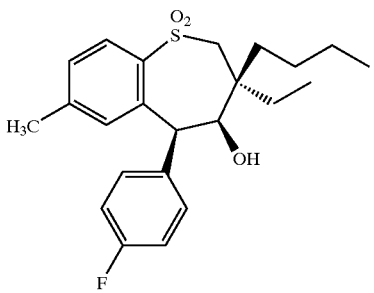

85

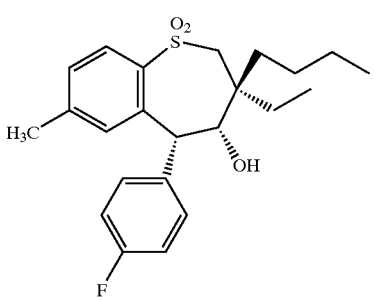

Alkylation of 4-methylphenol with 4-fluorobenzyl chloride according to the procedure described in J. Chem. Soc, 2431 (1958) gave 4-methyl-2-(4'-fluorobenzyl)phenol). This material was converted to compound 84 and compound 85 by the procedure similar to that in Example 18 method B.

Example 46

(3α,4β,5β)3-Butyl-3-ethyl-4-hydroxy-5-(4'-hydroxyphenyl)-7-methoxy-2,3,4,5-tetrahydrobenzothiepine-1,1-dioxide (86), and (3α,4β,5β)3-Butyl-3-ethyl-4,7-hydroxy-5-(4'-hydroxyphenyl)-2,3,4,5-tetrahydrobenzothiepine-1,1-dioxide (87)

86

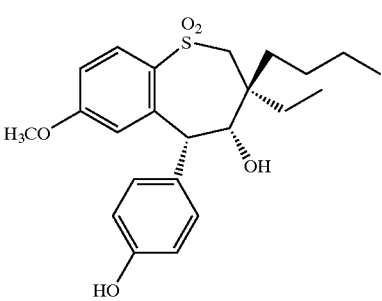

87

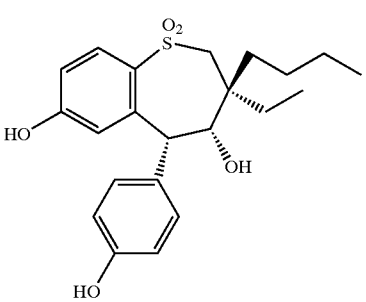

To a solution of 0.52 (1.2 mmol) of compound 66 in 20 ml of methylene chloride was added 1.7 g (6.78 mmol) of born tribromide. The reaction mixture was cooled to –78° C. and was stirred for 4 min. An additional 0.3 ml of boron tribromide was added to the reaction mixture and the reaction mixture was stirred at –78° C. for 1 h and quenched with 2 N HCl. The organic was extracted into ether. The ether layer was washed with brine, dried over MgSO$_4$, and concentrated in vacuo. The residue (0.48 g) was purified by HPLC (30% ethyl acetate in hexanes). The first fraction was 0.11 g of compound 86 as a white solid, mp 171.5–173° C. The second fraction was crystallized from chloroform to give 0.04 g of compound 87 as a white solid, mp 264° C. (dec).

Example 47

(3α,4β,5β)3-Butyl-3-ethyl-4,7-dihydroxy-5-(4'-fluorophenyl)-2,3,4,5-tetrahydrobenzothiepine-1,1-dioxide (88)

88

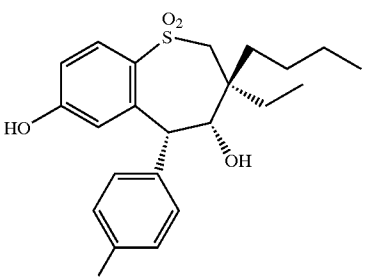

Reaction of compound 70 with excess boron tribromide at room temperature and worked up as in Example 46 gave compound 88 after an HPLC purification.

Example 48

(3α,4β,5β)3-Butyl-3-ethyl-5-(4'-fluorophenyl)-4-hydroxy-7-(1-azetidinyl)-2,3,4,5-tetrahydrobenzothiepine-1,1-dioxide (89)

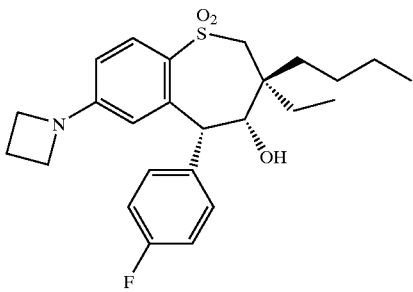

89

A mixture of 0.20 g (0.49 mmol) of compound 78, and 2.0 g (35 mmol) of aztidine was held at reflux for 3 h and concentrated in vacuo. The residue was diluted with ether (30 ml) and washed with water and brine and dried over MgSO$_4$. The ether solution was concentrated on a steam bath. The separated crystals were filtered to give 0.136 g of 89 as prisms, mp 196.5–199.5° C.

Example 49

(3α,4α,5α)3-Butyl-3-ethyl-5-(3'-methoxyphenyl)-4-hydroxy-7-methylthio-2,3,4,5-tetrahydrobenzothlepine-1,1-dioxide (90). (3α,4β,5β)3-Butyl-3-ethyl-5-(3'-methoxyphenyl)-4-hydroxy-7-methylthio-2,3,4,5-tetrahydrobenzothiepine-1,1-dioxide (91)

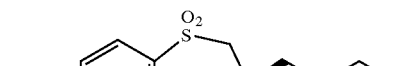

90

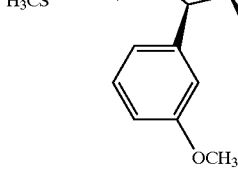

91

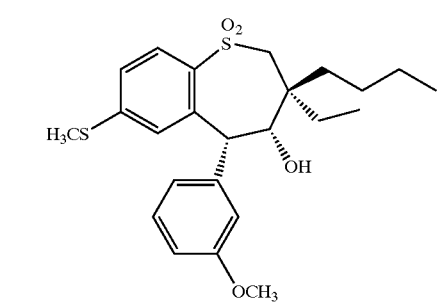

A mixture of 0.4 g (0.95 mmol) of compound 79, 0.08 g (1.14 mmol) of sodium methanethiolate and 15 ml of anhydrous DMF was stirred at 60° C. for 2 h. An additional 1.4 mmol of sodium methanethiolate was added to the reaction mixture and the mixture was stirred at 60° C. for an additional 2 h. The reaction mixture was triturated with 100 ml of water and extracted methylene chloride. The methylene chloride water mixture was filtered through Celite and the methylene chloride layer was dried over MgSO$_4$ and concentrated in vacuo. The first fraction (0.1 g) was compound 90, mp 117–121° C. The second fraction (0.16 g) was compound 91, mp 68–76° C.

Example 50

A. Preparation of Polyethyleneglycol Functionalized Benzothiepine

No. 141

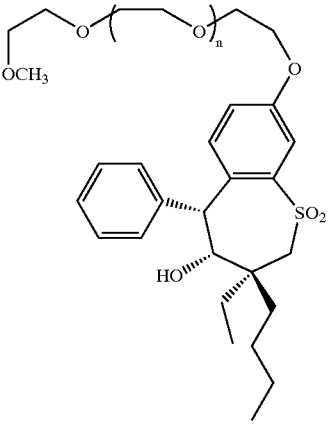

No. 136

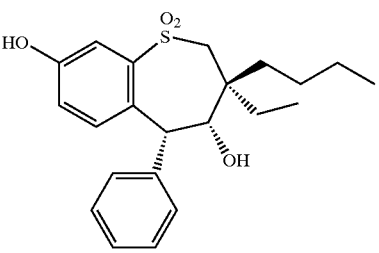

A 50 ml rb flash under a nitrogen atmosphere was charged with 0.54 g of M-Tres-5000 (Polyethyleneglycol Tresylate [methoxy-PEG-Tres,MW 5000] purchased from Shearwater Polymers Inc., 2130 Memorial Parkway, SW, Huntsville, Ala. 35801), 0.055 g Compound No. 136, 0.326 C$_s$CO$_3$ and 2 cc anhydrous acetonitrile. The reaction was stirred at 30° C. for 5 days and then the solution was filtered to remove salts. Next, the acetonitrile was removed under vacuum and the product was dissolved in THF and then precipitated by addition of hexane. The polymer precipitate was isolate by filtration from the solvent mixture (THF/hexane). This precipitation procedure was continued until no Compound No. 136 was detected in the precipitated product (by TLC SiO2). Next, the polymer precipitate was dissolved in water and filtered and the water soluble polymer was dialyzed for 48 hours through a cellulose dialysis tube (Spectrum® 7, 45 mm×0.5 ft, cutoff 1,000 MW). The polymer solution was then removed from the dialysis tube and lyophilized until dried. The NMR was consistent with the desired product A and gel permeation chromatography indicated the presence of a 4500 MW polymer and also verified that no free Compound No. 136 was present. This material was active in the IBAT in vitro cell assay.

Example 51

Preparation of Compound 140

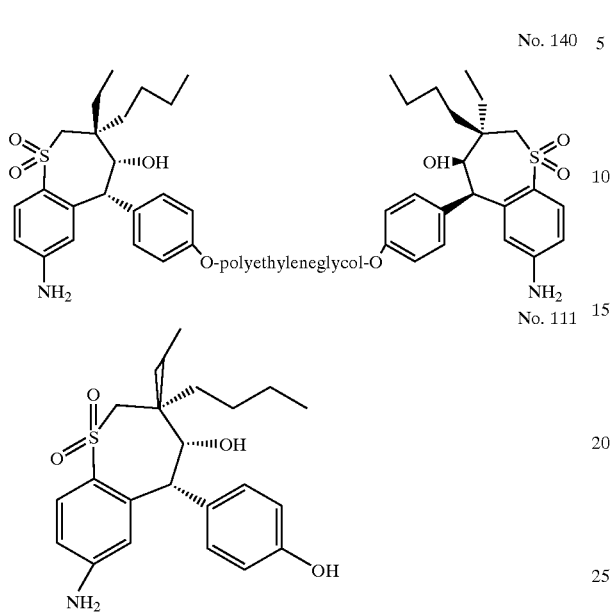

No. 140

No. 111

Example 52

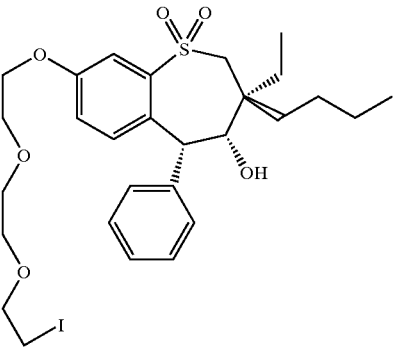

No. 134

A 10 cc vial was charged with 0.21 g of Compound No. 136 (0.5 mmoles), 0.17 g (1.3 mmoles) potassium carbonate, 0.6 g (1.5 mmoles) of 1,2-bis-2-iodoethoxy)-ethane and 10 cc DMF. The reaction was stirred for 4 days at room temperature and then worked up by washing with ether/water. The ether layer was stripped to dryness and the desired product Compound No. 134 was isolated on a silica gel column using 80/20 hexane ethyl acetate.

Example 53

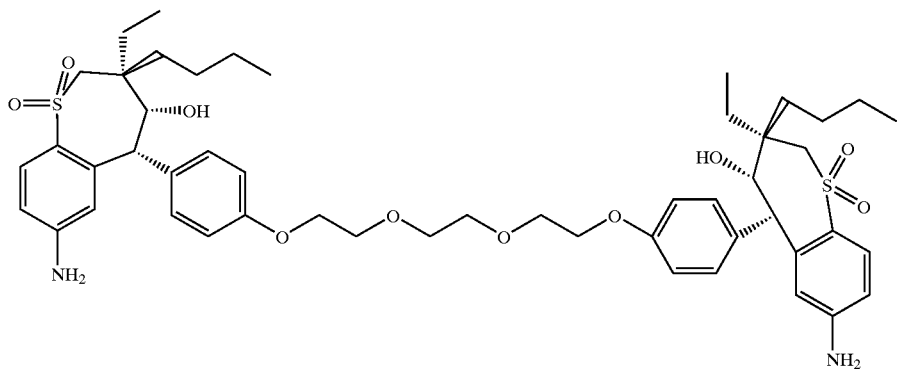

No. 112

Example 54

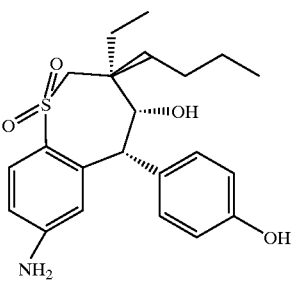

No. 113

Compound 140 is prepared as noted below. A 2-necked 50 ml round bottom Flask was charged with 0.42 g of Tres-3400 (Polyethyleneglycol Tresylate [Tres-PEG-Tres,MW 3400] purchased from Shearwater Polymers Inc., 2130 Memorial Parkway, SW, Huntsville, Ala. 35801), 0.1 potassium carbonate, 0.100 g of Compound No. 111 and 5 ml anhydrous DMF. Stir for 6 days at 27° C. TLC indicated the disappearance of the starting Compound No. 111. The solution was transferred to a separatory funnel and diluted with 50 cc methylene chloride and then extracted with water. The organic layer was evaporated to dryness by means of a rotary evaporator. Dry wgt. 0.4875 g. Next, the polymer was dissolved in water and then dialyzed for 48 hours at 40° C. through a cellulose dialysis tube (spectrum® 7, 45 mm×0.5 ft, cutoff 1,000 MW). The polymer solution was then removed from the dialysis tube and lyophilized until dried 0.341 g). NMR was consistent with the desired product 140.

Preparation of compound no. 112 is described below. A two necked 25 ml round bottom Flask was charged with 0.5 g (1.24 mmoles) of compound no. 134, infra, 13 mls of anhydrous DMF, 0.055 g of 60% NaH dispersion and 0.230 g (0.62 mmoles) of 1,2-Bis [2-iodoethoxylethane] at 10° C. under nitrogen. Next, the reaction was slowly heated to 40°

C. After 14 hours all of the Compound No. 113 was consumed and the reaction was cooled to room temperature and extracted with ether/water. The ether layer was evaporated to dryness and then chromatographed on Silicage (80/20 ethyl acetate/hexane). Isolated Compound No. 112 (0.28 g) was characterized by NMR and mass spec.

Example 55

No. 135

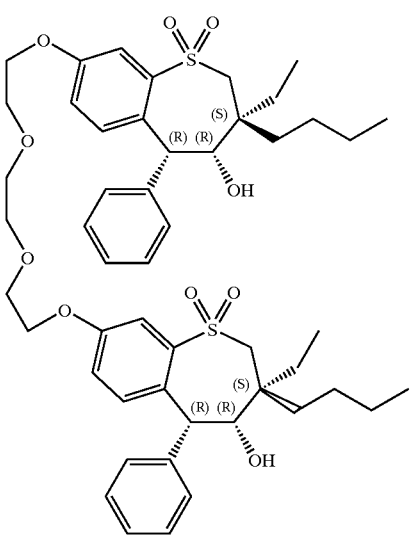

No. 136

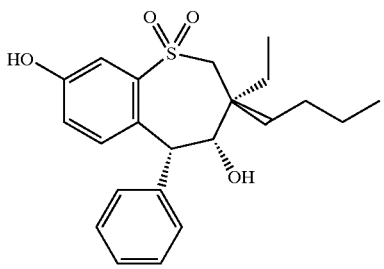

Preparation of compound no. 135 is described below. In a 50 ml round bottom Flask, add 0.7 g (1.8 mmoles) of Compound No. 136, 0.621 g of potassium carbonate, 6 ml DMF, and 0.33 g of 1,2-Bis [2-iodoethoxylethane]. Stir at 40° C. under nitrogen for 12 hours. The workup and isolation was the same procedure for Compound No. 112.

Examples 56 and 57 (Compound Nos. 131 and 137)

The compositions of these compounds are shown in Table 3, infra.

The same procedure as for Example 55 except appropriate benzothiepine was used.

Example 58 (Compound No. 139)

The composition of this compound is shown in Table 3 infra.

Same procedure as for Example 55 with appropriate benzothiepine 1,6 diiodohexane was used instead of 1,2-Bis [2-iodoethoxylethane].

Example 59 (Compound No. 101)

No. 101

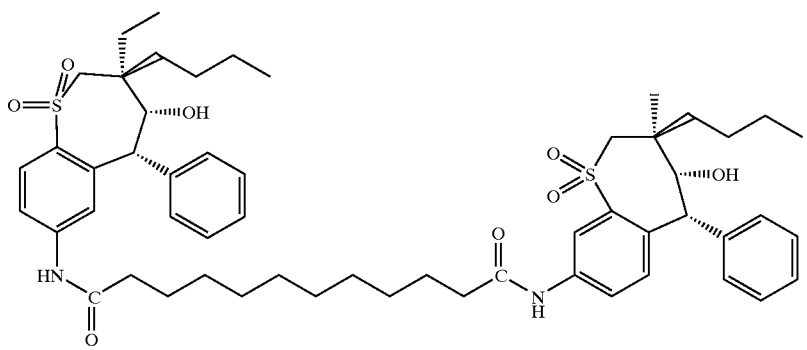

This compound is prepared by condensing the 7-NH$_2$ benzothiepine with the 1,12-dodecane dicarboxylic acid or acid halide.

Example 60 (Compound No. 104)

No. 104

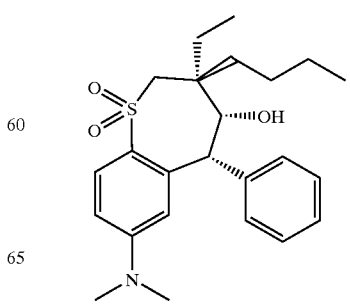

275
-continued

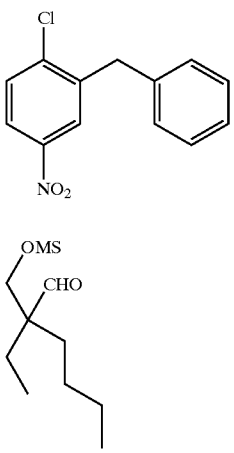

No. 32

Mesylate IV

276

2-Chloro-5-nitrobenzophenone is reduced with triethylsilane and trifluoromethane sulfonic acid to 2-chloro-5-nitrodiphenylmethane 32. Reaction of 32 (similar to S2-32 of Scheme 2, supra) with lithium sulfide followed by reacting the resulting sulfide with mesylate IV (similar to compound S2-33 of Scheme 2, supra) gives sulfide-aldehyde XXIII (similar to compound S2-34 of Scheme 2, supra) Oxidation of XXIII (not shown) with 2 equivalents of MCPBA yields sulfone-aldehyde XXIV (see Scheme 8 below). Reduction of the sulfone-aldehyde XXIV with 100 psi hydrogen and 55° C. for 12 hours catalyzed by palladium on carbon in the same reaction vessel together with $R^7CHO$ yields the substituted dimethylamine derivative XXVIII. Cyclization of XXVIII with potassium t-butoxide yields a mixture of substituted amino derivatives XXIXc and XXIXd.

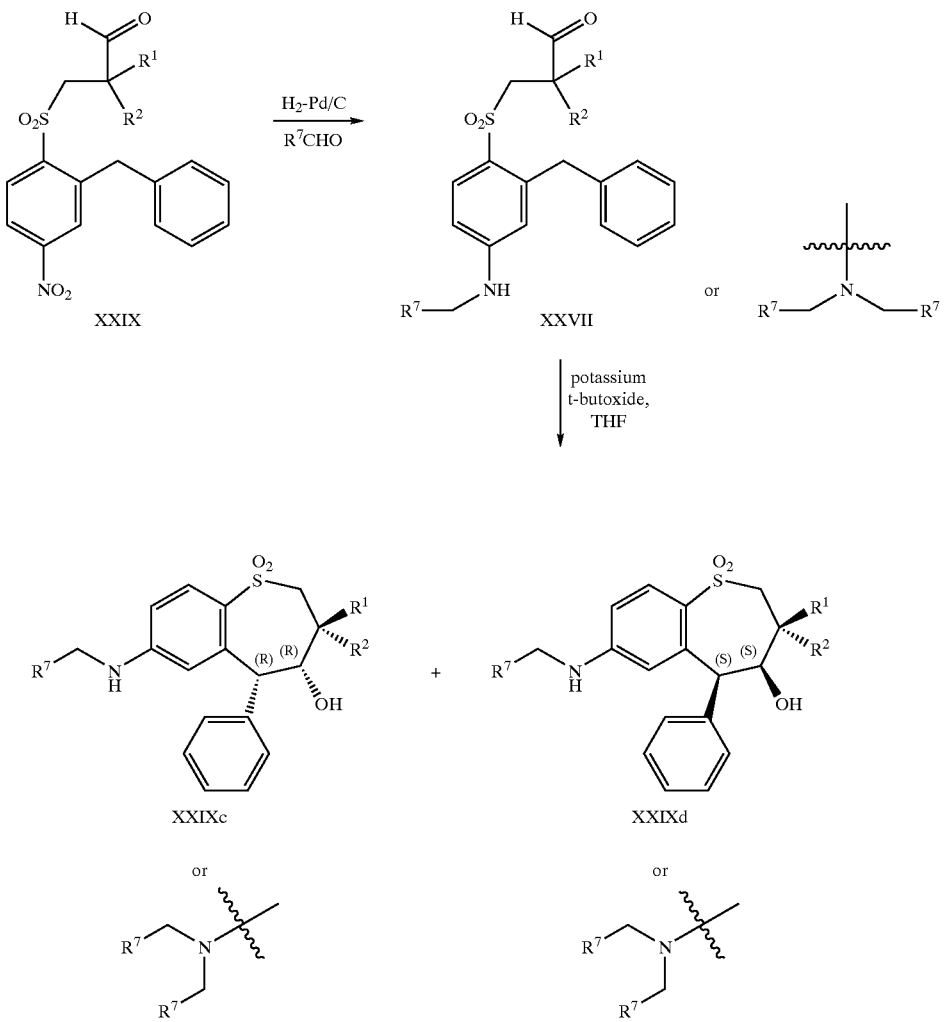

Example 61

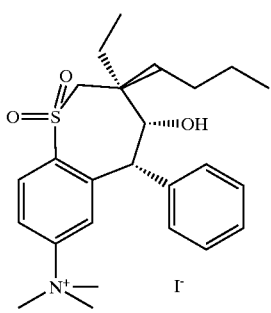

No. 102

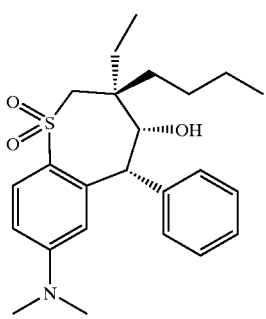

No. 70112

A 1 oz. Fisher-porter bottle was charged with 0.14 g (0.34 mmoles) of compound no. 70112, 0.97 gms (6.8 mmoles) of methyl iodide, and 7 ml of anhydrous acetonitrile. Heat to 50° C. for 4 days. The quat. Salt Compound No. 192 wasisolated by concentrating to 1 cc acetonitrile and then precipitating with diethyl ether.

Exampe 62

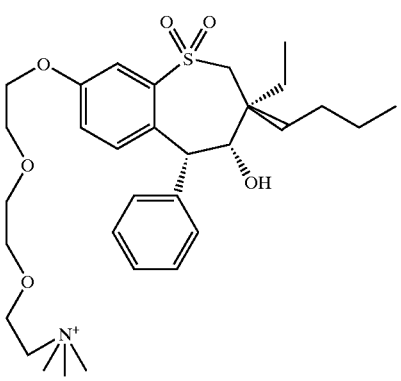

No. 125

A 0.1 g (0.159 mmoles) sample of Compound No. 134 was dissolved in 15 ml of anhydrous acetonitrile in a Fischer-porter bottle and then trimethylamine was bubbled through the solution for 5 minutes at 0° C. and then capped and warmed to room temperature. The reaction was stirred overnight and the desired product was isolated by removing solvent by rotary evaporation.

Example 63 (Comnound No. 295)

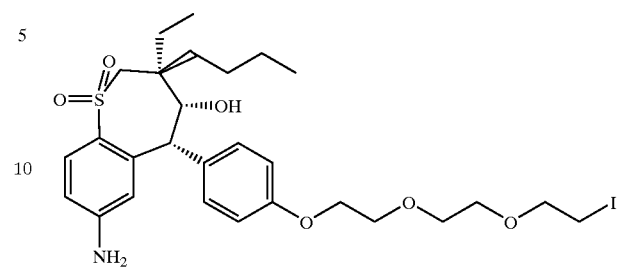

No. 295

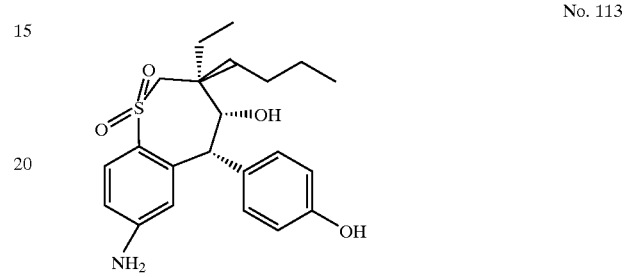

No. 113

Sodium Hydride 60% (11 mg, 0.27 mmoles) in 1 cc of acetonitrile at 0° C. was reacted with 0.248 mmoles (0.10 g) of Compound No. 113 in 2.5 cc of acetonitrile at 0° C. Next, 0.(980 g 2.48 mmoles) of 1,2-Bis [2-iodoethoxylethane]. After warming to room temperature, stir for 14 hours. The product was isolated by column chromatography.

Example 64 (Compound No. 286)

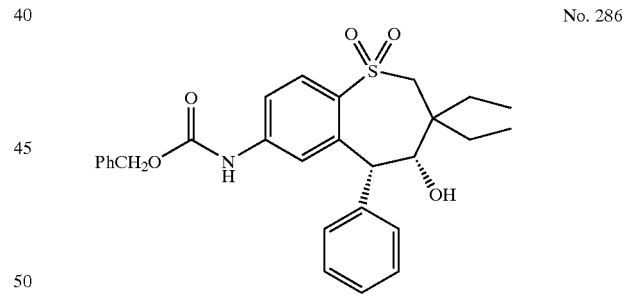

No. 286

Following a procedure similar to the one described in Example 86, infra (see Compound No. 118, Table 3, infra), the title compound was prepared and purified as a colorless solid; mp 180–181° C.; $^1$H NMR (CHCl$_3$) δ 0.85 (t, J=6 Hz, 3H, 0.92 (t, J=6 Hz, 3H), 1.24–1.42 (m, 2H), 1.46–1.56 (m, 1H), 1.64–1.80 (m, 1H), 2.24–2.38 (m, 1H), 3.15 (AB, $J_{AB}$=15 Hz, Δv=42 Hz, 2H), 4.20 (d, J=8 Hz, 1H), 5.13 (s, 2H), 5.53 (s, 1H), 6.46 (s, 1H), 6.68 (s, 1H), 7.29–7.51 (m, 10H), 7.74 (d, J=8 Hz, 1H), 8.06 (d, J=8 Hz, 1H). FABMS m/z 494 (M+H), HRMS calcd for (M+H) 494.2001, found 494.1993. Anal. Calcd. for $C_{28}H_{31}NO_5S$: C, 68.13; H, 6.33; N, 2.84. Found: C, 68.19; H, 6.56; N, 2.74.

Example 65 (Compound No. 287)

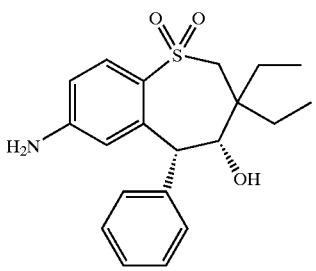

No. 287

Following a procedure similar to the one described in Example 89, infra (see Compound No. 121, Table 3, infra), the title compound was prepared and purified as a colorless solid: mp 245–246° C., $^1$H NMR (CDCl$_3$) δ 0.84 (t, J=6 Hz, 3H), 0.92 (t, J=6 Hz, 3H), 1.28, (d, J=8 Hz, 1H), 1.32–1.42 (m, 1H), 1.48–1.60 (m, 1H), 1.64–1.80 (m, 1H), 2.20–2.36 (m, 1H), 3.09 (AB, J$_{AB}$=15 Hz, Δv=42 Hz, 2H), 3.97 (bs, 2H), 4.15 (d, J=8 Hz, 1H), 5.49 (s, 1H), 5.95 (s, 1H), 6.54 (d, J=7 Hz, 1H), 7.29–7.53 (m, 5H), 7.88 (d, J=8 Hz, 1H); ESMS 366 (M+Li). Anal. Calcd. for C$_{20}$H$_{25}$NO$_3$S: C, 66.82; H, 7.01; N, 3.90. Found: C, 66.54; H, 7.20; N, 3.69.

Example 66 (Compound No. 288)

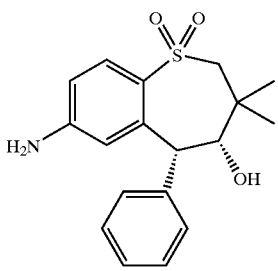

No. 288

Following a procedure similar to the one described in Example 89, infra (see Compound No. 121, Table 3, infra), the title compound was prepared and purified by silica gel chromatography to give the desired product as a colorless solid: mp 185–186° C.; $^1$H NMR (CDCl$_3$) δ 1.12 (s, 3H), 1.49 (s, 3H), 3.00 (d, J=15 Hz, 1H), 3.28 (d, J=15 Hz, 1H), 4.00 (s, 1H), 5.30 (s, 1H), 5.51 (s, 1H), 5.97 (s, 1H), 6.56 (dd, J=2.1, 8.4 Hz, 1H), 7.31–7.52 (m, 5H), 7.89 (d, J=8.4 Hz, 1H). MS (FAB+)(M+H) m/z 332.

Example 67 (Compound No. 289)

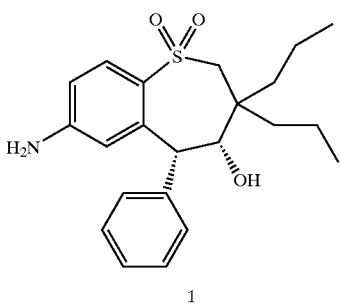

No. 289

Following a procedure similar to the one described in Example 89, infra (see Compound No. 121, Table 3, infra), the title compound was prepared and purified by silica gel chromatography to give the desired product as a white solid: mp 205–206° C.; $^1$H NMR (CDCl$_3$) δ 0.80–0.95 (m, 6H), 1.10–1.70 (m, 7H), 2.15 (m, 1H), 3.02 (d, J=15.3 Hz, 2H), 3.15 (d, J=15.1 Hz, 2H), 3.96 (s, br, 2H), 4.14 (d, J=7.8 Hz, 1H), 5.51 (s, 1H), 5.94 (d, J=2.2, 1H), 6.54 (dd, J=8.5, 2.2 Hz, 1H), 7.28–7.50 (m, 6H), 7.87 (d, J=8.5 Hz, 1H). MS (AB): m/z 388 (M+H).

Example 68 (Commound No. 290)

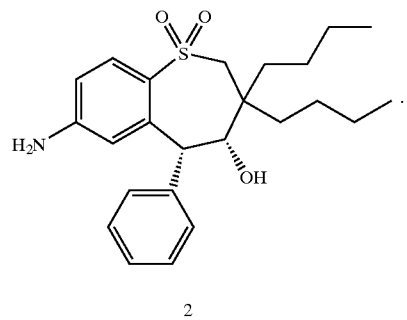

No. 290

Following a procedure similar to the one described in Example 89, infra (see Compound No. 121, Table 3, infra), the title compound was prepared and purified as a colorless solid: mp=96–98° C., $^1$H NMR (CDCl$_3$) δ 0.92 (t, J=7 Hz, 6H), 1.03–1.70 (m, 11H), 2.21 (t, J=8 Hz, 1H), 3.09 (AB, J$_{AB}$=18 Hz, Δv=38 Hz, 2H), 3.96 (bs, 2H), 4.14 (d, J=7 Hz, 1H), 5.51 (s, 1H), 5.94 (s, 1H), 6.56 (d, J=9 Hz, 1H), 7.41–7.53 (m, 6H), 7.87 (d, J=8 Hz, 1H); FABMS m/z 416 (M+H).

Example 69

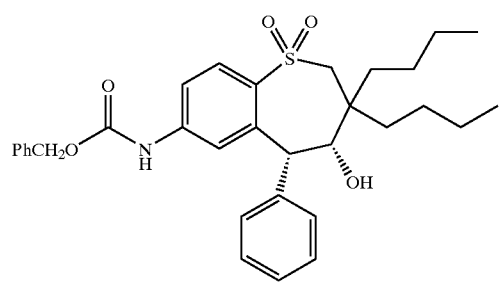

No. 291

Following a procedure similar to the one described in Example 86, infra (see Compound No. 118, Table 3, infra), the title compound was prepared and purified as a colorless solid: $^1$H NMR (CDCl$_3$) δ 0.91 (t, J=7 Hz, 6H), 1.02–1.52 (m, 11H), 1.60–1.70 (m, 1H), 2.23 (t, J=8 Hz, 1H), 3.12 (AB, J$_{AB}$=18 Hz, Δv=36 Hz, 2H), 4.18 (d, J=7 Hz, 1H), 5.13 (s, 2H), 5.53 (s, 1H), 6.43 (s, 1H), 6.65 (s, 1H), 7.29–7.52 (m, 10H), 7.74 (d, J=9 Hz, 1H), 8.03 (d, J=8 Hz, 1H); ESMS m/z 556 (M+Li).

Example 70 (Compound No. 292)

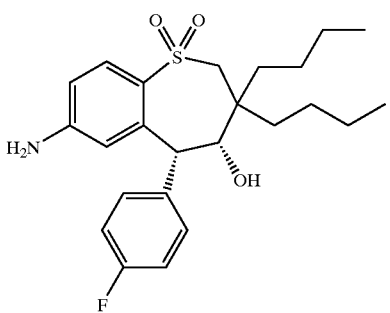

No. 292

Following a procedure similar to the one descried in Example 89, infra (see Compound No. 121, Table 3, infra), the title compound was prepared and purified as a colorless solid: mp=111–112.5° C., $^1$H NMR (CDCl$_3$) δ 0.90 (t, J=8 Hz, 6H), 1.03–1.50 (m, 10H), 1.55–1.70 (m, 2H), 2.18 (t, J=12 Hz, 2H), 3.07 (AB, J$_{AB}$=15 Hz, Δv=45 Hz, 2H), 4.09 (bs, 2H), 5.49 (s, 1H), 5.91 (s, 1H), 6.55 (d, J=9 Hz, 1H), 7.10 (t, J=7 Hz, 2H), 7.46 (t, J=6 Hz, 2H), 7.87 (d, J=9Hz, 1H).

Example 71 (Compound No. 293)

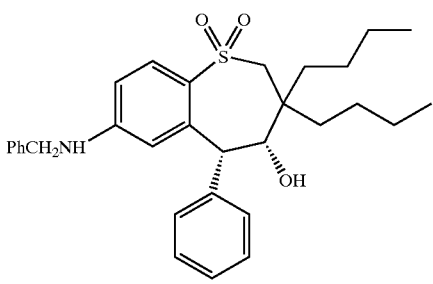

No. 293

During the preparation of Compound No. 290 from Compound No. 291 using BBr$_3$, the title compound was isolated: $^1$H NMR (CDCl$_3$) δ 0.85 (t, J=6 Hz, 6H), 0.98–1.60 (m, 10H), 1.50–1.66 (m, 2H), 2.16 (t, J=8 Hz, 1H), 3.04 (AB, J$_{AB}$=15 Hz, Δv=41 Hz, 2H), 4.08 (s, 1H), 4.12 (s, 1H), 5.44 (s, 1H), 5.84 (s, 1H), 6.42 (d, J=9 Hz, 1H), 7.12 (d, J=8 Hz, 2H), 7.16–7.26 (m, 10H), 7.83 (d, J=8 Hz, 1H); ESMS m/z 512 (M+Li).

Example 72 (Compound No. 294)

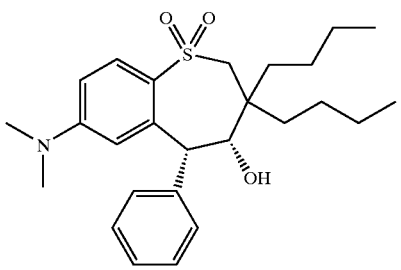

No. 294

Following a procedure similar to the one described in Example 60 (Compound No. 104), the title compound was prepared and purified as a colorless solid: $^1$H NMR (CDCl$_3$) δ 0.90 (t, J=6 Hz, 6H), 1.05–1.54 (m, 9H), 1.60–1.70 (m, 1H), 2.24 (t, J=8 Hz, 1H), 2.80 (s, 6H), 3.05 (AB, J$_{AB}$=15 Hz, Δv=42 Hz, 2H), 4.05–4.18 (m, 2H), 5.53 (s, 1H), 5.93 (s, 1H), 6.94 (d, J=9 Hz, 1H), 7.27–7.42 (m, 4H), 7.45 (d, J=8 Hz, 2H), 7.87 (d, J=9 Hz, 1H); ESMS m/z 444 (M+H).

Structures of the compounds of Examples 33 to 72 are shown in Tables 3 and 3A, infra.

Examples 73–79, 87, 88 and 91–102

Using in each instance a method generally described in those of Examples 1 to 72 appropriate to the substituents to be introduced, compounds were prepared having the structures set forth in Table 3, infra. The starting materials illustrated in the reaction schemes shown above were varied in accordance with principles of organic synthesis well known to the art to introduce the indicated substituents in the 4- and 5-positions (R$^{4A}$, R$^{4B}$, R$^{5A}$, R$^{5B}$) and in the indicated position on the benzo ring (R$^6$).

Structures of the the compounds produced in Examples 73–102 are set forth in Tables 3 and 3A, infra.

Examples 80–84

Preparation of 115, 116, 111, 113

Preparation of 4-Chloro-3-[4-methoxy-phenylmethyl]-nitrobenzene

In a 500 ml 2-necked rb flask weigh out 68.3 gms phosphorus pentachloride (0.328 mole 1.1 eq). Add 50 mls chlorobenzene. Slowly add 60 gms 2-chloro-5-nitrobenzoic acid (0.298 mole). Stir at room temp overnight under N2 then heat 1 hr at 50° C.

Remove chlorobenzene by high vaccuum. Wash residue with hexane. Dry wt=55.5 gms.

In the same rb flask, dissolve acid chloride (55.5 g 0.25 mole) from above with 100 mls anisole (about 3.4 eq). Chill solution with ice bath while purging with N2. Slowly add 40.3 g aluminum chloride (1.2 eq 0.3 mole). Stir under N$_2$ for 24 hrs.

After 24 hrs, the solution was poured into 300 mls 1N HCl soln. (cold). Stir this for 15 min. Extract several times with diethyl ether. Extract organic layer once with 2% aqueous NaOH then twice with water. Dry organic layer with MgSO$_4$, dry on vac line. Solid is washed well with ether and then ethanol before drying. Wt=34.57 g (mixture of meta, ortho and para).

| Elemental | Theory | found |
|---|---|---|
| C | 57.65 | 57.45 |
| H | 3.46 | 5.51 |
| N | 4.8 | 4.8 |
| Cl | 12.15 | 12.16 |

With the next step of the reduction of the ketone with trifluoromethane sulfonic aid and triethyl silane, crystallization with ethyl acetate/hexane affords pure 4-chloro-3-[4-methoxy-phenylmethyl]-nitrobenzene.

4-Chloro-3-[4-methoxy-phenylmethyl]-nitrobenzene was then reacted as specified in the synthesis of 117 and 118 from 2-chloro-4-nitrophenylmethane. From these procedures 115 and 116 can be synthesized. Compounds 111 and 113 can be synthesized from the procedure used to prepare Compound 121. See Table 3, infra.

Compound 114 can be prepared by reaction of 116 with ethyl mercaptan and aluminum trichloride.

Examples 85 and 86

Preparation of 117 and 118

2-Chloro-5-nitrobenzophenone is reduced with triethylsilane and trifluoromethane sulfonic acid to 2-chloro-5-nitrodiphenylmethane 32, supra. Reaction of 32 (similar to S2-32 of Scheme 2, supra) with lithium sulfide followed by reacting the resulting sulfide with mesylate IV (similar to compound S2-33 of Scheme 2, supra) gives sulfide-aldehyde XXIII (similar to compound S2-34 of Scheme 2, supra). Oxidation of XXIII (not shown) with 2 equivalents of MCPBA yields sulfone-aldehyde XXIV (see Scheme 8 below). Reduction of the sulfone-aldehyde XXIV with 100 psi hydrogen and 55° C. for 12 hours catalyzed by palladium on carbon in the same reaction vessel together with RCHO yields the substituted dimethylamine derivative XXVIII. Cyclization of XXVIII with potassium t-butoxide yields a mixture of substituted amino derivatives XXIXc and XXIXd. See SCHEME 8, supra.

The sulfone-aldehyde (31.8 g) was dissolved in ethanol/toluene and placed in a parr reactor with 100 ml toluene and 100 ml of ethanol and 3.2 g of 10% Pd/C and heated to 55° C. and 100 psi of hydrogen gas for 14 hours. The reaction was then filtered to remove the catalyst. The amine product (0.076 moles, 29.5 g) from this reaction was then reacted with benzyl chloroformate (27.4 g) in toluene in the presence of 35 g of potassium carbonate and stirred at room temperature overnight. After work up by extraction with water, the CBZ protected amine product was further purified by precipitation from toluene/hexane.

The CBZ protected amine product was then reacted with 3 equivalents of potassium t-butoxide in THF at 0° C. to yield compounds 117 and 118 which were separated by silica gel column chromatography.

Examples 89 and 90

Preparation of 121 or 122

Compound 118 (0.013 moles, 6.79 g) is dissolved in 135 ml of dry chloroform and cooled to −78° C., next 1.85 ml of boron tribromide (4.9 g) was added and the reaction is allowed to warm to room temperature. Reaction is complete after 1.5 hours. The reaction is quenched by addition of 10% potassium carbonate at 0° C. and extract with ether. Removal of ether yields Compound No. 121. See Table 3, infra. A similar procedure can be used to produce 122 from 117. See Table 3, infra.

Examples 93–96

Compounds 126, 127, 128 and 129 as set forth in Table 3 were prepared substantially in the manner described above for compounds 115, 116, 111 and 113, respectively, except that fluorobenzene was used as a starting material in place of anisole.

TABLE 3

Specific Compounds (#102–111, 113–130, 132–134, 136, 138, 142–144, 262–296)

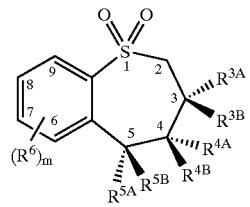

| Cp # | $R^{3A}$ | $R^{3B}$ | $R^{4A}$ | $R^{4B}$ | $R^{5A}$ | $R^{5B}$ | $(R^6)_m$ |
|---|---|---|---|---|---|---|---|
| 102 | Et— | n-Bu— | HO— | H— | Ph— | H— | I⁻, 7-(CH₃)₃N⁺— |
| 103 | n-Bu— | Et— | HO— | H— | Ph— | H— | I⁻, (CH₃)₃N⁺— |
| 104 | Et— | n-Bu— | HO— | H— | Ph— | H— | 7-(CH₃)₂N— |
| 105 | Et— | n-Bu— | HO— | H— | Ph— | H— | 7-CH₃SO₂NH— |
| 106 | Et— | n-Bu— | HO— | H— | Ph— | H— | 7-Br—CH₂—CONH— |
| 107 | n-Bu— | Et— | HO— | H— | p-n-C₁₀H₂₁—O—Ph— | H— | 7-NH₂— |
| 108 | Et— | n-Bu— | HO— | H— | Ph— | H— | 7-C₅H₁₁CONH— |
| 109 | Et— | n-Bu— | HO— | H— | p-n-C₁₀H₂₁—O—Ph— | H— | 7-NH₂— |
| 110 | Et— | n-Bu— | HO— | H— | Ph— | H— | 7-CH₃CONH— |
| 111 | n-Bu— | Et— | HO— | H— | p-HO—Ph— | H— | 7-NH₂— |
| 113 | Et— | n-Bu— | HO— | H— | p-HO—Ph— | H— | 7-NH₂— |
| 114 | Et— | n-Bu— | HO— | H— | p-CH₃O—Ph— | H— | 7-NH₂— |
| 115 | n-Bu— | Et— | HO— | H— | p-CH₃O—Ph— | H— | 7-NH—CBZ |
| 116 | Et— | n-Bu— | HO— | H— | p-CH₃O—Ph— | H— | 7-NH—CBZ |
| 117 | n-Bu— | Et— | HO— | H— | Ph— | H— | 7-NH—CBZ |
| 118 | Et— | n-Bu— | HO— | H— | Ph— | H— | 7-NH—CBZ |
| 119 | Et— | n-Bu— | HO— | H— | Ph— | H— | 7-NHCO₂-t-Bu |
| 120 | n-Bu— | Et— | HO— | H— | Ph— | H— | 7-NHCO₂-t-Bu |
| 121 | Et— | n-Bu— | HO— | H— | Ph— | H— | 7-NH₂— |
| 122 | n-Bu— | Et— | HO— | H— | Ph— | H— | 7-NH₂— |
| 123 | Et— | n-Bu— | HO— | H— | Ph— | H— | 7-n-C₆H₁₃—NH— |
| 124 | n-Bu— | Et— | HO— | H— | Ph— | H— | 7-n-C₆H₁₃—NH— |
| 125 | Et— | n-Bu— | HO— | H— | Ph— | H— | I⁻, 8-(CH₃)₃N⁺(CH₂CH₂O)₃— |
| 126 | n-Bu— | Et— | HO— | H— | p-F—Ph— | H— | 7-NH—CBZ |
| 127 | n-Bu— | Et— | HO— | H— | p-F—Ph— | H— | 7-NH₂— |

TABLE 3-continued

Specific Compounds (#102–111, 113–130, 132–134, 136, 138, 142–144, 262–296)

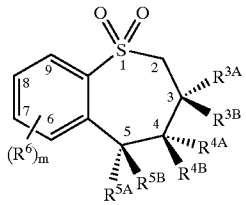

| Cp # | $R^{3A}$ | $R^{3B}$ | $R^{4A}$ | $R^{4B}$ | $R^{5A}$ | $R^{5B}$ | $(R^6)_m$ |
|---|---|---|---|---|---|---|---|
| 128 | Et— | n-Bu— | HO— | H— | p-F—Ph— | H— | 7-NH—CBZ |
| 129 | Et— | n-Bu— | HO— | H— | p-F—Ph— | H— | 7-NH$_2$— |
| 130 | Et— | n-Bu— | HO— | H— | Ph— | H— | I$^-$, 8-(CH$_3$)$_3$N$^+$C$_6$H$_{12}$O— |
| 132 | Et— | n-Bu— | HO— | H— | Ph— | H— | 8-phthalimidyl-C$_6$H$_{12}$O— |
| 133 | Et— | n-Bu— | HO— | H— | Ph— | H— | 8-n-C$_{10}$H$_{21}$— |
| 134 | Et— | n-Bu— | HO— | H— | Ph— | H— | 8-I-(C$_2$H$_4$O)$_3$— |
| 136 | Et— | n-Bu— | HO— | H— | Ph— | H— | 8-HO— |
| 138 | n-Bu— | Et— | HO— | H— | Ph— | H— | 8-CH$_3$CO$_2$— |
| 142 | Et— | n-Bu— | H— | HO— | H— | m-CH$_3$O—Ph— | 7-CH$_3$S— |
| 143 | Et— | n-Bu— | HO— | H— | m-CH$_3$O—Ph— | H— | 7-CH$_3$S— |
| 144 | Et— | n-Bu— | HO— | H— | p-F—Ph— | H— | 7-(N)-azetidine |
| 262 | Et— | n-Bu— | HO— | H— | m-CH$_3$O—Ph— | H— | 7-CH$_3$O— |
| 263 | Et— | n-Bu— | H— | HO— | H— | m-CH$_3$O—Ph— | 7-CH$_3$O— |
| 264 | Et— | n-Bu— | HO— | H— | m-CF$_3$—Ph— | H— | 7-CH$_3$O— |
| 265 | Et— | n-Bu— | H— | HO— | H— | m-CF$_3$—Ph— | 7-CH$_3$O— |
| 266 | Et— | n-Bu— | HO— | H— | m-HO—Ph— | H— | 7-HO— |
| 267 | Et— | n-Bu— | HO— | H— | m-HO—Ph— | H— | 7-CH$_3$O— |
| 268 | Et— | n-Bu— | HO— | H— | p-F—Ph— | H— | 7-CH$_3$O— |
| 269 | Et— | n-Bu— | H— | HO— | H— | p-F—Ph— | 7-CH$_3$O— |
| 270 | Et— | n-Bu— | HO— | H— | p-F—Ph— | H— | 7-HO— |
| 271 | Et— | n-Bu— | HO— | H— | m-CH$_3$O—Ph— | H— | 7-Br— |
| 272 | Et— | n-Bu— | H— | HO— | H— | m-CH$_3$O—Ph— | 7-Br— |
| 273 | Et— | n-Bu— | H— | HO— | H— | p-F—Ph— | 7-F— |
| 274 | Et— | n-Bu— | HO— | H— | p-F—Ph— | H— | 7-F— |
| 275 | Et— | n-Bu— | H— | HO— | H— | m-CH$_3$O—Ph— | 7-F— |
| 276 | Et— | n-Bu— | HO— | H— | m-CH$_3$O—Ph | H— | 7-F— |
| 277 | Et— | n-Bu— | HO— | H— | m-F—Ph— | H— | 7-CH$_3$O— |
| 278 | Et— | n-Bu— | H— | HO— | H— | o-F—Ph— | 7-CH$_3$O— |
| 279 | Et— | n-Bu— | H— | HO— | H— | m-F—Ph— | 7-CH$_3$O— |
| 280 | Et— | n-Bu— | HO— | H— | o-F—Ph— | H— | 7-CH$_3$O— |
| 281 | Et— | n-Bu— | HO— | H— | p-F—Ph— | H— | 7-CH$_3$S— |
| 282 | Et— | n-Bu— | HO— | H— | p-F—Ph— | H— | 7-CH$_3$— |
| 283 | Et— | n-Bu— | H— | HO— | H— | p-F—Ph— | 7-CH$_3$— |
| 284 | Et— | n-Bu— | HO— | H— | p-F—Ph— | H— | 7-(N)-morpholine |
| 285 | Et— | n-Bu— | HO— | H— | p-F—Ph— | H— | 7-(N)-pyrrolidine |
| 286 | Et— | Et— | HO— | H— | Ph— | H— | 7-NH—CBZ— |
| 287 | Et— | Et— | HO— | H— | Ph— | H— | 7-NH$_2$— |
| 288 | CH$_3$— | CH$_3$— | HO— | H— | Ph— | H— | 7-NH$_2$— |
| 289 | n-C$_3$H$_7$— | n-C$_3$H$_7$— | HO— | H— | Ph— | H— | 7-NH$_2$— |
| 290 | n-Bu— | n-Bu— | HO— | H— | Ph— | H— | 7-NH$_2$— |
| 291 | n-Bu— | n-Bu— | HO— | H— | Ph— | H— | 7-NH—CBZ— |
| 292 | n-Bu— | n-Bu— | HO— | H— | p-F—Ph— | H— | 7-NH$_2$— |
| 293 | n-Bu— | n-Bu— | HO— | H— | Ph— | H— | 7-PhCH$_2$N— |
| 294 | n-Bu— | n-Bu— | HO— | H— | Ph— | H— | 7-(CH$_3$)$_2$N— |
| 295 | Et— | n-Bu— | HO— | H— | p-I—(C$_2$H$_4$O)$_3$—Ph— | H— | 7-NH$_2$— |
| 296 | Et— | n-Bu— | HO— | H— | I$^-$, p-(CH$_3$)$_3$N$^+$(C$_2$H$_4$O)$_3$—Ph— | H— | 7-NH$_2$— |

TABLE 3A
Bridged Benzothiepines (#101, 112, 131, 135, 137, 139–141)
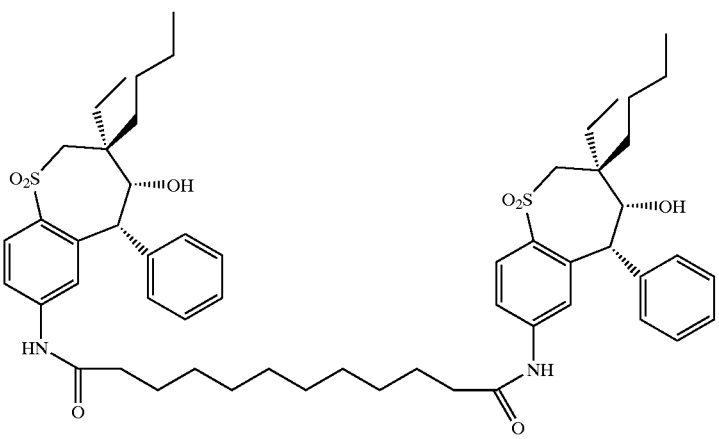
CPD #101 (Example 59)
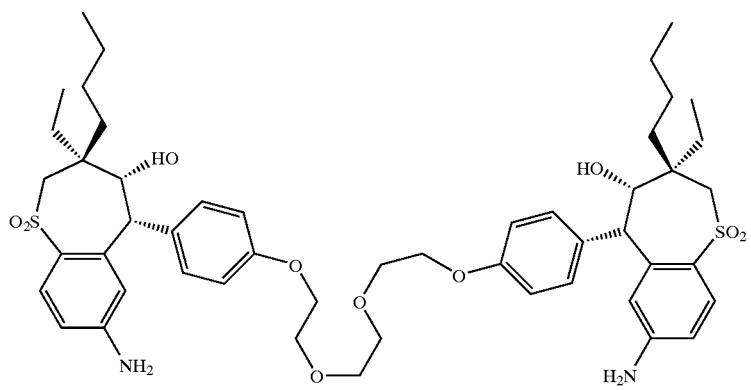
CPD #112 (Example 53)
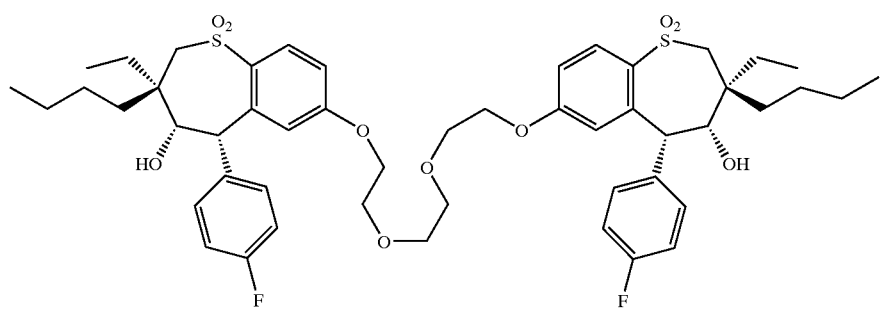
CPD #131 (Example 56)
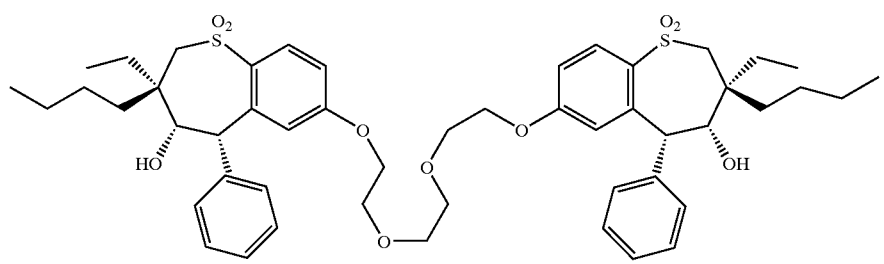
CPD #135 (Example 55)

TABLE 3A-continued
Bridged Benzothiepines (#101, 112, 131, 135, 137, 139–141)
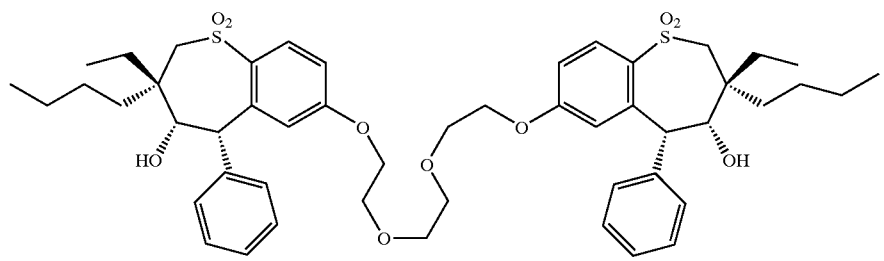
CPD #137 (Example 57)
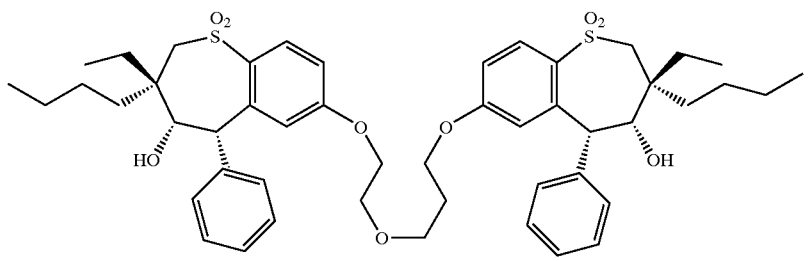
CPD #139 (Example 58)
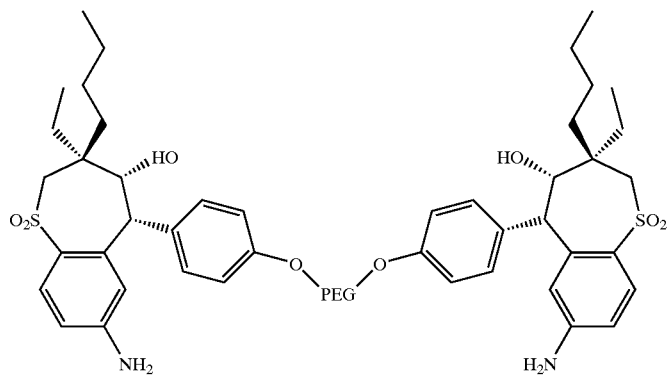
PEG = 3400 molecular weight polyethyleneglycol bridge
CPD #140 (Example 51)
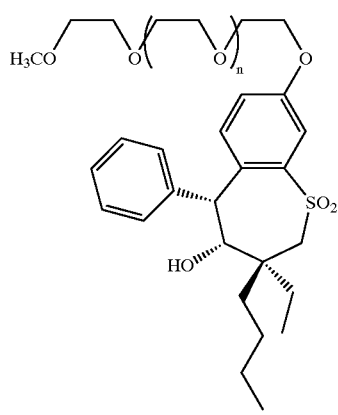
CPD #141 (Example 50)

Examples 104–231

Using in each instance a method generally described in those of Examples 1 to 72 appropriate to the substituents to be introduced, including where necessary other common synthesis expedients well known to the art, compounds are prepared having the structures set forth in Table 4 below. The starting materials illustrated in the reaction schemes shown above are varied in accordance with principles of organic synthesis well known to the art in order to introduce the indicated substituents in the 4- and 5-positions ($R^{3A}$, $R^{3B}$, $R^{4A}$, $R^{5A}$) and in the indicated position on the benzo ring ($R^6$). See Table 4 below.

TABLE 4

Alternative compounds #1 (#302–312, 314–430)

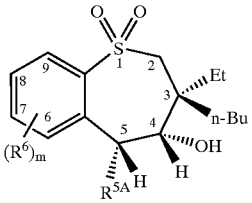

| Cpd # | $R^{5A}$ | $(R^6)_m$ |
|---|---|---|
| 302 | p-F—Ph— | 7-(1-aziridine) |
| 303 | p-F—Ph— | 7-EtS— |
| 304 | p-F—Ph— | 7-CH$_3$S(O)— |
| 305 | p-F—Ph— | 7-CH$_3$S(O)$_2$— |
| 306 | p-F—Ph— | 7-PhS— |
| 307 | p-F—Ph— | 7-CH$_3$S—<br>9-CH$_3$S— |
| 308 | p-F—Ph— | 7-CH$_3$O—<br>9-CH$_3$O— |
| 309 | p-F—Ph— | 7-Et— |
| 310 | p-F—Ph— | 7-iPr— |
| 311 | p-F—Ph— | 7-t-Bu— |
| 312 | p-F—Ph— | 7-(1-pyrazole)- |
| 314 | m-CH$_3$O—Ph | 7-(1-azetidine) |
| 315 | m-CH$_3$O—Ph— | 7-(1-aziridine) |
| 316 | m-CH$_3$O—Ph— | 7-EtS— |
| 317 | m-CH$_3$O—Ph— | 7-CH$_3$S(O)— |
| 318 | m-CH$_3$O—Ph— | 7-CH$_3$S(O)$_2$— |
| 319 | m-CH$_3$O—Ph— | 7-PhS— |
| 320 | m-CH$_3$O—Ph | 7-CH$_3$S—<br>9-CH$_3$S— |
| 321 | m-CH$_3$O—Ph | 7-CH$_3$O—<br>9-CH$_3$O— |
| 322 | m-CH$_3$O—Ph | 7-Et— |
| 323 | m-CH$_3$O—Ph | 7-iPr— |
| 324 | m-CH$_3$O—Ph | 7-t-Bu— |
| 325 | p-F—Ph— | 6-CH$_3$O—<br>7-CH$_3$O—<br>8-CH$_3$O— |
| 326 | p-F—Ph— | 7-(1-azetidine)<br>9-CH$_3$— |
| 327 | p-F—Ph— | 7-EtS—<br>9-CH$_3$— |
| 328 | p-F—Ph— | 7-CH$_3$S(O)—<br>9-CH$_3$— |
| 329 | p-F—Ph— | 7-CH$_3$S(O)$_2$—<br>9-CH$_3$— |
| 330 | p-F—Ph— | 7-PhS—<br>9-CH$_3$— |
| 331 | p-F—Ph— | 7-CH$_3$S—<br>9-CH$_3$— |
| 332 | p-F—Ph— | 7-CH$_3$O—<br>9-CH$_3$— |
| 333 | p-F—Ph— | 7-CH$_3$—<br>9-CH$_3$— |
| 334 | p-F—Ph— | 7-CH$_3$O—<br>9-CH$_3$O— |
| 335 | p-F—Ph— | 7-(1-pyrrole) |
| 336 | p-F—Ph— | 7-(N)N'-methylpiperazine |
| 337 | p-F—Ph— | Ph— |
| 338 | p-F—Ph— | 7-CH$_3$C(=CH$_2$)— |
| 339 | p-F—Ph— | 7-cyclpropyl |
| 340 | p-F—Ph— | 7-(CH$_3$)$_2$NHN— |
| 341 | p-F—Ph— | 7-(N)-azetidine<br>9-CH$_3$S— |
| 342 | p-F—Ph— | 7-(N-pyrrolidine)<br>9-CH$_3$S— |
| 343 | p-F—Ph— | 7-(CH$_3$)$_2$N—<br>9-CH$_3$S— |
| 344 | m-CH$_3$O—Ph— | 7-(1-pyrazole) |
| 345 | m-CH$_3$O—Ph— | 7-(N)N'-methylpiperazine |
| 346 | m-CH$_3$O—Ph— | Ph— |
| 347 | m-CH$_3$O—Ph— | 7-CH$_3$C(=CH$_2$)— |
| 348 | m-CH$_3$O—Ph— | 7-cyclopropyl |
| 349 | m-CH$_3$O—Ph— | 7-(CH$_3$)$_2$NHN— |
| 350 | m-CH$_3$O—Ph— | 7-(N)-azetidine<br>9-CH$_3$S— |
| 351 | m-CH$_3$O—Ph— | 7-(N-pyrrolidine)-<br>9-CH$_3$S— |
| 352 | m-CH$_3$O—Ph— | 7-(CH$_3$)$_2$N—<br>9-CH$_3$S— |
| 353 | m-CH$_3$O—Ph— | 6-CH$_3$O—<br>7-CH$_3$O—<br>8-CH$_3$O— |
| 354 | m-CH$_3$O—Ph— | 7-(1-azetidine)<br>9-CH$_3$— |
| 355 | m-CH$_3$O—Ph— | 7-EtS—<br>9-CH$_3$— |
| 356 | m-CH$_3$O—Ph— | 7-CH$_3$S(O)—<br>9-CH$_3$— |
| 357 | m-CH$_3$O—Ph— | 7-CH$_3$S(O)$_2$—<br>9-CH$_3$— |
| 358 | m-CH$_3$O—Ph— | 7-PhS—<br>9-CH$_3$— |
| 359 | m-CH$_3$O—Ph— | 7-CH$_3$S—<br>9-CH$_3$— |
| 360 | m-CH$_3$O—Ph— | 7-CH$_3$O—<br>9-CH$_3$— |
| 361 | m-CH$_3$O—Ph— | 7-CH$_3$—<br>9-CH$_3$— |
| 362 | m-CH$_3$O—Ph— | 7-CH$_3$O—<br>9-CH$_3$O— |
| 363 | thien-2-yl | 7-(1-aziridine) |
| 364 | thien-2-yl | 7-EtS— |
| 365 | thien-2-yl | 7-CH$_3$S(O)— |
| 366 | thien-2-yl | 7-CH$_3$S(O)$_2$— |
| 367 | thien-2-yl | 7-PhS— |
| 368 | thien-2-yl | 7-CH$_3$S—<br>9-CH$_3$S— |
| 369 | thien-2-yl | 7-CH$_3$O—<br>9-CH$_3$O— |
| 370 | thien-2-yl | 7-Et— |
| 371 | thien-2-yl | 7-iPr— |
| 372 | thien-2-yl | 7-t-Bu— |

TABLE 4-continued

Alternative compounds #1 (#302–312, 314–430)

| Cpd # | R⁵ᴬ | (R⁶)ₘ |
|---|---|---|
| 373 | thien-2-yl | 7-(1-pyrrole)- |
| 374 | thien-2-yl | 7-CH₃O— |
| 375 | thien-2-yl | 7-CH₃S— |
| 376 | thien-2-yl | 7-(1-azetidine) |
| 377 | thien-2-yl | 7-Me— |
| 378 | 5-Cl-thien-2-yl | 7-(1-azetidine) |
| 379 | 5-Cl-thien-2-yl | 7-(1-aziridine) |
| 380 | 5-Cl-thien-2-yl | 7-EtS— |
| 381 | 5-Cl-thien-2-yl | 7-CH₃S(O)— |
| 382 | 5-Cl-thien-2-yl | 7-CH₃S(O)₂— |
| 383 | 5-Cl-thien-2-yl | 7-PhS— |
| 384 | 5-Cl-thien-2-yl | 7-CH₃S— 9-CH₃S— |
| 385 | 5-Cl-thien-2-yl | 7-CH₃O— 9-CH₃O— |
| 386 | 5-Cl-thien-2-yl | 7-Et— |
| 387 | 5-Cl-thien-2-yl | 7-iPr— |
| 388 | 5-Cl-thien-2-yl | 7-t-Bu— |
| 389 | 5-Cl-thien-2-yl | 7-CH₃O— |
| 390 | 5-Cl-thien-2-yl | 7-CH₃S— |
| 391 | 5-Cl-thien-2-yl | 7-Me |
| 392 | thien-2-yl | 7-(1-azetidine) 9-CH₃— |
| 393 | thien-2-yl | 7-EtS— 9-CH₃— |
| 394 | thien-2-yl | 7-CH₃S(O)— 9-CH₃— |
| 395 | thien-2-yl | 7-CH₃S(O)₂— 9-CH₃— |
| 396 | thien-2-yl | 7-PhS— 9-CH₃— |
| 397 | thien-2-yl | 7-CH₃S— 9-CH₃— |
| 398 | thien-2-yl | 7-CH₃O— 9-CH₃— |
| 399 | thien-2-yl | 7-CH₃— 9-CH₃— |
| 400 | thien-2-yl | 7-CH₃O— 9-CH₃O— |
| 401 | thien-2-yl | 7-(1-pyrazrole) |
| 402 | thien-2-yl | 7-(N)N'-methylpiperazine |
| 403 | thien-2-yl | Ph— |
| 404 | thien-2-yl | 7-CH₃C(=CH₂)— |
| 405 | thien-2-yl | 7-cyclopropyl |
| 406 | thien-2-yl | 7-(CH₃)₂NHN— |
| 407 | thien-2-yl | 7-(N)-azetidine 9-CH₃S— |
| 408 | thien-2-yl | 7-(N-pyrrolidine) 9-CH₃S— |
| 409 | thien-2-yl | 7-(CH₃)₂N— 9-CH₃S— |
| 411 | 5-Cl-thien-2-yl | 7-(1-pyrazrole) |
| 412 | 5-Cl-thien-2-yl | 7-(N)N'-methylpiperazine |
| 413 | 5-Cl-thien-2-yl | Ph— |
| 414 | 5-Cl-thien-2-yl | 7-CH₃C(=CH₂)— |
| 415 | 5-Cl-thien-2-yl | 7-cyclopropyl |
| 416 | 5-Cl-thien-2-yl | 7-(CH₃)₂NHN— |
| 417 | 5-Cl-thien-2-yl | 7-(N)-azetidine 9-CH₃S— |
| 418 | 5-Cl-thien-2-yl | 7-(N-pyrrolidine)- 9-CH₃S— |
| 419 | 5-Cl-thien-2-yl | 7-(CH₃)₂N— 9-CH₃S— |
| 420 | 5-Cl-thien-2-yl | 7-(1-azetidine) 9-CH₃— |
| 421 | 5-Cl-thien-2-yl | 7-EtS— 9-CH₃— |
| 422 | 5-Cl-thien-2-yl | 7-CH₃S(O)— 9-CH₃— |
| 423 | 5-Cl-thien-2-yl | 7-CH₃S(O)₂— 9-CH₃— |
| 424 | 5-Cl-thien-2-yl | 7-PhS— 9-CH₃— |
| 425 | 5-Cl-thien-2-yl | 7-CH₃S— 9-CH₃— |
| 426 | 5-Cl-thien-2-yl | 7-CH₃O— 9-CH₃— |
| 427 | 5-Cl-thien-2-yl | 7-CH₃— 9-CH₃— |
| 428 | 5-Cl-thien-2-yl | 7-CH₃O— 9-CH₃O— |
| 429 | thien-2-yl | 6-CH₃O— 7-CH₃O— 8-CH₃O— |
| 430 | 5-Cl-thien-2-yl | 6-CH₃O— 7-CH₃O— 8-CH₃O— |

Examples 232–1394

Using in each instance a method generally described in those of Examples 1 to 72 appropriate to the substituents to be introduced, including where necessary other common synthesis expedients well known to the art, compounds are prepared having the structures set forth in Table 5–7 below. The starting materials illustrated in the reaction schemes shown above are varied in accordance with principles of organic synthesis well known to the art in order to introduce the indicated substituents in the 4- and 5-positions ($R^{3A}$, $R^{3B}$, $R^{4A}$, $R^{5A}$) and in the indicated position on the benzo ring ($R^6$).

TABLE 5

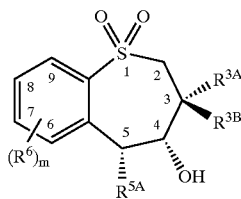

| Prefix (FFF.xxx) | Cpd # yyy | $R^{3A}=R^{3B}$ | $R^{5A}$ | $(R^6)_m$ |
|---|---|---|---|---|
| F101.001 | 01 | Ethyl | Ph- | 7-methyl |
| | 02 | Ethyl | Ph- | 7-ethyl |
| | 03 | Ethyl | Ph- | 7-iso-propyl |
| | 04 | Ethyl | Ph- | 7-tert-butyl |
| | 05 | Ethyl | Ph- | 7-OH |
| | 06 | Ethyl | Ph- | 7-OCH$_3$ |
| | 07 | Ethyl | Ph- | 7-O(iso-propyl) |
| | 08 | Ethyl | Ph- | 7-SCH$_3$ |
| | 09 | Ethyl | Ph- | 7-SOCH$_3$ |
| | 10 | ethyl | Ph- | 7-SO$_2$CH$_3$ |
| | 11 | ethyl | Ph- | 7-SCH$_2$CH$_3$ |
| | 12 | ethyl | Ph- | 7-NH$_2$ |
| | 13 | ethyl | Ph- | 7-NHOH |
| | 14 | ethyl | Ph- | 7-NHCH$_3$ |
| | 15 | ethyl | Ph- | 7-N(CH$_3$)$_2$ |
| | 16 | ethyl | Ph- | 7-N$^+$(CH$_3$)$_3$, I$^-$ |
| | 17 | ethyl | Ph- | 7-NHC(=O)CH$_3$ |
| | 18 | ethyl | Ph- | 7-N(CH$_2$CH$_3$)$_2$ |
| | 19 | ethyl | Ph- | 7-NMeCH$_2$CO$_2$H |
| | 20 | ethyl | Ph- | 7-N$^+$(Me)$_2$CH$_2$CO$_2$H, I$^-$ |
| | 21 | ethyl | Ph- | 7-(N)-morpholine |
| | 22 | ethyl | Ph- | 7-(N)-azetidine |
| | 23 | ethyl | Ph- | 7-(N)—N-methylazetidinium, I$^-$ |
| | 24 | ethyl | Ph- | 7-(N)-pyrrolidine |
| | 25 | ethyl | Ph- | 7-(N)—N-methyl-pyrrolidinium, I$^-$ |
| | 26 | ethyl | Ph- | 7-(N)—N-methyl-morpholinium, I$^-$ |
| | 27 | ethyl | Ph- | 7-(N)—N'-methylpiperazine |
| | 28 | ethyl | Ph- | 7-(N)—N'-dimethylpiperazinium, I$^-$ |
| | 29 | ethyl | Ph- | 7-NH—CBZ |
| | 30 | ethyl | Ph- | 7-NHC(O)C$_5$H$_{11}$ |
| | 31 | ethyl | Ph- | 7-NHC(O)CH$_2$Br |
| | 32 | ethyl | Ph- | 7-NH—C(NH)NH$_2$ |
| | 33 | ethyl | Ph- | 7-(2)-thiophene |
| | 34 | ethyl | Ph- | 8-methyl |
| | 35 | ethyl | Ph- | 8-ethyl |
| | 36 | ethyl | Ph- | 8-iso-propyl |
| | 37 | ethyl | Ph | 8-tert-butyl |
| | 38 | ethyl | Ph- | 8-OH |
| | 39 | ethyl | Ph- | 8-OCH$_3$ |
| | 40 | ethyl | Ph- | 8-O(iso-propyl) |
| | 41 | ethyl | Ph- | 8-SCH$_3$ |
| | 42 | ethyl | Ph- | 8-SOCH$_3$ |
| | 43 | ethyl | Ph- | 8-SO$_2$CH$_3$ |
| | 44 | ethyl | Ph- | 8-SCH$_2$CH$_3$ |
| | 45 | ethyl | Ph- | 8-NH$_2$ |
| | 46 | ethyl | Ph- | 8-NHOH |
| | 47 | ethyl | Ph- | 8-NHCH$_3$ |
| | 48 | ethyl | Ph- | 8-N(CH$_3$)$_2$ |
| | 49 | ethyl | Ph- | 8-N$^+$(CH$_3$)$_3$, I$^-$ |
| | 50 | ethyl | Ph- | 8-NHC(=O)CH$_3$ |
| | 51 | ethyl | Ph- | 8-N(CH$_2$CH$_3$)$_2$ |
| | 52 | ethyl | Ph- | 8-NMeCH$_2$CO$_2$H |
| | 53 | ethyl | Ph- | 8-N$^+$(Me)$_2$CH$_2$CO$_2$H, I$^-$ |
| | 54 | ethyl | Ph- | 8-(N)-morpholine |
| | 55 | ethyl | Ph- | 8-(N)-azetidine |
| | 56 | ethyl | Ph- | 8-(N)—N-methylazetidinium, I$^-$ |
| | 57 | ethyl | Ph- | 8-(N)-pyrrolidine |
| | 58 | ethyl | Ph- | 8-(N)—N-methyl-pyrrolidinium, I$^-$ |
| | 59 | ethyl | Ph- | 8-(N)—N-methyl-morpholinium, I$^-$ |
| | 60 | ethyl | Ph- | 8-(N)—N'-methylpiperazine |
| | 61 | ethyl | Ph- | 8-(N)—N'-dimethylpiperazinium, I$^-$ |
| | 62 | ethyl | Ph- | 8-NH—CBZ |
| | 63 | ethyl | Ph- | 8-NHC(O)C$_5$H$_{11}$ |
| | 64 | ethyl | Ph- | 8-NHC(O)CH$_2$Br |
| | 65 | ethyl | Ph- | 8-NH—C(NH)NH$_2$ |

TABLE 5-continued

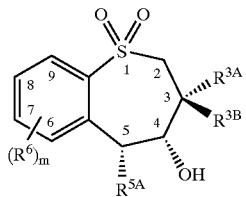

| Prefix (FFF.xxx. | Cpd # yyy) | $R^{3A}=R^{3B}$ | $R^{5A}$ | $(R^6)_m$ |
|---|---|---|---|---|
| | 66 | ethyl | Ph- | 8-(2)-thiophene |
| | 67 | ethyl | Ph- | 9-methyl |
| | 68 | ethyl | Ph- | 9-ethyl |
| | 69 | ethyl | Ph- | 9-iso-propyl |
| | 70 | ethyl | Ph- | 9-tert-butyl |
| | 71 | ethyl | Ph- | 9-OH |
| | 72 | ethyl | Ph- | 9-$OCH_3$ |
| | 73 | ethyl | Ph- | 9-O(iso-propyl) |
| | 74 | ethyl | Ph- | 9-$SCH_3$ |
| | 75 | ethyl | Ph- | 9-$SOCH_3$ |
| | 76 | ethyl | Ph- | 9-$SO_2CH_3$ |
| | 77 | ethyl | Ph- | 9-$SCH_2CH_3$ |
| | 78 | ethyl | Ph- | 9-$NH_2$ |
| | 79 | ethyl | Ph- | 9-NHOH |
| | 80 | ethyl | Ph- | 9-$NHCH_3$ |
| | 81 | ethyl | Ph- | 9-$N(CH_3)_2$ |
| | 82 | ethyl | Ph- | 9-$N^+(CH_3)_3$, $I^-$ |
| | 83 | ethyl | Ph- | 9-NHC(=O)$CH_3$ |
| | 84 | ethyl | Ph- | 9-$N(CH_2CH_3)_2$ |
| | 85 | ethyl | Ph- | 9-NMe$CH_2CO_2H$ |
| | 86 | ethyl | Ph- | 9-$N^+(Me)_2CH_2CO_2H$, $I^-$ |
| | 87 | ethyl | Ph- | 9-(N)-morpholine |
| | 88 | ethyl | Ph- | 9-(N)-azetidine |
| | 89 | ethyl | Ph- | 9-(N)—N-methylazetidinium, $I^-$ |
| | 90 | ethyl | Ph- | 9-(N)-pyrrolidine |
| | 91 | ethyl | Ph- | 9-(N)—N-methyl-pyrrolidinium, $I^-$ |
| | 92 | ethyl | Ph- | 9-(N)—N-methyl-morpolinium, $I^-$ |
| | 93 | ethyl | Ph- | 9-(N)—N'-methylpiperazine |
| | 93 | ethyl | Ph- | 9-(N)—N'-dimethylpiperazinium, $I^-$ |
| | 95 | ethyl | Ph- | 9-NH—CBZ |
| | 96 | ethyl | Ph- | 9-NHC(O)$C_5H_{11}$ |
| | 97 | ethyl | Ph- | 9-NHC(O)$CH_2$Br |
| | 98 | ethyl | Ph- | 9-NH—C(NH)$NH_2$ |
| | 99 | ethyl | Ph- | 9-(2)-thiophene |
| | 100 | ethyl | Ph- | 7-$OCH_3$, 8-$OCH_3$ |
| | 101 | ethyl | Ph- | 7-$SCH_3$, 8-$OCH_3$ |
| | 102 | ethyl | Ph- | 7-$SCH_3$, 8-$SCH_3$ |
| | 103 | ethyl | Ph- | 6-$OCH_3$, 7-$OCH_3$, 8-$OCH_3$ |
| F101.002 | 01 | n-propyl | Ph- | 7-methyl |
| | 02 | n-propyl | Ph- | 7-ethyl |
| | 03 | n-propyl | Ph- | 7-iso-propyl |
| | 04 | n-propyl | Ph- | 7-tert-butyl |
| | 05 | n-propyl | Ph- | 7-OH |
| | 06 | n-propyl | Pn- | 7-$OCH_3$ |
| | 07 | n-propyl | Ph- | 7-O(iso-propyl) |
| | 08 | n-propyl | Ph- | 7-$SCH_3$ |
| | 09 | n-propyl | Ph- | 7-$SOCH_3$ |
| | 10 | n-propyl | Ph- | 7-$SO_2CH_3$ |
| | 11 | n-propyl | Ph- | 7-$SCH_2CH_3$ |
| | 12 | n-propyl | Ph- | 7-$NH_2$ |
| | 13 | n-propyl | Ph- | 7-NHOH |
| | 14 | n-propyl | Ph- | 7-$NHCH_3$ |
| | 15 | n-propyl | Ph- | 7-$N(CH_3)_2$ |
| | 16 | n-propyl | Ph- | 7-$N^+(CH_3)_3$, $I^-$ |
| | 17 | n-propyl | Ph- | 7-NHC(=O)$CH_3$ |
| | 18 | n-propyl | Ph- | 7-$N(CH_2CH_3)_2$ |
| | 19 | n-propyl | Ph- | 7-NMe$CH_2CO_2H$ |
| | 20 | n-propyl | Ph- | 7-$N^+(Me)_2CH_2CO_2H$, $I^-$ |
| | 21 | n-propyl | Ph- | 7-(N)-morpholine |
| | 22 | n-propyl | Ph- | 7-(N)-azetidine |
| | 23 | n-propyl | Ph- | 7-(N)—N-methylazetidinium, $I^-$ |
| | 24 | n-propyl | Ph- | 7-(N)-pyrrolidine |
| | 25 | n-propyl | Ph- | 7-(N)—N-methyl-pyrrolidinium, $I^-$ |
| | 26 | n-propyl | Ph- | 7-(N)—N-methyl-morpholinium, $I^-$ |
| | 27 | n-propyl | Ph- | 7-(N)—N'-methylpiperazine |

TABLE 5-continued

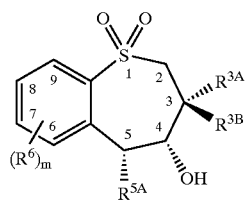

| Prefix (FFF.xxx. | Cpd # yyy) | $R^{3A}=R^{3B}$ | $R^{5A}$ | $(R^6)_m$ |
|---|---|---|---|---|
| | 28 | n-propyl | Ph- | 7-(N)—N'-dimethylpiperazinium, I⁻ |
| | 29 | n-propyl | Ph- | 7-NH—CBZ |
| | 30 | n-propyl | Ph- | 7-NHC(O)C$_5$H$_{11}$ |
| | 31 | n-propyl | Ph- | 7-NHC(O)CH$_2$Br |
| | 32 | n-propyl | Ph- | 7-NH—C(NH)NH$_2$ |
| | 33 | n-propyl | Ph- | 7-(2)-thiophene |
| | 34 | n-propyl | Ph- | 8-methyl |
| | 35 | n-propyl | Ph- | 8-ethyl |
| | 36 | n-propyl | Ph- | 8-iso-propyl |
| | 37 | n-propyl | Ph- | 8-tert-butyl |
| | 38 | n-propyl | Ph- | 8-OH |
| | 39 | n-propyl | Ph- | 8-OCH$_3$ |
| | 40 | n-propyl | Ph- | 8-O(iso-propyl) |
| | 41 | n-propyl | Ph- | 8-SCH$_3$ |
| | 42 | n-propyl | Ph- | 8-SOCH$_3$ |
| | 43 | n-propyl | Ph- | 8-SO$_2$CH$_3$ |
| | 44 | n-propyl | Ph- | 8-SCH$_2$CH$_3$ |
| | 45 | n-propyl | Ph- | 8-NH$_2$ |
| | 46 | n-propyl | Ph- | 8-NHOH |
| | 47 | n-propyl | Ph- | 8-NHCH$_3$ |
| | 48 | n-propyl | Ph- | 8-N(CH$_3$)$_2$ |
| | 49 | n-propyl | Ph- | 8-N⁺(CH$_3$)$_3$, I⁻ |
| | 50 | n-propyl | Ph- | 8-NHC(=O)CH$_3$ |
| | 51 | n-propyl | Ph- | 8-N(CH$_2$CH$_3$)$_2$ |
| | 52 | n-propyl | Ph- | 8-NMeCH$_2$CO$_2$H |
| | 53 | n-propyl | Ph- | 8-N⁺(Me)$_2$CH$_2$CO$_2$H, I⁻ |
| | 54 | n-propyl | Ph- | 8-(N)-morpholine |
| | 55 | n-propyl | Ph- | 8-(N)-azetidine |
| | 56 | n-propyl | Ph- | 8-(N)—N-methylazetidinium, I⁻ |
| | 57 | n-propyl | Ph- | 8-(N)-pyrrolidine |
| | 58 | n-propyl | Ph- | 8-(N)—N-methyl-pyrrolidinium, I⁻ |
| | 59 | n-propyl | Ph- | 8-(N)—N-methyl-morpholinium, I⁻ |
| | 60 | n-propyl | Ph- | 8-(N)—N'-methylpiperazine |
| | 61 | n-propyl | Ph- | 8-(N)—N'-dimethylpiperazinium, I⁻ |
| | 62 | n-propyl | Ph- | 8-NH—CBZ |
| | 63 | n-propyl | Ph- | 8-NHC(O)C$_5$H$_{11}$ |
| | 64 | n-propyl | Ph- | 8-NHC(O)CH$_2$Br |
| | 65 | n-propyl | Ph- | 8-NHC(NH)NH$_2$ |
| | 66 | n-propyl | Ph- | 8-(2)-thiophene |
| | 67 | n-propyl | Ph- | 9-methyl |
| | 68 | n-propyl | Ph- | 9-ethyl |
| | 69 | n-propyl | Ph- | 9-iso-propyl |
| | 70 | n-propyl | Ph- | 9-tert-butyl |
| | 71 | n-propyl | Ph- | 9-OH |
| | 72 | n-propyl | Ph- | 9-OCH$_3$ |
| | 73 | n-propyl | Ph- | 9-O(iso-propyl) |
| | 74 | n-propyl | Ph- | 9-SCH$_3$ |
| | 75 | n-propyl | Ph- | 9-SOCH$_3$ |
| | 76 | n-propyl | Ph- | 9-SO$_2$CH$_3$ |
| | 77 | n-propyl | Ph- | 9-SCH$_2$CH$_3$ |
| | 78 | n-propyl | Ph- | 9-NH$_2$ |
| | 79 | n-propyl | Ph- | 9-NHOH |
| | 80 | n-propyl | Ph- | 9-NHCH$_3$ |
| | 81 | n-propyl | Ph- | 9-N(CH$_3$)$_2$ |
| | 82 | n-propyl | Ph- | 9-N⁺(CH$_3$)$_3$, I⁻ |
| | 83 | n-propyl | Ph- | 9-NHC(=O)CH$_3$ |
| | 84 | n-propyl | Ph- | 9-N(CH$_2$CH$_3$)$_2$ |
| | 85 | n-propyl | Ph- | 9-NMeCH$_2$CO$_2$H |
| | 86 | n-propyl | Ph- | 9-N⁺(Me)$_2$CH$_2$CO$_2$H, I⁻ |
| | 87 | n-propyl | Ph- | 9-(N)-morpholine |
| | 88 | n-propyl | Ph- | 9-(N)-azetidine |
| | 89 | n-propyl | Ph- | 9-(N)—N-methylazetidinium, I⁻ |
| | 90 | n-propyl | Ph- | 9-(N)-pyrrolidine |
| | 91 | n-propyl | Ph- | 9-(N)—N-methyl-pyrrolidinium, I⁻ |
| | 92 | n-propyl | Ph- | 9-(N)—N-methyl-morpholinium, I⁻ |

TABLE 5-continued

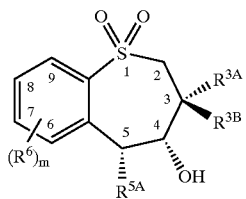

| Prefix (FFF.xxx) | Cpd # yyy | $R^{3A}=R^{3B}$ | $R^{5A}$ | $(R^6)_m$ |
|---|---|---|---|---|
| | 93 | n-propyl | Ph- | 9-(N)—N'-methylpiperazine |
| | 93 | n-propyl | Ph- | 9-(N)—N'-dimethylpiperazinium, I⁻ |
| | 95 | n-propyl | Ph- | 9-NH—CBZ |
| | 96 | n-propyl | Ph- | 9-NHC(O)C$_5$H$_{11}$ |
| | 97 | n-propyl | Ph- | 9-NHC(O)CH$_2$Br |
| | 98 | n-propyl | Ph- | 9-NHC(NH)NH$_2$ |
| | 99 | n-propyl | Ph- | 9-(2)-thiophene |
| | 100 | n-propyl | Ph- | 7-OCH$_3$, 8-OCH$_3$ |
| | 101 | n-propyl | Ph- | 7-SCH$_3$, 8-OCH$_3$ |
| | 102 | n-propyl | Ph- | 7-SCH$_3$, 8-SCH$_3$ |
| | 103 | n-propyl | Ph- | 6-OCH$_3$, 7-OCH$_3$, 8-OCH$_3$ |
| F101.003 | 01 | n-butyl | Ph- | 7-methyl |
| | 02 | n-butyl | Ph- | 7-ethyl |
| | 03 | n-butyl | Ph- | 7-iso-propyl |
| | 04 | n-butyl | Ph- | 7-tert-butyl |
| | 05 | n-butyl | Ph- | 7-OH |
| | 06 | n-butyl | Ph- | 7-OCH$_3$ |
| | 07 | n-butyl | Ph- | 7-O(iso-propyl) |
| | 08 | n-butyl | Ph- | 7-SCH$_3$ |
| | 09 | n-butyl | Ph- | 7-SOCH$_3$ |
| | 10 | n-butyl | Ph- | 7-SO$_2$CH$_3$ |
| | 11 | n-butyl | Ph- | 7-SCH$_2$CH$_3$ |
| | 12 | n-butyl | Ph- | 7-NH$_2$ |
| | 13 | n-butyl | Ph- | 7-NHOH |
| | 14 | n-butyl | Ph- | 7-NHCH$_3$ |
| | 15 | n-butyl | Ph- | 7-N(CH$_3$)$_2$ |
| | 16 | n-butyl | Ph- | 7-N⁺(CH$_3$)$_3$, I⁻ |
| | 17 | n-butyl | Ph- | 7-NHC(=O)CH$_3$ |
| | 18 | n-butyl | Ph- | 7-N(CH$_2$CH$_3$)$_2$ |
| | 19 | n-butyl | Ph- | 7-NMeCH$_2$CO$_2$H |
| | 20 | n-butyl | Ph- | 7-N⁺(Me)$_2$CH$_2$CO$_2$H, I⁻ |
| | 21 | n-butyl | Ph- | 7-(N)-morpholine |
| | 22 | n-butyl | Ph- | 7-(N)-azetidine |
| | 23 | n-butyl | Ph- | 7-(N)—N-methylazetidinium, I⁻ |
| | 24 | n-butyl | Ph- | 7-(N)-pyrrolidine |
| | 25 | n-butyl | Ph- | 7-(N)—N-methyl-pyrrolidinium, I⁻ |
| | 26 | n-butyl | Ph- | 7-(N)—N-methyl-morpholinium, I⁻ |
| | 27 | n-butyl | Ph- | 7-(N)—N'-methylpiperazine |
| | 28 | n-butyl | Ph- | 7-(N)—N'-dimethylpiperazinium, I⁻ |
| | 29 | n-butyl | Ph- | 7-NH—CBZ |
| | 30 | n-butyl | Ph- | 7-NHC(O)C$_5$H$_{11}$ |
| | 31 | n-butyl | Ph- | 7-NHC(O)CH$_2$Br |
| | 32 | n-butyl | Ph- | 7-NH—C(NH)NH$_2$ |
| | 33 | n-butyl | Ph- | 7-(2)-thiophene |
| | 34 | n-butyl | Ph- | 8-methyl |
| | 35 | n-butyl | Ph- | 8-ethyl |
| | 36 | n-butyl | Ph- | 8-iso-propyl |
| | 37 | n-butyl | Ph- | 8-tert-butyl |
| | 38 | n-butyl | Ph- | 8-OH |
| | 39 | n-butyl | Ph- | 8-OCH$_3$ |
| | 40 | n-butyl | Ph- | 8-O(iso-propyl) |
| | 41 | n-butyl | Ph- | 8-SCH$_3$ |
| | 42 | n-butyl | Ph- | 8-SOCH$_3$ |
| | 43 | n-butyl | Ph- | 8-SO$_2$CH$_3$ |
| | 44 | n-butyl | Ph- | 8-SCH$_2$CH$_3$ |
| | 45 | n-butyl | Ph- | 8-NH$_2$ |
| | 46 | n-butyl | Ph- | 8-NHOH |
| | 47 | n-butyl | Ph- | 8-NHCH$_3$ |
| | 48 | n-butyl | Ph- | 8-N(CH$_3$)$_2$ |
| | 49 | n-butyl | Ph- | 8-N⁺(CH$_3$)$_3$, I⁻ |
| | 50 | n-butyl | Ph- | 8-NHC(=O)CH$_3$ |
| | 51 | n-butyl | Ph- | 8-N(CH$_2$CH$_3$)$_2$ |
| | 52 | n-butyl | Ph- | 8-NMeCH$_2$CO$_2$H |
| | 53 | n-butyl | Ph- | 8-N⁺(Me)$_2$CH$_2$CO$_2$H, I⁻ |
| | 54 | n-butyl | Ph- | 8-(N)-morpholine |

TABLE 5-continued

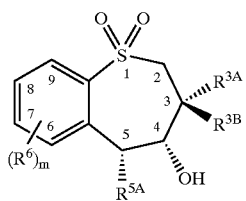

| Prefix (FFF.xxx. | Cpd # yyy) | $R^{3A}=R^{3B}$ | $R^{5A}$ | $(R^6)_m$ |
|---|---|---|---|---|
| | 55 | n-butyl | Ph- | 8-(N)-azetidine |
| | 56 | n-butyl | Ph- | 8-(N)—N-methylazetidinium, I⁻ |
| | 57 | n-butyl | Ph- | 8-(N)-pyrrolidine |
| | 58 | n-butyl | Ph- | 8-(N)—N-methyl-pyrrolidinium, I⁻ |
| | 59 | n-butyl | Ph- | 8-(N)—N-methyl-morpholinium, I⁻ |
| | 60 | n-butyl | Ph- | 8-(N)—N'-methylpiperazine |
| | 61 | n-butyl | Ph- | 8-(N)—N'-methylpiperazinium, I⁻ |
| | 62 | n-butyl | Ph- | 8-NH—CBZ |
| | 63 | n-butyl | Ph- | 8-NHC(O)C$_5$H$_{11}$ |
| | 64 | n-butyl | Ph- | 8-NHC(O)CH$_2$Br |
| | 65 | n-butyl | Ph- | 8-NH—C(NH)NH$_2$ |
| | 66 | n-butyl | Ph- | 8-(2)-thiophene |
| | 67 | n-butyl | Ph- | 9-methyl |
| | 68 | n-butyl | Ph- | 9-ethyl |
| | 69 | n-butyl | Ph- | 9-iso-propyl |
| | 70 | n-butyl | Ph- | 9-tert-butyl |
| | 71 | n-butyl | Ph- | 9-OH |
| | 72 | n-butyl | Ph- | 9-OCH$_3$ |
| | 73 | n-butyl | Ph- | 9-O(iso-propyl) |
| | 74 | n-butyl | Ph- | 9-SCH$_3$ |
| | 75 | n-butyl | Ph- | 9-SOCH$_3$ |
| | 76 | n-butyl | Ph- | 9-SO$_2$CH$_3$ |
| | 77 | n-butyl | Ph- | 9-SCH$_2$CH$_3$ |
| | 78 | n-butyl | Ph- | 9-NH$_2$ |
| | 79 | n-butyl | Ph- | 9-NHOH |
| | 80 | n-butyl | Ph- | 9-NHCH$_3$ |
| | 81 | n-butyl | Ph- | 9-N(CH$_3$)$_2$ |
| | 82 | n-butyl | Ph- | 9-N$^+$(CH$_3$)$_3$, I⁻ |
| | 83 | n-butyl | Ph- | 9-NHC(=O)CH$_3$ |
| | 84 | n-butyl | Ph- | 9-N(CH$_2$CH$_3$)$_2$ |
| | 85 | n-butyl | Ph- | 9-NMeCH$_2$CO$_2$H |
| | 86 | n-butyl | Ph- | 9-N$^+$(Me)$_2$CH$_2$CO$_2$H, I⁻ |
| | 87 | n-butyl | Ph- | 9-(N)-morpholine |
| | 88 | n-butyl | Ph- | 9-(N)-azetidine |
| | 89 | n-butyl | Ph- | 9-(N)—N-methylazetidinium, I⁻ |
| | 90 | n-butyl | Ph- | 9-(N)-pyrrolidine |
| | 91 | n-butyl | Ph- | 9-(N)—N-methyl-pyrrolidinium, I⁻ |
| | 92 | n-butyl | Ph- | 9-(N)—N-methyl-morpholinium, I⁻ |
| | 93 | n-butyl | Ph- | 9-(N)—N'-methylpiperazine |
| | 93 | n-butyl | Ph- | 9-(N)—N'-dimethylpiperazinium, I⁻ |
| | 95 | n-butyl | Ph- | 9-NH—CBZ |
| | 96 | n-butyl | Ph- | 9-NHC(O)C$_5$H$_{11}$ |
| | 97 | n-butyl | Ph- | 9-NHC(O)CH$_2$Br |
| | 98 | n-butyl | Ph- | 9-NH—C(NH)NH$_2$ |
| | 99 | n-butyl | Ph- | 9-(2)-thiophene |
| | 100 | n-butyl | Ph- | 7-OCH$_3$, 8-OCH$_3$ |
| | 101 | n-butyl | Ph- | 7-SCH$_3$, 8-OCH$_3$ |
| | 102 | n-butyl | Ph- | 7-SCH$_3$, 8-SCH$_3$ |
| | 103 | n-butyl | Ph- | 6-OCH$_3$, 7-OCH$_3$, 8-OCH$_3$ |
| F101.004 | 01 | n-pentyl | Ph- | 7-methyl |
| | 02 | n-pentyl | Ph- | 7-ethyl |
| | 03 | n-pentyl | Ph- | 7-iso-propyl |
| | 04 | n-pentyl | Ph- | 7-tert-butyl |
| | 05 | n-pentyl | Ph- | 7-OH |
| | 06 | n-pentyl | Ph- | 7-OCH$_3$ |
| | 07 | n-pentyl | Ph- | 7-O(iso-propyl) |
| | 08 | n-pentyl | Ph- | 7-SCH$_3$ |
| | 09 | n-pentyl | Ph- | 7-SOCH$_3$ |
| | 10 | n-pentyl | Ph- | 7-SO$_2$CH$_3$ |
| | 11 | n-pentyl | Ph- | 7-SCH$_2$CH$_3$ |
| | 12 | n-pentyl | Ph- | 7-NH$_2$ |
| | 13 | n-pentyl | Ph- | 7-NHOH |
| | 14 | n-pentyl | Ph- | 7-NHCH$_3$ |
| | 15 | n-pentyl | Ph- | 7-N(CH$_3$)$_2$ |
| | 16 | n-pentyl | Ph- | 7-N$^+$(CH$_3$)$_3$, I⁻ |

TABLE 5-continued

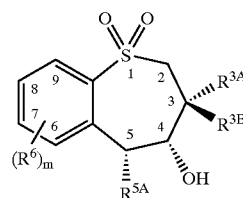

| Prefix (FFF.xxx. | Cpd # yyy) | $R^{3A}=R^{3B}$ | $R^{5A}$ | $(R^6)_m$ |
|---|---|---|---|---|
| | 17 | n-pentyl | Ph- | 7-NHC(=O)CH$_3$ |
| | 18 | n-pentyl | Ph- | 7-N(CH$_2$CH$_3$)$_2$ |
| | 19 | n-pentyl | Ph- | 7-NMeCH$_2$CO$_2$H |
| | 20 | n-pentyl | Ph- | 7-N$^+$(Me)$_2$CH$_2$CO$_2$H, I$^-$ |
| | 21 | n-pentyl | Ph- | 7-(N)-morpholine |
| | 22 | n-pentyl | Ph- | 7-(N)-azetidine |
| | 23 | n-pentyl | Ph- | 7-(N)—N-methylazetidinium, I$^-$ |
| | 24 | n-pentyl | Ph- | 7-(N)-pyrrolidine |
| | 25 | n-pentyl | Ph- | 7-(N)—N-methylpyrrolidinium, I$^-$ |
| | 26 | n-pentyl | Ph- | 7-(N)—N-methyl-morpholinium, I$^-$ |
| | 27 | n-pentyl | Ph- | 7-(N)—N'-methylpiperazine |
| | 28 | n-pentyl | Ph- | 7-(N)—N'-dimethylpiperazinium, I$^-$ |
| | 29 | n-pentyl | Ph- | 7-NH—CBZ |
| | 30 | n-pentyl | Ph- | 7-NHC(O)C$_5$H$_{11}$ |
| | 31 | n-pentyl | Ph- | 7-NHC(O)CH$_2$Br |
| | 32 | n-pentyl | Ph- | 7-NH—C(NH)NH$_2$ |
| | 33 | n-pentyl | Ph- | 7-(2)-thiophene |
| | 34 | n-pentyl | Ph- | 8-methyl |
| | 35 | n-pentyl | Ph- | 8-ethyl |
| | 36 | n-pentyl | Ph- | 8-iso-propyl |
| | 37 | n-pentyl | Ph- | 8-tert-butyl |
| | 38 | n-pentyl | Ph- | 8-OH |
| | 39 | n-pentyl | Ph- | 8-OCH$_3$ |
| | 40 | n-pentyl | Ph- | 8-O(iso-propyl) |
| | 41 | n-pentyl | Ph- | 8-SCH$_3$ |
| | 42 | n-pentyl | Ph- | 8-SOCH$_3$ |
| | 43 | n-pentyl | Ph- | 8-SO$_2$CH$_3$ |
| | 44 | n-pentyl | Ph- | 8-SCH$_2$CH$_3$ |
| | 45 | n-pentyl | Ph- | 8-NH$_2$ |
| | 46 | n-pentyl | Ph- | 8-NHOH |
| | 47 | n-pentyl | Ph- | 8-NHCH$_3$ |
| | 48 | n-pentyl | Ph- | 8-N(CH$_3$)$_2$ |
| | 49 | n-pentyl | Ph- | 8-N$^+$(CH$_3$)$_3$, I$^-$ |
| | 50 | n-pentyl | Ph- | 8-NHC(=O)CH$_3$ |
| | 51 | n-pentyl | Ph- | 8-N(CH$_2$CH$_3$)$_2$ |
| | 52 | n-pentyl | Ph- | 8-NMeCH$_2$CO$_2$H |
| | 53 | n-pentyl | Ph- | 8-N$^+$(Me)$_2$CH$_2$CO$_2$H, I$^-$ |
| | 54 | n-pentyl | Ph- | 8-(N)-morpholine |
| | 55 | n-pentyl | Ph- | 8-(N)-azetidine |
| | 56 | n-pentyl | Ph- | 8-(N)—N-methylazetidinium, I$^-$ |
| | 57 | n-pentyl | Ph- | 8-(N)-pyrrolidine |
| | 58 | n-pentyl | Ph- | 8-(N)—N-methyl-pyrrolidinium, I$^-$ |
| | 59 | n-pentyl | Ph- | 8-(N)—N-methyl-morpholinium, I$^-$ |
| | 60 | n-pentyl | Ph- | 8-(N)—N'-methylpiperazine |
| | 61 | n-pentyl | Ph- | 8-(N)—N'-dimethylpiperazinium, I$^-$ |
| | 62 | n-pentyl | Ph- | 8-NH—CBZ |
| | 63 | n-pentyl | Ph- | 8-NHC(O)C$_5$H$_{11}$ |
| | 64 | n-pentyl | Ph- | 8-NHC(O)CH$_2$Br |
| | 65 | n-pentyl | Ph- | 8-NH—C(NH)NH$_2$ |
| | 66 | n-pentyl | Ph- | 8-(2)-thiophene |
| | 67 | n-pentyl | Ph- | 9-methyl |
| | 68 | n-pentyl | Ph- | 9-ethyl |
| | 69 | n-pentyl | Ph- | 9-iso-propyl |
| | 70 | n-pentyl | Ph- | 9-tert-butyl |
| | 71 | n-pentyl | Ph- | 9-OH |
| | 72 | n-pentyl | Ph- | 9-OCH$_3$ |
| | 73 | n-pentyl | Ph- | 9-O(iso-propyl) |
| | 74 | n-pentyl | Ph- | 9-SCH$_3$ |
| | 75 | n-pentyl | Ph- | 9-SOCH$_3$ |
| | 76 | n-pentyl | Ph- | 9-SO$_2$CH$_3$ |
| | 77 | n-pentyl | Ph- | 9-SCH$_2$CH$_3$ |
| | 78 | n-pentyl | Ph- | 9-NH$_2$ |
| | 79 | n-pentyl | Ph- | 9-NHOH |
| | 80 | n-pentyl | Ph- | 9-NHCH$_3$ |
| | 81 | n-pentyl | Ph- | 9-N(CH$_3$)$_2$ |

TABLE 5-continued

| Prefix (FFF.xxx) | Cpd # yyy | R³ᴬ=R³ᴮ | R⁵ᴬ | (R⁶)ₘ |
|---|---|---|---|---|
| | 82 | n-pentyl | Ph- | 9-N⁺(CH₃)₃, I⁻ |
| | 83 | n-pentyl | Ph- | 9-NHC(=O)CH₃ |
| | 84 | n-pentyl | Ph- | 9-N(CH₂CH₃)₂ |
| | 85 | n-pentyl | Ph- | 9-NMeCH₂CO₂H |
| | 86 | n-pentyl | Ph- | 9-N⁺(Me)₂CH₂CO₂H, I⁻ |
| | 87 | n-pentyl | Ph- | 9-(N)-morpholine |
| | 88 | n-pentyl | Ph- | 9-(N)-azetidine |
| | 89 | n-pentyl | Ph- | 9-(N)—N-methylazetidinium, I⁻ |
| | 90 | n-pentyl | Ph- | 9-(N)-pyrrolidine |
| | 91 | n-pentyl | Ph- | 9-(N)—N-methyl-pyrrolidinium, I⁻ |
| | 92 | n-pentyl | Ph- | 9-(N)—N-methyl-morpholinium, I⁻ |
| | 93 | n-pentyl | Ph- | 9-(N)—N'-methylpiperazine |
| | 93 | n-pentyl | Ph- | 9-(N)—N'-dimethylpiperazinium, I⁻ |
| | 95 | n-pentyl | Ph- | 9-NH—CBZ |
| | 96 | n-pentyl | Ph- | 9-NHC(O)C₅H₁₁ |
| | 97 | n-pentyl | Ph- | 9-NHC(O)CH₂Br |
| | 98 | n-pentyl | Ph- | 9-NH—C(NH)NH₂ |
| | 99 | n-pentyl | Ph- | 9-(2)-thiophene |
| | 100 | n-pentyl | Ph- | 7-OCH₃, 8-OCH₃ |
| | 101 | n-pentyl | Ph- | 7-SCH₃, 8-OCH₃ |
| | 102 | n-pentyl | Ph- | 7-SCH₃, 8-SCH₃ |
| | 103 | n-pentyl | Ph- | 6-OCH₃, 7-OCH₃, 8-OCH₃ |
| F101.005 | 01 | n-hexyl | Ph- | 7-methyl |
| | 02 | n-hexyl | Ph- | 7-ethyl |
| | 03 | n-hexyl | Ph- | 7-iso-propyl |
| | 04 | n-hexyl | Ph- | 7-tert-butyl |
| | 05 | n-hexyl | Ph- | 7-OH |
| | 06 | n-hexyl | Ph- | 7-OCH₃ |
| | 07 | n-hexyl | Ph- | 7-O(iso-propyl) |
| | 08 | n-hexyl | Ph- | 7-SCH₃ |
| | 09 | n-hexyl | Ph- | 7-SOCH₃ |
| | 10 | n-hexyl | Ph- | 7-SO₂CH₃ |
| | 11 | n-hexyl | Ph- | 7-SCH₂CH₃ |
| | 12 | n-hexyl | Ph- | 7-NH₂ |
| | 13 | n-hexyl | Ph- | 7-NHOH |
| | 14 | n-hexyl | Ph- | 7-NHCH₃ |
| | 15 | n-hexyl | Ph- | 7-N(CH₃)₂ |
| | 16 | n-hexyl | Ph- | 7-N⁺(CH₃)₃, I⁻ |
| | 17 | n-hexyl | Ph- | 7-NHC(=O)CH₃ |
| | 18 | n-hexyl | Ph- | 7-N(CH₂CH₃)₂ |
| | 19 | n-hexyl | Ph- | 7-NMeCH₂CO₂H |
| | 20 | n-hexyl | Ph- | 7-N⁺(Me)₂CH₂CO₂H, I⁻ |
| | 21 | n-hexyl | Ph- | 7-(N)-morpholine |
| | 22 | n-hexyl | Ph- | 7-(N)-azetidine |
| | 23 | n-hexyl | Ph- | 7-(N)—N-methylazetidinium, I⁻ |
| | 24 | n-hexyl | Ph- | 7-(N)-pyrrolidine |
| | 25 | n-hexyl | Ph- | 7-(N)—N-methyl-pyrrolidinium, I⁻ |
| | 26 | n-hexyl | Ph- | 7-(N)—N-methyl-morpholinium, I⁻ |
| | 27 | n-hexyl | Ph- | 7-(N)—N'-methylpiperazine |
| | 28 | n-hexyl | Ph- | 7-(N)—N'-dimethylpiperazinium, I⁻ |
| | 29 | n-hexyl | Ph- | 7-NH—CBZ |
| | 30 | n-hexyl | Ph- | 7-NHC(O)C₅H₁₁ |
| | 31 | n-hexyl | Ph- | 7-NHC(O)CH₂Br |
| | 32 | n-hexyl | Ph- | 7-NH—C(NH)NH₂ |
| | 33 | n-hexyl | Ph- | 7-(2)-thiophene |
| | 34 | n-hexyl | Ph- | 8-methyl |
| | 35 | n-hexyl | Ph- | 8-ethyl |
| | 36 | n-hexyl | Ph- | 8-iso-propyl |
| | 37 | n-hexyl | Ph- | 8-tert-butyl |
| | 38 | n-hexyl | Ph- | 8-OH |
| | 39 | n-hexyl | Ph- | 8-OCH₃ |
| | 40 | n-hexyl | Ph- | 8-O(iso-propyl) |
| | 41 | n-hexyl | Ph- | 8-SCH₃ |
| | 42 | n-hexyl | Ph- | 8-SOCH₃ |
| | 43 | n-hexyl | Ph- | 8-SO₂CH₃ |

TABLE 5-continued

[Structure: benzothiepine sulfone with positions labeled 1-9, substituents R³ᴬ, R³ᴮ at position 3, R⁵ᴬ at position 5, OH at position 4, and (R⁶)ₘ on the aromatic ring]

| Prefix (FFF.xxx. | Cpd # yyy) | R³ᴬ=R³ᴮ | R⁵ᴬ | (R⁶)ₘ |
|---|---|---|---|---|
| | 44 | n-hexyl | Ph- | 8-SCH$_2$CH$_3$ |
| | 45 | n-hexyl | Ph- | 8-NH$_2$ |
| | 46 | n-hexyl | Ph- | 8-NHOH |
| | 47 | n-hexyl | Ph- | 8-NHCH$_3$ |
| | 48 | n-hexyl | Ph- | 8-N(CH$_3$)$_2$ |
| | 49 | n-hexyl | Ph- | 8-N$^+$(CH$_3$)$_3$, I$^-$ |
| | 50 | n-hexyl | Ph- | 8-NHC(=O)CH$_3$ |
| | 51 | n-hexyl | Ph- | 8-N(CH$_2$CH$_3$)$_2$ |
| | 52 | n-hexyl | Ph- | 8-NMeCH$_2$CO$_2$H |
| | 53 | n-hexyl | Ph- | 8-N$^+$(Me)$_2$CH$_2$CO$_2$H, I$^-$ |
| | 54 | n-hexyl | Ph- | 8-(N)-morpholine |
| | 55 | n-hexyl | Ph- | 8-(N)-azetidine |
| | 56 | n-hexyl | Ph- | 8-(N)—N-methylazetidinium, I$^-$ |
| | 57 | n-hexyl | Ph- | 8-(N)-pyrrolidine |
| | 58 | n-hexyl | Ph- | 8-(N)—N-methyl-pyrrolidinium, I$^-$ |
| | 59 | n-hexyl | Ph- | 8-(N)—N-methyl-morpholinium, I$^-$ |
| | 60 | n-hexyl | Ph- | 8-(N)—N'-methylpiperazine |
| | 61 | n-hexyl | Ph- | 8-(N)—N'-dimethylpiperazinium, I$^-$ |
| | 62 | n-hexyl | Ph- | 8-NH—CBZ |
| | 63 | n-hexyl | Ph- | 8-NHC(O)C$_5$H$_{11}$ |
| | 64 | n-hexyl | Ph- | 8-NHC(O)CH$_2$Br |
| | 65 | n-hexyl | Ph- | 8-NH—C(NH)NH$_2$ |
| | 66 | n-hexyl | Ph- | 8-(2)-thiophene |
| | 67 | n-hexyl | Ph- | 9-methyl |
| | 68 | n-hexyl | Ph- | 9-ethyl |
| | 69 | n-hexyl | Ph- | 9-iso-propyl |
| | 70 | n-hexyl | Ph- | 9-tert-butyl |
| | 71 | n-hexyl | Ph- | 9-OH |
| | 72 | n-hexyl | Ph- | 9-OCH$_3$ |
| | 73 | n-hexyl | Ph- | 9-O(iso-propyl) |
| | 74 | n-hexyl | Ph- | 9-SCH$_3$ |
| | 75 | n-hexyl | Ph- | 9-SOCH$_3$ |
| | 76 | n-hexyl | Ph- | 9-SO$_2$CH$_3$ |
| | 77 | n-hexyl | Ph- | 9-SCH$_2$CH$_3$ |
| | 78 | n-hexyl | Ph- | 9-NH$_2$ |
| | 79 | n-hexyl | Ph- | 9-NHOH |
| | 80 | n-hexyl | Ph- | 9-NHCH$_3$ |
| | 81 | n-hexyl | Ph- | 9-N(CH$_3$)$_2$ |
| | 82 | n-hexyl | Ph- | 9-N$^+$(CH$_3$)$_3$, I$^-$ |
| | 83 | n-hexyl | Ph- | 9-NHC(=O)CH$_3$ |
| | 84 | n-hexyl | Ph- | 9-N(CH$_2$CH$_3$)$_2$ |
| | 85 | n-hexyl | Ph- | 9-NMeCH$_2$CO$_2$H |
| | 86 | n-hexyl | Ph- | 9-N$^+$(Me)$_2$CH$_2$CO$_2$H, I$^-$ |
| | 87 | n-hexyl | Ph- | 9-(N)-morpholine |
| | 88 | n-hexyl | Ph- | 9-(N)-azetidine |
| | 89 | n-hexyl | Ph- | 9-(N)—N-methylazetidinium, I$^-$ |
| | 90 | n-hexyl | Ph- | 9-(N)-pyrrolidine |
| | 91 | n-hexyl | Ph- | 9-(N)—N-methyl-pyrrolidinium, I$^-$ |
| | 92 | n-hexyl | Ph- | 9-(N)—N-methyl-morpholinium, I$^-$ |
| | 93 | n-hexyl | Ph- | 9-(N)—N'-methylpiperazine |
| | 93 | n-hexyl | Ph- | 9-(N)—N'-dimethylpiperazinium, I$^-$ |
| | 95 | n-hexyl | Ph- | 9-NH—CBZ |
| | 96 | n-hexyl | Ph- | 9-NHC(O)C$_5$H$_{11}$ |
| | 97 | n-hexyl | Ph- | 9-NHC(O)CH$_2$Br |
| | 98 | n-hexyl | Ph- | 9-NH—C(NH)NH$_2$ |
| | 99 | n-hexyl | Ph- | 9-(2)-thiophene |
| | 100 | n-hexyl | Ph- | 7-OCH$_3$, 8-OCH$_3$ |
| | 101 | n-hexyl | Ph- | 7-SCH$_3$, 8-OCH$_3$ |
| | 102 | n-hexyl | Ph- | 7-SCH$_3$, 8-SCH$_3$ |
| | 103 | n-hexyl | Ph- | 6-OCH$_3$, 7-OCH$_3$, 8-OCH$_3$ |
| F101.006 | 01 | iso-propyl | Ph- | 7-methyl |
| | 02 | iso-propyl | Ph- | 7-ethyl |
| | 03 | iso-propyl | Ph- | 7-iso-propyl |
| | 04 | iso-propyl | Ph- | 7-tert-butyl |
| | 05 | iso-propyl | Ph- | 7-OH |

TABLE 5-continued

| Prefix (FFF.xxx. | Cpd # yyy) | $R^{3A}=R^{3B}$ | $R^{5A}$ | $(R^6)_m$ |
|---|---|---|---|---|
| | 06 | iso-propyl | Ph- | 7-OCH$_3$ |
| | 07 | iso-propyl | Ph- | 7-O(iso-propyl) |
| | 08 | iso-propyl | Ph- | 7-SCH$_3$ |
| | 09 | iso-propyl | Ph- | 7-SOCH$_3$ |
| | 10 | iso-propyl | Ph- | 7-SO$_2$CH$_3$ |
| | 11 | iso-propyl | Ph- | 7-SCH$_2$CH$_3$ |
| | 12 | iso-propyl | Ph- | 7-NH$_2$ |
| | 13 | iso-propyl | Ph- | 7-NHOH |
| | 14 | iso-propyl | Ph- | 7-NHCH$_3$ |
| | 15 | iso-propyl | Ph- | 7-N(CH$_3$)$_2$ |
| | 16 | iso-propyl | Ph- | 7-N$^+$(CH$_3$)$_3$, I$^-$ |
| | 17 | iso-propyl | Ph- | 7-NHC(=O)CH$_3$ |
| | 18 | iso-propyl | Ph- | 7-N(CH$_2$CH$_3$)$_2$ |
| | 19 | iso-propyl | Ph- | 7-NMeCH$_2$CO$_2$H |
| | 20 | iso-propyl | Ph- | 7-N$^+$(Me)$_2$CH$_2$CO$_2$H, I$^-$ |
| | 21 | iso-propyl | Ph- | 7-(N)-morpholine |
| | 22 | iso-propyl | Ph- | 7-(N)-azetidine |
| | 23 | iso-propyl | Ph- | 7-(N)—N-methylazetidinium, I$^-$ |
| | 24 | iso-propyl | Ph- | 7-(N)-pyrrolidine |
| | 25 | iso-propyl | Ph- | 7-(N)—N-methyl-pyrrolidinium, I$^-$ |
| | 26 | iso-propyl | Ph- | 7-(N)—N-methyl-morpholinium, I$^-$ |
| | 27 | iso-propyl | Ph- | 7-(N)—N'-methylpiperazine |
| | 28 | iso-propyl | Ph- | 7-(N)—N'-dimethylpiperazinium, I$^-$ |
| | 29 | iso-propyl | Ph- | 7-NH—CBZ |
| | 30 | iso-propyl | Ph- | 7-NHC(O)C$_5$H$_{11}$ |
| | 31 | iso-propyl | Ph- | 7-NHC(O)CH$_2$Br |
| | 32 | iso-propyl | Ph- | 7-NH—C(NH)NH$_2$ |
| | 33 | iso-propyl | Ph- | 7-(2)-thiophene |
| | 34 | iso-propyl | Ph- | 8-methyl |
| | 35 | iso-propyl | Ph- | 8-ethyl |
| | 36 | iso-propyl | Ph- | 8-iso-propyl |
| | 37 | iso-propyl | Ph- | 8-tert-butyl |
| | 38 | iso-propyl | Ph- | 8-OH |
| | 39 | iso-propyl | Ph- | 8-OCH$_3$ |
| | 40 | iso-propyl | Ph- | 8-O(iso-propyl) |
| | 41 | iso-propyl | Ph- | 8-SCH$_3$ |
| | 42 | iso-propyl | Ph- | 8-SOCH$_3$ |
| | 43 | iso-propyl | Ph- | 8-SO$_2$CH$_3$ |
| | 44 | iso-propyl | Ph- | 8-SCH$_2$CH$_3$ |
| | 45 | iso-propyl | Ph- | 8-NH$_2$ |
| | 46 | iso-propyl | Ph- | 8-NHOH |
| | 47 | iso-propyl | Ph- | 8-NHCH$_3$ |
| | 48 | iso-propyl | Ph- | 8-N(CH$_3$)$_2$ |
| | 49 | iso-propyl | Ph- | 8-N$^+$(CH$_3$)$_3$, I$^-$ |
| | 50 | iso-propyl | Ph- | 8-NHC(=O)CH$_3$ |
| | 51 | iso-propyl | Ph- | 8-N(CH$_2$CH$_3$)$_2$ |
| | 52 | iso-propyl | Ph- | 8-NMeCH$_2$CO$_2$H |
| | 53 | iso-propyl | Ph- | 8-N$^+$(Me)$_2$CH$_2$CO$_2$H, I$^-$ |
| | 54 | iso-propyl | Ph- | 8-(N)-morpholine |
| | 55 | iso-propyl | Ph- | 8-(N)-azetidine |
| | 56 | iso-propyl | Ph- | 8-(N)—N-methylazetidinium, I$^-$ |
| | 57 | iso-propyl | Ph- | 8-(N)-pyrrolidine |
| | 58 | iso-propyl | Ph- | 8-(N)—N-methyl-pyrrolidinium, I$^-$ |
| | 59 | iso-propyl | Ph- | 8-(N)—N-methyl-morpholinium, I$^-$ |
| | 60 | iso-propyl | Ph- | 8-(N)—N'-methylpiperazine |
| | 61 | iso-propyl | Ph- | 8-(N)—N'-dimethylpiperazinium, I$^-$ |
| | 62 | iso-propyl | Ph- | 8-NH—CBZ |
| | 63 | iso-propyl | Ph- | 8-NHC(O)C$_5$H$_{11}$ |
| | 64 | iso-propyl | Ph- | 8-NHC(O)CH$_2$Br |
| | 65 | iso-propyl | Ph- | 8-NH—C(NH)NH$_2$ |
| | 66 | iso-propyl | Ph- | 8-(2)-thiophene |
| | 67 | iso-propyl | Ph- | 9-methyl |
| | 68 | iso-propyl | Ph- | 9-ethyl |
| | 69 | iso-propyl | Ph- | 9-iso-propyl |
| | 70 | iso-propyl | Ph- | 9-tert-butyl |

TABLE 5-continued

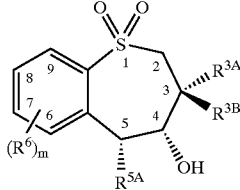

| Prefix (FFF.xxx.) | Cpd # yyy) | $R^{3A}=R^{3B}$ | $R^{5A}$ | $(R^6)_m$ |
|---|---|---|---|---|
| | 71 | iso-propyl | Ph- | 9-OH |
| | 72 | iso-propyl | Ph- | 9-OCH$_3$ |
| | 73 | isopropyl | Ph- | 9-O(iso-propyl) |
| | 74 | iso-propyl | Ph- | 9-SCH$_3$ |
| | 75 | iso-propyl | Ph- | 9-SOCH$_3$ |
| | 76 | iso-propyl | Ph- | 9-SO$_2$CH$_3$ |
| | 77 | iso-propyl | Ph- | 9-SCH$_2$CH$_3$ |
| | 78 | iso-propyl | Ph- | 9-NH$_2$ |
| | 79 | iso-propyl | Ph- | 9-NHOH |
| | 80 | iso-propyl | Ph- | 9-NHCH$_3$ |
| | 81 | iso-propyl | Ph- | 9-N(CH$_3$)$_2$ |
| | 82 | iso-propyl | Ph- | 9-N$^+$(CH$_3$)$_3$, I$^-$ |
| | 83 | iso-propyl | Ph- | 9-NHC(=O)CH$_3$ |
| | 84 | iso-propyl | Ph- | 9-N(CH$_2$CH$_3$)$_2$ |
| | 85 | iso-propyl | Ph- | 9-NMeCH$_2$CO$_2$H |
| | 86 | iso-propyl | Ph- | 9-N$^+$(Me)$_2$CH$_2$CO$_2$H, I$^-$ |
| | 87 | iso-propyl | Ph- | 9-(N)-morpholine |
| | 88 | iso-propyl | Ph- | 9-(N)-azetidine |
| | 89 | iso-propyl | Ph- | 9-(N)—N-methylazetidinium, I$^-$ |
| | 90 | iso-propyl | Ph- | 9-(N)-pyrrolidine |
| | 91 | iso-propyl | Ph- | 9-(N)—N-methyl-pyrrolidinium, I$^-$ |
| | 92 | iso-propyl | Ph- | 9-(N)—N-methyl-morpholinium, I$^-$ |
| | 93 | iso-propyl | Ph- | 9-(N)—N'-methylpiperazine |
| | 93 | iso-propyl | Ph- | 9-(N)—N'-dimethylpiperazinium, I$^-$ |
| | 95 | iso-propyl | Ph- | 9-NH—CBZ |
| | 96 | iso-propyl | Ph- | 9-NHC(O)C$_5$H$_{11}$ |
| | 97 | iso-propyl | Ph- | 9-NHC(O)CH$_2$Br |
| | 98 | iso-propyl | Ph- | 9-NH—C(NH)NH$_2$ |
| | 99 | iso-propyl | Ph- | 9-(2)-thiophene |
| | 100 | iso-propyl | Ph- | 7-OCH$_3$, 8-OCH$_3$ |
| | 101 | iso-propyl | Ph- | 7-SCH$_3$, 8-OCH$_3$ |
| | 102 | iso-propyl | Ph- | 7-SCH$_3$, 8-SCH$_3$ |
| | 103 | iso-propyl | Ph- | 6-OCH$_3$, 7-OCH$_3$, 8-OCH$_3$ |
| F101.007 | 01 | iso-butyl | Ph- | 7-methyl |
| | 02 | iso-butyl | Ph- | 7-ethyl |
| | 03 | iso-butyl | Ph- | 7-iso-propyl |
| | 04 | iso-butyl | Ph- | 7-tert-butyl |
| | 05 | iso-butyl | Ph- | 7-OH |
| | 06 | iso-butyl | Ph- | 7-OCH$_3$ |
| | 07 | iso-butyl | Ph- | 7-O(iso-propyl) |
| | 08 | iso-butyl | Ph- | 7-SCH$_3$ |
| | 09 | iso-butyl | Ph- | 7-SOCH$_3$ |
| | 10 | iso-butyl | Ph- | 7-SO$_2$CH$_3$ |
| | 11 | iso-butyl | Ph- | 7-SCH$_2$CH$_3$ |
| | 12 | iso-butyl | Ph- | 7-NH$_2$ |
| | 13 | iso-butyl | Ph- | 7-NHOH |
| | 14 | iso-butyl | Ph- | 7-NHCH$_3$ |
| | 15 | iso-butyl | Ph- | 7-N(CH$_3$)$_2$ |
| | 16 | iso-butyl | Ph- | 7-N$^+$(CH$_3$)$_3$, I$^-$ |
| | 17 | iso-butyl | Ph- | 7-NHC(=O)CH$_3$ |
| | 18 | iso-butyl | Ph- | 7-N(CH$_2$CH$_3$)$_2$ |
| | 19 | iso-butyl | Ph- | 7-NMeCH$_2$CO$_2$H |
| | 20 | iso-butyl | Ph- | 7-N$^+$(Me)$_2$CH$_2$CO$_2$H, I$^-$ |
| | 21 | iso-butyl | Ph- | 7-(N)-morpholine |
| | 22 | iso-butyl | Ph- | 7-(N)-azetidine |
| | 23 | iso-butyl | Ph- | 7-(N)—N-methylazetidinium, I$^-$ |
| | 24 | iso-butyl | Ph- | 7-(N)-pyrrolidine |
| | 25 | iso-butyl | Ph- | 7-(N)—N-methyl-pyrrolidinium, I$^-$ |
| | 26 | iso-butyl | Ph- | 7-(N)—N-methyl-morpholinium, I$^-$ |
| | 27 | iso-butyl | Ph- | 7-(N)—N'-methylpiperazine |
| | 28 | iso-butyl | Ph- | 7-(N)—N'-dimethylpiperazinium, I$^-$ |
| | 29 | iso-butyl | Ph- | 7-NH—CBZ |
| | 30 | iso-butyl | Ph- | 7-NHC(O)C$_5$H$_{11}$ |
| | 31 | iso-butyl | Ph- | 7-NHC(O)CH$_2$Br |
| | 32 | iso-butyl | Ph- | 7-NH—C(NH)NH$_2$ |

TABLE 5-continued

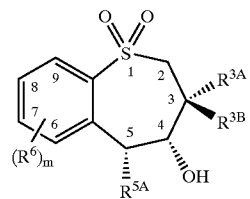

| Prefix (FFF.xxx. | Cpd # yyy) | $R^{3A}=R^{3B}$ | $R^{5A}$ | $(R^6)_m$ |
|---|---|---|---|---|
| | 33 | iso-butyl | Ph- | 7-(2)-thiophene |
| | 34 | iso-butyl | Ph- | 8-methyl |
| | 35 | iso-butyl | Ph- | 8-ethyl |
| | 36 | iso-butyl | Ph- | 8-iso-propyl |
| | 37 | iso-butyl | Ph- | 8-tert-butyl |
| | 38 | iso-butyl | Ph- | 8-OH |
| | 39 | iso-butyl | Ph- | 8-OCH$_3$ |
| | 40 | iso-butyl | Ph- | 8-O(iso-propyl) |
| | 41 | iso-butyl | Ph- | 8-SCH$_3$ |
| | 42 | iso-butyl | Ph- | 8-SOCH$_3$ |
| | 43 | iso-butyl | Ph- | 8-SO$_2$CH$_3$ |
| | 44 | iso-butyl | Ph- | 8-SCH$_2$CH$_3$ |
| | 45 | iso-butyl | Ph- | 8-NH$_2$ |
| | 46 | iso-butyl | Ph- | 8-NHOH |
| | 47 | iso-butyl | Ph- | 8-NHCH$_3$ |
| | 48 | iso-butyl | Ph- | 8-N(CH$_3$)$_2$ |
| | 49 | iso-butyl | Ph- | 8-N$^+$(CH$_3$)$_3$, I$^-$ |
| | 50 | iso-butyl | Ph- | 8-NHC(=O)CH$_3$ |
| | 51 | iso-butyl | Ph- | 8-N(CH$_2$CH$_3$)$_2$ |
| | 52 | iso-butyl | Ph- | 8-NMeCH$_2$CO$_2$H |
| | 53 | iso-butyl | Ph- | 8-N$^+$(Me)$_2$CH$_2$CO$_2$H, I$^-$ |
| | 54 | iso-butyl | Ph- | 8-(N)-morpholine |
| | 55 | iso-butyl | Ph- | 8-(N)-azetidine |
| | 56 | iso-butyl | Ph- | 8-(N)—N-methylazetidinium, I$^-$ |
| | 57 | iso-butyl | Ph- | 8-(N)-pyrrolidine |
| | 58 | iso-butyl | Ph- | 8-(N)—N-methyl-pyrrolidinium, I$^-$ |
| | 59 | iso-butyl | Ph- | 8-(N)—N-methyl-morpholinium, I$^-$ |
| | 60 | iso-butyl | Ph- | 8-(N)—N'-methylpiperazine |
| | 61 | iso-butyl | Ph- | 8-(N)—N'-dimethylpiperazinium, I$^-$ |
| | 62 | iso-butyl | Ph- | 8-NH—CBZ |
| | 63 | iso-butyl | Ph- | 8-NHC(O)C$_5$H$_{11}$ |
| | 64 | iso-butyl | Ph- | 8-NHC(O)CH$_2$Br |
| | 65 | iso-butyl | Ph- | 8-NH—C(NH)NH$_2$ |
| | 66 | iso-butyl | Ph- | 8-(2)-thiophene |
| | 67 | iso-butyl | Ph- | 9-methyl |
| | 68 | iso-butyl | Ph- | 9-ethyl |
| | 69 | iso-butyl | Ph- | 9-iso-propyl |
| | 70 | iso-butyl | Ph- | 9-tert-butyl |
| | 71 | iso-butyl | Ph- | 9-OH |
| | 72 | iso-butyl | Ph- | 9-OCH$_3$ |
| | 73 | iso-butyl | Ph- | 9-O(iso-propyl) |
| | 74 | iso-butyl | Ph- | 9-SCH$_3$ |
| | 75 | iso-butyl | Ph- | 9-SOCH$_3$ |
| | 76 | iso-butyl | Ph- | 9-SO$_2$CH$_3$ |
| | 77 | iso-butyl | Ph- | 9-SCH$_2$CH$_3$ |
| | 78 | iso-butyl | Ph- | 9-NH$_2$ |
| | 79 | iso-butyl | Ph- | 9-NHOH |
| | 80 | iso-butyl | Ph- | 9-NHCH$_3$ |
| | 81 | iso-butyl | Ph- | 9-N(CH$_3$)$_2$ |
| | 82 | iso-butyl | Ph- | 9-(N$^+$(CH$_3$)$_3$, I$^-$ |
| | 83 | iso-butyl | Ph- | 9-NHC(=O)CH$_3$ |
| | 84 | iso-butyl | Ph- | 9-N(CH$_2$CH$_3$)$_2$ |
| | 85 | iso-butyl | Ph- | 9-NMeCH$_2$CO$_2$H |
| | 86 | iso-butyl | Ph- | 9-N$^+$(Me)$_2$CH$_2$CO$_2$H, I$^-$ |
| | 87 | iso-butyl | Ph- | 9-(N)-morpholine |
| | 88 | iso-butyl | Ph- | 9-(N)-azetidine |
| | 89 | iso-butyl | Ph- | 9-(N)—N-methylazetidinium, I$^-$ |
| | 90 | iso-butyl | Ph- | 9-(N)-pyrrolidine |
| | 91 | iso-butyl | Ph- | 9-(N)—N-methyl-pyrrolidinium, I$^-$ |
| | 92 | iso-butyl | Ph- | 9-(N)—N-methyl-morpholinium, I$^-$ |
| | 93 | iso-butyl | Ph- | 9-(N)—N'-methylpiperazine |
| | 93 | iso-butyl | Ph- | 9-(N)—N'-dimethylpiperazinium, I$^-$ |
| | 95 | iso-butyl | Ph- | 9-NH—CBZ |
| | 96 | iso-butyl | Ph- | 9-NHC(O)C$_5$H$_{11}$ |
| | 97 | iso-butyl | Ph- | 9-NHC(O)CH$_2$Br |

TABLE 5-continued

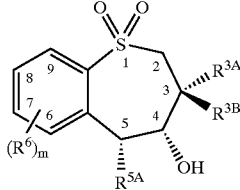

| Prefix (FFF.xxx. | Cpd # yyy) | $R^{3A}=R^{3B}$ | $R^{5A}$ | $(R^6)_m$ |
|---|---|---|---|---|
| | 98 | iso-butyl | Ph- | 9-NH—C(NH)NH$_2$ |
| | 99 | iso-butyl | Ph- | 9-(2)-thiophene |
| | 100 | iso-butyl | Ph- | 7-OCH$_3$, 8-OCH$_3$ |
| | 101 | iso-butyl | Ph- | 7-SCH$_3$, 8-OCH$_3$ |
| | 102 | iso-butyl | Ph- | 7-SCH$_3$, 8-SCH$_3$ |
| | 103 | iso-butyl | Ph- | 6-OCH$_3$, 7-OCH$_3$, 8-OCH$_3$ |
| F101.008 | 01 | iso-pentyl | Ph- | 7-methyl |
| | 02 | iso-pentyl | Ph- | 7-ethyl |
| | 03 | iso-pentyl | Ph- | 7-iso-propyl |
| | 04 | iso-pentyl | Ph- | 7-tert-butyl |
| | 05 | iso-pentyl | Ph- | 7-OH |
| | 06 | iso-pentyl | Ph- | 7-OCH$_3$ |
| | 07 | iso-pentyl | Ph- | 7-O(iso-propyl) |
| | 08 | iso-pentyl | Ph- | 7-SCH$_3$ |
| | 09 | iso-pentyl | Ph- | 7-SOCH$_3$ |
| | 10 | iso-pentyl | Ph- | 7-SO$_2$CH$_3$ |
| | 11 | iso-pentyl | Ph- | 7-SCH$_2$CH$_3$ |
| | 12 | iso-pentyl | Ph- | 7-NH$_2$ |
| | 13 | iso-pentyl | Ph- | 7-NHOH |
| | 14 | iso-pentyl | Ph- | 7-NHCH$_3$ |
| | 15 | iso-pentyl | Ph- | 7-N(CH$_3$)$_2$ |
| | 16 | iso-pentyl | Ph- | 7-N$^+$(CH$_3$)$_3$, I$^-$ |
| | 17 | iso-pentyl | Ph- | 7-NHC(=O)CH$_3$ |
| | 18 | iso-pentyl | Ph- | 7-N(CH$_2$CH$_3$)$_2$ |
| | 19 | iso-pentyl | Ph- | 7-NMeCH$_2$CO$_2$H |
| | 20 | iso-pentyl | Ph- | 7-N$^+$(Me)$_2$CH$_2$CO$_2$H, I$^-$ |
| | 21 | iso-pentyl | Ph- | 7-(N)-morpholine |
| | 22 | iso-pentyl | Ph- | 7-(N)-azetidine |
| | 23 | iso-pentyl | Ph- | 7-(N)—N-methylazetidinium, I$^-$ |
| | 24 | iso-pentyl | Ph- | 7-(N)-pyrrolidine |
| | 25 | iso-pentyl | Ph- | 7-(N)—N-methyl-pyrrolidinium, I$^-$ |
| | 26 | iso-pentyl | Ph- | 7-(N)—N-methyl-morpholinium, I$^-$ |
| | 27 | iso-pentyl | Ph- | 7-(N)—N'-methylpiperazine |
| | 28 | iso-pentyl | Ph- | 7-(N)—N'-dimethylpiperazinium, I$^-$ |
| | 29 | iso-pentyl | Ph- | 7-NH—CBZ |
| | 30 | iso-pentyl | Ph- | 7-NHC(O)C$_5$H$_{11}$ |
| | 31 | iso-pentyl | Ph- | 7-NHC(O)CH$_2$Br |
| | 32 | iso-pentyl | Ph- | 7-NH—C(NH)NH$_2$ |
| | 33 | iso-pentyl | Ph- | 7-(2)-thiophene |
| | 34 | iso-pentyl | Ph- | 8-methyl |
| | 35 | iso-pentyl | Ph- | 8-ethyl |
| | 36 | iso-pentyl | Ph- | 8-iso-propyl |
| | 37 | iso-pentyl | Ph- | 8-tert-butyl |
| | 38 | iso-pentyl | Ph- | 8-OH |
| | 39 | iso-pentyl | Ph- | 8-OCH$_3$ |
| | 40 | iso-pentyl | Ph- | 8-O(iso-propyl) |
| | 41 | iso-pentyl | Ph- | 8-SCH$_3$ |
| | 42 | iso-pentyl | Ph- | 8-SOCH$_3$ |
| | 43 | iso-pentyl | Ph- | 8-SO$_2$CH$_3$ |
| | 44 | iso-pentyl | Ph- | 8-SCH$_2$CH$_3$ |
| | 45 | iso-pentyl | Ph- | 8-NH$_2$ |
| | 46 | iso-pentyl | Ph- | 8-NHOH |
| | 47 | iso-pentyl | Ph- | 8-NHCH$_3$ |
| | 48 | iso-pentyl | Ph- | 8-N(CH$_3$)$_2$ |
| | 49 | iso-pentyl | Ph- | 8-N$^+$(CH$_3$)$_3$, I$^-$ |
| | 50 | iso-pentyl | Ph- | 8-NHC(=O)CH$_3$ |
| | 51 | iso-pentyl | Ph- | 8-N(CH$_2$CH$_3$)$_2$ |
| | 52 | iso-pentyl | Ph- | 8-NMeCH$_2$CO$_2$H |
| | 53 | iso-pentyl | Ph- | 8-N$^+$(Me)$_2$CH$_2$CO$_2$H, I$^-$ |
| | 54 | iso-pentyl | Ph- | 8-(N)-morpholine |
| | 55 | iso-pentyl | Ph- | 8-(N)-azetidine |
| | 56 | iso-pentyl | Ph- | 8-(N)—N-methylazetidinium, I$^-$ |
| | 57 | iso-pentyl | Ph- | 8-(N)-pyrrolidine |
| | 58 | iso-pentyl | Ph- | 8-(N)—N-methyl-pyrrolidinium, I$^-$ |
| | 59 | iso-pentyl | Ph- | 8-(N)—N-methyl-morpholinium, I$^-$ |

TABLE 5-continued

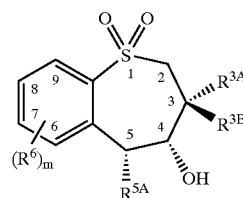

| Prefix (FFF.xxx) | Cpd # yyy | $R^{3A}=R^{3B}$ | $R^{5A}$ | $(R^6)_m$ |
|---|---|---|---|---|
| | 60 | iso-pentyl | Ph- | 8-(N)—N'-methylpiperazine |
| | 61 | iso-pentyl | Ph- | 8-(N)—N'-dimethylpiperazinium, I$^-$ |
| | 62 | iso-pentyl | Ph- | 8-NH—CBZ |
| | 63 | iso-pentyl | Ph- | 8-NHC(O)C$_5$H$_{11}$ |
| | 64 | iso-pentyl | Ph- | 8-NHC(O)CH$_2$Br |
| | 65 | iso-pentyl | Ph- | 8-NH—C(NH)NH$_2$ |
| | 66 | iso-pentyl | Ph- | 8-(2)-thiophene |
| | 67 | iso-pentyl | Ph- | 9-methyl |
| | 68 | iso-pentyl | Ph- | 9-ethyl |
| | 69 | iso-pentyl | Ph- | 9-iso-propyl |
| | 70 | iso-pentyl | Ph- | 9-tert-butyl |
| | 71 | iso-pentyl | Ph- | 9-OH |
| | 72 | iso-pentyl | Ph- | 9-OCH$_3$ |
| | 73 | iso-pentyl | Ph- | 9-O(iso-propyl) |
| | 74 | iso-pentyl | Ph- | 9-SCH$_3$ |
| | 75 | iso-pentyl | Ph- | 9-SOCH$_3$ |
| | 76 | iso-pentyl | Ph- | 9-SO$_2$CH$_3$ |
| | 77 | iso-pentyl | Ph- | 9-SCH$_2$CH$_3$ |
| | 78 | iso-pentyl | Ph- | 9-NH$_2$ |
| | 79 | iso-pentyl | Ph- | 9-NHOH |
| | 80 | iso-pentyl | Ph- | 9-NHCH$_3$ |
| | 81 | iso-pentyl | Ph- | 9-N(CH$_3$)$_2$ |
| | 82 | iso-pentyl | Ph- | 9-N$^+$(CH$_3$)$_3$, I$^-$ |
| | 83 | iso-pentyl | Ph- | 9-NHC(=O)CH$_3$ |
| | 84 | iso-pentyl | Ph- | 9-N(CH$_2$CH$_3$)$_2$ |
| | 85 | iso-pentyl | Ph- | 9-NMeCH$_2$CO$_2$H |
| | 86 | iso-pentyl | Ph- | 9-N$^+$(Me)$_2$CH$_2$CO$_2$H, I$^-$ |
| | 87 | iso-pentyl | Ph- | 9-(N)-morpholine |
| | 88 | iso-pentyl | Ph- | 9-(N)-azetidine |
| | 89 | iso-pentyl | Ph- | 9-(N)—N-methylazetidinium, I$^-$ |
| | 90 | iso-pentyl | Ph- | 9-(N)-pyrrolidine |
| | 91 | iso-pentyl | Ph- | 9-(N)—N-methyl-pyrrolidinium, I$^-$ |
| | 92 | iso-pentyl | Ph- | 9-(N)—N-methyl-morpholinium, I$^-$ |
| | 93 | iso-pentyl | Ph- | 9-(N)—N'-methylpiperazine |
| | 93 | iso-pentyl | Ph- | 9-(N)—N'-dimethylpiperazinium, I$^-$ |
| | 95 | iso-pentyl | Ph- | 9-NH—CBZ |
| | 96 | iso-pentyl | Ph- | 9-NHC(O)C$_5$H$_{11}$ |
| | 97 | iso-pentyl | Ph- | 9-NHC(O)CH$_2$Br |
| | 98 | iso-pentyl | Ph- | 9-NH—C(NH)NH$_2$ |
| | 99 | iso-pentyl | Ph- | 9-(2)-thiophene |
| | 100 | iso-pentyl | Ph- | 7-OCH$_3$, 8-OCH$_3$ |
| | 101 | iso-pentyl | Ph- | 7-SCH$_3$, 8-OCH$_3$ |
| | 102 | iso-pentyl | Ph- | 7-SCH$_3$, 8-SCH$_3$ |
| | 103 | iso-pentyl | Ph- | 6-OCH$_3$, 7-OCH$_3$, 8-OCH$_3$ |
| F101.009 | 01 | CH$_2$C(=O)C$_2$H$_5$ | Ph- | 7-methyl |
| | 02 | CH$_2$C(=O)C$_2$H$_5$ | Ph- | 7-ethyl |
| | 03 | CH$_2$C(=O)C$_2$H$_5$ | Ph- | 7-iso-propyl |
| | 04 | CH$_2$C(=O)C$_2$H$_5$ | Ph- | 7-tert-butyl |
| | 05 | CH$_2$C(=O)C$_2$H$_5$ | Ph- | 7-OH |
| | 06 | CH$_2$C(=O)C$_2$H$_5$ | Ph- | 7-OCH$_3$ |
| | 07 | CH$_2$C(=O)C$_2$H$_5$ | Ph- | 7-O(iso-propyl) |
| | 08 | CH$_2$C(=O)C$_2$H$_5$ | Ph- | 7-SCH$_3$ |
| | 09 | CH$_2$C(=O)C$_2$H$_5$ | Ph- | 7-SOCH$_3$ |
| | 10 | CH$_2$C(=O)C$_2$H$_5$ | Ph- | 7-SO$_2$CH$_3$ |
| | 11 | CH$_2$C(=O)C$_2$H$_5$ | Ph- | 7-SCH$_2$CH$_3$ |
| | 12 | CH$_2$C(=O)C$_2$H$_5$ | Ph- | 7-NH$_2$ |
| | 13 | CH$_2$C(=O)C$_2$H$_5$ | Ph- | 7-NHOH |
| | 14 | CH$_2$C(=O)C$_2$H$_5$ | Ph- | 7-NHCH$_3$ |
| | 15 | CH$_2$C(=O)C$_2$H$_5$ | Ph- | 7-N(CH$_3$)$_2$ |
| | 16 | CH$_2$C(=O)C$_2$H$_5$ | Ph- | 7-N$^+$(CH$_3$)$_3$, I$^-$ |
| | 17 | CH$_2$C(=O)C$_2$H$_5$ | Ph- | 7-NHC(=O)CH$_3$ |
| | 18 | CH$_2$C(=O)C$_2$H$_5$ | Ph- | 7-N(CH$_2$CH$_3$)$_2$ |
| | 19 | CH$_2$C(=O)C$_2$H$_5$ | Ph- | 7-NMeCH$_2$CO$_2$H |
| | 20 | CH$_2$C(=O)C$_2$H$_5$ | Ph- | 7-N$^+$(Me)$_2$CH$_2$CO$_2$H, I$^-$ |
| | 21 | CH$_2$C(=O)C$_2$H$_5$ | Ph- | 7-(N)-morpholine |

TABLE 5-continued

[Structure: benzothiepine sulfone with positions labeled 1-9, S at 1 with two =O, positions 2,3 with R³ᴬ and R³ᴮ, position 4 with OH, position 5 with R⁵ᴬ, and (R⁶)ₘ on the aromatic ring]

| Prefix (FFF.xxx. | Cpd # yyy) | R³ᴬ=R³ᴮ | R⁵ᴬ | (R⁶)ₘ |
|---|---|---|---|---|
| | 22 | CH₂C(=O)C₂H₅ | Ph- | 7-(N)-azetidine |
| | 23 | CH₂C(=O)C₂H₅ | Ph- | 7-(N)—N-methylazetidinium, I⁻ |
| | 24 | CH₂C(=O)C₂H₅ | Ph- | 7-(N)-pyrrolidine |
| | 25 | CH₂C(=O)C₂H₅ | Ph- | 7-(N)—N-methyl-pyrrolidinium, I⁻ |
| | 26 | CH₂C(=O)C₂H₅ | Ph- | 7-(N)—N-methyl-morpholinium, I⁻ |
| | 27 | CH₂C(=O)C₂H₅ | Ph- | 7-(N)—N'-methylpiperazine |
| | 28 | CH₂C(=O)C₂H₅ | Ph- | 7-(N)—N'-dimethylpiperazinium, I⁻ |
| | 29 | CH₂C(=O)C₂H₅ | Ph- | 7-NH—CBZ |
| | 30 | CH₂C(=O)C₂H₅ | Ph- | 7-NHC(O)C₅H₁₁ |
| | 31 | CH₂C(=O)C₂H₅ | Ph- | 7-NHC(O)CH₂Br |
| | 32 | CH₂C(=O)C₂H₅ | Ph- | 7-NHC(NH)NH₂ |
| | 33 | CH₂C(=O)C₂H₅ | Ph- | 7-(2)-thiophene |
| | 34 | CH₂C(=O)C₂H₅ | Ph- | 8-methyl |
| | 35 | CH₂C(=O)C₂H₅ | Ph- | 8-ethyl |
| | 36 | CH₂C(=O)C₂H₅ | Ph- | 8-iso-propyl |
| | 37 | CH₂C(=O)C₂H₅ | Ph- | 8-tert-butyl |
| | 38 | CH₂C(=O)C₂H₅ | Ph- | 8-OH |
| | 39 | CH₂C(=O)C₂H₅ | Ph- | 8-OCH₃ |
| | 40 | CH₂C(=O)C₂H₅ | Ph- | 8-O(iso-propyl) |
| | 41 | CH₂C(=O)C₂H₅ | Ph- | 8-SCH₃ |
| | 42 | CH₂C(=O)C₂H₅ | Ph- | 8-SOCH₃ |
| | 43 | CH₂C(=O)C₂H₅ | Ph- | 8-SO₂CH₃ |
| | 44 | CH₂C(=O)C₂H₅ | Ph- | 8-SCH₂CH₃ |
| | 45 | CH₂C(=O)C₂H₅ | Ph- | 8-NH₂ |
| | 46 | CH₂C(=O)C₂H₅ | Ph- | 8-NHOH |
| | 47 | CH₂C(=O)C₂H₅ | Ph- | 8-NHCH₃ |
| | 48 | CH₂C(=O)C₂H₅ | Ph- | 8-N(CH₃)₂ |
| | 49 | CH₂C(=O)C₂H₅ | Ph- | 8-N⁺(CH₃)₃, I⁻ |
| | 50 | CH₂C(=O)C₂H₅ | Ph- | 8-NHC(=O)CH₃ |
| | 51 | CH₂C(=O)C₂H₅ | Ph- | 8-N(CH₂CH₃)₂ |
| | 52 | CH₂C(=O)C₂H₅ | Ph- | 8-NMeCH₂CO₂H |
| | 53 | CH₂C(=O)C₂H₅ | Ph- | 8-N⁺(Me)₂CH₂CO₂H, I⁻ |
| | 54 | CH₂C(=O)C₂H₅ | Ph- | 8-(N)-morpholine |
| | 55 | CH₂C(=O)C₂H₅ | Ph- | 8-(N)-azetidine |
| | 56 | CH₂C(=O)C₂H₅ | Ph- | 8-(N)—N-methylazetidinium, I⁻ |
| | 57 | CH₂C(=O)C₂H₅ | Ph- | 8-(N)-pyrrolidine |
| | 58 | CH₂C(=O)C₂H₅ | Ph- | 8-(N)—N-methyl-pyrrolidinium, I⁻ |
| | 59 | CH₂C(=O)C₂H₅ | Ph- | 8-(N)—N-methyl-morpholinium, I⁻ |
| | 60 | CH₂C(=O)C₂H₅ | Ph- | 8-(N)—N'-methylpiperazine |
| | 61 | CH₂C(=O)C₂H₅ | Ph- | 8-(N)—N'-dimethylpiperazinium, I⁻ |
| | 62 | CH₂C(=O)C₂H₅ | Ph- | 8-NH—CBZ |
| | 63 | CH₂C(=O)C₂H₅ | Ph- | 8-NHC(O)C₅H₁₁ |
| | 64 | CH₂C(=O)C₂H₅ | Ph- | 8-NHC(O)CH₂Br |
| | 65 | CH₂C(=O)C₂H₅ | Ph- | 8-NH—C(NH)NH₂ |
| | 66 | CH₂C(=O)C₂H₅ | Ph- | 8-(2)-thiophene |
| | 67 | CH₂C(=O)C₂H₅ | Ph- | 9-methyl |
| | 68 | CH₂C(=O)C₂H₅ | Ph- | 9-ethyl |
| | 69 | CH₂C(=O)C₂H₅ | Ph- | 9-iso-propyl |
| | 70 | CH₂C(=O)C₂H₅ | Ph- | 9-tert-butyl |
| | 71 | CH₂C(=O)C₂H₅ | Ph- | 9-OH |
| | 72 | CH₂C(=O)C₂H₅ | Ph- | 9-OCH₃ |
| | 73 | CH₂C(=O)C₂H₅ | Ph- | 9-O(iso-propyl) |
| | 74 | CH₂C(=O)C₂H₅ | Ph- | 9-SCH₃ |
| | 75 | CH₂C(=O)C₂H₅ | Ph- | 9-SOCH₃ |
| | 76 | CH₂C(=O)C₂H₅ | Ph- | 9-SO₂CH₃ |
| | 77 | CH₂C(=O)C₂H₅ | Ph- | 9-SCH₂CH₃ |
| | 78 | CH₂C(=O)C₂H₅ | Ph- | 9-NH₂ |
| | 79 | CH₂C(=O)C₂H₅ | Ph- | 9-NHOH |
| | 80 | CH₂C(=O)C₂H₅ | Ph- | 9-NHCH₃ |
| | 81 | CH₂C(=O)C₂H₅ | Ph- | 9-N(CH₃)₂ |
| | 82 | CH₂C(=O)C₂H₅ | Ph- | 9-N⁺(CH₃)₃, I⁻ |
| | 83 | CH₂C(=O)C₂H₅ | Ph- | 9-NHC(=O)CH₃ |
| | 84 | CH₂C(=O)C₂H₅ | Ph- | 9-N(CH₂CH₃)₂ |
| | 85 | CH₂C(=O)C₂H₅ | Ph- | 9-NMeCH₂CO₂H |
| | 86 | CH₂C(=O)C₂H₅ | Ph- | 9-N⁺(Me)₂CH₂CO₂H, I⁻ |

TABLE 5-continued

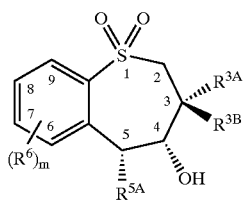

| Prefix (FFF.xxx) | Cpd # yyy | R³ᴬ=R³ᴮ | R⁵ᴬ | (R⁶)ₘ |
|---|---|---|---|---|
| | 87 | CH₂C(=O)C₂H₅ | Ph- | 9-(N)-morpholine |
| | 88 | CH₂C(=O)C₂H₅ | Ph- | 9-(N)-azetidine |
| | 89 | CH₂C(=O)C₂H₅ | Ph- | 9-(N)—N-methylazetidinium, I⁻ |
| | 90 | CH₂C(=O)C₂H₅ | Ph- | 9-(N)-pyrrolidine |
| | 91 | CH₂C(=O)C₂H₅ | Ph- | 9-(N)—N-methyl-pyrrolidinium, I⁻ |
| | 92 | CH₂C(=O)C₂H₅ | Ph- | 9-(N)—N-methyl-morpholinium, I⁻ |
| | 93 | CH₂C(=O)C₂H₅ | Ph- | 9-(N)—N'-methylpiperazine |
| | 93 | CH₂C(=O)C₂H₅ | Ph- | 9-(N)—N'-dimethylpiperazinium, I⁻ |
| | 95 | CH₂C(=O)C₂H₅ | Ph- | 9-NH—CBZ |
| | 96 | CH₂C(=O)C₂H₅ | Ph- | 9-NHC(O)C₅H₁₁ |
| | 97 | CH₂C(=O)C₂H₅ | Ph- | 9-NHC(O)CH₂Br |
| | 98 | CH₂C(=O)C₂H₅ | Ph- | 9-NH—C(NH)NH₂ |
| | 99 | CH₂C(=O)C₂H₅ | Ph- | 9-(2)-thiophene |
| | 100 | CH₂C(=O)C₂H₅ | Ph- | 7-OCH₃, 8-OCH₃ |
| | 101 | CH₂C(=O)C₂H₅ | Ph- | 7-SCH₃, 8-OCH₃ |
| | 102 | CH₂C(=O)C₂H₅ | Ph- | 7-SCH₃, 8-SCH₃ |
| | 103 | CH₂C(=O)C₂H₅ | Ph- | 6-OCH₃, 7-OCH₃, 8-OCH₃ |
| F101.010 | 01 | CH₂OC₂H₅ | Ph- | 7-methyl |
| | 02 | CH₂OC₂H₅ | Ph- | 7-ethyl |
| | 03 | CH₂OC₂H₅ | Ph- | 7-iso-propyl |
| | 04 | CH₂OC₂H₅ | Ph- | 7-tert-butyl |
| | 05 | CH₂OC₂H₅ | Ph- | 7-OH |
| | 06 | CH₂OC₂H₅ | Ph- | 7-OCH₃ |
| | 07 | CH₂OC₂H₅ | Ph- | 7-O(iso-propyl) |
| | 08 | CH₂OC₂H₅ | Ph- | 7-SCH₃ |
| | 09 | CH₂OC₂H₅ | Ph- | 7-SOCH₃ |
| | 10 | CH₂OC₂H₅ | Ph- | 7-SO₂CH₃ |
| | 11 | CH₂OC₂H₅ | Ph- | 7-SCH₂CH₃ |
| | 12 | CH₂OC₂H₅ | Ph- | 7-NH₂ |
| | 13 | CH₂OC₂H₅ | Ph- | 7-NHOH |
| | 14 | CH₂OC₂H₅ | Ph- | 7-NHCH₃ |
| | 15 | CH₂OC₂H₅ | Ph- | 7-N(CH₃)₂ |
| | 16 | CH₂OC₂H₅ | Ph- | 7-N⁺(CH₃)₃, I⁻ |
| | 17 | CH₂OC₂H₅ | Ph- | 7-NHC(=O)CH₃ |
| | 18 | CH₂OC₂H₅ | Ph- | 7-N(CH₂CH₃)₂ |
| | 19 | CH₂OC₂H₅ | Ph- | 7-NMeCH₂CO₂H |
| | 20 | CH₂OC₂H₅ | Ph- | 7-N⁺(Me)₂CH₂CO₂H, I⁻ |
| | 21 | CH₂OC₂H₅ | Ph- | 7-(N)-morpholine |
| | 22 | CH₂OC₂H₅ | Ph- | 7-(N)-azetidine |
| | 23 | CH₂OC₂H₅ | Ph- | 7-(N)—N-methylazetidinium, I⁻ |
| | 24 | CH₂OC₂H₅ | Ph- | 7-(N)-pyrrolidine |
| | 25 | CH₂OC₂H₅ | Ph- | 7-(N)—N-methyl-pyrrolidinium, I⁻ |
| | 26 | CH₂OC₂H₅ | Ph- | 7-(N)—N-methyl-morpholinium, I⁻ |
| | 27 | CH₂OC₂H₅ | Ph- | 7-(N)—N'-methylpiperazine |
| | 28 | CH₂OC₂H₅ | Ph- | 7-(N)—N'-dimethylpiperazinium, I⁻ |
| | 29 | CH₂OC₂H₅ | Ph- | 7-NH—CBZ |
| | 30 | CH₂OC₂H₅ | Ph- | 7-NHC(O)C₅H₁₁ |
| | 31 | CH₂OC₂H₅ | Ph- | 7-NHC(O)CH₂Br |
| | 32 | CH₂OC₂H₅ | Ph- | 7-NH—C(NH)NH₂ |
| | 33 | CH₂OC₂H₅ | Ph- | 7-(2)-thiophene |
| | 34 | CH₂OC₂H₅ | Ph- | 8-methyl |
| | 35 | CH₂OC₂H₅ | Ph- | 8-ethyl |
| | 36 | CH₂OC₂H₅ | Ph- | 8-iso-propyl |
| | 37 | CH₂OC₂H₅ | Ph- | 8-tert-butyl |
| | 38 | CH₂OC₂H₅ | Ph- | 8-OH |
| | 39 | CH₂OC₂H₅ | Ph- | 8-OCH₃ |
| | 40 | CH₂OC₂H₅ | Ph- | 8-O(iso-propyl) |
| | 41 | CH₂OC₂H₅ | Ph- | 8-SCH₃ |
| | 42 | CH₂OC₂H₅ | Ph- | 8-SOCH₃ |
| | 43 | CH₂OC₂H₅ | Ph- | 8-SO₂CH₃ |
| | 44 | CH₂OC₂H₅ | Ph- | 8-SCH₂CH₃ |
| | 45 | CH₂OC₂H₅ | Ph- | 8-NH₂ |
| | 46 | CH₂OC₂H₅ | Ph- | 8-NHOH |
| | 47 | CH₂OC₂H₅ | Ph- | 8-NHCH₃ |
| | 48 | CH₂OC₂H₅ | Ph- | 8-N(CH₃)₂ |

TABLE 5-continued

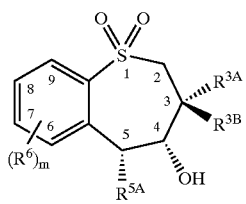

| Prefix (FFF.xxx) | Cpd # yyy) | $R^{3A}=R^{3B}$ | $R^{5A}$ | $(R^6)_m$ |
|---|---|---|---|---|
| | 49 | $CH_2OC_2H_5$ | Ph- | 8-$N^+(CH_3)_3$, $I^-$ |
| | 50 | $CH_2OC_2H_5$ | Ph- | 8-NHC(=O)CH$_3$ |
| | 51 | $CH_2OC_2H_5$ | Ph- | 8-N(CH$_2$CH$_3$)$_2$ |
| | 52 | $CH_2OC_2H_5$ | Ph- | 8-NMeCH$_2$CO$_2$H |
| | 53 | $CH_2OC_2H_5$ | Ph- | 8-$N^+$(Me)$_2$CH$_2$CO$_2$H, $I^-$ |
| | 54 | $CH_2OC_2H_5$ | Ph- | 8-(N)-morpholine |
| | 55 | $CH_2OC_2H_5$ | Ph- | 8-(N)-azetidine |
| | 56 | $CH_2OC_2H_5$ | Ph- | 8-(N)—N-methylazetidinium, $I^-$ |
| | 57 | $CH_2OC_2H_5$ | Ph- | 8-(N)-pyrrolidine |
| | 58 | $CH_2OC_2H_5$ | Ph- | 8-(N)—N-methyl-pyrrolidinium, $I^-$ |
| | 59 | $CH_2OC_2H_5$ | Ph- | 8-(N)—N-methyl-morpholinium, $I^-$ |
| | 60 | $CH_2OC_2H_5$ | Ph- | 8-(N)—N'-methylpiperzine |
| | 61 | $CH_2OC_2H_5$ | Ph- | 8-(N)—N'-dimethylpiperadinium, $I^-$ |
| | 62 | $CH_2OC_2H_5$ | Ph- | 8-NH—CBZ |
| | 63 | $CH_2OC_2H_5$ | Ph- | 8-NHC(O)C$_5$H$_{11}$ |
| | 64 | $CH_2OC_2H_5$ | Ph- | 8-NHC(O)CH$_2$Br |
| | 65 | $CH_2OC_2H_5$ | Ph- | 8-NH—C(NH)NH$_2$ |
| | 66 | $CH_2OC_2H_5$ | Ph- | 8-(2)-thiophene |
| | 67 | $CH_2OC_2H_5$ | Ph- | 9-methyl |
| | 68 | $CH_2OC_2H_5$ | Ph- | 9-ethyl |
| | 69 | $CH_2OC_2H_5$ | Ph- | 9-iso-propyl |
| | 70 | $CH_2OC_2H_5$ | Ph- | 9-tert-butyl |
| | 71 | $CH_2OC_2H_5$ | Ph- | 9-OH |
| | 72 | $CH_2OC_2H_5$ | Ph- | 9-OCH$_3$ |
| | 73 | $CH_2OC_2H_5$ | Ph- | 9-O(iso-propyl) |
| | 74 | $CH_2OC_2H_5$ | Ph- | 9-SCH$_3$ |
| | 75 | $CH_2OC_2H_5$ | Ph- | 9-SOCH$_3$ |
| | 76 | $CH_2OC_2H_5$ | Ph- | 9-SO$_2$CH$_3$ |
| | 77 | $CH_2OC_2H_5$ | Ph- | 9-SCH$_2$CH$_3$ |
| | 78 | $CH_2OC_2H_5$ | Ph- | 9-NH$_2$ |
| | 79 | $CH_2OC_2H_5$ | Ph- | 9-NHOH |
| | 80 | $CH_2OC_2H_5$ | Ph- | 9-NHCH$_3$ |
| | 81 | $CH_2OC_2H_5$ | Ph- | 9-N(CH$_3$)$_2$ |
| | 82 | $CH_2OC_2H_5$ | Ph- | 9-$N^+(CH_3)_3$, $I^-$ |
| | 83 | $CH_2OC_2H_5$ | Ph- | 9-NHC(=O)CH$_3$ |
| | 84 | $CH_2OC_2H_5$ | Ph- | 9-N(CH$_2$CH$_3$)$_2$ |
| | 85 | $CH_2OC_2H_5$ | Ph- | 9-NMeCH$_2$CO$_2$H |
| | 86 | $CH_2OC_2H_5$ | Ph- | 9-$N^+$(Me)$_2$CH$_2$CO$_2$H, $I^-$ |
| | 87 | $CH_2OC_2H_5$ | Ph- | 9-(N)-morpholine |
| | 88 | $CH_2OC_2H_5$ | Ph- | 9-(N)-azetidine |
| | 89 | $CH_2OC_2H_5$ | Ph- | 9-(N)—N-methylazetidinium, $I^-$ |
| | 90 | $CH_2OC_2H_5$ | Ph- | 9-(N)-pyrrolidine |
| | 91 | $CH_2OC_2H_5$ | Ph- | 9-(N)—N-methyl-pyrrolidinium, $I^-$ |
| | 92 | $CH_2OC_2H_5$ | Ph- | 9-(N)—N-methyl-morpholinium, $I^-$ |
| | 93 | $CH_2OC_2H_5$ | Ph- | 9-(N)—N'-methylpiperazine |
| | 93 | $CH_2OC_2H_5$ | Ph- | 9-(N)—N'-dimethylpiperazinium, $I^-$ |
| | 95 | $CH_2OC_2H_5$ | Ph- | 9-NH—CBZ |
| | 96 | $CH_2OC_2H_5$ | Ph- | 9-NHC(O)C$_5$H$_{11}$ |
| | 97 | $CH_2OC_2H_5$ | Ph- | 9-NHC(O)CH$_2$Br |
| | 98 | $CH_2OC_2H_5$ | Ph- | 9-NH—C(NH)NH$_2$ |
| | 99 | $CH_2OC_2H_5$ | Ph- | 9-(2)-thiophene |
| | 100 | $CH_2OC_2H_5$ | Ph- | 7-OCH$_3$, 8-OCH$_3$ |
| | 101 | $CH_2OC_2H_5$ | Ph- | 7-SCH$_3$, 8-OCH$_3$ |
| | 102 | $CH_2OC_2H_5$ | Ph- | 7-SCH$_3$, 8-SCH$_3$ |
| | 103 | $CH_2OC_2H_5$ | Ph- | 6-OCH$_3$, 7-OCH$_3$, 8-OCH$_3$ |
| F101.011 | 01 | CH$_2$CH(OH)C$_2$H$_5$ | Ph- | 7-methyl |
| | 02 | CH$_2$CH(OH)C$_2$H$_5$ | Ph- | 7-ethyl |
| | 03 | CH$_2$CH(OH)C$_2$H$_5$ | Ph- | 7-iso-propyl |
| | 04 | CH$_2$CH(OH)C$_2$H$_5$ | Ph- | 7-tert-butyl |
| | 05 | CH$_2$CH(OH)C$_2$H$_5$ | Ph- | 7-OH |
| | 06 | CH$_2$CH(OH)C$_2$H$_5$ | Ph- | 7-OCH$_3$ |
| | 07 | CH$_2$CH(OH)C$_2$H$_5$ | Ph- | 7-O(iso-propyl) |
| | 08 | CH$_2$CH(OH)C$_2$H$_5$ | Ph- | 7-SCH$_3$ |
| | 09 | CH$_2$CH(OH)C$_2$H$_5$ | Ph- | 7-SOCH$_3$ |
| | 10 | CH$_2$CH(OH)C$_2$H$_5$ | Ph- | 7-SO$_2$CH$_3$ |

TABLE 5-continued

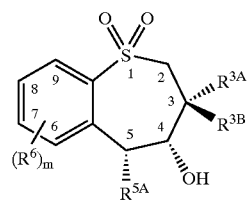

| Prefix (FFF.xxx. | Cpd # yyy) | $R^{3A}=R^{3B}$ | $R^{5A}$ | $(R^6)_m$ |
|---|---|---|---|---|
| | 11 | $CH_2CH(OH)C_2H_5$ | Ph- | 7-$SCH_2CH_3$ |
| | 12 | $CH_2CH(OH)C_2H_5$ | Ph- | 7-$NH_2$ |
| | 13 | $CH_2CH(OH)C_2H_5$ | Ph- | 7-NHOH |
| | 14 | $CH_2CH(OH)C_2H_5$ | Ph- | 7-$NHCH_3$ |
| | 15 | $CH_2CH(OH)C_2H_5$ | Ph- | 7-$N(CH_3)_2$ |
| | 16 | $CH_2CH(OH)C_2H_5$ | Ph- | 7-$N^+(CH_3)_3$, $I^-$ |
| | 17 | $CH_2CH(OH)C_2H_5$ | Ph- | 7-NHC(=O)$CH_3$ |
| | 18 | $CH_2CH(OH)C_2H_5$ | Ph- | 7-$N(CH_2CH_3)_2$ |
| | 19 | $CH_2CH(OH)C_2H_5$ | Ph- | 7-$NMeCH_2CO_2H$ |
| | 20 | $CH_2CH(OH)C_2H_5$ | Ph- | 7-$N^+(Me)_2CH_2CO_2H$, $I^-$ |
| | 21 | $CH_2CH(OH)C_2H_5$ | Ph- | 7-(N)-morpholine |
| | 22 | $CH_2CH(OH)C_2H_5$ | Ph- | 7-(N)-azetidine |
| | 23 | $CH_2CH(OH)C_2H_5$ | Ph- | 7-(N)—N-methylazetidinium, $I^-$ |
| | 24 | $CH_2CH(OH)C_2H_5$ | Ph- | 7-(N)-pyrrolidine |
| | 25 | $CH_2CH(OH)C_2H_5$ | Ph- | 7-(N)—N-methyl-pyrrolidinium, $I^-$ |
| | 26 | $CH_2CH(OH)C_2H_5$ | Ph- | 7-(N)—N-methyl-morpholinium, $I^-$ |
| | 27 | $CH_2CH(OH)C_2H_5$ | Ph- | 7-(N)—N'-methylpiperazine |
| | 28 | $CH_2CH(OH)C_2H_5$ | Ph- | 7-(N)—N'-dimethylpiperazinium, $I^-$ |
| | 29 | $CH_2CH(OH)C_2H_5$ | Ph- | 7-NH—CBZ |
| | 30 | $CH_2CH(OH)C_2H_5$ | Ph- | 7-$NHC(O)C_5H_{11}$ |
| | 31 | $CH_2CH(OH)C_2H_5$ | Ph- | 7-$NHC(O)CH_2Br$ |
| | 32 | $CH_2CH(OH)C_2H_5$ | Ph- | 7-NH—C(NH)$NH_2$ |
| | 33 | $CH_2CH(OH)C_2H_5$ | Ph- | 7-(2)-thiophene |
| | 34 | $CH_2CH(OH)C_2H_5$ | Ph- | 8-methyl |
| | 35 | $CH_2CH(OH)C_2H_5$ | Ph- | 8-ethyl |
| | 36 | $CH_2CH(OH)C_2H_5$ | Ph- | 8-iso-propyl |
| | 37 | $CH_2CH(OH)C_2H_5$ | Ph- | 8-tert-butyl |
| | 38 | $CH_2CH(OH)C_2H_5$ | Ph- | 8-OH |
| | 39 | $CH_2CH(OH)C_2H_5$ | Ph- | 8-$OCH_3$ |
| | 40 | $CH_2CH(OH)C_2H_5$ | Ph- | 8-O(iso-propyl) |
| | 41 | $CH_2CH(OH)C_2H_5$ | Ph- | 8-$SCH_3$ |
| | 42 | $CH_2CH(OH)C_2H_5$ | Ph- | 8-$SOCH_3$ |
| | 43 | $CH_2CH(OH)C_2H_5$ | Ph- | 8-$SO_2CH_3$ |
| | 44 | $CH_2CH(OH)C_2H_5$ | Ph- | 8-$SCH_2CH_3$ |
| | 45 | $CH_2CH(OH)C_2H_5$ | Ph- | 8-$NH_2$ |
| | 46 | $CH_2CH(OH)C_2H_5$ | Ph- | 8-NHOH |
| | 47 | $CH_2CH(OH)C_2H_5$ | Ph- | 8-$NHCH_3$ |
| | 48 | $CH_2CH(OH)C_2H_5$ | Ph- | 8-$N(CH_3)_2$ |
| | 49 | $CH_2CH(OH)C_2H_5$ | Ph- | 8-$N^+(CH_3)_3$, $I^-$ |
| | 50 | $CH_2CH(OH)C_2H_5$ | Ph- | 8-NHC(=O)$CH_3$ |
| | 51 | $CH_2CH(OH)C_2H_5$ | Ph- | 8-$N(CH_2CH_3)_2$ |
| | 52 | $CH_2CH(OH)C_2H_5$ | Ph- | 8-$NMeCH_2CO_2H$ |
| | 53 | $CH_2CH(OH)C_2H_5$ | Ph- | 8-$N^+(Me)_2CH_2CO_2H$, $I^-$ |
| | 54 | $CH_2CH(OH)C_2H_5$ | Ph- | 8-(N)-morpholine |
| | 55 | $CH_2CH(OH)C_2H_5$ | Ph- | 8-(N)-azetidine |
| | 56 | $CH_2CH(OH)C_2H_5$ | Ph- | 8-(N)—N-methylazetidinium, $I^-$ |
| | 57 | $CH_2CH(OH)C_2H_5$ | Ph- | 8-(N)-pyrrolidine |
| | 58 | $CH_2CH(OH)C_2H_5$ | Ph- | 8-(N)—N-methyl-pyrrolidinium, $I^-$ |
| | 59 | $CH_2CH(OH)C_2H_5$ | Ph- | 8-(N)—N-methyl-morpholinium, $I^-$ |
| | 60 | $CH_2CH(OH)C_2H_5$ | Ph- | 8-(N)—N'-methylpiperazine |
| | 61 | $CH_2CH(OH)C_2H_5$ | Ph- | 8-(N)—N'-dimethylpiperazinium, $I^-$ |
| | 62 | $CH_2CH(OH)C_2H_5$ | Ph- | 8-NH—CBZ |
| | 63 | $CH_2CH(OH)C_2H_5$ | Ph- | 8-$NHC(O)C_5H_{11}$ |
| | 64 | $CH_2CH(OH)C_2H_5$ | Ph- | 8-$NHC(O)CH_2Br$ |
| | 65 | $CH_2CH(OH)C_2H_5$ | Ph- | 8-NH—C(NH)$NH_2$ |
| | 66 | $CH_2CH(OH)C_2H_5$ | Ph- | 8-(2)-thiophene |
| | 67 | $CH_2CH(OH)C_2H_5$ | Ph- | 9-methyl |
| | 68 | $CH_2CH(OH)C_2H_5$ | Ph- | 9-ethyl |
| | 69 | $CH_2CH(OH)C_2H_5$ | Ph- | 9-iso-propyl |
| | 70 | $CH_2CH(OH)C_2H_5$ | Ph- | 9-tert-butyl |
| | 71 | $CH_2CH(OH)C_2H_5$ | Ph- | 9-OH |
| | 72 | $CH_2CH(OH)C_2H_5$ | Ph- | 9-$OCH_3$ |
| | 73 | $CH_2CH(OH)C_2H_5$ | Ph- | 9-O(iso-propyl) |
| | 74 | $CH_2CH(OH)C_2H_5$ | Ph- | 9-$SCH_3$ |
| | 75 | $CH_2CH(OH)C_2H_5$ | Ph- | 9-$SOCH_3$ |

TABLE 5-continued

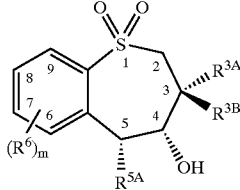

| Prefix (FFF.xxx) | Cpd # yyy | $R^{3A}=R^{3B}$ | $R^{5A}$ | $(R^6)_m$ |
|---|---|---|---|---|
| | 76 | $CH_2CH(OH)C_2H_5$ | Ph- | 9-$SO_2CH_3$ |
| | 77 | $CH_2CH(OH)C_2H_5$ | Ph- | 9-$SCH_2CH_3$ |
| | 78 | $CH_2CH(OH)C_2H_5$ | Ph- | 9-$NH_2$ |
| | 79 | $CH_2CH(OH)C_2H_5$ | Ph- | 9-NHOH |
| | 80 | $CH_2CH(OH)C_2H_5$ | Ph- | 9-$NHCH_3$ |
| | 81 | $CH_2CH(OH)C_2H_5$ | Ph- | 9-$N(CH_3)_2$ |
| | 82 | $CH_2CH(OH)C_2H_5$ | Ph- | 9-$N^+(CH_3)_3$, $I^-$ |
| | 83 | $CH_2CH(OH)C_2H_5$ | Ph- | 9-NHC(=O)$CH_3$ |
| | 84 | $CH_2CH(OH)C_2H_5$ | Ph- | 9-$N(CH_2CH_3)_2$ |
| | 85 | $CH_2CH(OH)C_2H_5$ | Ph- | 9-$NMeCH_2CO_2H$ |
| | 86 | $CH_2CH(OH)C_2H_5$ | Ph- | 9-$N^+(Me)_2CH_2CO_2H$, $I^-$ |
| | 87 | $CH_2CH(OH)C_2H_5$ | Ph- | 9-(N)-morpholine |
| | 88 | $CH_2CH(OH)C_2H_5$ | Ph- | 9-(N)-azetidine |
| | 89 | $CH_2CH(OH)C_2H_5$ | Ph- | 9-(N)—N-methylazetidinium, $I^-$ |
| | 90 | $CH_2CH(OH)C_2H_5$ | Ph- | 9-(N)-pyrrolidine |
| | 91 | $CH_2CH(OH)C_2H_5$ | Ph- | 9-(N)—N-methyl-pyrrolidinium, $I^-$ |
| | 92 | $CH_2CH(OH)C_2H_5$ | Ph- | 9-(N)—N-methyl-morpholinium, $I^-$ |
| | 93 | $CH_2CH(OH)C_2H_5$ | Ph- | 9-(N)—N'-methylpiperazine |
| | 93 | $CH_2CH(OH)C_2H_5$ | Ph- | 9-(N)—N'-dimethylpiperazinium, $I^-$ |
| | 95 | $CH_2CH(OH)C_2H_5$ | Ph- | 9-NH—CBZ |
| | 96 | $CH_2CH(OH)C_2H_5$ | Ph- | 9-NHC(O)$C_5H_{11}$ |
| | 97 | $CH_2CH(OH)C_2H_5$ | Ph- | 9-NHC(O)$CH_2Br$ |
| | 98 | $CH_2CH(OH)C_2H_5$ | Ph- | 9-NH—C(NH)$NH_2$ |
| | 99 | $CH_2CH(OH)C_2H_5$ | Ph- | 9-(2)-thiophene |
| | 100 | $CH_2CH(OH)C_2H_5$ | Ph- | 7-$OCH_3$, 8-$OCH_3$ |
| | 101 | $CH_2CH(OH)C_2H_5$ | Ph- | 7-$SCH_3$, 8-$OCH_3$ |
| | 102 | $CH_2CH(OH)C_2H_5$ | Ph- | 7-$SCH_3$, 8-$SCH_3$ |
| | 103 | $CH_2CH(OH)C_2H_5$ | Ph- | 6-$OCH_3$, 7-$OCH_3$, 8-$OCH_3$ |
| F101.012 | 01 | $CH_2O$-(4-picoline) | Ph- | 7-methyl |
| | 02 | $CH_2O$-(4-picoline) | Ph- | 7-ethyl |
| | 03 | $CH_2O$-(4-picoline) | Ph- | 7-iso-propyl |
| | 04 | $CH_2O$-(4-picoline) | Ph- | 7-tert-butyl |
| | 05 | $CH_2O$-(4-picoline) | Ph- | 7-OH |
| | 06 | $CH_2O$-(4-picoline) | Ph- | 7-$OCH_3$ |
| | 07 | $CH_2O$-(4-picoline) | Ph- | 7-O(iso-propyl) |
| | 08 | $CH_2O$-(4-picoline) | Ph- | 7-$SCH_3$ |
| | 09 | $CH_2O$-(4-picoline) | Ph- | 7-$SOCH_3$ |
| | 10 | $CH_2O$-(4-picoline) | Ph- | 7-$SO_2CH_3$ |
| | 11 | $CH_2O$-(4-picoline) | Ph- | 7-$SCH_2CH_3$ |
| | 12 | $CH_2O$-(4-picoline) | Ph- | 7-$NH_2$ |
| | 13 | $CH_2O$-(4-picoline) | Ph- | 7-NHOH |
| | 14 | $CH_2O$-(4-picoline) | Ph- | 7-$NHCH_3$ |
| | 15 | $CH_2O$-(4-picoline) | Ph- | 7-$N(CH_3)_2$ |
| | 16 | $CH_2O$-(4-picoline) | Ph- | 7-$N^+(CH_3)_3$, $I^-$ |
| | 17 | $CH_2O$-(4-picoline) | Ph- | 7-NHC(=O)$CH_3$ |
| | 18 | $CH_2O$-(4-picoline) | Ph- | 7-$N(CH_2CH_3)_2$ |
| | 19 | $CH_2O$-(4-picoline) | Ph- | 7-$NMeCH_2CO_2H$ |
| | 20 | $CH_2O$-(4-picoline) | Ph- | 7-$N^+(Me)_2CH_2CO_2H$, $I^-$ |
| | 21 | $CH_2O$-(4-picoline) | Ph- | 7-(N)-morpholine |
| | 22 | $CH_2O$-(4-picoline) | Ph- | 7-(N)-azetidine |
| | 23 | $CH_2O$-(4-picoline) | Ph- | 7-(N)—N-methylazetidinium, $I^-$ |
| | 24 | $CH_2O$-(4-picoline) | Ph- | 7-(N)-pyrrolidine |
| | 25 | $CH_2O$-(4-picoline) | Ph- | 7-(N)—N-methyl-pyrrolidinium, $I^-$ |
| | 26 | $CH_2O$-(4-picoline) | Ph- | 7-(N)—N-methyl-morpholinium, $I^-$ |
| | 27 | $CH_2O$-(4-picoline) | Ph- | 7-(N)—N'-methylpiperazine |
| | 28 | $CH_2O$-(4-picoline) | Ph- | 7-(N)—N'-dimethylpiperazinium, $I^-$ |
| | 29 | $CH_2O$-(4-picoline) | Ph- | 7-NH—CBZ |
| | 30 | $CH_2O$-(4-picoline) | Ph- | 7-NHC(O)$C_5H_{11}$ |
| | 31 | $CH_2O$-(4-picoline) | Ph- | 7-NHC(O)$CH_2Br$ |
| | 32 | $CH_2O$-(4-picoline) | Ph- | 7-NH—C(NH)$NH_2$ |
| | 33 | $CH_2O$-(4-picoline) | Ph- | 7-(2)-thiophene |
| | 34 | $CH_2O$-(4-picoline) | Ph- | 8-methyl |
| | 35 | $CH_2O$-(4-picoline) | Ph- | 8-ethyl |
| | 36 | $CH_2O$-(4-picoline) | Ph- | 8-iso-propyl |
| | 37 | $CH_2O$-(4-picoline) | Ph- | 8-tert-butyl |

TABLE 5-continued

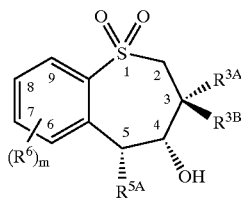

| Prefix (FFF.xxx. | Cpd # yyy) | $R^{3A}=R^{3B}$ | $R^{5A}$ | $(R^6)_m$ |
|---|---|---|---|---|
| | 38 | $CH_2O$-(4-picoline) | Ph- | 8-OH |
| | 39 | $CH_2O$-(4-picoline) | Ph- | 8-$OCH_3$ |
| | 40 | $CH_2O$-(4-picoline) | Ph- | 8-O(iso-propyl) |
| | 41 | $CH_2O$-(4-picoline) | Ph- | 8-$SCH_3$ |
| | 42 | $CH_2O$-(4-picoline) | Ph- | 8-$SOCH_3$ |
| | 43 | $CH_2O$-(4-picoline) | Ph- | 8-$SO_2CH_3$ |
| | 44 | $CH_2O$-(4-picoline) | Ph- | 8-$SCH_2CH_3$ |
| | 45 | $CH_2O$-(4-picoline) | Ph- | 8-$NH_2$ |
| | 46 | $CH_2O$-(4-picoline) | Ph- | 8-NHOH |
| | 47 | $CH_2O$-(4-picoline) | Ph- | 8-$NHCH_3$ |
| | 48 | $CH_2O$-(4-picoline) | Ph- | 8-$N(CH_3)_2$ |
| | 49 | $CH_2O$-(4-picoline) | Ph- | 8-$N^+(CH_3)_3$, $I^-$ |
| | 50 | $CH_2O$-(4-picoline) | Ph- | 8-NHC(=O)$CH_3$ |
| | 51 | $CH_2O$-(4-picoline) | Ph- | 8-$N(CH_2CH_3)_2$ |
| | 52 | $CH_2C$-(4-picoline) | Ph- | 8-$NMeCH_2CO_2H$ |
| | 53 | $CH_2O$-(4-picoline) | Ph- | 8-$N^+(Me)_2CH_2CO_2H$, $I^-$ |
| | 54 | $CH_2O$-(4-picoline) | Ph- | 8-(N)-morpholine |
| | 55 | $CH_2O$-(4-picoline) | Ph- | 8-(N)-azetidine |
| | 56 | $CH_2O$-(4-picoline) | Ph- | 8-(N)—N-methylazetidinium, $I^-$ |
| | 57 | $CH_2O$-(4-picoline) | Ph- | 8-(N)-pyrrolidine |
| | 58 | $CH_2O$-(4-picoline) | Ph- | 8-(N)—N-methyl-pyrrolidinium, $I^-$ |
| | 59 | $CH_2O$-(4-picoline) | Ph- | 8-(N)—N-methyl-morpholinium, $I^-$ |
| | 60 | $CH_2O$-(4-picoline) | Ph- | 8-(N)—N'-methylpiperazine |
| | 61 | $CH_2O$-(4-picoline) | Ph- | 8-(N)—N'-dimethylpiperazinium, $I^-$ |
| | 62 | $CH_2O$-(4-picoline) | Ph- | 8-NH—CBZ |
| | 63 | $CH_2O$-(4-picoline) | Ph- | 8-NHC(O)$C_5H_{11}$ |
| | 64 | $CH_2O$-(4-picoline) | Ph- | 8-NHC(O)$CH_2Br$ |
| | 65 | $CH_2O$-(4-picoline) | Ph- | 8-NH—C(NH)$NH_2$ |
| | 66 | $CH_2O$-(4-picoline) | Ph- | 8-(2)-thiophene |
| | 67 | $CH_2O$-(4-picoline) | Ph- | 9-methyl |
| | 68 | $CH_2O$-(4-picoline) | Ph- | 9-ethyl |
| | 69 | $CH_2O$-(4-picoline) | Ph- | 9-iso-propyl |
| | 70 | $CH_2O$-(4-picoline) | Ph- | 9-tert-butyl |
| | 71 | $CH_2O$-(4-picoline) | Ph- | 9-OH |
| | 72 | $CH_2O$-(4-picoline) | Ph- | 9-$OCH_3$ |
| | 73 | $CH_2O$-(4-picoline) | Ph- | 9-O(iso-propyl) |
| | 74 | $CH_2O$-(4-picoline) | Ph- | 9-$SCH_3$ |
| | 75 | $CH_2O$-(4-picoline) | Ph- | 9-$SOCH_3$ |
| | 76 | $CH_2O$-(4-picoline) | Ph- | 9-$SO_2CH_3$ |
| | 77 | $CH_2O$-(4-picoline) | Ph- | 9-$SCH_2CH_3$ |
| | 78 | $CH_2O$-(4-picoline) | Ph- | 9-$NH_2$ |
| | 79 | $CH_2O$-(4-picoline) | Ph- | 9-NHOH |
| | 80 | $CH_2O$-(4-picoline) | Ph- | 9-$NHCH_3$ |
| | 81 | $CH_2O$-(4-picoline) | Ph- | 9-$N(CH_3)_2$ |
| | 82 | $CH_2O$-(4-picoline) | Ph- | 9-$N^+(CH_3)_3$, $I^-$ |
| | 83 | $CH_2O$-(4-picoline) | Ph- | 9-NHC(=O)$CH_3$ |
| | 84 | $CH_2O$-(4-picoline) | Ph- | 9-$N(CH_2CH_3)_2$ |
| | 85 | $CH_2O$-(4-picoline) | Ph- | 9-$NMeCH_2CO_2H$ |
| | 86 | $CH_2O$-(4-picoline) | Ph- | 9-$N^+(Me)_2CH_2CO_2H$, $I^-$ |
| | 87 | $CH_2O$-(4-picoline) | Ph- | 9-(N)-morpholine |
| | 88 | $CH_2O$-(4-picoline) | Ph- | 9-(N)-azetidine |
| | 89 | $CH_2O$-(4-picoline) | Ph- | 9-(N)—N-methylazetidinium, $I^-$ |
| | 90 | $CH_2O$-(4-picoline) | Ph- | 9-(N)-pyrrolidine |
| | 91 | $CH_2O$-(4-picoline) | Ph- | 9-(N)—N-methyl-pyrrolidinium, $I^-$ |
| | 92 | $CH_2O$-(4-picoline) | Ph- | 9-(N)—N-methyl-morpholinium, $I^-$ |
| | 93 | $CH_2O$-(4-picoline) | Ph- | 9-(N)—N'-methylpiperazine |
| | 93 | $CH_2O$-(4-picoline) | Ph- | 9-(N)—N'-dimethylpiperazinium, $I^-$ |
| | 95 | $CH_2O$-(4-picoline) | Ph- | 9-NH—CBZ |
| | 96 | $CH_2O$-(4-picoline) | Ph- | 9-NHC(O)$C_5H_{11}$ |
| | 97 | $CH_2O$-(4-picoline) | Ph- | 9-NHC(O)$CH_2Br$ |
| | 98 | $CH_2O$-(4-picoline) | Ph- | 9-NH—C(NH)$NH_2$ |
| | 99 | $CH_2O$-(4-picoline) | Ph- | 9-(2)-thiophene |
| | 100 | $CH_2O$-(4-picoline) | Ph- | 7-$OCH_3$, 8-$OCH_3$ |

TABLE 5-continued

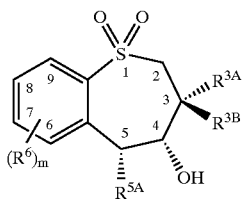

| Prefix (FFF.xxx. | Cpd # yyy) | R$^{3A}$=R$^{3B}$ | R$^{5A}$ | (R$^6$)$_m$ |
|---|---|---|---|---|
| | 101 | CH$_2$O-(4-picoline) | Ph- | 7-SCH$_3$, 8-OCH$_3$ |
| | 102 | CH$_2$O-(4-picoline) | Ph- | 7-SCH$_3$, 8-SCH$_3$ |
| | 103 | CH$_2$O-(4-picoline) | Ph- | 6-OCH$_3$, 7-OCH$_3$, 8-OCH$_3$ |

TABLE 6

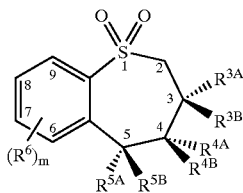

| Compound Number | R$^{3A}$ | R$^{3B}$ | R$^{4A}$ | R$^{4B}$ | R$^{5A}$ |
|---|---|---|---|---|---|
| 101 | ethyl | n-butyl | OH | H | phenyl |
| 102 | ethyl | n-butyl | OH | H | phenyl |
| 103 | n-butyl | Ethyl | OH | H | phenyl |
| 104 | ethyl | n-butyl | OH | H | phenyl |
| 105 | ethyl | n-butyl | OH | H | phenyl |
| 106 | ethyl | n-butyl | OH | H | phenyl |
| 107 | n-butyl | Ethyl | OH | H | 4-(decyloxy)phenyl |
| 108 | ethyl | n-butyl | OH | H | phenyl |
| 109 | ethyl | n-butyl | OH | H | 4-(decyloxy)phenyl |
| 110 | ethyl | n-butyl | OH | H | phenyl |
| 111 | n-butyl | Ethyl | OH | H | 4-hydroxyphenyl |
| 112 | ethyl | n-butyl | OH | H | 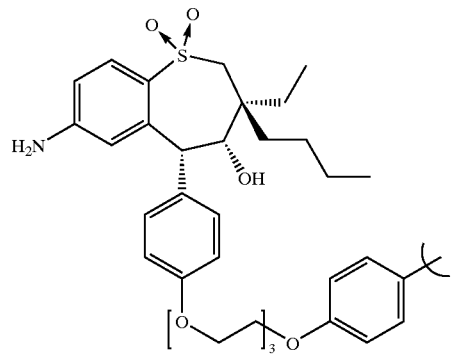 |
| 113 | ethyl | n-butyl | OH | H | 4-hydroxyphenyl |
| 114 | ethyl | n-butyl | OH | H | 4-methoxyphenyl |
| 115 | n-butyl | ethyl | OH | H | 4-methoxyphenyl |
| 116 | ethyl | n-butyl | OH | H | 4-methoxyphenyl |
| 117 | n-butyl | ethyl | OH | H | phenyl |
| 118 | ethyl | n-butyl | OH | H | phenyl |
| 119 | ethyl | n-butyl | OH | H | phenyl |
| 120 | n-butyl | ethyl | OH | H | phenyl |
| 121 | ethyl | n-butyl | OH | H | phenyl |
| 122 | n-butyl | ethyl | OH | H | phenyl |
| 123 | ethyl | n-butyl | OH | H | phenyl |
| 124 | n-butyl | ethyl | OH | H | phenyl |
| 125 | ethyl | n-butyl | OH | H | phenyl |
| 126 | n-butyl | ethyl | OH | H | 4-fluorophenyl |

TABLE 6-continued

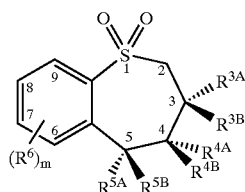

| Compound Number | R³ᴬ | R³ᴮ | R⁴ᴬ | R⁴ᴮ | R⁵ᴬ |
|---|---|---|---|---|---|
| 127 | n-butyl | ethyl | OH | H | 4-fluorophenyl |
| 128 | Ethyl | n-butyl | OH | H | 4-fluorophenyl |
| 129 | Ethyl | n-butyl | OH | H | 4-fluorophenyl |
| 131 | Ethyl | n-butyl | OH | H | 4-fluorophenyl |
| 132 | Ethyl | n-butyl | OH | H | phenyl |
| 133 | Ethyl | n-butyl | OH | H | phenyl |
| 134 | Ethyl | n-butyl | OH | H | phenyl |
| 135 | Ethyl | n-butyl | OH | H | phenyl |
| 136 | Ethyl | n-butyl | OH | H | phenyl |
| 137 | n-butyl | ethyl | OH | H | phenyl |
| 138 | n-butyl | ethyl | OH | H | phenyl |
| 139 | n-butyl | ethyl | OH | H | phenyl |
| 140 | | | | | |
| 141 | | | | | |
| 142 | Ethyl | n-butyl | H | OH | H |
| 143 | Ethyl | n-butyl | OH | H | 3-methoxyphenyl |
| 144 | Ethyl | n-butyl | OH | H | 4-fluorophenyl |
| 262 | Ethyl | n-butyl | OH | H | 3-methoxyphenyl |
| 263 | Ethyl | n-butyl | H | OH | H |
| 264 | Ethyl | n-butyl | OH | H | 3-trifluoromethylphenyl |
| 265 | Ethyl | n-butyl | H | OH | H |
| 266 | Ethyl | n-butyl | OH | H | 3-hydroxyphenyl |
| 267 | Ethyl | n-butyl | OH | H | 3-hydroxyphenyl |
| 268 | Ethyl | n-butyl | OH | H | 4-fluorophenyl |
| 269 | Ethyl | n-butyl | H | OH | H |
| 270 | Ethyl | n-butyl | OH | H | 4-fluorophenyl |
| 271 | Ethyl | n-butyl | OH | H | 3-methoxyphenyl |
| 272 | Ethyl | n-butyl | H | OH | H |
| 273 | Ethyl | n-butyl | H | OH | H |
| 274 | Ethyl | n-butyl | OH | H | 4-fluorophenyl |
| 275 | Ethyl | n-butyl | H | OH | H |
| 276 | Ethyl | n-butyl | OH | H | 3-methoxyphenyl |
| 277 | Ethyl | n-butyl | OH | H | 3-fluorophenyl |
| 278 | Ethyl | n-butyl | H | OH | 2-fluorophenyl |
| 279 | Ethyl | n-butyl | H | OH | 3-fluorophenyl |
| 280 | Ethyl | n-butyl | OH | H | 2-fluorophenyl |
| 281 | Ethyl | n-butyl | OH | H | 4-fluorophenyl |
| 282 | Ethyl | n-butyl | OH | H | 4-fluorophenyl |
| 283 | Ethyl | n-butyl | H | OH | H |
| 284 | Ethyl | n-butyl | OH | H | 4-fluorophenyl |
| 286 | Ethyl | ethyl | OH | H | phenyl |
| 287 | Ethyl | ethyl | OH | H | phenyl |
| 288 | methyl | methyl | OH | H | phenyl |
| 289 | n-butyl | n-butyl | OH | H | phenyl |
| 290 | n-butyl | n-butyl | OH | H | phenyl |
| 291 | n-butyl | n-butyl | OH | H | phenyl |
| 292 | n-butyl | n-butyl | OH | H | 4-fluorophenyl |
| 293 | n-butyl | n-butyl | OH | H | phenyl |
| 294 | n-butyl | n-butyl | OH | H | phenyl |
| 295 | Ethyl | n-butyl | OH | H | 3-I |
| 296 | Ethyl | n-butyl | OH | H | 3-N+(CH3)3 I⁻ |

TABLE 6-continued

[Structure: benzothiepine 1,1-dioxide core with positions labeled 1-9, substituents $R^{3A}$, $R^{3B}$ at position 3; $R^{4A}$, $R^{4B}$ at position 4; $R^{5A}$, $R^{5B}$ at position 5; $(R^6)_m$ on benzene ring]

| Compound Number | $R^{3A}$ | $R^{3B}$ | $R^{4A}$ | $R^{4B}$ | $R^{5A}$ |
|---|---|---|---|---|---|
| 1000 | Ethyl | n-butyl | OH | H | 3-(NH-CH₂CH₂CH₂-SO₃H)-phenyl |
| 1001 | Ethyl | n-butyl | OH | H | 4-(O-(CH₂)₃-N⁺(CH₂CH₃)₃) I⁻ -phenyl |
| 1002 | Ethyl | n-butyl | OH | H | 3-(CH₂-pyridinium) Br⁻ -phenyl |
| 1003 | Ethyl | n-butyl | OH | H | 3-(O-CH₂CH₂-N⁺(Et)₃) I⁻ -phenyl |
| 1004 | Ethyl | n-butyl | OH | H | 3-(NH-CO-(CH₂)₃-N⁺(CH₂CH₃)₃) CF₃COO⁻ -phenyl |
| 1005 | n-butyl | n-butyl | OH | H | 3-(NH-CO-(CH₂)₃-N⁺(CH₂CH₃)₃) CF₃COO⁻ -phenyl |
| 1006 | n-butyl | n-butyl | OH | H | 3-fluoro-4-(O-CH₂CH₂-O-CH₂CH₂-N⁺(Me)(4-methylpiperazinyl)) Br⁻ -phenyl |
| 1007 | n-butyl | n-butyl | OH | H | 3-(O-(CH₂)₃-N⁺(CH₂CH₃)₃) I⁻ -phenyl |

TABLE 6-continued

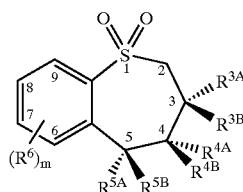

| Compound Number | R³ᴬ | R³ᴮ | R⁴ᴬ | R⁴ᴮ | R⁵ᴬ |
|---|---|---|---|---|---|
| 1008 | n-butyl | n-butyl | OH | H | *(3-(3-(pyridazinium-1-yl)propoxy)phenyl, iodide)* |
| 1009 | n-butyl | n-butyl | OH | H | *(3-(3-(4-dimethylaminopyridinium-1-yl)propoxy)phenyl, iodide)* |
| 1010 | n-butyl | n-butyl | OH | H | 3-fluoro-4-methoxyphenyl |
| 1011 | n-butyl | n-butyl | OH | H | 3-fluoro-4-(5-triethylammoniumpentyloxy)phenyl, trifluoroacetate salt |
| 1012 | n-butyl | n-butyl | OH | H | 4-hydroxyphenyl |
| 1013 | n-butyl | n-butyl | OH | H | *(3-fluoro-4-(3-trimethylammoniumpropoxy)phenyl, iodide)* |
| 1014 | n-butyl | n-butyl | OH | H | 4-methoxyphenyl |
| 1015 | n-butyl | n-butyl | OH | H | *(3-fluoro-4-(2-(1-methylpyrrolidinium-1-yl)ethoxy)phenyl, bromide)* |
| 1016 | n-butyl | n-butyl | OH | H | *(3-(3-(N,N-dimethyl-N-carboxymethylammonium)propoxy)phenyl, iodide)* |
| 1017 | n-butyl | n-butyl | OH | H | *(3-(3-(4-methylquinolinium-1-yl)propoxy)phenyl, iodide)* |
| 1018 | n-butyl | n-butyl | OH | H | *(3-(3-(N-(2-(N-methylbenzamido)ethyl)-N,N-dimethylammonium)propoxy)phenyl, iodide)* |

TABLE 6-continued
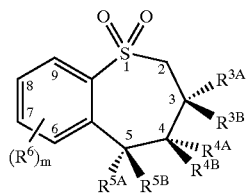
| Compound Number | R³ᴬ | R³ᴮ | R⁴ᴬ | R⁴ᴮ | R⁵ᴬ |
|---|---|---|---|---|---|
| 1019 | n-butyl | n-butyl | OH | H | 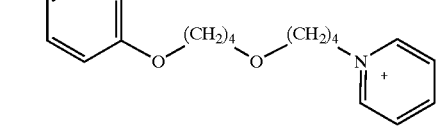 |
| 1020 | n-butyl | n-butyl | OH | H | 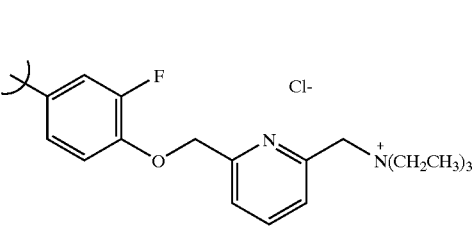 |
| 1021 | n-butyl | n-butyl | OH | H | 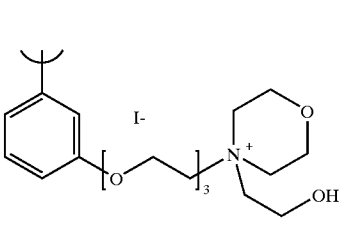 |
| 1022 | n-butyl | n-butyl | OH | H | 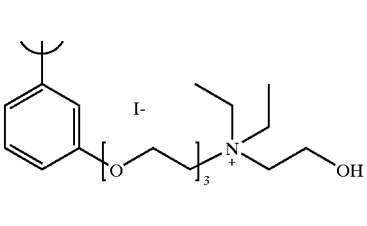 |
| 1023 | n-butyl | n-butyl | OH | H | 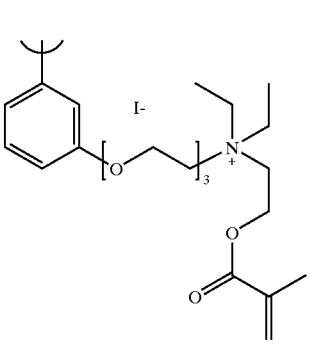 |

TABLE 6-continued

| Compound Number | R³ᴬ | R³ᴮ | R⁴ᴬ | R⁴ᴮ | R⁵ᴬ |
|---|---|---|---|---|---|
| 1024 | n-butyl | n-butyl | OH | H | |
| 1025 | n-butyl | n-butyl | OH | H | |
| 1026 | n-butyl | n-butyl | OH | H | |
| 1027 | n-butyl | n-butyl | OH | H | |
| 1028 | n-butyl | n-butyl | OH | H | |
| 1029 | n-butyl | n-butyl | OH | H | |

TABLE 6-continued
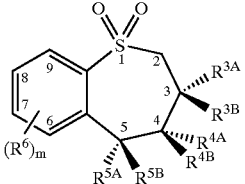
| Compound Number | R³ᴬ | R³ᴮ | R⁴ᴬ | R⁴ᴮ | R⁵ᴬ |
|---|---|---|---|---|---|
| 1030 | n-butyl | n-butyl | OH | H | 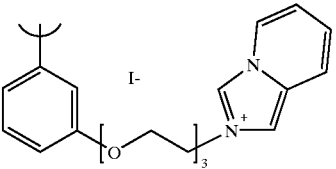 |
| 1031 | n-butyl | n-butyl | OH | H | 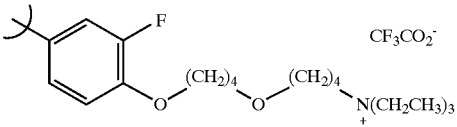 |
| 1032 | n-butyl | n-butyl | OH | H | 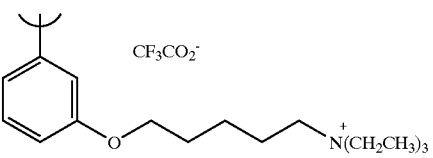 |
| 1033 | n-butyl | n-butyl | OH | H | 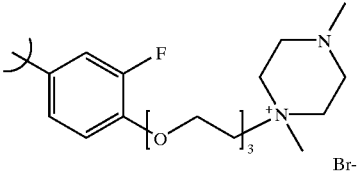 |
| 1034 | n-butyl | n-butyl | OH | H | 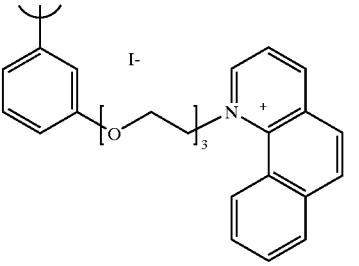 |
| 1035 | n-butyl | n-butyl | OH | H | 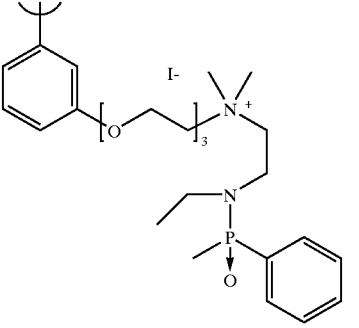 |

TABLE 6-continued
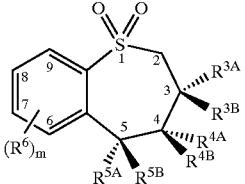
| Compound Number | R³ᴬ | R³ᴮ | R⁴ᴬ | R⁴ᴮ | R⁵ᴬ |
|---|---|---|---|---|---|
| 1036 | n-butyl | n-butyl | OH | H | 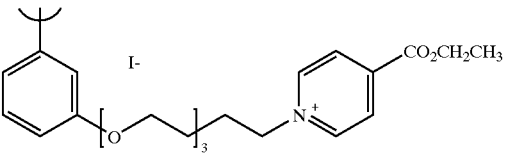 |
| 1037 | n-butyl | n-butyl | OH | H | 4-hydroxyphenyl |
| 1038 | n-butyl | n-butyl | OH | H | 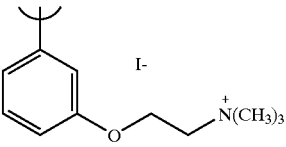 |
| 1039 | n-butyl | n-butyl | OH | H | phenyl |
| 1040 | n-butyl | n-butyl | OH | H | 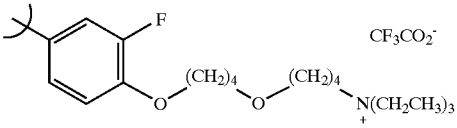 |
| 1041 | n-butyl | n-butyl | OH | H | 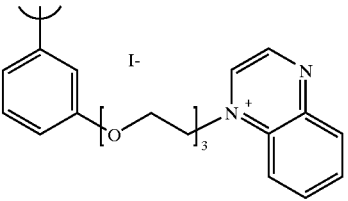 |
| 1042 | n-butyl | n-butyl | OH | H | 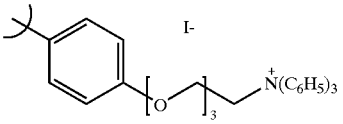 |
| 1043 | n-butyl | n-butyl | OH | H | 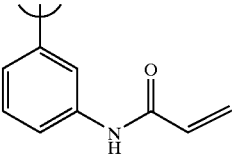 |
| 1044 | n-butyl | n-butyl | OH | H | 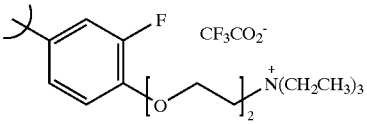 |

TABLE 6-continued
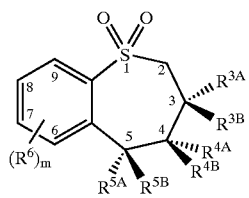
| Compound Number | R³ᴬ | R³ᴮ | R⁴ᴬ | R⁴ᴮ | R⁵ᴬ |
|---|---|---|---|---|---|
| 1045 | n-butyl | n-butyl | OH | H | 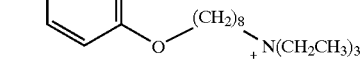 |
| 1046 | n-butyl | n-butyl | OH | H | 3-aminophenyl |
| 1047 | n-butyl | n-butyl | OH | H | 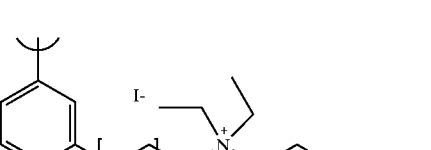 |
| 1048 | n-butyl | n-butyl | OH | H | 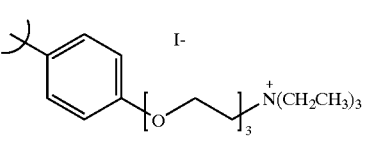 |
| 1049 | n-butyl | n-butyl | OH | H | 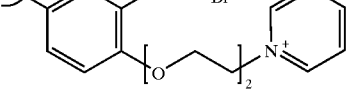 |
| 1050 | n-butyl | n-butyl | OH | H | 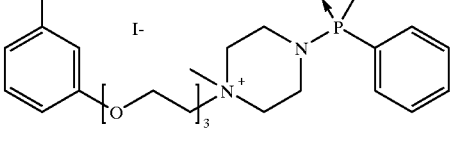 |
| 1051 | n-butyl | n-butyl | OH | H | 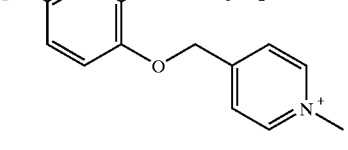 |
| 1052 | n-butyl | n-butyl | OH | H | 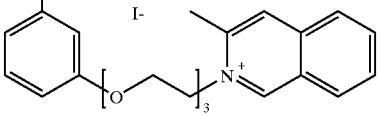 |

TABLE 6-continued

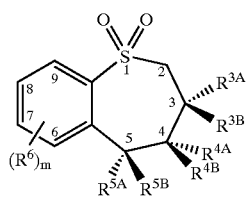

| Compound Number | R³ᴬ | R³ᴮ | R⁴ᴬ | R⁴ᴮ | R⁵ᴬ |
|---|---|---|---|---|---|
| 1053 | n-butyl | n-butyl | OH | H | *4-[(3-fluoro-4-(3-(4-dimethylamino-pyridinium-1-yl)propoxy)phenyl], CF₃CO₂⁻* |
| 1054 | n-butyl | n-butyl | OH | H | *3-[3-(isoquinolinium-2-yl)propoxy]phenyl, I⁻* |
| 1055 | n-butyl | n-butyl | OH | H | *4-[3-(1,4,8,11-tetramethyl-1,4,8,11-tetraazacyclotetradecan-1-ium-1-yl)propoxy]phenyl, I⁻* |
| 1056 | n-butyl | n-butyl | OH | H | *3-[3-(6,7,8,9-tetrahydro-5H-cyclohepta[c]pyridinium-2-yl)propoxy]phenyl, I⁻* |
| 1057 | n-butyl | n-butyl | OH | H | *3-[3-(pyrazinium-1-yl)propoxy]phenyl, I⁻* |
| 1058 | n-butyl | n-butyl | OH | H | *3-[3-(N,N-diethyl-N-(2-(N-methyl-N-benzoyl-amino)ethyl)ammonio)propoxy]phenyl, I⁻* |
| 1059 | n-butyl | n-butyl | OH | H | *4-[2-(1-ethylpiperidinium-1-yl)ethoxy]-3-fluorophenyl, Br⁻* |

TABLE 6-continued
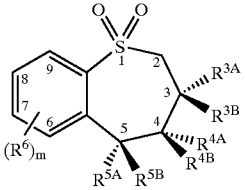
| Compound Number | R^3A | R^3B | R^4A | R^4B | R^5A |
|---|---|---|---|---|---|
| 1060 | Ethyl | n-butyl | OH | H | 3-fluoro-4-methoxyphenyl |
| 1061 | n-butyl | n-butyl | OH | H | 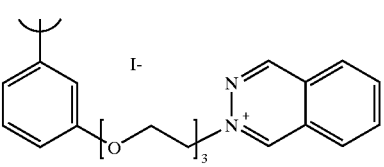 |
| 1062 | n-butyl | n-butyl | OH | H | 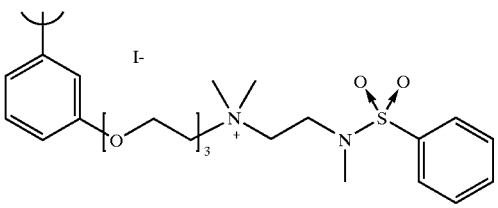 |
| 1063 | n-butyl | n-butyl | OH | H | 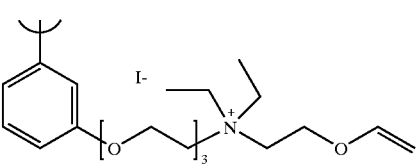 |
| 1064 | n-butyl | n-butyl | OH | H | 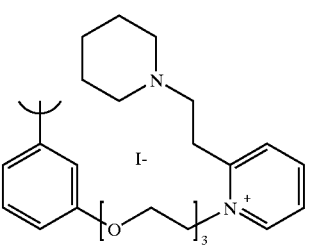 |
| 1065 | n-butyl | n-butyl | OH | H | 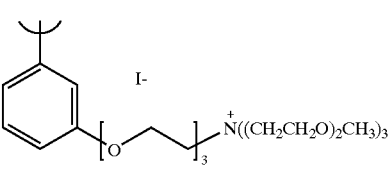 |
| 1066 | n-butyl | n-butyl | OH | H | 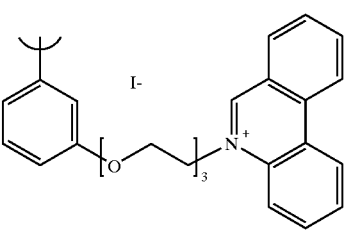 |
| 1067 | n-butyl | n-butyl | OH | H | thiophen-3-yl |

TABLE 6-continued

| Compound Number | R$^{3A}$ | R$^{3B}$ | R$^{4A}$ | R$^{4B}$ | R$^{5A}$ |
|---|---|---|---|---|---|
| 1068 | n-butyl | n-butyl | OH | H | [3-(pyridinium-1-yl)propoxy]phenyl, I$^-$ |
| 1069 | n-butyl | n-butyl | OH | H | phenyl |
| 1070 | n-butyl | n-butyl | OH | H | [2-(3-ethylimidazolium-1-yl)ethoxy]-2-fluorophenyl, CF$_3$CO$_2^-$ |
| 1071 | n-butyl | n-butyl | OH | H | phenyl with (OCH$_2$CH$_2$)$_3$-N$^+$(Et)$_2$-CH$_2$CH$_2$-N(Me)-P(=O)(Me)(Ph), I$^-$ |
| 1072 | n-butyl | n-butyl | OH | H | [3-(4-hydroxymethylpyridinium-1-yl)propoxy]phenyl, I$^-$ |
| 1073 | n-butyl | n-butyl | OH | H | [2-(DABCO-N$^+$)ethoxy]-2-fluorophenyl, Br$^-$ |
| 1074 | Ethyl | n-butyl | OH | H | 3-fluoro-4-methoxyphenyl |
| 1075 | n-butyl | n-butyl | OH | H | 4-fluorophenyl |
| 1076 | n-butyl | n-butyl | OH | H | 4-[3-(trimethylammonio)propoxy]phenyl, I$^-$ |
| 1077 | n-butyl | n-butyl | OH | H | 3-hydroxymethylphenyl |
| 1078 | Ethyl | n-butyl | OH | H | 4-hydroxyphenyl |

TABLE 6-continued
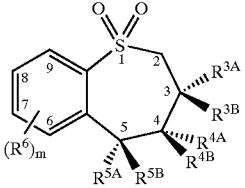
| Compound Number | R³ᴬ | R³ᴮ | R⁴ᴬ | R⁴ᴮ | R⁵ᴬ |
|---|---|---|---|---|---|
| 1079 | Ethyl | n-butyl | OH | H | 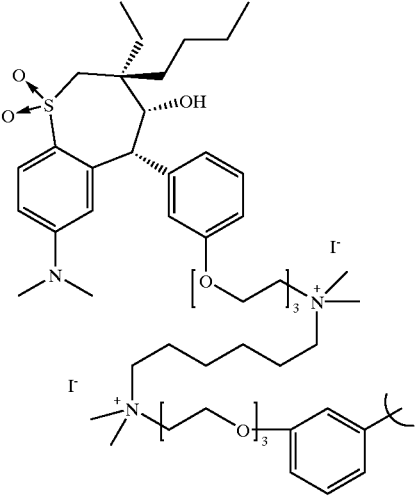 |
| 1080 | n-butyl | n-butyl | OH | H | 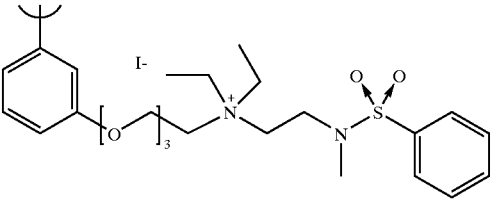 |
| 1081 | n-butyl | n-butyl | OH | H | 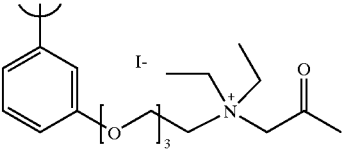 |
| 1082 | n-butyl | n-butyl | OH | H | 2-pyridyl |
| 1083 | n-butyl | n-butyl | OH | H | 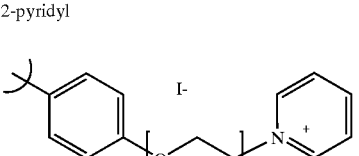 |
| 1084 | n-butyl | n-butyl | OH | H | 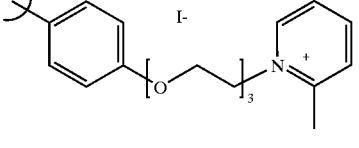 |
| 1085 | n-butyl | n-butyl | OH | H | thiophen-3-yl |

TABLE 6-continued

| Compound Number | R³ᴬ | R³ᴮ | R⁴ᴬ | R⁴ᴮ | R⁵ᴬ |
|---|---|---|---|---|---|
| 1086 | n-butyl | n-butyl | OH | H | |
| 1087 | n-butyl | n-butyl | OH | H | |
| 1088 | Ethyl | n-butyl | OH | H | 3,4-methylenedioxyphenyl |
| 1089 | Ethyl | n-butyl | OH | H | 4-methoxyphenyl |
| 1090 | n-butyl | n-butyl | OH | H | |
| 1091 | n-butyl | n-butyl | OH | H | |
| 1092 | n-butyl | n-butyl | OH | H | |
| 1093 | n-butyl | n-butyl | OH | H | |

TABLE 6-continued

[Structure: benzothiepine 1,1-dioxide core with positions 2,3,4,5 bearing R³ᴬ, R³ᴮ, R⁴ᴬ, R⁴ᴮ, R⁵ᴬ, R⁵ᴮ substituents and (R⁶)ₘ on the aromatic ring]

| Compound Number | R³ᴬ | R³ᴮ | R⁴ᴬ | R⁴ᴮ | R⁵ᴬ |
|---|---|---|---|---|---|
| 1094 | n-butyl | n-butyl | OH | H | 3-[2-(3-methoxycarbonylpyridinium-1-yl)ethoxy]phenyl, I⁻ |
| 1095 | n-butyl | n-butyl | OH | H | 3-[2-(1,4-diazabicyclo[2.2.2]octan-1-ium-1-yl)ethoxy]phenyl, I⁻ |
| 1096 | n-butyl | n-butyl | OH | H | 3-[2-(4-methylpyridinium-1-yl)ethoxy]phenyl, I⁻ |
| 1097 | n-butyl | n-butyl | OH | H | 3-(3-bromopropanamido)phenyl |
| 1098 | n-butyl | n-butyl | OH | H | 4-[2-(3-triethylammoniopropylthio)ethoxy]-3-fluorophenyl, I⁻ |
| 1099 | Ethyl | n-butyl | OH | H | 4-methoxyphenyl |
| 1100 | n-butyl | n-butyl | OH | H | 4-methoxyphenyl |
| 1101 | n-butyl | n-butyl | OH | H | 4-[2-(4-dimethylaminopyridinium-1-yl)ethoxy]-3-fluorophenyl, CF₃CO₂⁻ |
| 1102 | n-butyl | n-butyl | OH | H | 3-carboxymethylphenyl |
| 1103 | n-butyl | n-butyl | OH | H | 4-[3-(N,N-dimethyl-N-(2-trimethylammonioethyl)ammonio)propoxy]phenyl, 2 I⁻ |

TABLE 6-continued

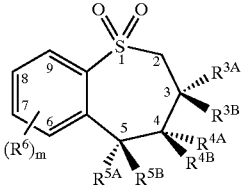

| Compound Number | R³ᴬ | R³ᴮ | R⁴ᴬ | R⁴ᴮ | R⁵ᴬ |
|---|---|---|---|---|---|
| 1104 | n-butyl | n-butyl | OH | H | 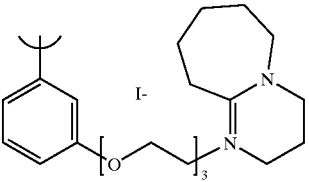 |
| 1105 | n-butyl | n-butyl | OH | H | 5-piperonyl |
| 1106 | n-butyl | n-butyl | OH | H | 3-hydroxyphenyl |
| 1107 | n-butyl | n-butyl | OH | H | 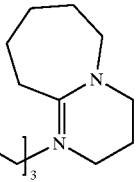 |
| 1108 | n-butyl | n-butyl | OH | H | 3-pyridyl |
| 1109 | n-butyl | n-butyl | OH | H | 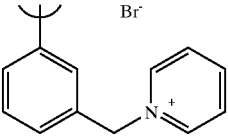 |
| 1110 | n-butyl | n-butyl | OH | H | 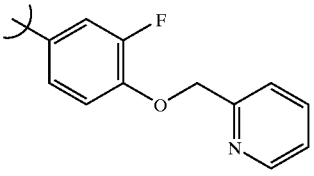 |
| 1111 | n-butyl | n-butyl | OH | H | 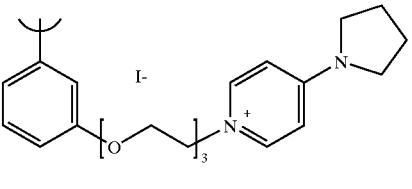 |
| 1112 | n-butyl | n-butyl | OH | H | 4-pyridyl |
| 1113 | n-butyl | n-butyl | OH | H | 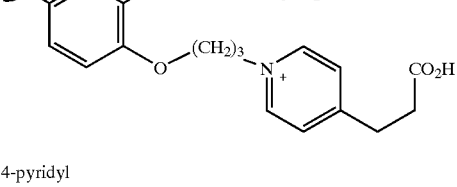 |
| 1114 | n-butyl | n-butyl | OH | H | 3-methoxyphenyl |
| 1115 | n-butyl | n-butyl | OH | H | 4-fluorophenyl |
| 1116 | Ethyl | n-butyl | OH | H | 3-tolyl |

TABLE 6-continued
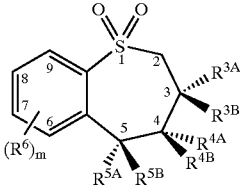
| Compound Number | R3A | R3B | R4A | R4B | R5A |
|---|---|---|---|---|---|
| 1117 | Ethyl | n-butyl | OH | H | 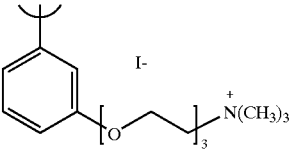 |
| 1118 | Ethyl | n-butyl | OH | H | 3-fluoro-4-hydroxyphenyl |
| 1119 | n-butyl | n-butyl | OH | H | 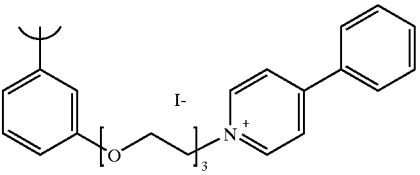 |
| 1120 | n-butyl | n-butyl | OH | H | 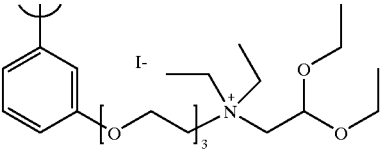 |
| 1121 | n-butyl | n-butyl | OH | H | 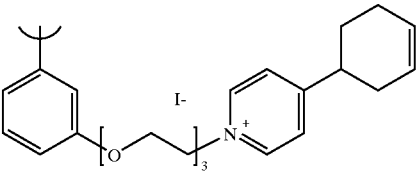 |
| 1122 | n-butyl | n-butyl | OH | H | 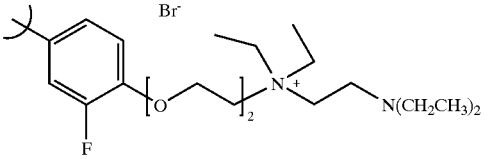 |
| 1123 | n-butyl | n-butyl | OH | H | phenyl |
| 1124 | n-butyl | n-butyl | OH | H | 3-methoxyphenyl |
| 1125 | n-butyl | n-butyl | OH | H | 3-chloro-4-methoxyphenyl |
| 1126 | Ethyl | n-butyl | OH | H | 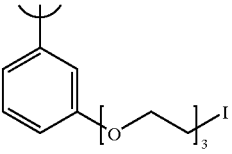 |
| 1127 | n-butyl | n-butyl | OH | H | 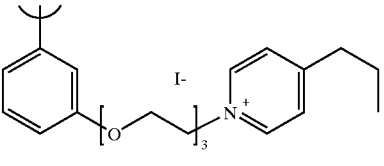 |

TABLE 6-continued

| Compound Number | R³ᴬ | R³ᴮ | R⁴ᴬ | R⁴ᴮ | R⁵ᴬ |
|---|---|---|---|---|---|
| 1128 | n-butyl | n-butyl | OH | H | 3-fluoro-4-hydroxyphenyl |
| 1129 | n-butyl | n-butyl | OH | H | 4-fluorophenyl |
| 1130 | n-butyl | n-butyl | OH | H | 3-chloro-4-fluorophenyl |
| 1131 | Ethyl | n-butyl | OH | H | 4-methoxyphenyl |
| 1132 | n-butyl | n-butyl | OH | H | (structure: 3-[O(CH₂)₂]₃-N⁺-tetrahydroisoquinolinium phenyl, I⁻) |
| 1133 | n-butyl | n-butyl | OH | H | 4-cyanomethylphenyl |
| 1134 | Ethyl | n-butyl | OH | H | (structure: phenyl-O-(CH₂)₄-O-C(=O)CH₃) |
| 1135 | n-butyl | n-butyl | OH | H | 3,4-dimethoxyphenyl |
| 1136 | n-butyl | n-butyl | OH | H | (structure: phenyl-[O(CH₂)₂]₃-I) |
| 1137 | n-butyl | n-butyl | OH | H | 4-fluorophenyl |
| 1138 | n-butyl | n-butyl | OH | H | (structure: phenyl-[O(CH₂)₂]₃-N⁺-(4-tert-butylpyridinium), I⁻) |
| 1139 | n-butyl | n-butyl | OH | H | 3,4-difluorophenyl |
| 1140 | n-butyl | n-butyl | OH | H | 3-methoxyphenyl |
| 1141 | n-butyl | n-butyl | OH | H | 4-fluorophenyl |
| 1142 | n-butyl | n-butyl | OH | H | (structure: 2-fluoro-4-substituted phenyl-[O(CH₂)₂]₂-S-CH₂CH₂-N(CH₂CH₃)₂) |
| 1143 | n-butyl | n-butyl | H | OH | H |
| 1144 | n-butyl | n-butyl | OH | H | 5-piperonyl |
| 1145 | n-butyl | n-butyl | OH | H | 4-methoxyphenyl |

TABLE 6-continued

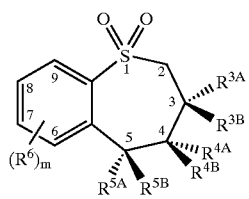

| Compound Number | $R^{3A}$ | $R^{3B}$ | $R^{4A}$ | $R^{4B}$ | $R^{5A}$ |
|---|---|---|---|---|---|
| 1146 | n-butyl | n-butyl | OH | H | ![4-((CH2)10-N(CH3)3+ I-)phenoxy] |
| 1147 | n-butyl | n-butyl | OH | H | 3-methoxyphenyl |
| 1148 | n-butyl | n-butyl | OH | H | 4-fluorophenyl |
| 1149 | n-butyl | n-butyl | OH | H | 4-fluorophenyl |
| 1150 | n-butyl | n-butyl | OH | H | 3-methoxyphenyl |
| 1151 | n-butyl | ethyl | OH | H | 3-fluoro-4-methoxyphenyl |
| 1152 | n-butyl | n-butyl | OH | H | phenyl |
| 1153 | n-butyl | n-butyl | OH | H | 4-fluorophenyl |
| 1154 | n-butyl | n-butyl | OH | H | 3-methoxyphenyl |
| 1155 | n-butyl | n-butyl | OH | H | 4-fluorophenyl |
| 1156 | n-butyl | n-butyl | OH | H | 4-fluorophenyl |
| 1157 | n-butyl | n-butyl | OH | H | 4-fluorophenyl |
| 1158 | n-butyl | n-butyl | OH | H | 4-pyridinyl, hydrochloride salt |
| 1159 | n-butyl | ethyl | OH | H | phenyl |
| 1160 | n-butyl | n-butyl | OH | H | 4-fluorophenyl |
| 1161 | n-butyl | n-butyl | OH | H | 3,5-dichloro-4-methoxyphenyl |
| 1162 | n-butyl | n-butyl | OH | H | phenyl |
| 1163 | n-butyl | n-butyl | OH | H | 3-(dimethylamino)phenyl |
| 1164 | n-butyl | n-butyl | OH | H | 4-pyridinyl |
| 1165 | n-butyl | n-butyl | OH | H | 3-fluoro-4-methoxyphenyl |
| 1166 | n-butyl | n-butyl | OH | H | 3-hydroxyphenyl |
| 1167 | n-butyl | n-butyl | OH | H | [3-chloro-4-(allyloxy)phenyl] |
| 1168 | n-butyl | n-butyl | OH | H | 4-hydroxyphenyl |
| 1169 | n-butyl | n-butyl | OH | H | phenyl |
| 1170 | n-butyl | n-butyl | OH | H | 3-methoxyphenyl |
| 1171 | n-butyl | n-butyl | OH | H | 4-(trifluoromethylsulfonyloxy)phenyl |
| 1172 | n-butyl | n-butyl | OH | H | 4-pyridinyl |
| 1173 | n-butyl | n-butyl | OH | H | 4-fluorophenyl |
| 1174 | Ethyl | n-butyl | OH | H | 3-methoxyphenyl |
| 1175 | Ethyl | n-butyl | OH | H | 3-methoxyphenyl |
| 1176 | n-butyl | n-butyl | OH | H | 4-fluorophenyl |
| 1177 | n-butyl | n-butyl | OH | H | 3-methoxyphenyl |
| 1178 | n-butyl | n-butyl | OH | H | 3-(trifluoromethylsulfonyloxy)phenyl |
| 1179 | n-butyl | n-butyl | OH | H | phenyl |
| 1180 | n-butyl | n-butyl | OH | H | phenyl |
| 1181 | n-butyl | n-butyl | OH | H | 4-fluorophenyl |
| 1182 | n-butyl | n-butyl | OH | H | 4-(dimethylamino)phenyl |
| 1183 | n-butyl | n-butyl | OH | H | 3-methoxyphenyl |
| 1184 | n-butyl | n-butyl | OH | H | 4-fluorophenyl |
| 1185 | n-butyl | n-butyl | OH | H | 4-fluorophenyl |
| 1186 | n-butyl | n-butyl | OH | H | phenyl |
| 1187 | n-butyl | n-butyl | OH | H | 4-fluorophenyl |
| 1188 | n-butyl | n-butyl | OH | H | 4-methoxyphenyl |
| 1189 | n-butyl | n-butyl | OH | H | 3,4-difluorophenyl |
| 1190 | n-butyl | n-butyl | OH | H | 2-bromophenyl |
| 1191 | n-butyl | n-butyl | OH | H | 4-(dimethylamino)phenyl |
| 1192 | n-butyl | n-butyl | OH | H | 3-(dimethylamino)phenyl |
| 1193 | n-butyl | n-butyl | OH | H | 4-(2-(2-methylpropyl))phenyl |

TABLE 6-continued
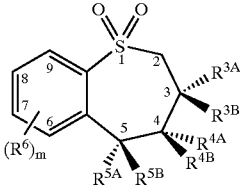
| Compound Number | R³ᴬ | R³ᴮ | R⁴ᴬ | R⁴ᴮ | R⁵ᴬ |
|---|---|---|---|---|---|
| 1194 | n-butyl | n-butyl | OH | H | 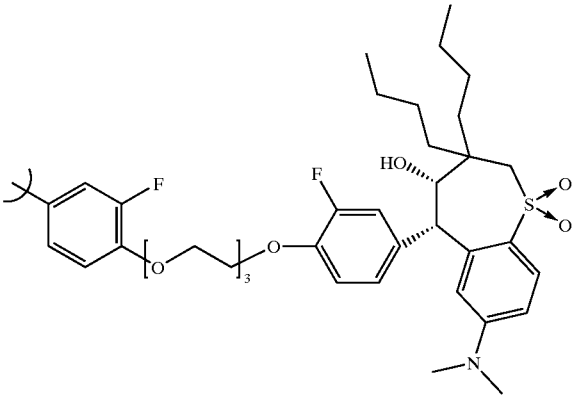 |
| 1195 | n-butyl | n-butyl | OH | H | 4-methoxyphenyl |
| 1196 | n-butyl | n-butyl | OH | H | 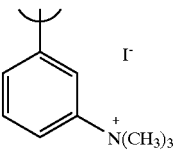 |
| 1197 | n-butyl | ethyl | R3 + R4 = oxo | R3 + R4 = oxo | phenyl |
| 1198 | n-butyl | n-butyl | OH | H | 4-(pyridinyl-N-oxide) |
| 1199 | n-butyl | n-butyl | OH | H | 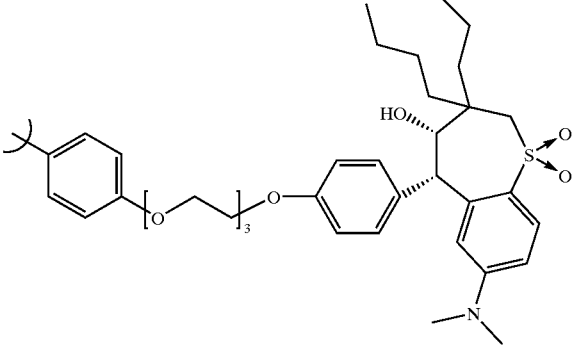 |
| 1200 | n-butyl | n-butyl | H | OH | H |
| 1201 | n-butyl | n-butyl | OH | H | H |
| 1202 | n-butyl | n-butyl | OH | H | 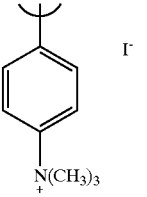 |

TABLE 6-continued

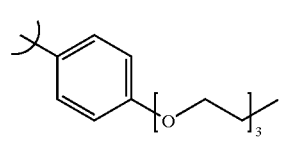

| Compound Number | R³ᴬ | R³ᴮ | R⁴ᴬ | R⁴ᴮ | R⁵ᴬ |
| --- | --- | --- | --- | --- | --- |
| 1203 | n-butyl | n-butyl | OH | H | 5-piperazinyl |
| 1204 | n-butyl | n-butyl | OH | H | 4-fluorophenyl |
| 1205 | n-butyl | n-butyl | OH | H | 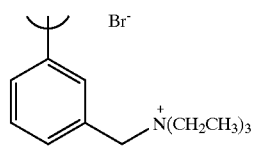 |
| 1206 | n-butyl | n-butyl | OH | H | 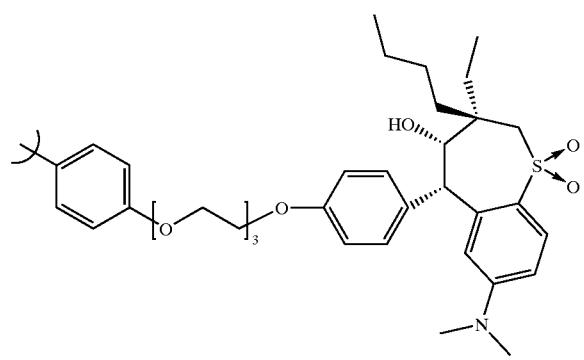 |
| 1207 | n-butyl | n-butyl | OH | H | 3,5-dichlorophenyl |
| 1208 | n-butyl | n-butyl | OH | H | 4-methoxyphenyl |
| 1209 | n-butyl | n-butyl | acetoxy | H | phenyl |
| 1210 | n-butyl | n-butyl | OH | H | 2-(dimethylamino)phenyl |
| 1211 | Ethyl | n-butyl | OH | H | 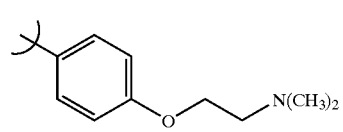 |
| 1212 | n-butyl | n-butyl | OH | H | 4-methoxyphenyl |
| 1213 | n-butyl | ethyl | H | OH | H |
| 1214 | n-butyl | ethyl | OH | H | phenyl |
| 1215 | n-butyl | n-butyl | OH | H | 4-methoxyphenyl |
| 1216 | Ethyl | n-butyl | OH | H | 5-piperonyl |
| 1217 | n-butyl | n-butyl | OH | H | 4-carboxyphenyl |
| 1218 | n-butyl | n-butyl | OH | H | 4-methoxyphenyl |
| 1219 | n-butyl | n-butyl | OH | H |  |
| 1220 | n-butyl | n-butyl | OH | H | 3-methoxyphenyl |

TABLE 6-continued

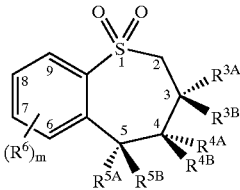

| Compound Number | $R^{3A}$ | $R^{3B}$ | $R^{4A}$ | $R^{4B}$ | $R^{5A}$ |
|---|---|---|---|---|---|
| 1221 | n-butyl | n-butyl | OH | H | 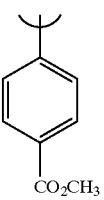 |
| 1222 | n-butyl | n-butyl | OH | H | 3-methoxyphenyl |
| 1223 | n-butyl | n-butyl | OH | H | phenyl |
| 1224 | n-butyl | n-butyl | OH | H | 3-nitrophenyl |
| 1225 | n-butyl | ethyl | OH | H | 3-methylphenyl |
| 1226 | Ethyl | n-butyl | OH | H | 5-piperonyl |
| 1227 | n-butyl | n-butyl | OH | H | 4-fluorophenyl |
| 1228 | n-butyl | n-butyl | OH | H | 2-pyrrolyl |
| 1229 | n-butyl | n-butyl | OH | H | 3-chloro-4-hydroxyphenyl |
| 1230 | n-butyl | n-butyl | OH | H | phenyl |
| 1231 | n-butyl | n-butyl | OH | H | 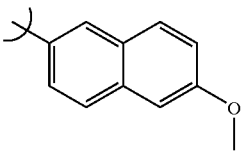 |
| 1232 | n-butyl | n-butyl | H | OH | 3-thiophenyl |
| 1233 | n-butyl | n-butyl | OH | H | 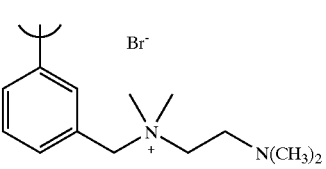 |
| 1234 | n-butyl | n-butyl | OH | H | 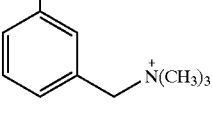 |
| 1235 | n-butyl | n-butyl | OH | H | 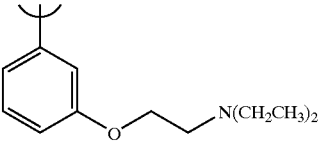 |
| 1236 | n-butyl | n-butyl | OH | H | 4-(bromomethyl)phenyl |
| 1237 | n-butyl | n-butyl | OH | H | 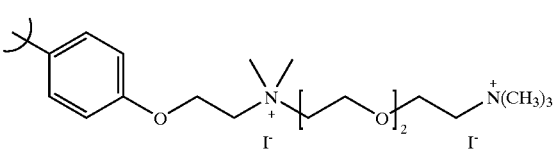 |

TABLE 6-continued

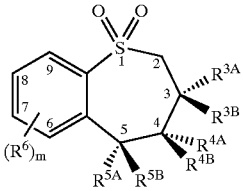

| Compound Number | R³ᴬ | R³ᴮ | R⁴ᴬ | R⁴ᴮ | R⁵ᴬ |
|---|---|---|---|---|---|
| 1238 | n-butyl | n-butyl | OH | H | 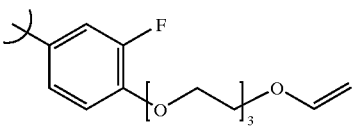 |
| 1239 | n-butyl | n-butyl | OH | H | 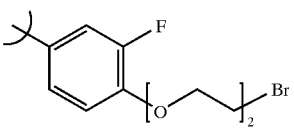 |
| 1240 | n-butyl | n-butyl | OH | H | 4-methoxy-3-methylphenyl |
| 1241 | n-butyl | n-butyl | OH | H | 3-(dimethylaminomethyl)phenyl |
| 1242 | n-butyl | n-butyl | OH | H | 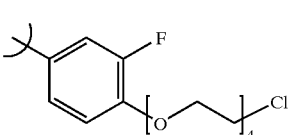 |
| 1243 | n-butyl | n-butyl | OH | H | 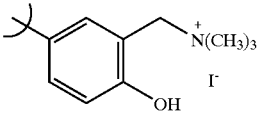 |
| 1244 | n-butyl | n-butyl | OH | H | 3-methoxyphenyl |
| 1245 | n-butyl | n-butyl | OH | H | 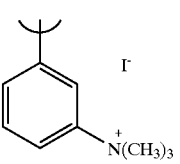 |
| 1246 | n-butyl | n-butyl | OH | H | 3-(bromomethyl)phenyl |
| 1247 | n-butyl | n-butyl | OH | H | 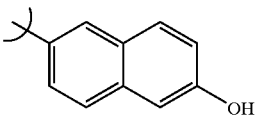 |
| 1248 | n-butyl | n-butyl | OH | H | 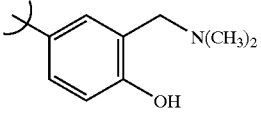 |
| 1249 | n-butyl | n-butyl | OH | H | 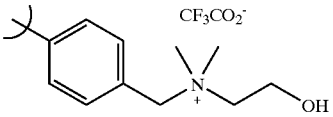 |
| 1250 | n-butyl | n-butyl | OH | H | 3-(dimethylamino)phenyl |
| 1251 | n-butyl | n-butyl | OH | H | 1-naphthyl |

TABLE 6-continued

| Compound Number | R³ᴬ | R³ᴮ | R⁴ᴬ | R⁴ᴮ | R⁵ᴬ |
|---|---|---|---|---|---|
| 1252 | n-butyl | n-butyl | OH | H | 4-(O(CH₂)₃N⁺(CH₂CH₃)₃) phenyl, I⁻ |
| 1253 | n-butyl | n-butyl | OH | H | 3-(CH₂N⁺(CH₃)₃)-4-methoxyphenyl, I⁻ |
| 1254 | n-butyl | n-butyl | OH | H | 4-(CH₂-pyridinium) phenyl, Br⁻ |
| 1255 | n-butyl | n-butyl | OH | H | 3-(CH₂N⁺(CH₃)₂CH₂CH₂N⁺(CH₃)₃) phenyl, 2 I⁻ |
| 1256 | n-butyl | n-butyl | OH | H | 3-nitrophenyl |
| 1257 | n-butyl | n-butyl | OH | H | phenyl |
| 1258 | n-butyl | n-butyl | OH | H | 4-fluorophenyl |
| 1259 | Ethyl | n-butyl | H | OH | H |
| 1260 | Ethyl | n-butyl | OH | H | 3-hydroxyphenyl |
| 1261 | n-butyl | n-butyl | OH | H | 4-(O(CH₂CH₂O)₃-4-(dimethylamino-benzothiepine-dioxide)phenyl)phenyl |
| 1262 | n-butyl | n-butyl | OH | H | 2-thiophenyl |
| 1263 | n-butyl | n-butyl | OH | H | 5-piperonyl |
| 1264 | n-butyl | n-butyl | OH | H | 4-fluorophenyl |
| 1265 | n-butyl | n-butyl | OH | H | 4-fluorophenyl |
| 1266 | n-butyl | n-butyl | OH | H | 3-(CH₂N⁺(CH₃)₃)-4-methoxyphenyl |
| 1267 | n-butyl | ethyl | OH | H | 5-piperonyl |

TABLE 6-continued
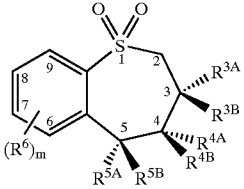
| Compound Number | $R^{3A}$ | $R^{3B}$ | $R^{4A}$ | $R^{4B}$ | $R^{5A}$ |
|---|---|---|---|---|---|
| 1268 | n-butyl | n-butyl | OH | H | 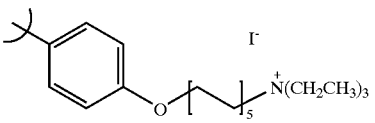 |
| 1269 | n-butyl | n-butyl | OH | H | 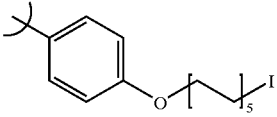 |
| 1270 | n-butyl | n-butyl | OH | H | 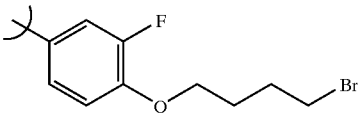 |
| 1271 | n-butyl | n-butyl | OH | H | 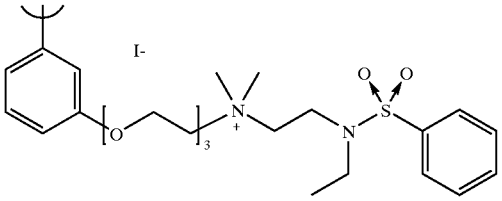 |
| 1272 | n-butyl | n-butyl | OH | H | 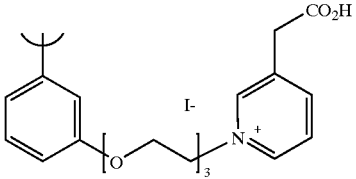 |
| 1273 | n-butyl | n-butyl | OH | H | 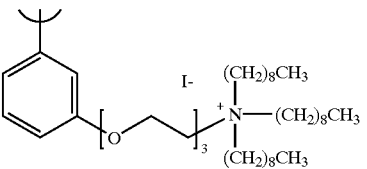 |
| 1274 | n-butyl | n-butyl | OH | H | 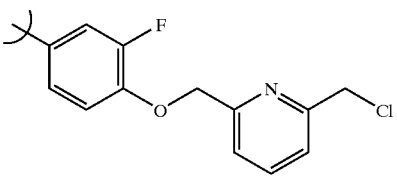 |

TABLE 6-continued

| Compound Number | R³ᴬ | R³ᴮ | R⁴ᴬ | R⁴ᴮ | R⁵ᴬ |
|---|---|---|---|---|---|
| 1275 | n-butyl | n-butyl | OH | H | 4-(2-(4-methylpiperazin-1-ium-1-yl)ethoxy)-3-fluorophenyl iodide (dimethylpiperazinium) |
| 1276 | n-butyl | n-butyl | OH | H | 3-(3-(tri(7-methyloctyl)ammonio)propoxy)phenyl iodide |
| 1277 | n-butyl | n-butyl | OH | H | 4-(2-(N-methyl-N-(carboxymethyl)amino)ethoxy)-3-fluorophenyl |
| 1278 | n-butyl | n-butyl | OH | H | 3-(3-(tripentylammonio)propoxy)phenyl iodide |
| 1279 | n-butyl | n-butyl | OH | H | 3-(3-(trihexylammonio)propoxy)phenyl iodide |
| 1280 | n-butyl | n-butyl | OH | H | 4-(N-methyl-N-((dimethylamino)methyl)aminocarbonylmethyl)-3-fluorophenyl |
| 1281 | n-butyl | n-butyl | OH | H | 4-(tripropoxy)phenyl |
| 1282 | Ethyl | n-butyl | OH | H | 3-fluoro-4-methoxyphenyl |
| 1283 | n-butyl | n-butyl | OH | H | 4-hydroxymethylphenyl |
| 1284 | n-butyl | n-butyl | OH | H | 4-fluorophenyl |
| 1285 | n-butyl | ethyl | OH | H | phenyl |

TABLE 6-continued
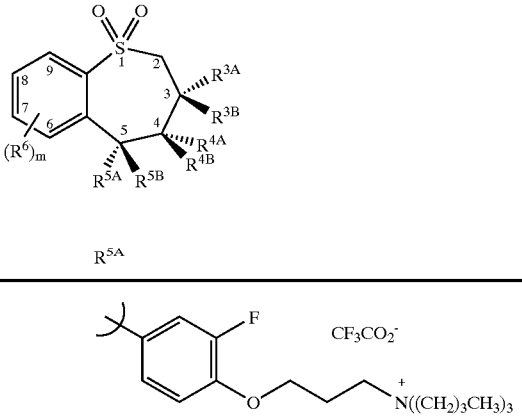
| Compound Number | R³ᴬ | R³ᴮ | R⁴ᴬ | R⁴ᴮ | R⁵ᴬ |
|---|---|---|---|---|---|
| 1286 | n-butyl | n-butyl | OH | H | 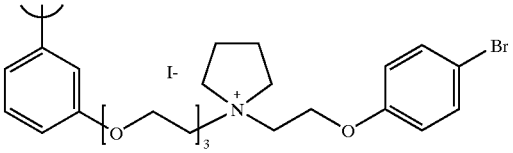 |
| 1287 | n-butyl | ethyl | OH | H | 4-hydroxyphenyl |
| 1288 | n-butyl | n-butyl | OH | H | 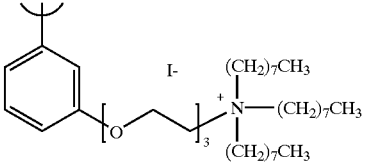 |
| 1289 | n-butyl | n-butyl | OH | H | 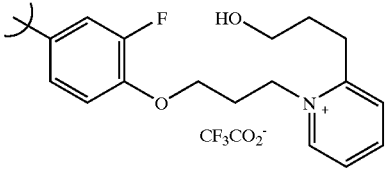 |
| 1290 | n-butyl | n-butyl | OH | H | 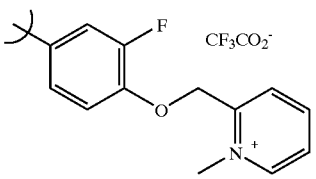 |
| 1291 | n-butyl | n-butyl | OH | H | 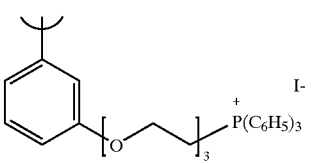 |
| 1292 | n-butyl | n-butyl | OH | H | 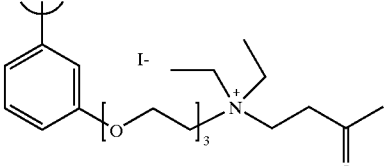 |
| 1293 | n-butyl | n-butyl | OH | H |  |

TABLE 6-continued
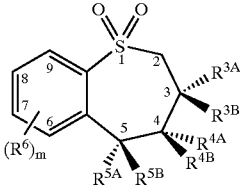
| Compound Number | R³ᴬ | R³ᴮ | R⁴ᴬ | R⁴ᴮ | R⁵ᴬ |
|---|---|---|---|---|---|
| 1294 | n-butyl | n-butyl | OH | H | 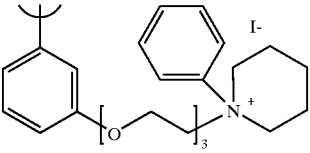 |
| 1295 | n-butyl | n-butyl | OH | H | 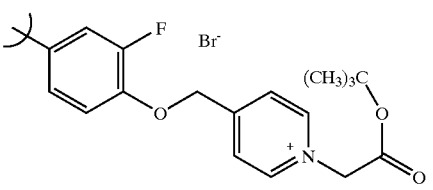 |
| 1296 | n-butyl | n-butyl | OH | H | 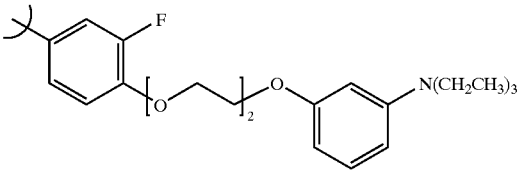 |
| 1297 | n-butyl | n-butyl | OH | H | 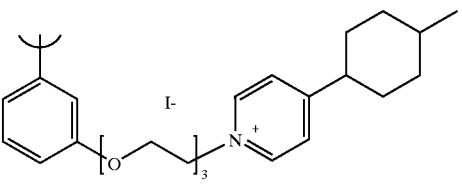 |
| 1298 | n-butyl | n-butyl | OH | H | 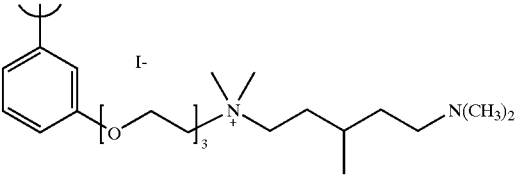 |
| 1299 | n-butyl | n-butyl | OH | H | 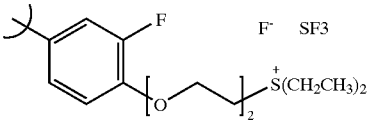 |
| 1300 | n-butyl | ethyl | H | OH | H |
| 1301 | n-butyl | n-butyl | OH | H | 3-methoxyphenyl |
| 1302 | n-butyl | n-butyl | OH | H | 3-hydroxyphenyl |
| 1303 | n-butyl | n-butyl | OH | H | 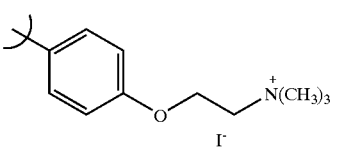 |
| 1304 | n-butyl | n-butyl | OH | H | 3-methoxyphenyl |

TABLE 6-continued

| Compound Number | R3A | R3B | R4A | R4B | R5A |
|---|---|---|---|---|---|
| 1305 | n-butyl | n-butyl | OH | H | 4-fluorophenyl |
| 1306 | n-butyl | n-butyl | OH | H | [4-(2-methoxy-2-phenyl-2-(trifluoromethyl)acetoxy)phenyl] |
| 1307 | n-butyl | n-butyl | OH | H | H |
| 1308 | Ethyl | n-butyl | OH | H | [2-fluoro-4-((7,7-dimethyl-2-oxobicyclo[2.2.1]hept-1-yl)methylsulfonyloxy)phenyl] |
| 1309 | n-butyl | n-butyl | OH | H | 4-methoxyphenyl |
| 1310 | Ethyl | n-butyl | OH | H | phenyl |
| 1311 | n-butyl | ethyl | OH | H | phenyl |
| 1312 | n-butyl | ethyl | OH | H | phenyl |
| 1313 | n-butyl | ethyl | OH | H | phenyl |
| 1314 | Ethyl | n-butyl | OH | H | phenyl |
| 1315 | Ethyl | n-butyl | OH | H | phenyl |
| 1316 | n-butyl | ethyl | OH | H | phenyl |
| 1317 | n-butyl | ethyl | OH | H | phenyl |
| 1318 | Ethyl | n-butyl | OH | H | phenyl |
| 1319 | Ethyl | n-butyl | OH | H | 3-methoxyphenyl |
| 1320 | Ethyl | n-butyl | OH | H | phenyl |
| 1321 | n-butyl | ethyl | OH | H | phenyl |
| 1322 | n-butyl | n-butyl | OH | H | [3-fluoro-4-(2-(pyrrolidin-1-yl)ethoxy)phenyl] |
| 1323 | n-butyl | n-butyl | OH | H | [2-methyl-5-(N-methylcarbamoyl)phenyl] (approx) |
| 1324 | n-butyl | n-butyl | OH | H | [3-(2-(2-(2-(pyrimidinium-1-yl)ethoxy)ethoxy)ethoxy)phenyl] I- |
| 1325 | n-butyl | n-butyl | OH | H | 4-((diethylamino)methyl)phenyl |

TABLE 6-continued

| Compound Number | R³ᴬ | R³ᴮ | R⁴ᴬ | R⁴ᴮ | R⁵ᴬ |
|---|---|---|---|---|---|
| 1326 | n-butyl | n-butyl | OH | H | 3-[2-[2-[2-(N,N-diethyl-N-(2,3-dihydroxypropyl)ammonio)ethoxy]ethoxy]ethoxy]phenyl iodide |
| 1327 | n-butyl | n-butyl | OH | H | 3-fluoro-4-hydroxy-5-iodophenyl |
| 1328 | n-butyl | n-butyl | OH | H | 3-[2-[2-[2-(N-methyl-N-(4-phenylsulfonylpiperidinio))ethoxy]ethoxy]ethoxy]phenyl iodide |
| 1329 | n-butyl | n-butyl | OH | H | 3-fluoro-4-[2-(N-ethylpyrrolidinio)ethoxy]phenyl trifluoroacetate |
| 1330 | n-butyl | n-butyl | OH | H | 3-[2-[2-[2-(N-methyl-N,N-bis(2-phenylethyl)ammonio)ethoxy]ethoxy]ethoxy]phenyl iodide |
| 1331 | n-butyl | n-butyl | OH | H | 3-fluoro-4-[4-(N,N,N-triethylammonio)-2-butynyloxy]phenyl trifluoroacetate |
| 1332 | n-butyl | n-butyl | OH | H | 3-[2-[2-[2-(N-methylmorpholinio)ethoxy]ethoxy]ethoxy]phenyl iodide |
| 1333 | n-butyl | n-butyl | OH | H | 4-[(N,N,N-triethylammonio)methyl]phenyl iodide |

TABLE 6-continued

| Compound Number | R³ᴬ | R³ᴮ | R⁴ᴬ | R⁴ᴮ | R⁵ᴬ |
|---|---|---|---|---|---|
| 1334 | n-butyl | n-butyl | OH | H | 3-(2-(N-ethylmorpholinium)ethoxy)phenyl, I⁻ |
| 1335 | n-butyl | n-butyl | OH | H | 3-(2-(N-methyl-N'-methylpiperazinium)ethoxy)phenyl, I⁻ |
| 1336 | n-butyl | n-butyl | OH | H | 3-(2-(N,N-dimethyl-N-(2-(dimethylamino)ethyl)ammonium)ethoxy)phenyl, I⁻ |
| 1337 | n-butyl | n-butyl | OH | H | 4-((trimethylammonio)methyl)phenyl, I⁻ |
| 1338 | n-butyl | n-butyl | OH | H | 4-methoxyphenyl |
| 1339 | n-butyl | n-butyl | OH | H | 2-(N-tert-butyl-N-methylcarbamoyl)-5-methylphenyl |
| 1340 | n-butyl | ethyl | OH | H | 5-piperonyl |
| 1341 | n-butyl | n-butyl | acetoxy | H | 3-methoxyphenyl |
| 1342 | n-butyl | n-butyl | OH | H | 5-piperonyl |
| 1343 | Ethyl | n-butyl | OH | H | phenyl |
| 1344 | n-butyl | n-butyl | OH | H | 3-fluoro-4-methoxyphenyl |
| 1345 | Ethyl | n-butyl | OH | H | phenyl |
| 1346 | Ethyl | n-butyl | OH | H | phenyl |
| 1347 | n-butyl | n-butyl | OH | H | 3-fluoro-4-methoxyphenyl |
| 1348 | isobutyl | isobutyl | OH | H | phenyl |
| 1349 | Ethyl | n-butyl | OH | H | phenyl |
| 1350 | n-butyl | n-butyl | OH | H | 3-fluoro-4-methoxyphenyl |

TABLE 6-continued

| Compound Number | R³ᴬ | R³ᴮ | R⁴ᴬ | R⁴ᴮ | R⁵ᴬ |
|---|---|---|---|---|---|
| 1351 | n-butyl | n-butyl | OH | H | (4-phenoxy)-O-(CH₂)₅-O-(2-phenyl)-N⁺(CH₂CH₃)(CH₃)₂, CF₃CO₂⁻ |
| 1352 | n-butyl | n-butyl | OH | H | (4-phenoxy)-O-(CH₂)₃-N⁺(CH₂CH₂CH₂CH₃)₃, Br⁻ |
| 1353 | n-butyl | n-butyl | OH | H | (3-fluoro-4-phenoxy)-O-(CH₂)₃-N⁺(CH₂CH₃)₃, CF₃CO₂⁻ |
| 1354 | n-butyl | n-butyl | OH | H | (3-fluoro-4-phenoxy)-O-(CH₂)₃-N⁺(CH₃)(piperazine)N⁺(CH₃)₂, 2 I⁻ |
| 1355 | n-butyl | n-butyl | OH | H | (3-phenoxy)-O-(CH₂)₃-N⁺(pyridinium), I⁻ |
| 1356 | n-butyl | n-butyl | OH | H | (N-methylpyridinium-3-yl), I⁻ |
| 1357 | n-butyl | n-butyl | OH | H | (3-fluoro-4-phenoxy)-O-(CH₂)₃-Br |
| 1358 | n-butyl | n-butyl | OH | H | (3-phenoxy)-O-(CH₂)₃-P⁺(CH₂CH₃)₃, I⁻ |

TABLE 6-continued

| Compound Number | R³ᴬ | R³ᴮ | R⁴ᴬ | R⁴ᴮ | R⁵ᴬ |
|---|---|---|---|---|---|
| 1359 | n-butyl | n-butyl | OH | H | |
| 1360 | n-butyl | n-butyl | OH | H | |
| 1361 | n-butyl | n-butyl | OH | H | |
| 1362 | n-butyl | n-butyl | OH | H | |
| 1363 | n-butyl | n-butyl | OH | H | |
| 1364 | n-butyl | n-butyl | OH | H | |

TABLE 6-continued

| Compound Number | R³ᴬ | R³ᴮ | R⁴ᴬ | R⁴ᴮ | R⁵ᴬ |
|---|---|---|---|---|---|
| 1365 | n-butyl | n-butyl | OH | H | |
| 1366 | n-butyl | n-butyl | OH | H | |
| 1367 | n-butyl | n-butyl | OH | H | |
| 1368 | n-butyl | n-butyl | OH | H | |
| 1369 | n-butyl | n-butyl | OH | H | |
| 1370 | n-butyl | n-butyl | OH | H | |

TABLE 6-continued
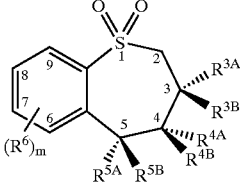
| Compound Number | $R^{3A}$ | $R^{3B}$ | $R^{4A}$ | $R^{4B}$ | $R^{5A}$ |
|---|---|---|---|---|---|
| 1371 | n-butyl | n-butyl | OH | H | 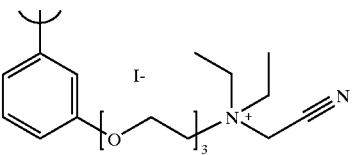 |
| 1372 | n-butyl | n-butyl | OH | H | 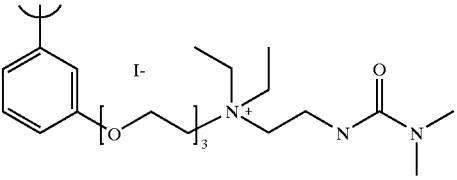 |
| 1373 | n-butyl | n-butyl | OH | H | 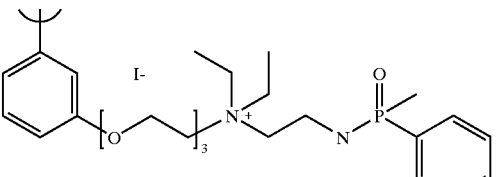 |
| 1374 | n-butyl | n-butyl | OH | H | 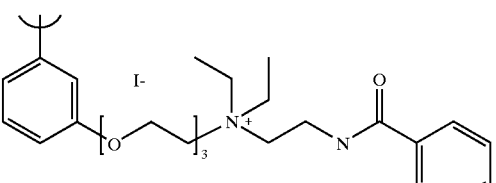 |
| 1375 | n-butyl | n-butyl | OH | H | 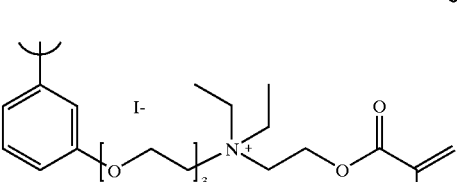 |
| 1376 | n-butyl | n-butyl | OH | H | 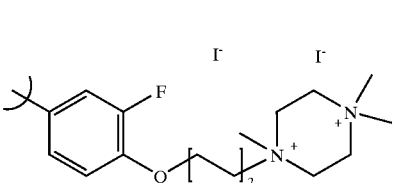 |
| 1377 | n-butyl | n-butyl | OH | H | 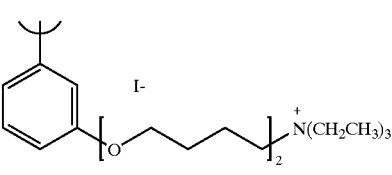 |

TABLE 6-continued

| Compound Number | R³ᴬ | R³ᴮ | R⁴ᴬ | R⁴ᴮ | R⁵ᴬ |
|---|---|---|---|---|---|
| 1378 | n-butyl | n-butyl | OH | H | 3-substituted benzyl-O-CH₂CH₂-N⁺(CH₂CH₃)₃ |
| 1379 | n-butyl | n-butyl | OH | H | 4-substituted benzyl-O-CH₂CH₂-N⁺(CH₂CH₃)₃ I⁻ |
| 1380 | n-butyl | n-butyl | OH | H | 3-substituted phenyl-CH₂CH₂-N⁺(CH₂CH₃)₃ I⁻ |
| 1381 | n-butyl | n-butyl | OH | H | 4-substituted-2-fluorophenyl-O-CH₂-(1-ethylpyridinium-4-yl) I⁻ |
| 1382 | n-butyl | n-butyl | OH | H | 3-substituted phenyl-CH₂-(1-ethylpyridinium-3-yl) I⁻ |
| 1383 | n-butyl | n-butyl | OH | H | 4-substituted-2-fluorophenyl-O-(1-methylpyridinium-2-yl) I⁻ |
| 1384 | n-butyl | n-butyl | OH | H | 4-substituted-2-fluorophenyl-O-(CH₂CH₂O)₃-piperazinium-N,N,N-trimethyl 2 I⁻ |

TABLE 6-continued
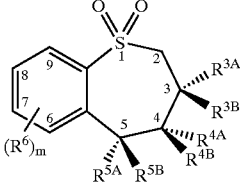
| Compound Number | $R^{3A}$ | $R^{3B}$ | $R^{4A}$ | $R^{4B}$ | $R^{5A}$ |
|---|---|---|---|---|---|
| 1385 | n-butyl | n-butyl | OH | H | 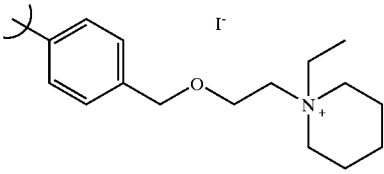 |
| 1386 | n-butyl | n-butyl | OH | H |  |
| 1387 | n-butyl | n-butyl | OH | H | 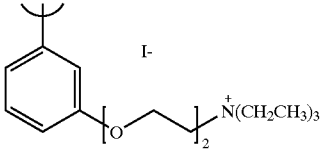 |
| 1388 | n-butyl | n-butyl | OH | H |  |
| 1389 | n-butyl | n-butyl | OH | H | 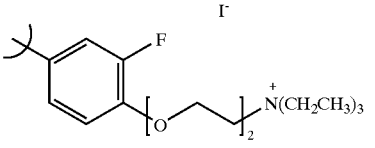 |
| 1390 | n-butyl | n-butyl | OH | H |  |
| 1391 | n-butyl | n-butyl | OH | H | 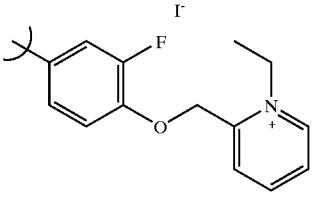 |

TABLE 6-continued
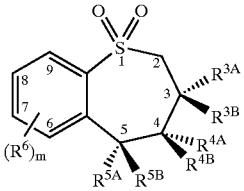
| Compound Number | R³ᴬ | R³ᴮ | R⁴ᴬ | R⁴ᴮ | R⁵ᴬ |
|---|---|---|---|---|---|
| 1392 | n-butyl | n-butyl | OH | H | |
| 1393 | n-butyl | n-butyl | OH | H | |
| 1394 | n-butyl | n-butyl | OH | H | |
| 1395 | n-butyl | n-butyl | OH | H | |
| 1396 | n-butyl | n-butyl | OH | H | |
| 1397 | n-butyl | n-butyl | OH | H | |

TABLE 6-continued

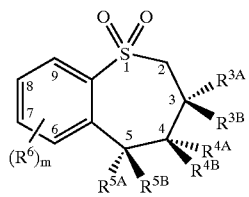

| Compound Number | R³ᴬ | R³ᴮ | R⁴ᴬ | R⁴ᴮ | R⁵ᴬ |
|---|---|---|---|---|---|
| 1398 | n-butyl | n-butyl | OH | H | 3-(2-pyridinium-1-yl-ethyl)phenyl, I⁻ |
| 1399 | n-butyl | n-butyl | OH | H | 4-(2-fluoro)-phenyl-O-(CH₂)₃-N⁺(CH₃)-piperazine-N⁺(CH₃)₂, 2 I⁻ |
| 1400 | n-butyl | n-butyl | OH | H | 4-(2-fluoro)-phenyl-O-(CH₂)₄-N⁺(CH₃)₃, I⁻ |
| 1401 | n-butyl | n-butyl | OH | H | 4-(2-fluoro)-phenyl-O-(CH₂)₂-N⁺-morpholine-(CH₂)₃SO₃H, I⁻ |
| 1402 | n-butyl | n-butyl | OH | H | 4-[O-(CH₂)₂-pyridinium]phenyl, I⁻ |
| 1403 | n-butyl | n-butyl | OH | H | 3-[O-(CH₂)₂-pyridinium]phenyl, I⁻ |
| 1404 | n-butyl | n-butyl | OH | H | 3-[CH₂-O-(CH₂)₂-pyridinium]phenyl, I⁻ |

TABLE 6-continued
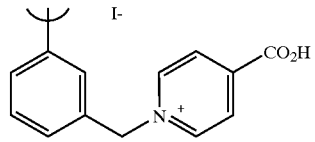
| Compound Number | R³ᴬ | R³ᴮ | R⁴ᴬ | R⁴ᴮ | R⁵ᴬ |
|---|---|---|---|---|---|
| 1405 | n-butyl | n-butyl | OH | H |  |
| 1406 | n-butyl | n-butyl | OH | H | 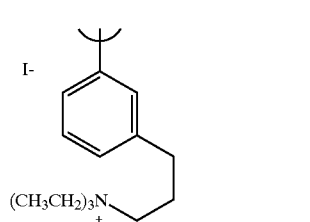 |
| 1407 | n-butyl | n-butyl | OH | H | 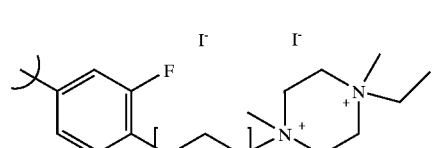 |
| 1408 | n-butyl | n-butyl | OH | H | 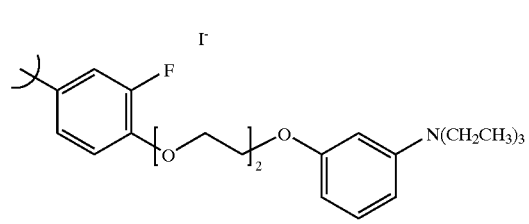 |
| 1409 | n-butyl | n-butyl | OH | H | 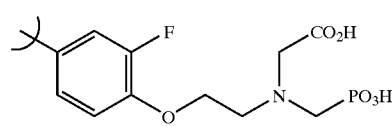 |
| 1410 | n-butyl | n-butyl | OH | H | 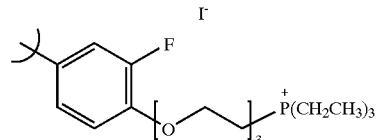 |
| 1411 | n-butyl | n-butyl | OH | H |  |

TABLE 6-continued

| Compound Number | R³ᴬ | R³ᴮ | R⁴ᴬ | R⁴ᴮ | R⁵ᴬ |
| --- | --- | --- | --- | --- | --- |
| 1412 | n-butyl | n-butyl | OH | H | 3-(N-ethylpyridinium-2-ylmethylamino)phenyl, I⁻ |
| 1413 | n-butyl | n-butyl | OH | H | 3-(N-ethylpyridinium-3-ylmethylamino)phenyl, I⁻ |
| 1414 | n-butyl | n-butyl | OH | H | 3-(N-ethylpyridinium-4-ylmethylamino)phenyl, I⁻ |
| 1415 | n-butyl | n-butyl | OH | H | 2-(N-ethylpyridinium-3-ylamino)pyridin-4-yl, I⁻ |
| 1416 | n-butyl | n-butyl | OH | H | 2-(3-triethylammoniopropylamino)pyridin-4-yl, I⁻ |
| 1417 | n-butyl | n-butyl | OH | H | 2-(triethylammoniomethyl)pyridin-4-yl, I⁻ |

TABLE 6-continued
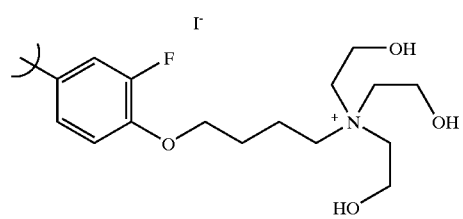
| Compound Number | $R^{3A}$ | $R^{3B}$ | $R^{4A}$ | $R^{4B}$ | $R^{5A}$ |
|---|---|---|---|---|---|
| 1418 | n-butyl | n-butyl | OH | H | 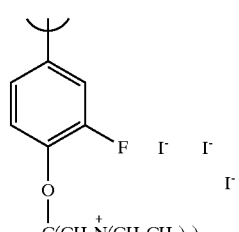 |
| 1419 | n-butyl | n-butyl | OH | H | 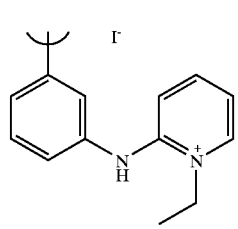 |
| 1420 | n-butyl | n-butyl | OH | H | 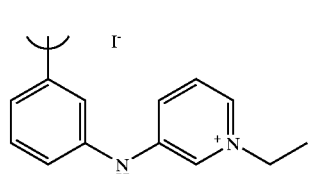 |
| 1421 | n-butyl | n-butyl | OH | H | 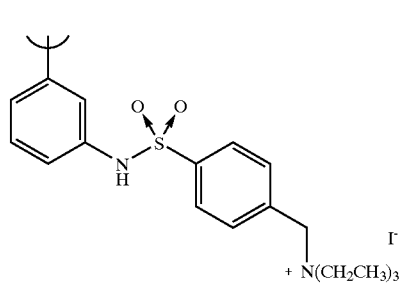 |
| 1422 | n-butyl | n-butyl | OH | H | 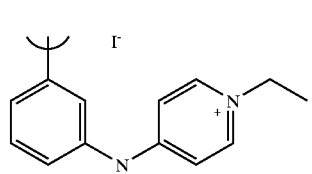 |
| 1423 | n-butyl | n-butyl | OH | H |  |

TABLE 6-continued

| Compound Number | R³ᴬ | R³ᴮ | R⁴ᴬ | R⁴ᴮ | R⁵ᴬ |
|---|---|---|---|---|---|
| 1424 | n-butyl | n-butyl | OH | H | 4-[(1-ethylpyridinium-4-yl)amino]pyridin-2-yl, I⁻ |
| 1425 | n-butyl | n-butyl | OH | H | 2-[5-(triethylammonio)pentyloxy]pyridin-4-yl, I⁻ |
| 1426 | n-butyl | n-butyl | OH | H | 2-[4-(triethylammonio)butylamino]pyridin-4-yl, I⁻ |
| 1427 | n-butyl | n-butyl | OH | H | 3-{[2-(2-{2-[(3-hydroxyphenyl)(dimethyl)ammonio]ethoxy}ethoxy)ethoxy]}phenyl, I⁻ |
| 1428 | n-butyl | n-butyl | OH | H | 3-[(3-sulfopropyl)amino]phenyl |
| 1429 | n-butyl | n-butyl | OH | H | 3-(triphenylammonio)phenyl, Br⁻ |

TABLE 6-continued
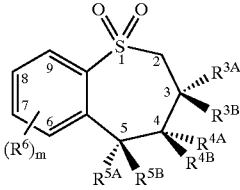
| Compound Number | R³ᴬ | R³ᴮ | R⁴ᴬ | R⁴ᴮ | R⁵ᴬ |
|---|---|---|---|---|---|
| 1430 | n-butyl | n-butyl | OH | H | 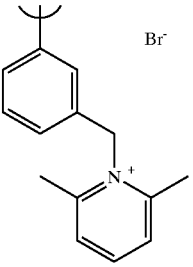 |
| 1431 | n-butyl | n-butyl | OH | H | 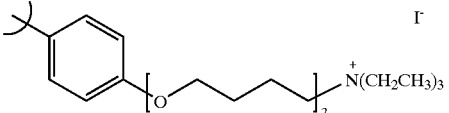 |
| 1432 | n-butyl | n-butyl | OH | H | 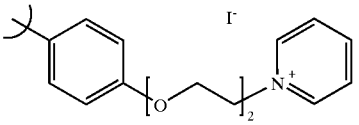 |
| 1433 | n-butyl | n-butyl | OH | H | 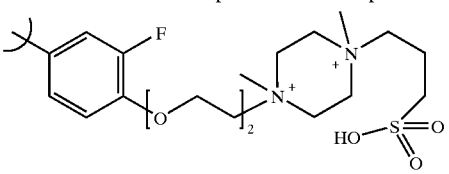 |
| 1434 | n-butyl | n-butyl | OH | H | 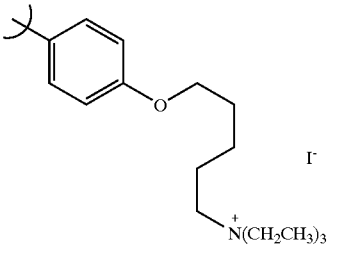 |
| 1435 | n-butyl | n-butyl | OH | H | 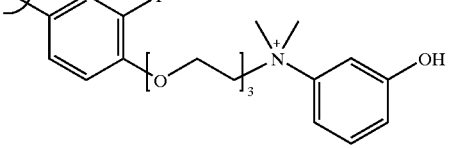 |
| 1436 | n-butyl | n-butyl | OH | H | 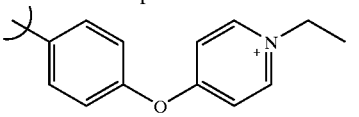 |

TABLE 6-continued
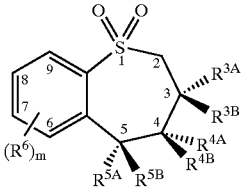
| Compound Number | R3A | R3B | R4A | R4B | R5A |
|---|---|---|---|---|---|
| 1437 | n-butyl | n-butyl | OH | H | 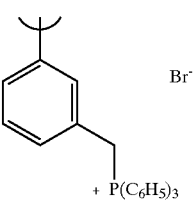 |
| 1438 | n-butyl | n-butyl | OH | H | 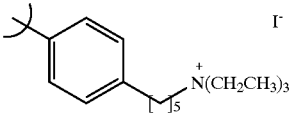 |
| 1439 | n-butyl | n-butyl | OH | H | 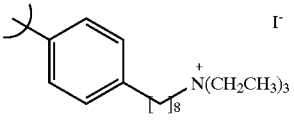 |
| 1440 | n-butyl | n-butyl | OH | H | 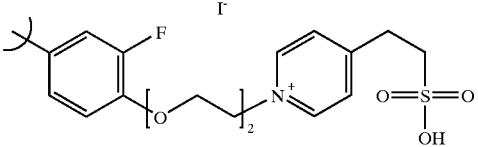 |
| 1441 | n-butyl | n-butyl | OH | H | 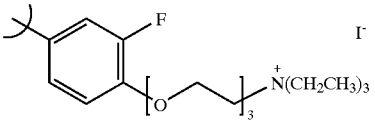 |
| 1442 | n-butyl | n-butyl | OH | H | 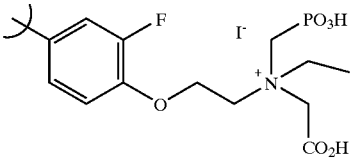 |
| 1443 | n-butyl | n-butyl | OH | H | 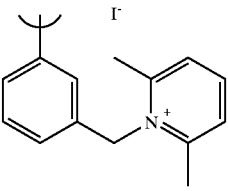 |

TABLE 6-continued
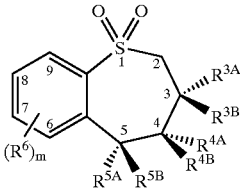
| Compound Number | R³ᴬ | R³ᴮ | R⁴ᴬ | R⁴ᴮ | R⁵ᴬ |
|---|---|---|---|---|---|
| 1444 | n-butyl | n-butyl | OH | H | 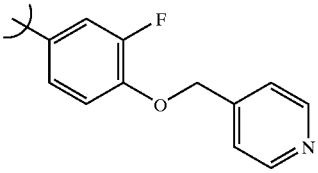 |
| 1445 | n-butyl | n-butyl | OH | H | 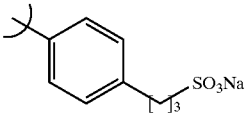 |
| 1446 | n-butyl | n-butyl | OH | H | 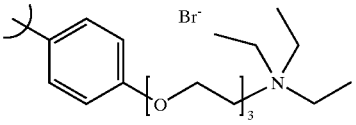 |
| 1447 | n-butyl | n-butyl | OH | H | 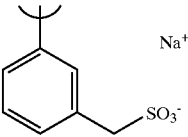 |
| 1448 | n-butyl | n-butyl | OH | H | 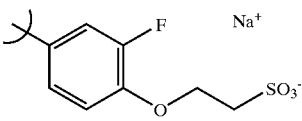 |
| 1449 | n-butyl | n-butyl | OH | H | 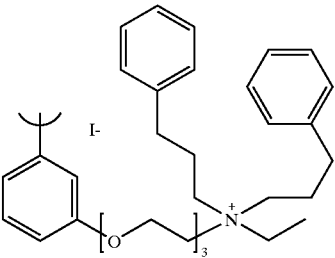 |
| 1450 | n-butyl | n-butyl | OH | H | phenyl |
| 1451 | n-butyl | n-butyl | OH | H | 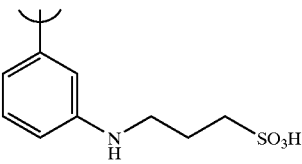 |

TABLE 7

| Compound Number | R^5B | (R^6)_m |
|---|---|---|
| 101 | H | (structure shown) at the 7-position |
| 102 | H | 7-trimethylammonium iodide |
| 103 | H | 7-trimethylammonium iodide |
| 104 | H | 7-dimethylamino |
| 105 | H | 7-methanesulfonamido |
| 106 | H | 7-(2'-bromoacetamido) |
| 107 | H | 7-amino |
| 108 | H | 7-(hexylamido) |
| 109 | H | 7-amino |
| 110 | H | 7-acetamido |
| 111 | H | 7-amino |
| 112 | H | 7-amino |
| 113 | H | 7-amino |
| 114 | H | 7-amino |
| 115 | H | 7-(O-benzylcarbamato) |
| 116 | H | 7-(O-benzylcarbamato) |
| 117 | H | 7-(O-benzylcarbamato) |
| 118 | H | 7-(O-benzylcarbamato) |
| 119 | H | 7-(O-tert-butylcarbamato) |
| 120 | H | 7-(O-benzylcarbamato) |
| 121 | H | 7-amino |
| 122 | H | 7-amino |
| 123 | H | 7-hexylamino |
| 124 | H | 7-(hexylamino) |
| 125 | H | (structure shown) at the 8-position |
| 126 | H | 7-(O-benzylcarbamato) |
| 127 | H | 7-amino |
| 128 | H | 7-(O-benzylcarbamato) |
| 129 | H | 7-amino |
| 131 | H | (structure shown) at the 7-position |

TABLE 7-continued
| Compound Number | $R^{5B}$ | $(R^6)_m$ |
|---|---|---|
| 132 | H | 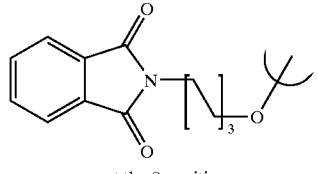 at the 8-position |
| 133 | H | 8-(hexyloxy) |
| 134 | H | 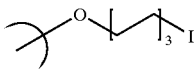 at the 8-position |
| 135 | H | 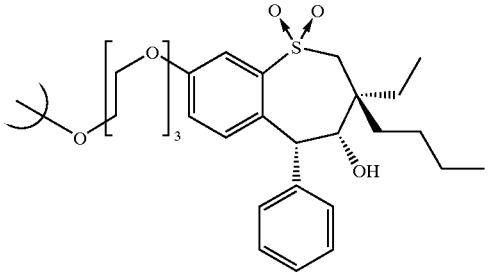 at the 8-position |
| 136 | H | 8-hydroxy |
| 137 | H | 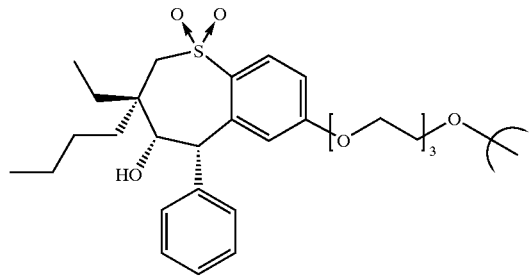 at the 7-position |
| 138 | H | 8-acetoxy |
| 139 | H | 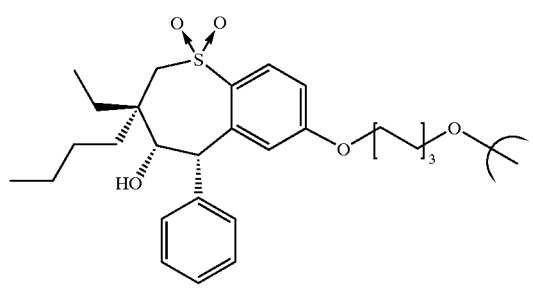 at the 7-position |
| 140 | | |
| 141 | | |
| 142 | 3-methoxy-phenyl | 7-methylmercapto |
| 143 | H | 7-methylmercapto |
| 144 | H | 7-(N-azetidinyl) |
| 262 | H | 7-methoxy |

TABLE 7-continued

| Compound Number | R$^{5B}$ | (R$^6$)$_m$ |
|---|---|---|
| 263 | 3-methoxy-phenyl | 7-methoxy |
| 264 | H | 7-methoxy |
| 265 | 3-trifluoro-methyl-phenyl | 7-methoxy |
| 266 | H | 7-hydroxy |
| 267 | H | 7-methoxy |
| 268 | H | 7-methoxy |
| 269 | 4-fluoro-phenyl | 7-methoxy |
| 270 | H | 7-hydroxy |
| 271 | H | 7-bromo |
| 272 | 3-methoxy-phenyl | 7-bromo |
| 273 | 4-fluoro-phenyl | 7-fluoro |
| 274 | H | 7-fluoro |
| 275 | 3-methoxy-phenyl | 7-fluoro |
| 276 | H | 7-fluoro |
| 277 | H | 7-methoxy |
| 278 | H | 7-methoxy |
| 279 | H | 7-methoxy |
| 280 | H | 7-methoxy |
| 281 | H | 7-methylmercapto |
| 282 | H | 7-methyl |
| 283 | 4-fluoro-phenyl | 7-methyl |
| 284 | H | 7-(4'-morpholino) |
| 286 | H | 7-(O-benzylcarbamato) |
| 287 | H | 7-amino |
| 288 | H | 7-amino |
| 289 | H | 7-amino |
| 290 | H | 7-amino |
| 291 | H | 7-(O-benzylcarbamato) |
| 292 | H | 7-amino |
| 293 | H | 7-benzylamino |
| 294 | H | 7-dimethylamino |
| 295 | H | 7-amino |
| 296 | H | 7-amino |
| 1000 | H | 7-dimethylamino |
| 1001 | H | 7-dimethylamino |
| 1002 | H | 7-dimethylamino |
| 1003 | H | 7-dimethylamino |
| 1004 | H | 7-dimethylamino |
| 1005 | H | 7-dimethylamino |
| 1006 | H | 7-dimethylamino |
| 1007 | H | 7-dimethylamino |
| 1008 | H | 7-dimethylamino |
| 1009 | H | 7-dimethylamino |
| 1010 | H | 7-dimethylamino |
| 1011 | H | 7-dimethylamino |
| 1012 | H | 7-dimethylamino; 9-methoxy |
| 1013 | H | 7-dimethylamino |
| 1014 | H | 7-dimethylamino; 9-methoxy |
| 1015 | H | 7-dimethylamino |
| 1016 | H | 7-dimethylamino |
| 1017 | H | 7-dimethylamino |
| 1018 | H | 7-dimethylamino |
| 1019 | H | 7-dimethylamino |
| 1020 | H | 7-dimethylamino |
| 1021 | H | 7-dimethylamino |
| 1022 | H | 7-dimethylamino |
| 1023 | H | 7-dimethylamino |
| 1024 | H | 7-dimethylamino |
| 1025 | H | 7-dimethylamino |
| 1026 | H | 7-dimethylamino |
| 1027 | H | 7-dimethylamino |
| 1028 | H | 7-dimethylamino |
| 1029 | H | 7-dimethylamino |
| 1030 | H | 7-dimethylamino |
| 1031 | H | 7-dimethylamino |
| 1032 | H | 7-dimethylamino |
| 1033 | H | 7-dimethylamino |
| 1034 | H | 7-dimethylamino |
| 1035 | H | 7-dimethylamino |
| 1036 | H | 7-dimethylamino |
| 1037 | H | 7-dimethylamino |
| 1038 | H | 7-dimethylamino |

TABLE 7-continued

| Compound Number | R⁵ᴮ | (R⁶)ₘ |
|---|---|---|
| 1039 | H | 7-dimethylamino |
| 1040 | H | 7-dimethylamino |
| 1041 | H | 7-dimethylamino |
| 1042 | H | 7-dimethylamino |
| 1043 | 3-Fluoro-4-methoxy-phenyl | 7-dimethylamino |
| 1044 | H | 7-dimethylamino |
| 1045 | H | 7-dimethylamino |
| 1046 | H | 7-dimethylamino |
| 1047 | H | 7-dimethylamino |
| 1048 | H | 7-dimethylamino |
| 1049 | H | 7-dimethylamino |
| 1050 | H | 7-dimethylamino |
| 1051 | H | 7-dimethylamino |
| 1052 | H | 7-dimethylamino |
| 1053 | H | 7-dimethylamino |
| 1054 | H | 7-dimethylamino |
| 1055 | H | 7-dimethylamino |
| 1056 | H | 7-dimethylamino |
| 1057 | H | 7-dimethylamino |
| 1058 | H | 7-dimethylamino |
| 1059 | H | 7-dimethylamino |
| 1060 | H | 7-methylamino |
| 1061 | H | 7-methylamino |
| 1062 | H | 7-methylamino |
| 1063 | H | 7-methylamino |
| 1064 | H | 7-methylamino |
| 1065 | H | 7-dimethylamino |
| 1066 | H | 7-dimethylamino |
| 1067 | H | 9-dimethylamino |
| 1068 | H | 7-dimethylamino |
| 1069 | H | 7-dimethylamino; 9-dimethylamino |
| 1070 | H | 7-dimethylamino |
| 1071 | H | 7-dimethylamino |
| 1072 | H | 7-dimethylamino |
| 1073 | H | 7-dimethylamino |
| 1074 | H | 7-dimethylamino |
| 1075 | H | 7-dimethylamino; 9-dimethylamino |
| 1076 | H | 7-dimethylamino |
| 1077 | H | 7-dimethylamino |
| 1078 | H | 7-dimethylamino |
| 1079 | H | 7-dimethylamino |
| 1080 | H | 7-dimethylamino |
| 1081 | H | 7-dimethylamino |
| 1082 | H | 7-dimethylamino |
| 1083 | H | 7-dimethylamino |
| 1084 | H | 7-dimethylamino |
| 1085 | H | 7-dimethylamino |
| 1086 | H | 7-dimethylamino |
| 1087 | H | 7-dimethylamino |
| 1088 | H | 7-dimethylamino |
| 1089 | H | 7-dimethylamino |
| 1090 | H | 7-dimethylamino |
| 1091 | H | 7-dimethylamino |
| 1092 | H | 7-dimethylamino |
| 1093 | H | 7-dimethylamino |
| 1094 | H | 7-dimethylamino |
| 1095 | H | 7-dimethylamino |
| 1096 | H | 7-dimethylamino |
| 1097 | H | 7-dimethylamino |
| 1098 | H | 7-dimethylamino |
| 1099 | H | 7-dimethylamino |
| 1100 | H | 7-dimethylamino |
| 1101 | H | 7-dimethylamino |
| 1102 | H | 7-dimethylamino |
| 1103 | H | 7-dimethylamino |
| 1104 | H | 7-dimethylamino |
| 1105 | H | 7-dimethylamino |
| 1106 | H | 7-dimethylamino |
| 1107 | H | 7-dimethylamino |
| 1108 | H | 7-dimethylamino |
| 1109 | H | 7-dimethylamino |
| 1110 | H | 7-dimethylamino |
| 1111 | H | 7-dimethylamino |

TABLE 7-continued

| Compound Number | R$^{5B}$ | (R$^6$)$_m$ |
|---|---|---|
| 1112 | H | 7-dimethylamino |
| 1113 | H | 7-dimethylamino |
| 1114 | H | 7-methylamino |
| 1115 | H | 7-dimethylamino |
| 1116 | H | 7-dimethylamino |
| 1117 | H | 7-dimethylamino |
| 1118 | H | 7-dimethylamino |
| 1119 | H | 7-dimethylamino |
| 1120 | H | 7-dimethylamino |
| 1121 | H | 7-dimethylamino |
| 1122 | H | 7-dimethylamino |
| 1123 | H | 7-dimethylamino |
| 1124 | H | 7-dimethylamino |
| 1125 | H | 7-dimethylamino |
| 1126 | H | 7-dimethylamino |
| 1127 | H | 7-dimethylamino |
| 1128 | H | 7-dimethylamino |
| 1129 | H | 9-dimethylamino |
| 1130 | H | 7-dimethylamino |
| 1131 | H | 7-dimethylamino |
| 1132 | H | 7-dimethylamino |
| 1133 | H | 7-dimethylamino |
| 1134 | H | 7-dimethylamino |
| 1135 | H | 7-dimethylamino |
| 1136 | H | 7-dimethylamino |
| 1137 | H | 9-(2',2'-dimethylhydrazino) |
| 1138 | H | 7-dimethylamino |
| 1139 | H | 7-dimethylamino |
| 1140 | H | 7-(2',2'-dimethylhydrazino) |
| 1141 | H | 7-ethylmethylamino |
| 1142 | H | 7-dimethylamino |
| 1143 | H | 7-dimethylamino |
| 1144 | H | 7-dimethylamino |
| 1145 | H | 9-dimethylamino |
| 1146 | H | 7-dimethylamino |
| 1147 | H | 7-diethylamino |
| 1148 | H | 7-dimethylsulfonium, fluoride salt |
| 1149 | H | 7-ethylamino |
| 1150 | H | 7-ethylmethylamino |
| 1151 | H | 7-dimethylamino |
| 1152 | H | 7-(ethoxymethyl)methylamino |
| 1153 | H | 7-methylamino |
| 1154 | H | 9-methoxy |
| 1155 | H | 7-methyl |
| 1156 | H | 7-methylmercapto |
| 1157 | H | 7-fluoro; 9-dimethylamino |
| 1158 | H | 7-methoxy |
| 1159 | H | 7-dimethylamino |
| 1160 | H | 7-diethylamino |
| 1161 | H | 7-dimethylamino |
| 1162 | H | 7-dimethylamino |
| 1163 | H | 7-methoxy |
| 1164 | H | 7-methoxy |
| 1165 | H | 7-trimethylammonium iodide |
| 1166 | H | 7-trimethylammonium iodide |
| 1167 | H | 7-dimethylamino |
| 1168 | H | 7-trimethylammonium iodide |
| 1169 | H | 8-dimethylamino |
| 1170 | H | 7-ethylpropylamino |
| 1171 | H | 7-dimethylamino |
| 1172 | H | 7-methoxy |
| 1173 | H | 7-ethylpropylamino |
| 1174 | H | 7-phenyl |
| 1175 | H | 7-methylsulfonyl |
| 1176 | H | 9-fluoro |
| 1177 | H | 7-butylmethylamino |
| 1178 | H | 7-dimethylamino |
| 1179 | H | 8-methoxy |
| 1180 | H | 7-trimethylammonium iodide |
| 1181 | H | 7-butylmethylamino |
| 1182 | H | 7-methoxy |
| 1183 | H | 7-fluoro |
| 1184 | H | 7-fluoro; 9-fluoro |
| 1185 | H | 7-fluoro |
| 1186 | H | 7-fluoro; 9-fluoro |

TABLE 7-continued

| Compound Number | $R^{5B}$ | $(R^6)_m$ |
|---|---|---|
| 1187 | H | 7-methyl |
| 1188 | H | 7-trimethylammonium iodide |
| 1189 | H | 7-trimethylammonium iodide |
| 1190 | H | 7-bromo |
| 1191 | H | 7-hydroxy |
| 1192 | H | 7-hydroxy |
| 1193 | H | 7-dimethylamino |
| 1194 | H | 7-dimethylamino |
| 1195 | H | 7-(4'-methylpiperazin-1-yl) |
| 1196 | H | 7-methoxy |
| 1197 | H | 7-(N-methylformamido) |
| 1198 | H | 7-methoxy |
| 1199 | H | 7-dimethylamino |
| 1200 | phenyl | 7-dimethylamino |
| 1201 | H | 7-methyl |
| 1202 | H | 7-methoxy |
| 1203 | H | 7-(4'-tert-butylphenyl) |
| 1204 | H | 7-methoxy |
| 1205 | H | 7-dimethylamino |
| 1206 | H | 7-dimethylamino |
| 1207 | H | 7-dimethylamino |
| 1208 | H | 7-dimethylamino |
| 1209 | H | 7-dimethylphenyl |
| 1210 | H | 7-dimethylamino |
| 1211 | H | 7-dimethylamino |
| 1212 | H | 9-(4'-morpholino) |
| 1213 | 3-fluoro-4-methoxy-phenyl | 7-dimethylamino |
| 1214 | H | 7-(N-methylformamido) |
| 1215 | H | 9-methylmercapto |
| 1216 | H | 7-bromo |
| 1217 | H | 7-dimethylamino |
| 1218 | H | 9-methylsulfonyl |
| 1219 | H | 7-dimethylamino |
| 1220 | H | 7-isopropylamino |
| 1221 | H | 7-dimethylamino |
| 1222 | H | 7-ethylamino |
| 1223 | H | 8-bromo; 7-methylamino |
| 1224 | H | 7-fluoro |
| 1225 | H | 7-dimethylamino |
| 1226 | H | 7-bromo |
| 1227 | H | 7-(tert-butylamino |
| 1228 | H | 8-bromo; 7-dimethylamino |
| 1229 | H | 7-dimethylamino |
| 1230 | H | 9-dimethylamino; 7-fluoro |
| 1231 | H | 7-dimethylamino |
| 1232 | H | 9-dimethylamino |
| 1233 | H | 7-dimethylamino |
| 1234 | H | 7-dimethylamino |
| 1235 | H | 7-dimethylamino |
| 1236 | H | 7-dimethylamino |
| 1237 | H | 7-dimethylamino |
| 1238 | H | 7-dimethylamino |
| 1239 | H | 7-dimethylamino |
| 1240 | H | 7-dimethylamino |
| 1241 | H | 7-dimethylamino |
| 1242 | H | 7-dimethylamino |
| 1243 | H | 7-dimethylamino |
| 1244 | H | 7-(1'-methylhydrazido) |
| 1245 | H | 7-dimethylamino |
| 1246 | H | 7-dimethylamino |
| 1247 | H | 7-dimethylamino |
| 1248 | H | 7-dimethylamino |
| 1249 | H | 7-dimethylamino |
| 1250 | H | 7-dimethylamino |
| 1251 | H | 7-dimethylamino |
| 1252 | H | 7-dimethylamino |
| 1253 | H | 7-dimethylamino |
| 1254 | H | 7-dimethylamino |
| 1255 | H | 7-dimethylamino |
| 1256 | H | 7-dimethylamino |
| 1257 | H | 8-bromo; 7-dimethylamino |

TABLE 7-continued

| Compound Number | $R^{5B}$ | $(R^6)_m$ |
|---|---|---|
| 1258 | H | 9-(tert-butylamino) |
| 1259 | phenyl | 7-dimethylamino |
| 1260 | H | 7-dimethylamino |
| 1261 | H | 7-dimethylamino |
| 1262 | H | 7-dimethylamino |
| 1263 | H | 7-bromo |
| 1264 | H | 7-isopropylamino |
| 1265 | H | 9-isopropylamino |
| 1266 | H | 7-dimethylamino |
| 1267 | H | 7-carboxy, methyl ester |
| 1268 | H | 7-dimethylamino |
| 1269 | H | 7-dimethylamino |
| 1270 | H | 7-dimethylamino |
| 1271 | H | 7-dimethylamino |
| 1272 | H | 7-dimethylamino |
| 1273 | H | 7-dimethylamino |
| 1274 | H | 7-dimethylamino |
| 1275 | H | 7-dimethylamino |
| 1276 | H | 7-dimethylamino |
| 1277 | H | 7-dimethylamino |
| 1278 | H | 7-dimethylamino |
| 1279 | H | 7-dimethylamino |
| 1280 | H | 7-dimethylamino |
| 1281 | H | 7-dimethylamino |
| 1282 | H | 7-trimethylammonium iodide |
| 1283 | H | 7-dimethylamino |
| 1284 | H | 9-ethylamino |
| 1285 | H | 7-dimethylamino |
| 1286 | H | 7-dimethylamino |
| 1287 | H | 7-dimethylamino |
| 1288 | H | 7-dimethylamino |
| 1289 | H | 7-dimethylamino |
| 1290 | H | 7-dimethylamino |
| 1291 | H | 7-dimethylamino |
| 1292 | H | 7-dimethylamino |
| 1293 | H | 7-dimethylamino |
| 1294 | H | 7-dimethylamino |
| 1295 | H | 7-dimethylamino |
| 1296 | H | 7-dimethylamino |
| 1297 | H | 7-dimethylamino |
| 1298 | H | 7-dimethylamino |
| 1299 | H | 7-dimethylamino |
| 1300 | phenyl | 7-dimethylamino |
| 1301 | H | 7-trimethylammonium iodide |
| 1302 | H | 9-hydroxy |
| 1303 | H | 7-dimethylamino |
| 1304 | H | 7-tert-butylamino |
| 1305 | H | 9-methylamino |
| 1306 | H | 7-dimethylamino |
| 1307 | 4-methoxy-phenyl | 9-(4'-morpholino) |
| 1308 | H | 7-dimethylamino |
| 1309 | H | 9-fluoro |
| 1310 | H | 7-amino |
| 1311 | H | 7-(hydroxylamino) |
| 1312 | H | 8-hexyloxy |
| 1313 | H | 8-ethoxy |
| 1314 | H | 7-(hydroxylamino) |
| 1315 | H | 7-(hexyloxy) |
| 1316 | H | 8-hydroxy |
| 1317 | H | 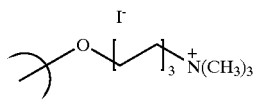 at the 8-position |
| 1318 | H | 7-dimethylamino |
| 1319 | H | 7-fluoro |
| 1320 | H | 7-amino |

TABLE 7-continued

| Compound Number | $R^{5B}$ | $(R^6)_m$ |
|---|---|---|
| 1321 | H | 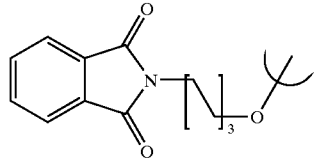 at the 8-position |
| 1322 | H | 7-dimethylamino |
| 1323 | H | 7-dimethylamino |
| 1324 | H | 7-dimethylamino |
| 1325 | H | 7-dimethylamino |
| 1326 | H | 7-dimethylamino |
| 1327 | H | 7-dimethylamino |
| 1328 | H | 7-dimethylamino |
| 1329 | H | 7-dimethylamino |
| 1330 | H | 7-dimethylamino |
| 1331 | H | 7-dimethylamino |
| 1332 | H | 7-dimethylamino |
| 1333 | H | 7-dimethylamino |
| 1334 | H | 7-dimethylamino |
| 1335 | H | 7-dimethylamino |
| 1336 | H | 7-dimethylamino |
| 1337 | H | 7-dimethylamino |
| 1338 | H | 7-(4'-methylpiperazinyl) |
| 1339 | H | 7-dimethylamino |
| 1340 | H | 7-methyl |
| 1341 | H | 7-dimethylamino |
| 1342 | H | 7-(4'-fluorophenyl) |
| 1343 | H | 7-amino |
| 1344 | H | 7-dimethylamino |
| 1345 | H | 7-trimethylammonium iodide |
| 1346 | H | 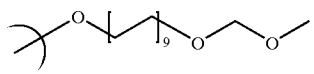 at the 8-position |
| 1347 | H | 7-dimethylamino |
| 1348 | H | 7-dimethylamino |
| 1349 | H | 7-dimethylamino |
| 1350 | H | 7-trimethylammonium iodide |
| 1351 | H | 7-dimethylamino |
| 1352 | H | 7-dimethylamino |
| 1353 | H | 7-dimethylamino |
| 1354 | H | 7-dimethylamino |
| 1355 | H | 7-dimethylamino |
| 1356 | H | 7-dimethylamino |
| 1357 | H | 7-dimethylamino |
| 1358 | H | 7-dimethylamino |
| 1359 | H | 7-dimethylamino |
| 1360 | H | 7-dimethylamino |
| 1361 | H | 7-dimethylamino |
| 1362 | H | 7-dimethylamino |
| 1363 | H | 7-dimethylamino |
| 1364 | H | 7-dimethylamino |
| 1365 | H | 7-dimethylamino |
| 1366 | H | 7-dimethylamino |
| 1367 | H | 7-dimethylamino |
| 1368 | H | 7-dimethylamino |
| 1369 | H | 7-dimethylamino |
| 1370 | H | 7-dimethylamino |
| 1371 | H | 7-dimethylamino |
| 1372 | H | 7-dimethylamino |
| 1373 | H | 7-dimethylamino |
| 1374 | H | 7-dimethylamino |
| 1375 | H | 7-dimethylamino |
| 1376 | H | 7-dimethylamino |
| 1377 | H | 7-dimethylamino |
| 1378 | H | 7-dimethylamino |
| 1379 | H | 7-dimethylamino |
| 1380 | H | 7-dimethylamino |

TABLE 7-continued

| Compound Number | R$^{5B}$ | (R$^6$)$_m$ |
|---|---|---|
| 1381 | H | 7-dimethylamino |
| 1382 | H | 7-dimethylamino |
| 1383 | H | 7-dimethylamino |
| 1384 | H | 7-dimethylamino |
| 1385 | H | 7-dimethylamino |
| 1386 | H | 7-dimethylamino |
| 1387 | H | 7-dimethylamino |
| 1388 | H | 7-dimethylamino |
| 1389 | H | 7-dimethylamino |
| 1390 | H | 7-dimethylamino |
| 1391 | H | 7-dimethylamino |
| 1392 | H | 7-dimethylamino |
| 1393 | H | 7-dimethylamino |
| 1394 | H | 7-dimethylamino |
| 1395 | H | 7-dimethylamino |
| 1396 | H | 7-dimethylamino |
| 1397 | H | 7-dimethylamino |
| 1398 | H | 7-dimethylamino |
| 1399 | H | 7-dimethylamino |
| 1400 | H | 7-dimethylamino |
| 1401 | H | 7-dimethylamino |
| 1402 | H | 7-dimethylamino |
| 1403 | H | 7-dimethylamino |
| 1404 | H | 7-dimethylamino |
| 1405 | H | 7-dimethylamino |
| 1406 | H | 7-dimethylamino |
| 1407 | H | 7-dimethylamino |
| 1408 | H | 7-dimethylamino |
| 1409 | H | 7-dimethylamino |
| 1410 | H | 7-dimethylamino |
| 1411 | H | 7-dimethylamino |
| 1412 | H | 7-dimethylamino |
| 1413 | H | 7-dimethylamino |
| 1414 | H | 7-dimethylamino |
| 1415 | H | 7-dimethylamino |
| 1416 | H | 7-dimethylamino |
| 1417 | H | 7-dimethylamino |
| 1418 | H | 7-dimethylamino |
| 1419 | H | 7-dimethylamino |
| 1420 | H | 7-dimethylamino |
| 1421 | H | 7-dimethylamino |
| 1422 | H | 7-dimethylamino |
| 1423 | H | 7-dimethylamino |
| 1424 | H | 7-dimethylamino |
| 1425 | H | 7-dimethylamino |
| 1426 | H | 7-dimethylamino |
| 1427 | H | 7-dimethylamino |
| 1428 | H | 7-dimethylamino |
| 1429 | H | 7-dimethylamino |
| 1430 | H | 7-dimethylamino |
| 1431 | H | 7-dimethylamino |
| 1432 | H | 7-dimethylamino |
| 1433 | H | 7-dimethylamino |
| 1434 | H | 7-dimethylamino |
| 1435 | H | 7-dimethylamino |
| 1436 | H | 7-dimethylamino |
| 1437 | H | 7-dimethylamino |
| 1438 | H | 7-dimethylamino |
| 1439 | H | 7-dimethylamino |
| 1440 | H | 7-dimethylamino |
| 1441 | H | 7-dimethylamino |
| 1442 | H | 7-dimethylamino |
| 1443 | H | 7-dimethylamino |
| 1444 | H | 7-dimethylamino |
| 1445 | H | 7-dimethylamino |
| 1446 | H | 7-methoxy; 8-methoxy |
| 1447 | H | 7-dimethylamino |
| 1448 | H | 7-dimethylamino |
| 1449 | H | 7-dimethylamino |
| 1450 | H | 7-dimethylamino |
| 1451 | H | 7-dimethylamino |

Example 1395

Dibutyl 4-Fluorobenzene Dialdehyde

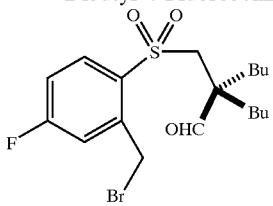

Step 1: Preparation of Dibutyl 4-Fluoro Benzene Dialdehyde

To a stirred solution of 17.5 g (123 mmol) of 2,5-difluorobenzaldehyde (Aldrich) in 615 mL of DMSO at ambient temperature was added 6.2 g (135 mmol) of lithium sulfide (Aldrich). The dark red solution was stirred at 75° C. for 1.5 hours, or until the starting material was completely consumed, and then 34 g (135 mmol) of dibutyl mesylate aldehyde was added at about 50° C. The reaction mixture was stirred at 75° C. for three hours or until the reaction was completed. The cooled solution was poured into water and extracted with ethyl acetate. The combined extracts were washed with water several times, dried ($MgSO_4$) and concentrated in vacuo. Silica gel chromatographic purification of the crude product gave 23.6 g (59%) of fluorobenzene dialdehyde as a yellow oil: $^1$H NMR ($CDCl_3$) d 0.87 (t, J=7.05 Hz, 6H), 1.0–1.4 (m, 8H), 1.5–1.78 (m, 4H), 3.09 (s, 2H), 7.2–7.35 (m, 1H), 7.5–7.6 (m, 2H), 9.43 (s, 1H), 10.50 (d, J=2.62 Hz, 1H).

Step 2: Preparation of Dibutyl 4-Fluorobenzyl Alcohol

To a solution of 22.6 g (69.8 mmol) of the dialdehyde obtained from Step 1 in 650 mL of THF at −60° C. was added 69.8 mL (69.8 mmol) of DIBAL (1M in THF) via a syringe. The reaction mixture was stirred at −4° C. for 20 hours. To the cooled solution at −40° C. was added sufficient amount of ethyl acetae to quench the excess of DIBAL, followed by 3 N HCl. The mixture was extracted with ethyl acetate, washed with water, dried ($MgSO_4$), and concentrated in vacuo. Silica gel chromatographic purification of the crude product gave 13.5 g (58%) of recovered starting material, and 8.1 g (36%) of the desired fluorobenzyl alcohol as a colorless oil: $^1$H NMR ($CDCl_3$) d 0.88 (t, J=7.05 Hz, 6H), 1.0–1.4 (m, 8H), 1.5–1.72 (m, 4H), 1.94 (br s, 1H), 3.03 (s, 2H), 4.79 (s, 2H), 6.96 (dt, J=8.46, 3.02 Hz, 1H), 7.20 (dd, J=9.47, 2.82 Hz, 1H), 7.42 (dd, J=8.67, 5.64 Hz, 1H), 9.40 (s, 1H).

Step 3: Preparation of Dibutyl 4-Fluorobenzyl Bromide

To a solution of 8.1 g (25 mmol) of benzyl alcohol obtained from Step 2 in 100 mL of DMF at −40° C. was added 47 g (50 mmol) of bromotriphenyphosphonium bromide (Aldrich). The resulting solution was stirred cold for 30 min, then was allowed to warm to 0° C. To the mixture was added 10% solution of sodium sulfite and ethyl acetate. The extract was washed a few times with water, dried (MgSO4), and concentrated in vacuo. The mixture was stirred in small amount of ethyl acetate/hexane mixture (1:4 ratio) and filtered through a pad of silica gel, eluting with same solvent mixture. The combined filtrate was concentrated in vacuo to give 9.5 g (98%) of the desired product as a colorless oil: $^1$H NMR ($CDCl_3$) d 0.88 (t, J=7.05 Hz, 6H), 1.0–1.4 (m, 8H), 1.55–1.78 (m, 4H), 3.11 (s, 2H), 4.67 (s, 2H), 7.02 (dt, J=8.46, 3.02 Hz, 1H), 7.15 (dd, J=9.47, 2.82 Hz, 1H), 7.46 (dd, J=8.67, 5.64, 1H), 9.45 (s, 1H).

Step 4: Preparation of Sulfonyl 4-Fluorobenzyl Bromide

To a solution of 8.5 g (25 mmol) of sulfide obtained from Step 3 in 200 mL of $CH_2Cl_2$ at 0° C. was added 15.9 g (60 mmol) of mCPBA (64% peracid). The resulting solution was stirred cold for 10 min, then was allowed to stirred ambient temperature for 5 hours. To the mixture was added 10% solution of sodium sulfite and ethyl acetate. The extract was washed several times with saturated $Na_2CO_3$, dried ($MgSO_4$), and concentrated in vacuo to give 10.2 g (98%) of the desired product as a colorless oil: $^1$H NMR ($CDCl_3$) d 0.91 (t, J=7.05 Hz, 6H), 1.03–1.4 (m, 8H), 1.65–1.82 (m, 2H), 1.90–2.05 (m, 2H), 3.54 (s, 2H), 5.01 (s, 2H), 7.04–7.23 (m, 1H), 7.30 (dd, J=8.87, 2.42 Hz, 1H), 8.03 (dd, J=8.86, 5.64, 1H), 9.49 (s, 1H).

Example 1396

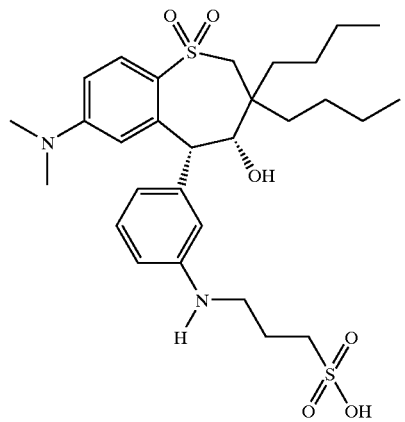

Generic Scheme 9

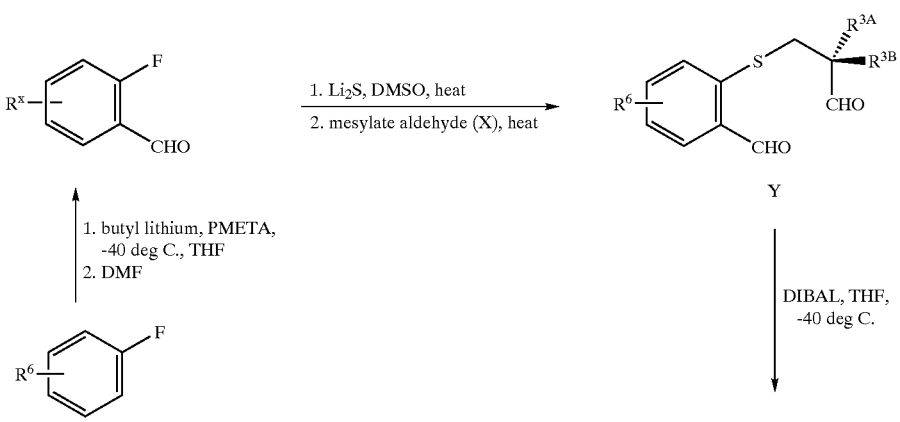

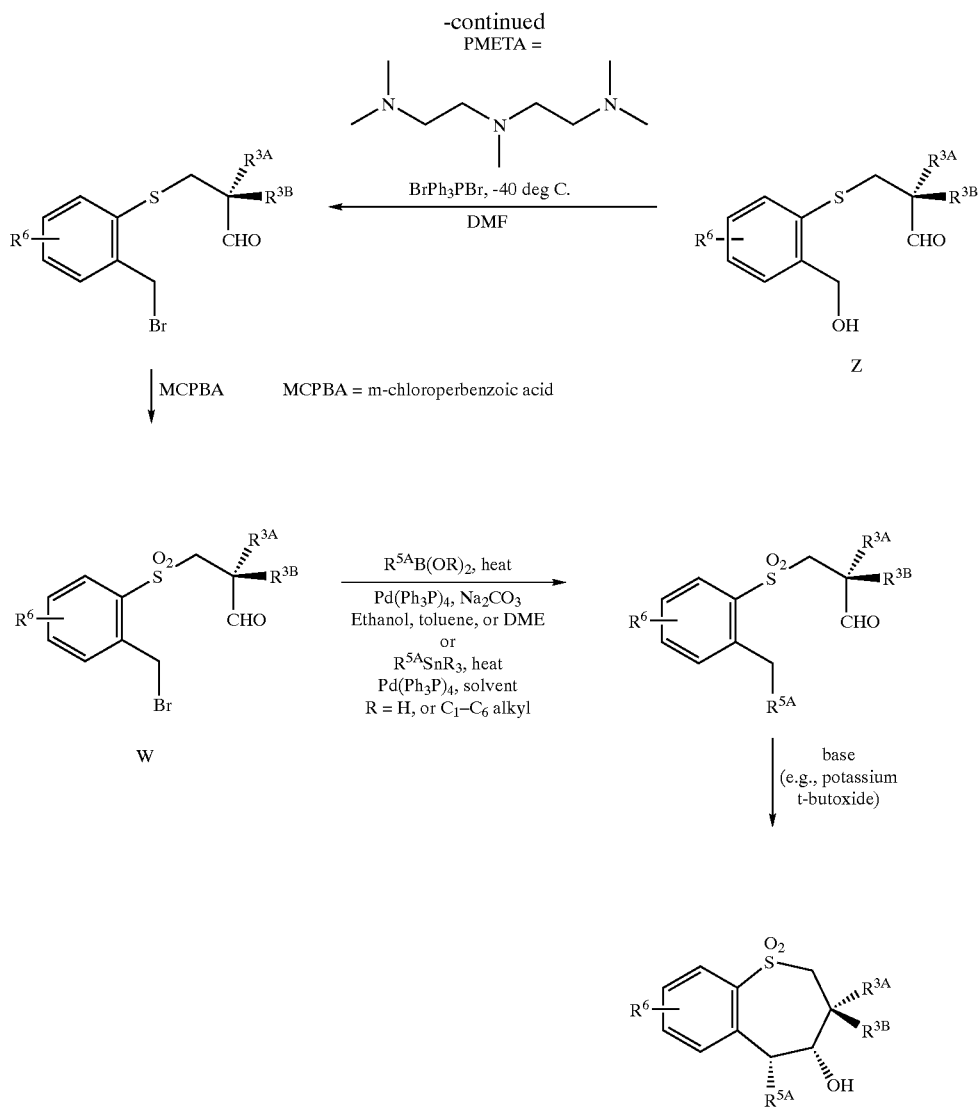

Generic Scheme 9: The nucleophilic substitution of an appropriately substituted 2-fluorobenzaldehyde with lithium sulfide or other nucleophilic sulfide anion in polar solvent (such as DMF, DMA, DMSO . . . etc), followed by the addition of dialkyl mesylate aldehyde (X), provided a dialkyl benzene dialdehyde Y. DIBAL reduction of the dialdehyde at low temperature yielded benzyl alcohol monoaldehyde Z. Conversion of benzyl alcohol to benzyl bromide, followed by oxidation of sulfide to sulfone yielded the key intermediate W.

Example 1397

The 7-fluoro, 9-fluoro and 7,9-difluoro analogs of benzothiepine compounds can be reacted with sulfur and nitrogen nucleophiles to give the corresponding sulfur and nitrogen substituted analogs. The following example demonstrates the synthesis of these analogs.

3,3-Dibutyl-5a-(4'-fluorophenyl)-4a-hydroxy-7-methylthio-2,3,4,5-tetrahydrobenzothiepine-1,1-dioxide

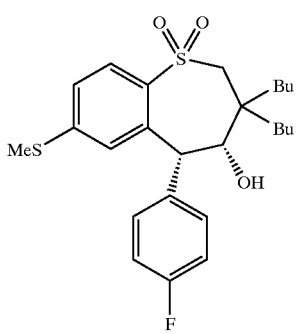

A mixture of 0.4 g Of 3,3-dibutyl-7-fluoro-5a-4'-fluorophenyl)-4a-hydroxy-2,3,4,5-tetrahydrobenzothiepine-1,1-dioxide, prepared by previously described method, 0.12 g of sodium methanethiolate and 20 ml of DMF was stirred at 50° C. for 3 days. An additional 0.1 g of sodium methanethiolate was added to the reaction mixture and the mixture was stirred for additional 20 h at 50° C. then was concentrated in vacuo. The residue was triturated with water and extracte with ether. The ether extract was dried over MgSO₄ and concentrated in vacuo to 0.44 g of an oil. Purification by HPLC (10% EtOAc in hexane) gave 0.26 g of needles, mp 164–165.5%C.

3,3-Dibutyl-9-dimethylamino-7-fluoro-5a-(4'-fluorophenyl)-4a-hydroxy-2,3,4,5-tetrahydrobenzothiepine-1,1-fioxide and 7,9-bis (Dimethylamino)-3,3-dibutyl-5a-(4'-fluorophenyl)-4a-hydroxy-2,3,4,5-tetrabydrobenzothiepine-1,1-dioxide

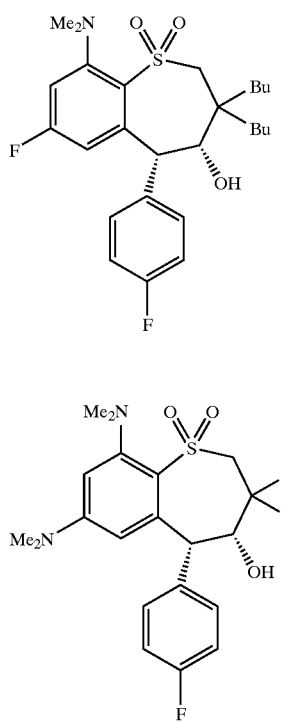

A solution of 0.105 g of 3,3-dibutyl-7,9-difluoro-5a-(4'-fluorophenyl)-4a-hydroxy-2,3,4,5-tetrahydrobenzothiepine-1,1-dioxide, prepared by the method described previously, in 20 ml of 2 N dimethylamine in THF was heated at 160° C. in a sealed Parr reactor overnight. The reaction mixture was cooled and concentrated in vacuo. The residue was triturated with 25 ml of water and extracted with ether. The ether extract was dried over MgSO₄ and concentrated in vacuo. The resdue was purified by HPLC (10% EtOAc in hexane) to give 35 mg of an earlier fraction which was identified as 3,3-dibutyl-9-dimethylamino-7-fluoro-5a-(4'-fluorophenyl)-4a-hydroxy-2,3,4,5-tetrahydrobenzothiepine-1,1-dioxide, MS (CI) m/e 480 (M⁺+1), and 29 mg of a later fraction which was identified as 7,9-bis(dimethylamnino)-3,3-dibutyl-5a-(4'-fluorophenyl)-4a-hydroxy-2,3,4,5-tetrahydrobenzothiepine-1,1-dioxide, MS (CI) m/e 505 (M⁺+1).

The compounds of this invention can also be synthesized using cyclic sulfate (XL, below) as the reagent as shown in the following schemes XI and XII. The following examples describe a procedure for using the cyclic sulfate as the reagent.

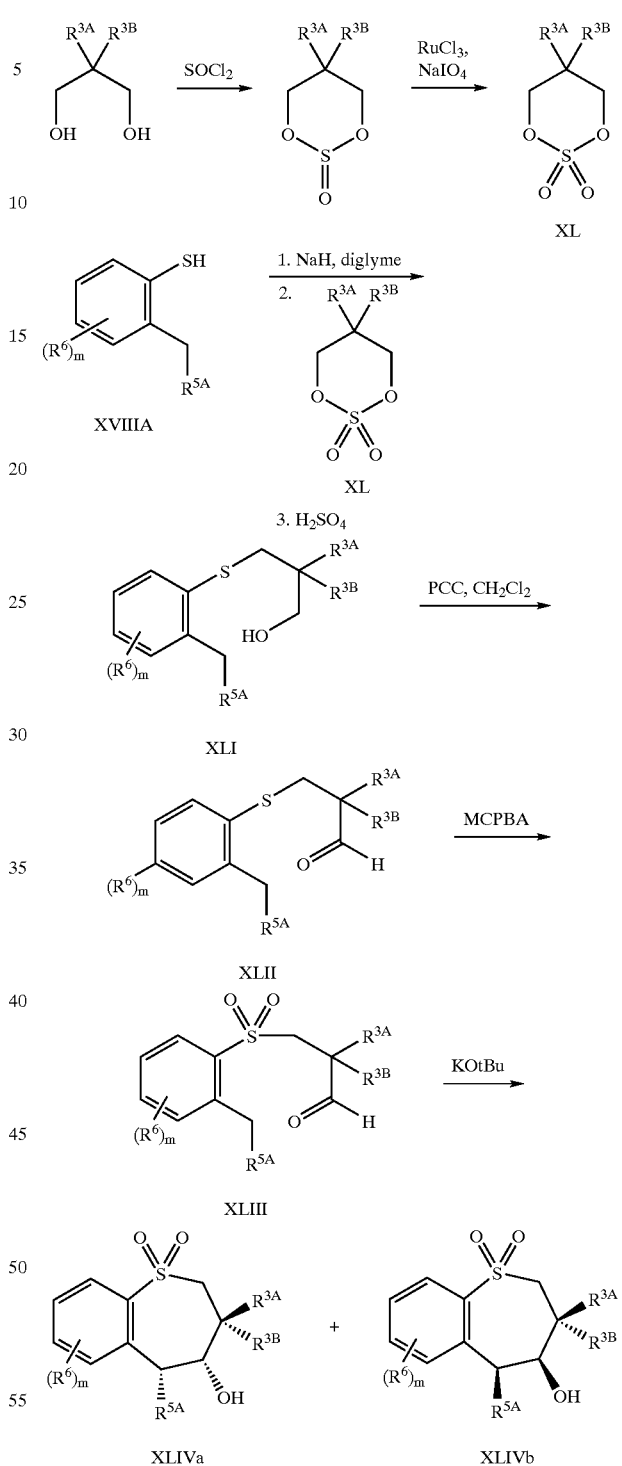

Scheme 10 illustrates yet another route to benzothiepine-1,1-dioxides, particularly 3,3-dialkyl analogs, starting from the thiophenol XVIIIA. Thiophenol XVIIIA can be reacted with cyclic sulfate XL to give the alcohol XLI which can be oxidized to yield the aldehyde XLII. Aldehyde XLII itself can be further oxidized to give the sulfone XLIII which can be cyclized to give a stereoisomeric mixture of benzothiepine XLIVa and XLIVb.

Thiophenol XVIIIA can be prepared according to Scheme 7 as previously discussed and has the following formula:

XVIIIA wherein $R^{5A}$, $R^6$ and are as previously described in connection with Formulas I-1 to I-24, where similar substituents $R^{5A}$ and $R^6$ are described. Cyclic sulfate XL can be prepared according to synthetic procedures known in the art and has the following formula:

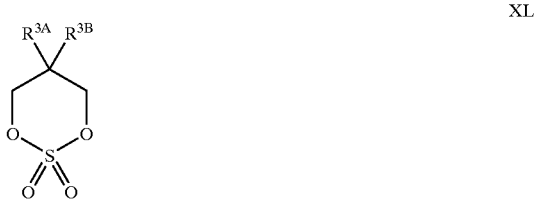

XL wherein $R^{3A}$ and $R^{3B}$ are as previously described in connection with Formulas I-1 to I-24 wherein similar substituents $R^{3A}$ and $R^{3B}$ are described fined for the compounds of formula I. Preferably, $R^1$ and $R^2$ are alkyl; more preferably, they are selected from the group consisting of methyl, ethyl, propyl, isopropyl, n-butyl, iso-butyl, sec-butyl, tert-butyl, and pentyl; and still more preferably, $R^1$ and $R^2$ are n-butyl.

In the process of Scheme XI, thiophenol XVIIIA is initially reacted with cyclic sulfate XL. This reaction preferably is conducted in an aprotic solvent such as methoxyethyl ether. While the reaction conditions such as temperature and time are not narrowly critical, the reaction preferably is allowed to proceed at about room temperature for about two hours. The reaction preferably employs an approximately stoichiometric ratio of the starting materials, with a slight excess of cyclic sulfate XL being preferred. Reaction time and yield can be improved by using about 1.01 to 1.3 equivalents of cyclic sulfate XL for each equivalent of thiophenol XVIIIA present. More preferably, this ratio is about 1.1 equivalents of cyclic sulfate XL for each equivalent of thiophenol XVIIIA present.

In the process of the invention, thiophenol XVIIIA also is treated with an abstracting agent. The abstracting agent can be added to the solvent containing thiophenol XVIIIA prior to, concurrently with, or after the addition of cyclic sulfate XL. Without being held to a particular theory, it is believed the abstracting agent removes the hydrogen atom from the mercaptan group attached to the benzene ring of thiophenol XVIIIA. The resulting sulfur anion of the thiophenol then reacts with cyclic sulfate XL to open the sulfate ring. The sulfur anion of the thiophenol then bonds with a terminal carbon atom of the open ring sulfate. The terminal group at the unbonded end of the open ring sulfate is the sulfate group.

The abstracting agent generally is a base having a pH greater than about 10. Preferably, the base is an alkali metal hydride such as sodium hydride, lithium hydride or potassium hydride; more preferably, the base is sodium hydride. A slight excess of abstracting agent is preferred relative to thiophenol XVIIIA. Reaction time and yield is improved by using about 1.0 to about 1.1 equivalents of abstracting agent for each equivalent of thiophenol XVIIIA present. More preferably, this ratio is about 1.1 equivalents of abstracting agent for each equivalent of thiophenol XVIIIA present.

The sulfate group of the intermediate product of the reaction of thiophenol XVIIIA with cyclic sulfate XL is then removed, preferably by hydrolysis, to yield alcohol XLI. Suitable hydrolyzing agents include mineral acids, particularly hydrochloric acid and sulfuric acid.

The several reactions involving thiophenol XVIIIA, cyclic sulfate XL, the abstracting agent and the hydrolyzing agent can take place in situ without the need for isolation of any of the intermediates produced.

Alcohol XLI is then isolated by conventional methods (for example, extraction with aqueous methyl salicylate) and oxidized using standard oxidizing agents to aldehyde XLII. Preferably, the oxidizing agent is sulfur trioxide or pyridinium chlorochromate, and more preferably, it is pyridinium chlorochromate. The reaction is conducted in a suitable organic solvent such as methylene chloride or chloroform.

Aldehyde XLII is then isolated by conventional methods and further oxidized using standard oxidizing agents to sulfone-aldehyde XLIII. Preferably, the oxidizing agent is metachloroperbenzoic acid.

Sulfone-aldehyde XLIII likewise is isolated by conventional methods and then cyclized to form the stereoisomeric benzothiepines XLIVa and XLIVb. The cyclizing agent preferably is a base having a pH between about 8 and about 9. More preferably, the base is an alkoxide base, and still more preferably, the base is potassium tert-butoxide.

The two oxidation steps of Scheme 10 can be reversed without adversely affecting the overall reaction. Alcohol XLI can be oxidized first to yield a sulfone-alcohol which is then oxidized to yield a sulfone-aldehyde.

SCHEME 11

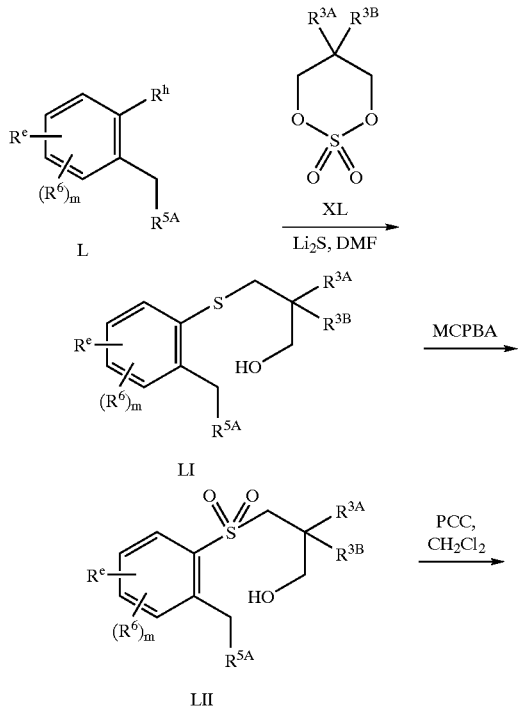

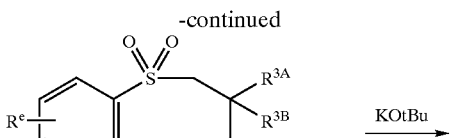

LIII

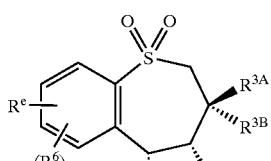

LIVa

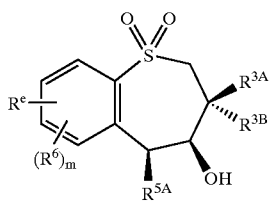

LIVb

Scheme 11 illustrates still another route to benzothiepine-1,1-dioxides, particularly 3,3-dialkyl analogs, starting from the halobenzene L. Halobenzene L can be reacted with cyclic sulfate XL disclosed above to give the alcohol LI which can be oxidized to yield the sulfone-alcohol LII. Sulfone-alcohol LII itself can be further oxidized to give the sulfone-aldehyde LIII which can be cyclized to give a stereoisomeric mixture of benzothiepine LIVa and LIVb.

Halobenzene L (which is commercially available or can be synthesized from commercially available halobenzenes by one skilled in the art) has the following formula:

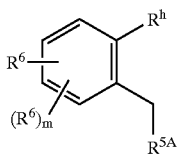

L wherein $R^{5A}$, $R^6$, and m are as previously described in connection with compounds of Formulas I-1 to I-24, where substituents $R^{5A}$ and $R^6$ are described. $R_h$ is a halogen such as chloro, bromo, fluoro or iodo; and $R^e$ is an electron withdrawing group at the ortho or para position of the halobenzene, and is preferably a p-nitro or o-nitro group. Cyclic sulfate XL can be prepared as set forth in Scheme XI and can have the following formula:

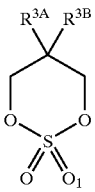

XL wherein $R^{3A}$ and $R^{3B}$ are as previously described in connection with compounds of Formulas I-1 to I-24, where substituents $R^{3A}$ and $R^{3B}$ are described. Preferably, $R^{3A}$ and $R^{3B}$ are alkyl; more preferably, they are selected from the group consisting of methyl, ethyl, propyl, isopropyl, n-butyl, iso-butyl, sec-butyl, tert-butyl, and pentyl; and still more preferably, $R^{3A}$ and $R^{3B}$ are n-butyl.

In the process of Scheme 11, halobenzene L is initially reacted with cyclic sulfate XL. This reaction preferably is conducted in an aprotic solvent such as dimethyl formamide or N:N-dimethylacetamide, and more preferably, in dimethyl formamide. Although the reaction conditions such as temperature and time are not narrowly critical, the reaction preferably is allowed to proceed at between about 70° C. and about 90° C. for about 8 to 12 hours. More preferably, the reaction temperature is maintained at about 80° C. The reaction preferably employs an approximately stoichiometric ratio of the starting materials, with a slight excess of cyclic sulfate XL being preferred. Reaction time and yield is improved by using about 1.1 to 1.3 equivalents of cyclic sulfate XL for each equivalent of halobenzene L present. More preferably, this ratio is about 1.1 equivalents of cyclic sulfate XL for each equivalent of halobenzene L present.

In the above-noted process in connection with the claimed invention, halobenzene L also is treated with an abstracting agent. The abstracting agent can be added to the solvent containing halobenzene L prior to, concurrently with, or after the addition of cyclic sulfate XL. Without being held to a particular theory, it is believed the abstracting agent removes the halogen atom attached to the benzene ring of halobenzene L and replaces that atom with a divalent sulfur atom. The resulting sulfur anion reacts with cyclic sulfate XL to open the sulfate ring. The sulfur anion of the halobenzene then bonds with a terminal carbon atom of the open ring sulfate. The terminal group at the unbonded end of the open ring sulfate is the sulfate group. The abstracting agent generally is a dialkali metal sulfide, and preferably it is dilithium sulfide. A slight excess of the abstracting agent is preferred relative to halobenzene L. Reaction time and yield is improved by using about 1.01 to 1.3 equivalents of abstracting agent for each equivalent of halobenzene L present. More preferably, this ratio is about 1.05 equivalents of abstracting agent for each equivalent of halobenzene L present.

The sulfate group of the product of the reaction of thiophenol XVIIIA with cyclic sulfate XL is then removed, preferably by hydrolysis, to yield a mixture of an ester and alcohol LI. Suitable hydrolyzing agents include mineral acids, particularly hydrochloric acid and sulfuric acid. The ester is then converted to alcohol LI by treatment with an alkali metal hydroxide, preferably sodium hydroxide.

The several reactions involving halobenzene L, cyclic sulfate XL, the abstracting agent and the hydrolyzing agent can take place in situ without the need to isolate any of the intermediates produced.

Alcohol LI is then isolated by conventional methods (for example, extraction with aqueous methyl salicylate) and oxidized using standard oxidizing agents to sulfone-alcohol LII. Preferably, the oxidizing agent is metachloroperbenzoic acid. The reaction is conducted in a suitable organic solvent such as methylene chloride or chloroform.

Sulfone-alcohol LII is then isolated by conventional methods and further oxidized using standard oxidizing agents to sulfone-aldehyde LIII. Preferably, the oxidizing agent is sulfur trioxide or pyridinium chlorochromate, and more preferably, it is pyridinium chlorochromate. The reaction is conducted in a suitable organic solvent such as methylene chloride or chloroform.

Sulfone-aldehyde XLII is then converted to the desired benzothiepine-1,1-dioxides according to the procedure previously set forth in Scheme 10.

The two oxidation steps can be reversed without adversely affecting the overall reaction. Alcohol XLI can be oxidized first to yield an aldehyde which is then oxidized to yield a sulfone-aldehyde.

Use of the cyclic sulfate reagent instead of a mesylate reagent in Schemes 10 and 11 improves the overall yield and avoids many of the purification difficulties encountered relative to those reaction schemes proceeding through a mesylate intermediate. Overall yields are significantly improved when a cyclic sulfate is used instead of a mesylate reagent. In addition, chromatographic separation of the intermediate product of the cyclic sulfate coupling step of the reaction is not necessary. For example, in Schemes XI and XII the intermediate is a water soluble alkali metal salt and the impurities can be removed by extraction with ether. The intermediate is then hydrolyzed to the desired alcohol.

Example Corresponding to Scheme 10
Step 1: Preparation of 2,2-Dibutyl-1,3-propanediol:

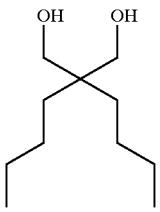

Lithium aluminum hydride (662 ml, 1.2 equivalents, 0.66 mol) in 662 mL of 1M THF was added dropwise to a stirred solution of dibutyl-diethylmalonate (150 g, 0.55 mol) (Aldrich) in dry THF (700 ml) while maintaining the temperature of the reaction mixture at between about −20° C. to about 0° C. using an acetone/dry ice bath. The reaction mixture was then stirred at room temperature overnight. The reaction was cooled to −20° C. and 40 ml of water, 80 ml of 10% NaOH and 80 ml of water were successively added dropwise. The resulting suspension was filtered. The filtrate was dried over sodium sulphate and concentrated under vacuum to give 98.4 g (yield 95%) of the diol as an oil. Proton NMR, carbon NMR and MS confirmed the product.

Step 2: Dibutyl-cyclic-sulfite:

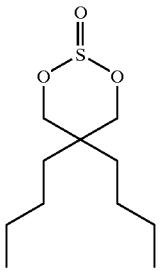

A solution of the dibutyl-diol of step 1 (103 g, 0.5478 mol) in anhydrous methylene chloride (500 ml) and triethylamine (221 g, 4 equivalents, 2.19 mol) was stirred at 0C under nitrogen. Thionyl chloride (97.78 g, 0.82 mol) was added dropwise to the mixture. Within 5 minutes the solution turned to yellow and then to black when the addition was completed within about half an hour. The reaction was completed within 3 hours (gas chromatography confirmed no starting material was left). The mixture was washed with ice water twice, and brine twice. The organic phase was dried over magnesium sulphate and concentrated under vacuum to give 128 g (yield 100%) of the dibutyl-cyclic-sulfite as a black oil. NMR and MS were consistent with the product.

Step 3: Dibutyl-cyclic sulfate:

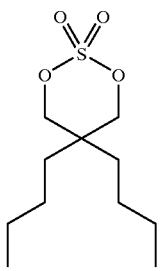

To a solution of the dibutyl-cyclic-sulfite of step 2 (127.5 g, 0.54 mol) in 600 ml acetonitrile and 500 ml of water cooled in an ice bath under nitrogen was added ruthenium (III) chloride (1 g) and sodium periodate (233 g, 1.08 mol). The reaction was stirred overnight and the color of the solution turned black. Gas chromatography confirmed there was no starting material left. The mixture was extracted once with 300 ml of ether and three times with brine. The organic phase was dried over magnesium sulphate and passed through celite. The filtrate was concentrated under vacuum and gave 133 g (yield 97.8%) of the dibutyl-cyclic-sulfate as an oil. Proton NMR, carbon NMR and MS confirmed the product.

Step 4: 2-[(2-4'-Fluorobenzyl-4-methylphenylthio)methyl]-2-butylhexanol:

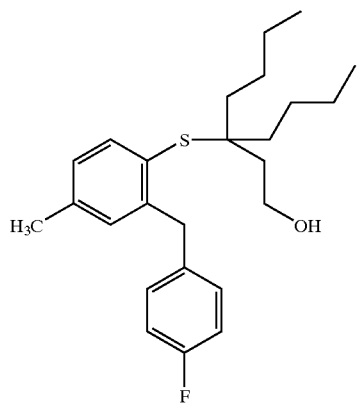

A 60% oil dispersion of sodium hydride (0.27 g, 6.68 mmole) was washed with hexane. The hexane was decanted and 20 ml of methoxyethyl ether was added to the washed sodium hydride and cooled in an ice bath. A mixture of diphenylmethane thiophenol (1.55 g, 6.68 mmole) in 10 ml of methoxyethyl ether was added dropwise over a period of 15 minutes. A mixture of the dibutyl-cyclic-sulfate of step 3 (2.17 g, 8.66 mmole) in 10 ml of methoxyethyl ether was then added. The resulting mixture was stirred for 30 minutes at 0° C. and 1 hour at room temperature under nitrogen. Gas chromatography confirmed there was no thiol left. The solvent was evaporated and washed with water and ether two times. The water layer was separated and 20 ml of 10% NaOH was added. This aqueous mixture was boiled for 30 minutes, cooled, acidified with 6N HCl, and boiled for 10 minutes. The mixture was cooled and extracted with ether. The organic layer was washed successively with water and brine, dried over magnesium sulphate, and concentrated under vacuum to give 2.47 g (yield 92.5%) of the hexanol as an oil. Proton NMR, C13-NMR and MS confirmed the product.

Step 5: 2-[(2-4'-Fluorobenzyl-4-methylphenylthio)methyl]-2-butylhexanal:

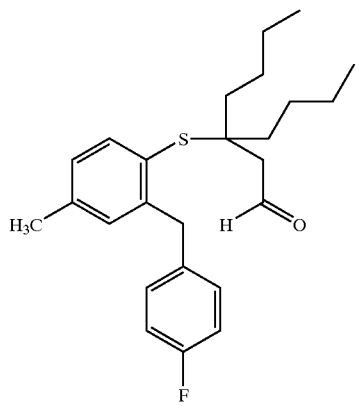

To a solution of the hexanol of step 4 (2 g, 4.9 mmole) in 40 ml of methylene chloride cooled in an ice bath under nitrogen was added pyridinium chlorochromate (2.18 g, 9.9 mmole). The reaction mixture was stirred for 3 hours and filtered through silica gel. The filtrate was concentrated under vacuum to give 1.39 g (yield 70%) of the hexanal as an oil. Proton NMR, carbon NMR and MS confirmed the product.

Step 6: 2-[(2-4'-Fluorobenzyl-4-methylphenylsulfonyl)methyl]-2-butylhexanal

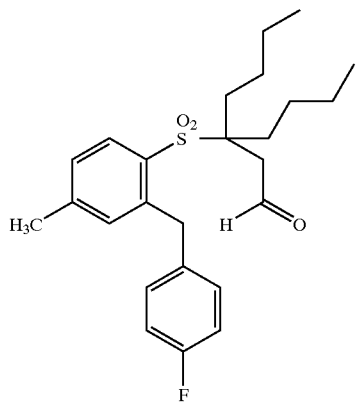

To a solution of the hexanal of step 5 (0.44 g, 1.1 mmole) in 20 ml of methylene chloride cooled by an ice bath under nitrogen was added 70% metachloroperbenzoic acid (0.54 g, 2.2 mmole). The reaction mixture was stirred for 18 hours and filtered. The filtrate was washed successively with 10% NaOH (3×), water, and brine, dried over magnesium sulphate, and concentrated under vacuum to give 0.42 g (yield 90%) of the hexanal as an oil. Proton NMR, carbon NMR and MS confirmed the product.

Step 7: cis3,3-Butyl-7-methyl-5-(4'-fluoro-phenyl)-2,3,4,5-tetrahydrobenzothiepine-1,1-oxide:

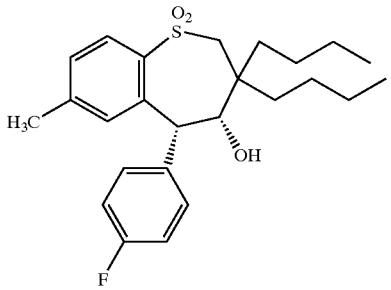

A mixture of the hexanal of step 6 (0.37 g, 0.85 mmole) in 30 ml of anhydrous THF was stirred in an ice bath at a temperature of about 0° C. Potassium-tert-butoxide (102 mg, 0.85 mmole) was then added. After 3 hours thin layer chromatography confirmed the presence of the product and a small amount of the starting material. The crude reaction mixture was acidified with 10% HCl, extracted with ether, washed successively with water and brine, dried with $MgSO_4$, and concentrated under vacuum. This concentrate was purified by HPLC (10% EtOAc-Hexane). The first fraction came as 0.1 g of the starting material in the form of an oil. The second fraction yielded 0.27 g (75% yield) of the desired benzothiepine as a white solid. Proton NMR, carbon NMR and MS confirmed the product. (M+H=433).

Example Corresponding to Scheme 11

Step 1: 2-[(2-4'-Methoxybenzyl-4-nitrophenylthio)-methyl]-2-butylhexanol:

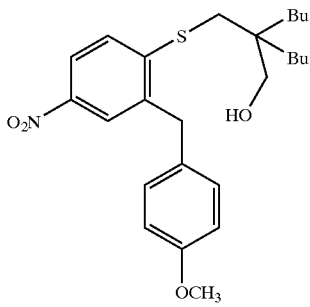

Chlorodiphenylmethane (10 g) was dissolved in 25 ml of DMF and lithium sulfide [1.75 g, 1.05 equivalents] was added. The solution color changed to red. The reaction mixture was heated at 80° C. overnight. The solution was cooled to 0° C. and dibutyl-cyclic-sulfate (9.9 g; prepared as set forth in Step 3 of the Scheme XI examples) in 10 ml of DMF was added and stirred at room temperature overnight. The solvent was evaporated and washed successively with water and ether (three times). The water layer was separated and 40 ml of concentrated sulfuric acid was added and the reaction mixture boiled overnight. The mixture was cooled and extracted with ethyl acetate. The organic layer was washed successively with water and brine, dried over magnesium sulphate, and concentrated under vacuum. The product was boiled with 3M of NaOH for 1 hour. The mixture was cooled and extracted with ethyl acetate. The organic layer was washed successively with water and brine, dried over magnesium sulphate, and concentrated under vacuum. The concentrate was dissolved in methylene chloride, filtered through silica gel, eluted with 20% ethyl acetate and hexane, and concentrated under vacuum to give 11.9 g (yield 74%) of the hexanol as an oil. Proton No, C13-NMR and MS confirmed the product.

Step 2: 2-[2-4'-Methoxybenzyl-4-nitrophenylthio)methyl]-2-butylhexanal:

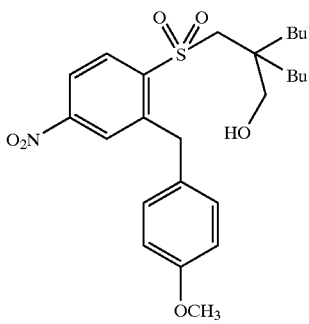

To a solution of the hexanol of step 1 (6 g, 13 mmole) in 50 ml methylene chloride cooled in ice bath under nitrogen was added 70% MCPBA (8.261 g, 33 mmole). The reaction was stirred for 18 hours at room temperature and filtered. The filtrate was washed successively with 10% NaOH (3×), water and brine, dried over magnesium sulphate, and concentrated under vacuum. The concentrate was dissolved in methylene chloride, filtered through silica gel, eluted with 20% ethyl acetate and hexane, and concentrated under vacuum to give 5 g (yield 77.7%) of the hexanal as a white solid, MP 58–60° C. Proton NMR, C13-NMR and MS confirmed the product.

Example 1398

Step 1. Preparation of 2

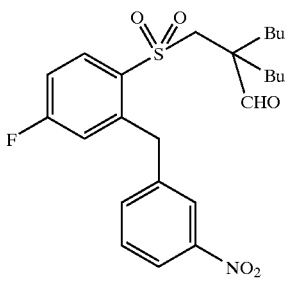

To a solution of 6.0 g of dibutyl 4-fluorobenzene dialdehyde of Example 1395 (14.3 mmol) in 72 mL of toluene and 54 mL of ethanol was added 4.7 g 3-nitrobenzeneboronic acid (28.6 mmol), 0.8 g of tetrakis (triphenylphosphine) palladium(0) (0.7 mmol) and 45 mL of a 2 M solution of sodium carbonate in water. This heterogeneous mixture was refluxed for three hours, then cooled to ambient temperature and partitioned between ethyl acetate and water. The organic layer was dried over $MgSO_4$ and concentrated in vacuo. Purification by silica gel chromatography (Waters Prep-2000) using ethyl acetate/hexanes (25/75) gave 4.8 g (73%) of the title compound as a yellow solid. $^1$H NMR (CDCl$_3$) d 0.88 (t, J=7.45 Hz, 6H), 0.99–1.38 (m, 8H), 1.62–1.75 (m, 2H), 1.85–2.00 (m, 2H), 3.20 (s, 2H), 4.59 (s, 2H), 6.93 (dd, J=10.5 and 2.4 Hz, 1H), 7.15 (dt, J=8.4 and 2.85 Hz, 1H), 7.46–7.59 (m, 2H), 8.05–8.16 (m, 3H), 9.40 (s, 1H).

Step 3. Preparation of 3

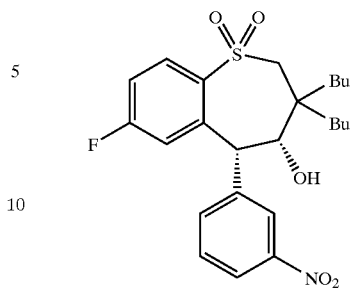

A solution of 4.8 g (10.4 mmol) of 2 in 500 mL THF was cooled to 0° C. in an ice bath. 20 mL of a 1 M solution of potassium t-butoxide was added slowly, maintaining the temperature at <5° C. Stirring was continued for 30 minutes, then the reaction was quenched with 100 mL of saturated ammonium chloride. The mixture was partitioned between ethyl acetate and water, the organic layer was washed with brine, then dried (MgSO$_4$) and concentrated in vacuo.

Purification by silica gel chromatography through a 100 ml plug using CH$_2$Cl$_2$ as eluent yielded 4.3 g (90%) of 3 as a pale yellow foam. $^1$H NMR (CDCl$_3$) d 0.93 (t, J=7.25 Hz, 6H), 1.00–1.55 (m, 8H), 1.59–1.74 (m, 3H), 2.15–2.95 (m, 1H), 3.16 (q$_{AB}$, J$_{AB}$=15.0 Hz, ΔV=33.2 Hz, 2H), 4.17 (d, J=6.0 Hz, 1H), 5.67 (s, 1H), 6.34 (dd, J=9.6 and 3.0 Hz, 1H), 7.08 (dt, J=8.5 and 2.9 Hz, 1H), 7.64 (t, J=8.1 Hz, 1H), 7.81 (d, J=8.7 Hz, 1H), 8.13 (dd, J=9.9 and 3.6 Hz, 1H), 8.23–8.30 (m, 1H), 8.44 (s, 1H). MS(FABH$^+$) m/e (relative intensity) 464.5 (100), 446.6 (65). HRMS calculated for M+H 464.1907. Found 464.1905.

Step 4. Preparation of 4

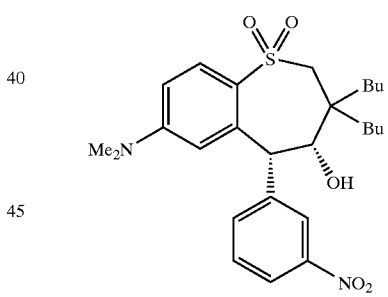

To a cooled (0° C.) solution of 4.3 g (9.3 mmol) of 3 in 30 ml THF contained in a stainless steel reaction vessel was added 8.2 g dimethyl amine (182 mmol). The vessel was sealed and heated to 110° C. for 16 hours. The reaction vessel was cooled to ambient temperature and the contents concentrated in vacuo. Purification by silica gel chromatography (Waters Prep-2000) using an ethyl acetate/hexanes gradient (10–40% ethyl acetate) gave 4.0 g (88%) of 4 as a yellow solid. $^1$H NMR (CDCl$_3$) d 0.80–0.95 (m, 6H), 0.96–1.53 (m, 8H), 1.60–1.69 (m, 3H), 2.11–2.28 (m, 1H), 2.79 (s, 6H), 3.09 (q$_{AB}$, J$_{AB}$=15.0 Hz, DV=45.6 Hz, 2H), 4.90 (d, J=9.0 Hz, 1H), 5.65 (s, 1H), 5.75 (d, J=2.1 Hz, 1H), 6.52 (dd, J=9.6 and 2.7 Hz, 1H), 7.59 (t, J=8.4 Hz, 1H), 7.85 (d, J=7.80 Hz, 1H), 7.89 (d, J=9.0 Hz, 1H), 8.20 (dd, J=8.4 and 1.2 Hz, 1H), 8.43 (s, 1H). MS(FABH$^+$) m/e (relative intensity) 489.6 (100), 471.5 (25). HRMS calculated for M+H 489.2423. Found 489.2456.

Step 5. Preparation of 5

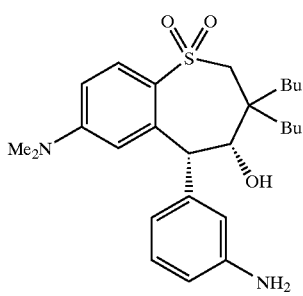

To a suspension of 1.0 g (2.1 mmol) of 4 in 100 ml ethanol in a stainless steel Parr reactor was added 1 g 10% palladium on carbon. The reaction vessel was sealed, purged twice with $H_2$, then charged with $H_2$ (100 psi) and heated to 45° C. for six hours. The reaction vessel was cooled to ambient temperature and the contents filtered to remove the catalyst. The filtrate was concentrated in vacuo to give 0.9 g (96%) of 5. $^1$H NMR (CDCl$_3$) d 0.80–0.98 (m, 6H), 1.00–1.52 (m, 10H), 1.52–1.69 (m, 1H), 2.15–2.29 (m, 1H), 2.83 (s, 6H), 3.07 ($q_{AB}$, $J_{AB}$=15.1 Hz, DV=44.2 Hz, 2H), 3.70 (s, 2H), 4.14 (s, 1H), 5.43 (s, 1H), 6.09 (d, J=2.4 Hz, 1H), 6.52 (dd, J=12.2 and 2.6 Hz, 1H), 6.65 (dd, J=7.8 and 1.8 Hz, 1H), 6.83 (s, 1H), 6.93 (d, J=7.50 Hz, 1H), 7.19 (t, J=7.6 Hz, 1H), 7.89 (d, J=8.9 Hz, 1H). MS(FABH+) m/e (relative intensity) 459.7 (100). HRMS calculated for M+H 459.2681. Found 459.2670.

Step 6. Preparation of 6

To a solution of 914 mg (2.0 mmol) of 5 in 50 ml THF was added 800 mg (4.0 mmol) 5-bromovaleroyl chloride. Next was added 4 g (39.6 mmol) TEA. The reaction was stirred 10 minutes, then partitioned between ethyl acetate and brine. The organic layer was dried (MgSO$_4$) and concentrated in vacuo. Purification by silica gel chromatography through a 70 ml MPLC column using a gradient of ethyl acetate (20–50%) in hexane as eluent yielded 0.9 g (73%) of 6 as a pale yellow oil. $^1$H NMR (CDCl$_3$) d 0.84–0.95 (m, 6H), 1.02–1.53 (m, 10H), 1.53–1.68 (m, 1H), 1.80–2.00 (m, 4H), 2.12–2.26 (m, 4H), 2.38 (t, J=6.9 Hz, 2H), 2.80 (s, 6H), 3.07 ($q_{AB}$, $J_{AB}$=15.6 Hz, DV=40.4 Hz, 2H), 3.43 (t, J=6.9 Hz, 2H), 4.10 (s, 1H), 5.51 (s, 1H), 5.95 (d, J=2.4 Hz, 1H), 6.51 (dd, J=9.3 and 2.7 Hz, 1H), 7.28 (s, 1H), 7.32–7.41 (m, 2H), 7.78 (d, J=8.1 Hz, 1H), 7.90 (d, J=9.0 Hz, 1H).

Step 7. Preparation of 7

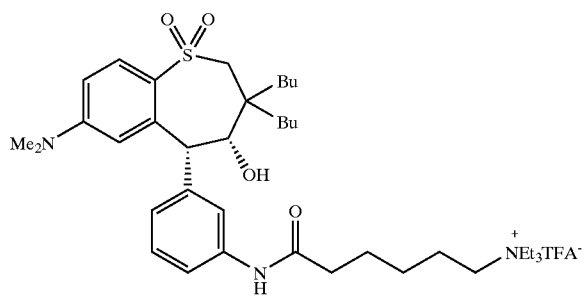

To a solution of 0.9 g (1.45 mmol) of 6 in 25 ml acetonitrile add 18 g (178 mmol) TEA. Heat at 55° C. for 16 hours. The reaction mixture was cooled to ambient temperature and concentrated in vacuo. Purification by reverse-phase silica gel chromatography (Waters Delta Prep 3000) using an acetonitrile/water gradient containing 0.05% TFA (20–65% acetonitrile) gave 0.8 g (73%) of 7 as a white foam.

$^1$H NMR (CDCl$_3$) d 0.80–0.96 (m, 6H), 0.99–1.54 (m, 19H), 1.59–1.84 (m, 3H), 2.09–2.24 (m, 1H), 2.45–2.58 (in, 2H), 2.81 (s, 6H), 3.09 ($q_{AB}$, $J_{AB}$=15.6 Hz, DV=18.5 Hz, 2H), 3.13–3.31 (m, 8H), 4.16 (s, 1H), 5.44 (s, 1H), 6.08 (d, J=1.8 Hz, 1H), 6.57 (dd, J=9.3 and 2.7 Hz, 1H), 7.24 (t, J=7.5 Hz, 1H), 7.34 (t, J=8.4 Hz, 1H), 7.56 (d, J=8.4 Hz, 1H), 7.74 (s, 1H), 7.88 (d, J=9.0 Hz, 1H), 9.22 (s, 1H). HRMS calcd 642.4304; observed 642.4343.

Example 1398a

Step 1

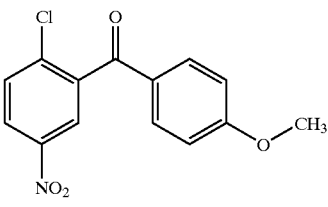

$C_{14}H_{10}ClNO_4$ fw = 291.69

In an inert atmosphere, weigh out 68.3 gms phosphorus pentachloride (0.328 mole Aldrich 15,777-5) into a 2-necked 500 ml round bottom flask. Fit flask with a $N_2$ inlet adapter and suba seal. Remove from inert atmosphere and begin $N_2$ purge. Add 50 mls anhydrous chlorobenzene (Aldrich 28,451-3) to the PCl$_5$ via syringe and begin stirring with magnetic stir bar.

Weigh out 60 gms 2-chloro-5-nitrobenzoic acid (0.298 mole Aldrich 12,511-3). Slowly add to the chlorobenzene solution while under $N_2$ purge. Stir at room temperature overnight. After stirring at room temperature for 20 hrs, place in oil bath and heat at 50° C. for 1 hr. Remove chlorobenzene by high vacuum. Wash residue with anhydrous hexane. Dry acid chloride wt=61.95 gms. Store in inert and dry atmosphere.

In inert atmosphere, dissolve acid chloride with 105 mls anhydrous anisole (0.97 mole Aldrich 29,629-5). Place solution in a 2-necked 500 ml round bottom flask.

Weigh out 45.1 gms aluminum chloride (0.34 moles Aldrich 29,471-3) and place in a solid addition funnel. Fit reaction flask with addition funnel and a $N_2$ inlet adapter. Remove from inert atmosphere. Chill reaction solution with ice bath and begin $N_2$ purge. Slowly add AlCl$_3$ to chilled solution. After addition is complete, allow to warm to room temperature. Stir overnight.

Quench reaction by pouring into a solution of 300 mls 1N HCl and ice. Stir 15 min. Extract twice with ether. Combine organic layers and extract twice with 2% NaOH, then twice with deionized $H_2O$. Dry with MgSO$_4$, filter and rotovap to dryness. Remove anisole by high vacuum. Crystalize product from 90% ethanol 10% ethyl acetate. Dry on vacuum line. Wt=35.2 gms. Yield 41%. Obtain NMR and mass spec (m/z=292).

Step 2

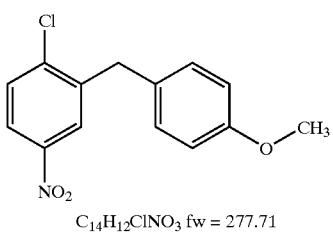

C₁₄H₁₂ClNO₃ fw = 277.71

Dissolve 38.10 gms (0.131 moles) of the benzophenone from step 1 in 250 mls anhydrous methylene chloride. Place in a 3 liter flask fitted with $N_2$ inlet, addition funnel and stopper. Stir with magnetic stir bar. Chill solution with ice bath.

Prepare a solution of 39.32 gms trifluoromethane sulfonic acid (0.262 mole Aldrich 15,853-4) and 170 mls anhydrous methylene chloride. Place in addition funnel and add dropwise to chilled solution under $N_2$. Stir 5 minutes after addition is complete.

Prepare a solution of 22.85 gms triethyl silane (0.197 mole Aldrich 23,019-7) and 170 mls anhydrous methylene chloride. Place in addition funnel and add dropwise to chilled solution under $N_2$. Stir 5 minutes after addition is complete.

Prepare a second solution of 39.32 gms trifluoromethane sulfonic acid and 170 mls anhydrous methylene chloride. Place in addition funnel and add dropwise to chilled solution under $N_2$. Stir 5 minutes after addition is complete.

Prepare a second solution of 22.85 gms triethyl silane and 170 mls anhydrous methylene chloride. Place in addition funnel and add dropwise to chilled solution under $N_2$. After all additions are made allow to slowly warm to room temperature overnight. Stir under $N_2$ overnight.

Prepare 1300 mls saturated $NaHCO_3$ in a 4 liter beaker. Chill with ice bath. While stirring vigorously, slowly add reaction mixture. Stir at chilled temperature for 30 min. Pour into a separatory funnel and allow separation. Remove organic layer and extract aqueous layer 2 times with methylene chloride. Dry organic layers with $MgSO_4$. Crystallize from ethanol. Dry on vacuum line. Dry wt=28.8 gms. Confirm by NMR and mass spec (m/z=278).

Step 3

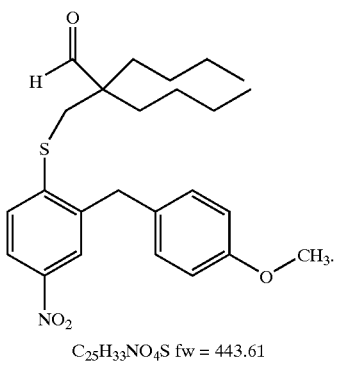

C₂₅H₃₃NO₄S fw = 443.61

Dissolve 10.12 gms (0.036 moles) of product 2 with 200 mls anhydrous DMSO. Place in a 500 ml round bottom flask with magnetic stir bar. Fit flask with water condenser, $N_2$ inlet, and stopper. Add 1.84 gms $Li_2S$ (0.040 moles Aldrich 21,3241). Place flask in oil bath and heat at 75° C. under $N_2$ overnight then cool to room temperature.

Weigh out 10.59 gms dibutyl mesylate (0.040 moles). Dissolve with anhydrous DMSO and add to reaction solution. Purge well with $N_2$, heat overnight at 80° C.

Cool to room temperature. Prepare 500 mls of 5% acetic acid in a 2 liter beaker. While stirring, slowly add reaction mixture. Stir 30 min. Extract with ether 3 times. Combine organic layers and extract with water and sat'd NaCl. Dry organic layer with $MgSO_4$, filter and rotovap to dryness. Dry oil on vacuum line. Obtain pure product by column chromatography using 95% hexane and 5% ethyl acetate as the mobile phase. Dry wt=7.8 gms. Obtain NMR and mass spec (m/z=444).

Step 4

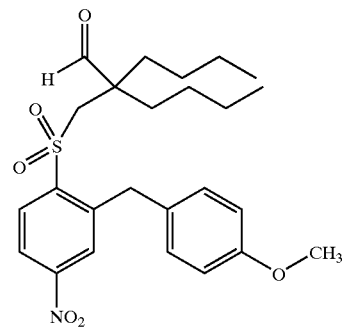

C₂₅H₃₃NO₆S fw = 475.61

Dissolve 9.33 gms (0.021 moles) of product 3 with 120 mls anhydrous methylene chloride. Place in a 250 ml round bottom flask with magnetic stir bar. Fit flask with $N_2$ inlet and stopper. Chill solution with ice bath under $N_2$ purge. Slowly add 11.54 gms 3-chloroperbenzoic acid (0.0435 moles, Fluka 25800, ~65%). After addition is complete warm to room temperature and monitor reaction by TLC. Reaction goes quickly to the sulphoxide intermediate but takes 8 hrs to convert to the sulphone. Chill solution over night in freezer. Filter solid from reaction, extract filtrate with 10% $K_2CO_3$. Extract aqueous layer twice with methylene choride. Combine organic layers and dry with $MgSO_4$. Filter and rotovap to dryness. Obtain pure product by crystallizing from ethanol or isolating by column chromatography. Obtain NMR and mass spec (m/z=476).

Step 5

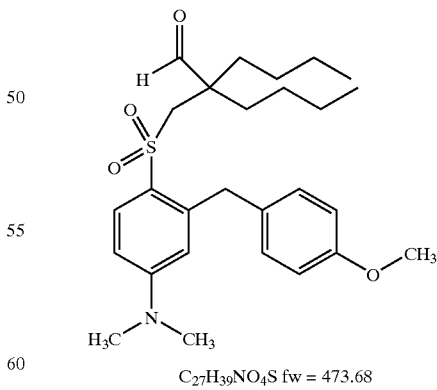

C₂₇H₃₉NO₄S fw = 473.68

Reaction is done in a 300 ml stainless steel Parr stirred mini reactor. Place 9.68 gms (0.0204 moles) of product 4 in reactor base. Add 160 mls ethanol. For safety reasons next two compounds are added in a $N_2$ atmosphere glove bag. In glove bag, add 15.3 mls formaldehyde (0.204 moles, Aldrich 25,254-9, about 37 wt % in water) and 1.45 gms 10% Pd/Carbon (Aldrich 20,569-9). Seal reactor before removing from glove bag. Purge reactor three times with H₂. Heat to 55° C. under H₂. Run reaction at 200 psig H₂, 55° C., and a stir rate of 250 rpm. Run overnight under these conditions.

Cool reactor and vent H₂. Purge with N₂. Check progress of run by TLC. Reaction is a mixture of desired product and intermediate. Filter reaction mixture over a bed of celite washing well with ether. Rotovap and redissolve with ether. Extract with water. Dry organic layer with MgSO₄, filter and rotovap to dryness. Dry on vacuum line.

Charge reactor again with same amounts, seal reactor and run overnight under same conditions. After second run all of the material has been converted to the desired product. Cool and vent H₂ pressure. Purge with N₂. Filter over a bed of celite, washing well with ether. Rotovap to dryness. Dissolve with ether and extract with water. Dry organic layer with MgSO₄, filter and rotovap to dryness. Dry on vacuum line. Obtain NMR and mass spec (m/z=474).
Step 6

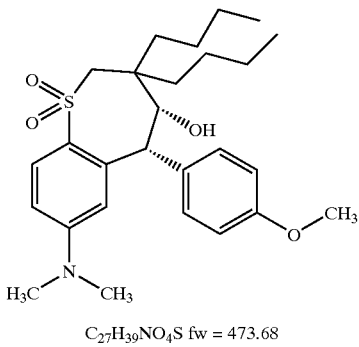

C$_{27}$H$_{39}$NO$_4$S fw = 473.68

Dissolve 8.97 gms (0.0189 mole) of product 5 with 135 mls anhydrous THF. Place in a 250 ml round bottom flask with magnetic stir bar. Fit flask with N₂ inlet and stopper. Chill solution with ice/salt bath under N₂ purge. Slowly add 2.55 gms potassium t-butoxide (0.227 mole Aldrich 15,667-1). After addition is complete, continue to stir at -10° C. monitoring by TLC. Once reaction is complete, quench by adding 135 mls 10% HCl stirring 10 min. Extract three times with ether. Dry organic layer with MgSO₄, filter and rotovap to dryness. Crystallize from ether. Obtain NMR and mass spec (m/z=74).
Step 7

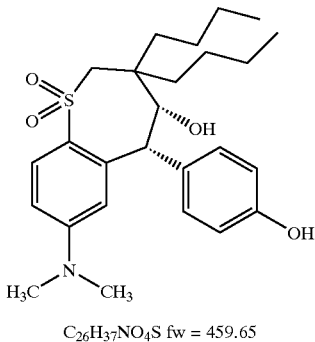

C$_{26}$H$_{37}$NO$_4$S fw = 459.65

Dissolve 4.67 gms (0.01 moles) of product 6 with 100 mls anhydrous chloroform. Place in a 250 ml round bottom flask with magnetic stir bar. Fit flask with N₂ inlet adapter and suba seal. Chill solution with dry ice/acetone bath under a N₂ purge. Slowly add, via syringe, 2.84 mls boron tribromide (0.03 moles Aldrich 20,220-7). Stir at cold temperature for 15 min after addition then allow to warm to room temperature. Monitor reaction progress by TLC. Reaction is usually complete in 3 hrs.

Chill solution with ice bath. Quench with 100 mls 10% K₂CO₃ while stirring rapidly. Stir 10 min. then transfer to sep funnel and allow, separation. Remove aqueous layer. Extract organic layer once with 10% HCl, once H₂O, and once with saturated NaCl solution. Dry organic layer with MgSO₄, filter and rotovap to dryness. Crystallize product from ether. Obtain NMR and mass spec (m/z=460).
Step 8

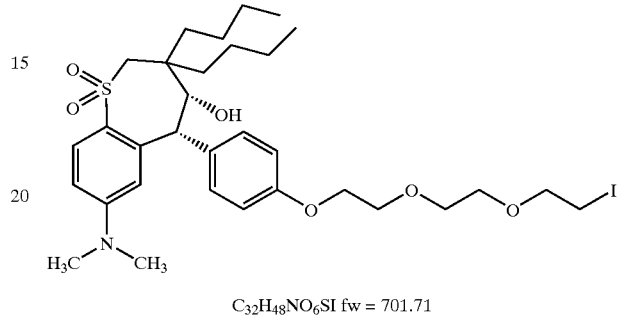

C$_{32}$H$_{48}$NO$_6$SI fw = 701.71

Weigh 0.38 gms NaH (9.57 mmoles Aldrich 19,923-0 60% disp. in mineral oil) in a 250 ml round bottom flask with magnetic stir bar. Fit flask with N₂ inlet and stopper. Chill NaH with ice bath and begin N₂ purge.

Dissolve 4.0 gms (8.7 mmoles) of product 7 with 60 mls anhydrous DMF. Add to the cold NaH. Stir at cold temperature for 30 min Add 1.33 gms K₂CO₃ (9.57 mmoles Fisher P-208).

Dissolve 16.1 gms 1,2-bis-(2-iodoethoxy)ethane (43.5 mmoles Aldrich 33,343-3) with 60 mls anhydrous DMF. Add to cold reaction mixture. Warm to room temperature then heat to 40° C. overnight under N₂.

Cleanup by diluting with ether and extracting sequentially with 5% NaOH, H₂O, and saturated NaCl. Dry organic layer with MgSO₄, filter and dry. Obtain pure product by column chromatography using 75% hexane 25% ethyl acetate as the mobile phase. Obtain NMR and mass spec (m/z=702).
Step 9

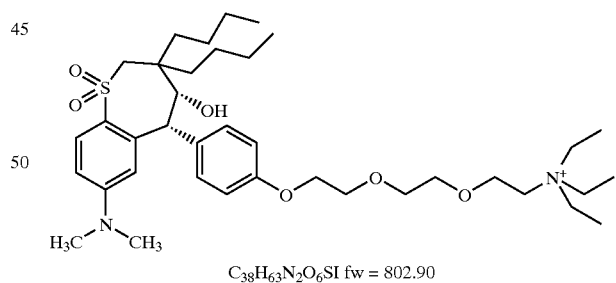

C$_{38}$H$_{63}$N$_2$O$_6$SI fw = 802.90

Dissolve 1.0 gms (1.43 mmoles) of product 8 with 10 mls anhydrous acetonitrile. Place in a 3 ounce Fischer-Porter pressure reaction vessel with magnetic stir bar. Add 2.9 gms triethyl amine (28.6 mmoles Aldrich 23,962-3) dissolved in 10 mls anhydrous acetonitrile. Purge well with N₂ then close system. Heat at 45° C. Monitor reaction by TLC. Reaction is usually complete in 48 hrs.

Perform cleanup by removing acetonitrile under vacuum. Redissolve with anhydrous chloroform and precipitate quaternary ammonium salt with ether. Repeat several times. Dry to obtain crystalline product. Obtain NMR and mass spec (m/z=75).

Example 1399
Step 1. Preparation of 1

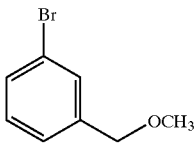

To a solution of 144 g of KOH (2560 mmol) in 1.1 L of DMSO was added 120 g of 2-bromobenzyl alcohol (641 mmol) slowly via addition funnel. Then was added 182 g of methyliodide (80 mL, 1282 mmol) via addition funnel. Stirred at ambient temperature for fifteen minutes. Poured reaction contents into 1.0 L of water and extracted three times with ethyl acetate. The organic layer was dried over MgSO$_4$ and concentrated in vacuo. Purified by silica-gel chromatography through a 200 mL plug using hexanes (100%) as elutant yielded 103.2 g (80%) of 1 as a clear colorless liquid. $^1$H NMR (CDCl$_3$) d 3.39 (s, 3H), 4.42 (s, 2H), 7.18–7.27 (m, 2H), 7.12 (d, J=7.45, 1H), 7.50 (s, 1H).

Step 2. Preparation of 2

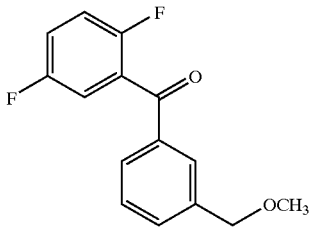

To a cooled (−78° C.) solution of 95 g (472 mmol) of 1 in 1.5 L THF was added 240 mL of 2.5 M n-butyl lithium (576 mmol). The mixture was stirred for one hour, and then to it was added 180 g of zinc iodide (566 mmol) dissolved in 500 ml THF. The mixture was stirred thirty minutes, allowed to warm to 5° C., cooled to −10° C. and to it was added 6 g of Pd(PPh$_3$)$_4$ (5.2 mmol) and 125 g 2,5-difluorobenzoyl chloride (708 mmol). The mixture was stirred at ambient temperature for 18 hours and then cooled to 10° C., quenched with water, partitioned between ethyl acetate and water, and washed organic layer with 1N HCL and with 1N NaOH. The organic layer was dried over MgSO$_4$ and concentrated in vacuo. Purification by silica gel chromatography (Waters Pre-500) using 5% ethyl acetate/hexanes as elutant gave 53.6 g (43%) of 2 as an orange oil. $^1$H NMR (CDCl$_3$) d 3.40 (s, 3H), 4.51 (s, 2H), 7.12–7.26 (m, 3H), 7.47 (t, J=7.50, 1H), 7.57 (d, J=7.45, 1H), 7.73 (d, J=7.45, 1H), 7.80 (s, 1H).

Step 3. Preparation of 3

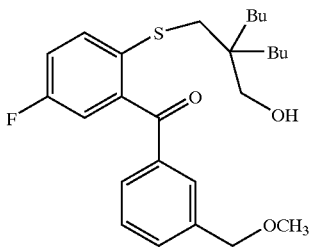

A solution of 53 g (202.3 mmol) of 2 and 11.2 g Li2S (242.8 mmol) in 250 mL DMF was heated to 100° C. for 18 hours. The reaction was cooled (0° C.) and 60.7 g of X' (the cyclic sulfate compound of example 1397) (242.8 mmol) in 50 mL DMF was added. Stirred at ambient temperature for 18 hours then condensed in vacuo. Added 1 L water to organic residue and extracted twice with diethyl ether. Aqueous layer acidified (pH 1) and refluxed 2 days. Cooled to ambient temperature and extracted with methylene chloride, dried organic layer over MgSO$_4$ and condensed in vacuo. Purification by silica gel chromatography (Waters Prep-500) using 10% ethyl acetate/hexanes as elutant gave 42.9 g (48%) of 3 as a yellow oil. $^1$H NMR (CDCl$_3$)d 0.86 (t, J=7.25 Hz, 6H), 1.10–1.26 (m, 12H), 2.83 (s, 2H), 3.32 (s, 2H), 3.40 (s, 3H), 4.48 (s, 3H), 7.02 (dd, J=8.26 Hz and 2.82 Hz, 1H), 7.16 (dt, J=8.19 Hz and 2.82 Hz, 1H), 7.45 (t, J=7.65 Hz, 1H), 7.56–7.61 (m, 2H), 7.69 (d, J=7.85 Hz, 1H), 7.74 (s, 1H).

Step 4. Preparation of 4

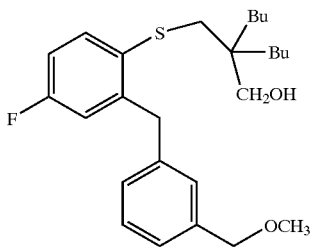

To a cooled (−40° C.) solution of 42.9 g (96.2 mmol) of 3 in 200 mL of methylene chloride was added 21.6 g trifluoromethane sulfonic acid (12.8 mL, 144 mmol) followed by the addition of 22.4 g triethyl silane (30.7 mL, 192.4 mmol). Stirred at −20° C. for two hours, quenched with water and warmed to ambient temperature. Partitioned between methylene chloride and water, dried the organic layer over MgSO$_4$ and condensed in vacuo. Purification by silica gel chromatography (Waters Prep-500) using 10% ethyl acetate/hexanes as elutant gave 24.2 g (60%)of 4 as a oil. $^1$H NMR (CDCl$_3$) d 0.89 (t, J=7.05 Hz, 6H), 1.17–1.40 (m, 12H), 1.46 (t, J=5.84 Hz, 1H), 2.81 (s, 2H), 3.38 (s, 3H), 3.43 (d, J=5.23 Hz, 2H), 4.16 (s, 2H), 4.42 (s, 2H), 6.80 (d, J=9.67 Hz, 1H), 6.90 (t, J=8.46 Hz, 1H), 7.09 (d, J=7.45 Hz, 1H), 7.15–7.21 (m, 2H), 7.25–7.32 (m, 2H), 7.42 (m, 1H).

Step 5. Preparation of 5

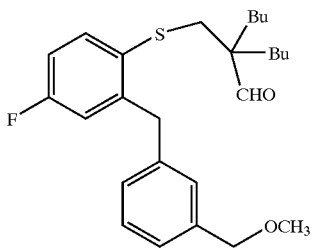

To a cooled (15–18° C.) solution of 24.2 g (55.8 mmol) of 4 in 100 mL DMSO was added 31.2 g sulfur trioxide pyridine complex (195 mmol). Stirred at ambient temperature for thirty minutes. Poured into cold water and extracted three times with ethyl acetate. Washed organics with 5% HCl (300 mL) and then with brine (300 mL), dired organics over MgSO$_4$ and condensed in vacuo to give 23.1 g (96%) of 5 as a light brown oil. $^1$H NMR (CDCl$_3$) d 0.87 (t, J=7.05 Hz, 6H), 1.01–1.32 (m, 8H), 1.53–1.65 (m, 4H), 2.98 (s, 2H), 3.38 (s, 3H), 4.15 (s, 2H), 4.43 (s, 2H), 6.81 (dd, J=9.66 Hz and 2.82 Hz, 1H), 6.91 (t, J=8.62 Hz, 1H), 7.07 (d, J=7.46 Hz, 1H), 7.14 (s, 1H), 7.19 (d, J=7.65 Hz, 1H), 7.26–7.32 (m, 1H), 7.42 (dd, J=8.66 Hz and 5.64 Hz, 1H), 9.40 (s, 1H).

Step 6. Preparation of 6

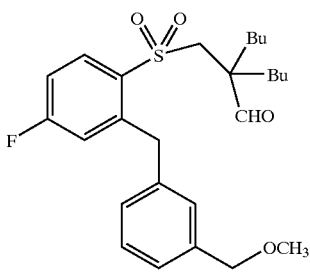

To a cooled (0° C.) solution of 23.1 g (53.6 mmol) of 5 in 200 mL methylene chloride was added 28.6 g meta cholorperoxy-benzoic acid (112.6 mmol). Stirred at ambient temperature for 24 hours. Quenched with 100 mL 10% $Na_2SO_3$, partitioned between water and methylene chloride. Dried organic layer over $MgSO_4$ and condensed in vacuo to give 24.5 g (98%) of 6 as a light yellow oil. $^1$H NMR ($CDCl_3$) d 0.86–1.29 (m, 14H), 1.58–1.63 (m, 2H), 1.82–1.91 (m, 2H), 3.13 (s, 2H), 3.39 (s, 3H), 4.44 (s, 2H), 4.50 (s, 2H), 6.93 (d, J=9.07 Hz, 1H), 7.10–7.33 (m, 5H), 8.05 (s, 1H), 9.38 (s, 1H).

Step 7. Preparation of 7

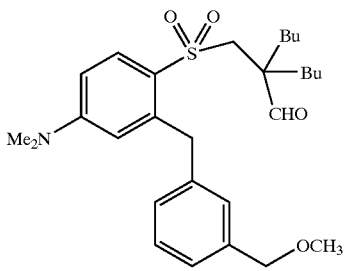

To a solution of 24.5 g (52.9 mmol) of 6 in 20 mL of THF contained in a stainless steel reaction vessel was added 100 mL of a 2.0 M solution of dimethyl amine and 20 mL of neat dimethyl amine. The vessel was sealed and heated to 110° C. for 16 hours. The reaction vessel was cooled to ambient temperature and the contents concentrated in vacuo. Purification by silica gel chromatography (Waters Prep-500) using 15% ethyl acetate/hexanes gave 21.8 g (84%) of 7 as a clear colorless oil. $^1$H NMR ($CDCl_3$) d 0.85 (t, J=7.25 Hz, 6H), 0.93–1.29 (m, 8H), 1.49–1.59 (m, 2H), 1.70–1.80 (m, 2H), 2.98 (s, 8H), 3.37 (s, 3H), 4.41 (s, 2H), 4.44 (s, 2H), 6.42 (s, 1H), 6.58 (dd, J=9.0 Hz and 2.61 Hz, 1H), 7.13 (d, J=7.45 Hz, 1H), 7.21 (s, 1H), 7.28 (t, J=7.85 Hz, 1H), 7.82 (d, J=9.06 Hz, 1H), 9.36 (s, 1H).

Step 8. Preparation of 8

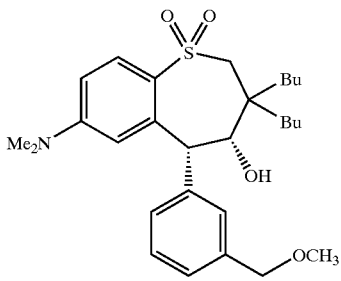

A solution of 21.8 g (44.8 mmol) of 7 in 600 mL of THF was cooled to 0° C. 58.2 mL of a 1 M solution of potassium t-butoxide was added slowly, maintaining the temperature at <5° C. Stirred for 30 minutes, then quenched with 50 mL of saturated ammonium chloride. The organic layer was partitioned between ethyl acetate and water, dried over $MgSO_4$ and concentrated in vacuo. Purification by recrystalization from 10% ethyl acetate/hexanes gave 15.1 g of 8 as a white solid. The mother liquor was purified by silica gel chromatography (Waters Prep-500) using 30% ethyl acetate/hexanes as the elutant to give 3.0 g of 8 as a white solid. MS (FABLi$^+$) m/e 494.6. HRMS (EI$^+$) calculated for M+H 487.2756. Found 487.2746.

Step 9. Preparation of 9

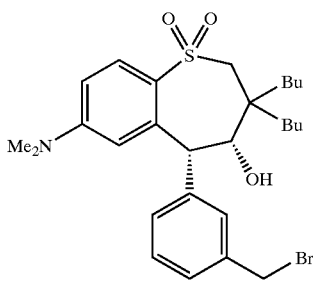

A solution of 2.0 g (4.1 mmol) of 8 in 20 mL of methylene chloride was cooled to 60° C. 4.1 mL of a 1M solution of boron tribromide was added. Stirred at ambient temperature for thirty minutes. Cooled reaction to ~10° C. and quenched with 50 mL of water. The organic layer was partitioned between methylene chloride and water, dried over $MgSO_4$ and concentrated in vacuo. Purification by recrystallization from 50% ethyl acetate/methylene chloride gave 1.95 g (89%) of 9 as a white solid. MS (FABH$^+$) m/e 537. HRMS (FAB) calculated for M 536.1834. Found 536.1822.

Step 10. Preparation of 10

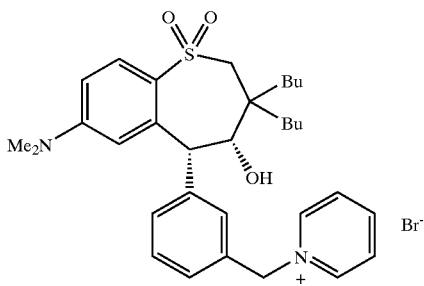

A solution of 1.09 g (2.0 mmol) of 9 and 4.9 g (62 mmol) of pyridine in 30 mL of acetonitrile was stirred at ambient temperature for 18 hours. The reaction was concentrated in vacuo. Purification by recrystallization from methanol/diethyl ether gave 1.19 g (96%) of 10 as an off white solid. MS (FAB$^+$) m/e 535.5.

Example 1400

Step 1

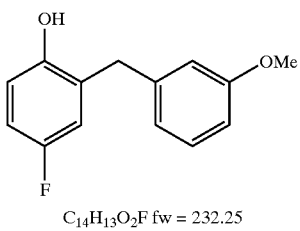

C₁₄H₁₃O₂F fw = 232.25

A 12-liter, 4-neck round-bottom flask was equipped with reflux condenser, N₂ gas adaptor, mechanical stirrer, and an addition funnel. The system was purged with N₂. A slurry of sodium hydride (126.0 g/4.988 mol) in toluene (2.5 L) was added, and the mixture was cooled to 6° C. A solution of 4-fluorophenol (560.5 g/5.000 mol) in toluene (2.5 L) was added via addition funnel over a period of 2.5 h. The reaction mixture was heated to reflux (100 C) for 1 h. A solution of 3-methoxybenzyl chloride (783.0 g/5.000 mol) in toluene (750 mL) was added via addition funnel while maintaining reflux. After 15 h. refluxing, the mixture was cooled to room temperature and poured into H₂O (2.5 L). After 20 min. stirring, the layers were separated, and the organic layer was extracted with a solution of potassium hydroxide (720 g) in MeOH (2.5 L). The MeOH layer was added to 20% aqueous potassium hydroxide, and the mixture was stirred for 30 min. The mixture was then washed 5 times with toluene. The toluene washes were extracted with 20% aq. KOH. All 20% aq. KOH solutions were combined and acidified with concentrated HCl. The acidic solution was extracted three times with ethyl ether, dried (MgSO₄), filtered and concentrated in vacuo. The crude product was purified by Kugelrohr distillation to give a clear, colorless oil (449.0 g/39% yield). b.p.: 120–130 C/50 mtorrHg. ¹H NMR and MS [(M+H)⁺=233] confirmed desired structure.

Step 2

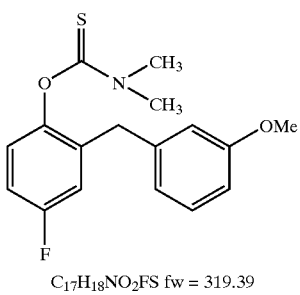

C₁₇H₁₈NO₂FS fw = 319.39

A 12-liter, 3-neck round-bottom flask was fitted with mechanical stirrer and N₂ gas adaptor. The system was purged with N₂. 4-Fluoro-2-(3-methoxybenzyl)-phenol (455.5 g/1.961 mol) and dimethylformamide were added. The solution was cooled to 6 C, and sodium hydride (55.5 g/2.197 mol) was added slowly. After warming to room temperature, dimethylthiocarbamoyl chloride (242.4 g/1.961 mol) was added. After 15 h, the reaction mixture was poured into H₂O (4.0 L), and extracted two times with ethyl ether. The combined organic layers were washed with H₂O and saturated aqueous NaCl, dried (MgSO₄), filtered, and concentrated in vacuo to give the product (605.3 g, 97% yield). ¹H NMR and MS [(M+H)⁺=320] confirm desired structure.

Step 3

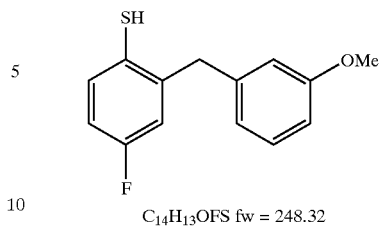

C₁₄H₁₃OFS fw = 248.32

A 12-liter, round-bottom flask was equipped with N₂ gas adaptor, mechanical stirrer, and reflux condenser. The system was purged with N₂. 4-Fluoro-2-(3-methoxybenzyl)-phenyldimethylthiocarbamate (605.3 g/1.895 mol) and phenyl ether (2.0 kg) were added, and the solution was heated to reflux for 2 h. The mixture was stirred for 64 h. at room temparature and then heated to reflux for 2 h. After cooling to room temperature, MeOH (2.0 L) and THF (2.0 L) were added, and the solution was stirred for 15 h. Potassium hydroxide (425.9 g/7.590 mol) was added, and the mixture was heated to reflux for 4 h. After cooling to room temparature, the mixture was concentrated by rotavap, dissolved in ethyl ether (1.0 L), and extracted with H₂O. The aqueous extracts were combined, acidified with concentrated HCl, and extracted with ethyl ether. The ether extracts were dried (MgSO₄), filtered, and concentrated in vacuo to give an amber oil (463.0 g, 98% yield). ¹H NMR confirmed desired structure.

Step 4

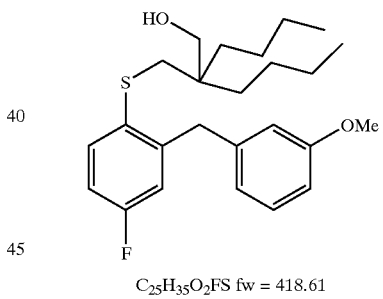

C₂₅H₃₅O₂FS fw = 418.61

A 5-liter, 3-neck, round-bottom flask was equipped with N₂ gas adaptor and mechanical stirrer. The system was purged with N₂. 4-Fluoro-2-(3-methoxybenzyl)-thiophenol (100.0 g/403.2 mmol) and 2-methoxyethyl ether (1.0 L) were added and the solution was cooled to 0° C. Sodium hydride (9.68 g/383.2 mmol) was added slowly, and the mixture was allowed to warm to room temparature, 2,2-Dibutylpropylene sulfate (110.89 g/443.6 mmol) was added, and the mixture was stirred for 64 h. The reaction mixture was concentrated by rotavap and dissolved in H₂O. The aqueous solution was washed with ethyl ether, and concentrated H₂SO₄ was added. The aqueous solution was heated to reflux for 30 min, cooled to room temperature, and extracted with ethyl ether. The ether solution was dried (MgSO₄), filtered, and conc'd in vacuo to give an amber oil (143.94 g/85% yield). ¹H NMR and MS [(M+H)⁺=419] confirm the desired structure.

Step 5

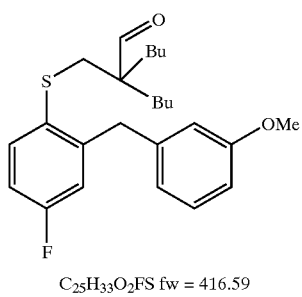

C25H33O2FS fw = 416.59

Step 7

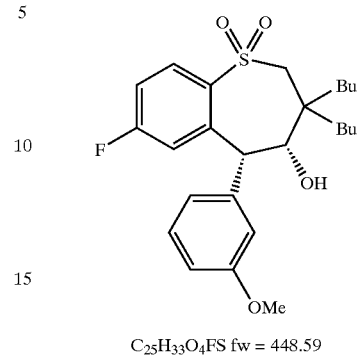

C25H33O4FS fw = 448.59

A 2-liter, 4-neck, round-bottom flask was equipped with N₂ gas adaptor, and mechanical stirrer. The system was purged with N₂. The corresponding alcohol (143.94 g/343.8 mmol) and CH₂Cl₂ (1.0 L) were added and cooled to 0° C. Pyridinium chlorochromate (140.53 g/651.6 mmol) was added. After 6 h., CH₂Cl₂ was added. After 20 min, the mixture was filtered through silica gel, washing with CH₂Cl₂. The filtrate was concentrated in vacuo to give a dark yellow-red oil (110.6 g, 77% yield). ¹H NMR and MS [(M+H)⁺=417] confirm the desired structure.

Step 6

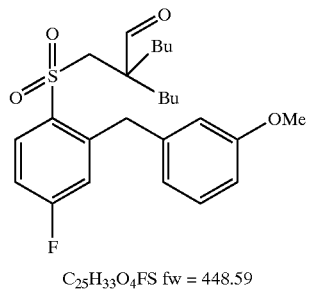

C25H33O4FS fw = 448.59

A 2-liter, 4-neck, round-bottom flask was equipped with N₂ gas adaptor and mechanical stirrer. The system was purged with N₂. The corresponding sulfide (110.6 g/265.5 mmol) and CH₂Cl₂ (1.0 L) were added. The solution was cooled to 0 C, and 3-chloroperbenzoic acid (158.21 g/531.7 mmol) was added portionwise. After 30 min, the reaction mixture was allowed to warm to room temperature After 3.5 h, the reaction mixture was cooled to 0° C. and filtered through a fine fritted funnel. The filtrate was washed with 10% aqueous K₂CO₃. An emulsion formed which was extracted with ethyl ether. The organic layers were combined, dried (MgSO₄), filtered, and concentrated in vacuo to give the product (93.2 g, 78% yield). ¹H NMR confirmed the desired structure.

A 2-liter, 4neck, round-bottom flask was equipped with N₂ gas adaptor, mechanical stirrer, and a powder addition funnel. The system was purged with N₂. The corresponding aldehyde (93.2 g/208 mmol) and THF (1.0 L) were added, and the mixture was cooled to 0° C. Potassium tert-butoxide (23.35 g/208.1 mmol) was added via addition funnel. After 1 h, 10% aq/HCl (1.0 L) was added. After 1 h, the mixture was extracted three times with ethyl ether, dried (MgSO₄), filtered, and concentrated in vacuo. The crude product was purified by recryst. from 80/20 hexane/ethyl acetate to give a white solid (32.18 g). The mother liquor was concentrated in vacuo and recrystelized from 95/5 toluene/ethyl acetate to give a white solid (33.60 g/combined yield: 71%). ¹H NMR confirmed the desired product.

Step 8

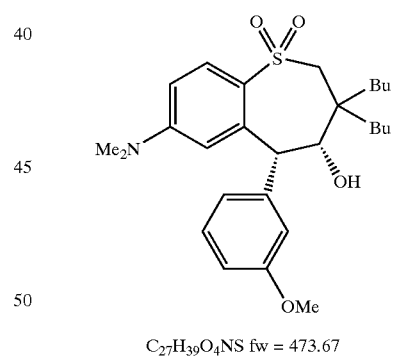

C27H39O4NS fw = 473.67

A Fisher porter bottle was fitted with N₂ line and magnetic stirrer. The system was purged with N₂. The corresponding fluoro-compound (28.1 g/62.6 mmol) was added, and the vessel was sealed and cooled to −78° C. Dimethylamine (17.1 g/379 mmol) was condensed via a CO₂/acetone bath and added to the reaction vessel. The mixture was allowed to warm to room temperature and was heated to 60° C. After 20 h, the reaction mixture was allowed to cool and was dissolved in ethyl ether. The ether solution was washed with H₂O, saturated aqueous NaCl, dried (MgSO₄), filtered, and concentrated in vacuo to give a white solid (28.5 g/96% yield). ¹H NMR confirmed the desired structure.

Step 9

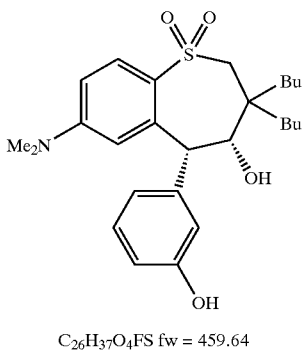

C₂₆H₃₇O₄FS fw = 459.64

A 250-mL, 3-neck, round-bottom flask was equipped with N$_2$ gas adaptor and magnetic stirrer. The system was purged with N$_2$. The corresponding methoxy-compound (6.62 g/14.0 mmol) and CHCl$_3$ (150 mL) were added. The reaction mixture was cooled to −78 C, and boron tribromide (10.50 g/41.9 mmol) was added. The mixture was allowed to warm to room temperature After 4 h, the reaction mixture was cooled to 0° C. and was quenched with 10% K$_2$CO$_3$ (100 mL). After 10 min, the layers were separated, and the aqueous layer was extracted two times with ethyl ether. The CHCl$_3$ and ether extracts were combined, washed with saturated aqueous NaCl, dried (MgSO$_4$), filtered, and concentrated in vacuo to give the product (6.27 g/98% yield). $^1$H NMR confirmed the desired structure.

Step 10

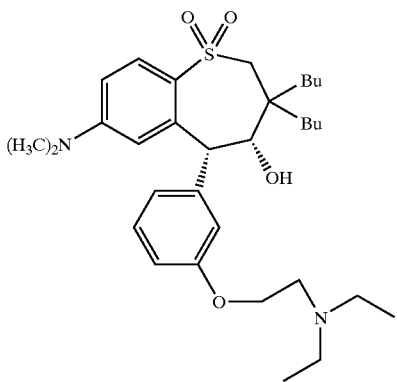

In a 250 ml single neck round bottom Flask with stir bar place 2-diethylamineoethyl chloride hydochloride (fw 172.10 g/mole) Aldrich D8, 720-1 (2.4 mmol, 4.12 g), 34 ml dry ether and 34 ml of 1N KOH (aqueous). Stir 15 minutes and then separate by ether extraction and dry over anhydrous potassium carbonate.

In a separate 2-necked 250 ml round bottom flask with stir bar add sodium hydride (60% dispersion in mineral oil, 100 mg, 2.6 mmol) and 34 ml of DMF. Cool to ice temperature. Next add phenol product (previous step) 1.1 g (2.4 mmilomoles in 5 ml DMF and the ether solution prepared above. Heat to 40° C. for 3 days. The product which contained no starting material by TLC was diluted with ether and extracted with 1 portion of 5% NaOH, followed by water and then brine. The ether layer was dried over magnesium sulfate and isolated by removing ether by rotary evaporation (1.3 gms). The product may be further purified by chromatography (SiO2 99% ethyl acetate/1% NH4OH at 5 ml/min.). Isolated yield: 0.78 g (mass spec, and H1NMR)

Step 11

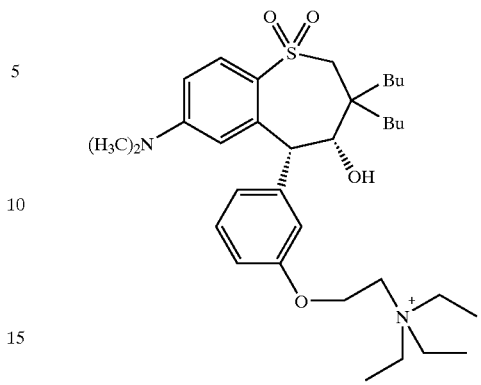

The product from step 10 (0.57 gms, 1.02 millimole fw 558.83 g/mole) and 1.6 gms iodoethane (10.02 mmol) was placed in 5 ml acetonitrile in a fischer-porter bottle and heated to 45° C. for 3 days. The solution was evaporated to dryness and redissolved in 5 mls of chloroform. Next ether was added to the chloroform solution and the resulting mixture was chilled. The desired product is isolated as a precipitate 0.7272 gms. Mass spec M−I=587.9, H NMR).

Example 1401
Step 1

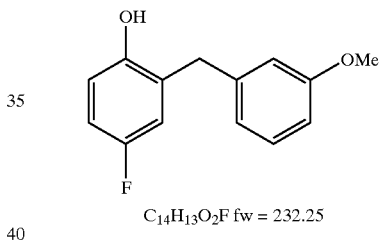

C₁₄H₁₃O₂F fw = 232.25

A 12-liter, 4neck round-bottom flask was equipped with reflux condenser, N$_2$ gas adaptor, mechanical stirrer, and an addition funnel. The system was purged with N$_2$. A slurry of sodium hydride (126.0 g/4.988 mol) in toluene (2.5 L) was added, and the mixture was cooled to 6° C. A solution of 4-fluorophenol (560.5 g/5.000 mol) in toluene (2.5 L) was added via addition funnel over a period of 2.5 h. The reaction mixture was heated to reflux (100 C) for 1 h. A solution of 3-methoxybenzyl chloride (783.0 g/5.000 mol) in toluene (750 mL) was added via addition funnel while maintaining reflux. After 15 h. refluxing, the mixture was cooled to room temperature and poured into H$_2$O (2.5 L). After 20 min. stirring, the layers were separated, and the organic layer was extracted with a solution of potassium hydroxide (720 g) in MeOH (2.5 L). The MeOH layer was added to 20% aqueous potassium hydroxide, and the mixture was stirred for 30 min. The mixture was then washed 5 times with toluene. The toluene washes were extracted with 20% aq. KOH. All 20% aqueous KOH solutions were combined and acidified with concentrated HCl. The acidic solution was extracted three times with ethyl ether, dried over MgSO$_4$, filtered and concentrated in vacuo. The crude product was purified by Kugelrohr distillation to give a clear, colorless oil (449.0 g/39% yield). b.p.: 120–130 C/50 mtorrHg. $^1$H NMR and MS [(M+H)$^+$=233] confirmed desired structure.

Step 2

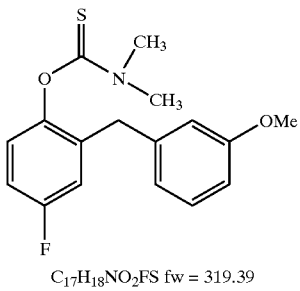

C₁₇H₁₈NO₂FS fw = 319.39

A 12-liter, 3-neck round-bottom flask was fitted with mechanical stirrer and N₂ gas adaptor. The system was purged with N₂. 4-Fluoro-2-(3-methoxybenzyl)-phenol (455.5 g/1.961 mol) and dimethylformamide were added. The solution was cooled to 6 C, and sodium hydride (55.5 g/2.197 mol) was added slowly. After warming to room temperature, dimethylthiocarbamoyl chloride (242.4 g/1.961 mol) was added. After 15 h, the reaction mixture was poured into H₂O (4.0 L), and extracted two times with ethyl ether. The combined organic layers were washed with H₂O and saturated aqueous NaCl, dried over MgSO₄, filtered, and concentrated in vacuo to give the product (605.3 g, 97% yield). ¹H NMR and MS [(M+H)⁺=320] confirm desired structure.

Step 3

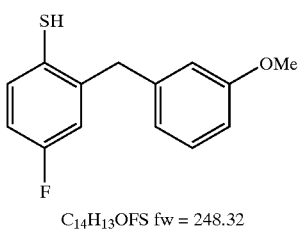

C₁₄H₁₃OFS fw = 248.32

A 12-liter, round-bottom flask was equipped with N₂ gas adaptor, mechanical stirrer, and reflux condenser. The system was purged with N₂. 4-Fluoro-2-(3-methoxybenzyl)-phenyldimethylthiocarbamate (605.3 g/1.895 mol) and phenyl ether (2.0 kg) were added, and the solution was heated to reflux for 2 h. The mixture was stirred for 64 h. at room temperature and then heated to reflux for 2 h. After cooling to room temperature, MeOH (2.0 L) and THF (2.0 L) were added, and the solution was stirred for 15 h. Potassium hydroxide (425.9 g/7.590 mol) was added, and the mixture was heated to reflux for 4 h. After cooling to room temperature, the mixture was concentrated by rotavap, dissolved in ethyl ether (1.0 L), and extracted with H₂O. The aqueous extracts were combined, acidified with conc. HCl, and extracted with ethyl ether. The ether extracts were dried (MgSO₄), filtered, and concentrated in vacuo to give an amber oil (463.0 g, 98% yield). ¹H NMR confirmed desired structure.

Step 4

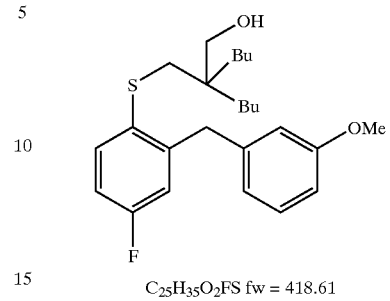

C₂₅H₃₅O₂FS fw = 418.61

A 5-liter, 3-neck, round-bottom flask was equipped with N₂ gas adaptor and mechanical stirrer. The system was purged with N₂. 4-Fluoro-2-(3-methoxybenzyl)-thiophenol (100.0 g/403.2 mmol) and 2-methoxyethyl ether (1.0 L) were added and the solution was cooled to 0° C. Sodium hydride (9.68 g/383.2 mmol) was added slowly, and the mixture was allowed to warm to room temperature 2,2-Dibutylpropylene sulfate (110.89 g/443.6 mmol) was added, and the mixture was stirred for 64 h. The reaction mixture was concentrated by rotavap and dissolved in H₂O. The aqueous solution was washed with ethyl ether, and conc. H₂SO₄ was added. The aqueous solution was heated to reflux for 30 min, cooled to room temperature, and extracted with ethyl ether. The ether solution was dried (MgSO₄), filtered, and concentrated in vacuo to give an amber oil (143.94 g/85% yield). ¹H NMR and MS [(M+H)⁺=419] confirm the desired structure.

Step 5

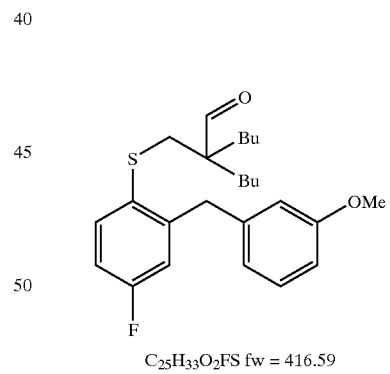

C₂₅H₃₃O₂FS fw = 416.59

A 2-liter, 4-neck, round-bottom flask was equipped with N₂ gas adaptor, and mechanical stirrer. The system was purged with N₂. The corresponding alcohol (143.94 g/343.8 mmol) and CH₂Cl₂ (1.0 L) were added and cooled to 0° C. Pyridinium chlorochromate (140.53 g/651.6 mmol) was added. After 6 h., CH₂Cl₂ was added. After 20 min, the mixture was filtered through silica gel, washing with CH₂Cl₂. The filtrate was concentrated in vacuo to give a dark yellow-red oil (110.6 g, 77% yield). ¹H NMR and MS [(M+H)⁺=417] confirm the desired structure.

Step 6

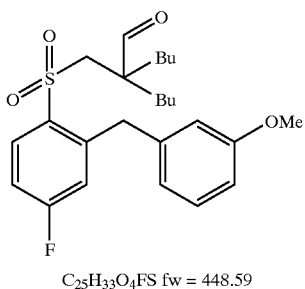

C25H33O4FS fw = 448.59

A 2-liter, 4-neck, round-bottom flask was equipped with N₂ gas adaptor and mechanical stirrer. The system was purged with N₂. The corresponding sulfide (110.6 g/265.5 mmol) and CH₂Cl₂ (1.0 L) were added. The solution was cooled to 0 C, and 3-chloroperbenzoic acid (158.21 g/531.7 mmol) was added portionwise. After 30 min, the reaction mixture was allowed to warm to room temperature After 3.5 h, the reaction mixture was cooled to 0° C. and filtered through a fine fritted funnel. The filtrate was washed with 10% aqueous K₂CO₃. An emulsion formed which was extracted with ethyl ether. The organic layers were combined, dried (MgSO₄), filtered, and concentrated in vacuo to give the product (93.2 g, 78% yield). ¹H NMR confirmed the desired structure.

Step 7

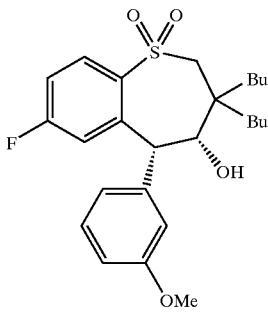

C25H33O4FS fw = 448.59

A 2-liter, 4neck, round-bottom flask was equipped with N₂ gas adaptor, mechanical stirrer, and a powder addition funnel. The system was purged with N₂. The corresponding aldehyde (93.2 g/208 mmol) and THF (1.0 L) were added, and the mixture was cooled to 0° C. Potassium tert-butoxide (23.35 g/208.1 mmol) was added via addition funnel. After 1 h, 10% aq/HCl (1.0 L) was added. After 1 h, the mixture was extracted three times with ethyl ether, dried (MgSO₄), filtered, and concentrated in vacuo. The crude product was purified by recrystallized from 80/20 hexane/ethyl acetate to give a white solid (32.18 g). The mother liquor was concentrated in vacuo and recrystallized from 95/5 toluene/ethyl acetate to give a white solid (33.60 g, combined yield: 71%). ¹H NMR confirmed the desired product.

Step 8

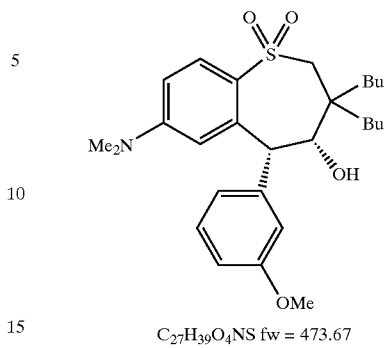

C27H39O4NS fw = 473.67

A Fisher porter bottle was fitted with N₂ line and magnetic stirrer. The system was purged with N₂. The corresponding fluoro-compound (28.1 g/62.6 mmol) was added, and the vessel was sealed and cooled to −78° C. Dimethylamine (17.1 g/379 mmol) was condensed via a CO₂/acetone bath and added to the reaction vessel. The mixture was allowed to warm to room temperature and was heated to 60° C. After 20 h, the reaction mixture was allowed to cool and was dissolved in ethyl ether. The ether solution was washed with H₂O, saturated aqueous NaCl, dried over MgSO₄, filtered, and concentrated in vacuo to give a white solid (28.5 g/96% yield). ¹H NMR confirmed the desired structure.

Step 9

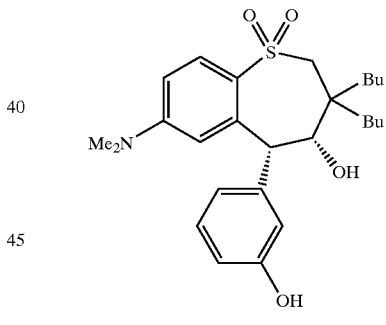

C26H37O4NS fw = 459.64

A 250-mL, 3-neck, round-bottom flask was equipped with N₂ gas adaptor and magnetic stirrer. The system was purged with N₂. The corresponding methoxy-compound (6.62 g/14.0 mmol) and CHCl₃ (150 mL) were added. The reaction mixture was cooled to −78 C, and boron tribromide (10.50 g/41.9 mmol) was added. The mixture was allowed to warm to room temperature After 4 h, the reaction mixture was cooled to 0° C. and was quenched with 10% K₂CO₃ (100 mL). After 10 min, the layers were separated, and the aqueous layer was extracted two times with ethyl ether. The CHCl₃ and ether extracts were combined, washed with saturated aqueous NaCl, dried over MgSO₄, filtered, and concentrated in vacuo to give the product (6.27 g/98% yield). ¹H NMR confirmed the desired structure.

Step 10

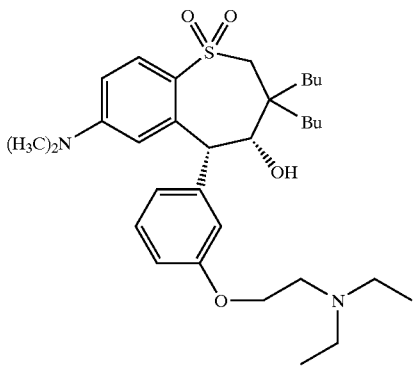

In a 250 ml single neck round bottom flask with stir bar place 2-diethylamineoethyl chloride hydochloride (fw 172.10 g/mole) Aldrich D8, 720-1 (2.4 millimoles, 4.12 g), 34 ml dry ether and 34 ml of 1N KOH (aqueous). Stir 15 minutes and then separate by ether extraction and dry over anhydrous potassium carbonate.

In a separate 2-necked 250 ml round bottom flask with stir bar add sodium hydride (60% dispersion in mineral oil, 100 mg, (2.6 mmol) and 34 ml of DMF. Cool to ice temperature. Next add phenol product (previous step) 1.1 g (2.4 mmol in 5 ml DMF and the ether solution prepared above. Heat to 40° C. for 3 days. The product which contained no starting material by TLC was diluted with ether and extracted with 1 portion of 5% NaOH, followed by water and then brine. The ether layer was dried over Magnesium sulfate and isolated by removing ether by rotary evaporation (1.3 gms). The product may be further purified by chromatography (silica 99% ethyl acetate/1% NH4OH at 5 ml/min.). Isolated yield: 0.78 g (mass spec, and H1 NMR)

Step 11

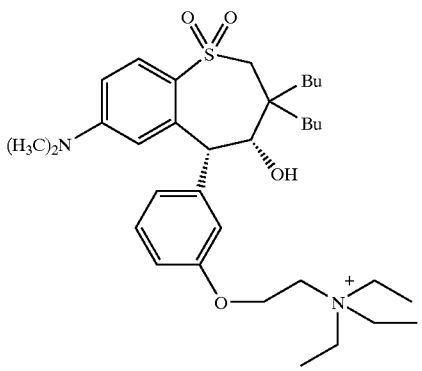

The product from step 10 (0.57 gms, 1.02 millimole fw 558.83 g/mole) and iodoethane (1.6 gms (10.02 mmilimoles) was place in 5 ml acetonitrile in a Fischer-Porter bottle and heated to 45° C. for 3 days. The solution was evaporated to dryness and redissolved in 5 mls of chloroform. Next ether was added to the chloroform solution and the resulting mixture was chilled. The desired product is isolated as a precipitate 0.7272 gms. Mass spec M−I=587.9, $^1$H NMR).

Example 1402

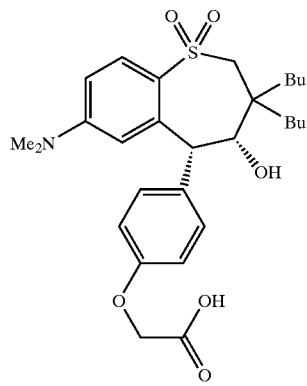

(4R-cis)-5-[[5-[4-[3,3-Dibutyl-7-(dimethylamino)-2, 3,4,5-tetrahydro-4-hydroxy-1,1-dioxido-1-benzothiepin-5-yl]phenoxy]pentyl]thio]-1H-tetrazole-1-acetic Acid Step 1. Preparation of 4-Fluoro-2-((4-methoxyphenyl)methyl)-phenol To a stirred solution of 23.66 g of 95% sodium hydride (0.94 mol) in 600 mL of dry toluene was added 100.0 g of 4-fluorophenol (0.89 mol) at 0° C. The mixture was stirred at 90° C. for 1 hour until gas evolution stopped. The mixture was cooled down to room temperature and a solution of 139.71 g of 3-methoxybenzyl chloride (0.89 mol) in 400 mL of dry toluene was added. After refluxing for 24 hours, the mixture was cooled to room temperature and quenched with 500 mL of water. The organic layer was separated, dried over $MgSO_4$, and concentrated under high vacuum. The remaining starting materials were removed by distillation. The crude dark red oil was filtered through a layer of 1 L of silica gel with neat hexane to yield 53.00 g (25.6%) of the product as a pink solid: $^1$H NMR (CDCl$_3$) δ 3.79 (s, 3H), 3.90 (s, 2H), 4.58 (s, 1H), 6.70–6.74 (m, 1H), 6.79–6.88 (m, 4H), 7.11–7.16 (m, 2H).

Step 2. Preparation of 4-Fluoro-2-((4-methoxyphenyl)methyl)-thiophenol

Step 2a. Preparation of Thiocarbamate

To a stirred solution of 50.00 g (215.30 mmol) of 4-fluoro-2-((4-methoxyphenyl)methyl)-phenol in 500 mL of dry DMF was added 11.20 g of 60% sodium hydride dispersion in mineral oil (279.90 mmol) at 2° C. The mixture was allowed to warm to room temperature and 26.61 g of dimethylthiocarbamoyl chloride (215.30 mmol) was added. The reaction mixture was stirred at room temperature overnight. The mixture was quenched with 100 mL of water in an ice bath The solution was extracted with 500 mL of diethyl ether. The ether solution was washed with 500 mL of water and 500 mL of brine. The ether solution was dried over $MgSO_4$ and stripped to dryness. The crude product was filtered through a plug of 500 mL silica gel using 5% ethyl acetate/hexane to yield 48.00 g (69.8%) of the product as a pale white solid: $^1$H NMR (CDCl$_3$) δ 3.21 (s, 3H), 3.46 (s, 3H), 3.80 (s, 3H), 3.82 (s, 2H), 6.78–6.86 (m, 3H), 6.90–7.00 (m, 2H), 7.09 (d, J=8.7 Hz, 2H).

Step 2b. Rearrangement and Hydrolysis of Thiocarbamate to 4-Fluoro-2-((4-methoxyphenyl)methyl)-thiophenol A stirred solution of 48.00 g (150.29 mmol) of thiocarbamate (obtained from Step 2a) in 200 mL of diphenyl ether was refluxed at 270° C. overnight. The solution was cooled down to room temperature and filtered through 1 L of silica gel with 2 L of hexane to remove phenyl ether. The rearrangement product was washed with 5% ethyl acetate/hexane to give 46.00 g (95.8%) of the product as a pale yellow solid: $^1$H NMR (CDCl$_3$) δ 3.02 (s, 3H), 3.10 (s, 3H), 3.80 (s, 3H), 4.07 (s, 2H), 6.82–6.86 (m, 3H), 6.93 (dt, J=8.4 Hz, 2.7 Hz, 1H), 7.08 (d, J=8.7 Hz, 2H), 7.49 (dd, J=6.0 Hz, 8.7 Hz, 1H).

To a solution of 46.00 g (144.02 mmol) of the rearrangement product (above) in 200 mL of methanol and 200 mL of THF was added 17.28 g of NaOH (432.06 mmol). The mixture was refluxed under nitrogen overnight. The solvents were evaporated off and 200 mL of water was added. The aqueous solution was washed with 200 mL of diethyl ether twice and placed in an ice bath. The aqueous mixture was acidified to pH 6 with concentrated HCl solution. The solution was extracted with 300 mL of diethyl ether twice. The ether layers were combined, dried over MgSO$_4$ and stripped to dryness to afford 27.00 g (75.5%) of the product as a brown oil: $^1$H NMR (CDCl$_3$) δ 3.24 (s, 1H), 3.80 (s, 3H), 3.99 (s, 2H), 6.81–6.87 (m, 4H), 7.09 (d, J=8.7 Hz, 2H), 7.27–7.33 (m, 1H).

Step 3. Preparation of Dibutyl Cyclic Sulfate

Step 3a. Preparation of 2,2-Dibutyl-1,3-propanediol.

To a stirred solution of di-butyl-diethylmalonate (Aldrich) (150 g, 0.55 mol in dry THF (700 ml) in an acetone/dry ice bath was added LAH (1 M THF) 662 ml (1.2 eq., 0.66 mol) dropwise maintaining the temperature between −20 to 0° C. The reaction was stirred at RT overnight. The reaction was cooled to −20° C. and 40 ml of water, and 80 mL of 10% NaOH and 80 ml of water were added dropwise. The resulting suspension was filtered. The filtrate was dried over sodium sulphate and concentrated in vacuo to give diol 98.4 g (yield 95%) as an oil. MS spectra and proton and carbon NMR spectra were consistent with the product.

Step 3b. Preparation of Dibutyl Cyclic Sulfite

A solution of 2,2-dibutyl-1,3-propanediol (103 g, 0.548 mol, obtained from Step 3a) and triethylamine (221 g, 2.19 mol) in anhydrous methylene chloride (500 ml) was stirred at 0° C. under nitrogen. To the mixture, thionyl chloride (97.8 g, 0.82 mol) was added dropwise and within 5 min the solution turned yellow and then black when the addition was completed within half an hour. The reaction mixture was stirred for 3 hrs. at 0° C. GC showed that there was no starting material left. The mixture was washed with ice water twice then with brine twice. The organic phase was dried over magnesium sulfate and concentrated under vacuum to give 128 g (100%) of the dibutyl cyclic sulfite as a black oil. Mass spectrum (MS) was consistent with the product.

Step 3c. Oxidation of Dibutyl Cyclic Sulfite to Dibutyl Cyclic Sulfate

To a solution of the dibutyl cyclic sulfite (127.5 g, 0.54 mol, obtained from Step 3b) in 600 ml acetonitrile and 500 ml of water cooled in an ice bath under nitrogen was added ruthenium (III) chloride (1 g) and sodium periodate (233 g, 1.08 mol). The reaction was stirred overnight and the color of the solution turned black. GC showed that there was no starting material left. The mixture was extracted with 300 ml of ether and the ether extract was washed three times with brine. The organic phase was dried over magnesium sulfate and passed through celite. The filtrate was concentrated under vacuum and to give 133 g (97.8%) of the dibutyl cyclic sulfate as an oil. Proton and carbon NMR and MS were consistent with the product.

Step 4. Preparation of Aryl-3-hydroxypropylsulfide

To a stirred solution of 27.00 g (108.73 mmol) of 4-fluoro-2-((4-methoxyphenyl)methyl)thiophenol (obtained from Step 2) in 270 mL of diglyme was added 4.35 g of 60% sodium hydride dispersion in mineral oil (108.73 mmol) at 0° C. After gas evolution ceased, 29.94 g (119.60 mmol) of the dibutyl cyclic sulfate (obtained from Step 3c) was added at 0° C. and stirred for 10 minutes. The mixture was allowed to warm up to room temperature and stirred overnight. The solvent was evaporated and 200 mL of water was added. The solution was washed with 200 mL of diethyl ether and added 25 mL of concentrated sulfuric acid to make a 2.0 M solution that was refluxed overnight. The solution was extracted with ethyl acetate and the organic solution was dried over MgSO$_4$ and concentrated in vacuo. The crude aryl-3-hydroxypropylsulfide was purified by silica gel chromatography (Waters Prep 500) using 8% ethyl acetate/hexane to yield 33.00 g (72.5%) of the product as a light brown oil: $^1$H NMR (CDCl$_3$) δ 0.90 (t, J=7.1 Hz, 6H), 1.14–1.34 (m, 12H), 2.82 (s, 2H), 3.48 (s, 2H), 3.79 (s, 3H), 4.10 (s, 2H), 6.77–6.92 (m, 4H), 7.09 (d, J=8.7 Hz, 2H), 7.41 (dd, J=8.7 Hz, 5.7 Hz, 1H).

Step 5. Preparation of Enantiomerically-enriched Aryl-3-hydroxypropylsulfide

To a stirred solution of 20.00 g (47.78 mmol) of aryl-3-hydroxypropylsulfide (obtained from Step 4) in 1 L of methylene chloride was added 31.50 g of 96% (1R)-(−)-(8,8-dichloro-10-camphor-sulfonyl)oxaziridine (100.34 mmol, Aldrich) at 2° C. After all the oxaziridine dissolved the mixture was placed into a −30° C. freezer for 72 hours. The solvent was evaporated and the crude solid was washed with 1 L of hexane. The white solid was filtered off and the hexane solution was concentrated in vacuo. The crude oil was purified on a silica gel column (Waters Prep 500) using 15% ethyl acetate/hexane to afford 19.00 g (95%) of the enantiomerically-enriched aryl-3-hydroxypropylsulfoxide as a colorless oil: $^1$H NMR (CDCl$_3$) δ 0.82–0.98 (m, 6H), 1.16–1.32 (m, 12H), 2.29 (d, J=13.8 Hz, 1H), 2.77 (d, J=13.5 Hz, 1H), 3.45 (d, J=12.3 Hz, 1H), 3.69 (d, J=12.3 Hz, 1H), 3.79 (s, 3H), 4.02 (q, J=15.6 Hz, 1H), 6.83–6.93 (m, 3H), 7.00 (d, J=8.1 Hz, 2H), 7.18–7.23 (m, 1H), 7.99–8.04 (m, 1H). Enantiomeric excess was determined by chiral HPLC on a (R,R)-Whelk-O column using 5% ethanol/hexane as the eluent. It showed to be 78% e.e. with the first eluting peak as the major product.

Step 6. Preparation of Enantiomerically-enriched Aryl-3-propanalsulfoxide

To a stirred solution of 13.27 g of triethylamine (131.16 mmol, Aldrich) in 200 mL dimethyl sulfoxide were added 19.00 g (43.72 mmol) of enantiomerically-enriched aryl-3-hydroxypropylsulfoxide (obtained from Step 5) and 20.96 g of sulfur trioxide-pyridine (131.16 mmol, Aldrich) at room temperature. After the mixture was stirred at room temperature for 48 hours, 500 mL of water was added to the mixture and stirred vigorously. The mixture was then extracted with 500 mL of ethyl acetate twice. The ethyl acetate layer was separated, dried over MgSO$_4$, and concentrated in vacuo. The crude oil was filtered through 500 mL of silica gel using 15% ethyl acetate/hexane to give 17.30 g (91%) of the enantiomerically-enriched aryl-3-propanalsulfoxide as a light orange oil: $^1$H NMR (CDCl$_3$) δ 0.85–0.95 (m, 6H), 1.11–1.17 (m, 4H), 1.21–1.39 (m, 4H), 1.59–1.76 (m, 4H), 1.89–1.99 (m, 1H), 2.57 (d, J=14.1 Hz, 1H), 2.91 (d, J=13.8 Hz, 1H), 3.79 (s, 3H), 3.97 (d, J=15.9 Hz, 1H), 4,12 (d, J=15.9 Hz, 1H), 6.84–6.89 (m, 3H), 7.03 (d, J=8.4 Hz, 2H), 7.19 (dt, J=8.4 Hz, 2.4 Hz, 1H), 8.02 (dd, J=8.7 Hz, 5.7 Hz, 1H), 9.49 (s, 1H).

Step 7. Preparation of the Enantiomerically-enriched Tetrahydrobenzothiepine-1-oxide (4R,5R)

To a stirred solution of 17.30 g (39.99 mmol) of enantiomerically-enriched aryl-3-propanalsulfoxide (obtained from Step 6) in 300 mL of dry THF at −15° C. was added 48 mL of 1.0 M potassium t-butoxide in THF (1.2 equivalents) under nitrogen. The solution was stirred at −15° C. for 4 hours. The solution was then quenched with 100 mL of water and neutralized with 4 mL of concentrated HCl solution at 0° C. The THF layer was separated, dried over $MgSO_4$, and concentrated in vacuo. The enantiomerically-enriched tetrahydrobenzothiepine-1-oxide (4R,5R) was purified by silica gel chromatography (Waters Prep 500) using 15% ethyl acetate/hexane to give 13.44 g (77.7%) of the product as a white solid: $^1$H NMR (CDCl$_3$) δ 0.87–0.97 (m, 6H), 1.16–1.32 (m, 4H), 1.34–1.48 (m, 4H), 1.50–.69 (m, 4H), 1.86–1.96 (m, 1H), 2.88 (d, J=13.0 Hz, 1H), 3.00 (d, J=13.0 Hz, 1H), 3.85 (s, 3H), 4.00 (s, 1H), 4.48 (s, 1H), 6.52 (dd, J=9.9 Hz, 2.4 Hz, 1H), 6.94 (d, J=9 Hz, 2H), 7.13 (dt, J=8.4 Hz, 2.4 Hz, 1H), 7.38 (d, J=8.7 Hz, 2H), 7.82 (dd, J=8.7 Hz, 5.7 Hz, 1H).

Step 8. Preparation of Enantiomerically-enriched Tetrahydrobenzothiepine-1,1-dioxide (4R,5R)

To a stirred solution of 13.44 g (31.07 mmol) of enantiomerically-enriched tetrahydrobenzothiepine-1-oxide (obtained from Step 7) in 150 mL of methylene chloride was added 9.46 g of 68% m-chloroperoxybenzoic acid (37.28 mmol, Sigma) at 0° C. After stirring at 0° C. for 2 hours, the mixture was allowed to warm up to room temperature and stirred for 4 hours. 50 mL of saturated $Na_2SO_3$ was added into the mixture and stirred for 30 minutes. The solution was then neutralized with 50 mL of saturated $NaHCO_3$ solution. The methylene chloride layer was separated, dried over $MgSO_4$, and concentrated in vacuo to give 13.00 g (97.5%) of the enantiomerically-enriched tetrahydrobenzothiepine-1,1-dioxide (4R,5R) as a light yellow solid: $^1$H NMR (CDCl$_3$) δ 0.89–0.95 (m, 6H), 1.09–1.42 (m, 12H), 2.16–2.26 (m, 1H), 3.14 (q, J=15.6 Hz, 1H), 3.87 (s, 3H), 4.18 (s, 1H), 5.48 (s, 1H), 6.54 (dd, J=10.2 Hz, 2.4 Hz, 1H), 6.96–7.07 (m, 3H), 7.40 (d, J=8.1 Hz, 2H), 8.11 (dd, J=8.6 Hz, 5.9 Hz, 1H).

Step 9. Preparation of Enantiomerically-enriched 7-(Dimethylamino)tetrahydrobenzothiepine-1,1-dioxide (4R,5R)

To a solution of 13.00 g (28.98 mmol) of enantiomerically-enriched tetrahydrobenzothiepine-1,1-dioxide (obtained from Step 8) in 73 mL of dimethylamine (2.0 M in THF, 146 mmol) in a Parr Reactor was added about 20 mL of neat dimethylamine. The mixture was sealed and stirred at 110° C. overnight, and cooled to ambient temperature. The excess dimethylamine was evaporated. The crude oil was dissolved in 200 mL of ethyl acetate and washed with 100 mL of water, dried over $MgSO_4$ and concentrated in vacuo. Purification on a silica gel column (Waters Prep 500) using 20% ethyl acetate/hexane gave 12.43 g (90.5%) of the enantiomerically-enriched 7-(dimethylamino)tetrahydrobenzothiepine-1,1-dioxide (4R,5R) as a colorless solid: $^1$H NMR (CDCl$_3$) δ 0.87–0.93 (m, 6H), 1.10–1.68 (m, 12H), 2.17–2.25 (m, 1H), 2.81 (s, 6H), 2.99 (d, J=15.3 Hz, 1H), 3.15 (d, J=15.3 Hz, 1H), 3.84 (s, 3H), 4.11 (d, J=7.5 Hz, 1H), 5.49 (s, 1H), 5.99 (d, J=2.4 Hz, 1H), 6.51 (dd, J=8.7 Hz, 2.4 Hz, 1H), 6.94 (d, J=8.7 Hz, 2H), 7.42 (d, J=8.4 Hz, 2H), 7.90 (d, J=8.7 Hz, 1H). The product was determined to have 78% e.e. by chiral HPLC on a Chiralpak AD column using 5% ethanol/hexane as the eluent. Recrystallization of this solid from ethyl acetate/hexane gave 1.70 g of the racemic product. The remaining solution was concentrated and recrystallized to give 9.8 g of colorless solid. Enantiomeric excess of this solid was determined by chiral HPLC on a Chiralpak AD column using 5% ethanol/hexane as the eluent. It showed to have 96% e.e with the first eluting peak as the major product.

Step 10: Demethylation of 5-(4'-Methoxyphenyl)-7-(dimethylamino)tetrahydrobenzothiepine-1,1-dioxide (4R, 5R)

To a solution of 47 g (99 mmol) of enantiomeric-enriched (dimethylamino)tetrahydrobenzothiepine-1,1-dioxide (obtained from Step 9) in 500 mL of methylene chloride at −10° C. was added dropwise a solution of boron tribromide (297 mL, 1M in methylene chloride, 297 mmol), and the resulting solution was stirred cold (−5° C. to 0° C.) for 1 hour or until the reaction was complete. The reaction was cooled in an acetone-dry ice bath at −10° C., and slowly quenched with 300 mL of water. The mixture was warmed to 10° C., and further diluted with 300 mL of saturated sodium bicarbonate solution to neutralize the mixture. The aqueous layer was separated and extracted with 300 mL of methylene chloride, and the combined extracts were washed with 200 mL of water, brine, dried over $MgSO_4$ and concentrated in vacuo. The residue was dissolved in 500 mL of ethyl acetate and stirred with 50 mL of glacial acetic acid for 30 minutes at ambient temperature. The mixture was washed twice with 200 mL of water, 200 mL of brine, dried over $MgSO_4$ and concentrated in vacuo to give the crude 4-hydroxyphenyl intermediate. The solid residue was recrystallized from methylene chloride to give 37.5 g (82%) of the desired 5-(4'-hydroxyphenyl)-7-(dimethylamino) tetrahydrobenzothiepine-1,1-dioxide as a white solid: $^1$H NMR (CDCl$_3$) δ 0.84–0.97 (m, 6H), 1.1–1.5 (m, 10H), 1.57–1.72 (m, 1H), 2.14–2.28 (m, 1H), 2.83 (s, 6H), 3.00 (d, J=15.3 Hz, 1H), 3.16 (d, J=15.3 Hz, 1H), 4.11 (s, 2H), 5.48 (s, 1H), 6.02 (d, J=2.4 Hz, 1H), 6.55 (dd, J=9, 2.4 Hz, 1H), 6.88 (d, 8,7 Hz, 2H), 7.38 (d, J=8.7 Hz, 2H), 7.91 (d, J=9 Hz, 2H).

Alternatively, enantiomeric-enriched 5-(4'-hydroxyphenyl)-7-(dimethylamino)tetrahydrobenzothiepine-1,1-dioxide, the intermediate just described, can be prepared via non-enantioselective synthesis followed by chiral chromatography separation. Oxidation of aryl-3-hydroxypropyl-sulfide (obtained from Step 4) with m-chloroperbenzoic acid (under the similar conditions as in Step 8, but with 2.2 equivalent of m-CPBA) gave the racemic sulfone intermediate. The sulfone was carried through the synthetic sequences (under the same conditions as in Step 7 and Step 9) to give the racemic 5-(4'-hydroxyphenyl)-7-(dimethylamino)tetrahydrobenzothiepine-1,1-dioxide. The two enantiomers were further separated into the desired enantiomeric-enriched 5-(4'-hydroxyphenyl)-7-(dimethylamino)tetrahydrobenzothiepine-1,1-dioxide by appropriate chiral chromatographic purification.

Step 11: Preparation of Ester Intermediate

To a solution of 1.0 g (2.18 mmol) of 5-(4'-hydroxyphenyl)-7-(dimethylamino)tetrahydrobenzo-thiepin-1,1-dioxide (obtained from Step 10) in 10 mL dimethylformamide was added 60 mg (2.38 mmol) of 95% sodium hydride and stirred for 15 minutes. To the reaction mixture was added 400 μL (2.52 mmol) of benzyl 2-bromoacetate and stirred for two hours. Water was added to the reaction mixture, extracted with ethyl acetate, washed with brine, dried over magnesium sulfate, filtered and the solvent evaporated to afford 1.30 g (98%) of the ester intermediate: $^1$H NMR (CDCl$_3$) δ 0.88–0.94 (m, 6H), 1.13–1.46 (m, 10H), 1.60–1.64 (m, 1H), 2.20–2.24 (m, 1H), 2.81 (s, 6H), 3.00 (d, J=15.1 Hz, 1H), 3.16 (t, J=15.1 Hz, 1H), 4.11 (s, 1H), 5.26 (s, 2H), 5.49 (s, 1H), 6.04 (d, J=2.4 Hz, 1H), 6.63 (dd, J=8.9, 2.4 Hz, 1H), 6.95 (d, J=8.7 Hz, 2H), 7.37 (s, 5H), 7.42 (d, J=8.5 Hz, 2H), 7.93 (d, J=8.9 Hz, 1H).

485

Step 12: Preparation of Acid

A solution of 1.30 g (2.14 mmol) of ester intermediate (obtained from Step 1) in 40 mL ethanol with 10% palladium on carbon was placed under an atmosphere of hydrogen gas (40 psi) for three hours. The reaction mixture was filtered through celite and the solvent was evaporated to afford the desired title compound as a white solid: mp 119–123° C.; $^1$H NMR (CDCl$_3$) δ 0.89–0.94 (m, 6H), 1.19–1.43 (m, 10H), 1.61–1.65 (m, 1H), 2.17–2.21 (m, 1H), 2.85 (s, 6H), 3.02 (d, J=15.1 Hz, 1H), 3.17 (t, J=14.9 Hz, 1H), 4.12 (s, 1H), 4.72 (s, 2H), 5.51 (s, 1H), 6.17 (s, 1H), 6.74 (d, J=9.1 Hz, 1H), 6.99 (d, J=8.3 Hz, 2H), 7.46 (d, J=8.5 Hz, 2H), 7.97 (d, J=8.7 Hz, 1H). HRMS. Calc'd for C$_{28}$H$_{40}$NO$_6$S: 518.2576. Found: 518.2599.

Example 1403

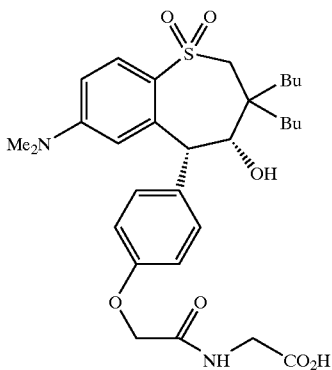

(4R-cis)-N-[[4-[3,3-Dibutyl-7-(dimethylamino)-2,3,4,5-tetrahydro-4-hydroxy-1,1-dioxido-1-benzothiepin-5-yl]phenoxyacetyl]glycine Step 1: Preparation of Glycine Ester Intermediate To a solution of 6.4 g (13.9 mmol) of 5-(4'-hydroxyphenyl)-7-(dimethylamino)tetrahydrobenzothiepine-1,1-dioxide (obtained from Example 1402, Step 10) and 2.9 g (21.0 mmol) of potassium carbonate in 100 ml of acetone was added 3.8 g (21.0 mmol) of N-(chloroacetyl) glycine ethyl ester and 50 mg (0.14 mmol) of tetrabutylammonium iodide. The reaction was heated to reflux for 2 days, cooled to ambient temperature and stirred for 20 hours, then partitioned between ethyl acetate and water. The organic layer was washed with brine, dried over MgSO$_4$, and concentrated in vacuo. Purification by silica gel chromatography (Waters Prep-500) using 50% ethyl acetate/hexanes afforded 7.5 g (90%) of glycine ester intermediate as a white foam: $^1$H NMR (CDCl$_3$) δ 0.86–0.98 (m, 6H), 1.04–1.56 (m, 13H), 1.58–1.71 (m, 1H), 2.14–2.29 (m, 1H), 2.73 (s, 6H), 3.08 (AB$_q$, J$_{AB}$=15.3 Hz, J=48.9 Hz, 2H), 4.06–4.19 (m, 6H), 4.25 (q, J=7.0 Hz, 2H), 4.57 (s, 2H), 5.50 (s, 1H), 5.98 (s, 1H), 6.56 (d, J=8.6 Hz, 1H), 6.98 (d, J=8.5 Hz, 2H), 7.17 (s, 1H), 7.47 (d, J=8.3 Hz, 2H), 7.91 (d, J=8.7 Hz, 1H).

Step 2: Preparation of Acid

A solution of 7.3 g (12.1 mmol) of glycine ester intermediate (obtained from Step 1) and 1.5 g LiOH.H$_2$O (36.3 mmol) in 60 mL of THF and 60 mL of water was heated to 45° C. for 2 hours. This was then cooled to ambient temperature, acidified with 1 N HCl and partitioned between ethyl acetate and water. The organic layer was washed with brine, dried over MgSO$_4$, and concentrated in vacuo. Purification by recrystallization from ethyl acetate gave 5.45 g (78%) of the desired title compound as a white crystalline solid: mp 149–150° C.; $^1$H NMR (CD$_3$OD) δ 0.88–0.98 (m, 6H), 1.06–1.56 (m, 10H), 1.70–1.84 (m, 1H), 2.06–2.20 (m, 1H), 2.79 (s, 6H), 3.11 (AB$_q$, J$_{AB}$=15.3 Hz, J=21.6 Hz, 2H), 4.01 (s, 2H), 4.07 (s, 1H), 4.61 (s, 2H), 5.31 (s, 1H), 6.04 (s, 1H), 6.57 (d, J=9.0 Hz, 1H), 7.08 (d, J=7.8 Hz, 2H), 7.44 (d, J=8.1 Hz, 2H), 7.76 (d, J=9.0 Hz, 1H), 8.42 (m 1H). HRMS(ES+) Calc'd for C$_{30}$H$_{42}$N$_2$O$_7$S: 575.2712. Found: 575.2790. Anal. Calc'd for: C$_{30}$H$_{42}$N$_2$O$_7$S C, 62.69; H, 7.37; N, 4.87. Found: C, 62.87; H, 7.56; N, 4.87.

Example 1403

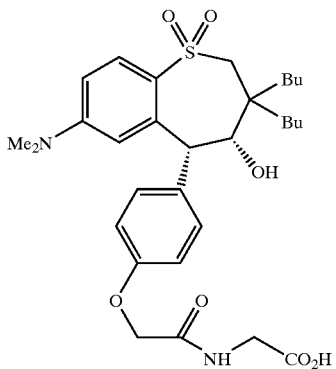

(4R-cis)-N-[[4-[3,3-Dibutyl-7-(dimethylamino)-2,3,4,5-tetrahydro-4-hydroxy-1,1-dioxido-1-benzothiepin-5-yl]phenoxyacetyl]glycine Step 1: Preparation of Glycine Ester Intermediate To a solution of 6.4 g (13.9 mmol) of 5-(4'-hydroxyphenyl)-7-(dimethylamino)tetrahydrobenzothiepine-1,1-dioxide (obtained from Example 1402, Step 10) and 2.9 g (21.0 mmol) of potassium carbonate in 100 ml of acetone was added 3.8 g (21.0 mmol) of N-(chloroacetyl) glycine ethyl ester and 50 mg (0.14 mmol) of tetrabutylammonium iodide. The reaction was heated to reflux for 2 days, cooled to ambient temperature and stirred for 20 hours, then partitioned between ethyl acetate and water. The organic layer was washed with brine, dried over MgSO$_4$, and concentrated in vacuo. Purification by silica gel chromatography (Waters Pre-500) using 50% ethyl acetate/hexanes afforded 7.5 g (90%) of glycine ester intermediate as a white foam: $^1$H NMR (CDCl$_3$) δ 0.86–0.98 (m, 6H), 1.04–1.56 (m, 13H), 1.58–1.71 (m, 1H), 2.142.29 (m, 1H), 2.73 (s, 6H), 3.08 (AB$_q$, J$_{AB}$=15.3 Hz, J=48.9 Hz, 2H), 4.06–4.19 (m, 6H), 4.25 (q, J=7.0 Hz, 2H), 4.57 (s, 2H), 5.50 (s, 1H), 5.98 (s, 1H), 6.56 (d, J=8.6 Hz, 1H), 6.98 (d, J=8.5 Hz, 2H), 7.17 (s, 1H), 7.47 (d, J=8.3 Hz, 2H), 7.91 (d, J=8.7 Hz, 1H).

Step 2: Preparation of Acid

A solution of 7.3 g (12.1 mmol) of glycine ester intermediate (obtained from Step 1) and 1.5 g LiOH.H$_2$O (36.3 mmol) in 60 mL of THF and 60 mL of water was heated to 45° C. for 2 hours. This was then cooled to ambient temperature, acidified with 1 N HCl and partitioned between ethyl acetate and water. The organic layer was washed with brine, dried over MgSO$_4$, and concentrated in vacuo. Purification by recrystallization from ethyl acetate gave 5.45 g (78%) of the desired title compound as a white crystalline solid: mp 149–150° C.; $^1$H NMR (CD$_3$OD) δ 0.88–0.98 (m, 6H), 1.06–1.56 (m, 10H), 1.70–1.84 (m, 1H), 2.06–2.20 (m, 1H), 2.79 (s, 6H), 3.11 (AB$_q$, J$_{AB}$=15.3 Hz, J=21.6 Hz, 2H), 4.01 (s, 2H), 4.07 (s, 1H), 4.61 (s, 2H), 5.31 (s, 1H), 6.04 (s, 1H), 6.57 (d, J=9.0 Hz, 1H), 7.08 (d, J=7.8 Hz, 2H), 7.44 (d, J=8.1 Hz, 2H), 7.76 (d, J=9.0 Hz, 1H), 8.42 (m, 1H).

HRMS(ES+) Calc'd for $C_{30}H_{42}N_2O_7S$: 575.2712. Found: 575.2790. Anal. Calc'd for: $C_{30}H_{42}N_2O_7S$ C, 62.69; H, 7.37; N, 4.87. Found: C, 62.87; H, 7.56; N, 4.87.

Example 1404

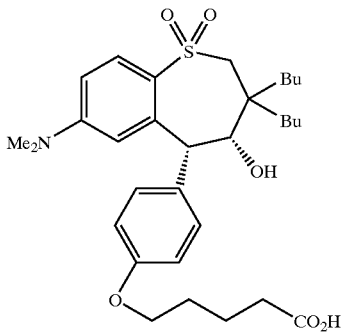

(4R-cis)-5-[4-[3,3-Dibutyl-7-(dimethylamino)-2,3,4,5-tetrahydro-4-hydroxy-1,1-dioxido-1-benzothiepin-5-yl]phenoxy]pentanoic Acid Step 1: Preparation of Ester Intermediate A solution of 5-(4'-hydroxyphenyl)-7-(dimethylamino)tetrahydrobenzothiepine-1,1-dioxide (1.0 g, 2.2 mmol, obtained from Example 1402, Step 10) in acetone (10 mL) at 25° C. under $N_2$ was treated with powdered $K_2CO_3$ (0.45 g, 3.3 mmol, 1.5 eq.), benzyl 5-bromovalerate (0.88 g, 3.3 mmol, 1.5 eq.) and a catalytic amount of tetra-n-butylammonium iodide (2 mg), and the resulting solution was stirred at 65° C. for 24 hours. The pale amber slurry was cooled to 25° C. and was concentrated in vacuo to provide a yellow residue. Purification by flash chromatography (2.4×30 cm silica, 20–40% EtOAc/hexane) afforded the ester intermediate (1.2 g, 86%) as a colorless oil: $^1$H NMR (CDCl$_3$) δ 0.91 (m, 6H), 1.11–1.47 (br m, 10H), 1.64 (m, 1H), 1.86 (m, 2H), 2.21 (m, 1H), 2.47 (m, 2H), 2.81 (s, 6H), 3.05 (AB$_q$, J=15.1 Hz, J=47.7 Hz, 2H), 4.10 (d, J=7.9 Hz, 1H), 5.13 (s, 2H), 5.47 (s, 1H), 6.00 (d, J=2.5 Hz, 1H), 6.50 (dd, J=8.9, 2.5 Hz, 1H), 6.91 (d, J=8.7 Hz, 2H), 7.36 (m, 5H), 7.40 (d, J=8.5 Hz, 2H), 7.86 (d, J=8.9 Hz, 1H); HRMS. Calc'd for $C_{38}H_{51}NO_6S$: 650.3515. Found: 650.3473.

Step 2: Preparation of Acid

A solution of the ester intermediate (0.99 g, 1.5 mmol, obtained from Step 1) in ethanol (7.5 mL) at 25° C. was treated with 5% palladium on carbon (0.15 g, 10 wt %) then stirred under an atmosphere (1 atm) of $H_2$ via hydrogen balloon. Every 10 min, hydrogen gas was bubbled through the slurry for 1 min, for a total reaction time of 4 hours. The slurry was placed under an atmosphere of $N_2$ and nitrogen was bubbled through the reaction mixture for 10 min. The mixture was filtered through a plug of Celite® (10 g) and concentrated in vacuo to give a white foam. Purification by flash chromatography (2.6×25 cm silica, 1.5% EtOH/CH$_2$Cl$_2$) afforded the desired title compound (0.54 g, 63%) as a white foam: mp: 76–79° C.; $^1$H NMR (CDCl$_3$) δ 0.90 (m, 6H), 1.10–1.46 (br m, 10H), 1.62 (m, 1H), 1.87 (m, 4H), 2.20 (m, 1H), 2.45 (m, 2H), 2.81 (s, 6H), 3.05 (AB$_q$, J=15.1 Hz, J=49.7 Hz, 2H), 4.00 (s, 2H), 4.09 (s, 1H), 5.45 (s, 1H), 5.99 (d, J=2.4 Hz, 1H), 6.48 (dd, J=8.9, 2.4 Hz, 1H), 6.91 (d, J=8.7 Hz, 2H), 7.39 (m, 5H), 7.39 (d, J=8.3 Hz, 2H), 7.84 (d, J=8.9 Hz, 11H); HRMS. Calc'd for $C_{31}H_{45}NO_6S$: 560.3046. Found: 560.3043.

Example 1405

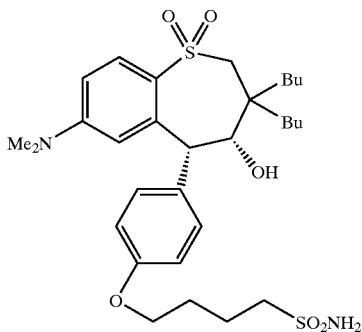

(4R-cis)-4-[4-[3,3-Dibutyl-7-(dimethylamino)-2,3,4,5-tetrahydro-4-hydroxy-1,1-dioxido-1-benzothiepin-5-yl]phenoxy-1-butanesulfonamide Step 1: Preparation of Sulfonic Acid Intermediate A solution of 7.4 g (16.1 mmol) of 5-(4'-hydroxyphenyl)-7-(dimethylamino)tetrahydrobenzo-thiepine-1,1-dioxide (obtained from Example 1402, Step 10) in acetone (35 mL) at 25° C. under $N_2$ was treated with powdered potassium carbonate (3.3 g, 24.1 mmol, 1.5 equiv.) and 1,4-butane sultone (2.5 mL, 24.1 mmol, 1.5 equiv.) and stirred and heated at 65° C. for 64 h. The solution was allowed to cool to 25° C. and quenched by the addition of water (50 mL), until a homogeneous mixture was obtained. The clear and colorless solution was added dropwise to a 4 N HCl solution cooled to 0° C. over a 30 min period. The mixture was vigorously stirred for 4 h then allowed to warm to ambient temperature and stirred for an additional 16 h The resultant white precipitate was filtered and washed with water and dried in vacuo to provide 8.8 g (92%) of the desired sulfonic acid as a white solid. A portion of the white solid was recrystallized from CH$_3$CN/hexane to give the desired sulfonic acid as colorless needles: mp 229–236° C. (decomposed); $^1$H NMR (DMSO-d$_6$) δ 0.82 (m, 6H), 1.02–1.33 (br m, 10H), 1.59 (m, 1H), 1.73 (m, 4H), 2.00 (s, 1H), 2.48 (m, 2H), 2.71 (s, 6H), 2.98 (s, 1M), 3.86 (s, 1H), 3.93 (m, 2H), 5.08 (s, 1H), 5.89 (s, 1H), 6.52 (dd, J=8.9, 2.4 Hz, 1H), 6.92 (d, J=8.3 Hz, 2H), 7.29 (d, J=8.1 Hz, 2H), 7.60 (d, J=8.9 Hz, 1H); Anal. Calc'd for $C_{30}H_{45}NO_7S_2$: C, 60.48; H, 7.61; N, 2.35. Found: C, 60.53; H, 7.70; N, 2.42.

Step 2: Preparation of 7-(Dimethylamino)-benzothiepin-5-yl]phenoxy-1-butanesulfonamide To a solution of 1.12 g (1.88 mmol) of the sulfonic acid (obtained from Step 1) in 10 mL CH$_2$Cl$_2$ was added 785 mg (3.77 mmol) PCl$_5$ and stirred for 1 hour. Water was added and the mixture was extracted and washed with brine. Dried with MgSO$_4$, filtered and solvent evaporated. To the residue was added 30 mL of 0.5M NH$_3$ in dioxane and stirred 16 hours. The precipitate was filtered and the solvent evaporated. The residue was purified by MPLC (33% EtOAc in hexane) to afford the desired title compound as a beige solid (125 mg, 11%): mp 108–110° C.; $^1$H NMR (CDCl$_3$) δ 0.85–0.93 (m, 6H), 1.13–1.59 (m, 10H), 1.60–1.67 (m, 1H), 1.94–2.20 (m, 5H), 2.82 (s, 6H), 2.99 (d, J=15.3 Hz, 1H), 3.15 (t, J=15.3 Hz, 1H), 3.23 (t, J=7.7 Hz, 2H), 4.03 (t, J=5.8 Hz, 2H), 4.084.10 (m, 1H), 4.79 (s, 2H), 5.47 (s, 1H), 6.02 (d, J=2.4 Hz, 1H), 6.52 (dd, J=8.9, 2.6 Hz, 1H), 6.91 (d, J=8.9 Hz, 2H), 7.41 (d, J=8.5 Hz, 2H), 7.89 (d, J=8.9 Hz, 1H). HRMS. Calc'd for $C_{30}H_{47}N_2O_6S_2$: 595.2876. Found: 595.2874.

Example 1406

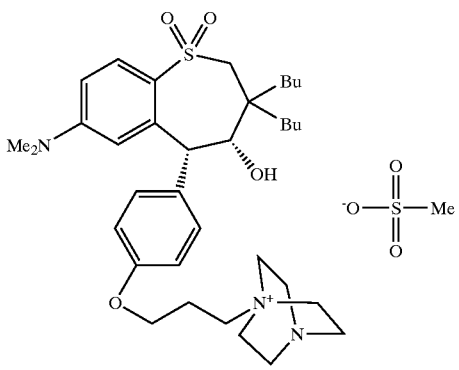

(4R-cis)-1-[3-[4-[3,3-Dibutyl-7-dimethylamino)-2,3,
4,5-tetrahydro-4-hydroxy-1,1-dioxido-1-
benzothiepin-5-yl]phenoxy]propyl]-4-aza-1-
azoniabicyclo[2.2.2]octane, Methanesulfonate (Salt)

Step 1: Preparation of Dimesylate Intermediate

To a cooled (−20° C.) solution of 5.0 g (65.7 mmol) of 1,3-propanediol in 50 mL of triethylamine and 200 mL of methylene chloride was added 15.8 g (137.9 mmol) of methanesulfonyl chloride. The mixture was stirred for 30 minutes, then warmed to ambient temperature and partitioned between ethyl acetate and 1N HCl. The organic layer was washed with brine, dried over $MgSO_4$, and concentrated in vacuo to give 13.5 g (89%) of dimesylate intermediate as a clear yellowish oil: $^1$H NMR ($CDCl_3$) δ 2.12 (quintet, J=4.5 Hz, 4H), 3.58 (s, 6H), 4.38 (t, J=5.4 Hz).

Step 2: Preparation of Propyl Mesylate Intermediate

To a solution of 2.4 g (5.2 mmol) of 5-(4'-hydroxyphenyl)-7-(dimethylamino)tetrahydrobenzothiepine-1,1-dioxide (obtained from Example 1402, Step 10) and 6.0 g (26.1 mmol) of dimesylate intermediate (obtained from Step 1) in 50 mL of acetone was added 3.6 g (26.1 mmol) of $K_2CO_3$. The reaction was heated to reflux overnight then cooled to ambient temperature and concentrated in vacuo. The residue was partitioned between ethyl acetate and water. The organic layer was washed with brine, dried over $MgSO_4$, and concentrated in vacuo. Purification by silica gel chromatography (Waters-Prep 500) using 36% ethyl acetate/hexanes afforded 2.8 g (90%) of the propyl mesylate intermediate as a white foam: $^1$H NMR ($CDCl_3$) δ 0.86–0.95 (m, 6H), 1.06–1.52 (m, 10H), 1.57–1.70 (m, 1H), 2.14–2.32 (m, 3H), 2.84 (s, 6H), 3.02 (s, 3H), 3.08 ($AB_q$, $J_{AB}$=15.0 Hz, J=46.9 Hz, 4.09–4.18 (m, 3H), 4.48 (t, J=6.0 Hz, 2H), 5.49 (s, 1H), 6.11 (s, 1H), 6.65 (d, J=8.7 Hz, 1H), 6.94 (d, J=8.6 Hz, 2H), 7.43 (d, J=8.5 Hz, 2H), 7.94 (d, J=8.9 Hz, 1H).

Step 3: Preparation of Quaternary Salt

To a solution of 1.2 g (2.0 mmol) of propyl mesylate intermediate (obtained from Step 2) in 20 ml of acetonitrile was added 0.3 g (2.9 mmol) of 1,4-diazabicyclo[2.2.2]octane (DABCO). The reaction mixture was stirred at 60° C. for three hours, then cooled to ambient temperature and concentrated in vacuo. Purification by trituration with methylene chloride/ethyl ether gave 1.3 g (91%) of the desired title compound as a white solid: mp. (dec) 230–235° C.; $^1$H NMR ($CDCl_3$) δ 0.860.95 (m, 6H), 1.041.52 (m, 10H), 1.57–1.70 (m, 1H), 2.12–2.25 (m, 3H), 2.28–2.39 (m, 2H), 2.83 (s, 6H), 3.04 (s, 3H), 3.09 ($AB_q$, $J_{AB}$=15.6 Hz, J=42.2 Hz, 2H) 3.22–3.32 (m, 6H), 3.56–3.66 (m, 6H), 3.73–3.83 (m, 2H), 4.064.17 9 m, 3H), 5.47 (s, 1H), 5.97 (s, 1H), 6.51 (d, J=8.6 Hz, 1H), 6.90 (d, J=8.6 Hz, 2H), 7.41 (d, J=8.7 Hz, 2H), 7.89 (d, J=8.9 Hz, 1H). MS (ES+) m/e 612.4. HRMS (ES+) Calc'd for $C_{35}H_{54}N_3O_4S^+$: 612.3835. Found: 612.3840.

Example 1407

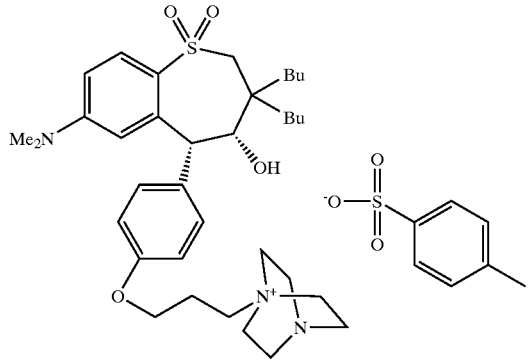

(4R-cis)-1-[3-[4-[3,3-Dibutyl-7-(dimethylamino)-2,
3,4,5-tetrahydro-4-hydroxy-1,1-dioxido-1-
benzothiepin-5-yl]phenoxy]propyl]-4-aza-1-
azoniabicyclo[2.2.2]octane, 4-
Methylbenzenesulfonate (Salt)

Step 1: Preparation of Propyl Tosylate Intermediate

A solution of 5-(4'-hydroxyphenyl)-7-(dimethylamino) tetrahydrobenzothiepine-1,1-dioxide (5.0 g, 10.9 mmol, obtained from Example 1402, Step 10) in acetone (100 mL) at 25° C. under $N_2$ was treated with powdered $K_2CO_3$ (3.8 g, 27.2 mmol, 2.5 eq.) and 1,3-propanediol di-p-tosylate (13.0 g, 32.6 mmol, 3.0 eq.), and the resulting mixture was stirred at 65° C. for 21 hours. The cream-colored slurry was cooled to 25° C. and was filtered through a sintered glass funnel. The filtrate was concentrated and the residue was dissolved in EtOAc (150 mL). The organic layer was washed with saturated aqueous $NaHCO_3$ (2×150 mL) and saturated aqueous NaCl (2×150 mL), and was dried ($MgSO_4$) and concentrated in vacuo to provide a pale orange oil. Purification by flash chromatography (4.4×35 cm silica, 20–30% EtOAc/hexane) afforded the propyl tosylate intermediate (6.0 g, 80%) as a white foam: $^1$H NMR ($CDCl_3$) δ 0.91 (m, 6H), 1.11–1.47 (br m, 10H), 1.63 (m, 1H), 2.14 (m, 2H), 2.21 (m, 1H), 2.41 (s, 3H), 2.81 (s, 6H), 3.06 (ABq, J=15.1 Hz, J=49.0 Hz, 2H), 4.01 (t, J=5.3 Hz, 2H), 4.10 (m, 1H), 4.26 (t, J=5.9 Hz, 2H), 5.29 (s, 1H), 5.48 (s, 1H), 5.98 (s, 1H), 6.51 (dd, J=8.9, 1.8 Hz, 1H), 6.83 (d, J=8.4 Hz, 2H), 7.30 (d, J=8.1 Hz, 2H), 7.39 (d, J=8.3 Hz, 2H), 7.78 (d, J=8.3 Hz, 2H), 7.88 (d, J=8.9 Hz, 1H).

Step 2: Preparation of Quaternary Salt

A solution of the propyl tosylate intermediate (1.05 g, 1.56 mmol, obtained from Step 1) in acetonitrile (15 mL) at 25° C. under $N_2$ was treated with diazabicyclo[2.2.2]octane (DABCO, 0.26 g, 2.34 mmol, 1.5 eq.) and stirred at 50° C. for 6 hours, then at 25° C. for 14 hours. The pale amber solution was cooled to 25° C. and concentrated in vacuo to provide an amber oil. The residue was dissolved in a minimal amount of $CH_2Cl_2$ (5 mL) and diluted with $Et_2O$ (100 mL) while vigorously stirring for 4 hours, during which time a white solid precipitated. The white solid was collected ($Et_2O$ wash) to give the desired title compound (1.11 g, 90%) as a white amorphous solid: mp 136.5–142° C. (decomposed); $^1$H NMR ($CDCl_3$) δ 0.89 (m, 6H), 1.12–1.43 (br m, 9H), 1.61 (m, 1H), 1.65 (m, 1H), 2.18 (m, 1H), 2.22 (m, 2H), 2.27 (s, 3H), 2.78 (s, 6H), 3.07 (ABq, J=15.1 Hz, J=39.5 Hz, 2H), 3.49 (br s, 6H), 3.68 (m, 1H), 3.74 (br s, 6H), 3.96 (br s, 2H), 4.09 (d, J=7.3 Hz, 1H), 5.46 (s, 1H), 5.96 (d, J=2.4 Hz, 1H), 6.49 (dd, J=8.9, 2.4 Hz, 1H), 6.83 (d, J=8.5 Hz, 2H), 7.11 (d, J=8.1 Hz, 2H), 7.40 (d, J=8.3 Hz, 2H), 7.74 (d, J=8.1 Hz, 2H), 7.87 (d, J=8.9 Hz, 1H); HRMS. Calc'd for $C_{35}H_{54}N_3O_4S$: 612.3835. Found: 612.3832.

Example 1408

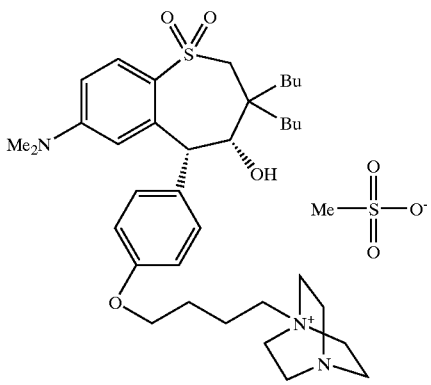

(4R-cis)-1-[4-[4-[3,3-Dibutyl-7-(dimethylamino)-2,3,4,5-tetrahydro-4-hydroxy-1,1-dioxido-1-benzothiepin-5-yl]phenoxy]butyl]-4-aza-1-azoniabicyclo[2.2.2]octanemethanesulfonate (Salt)

Step 1: Preparation of Butyl Mesylate Intermediate

A mixture of 1.00 g (2.18 mmol) of 5-(4'-hydroxyphenyl)-7-(dimethylamino)tetrahydrobenzo-thiepine-1,1-dioxide (obtained from Example 1402, Step 10), 2.68 g (10.88 mmol) of busulfan, and 1.50 g (10.88 mmol) of potassium carbonate in 20 mL of acetone was stirred at reflux overnight. The mixture was concentrated in vacuo and the crude was dissolved in 30 mL of ethyl acetate. The insoluble solid was filtered off and the filtrate was concentrated in vacuo. The resulting white foam was chromatographed through silica gel column, and eluted with 30% ethyl acetate/hexane to give 1.02 g (77%) of butyl mesylate intermediate as a white solid: $^1$H NMR (CDCl$_3$) δ 0.90 (m, 6H), 1.20–1.67 (m, 12H), 1.98 (m, 4H), 2.22 (m, 1H), 2.83 (s, 6H), 3.04 (s, 3H), 3.08 (ABq, 2H), 4.05 (t, J=5.55 Hz, 2H), 4.11 (d, J=6.90 Hz, 1H), 4.35 (t, J=6.0 Hz, 2H), 5.49 (s, 1H), 6.00 (d, J=2.4 Hz, 1H), 6.52 (dd, J=9.0 Hz, 2.7 Hz, 1H), 6.93 (d, J=9.0 Hz, 2H), 7.42 (d, J=8.4 Hz, 2H), 7.90 (d, J=9.0 Hz, 1H).

Step 2: Preparation of Ester Intermediate

A solution of 520 mg (0.85 mmol) of butyl mesylate intermediate (obtained from Step 1) and 191 mg (1.71 mmol) of DABCO in 10 mL of acetonitrile was stirred at 80° C. for 4 hours. The reaction mixture was concentrated in vacuo to yield a white foam. The foam was crushed and washed with ether. The solid was filtered off and dried in vacuo to give 540 mg (88%) of the desired title compound which was recrystallized from methylene chloride and acetone as a white solid: mp 248–251° C.; $^1$H NMR (CDCl$_3$) δ 0.91 (m, 6H), 1.14–1.47 (m, 14H), 1.63 (m, 1H), 1.96 (m, 4H), 2.21 (m, 1H), 2.77 (s, 3H), 2.82 (s, 3H), 3.07 (ABq, 2H), 3.26 (t, J=7.1 Hz, 6H), 3.60 (m, 8H), 4.08 (m, 3H), 5.47 (s, 1H), 5.99 (d, J=2.4 Hz, 1H), 6.51 (dd, J=8.9 Hz, 2.6 Hz, 1H), 6.91 (d, J=8.7 Hz, 2H), 7.41 (d, J=8.1 Hz, 2H), 7.89 (d, J=9.0 Hz, 1H).

Example 1409

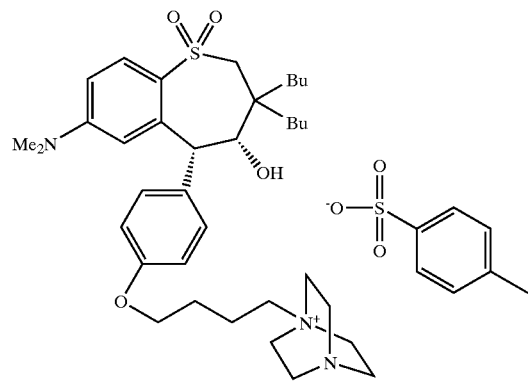

(4R-cis)-1-[4-[4-[3,3-Dibutyl-7-(dimethylamino)-2,3,4,5-tetrahydro-4-hydroxy-1,1-dioxido-1-benzothiepin-5-yl]phenoxy]butyl]-4-aza-1-azoniabicyclo[2.2.2]octane-4-methylbenzenesulfonate (Salt)

Step 1: Preparation of Propyl Tosylate Intermediate

A solution of 5-(4'-hydroxyphenyl)-7-(dimethylamino)tetrahydrobenzothiepine-1,1-dioxide (5.0 g, 10.9 mmol, obtained from Example 1402, Step 10) in acetone (100 mL) at 25° C. under $N_2$ was treated with powdered $K_2CO_3$ (3.8 g, 27.2 mmol, 2.5 eq.) and 1,4 butanediol di-p-tosylate (13.0 g, 32.6 mmol, 3.0 eq.), and the resulting solution was stirred at 65° C. for 21 hours. The cream-colored slurry was cooled to 25° C. and filtered through a sintered glass funnel. The filtrate was concentrated and the residue was dissolved in EtOAc (150 mL). The organic layer was washed with saturated aqueous NaHCO$_3$ (2×150 mL) and saturated aqueous NaCl (2×150 mL). The extract was dried (MgSO$_4$) and concentrated in vacuo to provide a pale orange oil. Purification by flash chromatography (4.4×35 cm silica, 20–30% EtOAc/hexane) afforded the propyl tosylate intermediate (6.0 g, 80%) as a white foam: $^1$H NMR (CDCl$_3$) δ 0.89 (m, 6H), 1.10–1.44 (br m, 10H), 1.61 (m, 1H), 1.84 (m, 4H), 2.19 (m, 1H), 2.43 (s, 3H), 2.80 (s, 6H), 3.03 (ABq, J=15.1 Hz, J=46.3 Hz, 2H), 3.93 (m, 2H), 4.06–4.13 (m, 4H), 5.44 (s, 1H), 5.96 (s, 1H), 6.46 (dd, J=8.9, 1.4 Hz, 1H), 6.85 (d, J=8.1 Hz, 2H), 7.33 (d, J=8.1 Hz, 2H), 7.38 (d, J=8.1 Hz, 2H), 7.78 (d, J=8.9 Hz, 2H), 7.83 (m, 1H).

Step 2: Preparation of Quaternary Salt

A solution of propyl tosylate intermediate (5.8 g, 8.5 mmol, obtained from Step 1) in acetonitrile (100 mL) at 25° C. under $N_2$ was treated with diazabicyclo[2.2.2]octane (DABCO, 1.1 g, 10.1 mmol, 1.2 eq.) and stirred at 45° C. for 6 hours. The pale yellow solution was cooled to 25° C. and concentrated in vacuo to provide an off-white solid. The residue was dissolved in a minimal amount of CH$_2$Cl$_2$ (5 mL) and diluted with Et$_2$O (100 mL) while vigorously stirring for 3 hours, during which time a white solid precipitated. The white solid was collected and recrystallized from EtOAc/hexane to give the desired title compound (5.7 g, 85%) as colorless needles: mp 223–231° C. (decomposed); $^1$H NMR (CDCl$_3$) δ 0.86 (m, 6H), 1.09–1.43 (br m, 12H), 1.61–1.90 (br m, 5H), 2.13 (m, 1H), 2.25 (s, 3H), 2.75 (s, 6H), 3.03 (ABq, J=15.1 Hz, J=30.0 Hz, 2H), 3.05 (br s, 6H), 3.37 (br s, 6H), 3.89 (m, 2H), 4.07 (d, J=7.5 Hz, 1H), 5.39 (s, 2H), 5.97 (d, J=1.6 Hz, 1H), 6.44 (dd, J=8.9, 2.0 Hz, 1H), 6.87 (d, J=8.3 Hz, 2H), 7.08 (d, J=8.1 Hz, 2H), 7.37 (d, J=8.3 Hz, 2H), 7.71 (d, J=8.1 Hz, 2H), 7.80 (d, J=8.9 Hz, 1H); HRMS. Calc'd for $C_{36}H_{56}N_3O_4S$: 626.3992.

Found: 626.3994. Anal. Calc'd for $C_{43}H_{63}N_3O_7S_2$: C, 64.71; H, 7.96; N, 5.27. Found: C, 64.36; H, 8.10; N, 5.32.

Example 1410

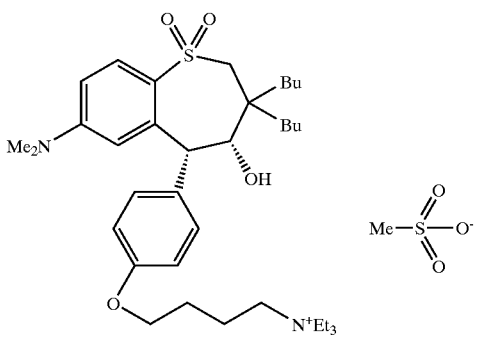

(4R-cis)-4-[4-[3,3-Dibutyl-7-dimethylamino)-2,3,4,
5-tetrahydro-4-hydroxy-1,1-dioxido-1-benzothiepin-
5-yl]phenoxy]-N,N,N-triethyl-1-butanaminium A solution of 1 g (1.64 mmol) of the butyl mesylate intermediate (obtained from Example 1408, Step 1) and 15 mL of triethylamine in 10 mL of acetonitrile was heated at 50° C. for 2 days. The solvent was evaporated and the residue was triturated with ether and ethyl acetate to afford 500 mg (43%) of product as a semi-solid. $^1$H NMR (CDCl$_3$) δ 0.8 (m, 6H), 1–1.6 (m, 24H), 2.1 (m, 1H), 2.6 (s, 3H), 2.7 (s, 6H), 2.9 (d, J=15 Hz, 1H), 3.0 (d, J=15 Hz, 1H), 3.3 (m, 8H), 4.0 (m, 4H), 5.3 (s, 1H), 5.9 (s, 1H), 6.4 (m, 1H), 6.8 (d, J=9 Hz, 2H), 7.4 (d, J=9 Hz, 2H), 7.8 (d, J=7 Hz, 1H). MS m/e 615.

Example 1411

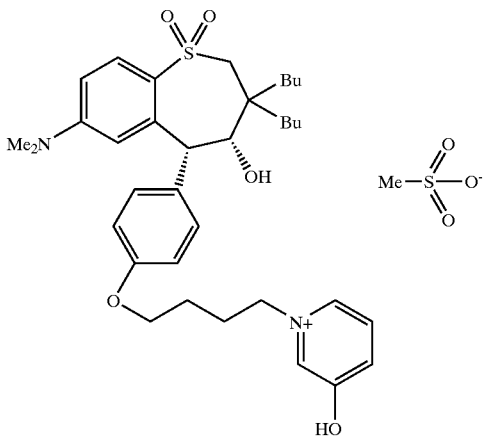

(4R-cis)-1-[4-[4-[3,3-Dibutyl-7-(dimethylamino)-2,
3,4,5-tetrahydro-4-hydroxy-1,1-dioxido-1-
benzothiepin-5-yl]phenoxy]butyl]-3-
hydroxypyridinium, Methanesulfonate (Salt)

A solution of 1 g (1.64 mmol) of the butyl mesylate intermediate (obtained from Example 1408, Step 1) and 234 mg (2.46 mmol) of 3-hydroxy pyridine in 1 mL of dimethylformamide was heated at 70° C. for 20 hours. The solvent was evaporated and the residue was triturated with ether and ethyl acetate to afford 990 mg (86%) of product as a semi-solid: $^1$H NMR (CDCl$_3$) δ 0.9 (m, 6H), 1–1.5 (m, 10H), 1.7 (m, 1H), 1.9 (m, 2H), 2–2.4 (m, 3H), 2.9 (s, 6H), 3.1 (d, J,=15 Hz, 1H), 3.2 (d, J=15 Hz, 1H), 4.1 (m, 3H), 4.7 (m, 2H), 5.5 (s, 1H), 6.1 (s, 1H), 6.6 (m, 1H), 6.9 (d, J=9 Hz, 2H), 7.4 (d, J=9 Hz, 2H), 7.7 (m, 1H), 8.0 (m, 2H), 8.2 (m, 1H), 9.1 (s, 1H). MS m/e 609.

Example 1412

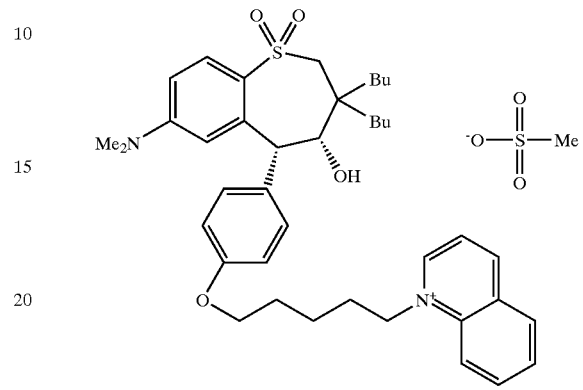

(4R-cis)-1-[5-[4-[3,3-Dibutyl-7-(dimethylamino)-2,
3,4,5-tetrahydro-4-hydroxy-1,1-dioxido-1-
benzothiepin-5-yl]phenoxy]pentyl]quinolinium,
Methanesulfonate (Salt)

Step 1: Preparation of Pentyl Mesylate Intermediate

To a stirred solution of 231 mg (5.79 mmol, 60% disp.) of NaH in 22 mL of DMF was added 2.05 g (4.45 mmol) of 5-(4'-hydroxyphenyl)-7-(dimethylamino)tetrahydrobenzothiepine-1,1-dioxide (obtained from Example 1402, Step 10), and the resulting solution was stirred at ambient temperature for 1 hour. To the mixture was added 18.02 g (55.63 mmol) of 1,5-diiodopentane and the solution was stirred overnight at ambient temperature. DMF was removed by high vacuum and the residue was extracted with ethyl acetate and washed with brine. The extract was dried over MgSO$_4$, and the concentrated residue was purified by column chromatography to give the pentyl mesylate intermediate: $^1$H NMR (CDCl$_3$) δ 0.90 (q, 6H), 1.05–2.0 (m, 17H), 2.2 (t, 1H), 2.8 (s, 6h), 3.0 (q, 2H), 3.22 (t, 2H), 3.95 (t, 2H), 4.1 (s, 1H), 5.42 (s, 1H), 6.1 (d, 1H), 6.6 (d, 1H), 6.9 (d, 2H), 7.4 (d, 2H), 7.9 (d, 1H).

Step 2: Preparation of Quaternary Salt

To 1.0 g (1.53 mmol) of the pentyl mesylate intermediate (obtained from Step 1) was added 3.94 g (30.5 mmol) of quinoline and 30 mL of acetonitrile. The solution was heated at 45° C. under N$_2$ for 10 days. The concentrated residue was purified by reverse phase C18 column chromatography. The obtained material was exchanged to its mesylate anion by ion exchange chromatography to give the desired title compound as a solid: mp 136° C.; $^1$H NMR (CDCl$_3$) δ 0.95 (q, 6H), 1.05–2.25 (m, 18H), 2.8 (s, 9H), 3.0 (q, 2H), 3.95 (t, 2H), 4.1 (s, 1H), 5.28 (t, 2H), 5.42 (s, 1H), 5.95 (s, 1H), 6.45 (d, 1H), 6.82 (d, 2H), 7.4 (d, 2H), 7.82 (d, 1H), 7.9 (t, 1H), 8.2 (t, 2H), 8.3 (q, 2H), 8.98 (d, 1H), 10.2 (d, 1H). HRMS. Calc'd for $C_{40}H_{53}N_2O_4S$: 657.3726. Found: 657.3736. Anal. Calc'd for $C_{40}H_{53}N_2O_4S \cdot CH_3O_3S$: C, 65.40; H, 7.50; N, 3.72; S, 8.52. Found: C, 62.9; H, 7.42; N, 3.56; S, 8.41.

Example 1413

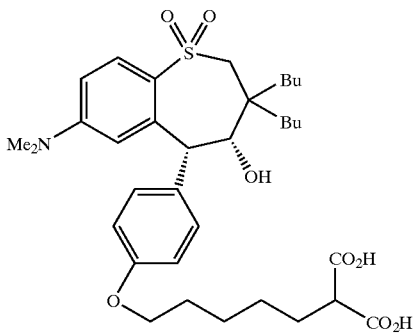

(4S-cis)-[5-[4-[3,3-Dibutyl-7-(dimethylamino)-2,3,4,5-tetrahydro-4-hydroxy-1,1-dioxido-1-benzothiepin-5-yl]phenoxy]pentyl]propanedioic Acid Step 1: Preparation of Pentyl Bromide Intermediate To a stirred solution of 0.63 g (15.72 mmol, 60% disp) of NaH in 85 mL of DMF was added 6.0 g (13.1 mmol) of 5-(4'-hydroxyphenyl)-7-(dimethylamino)tetra-hydrobenzothiepine-1,1-dioxide (obtained from 657 Example 1402, Step 10), and the resulting solution was stirred at ambient temperature for 1 hour. To the solution was added 37.7 g (163.75 mmol) of 1,5-dibromopentane, and the mixture was stirred overnight at ambient temperature. DMF was removed in vacuo and the residue was extracted with ethyl acetate and washed with brine. The extract was dried over $MgSO_4$, and the concentrated residue was purified by column chromatography to give the pentyl bromide intermediate: $^1$H NMR ($CDCl_3$) δ 0.90 (q, 6H), 1.05–2.0 (m, 17H), 2.2 (t, 1H), 2.8 (s, 6H), 3.0 (q, 2H), 3.4 (t, 2H), 3.95 (t, 2H), 4.1 (s, 1H), 5.42 (s, 1H), 6.0 (s, 1H), 6.5 (d, 1H), 6.9 (d, 2H), 7.4 (d, 2H), 7.9 (d, 1H).

Step 2: Preparation of Dibenzyl Ester Intermediate

To the mixture of 59 mg (1.476 mmol, 60% disp) of NaH in 27 mL of THF and 9 mL of DMF at 0° C. was added 0.84 g (2.952 mmol) of dibenzyl malonate (Aldrich), and the resulting solution was stirred at ambient temperature for 15 min. To the solution was added 0.5987 g (0.984 mmol) of the pentyl bromide intermediate, and the mixture was stirred at 80° C. overnight. Solvent was removed in vacuo, and the residue was extracted with methylene chloride and washed with brine. The extract was dried over $MgSO_4$, and the concentrated residue was purified by column chromatography to give the dibenzyl ester intermediate: $^1$H NMR ($CDCl_3$) δ 0.90 (q, 6H), 1.05–2.0 (m, 19H), 2.2 (t, 1H), 2.8 (s, 6H), 3.0 (q, 2H), 3.4 (t, 1H), 3.9 (t, 2H), 4.1 (d, 1H), 5.18 (s, 4H), 5.42 (s, 1H), 5.95 (s, 1H), 6.5 (d, 1H), 6.9 (d, 2H), 7.2–7.4 (m, 12H), 7.85 (d, 1H).

Step 3: Preparation of Diacid

A suspension of 0.539 g (0.664 mmol) of the dibenzyl ester intermediate (obtained from Step 2) and 25 mg of 10% Pd/C in 30 mL of ethanol was agitated at ambient temperature under 20 psi of hydrogen gas for 2 hours. The catalyst was filtered off, and the filtrate was concentrated to give the desired title compound as a solid: mp 118° C.; $^1$H NMR ($CDCl_3$) δ 0.9 (d, 6H), 1.05–2.2 (m, 20H), 2.8 (s, 6H), 3.0 (q, 2H), 3.4 (s, 1H), 3.95 (s, 2H), 4.1 (s, 1H), 5.42 (s, 1H), 5.95 (s, 1H), 6.5 (d, 1H), 6.9 (d, 2H), 7.4 (d, 2H), 7.85 (d, 1H). HRMS. Calc'd for $C_{34}H_{49}NO_8S$: 632.3257. Found: 632.3264. Anal. Calc'd for $C_{34}H_{49}NO_8S$: C, 64.63; H, 7.82; N, 2.22; S, 5.08. Found: C, 63.82; H, 7.89; N, 2.14; S, 4.93.

Example 1414

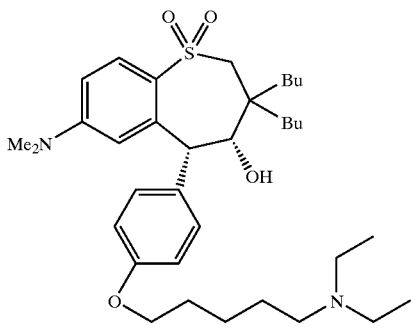

(4R-cis)-3,3-Dibutyl-5-[4-[[5-(diethylamino)pentyl]oxy]phenyl]-7-(dimethylamino)-2,3,4,5-tetrahydro-1-benzothiepin-4-ol 1,1-Dioxide Step 1: Preparation of Pentyl Iodide Intermediate To a solution of 5-(4'-hydroxyphenyl)-7-(dimethylamino)tetrahydrobenzothiepine-1,1-dioxide (3 g, 6.53 mmol, obtained from Example 1402, Step 10) in 100 mL of dimethylformamide was added 198 mg (7.83 mmol) of 95% sodium hydride. The mixture was stirred 15 minutes at room temperature and diiodopentane was added. After one hour at room temperature the mixture was diluted in ethyl acetate and water. The aqueous layer was extracted with ethyl acetate and the combined organic layer was washed with brine, dried over magnesium sulfate and concentrated in vacuo. The residue was chromatographed over silica gel, eluting with hexane/ethyl acetate (1/5) to afford 2.92 g (4.46 mmol) of the pentyl iodide intermediate: $^1$H NMR ($CDCl_3$) δ 0.9 (m, 6H), 1–1.5 (m, 11H), 1.6 (m, 3H), 1.8 (m, 4H), 2.2 (m, 1H), 2.8 (s, 6H), 3.0 (d, J=15 Hz, 1H), 3.2 (d, J=15 Hz, 1H), 3.3 (m, 2H), 4.0 (m, 1H), 4.1 (s, 1H), 5.5 (s, 1H), 6.1 (s, 1H), 6.6 (m, 1H), 6.9 (d, J=9 Hz, 2H), 7.4 (d, J=9 Hz, 2H), 7.9 (d, J=7 Hz, 1H).

Step 2: Preparation of Amine

A solution of 550 mg (0.76 mmol) of the pentyl iodide intermediate (obtained from Step 1) and 279 mg (3.81 mmol) of diethylamine in 3 mL of acetonitrile was stirred at 100° C. overnight. The mixture was concentrated in vacuo to yield a yellowish brown foam. The foam was dissolved in 10 mL of ethyl acetate and washed with 50 mL of saturated sodium carbonate solution twice. The ethyl acetate layer was dried over magnesium sulfate and concentrated to yield 390 mg (85%) of the desired title compound as a yellow foamy solid: $^1$H NMR ($CDCl_3$) δ 0.89 (m, 6H), 1.20–1.47 (m, 12H), 1.53–1.67 (m, 4H), 1.76–1.90 (m, 8H), 2.21 (m, 1H), 2.74–2.92 (m, 12H), 3.07 (ABq, 2H), 4.00 (t, J=6.3 Hz, 2H), 4.10 (d, J=7.8 Hz, 1H), 5.48 (s, 1H), 6.00 (d, J=2.4 Hz, 1H), 6.51 (dd, J=9.2 Hz, 2.6 Hz, 1H), 6.92 (d, J=8.7 Hz, 2H), 7.41 (d, J=8.4 Hz, 2H), 7.90 (d, J=9.0 Hz, 1H).

Example 1415

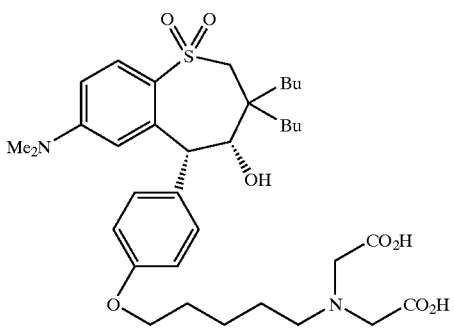

(4-cis)-N-(Carboxymethyl)-N-[5-[4-[3,3-dibutyl-7-(dimethylamnino)-2,3,4,5-tetrahydro-4-hydroxy-1,1-dioxido-1-benzothiepin-5-yl]phenoxy]pentyl]glycine Step 1: Preparation of Diester Intermediate A mixture of 8.6 g (14.1 mmol) of pentyl bromide intermediate (obtained from Example 1413, Step 1), 65 g (0.35 mol) of diethylaminodiacetate and 7.5 g (71 mmol) of anhydrous $Na_2CO_3$ was stirred at 160° C. for 3 hours. The reaction mixture was diluted with water and extracted with methylene chloride. The volatiles was removed in vacuo to give 9.6 g (95%) of the diester intermediate. $^1$H NMR spectrum was consistent with the structure; MS (M+H) m/e 717.

Step 2: Preparation of Diacid

The mixture of the diester intermediate (obtained from Step 1) and 2.7 g (64.3 mmol) of LiOH in THF (75 mL) and water (50 mL) was stirred at 40° C. for 18 hours. The reaction mixture was acidified with 1% HCl and extracted with dichloromethane. The residue was triturated with hexane, filtered to give 8.9 g (93%) of the desired title compound as a solid: mp 148–162° C.; $^1$H NMR ($CD_3OD$) δ 0.92 (t, 6H), 1.1–1.9 (m, 31H), 2.15 (t, 1H), 2.8 (s, 6H), 3.15 (ABq, 2H), 3.75(m, 1H), 4.1 (m, 6H), 5.3 (s, 1H), 6.1 (s, 1H), 6.6 (d, 1H), 7.0 (d, 2H), 7.4 (d, 2H), 7.8 (d, 1H); MS (M+H) m/e 661. Anal. Calc'd for [$C_{35}H_{52}N_2O_8S+1.5H_2O$]: C, 61.11; H, 8.06; N, 4.07; S, 4.66. Found: C, 61.00; H, 7.72; N, 3.89; S, 4.47.

Example 1416

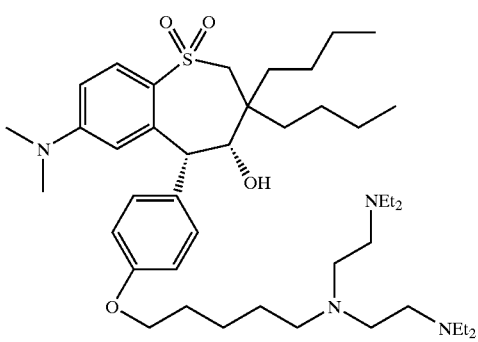

(4R-cis)-5-[4-[[5-[bis[2-(Diethylamino)ethyl]amino]pentyl]oxy]phenyl]-3,3-dibutyl-7-(dimethylamino)-2,3,4,5-tetrahydro-1-benzothiepin-4-ol 1,1-Dioxide A solution of 1 g of pentyl iodide intermediate (1.53 mmol, obtained from Example 1414, Step 1) in N,N,N',N'-tetraethyl diethylenetriamine was heated to 80° C. for 4 hours. The mixture was dissolved in ethyl acetate and saturated $NaHCO_3$. The organic layer was washed with brine, dried over magnesium sulfate, and concentrated in vacuo. The residue was purified by reverse phase chromatography. The fractions containing the product were concentrated in vacuo, dissolved in ethyl acetate and washed with saturated $NaHCO_3$. The residue was dried and concentrated in vacuo to afford 840 mg (74%) of the desired title compound as a thick oil. $^1$H NMR ($CDCl_3$) δ 0.8 (m, 6H), 1–1.6 (m, 28H), 1.8 (m, 2H), 2.1 (m, 1H), 2.5 (m, 18H), 2.7 (s, 6H), 2.9 (d, J=15 Hz, 1H), 3.1 (d, J=15 Hz, 1H), 3.9 (m, 2H), 4.0 (m, 1H), 4.1 (s, 1H), 5.4 (s, 1H), 6.0 (s, 1H), 6.4 (m, 1H), 6.9 (d, J=9 Hz, 2H), 7.4 (d, J=9 Hz, 2H), 7.8 (d, J=7 Hz, 1H). MS (M+H) m/e 743.

Example 1417

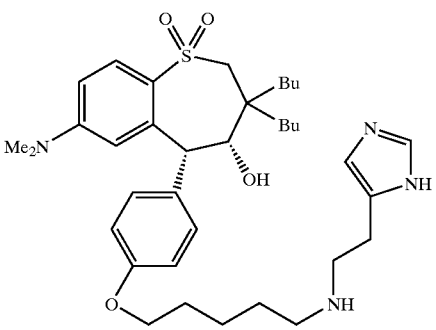

(4R-cis)-3,3-Dibutyl-7-(dimethylamino)-2,3,4,5-tetrahydro-5-[4-[[5-[[2-(1H-imidazol-4-yl)ethyl]amino]pentyl]oxy]phenyl]-1-benzothiepin-4-ol 1,1-Dioxide A solution of 1 g of pentyl iodide intermediate (1.53 mmol, obtained from Example 1414, Step 1) and 3.4 g (30.6 mmol) of histamine was heated to 50° C. for 17 hours. The mixture was dissolved in ethyl acetate and saturated $NaHCO_3$. The organic layer was washed with brine, dried over magnesium sulfate, and concentrated in vacuo. The residue was triturated with ether to afford 588 mg (60%) of the desired title compound as a semi-solid: $^1$H NMR ($CDCl_3$) δ 0.9 (m, 6H), 1–1.7 (m, 14H), 1.9 (m, 3H), 2.0 (m, 2H), 2.2 (m, 1H), 2.8 (s, 6H), 3.0 (m, 3H), 3.2 (m, 2H), 4.0 (m, 2H), 4.1 (m, 3H), 5.5 (s, 1H), 6.0 (s, 1H), 6.5 (m, 1H), 6.8 (s, 1H), 6.9 (d, J=9 Hz, 2H), 7.4 (m, 3H), 7.9 (d, J=8 Hz, 1H). MS (M+H) m/e 639.

Example 1418

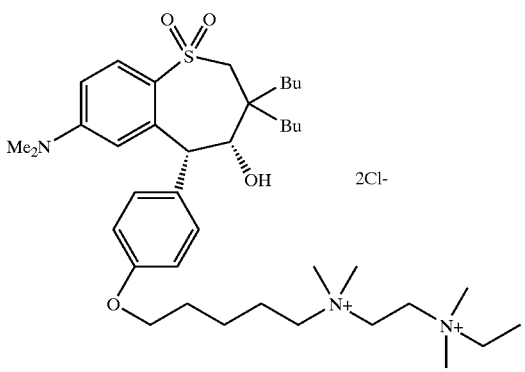

(4R-cis)-N-[5-[4-[3,3-Dibutyl-7-(dimethylamino)-2,
3,4,5-tetrahydro-4-hydroxy-1,1-dioxido-1-
benzothiepin-5-yl]phenoxy]pentyl]-N'-ethyl-N,N,N',
N'-tetramethyl-1,2-ethanediaminium Dichloride Step 1: Preparation of Pentyl Bromide Intermediate A mixture of 5-(4'-hydroxyphenyl)-7-(dimethylamino) tetrahydrobenzothiepine-1,1-dioxide (1.680 g, 3.66 mmol, obtained from Example 1402, Step 10) and sodium hydride (0.250 g, 6.25 mmol) in 30 mL of DMF was stirred in a dry 100 mL round-bottom flask under $N_2$. To this solution was added 1,5-dibromopentane (6.0 mL/44.0 mmol), and the resulting mixture was stirred for 18 hours. The reaction was diluted with brine (100 mL) and $H_2O$ (20 mL), and the mixture was extracted with EtOAc (3×50 mL). Organic layers were combined, dried ($MgSO_4$), filtered and concentrated in vacuo. Purification by filtration through silica gel eluting with 20% EtOAc/hexane and evaporation in vacuo gave pentyl bromide intermediate as a white foamy solid (1.783 g, 80%): $^1$H NMR (CDCl$_3$) δ 0.84–0.95 (m, 6H), 1.02–1.56 (m, 10H), 1.58–1.70 (m, 3H), 1.78–2.03 (m, 4H), 2.15–2.24 (m, 1H), 2.77 (s, 1H), 2.80 (s, 6H), 3.05 (ABq, 2H), 3.42 (t, 2H), 3.98 (t, 2H), 4.10 (s, 1H), 5.47 (s, 1H), 5.99 (d, 1H), 6.50 (dd, 1H), 6.91 (d, 2H), 7.40 (d, 2H), 7.88 (d, 1H).

Step 2: Preparation of mono-Quaternary Salt

The mixture of pentyl bromide intermediate (0.853 g, 1.40 mmol, obtained from Step 1), N,N,N',N'-tetramethylethylenediamine (1.0 mL/6.62 mmol) in 30 mL of acetonitrile was stirred at 40° C. for 12 hours, and the reaction mixture was concentrated in vacuo to give an off-white foamy solid (1.052 g).

The crude product was dissolved in acetonitrile (1.5 mL) and triturated with ethyl ether. The solvent was decanted to yield a sticky solid. This trituration method was repeated twice, and the resulting sticky solid was concentrated in vacuo to give the mono-quaternary salt as an off-white foamy solid (0.951 g, 94%): $^1$H NMR (CDCl$_3$) δ 0.81 (t, 6H), 0.96–1.64 (m, 13H), 1.62–1.85 (m, 4H), 2.03–2.18 (m, 1H), 2.20 (s, 6H), 2.67 (t, 2H), 2.74 (s, 6H), 2.98 (ABq, 2H), 3.30–3.42 (m, 1H), 3.38 (s, 6H), 3.60–3.75 (m, 4H), 3.90 (t, 2H), 4.01 (s, 1H), 5.37 (s, 1H), 5.92 (s, 1H), 6.41 (dd, 1H), 6.81 (d, 2H), 7.32 (d, 2H), 7.77 (d, 1H).

Step 3: Preparation of di-Quaternary Salt

The mono-quaternary salt (0.933 g, 1.29 mmol, obtained from Step 2), iodoethane (0.300 mL/3.75 mmol), and acetonitrile (30.0 mL) were combined in a 4 oz. Fischer Porter bottle. The reaction vessel was purged with $N_2$, sealed, equipped with magnetic stirrer, and heated to 50° C. After 24 hours, the reaction mixture was cooled to ambient temperature and concentrated in vacuo to give a yellow foamy solid (1.166 g). The solid was dissolved in methylene chloride/acetonitrile and precipitated with ethyl ether. After cooling to 0° C. overnight, the resulting solid was filtered, washed with ethyl ether and concentrated in vacuo to yield the di-quatenary salt as an off-white solid (1.046 g, 92%): $^1$H NMR (CD$_3$OD) δ 0.59 (t, 6H), 0.70–1.10 (m, 9H), 1.16 (t, 3H), 1.22–1.80 (m, 9H), 2.42 (s, 6H), 2.78 (d, 2H), 2.98 (s, 6H), 3.02 (s, 6H), 3.22–3.37 (m, 4H), 3.63–3.78 (m, 4H), 3.80 (s, 4H), 4.93 (s, 1H), 5.71 (s, 1H), 6.22 (dd, 1H), 6.61 (d, 2H), 7.02 (d, 2H), 7.40 (d, 1H).

Step 4: Preparation of Quaternary Dichloride Salt

The iodobromosalt (obtained from Step 3) was converted to its corresponding dichloride salt using Biorad AG 2X 8 resin and eluting with 70% $H_2O$/acetonitrile to give the desired title compound as a white foamy solid (0.746 g, 84%): mp 193.0–197.0° C.; $^1$H NMR (CD$_3$OD) δ 0.59 (t, J=6.0 Hz, 6H), 0.70–1.12 (m, 9H), 1.16 (t, J=6.6 Hz, 3H), 1.24–1.90 (m, 9H), 2.50 (s, 6H), 2.78 (s, 2H), 3.08 (s, 6H), 3.11 (s, 6H), 3.24–3.50 (m, 4H), 3.68 (s, 2H), 3.81 (s, 2H), 4.16 (s, 4H), 5.02 (s, 1H), 5.72 (s, 1H), 6.19 (d, J=8.4 Hz, 1H), 6.61 (d, J=8.1 Hz, 2H), 7.10 (d, J=7.8 Hz, 2H), 7.46 (d, J=8.7 Hz, 1H). HRMS. Calc'd for $C_{39}H_{67}N_3O_4$SCl: 708.4541. Found: 708.4598.

Example 1419

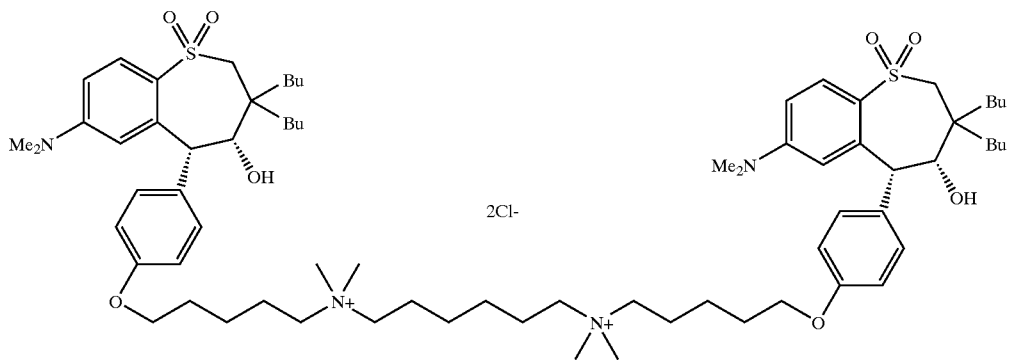

[4R-[4a,5a(4R*,5R*)]]-N,N'-bis[5-[4-[3,3-Dibutyl-7-(dimethylamino)-2,3,4,5-tetrahydro-4-hydroxy-1,1-dioxido-1-benzothiepin-5-yl]phenoxy]pentyl]-N,N,N'N'-tetramethyl-1,6-hexanediaminium Dichloride The pentyl bromide intermediate (1.002 g, 1.64 mmol, obtained from Example 1418, Step 1) and N,N,N',N'-tetramethyl-1,6-hexanediamine (0.100 g, 0.580 mmol) in 5 mL of acetonitrile were placed in a 4 oz. Fischer Porter bottle. The reaction vessel was purged with $N_2$, sealed, equipped with magnetic stirrer and heated to 50° C. After 15 hours, the reaction mixture was cooled to ambient temperature and concentrated in vacuo to give an off-white foamy solid (1.141 g). The solid was dissolved in acetonitrile and precipitated with ethyl ether. After cooling to 0° C., the solvent was decanted to yield a sticky off-white solid. This trituration method was repeated, and the resulting sticky solid was concentrated in vacuo to give the desired dibromide salt as an off-white foamy solid (0.843 g, quantitative): $^1$H NMR (CDCl$_3$) δ 0.85 (m, 12H), 1.01–1.70 (m, 30H), 1.76–2.08 (m, 12H), 2.18 (t, J=12.3 Hz, 2H), 2.79 (s, 12H), 3.03 (ABq, 4H), 3.35 (s, 12H), 3.52 (br s, 6H), 3.72 (br s, 4H), 3.97 (br s, 4H), 4.08 (br s, 2H), 5.42 (s, 2H), 6.00 (s, 2H), 6.51 (d, J=9.0 Hz, 2H), 6.86 (d, J=7.8 Hz, 4H), 7.38 (d, J=7.8 Hz, 4H), 7.83 (d, J=8.7 Hz, 2H). The dibromide salt was converted to its corresponding dichloride salt using Biorad AG 2x8 resin and eluting with 70% $H_2O/CH_3CN$ to give the desired title compound as a white foamy solid (0.676 g, 86%): mp 178.0–182.0° C.; $^1$H NMR (CDCl$_3$) δ 0.80–0.90 (m, 12H), 1.01–1.70 (m, 30H), 1.75–2.06 (m, 12H), 2.16 (t, J=12.9 Hz, 2H), 2.79 (s, 12H), 3.03 (ABq, 4H), 3.33 (s, 12H), 3.49 (br s, 6H), 3.70 (br s, 4H), 3.96 (t, J=5.4 Hz, 4H), 4.08 (s, 2H), 5.42 (s, 2H), 5.986 (s, 1H), 5.993 (s, 1H), 6.49 (d, J=9.0 Hz, 1H), 6.50 (d, J=9.0 Hz, 1H), 6.87 (d, J=8.4 Hz, 4H), 7.38 (d, J=8.1 Hz, 4H), 7.84 (d, J=8.7 Hz, 2H). HRMS. Calc'd for $C_{36}H_{58}N_2O_4S$: 614.4118. Found: 614.4148.

Example 1420

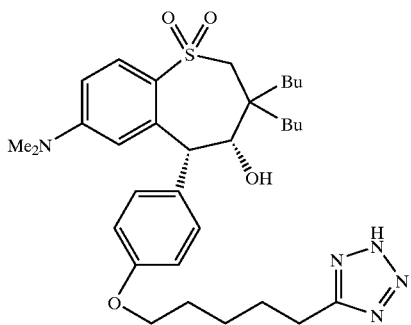

(4R-cis)-3,3-Dibutyl-7-(dimethylamino)-2,3,4,5-tetrahydro-5-[4-[[5-(1H-tetrazol-5-yl)pentyl]oxy]phenyl]-1-benzothiepin-4-ol 1,1-Dioxide Step 1: Preparation of Pentyl Bromide Intermediate To a stirred suspension of 1.01 g (25.4 mmol, 60% oil dispersion) of sodium hydride in 150 mL of DMF was added 9.0 g (19.5 mmol) of 5-(4'-hydroxyphenyl)-7-(dimethylamino)tetrahydrobenzothiepine-1,1-dioxide (obtained from Example 1402, Step 10) in portions. After 30 minutes the reaction was cooled in a water bath (15° C.) and 4.48 g (195 mmol) of 1,5-dibromopropane was added. The reaction was stirred at ambient temperature for 1.5 hours and quenched with 50 mL of saturated NH$_4$Cl. The reaction was diluted with ethyl acetate, washed with water, brine, dried over MgSO$_4$, filtered and concentrated in vacuo. Purification by silica gel chromatography (Waters-Prep 500) using 25% ethyl acetate/hexanes afforded 10.17 g (85%) of the pentyl bromide intermediate as a colorless foam: mp 65–70° C.; $^1$H NMR (CDCl$_3$) δ 0.84–0.98 (M, 6H), 1.04–1.52 (m, 10H), 1.58–1.65 (m, 3H), 1.82 (p, J=6.8 Hz, 2H), 1.94 (p, J=7.0 Hz, 2H), 2.12–2.26 (m, 1H), 2.82 (s, 6H), 3.06 (AB$_q$, J$_{AB}$=15.2, 45.3 Hz, 2H), 3.44 (t, J=6.7 Hz, 2H), 3.99 (t, J=6.3 Hz, 2H), 4.10 (s, 1H), 5.47 (s, 1H), 6.15 (d, J=2.7 Hz, 1H), 6.68 (dd, J=2.5, 8.4 Hz, 1H), 6.91 (d, J=8.4 Hz, 2H), 7.39 (d, J=8.4 Hz, 2H), 7.93 (d, J=8.7 Hz, 1H).

Step 2: Preparation of Pentyl Nitrile Intermediate

To a stirred solution of 378 mg (0.621 mmol) of the pentyl bromide intermediate (obtained from Step 1) in 1 mL of DMSO was added 37 mg (0.745 mmol) of sodium cyanide. The reaction was stirred at ambient temperature for 16 hours. The reaction was concentrated under a nitrogen stream and the residue partitioned between ethyl acetate and water. The organic layer was washed with brine, dried over MgSO$_4$, filtered, and concentrated in vacuo to afford 278 mg (93% RPHPLC purity, ca. 75%) of the pentyl nitrile intermediate as a colorless foam: $^1$H NMR (CDCl$_3$) δ 0.0.86–0.96 (m, 6H), 1.02–1.21(m, 1H), 1.21–1.52 (m, 19H), 1.58–1.92 (m, 7H), 2.16–2.28 (m, 1H), 2.41 (t, J=6.9 Hz, 2H), 2.83 (s, 6H), 3.08 (AB$_q$, 15.0, 47.5 Hz, 2H), 4.01 (t, J=6.2 Hz, 2H), 4.1 (s, 1H), 5.49 (s, 1H), 6.07 (d, J=2.1 Hz, 1H), 6.59 (dd, J=2.4, 8.7 Hz, 1H), 6.92 (d, J=8.1 Hz, 2H), 7.42 (d, J=8.4 Hz, 2H), 7.92 (d, J=8.7 Hz, 1H). MS (ES, M+H) m/e 555.

Step 3: Preparation of Tetrazole

A solution of 275 mg (0.5 mmol) of the nitrile intermediate (obtained from Step 2) and 666 mg (3.23 mmol) of azidotrimethyltin in 5 mL of toluene was stirped with heating at 80° C. for 60 hours. The reaction was concentrated under a nitrogen stream. Purification by reversed phase chromatography (Waters-Delta prep) using 60% water/acetonitrile afforded 226 mg of the desired title compound (75%) as a colorless foam: mp 80–85° C.; $^1$H NMR (CDCl$_3$) δ 0.83–0.95 (m, 6H), 1.30–1.52 (m, 10H), 1.52–1.73 (m, 3H), 1.79–1.99 (m, 4H), 2.14–2.26 (m, 1H), 2.91 (s, 6H), 3.02–3.22 (m, 4H), 3.92–4.06 (m, 2H), 4.16 (s, 1H), 5.47 (s, 1H), 6.28 (d, J=2.4 Hz, 1H), 6.74 (dd, J=2.7, 8.8 Hz, 1H), 6.89 (d, J=8.7 Hz, 2H), 7.37 (d, J=8.1 Hz, 2H), 7.98 (d, J=8.7 Hz, 1H). HRMS Calc'd for $C_{32}H_{48}N_5O_4S$: 598.3427. Found: 598.3443.

Example 1421

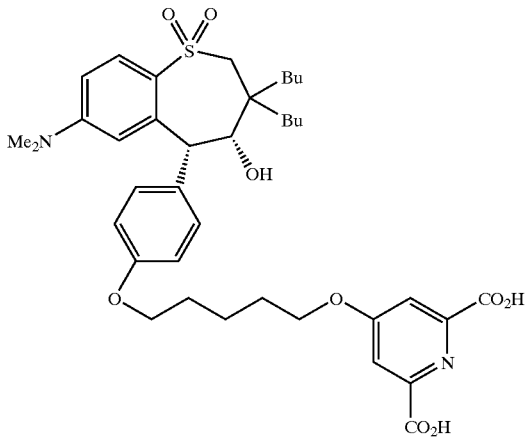

(4R-cis)-4-[[5-[4-[3,3-Dibutyl-7-(dimethylamino)-2,3,4,5-tetrahydro-4-hydroxy-1,1-dioxido-1-1benzothiepin-5-yl]phenoxy]pentyl]oxy]-2,6-pyridinecarboxylic Acid Step 1: Preparation of Pentyl Bromide Intermediate To a solution of 0.63 g (15.72 mmol, 60% disp) of NaH in 85 mL of DMF was add 6.0 g (13.1 mmol) of 5-(4'- hydroxyphenyl)-7-(dimethylamino)tetrahydrobenzo-thiepine-1,1-dioxide (obtained from Example 1402, Step 10), and the resulting solution was stirred at ambient temperature for 1 hour. To the solution was added 37.7 g (163.75 mmol) of 1,5-dibromopentane, and stirred overnight at ambient temperature. DMF was removed in vacuo and the residue was extracted with ethyl acetate and washed with brine. The extract was dried over $MgSO_4$, and the concentrated residue was purified by column chromatography to give the pentyl bromide intermediate: $^1$H NMR ($CDCl_3$) δ 0.90 (q, 6H), 1.05–2.0 (m, 17H), 2.2 (t, 1H), 2.8 (s, 6H), 3.0 (q, 2H), 3.4 (t, 2H), 3.95 (t, 2H), 4.1 (s, 1H), 5.42 (s, 1H), 6.0 (s, 1H), 6.5 (d, 1H), 6.9 (d, 2H), 7.4 (d, 2H), 7.9 (d, 1H).

Step 2: Esterification of Chelidamic Acid

A solution of 10 g (54.6 mmol) of chelidamic acid, 23.0 g (120.12 mmol) of 1-(3-dimethyl amino propyl)-3 ethyl carbodiimide hydrochloride, 1.33 g (10.8 mmol) of 4-dimethyl amino pyridine, and 12.4 mL (120.12 mmol) of benzyl alcohol in 100 mL of DMF was stirred at ambient temperature overnight under $N_2$. DMF was removed in vacuo and the residue was extracted with methylene chloride, washed with 5% $NaHCO_3$, 5% acetic acid, $H_2O$, and brine. The extract was dried over $MgSO_4$, and the concentrated residue was purified by column chromatography to give dibenzyl chelidamic ester $^1$H NMR ($CDCl_3$) δ 5.4 (s, 4H), 7.4 (m, 12H).

Step 3: Preparation of Pyridinyl Benzyl Ester Intermediate

A solution of 79 mg (1.972 mmol, 60% disp) of NaH and 0.716 g (1.972 mmol) of dibenzyl chelidamic ester (obtained from Step 2) in 17.5 mL of DMF was stirred at ambient temperature for 1 hour. To the solution was added 1.0 g (1.643 mmol) of the pentyl bromide intermediate and the mixture was stirred under $N_2$ overnight at 40° C. DMF was removed in vacuo, and the residue was extracted with ethyl acetate and washed with brine. The extract was dried over $MgSO_4$, and the concentrated residue was purified by column chromatography to give the pyridinyl dibenzyl ester intermediate: $^1$H NMR ($CDCl_3$) δ 0.90 (q, 6H), 1.05–2.0 (m, 19H), 2.2 (t, 1H), 2.8 (s, 6H), 3.0 (q, 2H), 4.0 (t, 2H), 4.1 (s, 1H), 5.4 (s, 4H), 5.42 (s, 1H), 6.0 (s, 1H), 6.5 (d, 1H), 6.9 (d, 2H), 7.3–7.5 (m, 12H), 7.78 (s, 2H), 7.9 (d, 1H).

Step 4: Preparation of Pyridinyl Diacid

A suspension of 0.8813 g (0.99 mmole) of dibenzyl ester (obtained from Step 3) and 40 mg of 10% Pd/C in 35 mL of ethanol and 5 mL of THF was agitated at ambient temperature under 20 psi of hydrogen gas for 2 hours. The catalyst was filtered off, and the filtrate was concentrated to give the desired title compound as a solid: mp 143° C.; 1H NMR (THF-d8) 0.95 (q, 6H), 1.05–1.65 (m, 15H), 1.9 (m, 4H), 2.22 (t, 1H), 2.8 (s, 6H), 3.0 (t, 2H), 4.1 (s, 3H), 4.3 (s, 2H), 5.4 (s, 1H), 6.05 (s, 1H), 6.5 (d, 1H), 6.9 (d, 2H), 7.4 (d, 2H), 7.78 (d, 1H), 7.82 (s, 2H). HRMS. Calc'd for $C_{38}H_{50}N_2O_9S$: 711.3315. Found: 711.3322. Anal. Calc'd for $C_{38}H_{50}N_2O_9S$: C, 64.20; H, 7.09; N, 3.94; S, 4.51. Found: C, 62.34; H, 6.97; N, 4.01; S, 4.48.

Example 1422

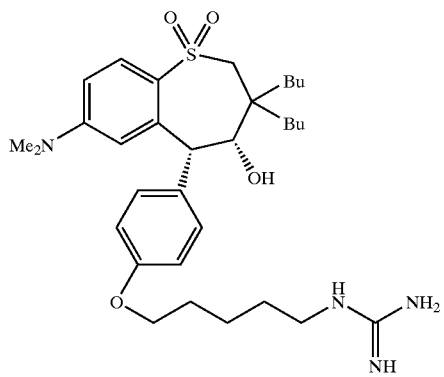

(4R-cis)-[5-[4-[3,3-Dibutyl-7-(dimethylamino)-2,3,4,5-tetrahydro-4-hydroxy-1,1-dioxido-1-benzothiepin-5-yl]phenoxy]pentyl]guanidine Step 1: Preparation of Pentyl Azide Intermediate To a stirred solution of 200 mg (0.328 mmol) of the pentyl bromide intermediate (obtained from Example 1420, Step 1) in 0.75 mL of DMSO was added 32 mg (0.493 mmol) of sodium azide and a catalytic amount of sodium iodide. The reaction was stirred at ambient temperature for 64 hours. The reaction was concentrated under a nitrogen stream and the residue partitioned between ethyl acetate and water. The organic layer was washed with brine, dried over $MgSO_4$, filtered, and concentrated in vacuo to afford 155 mg (92% RPHPLC purity, about 76% yield) of the pentyl azide intermediate as a colorless foam. Sample was used without further purification: mp 45–50° C; $^1$H NMR ($CDCl_3$) δ 0.83–0.93 (m, 6H), 1.03–1.48 (m, 10H), 1.54–1.74 (m, 5H), 1.78–1.86 (m, 1H), 2.14–2.26 (m, 1H), 2.81 (s, 6H), 3.06 ($AB_q$, $J_{AB}$=15.0, 48.0 Hz, 2H), 3.31 (t, J=6.3 Hz, 2H), 3.98 (t, J=6.3 Hz, 2H), 4.09 (s, 1H), 5.47 (s, 1H), 6.10 (d, J=1.8 Hz, 1H), 6.63 (dd, J=2.7, 9.0 Hz, 1H), 6.91 (d, J=9.0 Hz, 2H), 7.39 (d, J=8.4 Hz, 2H), 7.91 (d, J=8.7 Hz, 1H). MS (FAB, M+H) m/e 571.

Step 2: Preparation of Pentyl Amine Intermediate

To a solution of 0.67 g (1.17 mmol) of the azide intermediate (obtained from Step 1) in 75 mL of ethanol was added 0.10 g of 10% palladium on carbon and the mixture shaken under 49 psi of hydrogen at ambient temperature for 3.5 hours. The reaction was filtered through celite and concentrated in vacuo to give 0.62 g (86% RPHPLC purity, ca. 84%) of pentyl amine intermediate as an off-white foam. The sample was used without further purification: mp 70–85° C.; $^1$H NMR ($CDCl_3$) δ 0.86–0.96 (m, 6H), 1.06–1.75 (m, 15H), 1.79–1.93 (m, 4H), 2.15–2.28 (m, 1H), 2.82 (s, 6H), 2.96–3.20 (m, 4H), 3.99 (t, J=6.0 Hz, 2H), 4.04–4.14 (m, 1H), 5.49 (s, 1H), 6.00 (d, J=1.5 Hz, 1H), 6.51 (d, J=9.0 Hz, 1H), 6.91 (d, J=8.4 Hz, 2H), 7.41 (d, J=8.1 Hz, 2H), 7.90 (d, J=8.7 Hz, 1H). MS (ES, M+H) m/e 545.

Step 3: Preparation of Guanidine

To a stirred solution of 258 mg (0.474 mmol) of pentyl amino intermediate (obtained from Step 2) and 81 mg (0.551 mmol) of 1H-pyrazole-1-carboxamidine hydrochloride in 1.5 mL of DMF was added 71 mg (0.551 mmol) of diisopropylethylamine. The reaction was stirred at ambient temperature for 16 hours. Purification by reversed phase chromatography (Waters-Delta prep) using 60% water/acetonitrile afforded 120 mg (43%) of the desired title compound as colorless foamy solid: mp 67.0–72.5° C.; 1H NMR ($CDCl_3$) δ 0.89–0.93 (m, 6H), 1.05–1.17 (m, 1H), 1.26–1.90 (m, 16H), 2.07–2.24 (m, 1H), 2.81 (s, 6H), 2.99–3.19 (m, 4H), 3.98 (br s, 2H), 4.12 (s, 1H), 5.46 (s, 1H), 6.01 (d, J=2.1 Hz, 1H), 6.51 (dd, J=2.1,.8.0 Hz, 1H), 6.92 (d, J=8.1 Hz, 2H), 7.41 (d, J=7.8 Hz, 2H), 7.89 (d, J=8.7 Hz, 1H). HRMS. Calc'd for $C_{32}H_{50}N_4O_4S$: 586.3552. Found (M+H): 587.3620.

Example 1423

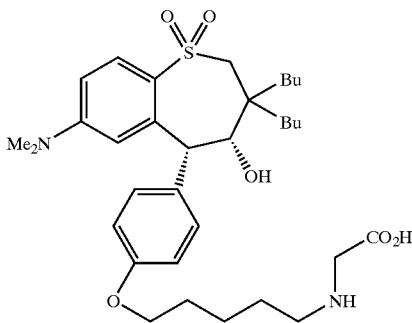

(4R-cis)-N-[5-[4-[3,3-Dibutyl-7-(dimethylamino)-2,3,4,5-tetrahydro-4-hydroxy-1,1-dioxido-1-benzothiepin-5-yl]phenoxy]pentyl]glycine Step 1: Preparation of Pentyl Azide Intermediate To a solution of pentyl bromide intermediate (400 mg, 0.657 mmol, obtained from Example 1420, Step 1) in dimethyl sulfoxide (20 mL) was added sodium azide (47 mg, 0.723 mmol, 1.1 eq), and the resulting clear solution was stirred at 23° C. for 16 h. The reaction solution was diluted with 100 mL ethyl acetate, then washed with water (2×100 mL) and brine (1×100 mL). The organic layer was dried ($MgSO_4$) and concentrated in vacuo to give 390 mg (quantitative) of pentyl azide intermediate as a yellow oil: $^1H$ NMR ($CDCl_3$) δ 0.82–0.90 (m, 7H), 1.05–1.56 (m, 12H), 1.59–1.71 (m, 3H), 1.78–2.01 (m, 4H), 2.20 (t, J=8.3 Hz, 1H), 2.82 (s, 6H), 3.08 (q, 2H), 3.44 (t, J=7.7 Hz, 2H), 3.99 (t, J=7.7 Hz, 2H), 4.91 (br s, 1H), 5.47 (s, 1H), 6.13 (d, J=7.58 Hz, 1H), 6.68 (d, J=7.7 Hz, 1H), 7.14 (ABq, 4H), 7.91 (d, J=7.8 Hz, 1H).

Step 2: Preparation of Amino Ester Intermediate

A suspension of pentyl azide intermediate (390 mg, 0.684 mmol, obtained from Step 1) and 100 mg of palladium on carbon in ethanol (15 mL) was agitated under an atmosphere of hydrogen gas (48 psi) for 4.5 hours. The ethanolic suspension was filtered through celite and concentrated in vacuo to give a yellow oil. The oil was immediately diluted with acetonitrile (15 mL), followed by the addition of triethylamine (0.156 g, 1.54 mmol, 2.25 eq) and bromo acetic acid benzyl ester (0.212 g, 0.925 mmol, 1.35 eq). The reaction was stirred at 23° C. for 48 hours. The reaction was concentrated in vacuo, and the residue was dissolved in ethyl acetate (20 mL) and washed with water (2×20 mL) and brine (1×20 mL). The organic layer was dried ($MgSO_4$) and dried in vacuo to give 420 mg (89%) of the amino ester intermediate as a yellow oil: $^1H$ NMR ($CDCl_3$) δ 0.82–0.90 (m, 6H), 1.05–1.56 (m, 14H), 1.58–1.71 (m, 3H), 1.78–2.01 (m, 4H), 2.20 (t, 8.3 Hz, 1H), 2.75 (d, J=7.83 Hz, 1H), 2.795 (s, 6H), 3.08 (q, 2H), 3.68–3.85 (m, 2H), 3.87–4.04 (m, 2H), 4.09 (s, 1H), 5.147 (s, 1H), 5.46 (s, 1H), 5.98 (d, J=7.58 Hz, 1H), 6.50 (dd, 1H), 6.85–6.87 (m, 2H), 7.28–7.45 (m, 5H), 7.89 (d, J=8.0 Hz, 1H). MS (ES) m/e 693.

Step 3: Preparation of Acid A suspension of benzyl ester intermediate (0.420 g, 0.61 mmol, obtained from Step 2) and 100 mg of palladium on carbon in ethanol (15 mL) was agitated under an atmosphere of hydrogen gas (48 psi) for 16 h. The suspension was filtered through celite, and concentrated in vacuo to give 0.330 g of a yellow semi-solid. The material was triturated with diethyl ether and the remaining semi-solid was dried in vacuo to give 0.19 g (52%) of the desired title compound as a yellow semi solid: $^1H$ NMR ($CDCl_3$) δ 0.86 (br s, 7H), 1.0–1.72 (m, 18H), 1.79 (br s, 2H), 1.98 (s, 2H), 2.09–2.24 (m, 2H), 2.78 (s, 6H), 2.99 (q, 2H), 3.96 (bs, 2H), 4.08 (s, 1H), 5.46 (s, 1H), 5.97 (s, 1H), 6.40–6.49 (m, 1H), 7.14 (ABq, 4H), 7.85 (t, J=7.93 Hz, 1H). MS (ES) m/e 603.

Example 1424

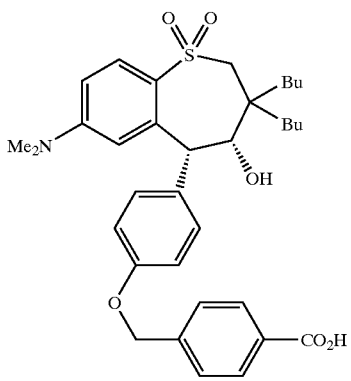

(4R-cis)-4-[[4-[3,3-Dibutyl-7-(dimethylamino)-2,3,4,5-tetrahydro-4-hydroxy-1,1-dioxido-1-benzothiepin-5-yl]phenoxy]methyl]benzoic Acid Step 1: Preparation of Benzoate Intermediate To a solution of 0.53 g (1.15 mmol) of 5-(4'-hydroxyphenyl)-7-(dimethylamino)tetrahydrobenzothiepine-1,1-dioxide (obtained from Example 1402, Step 10) in 10 mL dimethylformamide was added 35 mg (1.39 mmol) of 95% sodium hydride and stirred for 10 minutes. To the reaction mixture was added 525 mg (2.29 mmol) methyl 4-(bromomethyl)-benzoate and stirred for 16 hours. Water was added to the reaction mixture, extracted with ethyl acetate, washed with brine, dried over magnesium sulfate, filtered and the solvent evaporated to afford 0.51 g (73%) of the benzoate intermediate: $^1H$ NMR ($CDCl_3$) δ 0.86–0.96 (m, 6H), 1.14–1.47 (m, 10H), 1.60–1.64 (m, 1H), 2.20–2.23 (m, 1H), 2.80 (s, 6H), 2.99 (d, J=15.1 Hz, 1H), 3.15 (t, J=15.1 Hz, 1H), 3.92 (s, 3H), 4.09.4.15 (m, 1H), 5.17 (s, 2H), 5.49 (s, 1H), 5.94 (d, J=2.2 Hz, 1H), 6.50 (dd, J=8.9, 2.6 Hz, 1H), 7.00 (d, J=8.7 Hz, 2H), 7.43 (d, J=8.5 Hz, 2H), 7.53 (d, J=8.5 Hz, 2H), 7.93 (d, J=8.9 Hz, 1H), 8.06 (d, J=8.5 Hz, 2H).

Step 2: Preparation of Acid

A solution of 0.51 g (0.84 mmol) of the benzoate intermediate (obtained from Step 1) and 325 mg (2.53 mmol) of $KOSi(CH_3)_3$ (Aldrich) in 16 mL THF was stirred for 3.5 hours. The THF was evaporated, water added, extracted with ethyl acetate, dried over magnesium sulfate, filtered and the solvent evaporated to afford 0.30 g (60%) of the desired title compound as a white solid: mp 156–159° C.; $^1H$ NMR ($CDCl_3$) δ 0.89–0.94 (m, 6H), 1.24–1.43 (m, 10H), 1.62–1.66 (m, 1H), 2.20–2.24 (m, 1H), 2.84 (s, 6H), 3.02 (d, J=15.1 Hz, 1H), 3.17 (d, J=15.1 Hz, 1H), 4.14 (s, 1H), 5.20 (s, 2H), 5.50 (s, 1H), 6.16 (s, 1H), 6.71 (d, J=9.1 Hz, 2H), 7.03 (d, J=8.3 Hz, 2H), 7.44 (d, J=8.1 Hz, 2H), 7.57 (d, J=8.3 Hz, 2H), 7.95 (d, J=8.9 Hz, 1H), 8.13 (d, J=8.1 Hz, 2H). HRMS. Calc'd for $C_{34}H_{44}NO_6S$: 594.2889. Found: 594.2913.

Example 1425

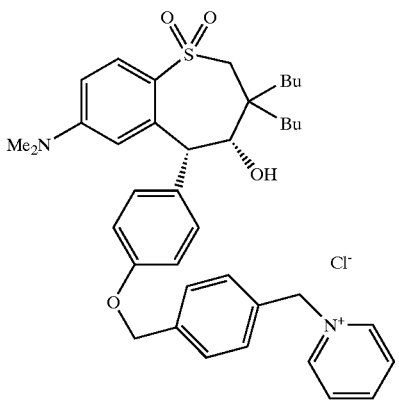

(4R-cis)-1-[[4-[[4-[3,3-Dibutyl-7-dimethylamino)-2,
3,4,5-tetrahydro-4-hydroxy-1,1-dioxido-1-
benzothiepin-5-yl]phenoxy]methyl]phenyl]methyl]-
pyridinium Chloride Step 1: Preparation of Chlorobenzyl Intermediate A solution of 5-(4'-hydroxyphenyl)-7-(dimethylamino) tetrahydrobenzothiepine-1,1-dioxide (5.0 g, 10.9 mmol, obtained from Example 1402, Step 10) in acetone (100 mL) at 25° C. under $N_2$ was treated with powdered $K_2CO_3$ (2.3 g, 16.3 mmol, 1.5 eq.) and α,α'-dichloro-p-xylene (6.7 g, 38.1 mmol, 3.5 eq.) and the resulting solution was stirred at 65° C. for 48 hours. The reaction mixture was cooled to 25° C. and concentrated to ⅓ of original volume. The residue was dissolved in EtOAc (150 mL) and washed with water (2×150 mL). The aqueous layer was extracted with EtOAc (2×150 mL) and the combined organic extracts were washed with saturated aqueous NaCl (2×150 mL. The combined extracts were dried ($MgSO_4$) and concentrated in vacuo to provide a yellow oil. Purification by flash chromatography (5.4×45 cm silica, 2540% EtOAc/hexane) afforded the chlorobenzyl intermediate (4.7 g, 72%) as a white foam: $^1$H NMR (CDCl$_3$) δ 0.89–0.94 (m, 6H), 1.12–1.48 (br m, 10H), 1.63 (m, 1H), 2.22 (m, 1H), 2.81 (s, 6H), 3.05 (ABq, J=15.1 Hz, J=50.0 Hz, 2H), 4.11 (d, J=8.1 Hz, 1H), 4.60 (s, 2H), 5.11 (s, 2H), 5.48 (s, 1H), 5.96 (d, J=2.4 Hz, 1H), 6.48 (dd, J=8.9, 2.6 Hz, 1H), 7.00 (d, J=8.9 Hz, 2H), 7.36–7.47 (m, 5H), 7.85 (d, J=8.9 Hz, 1H).

Step 2: Preparation of Quaternary Salt

A solution of the chlorobenzyl intermediate (1.0 g, 1.7 mmol, obtained from Step 1) in acetonitrile (5 mL) at 25° C. under $N_2$ was treated with pyridine (5 mL) and stirred at 35° C. for 36 hours. The pale amber solution was cooled to 25° C. and concentrated in vacuo to give the desired title compound (1.08 g, 96%) as a yellow solid: mp 154–156° C.; $^1$H NMR (CDCl$_3$) δ 0.83 (m, 6H), 1.06–1.44 (br m, 10H), 1.60 (m, 1H), 2.13 (m, 1H), 2.71 (s, 6H), 3.02 (ABq, J=15.1 Hz, J=28.4 Hz, 2H), 4.09 (s, 1H), 5.00 (s, 2H), 5.38 (s, 1H), 5.91 (d, J=2.4 Hz, 1H), 6.26 (s, 2H), 6.41 (dd, J=8.9, 2.4 Hz, 1H), 6.91 (d, J=8.7 Hz, 2H), 7.26 (m, 1H), 7.40 (d, J=7.7 Hz, 4H), 7.73 (d, J=7.9 Hz, 2H), 7.78 (d, J=8.9 Hz, 2H), 7.93 (t, J=6.8 Hz, 1H), 8.34 (t, J=7.7 Hz, 1H), 8.58 (br s, 1H), 9.69 (d, J=5.8 Hz, 2H); HRMS. Calc'd for $C_{39}H_{49}N_2O_4S$: 641.3413. Found: 641.3425.

Example 1426

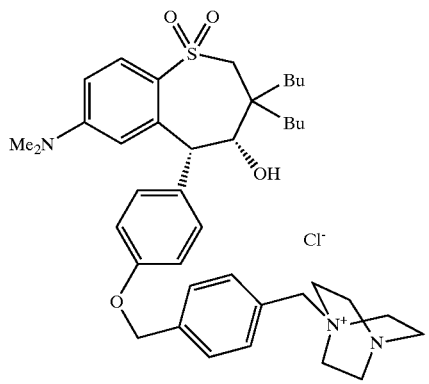

(4R-cis)-1-[[4-[[4-[3,3-Dibutyl-7-(dimethylamino-2,
3,4,5-tetrahydro-4-hydroxy-1,1-dioxido-1-
benzothiepin-5-yl]phenoxy]methyl]phenyl]methyl]-
4-aza-1-azoniabicyclo[2.2.2]octane Chloride Under $N_2$, a solution of 8.7 g (14.5 mmol) of the chlorobenzyl intermediate (obtained from a procedure similar to the one outlined in Example 1425, Step 1) in 60 mL of acetonitrile was added dropwise over a 30 min period to a solution of 2.9 g (26.2 mmol) of diazabicyclo[2.2.2]octane (DABCO) in 40 mL of acetonitrile at 35° C.; during the addition, a colorless precipitate was formed. The slurry was stirred at 35° C. for an additional 2 h. The product was collected and washed with 1 L of acetonitrile to give 9.6 g (93%) the title compound as a colorless crystalline solid: mp 223–230° C. (decomposed); $^1$H NMR (CDCl$_3$) δ 0.89 (m, 6H), 1.27–1.52 (br m, 10H), 1.63 (m, 11H), 2.20 (m, 1H), 2.81 (s, 6H), 3.06 (ABq, J=15.1 Hz, J=43.3 Hz, 2H), 3.16 (s, 6H), 3.76 (s, 6H), 4.11 (d, J=7.7 Hz, 1H), 5.09 (s, 2H), 5.14 (s, 2H), 5.48 (s, 1H), 5.96 (s, 1H), 6.49 (d, J=8.9 Hz, 1H), 6.99 (d, J=8.0 Hz, 2H), 7.26 (m, 1H), 7.44 (d, J=8.0 Hz, 2H), 7.52 (d, J=7.4 Hz, 2H), 7.68 (d, J=7.4 Hz, 2H), 7.87 (d, J=8.9 Hz, 1H); HRMS. Calc'd for $C_{40}H_{56}N_3O_4S$: 674.3992. Found: 674.4005.

Example 1426a

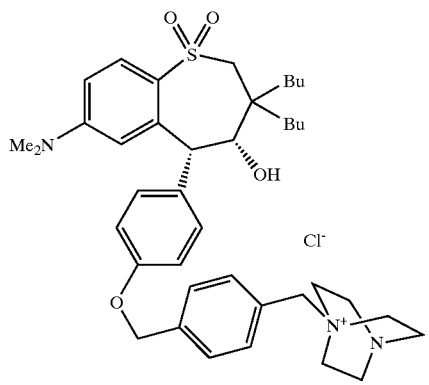

(4R-cis)-1-[[4-[[4-[3,3-Dibutyl-7-(dimethylamino)-
2,3,4,5-tetrahydro-4-hydroxy-1,1-dioxido-1-
benzothiepin-5-yl]phenoxy]methyl]phenyl]methyl]-
4-aza-1-azoniabicyclo[2.2.2]octane Chloride A solution of the chlorobenzyl intermediate (4.6 g, 7.7 mmol, obtained from Example 1425, Step 1) in acetonitrile (100 mL) at 25° C. under N₂ was treated with diazabicyclo [2.2.2]octane (DABCO, 0.95 g, 8.5 mmol, 1.1 eq.) and stirred at 35° C. for 2 hours, during which time a white solid precipitated out The white solid was collected, washed with CH₃CN and recrystallized from CH₃OH/Et₂O to give the title compound (4.95 g, 91%) as a white solid: mp 223–230° C. (decomposed); $^1$H NMR (CDCl₃) δ 0.89 (m, 6H), 1.27–1.52 (br m, 10H), 1.63 (m, 1H), 2.20 (m, 1H), 2.81 (s, 6H), 3.06 (ABq, J=15.1 Hz, J=43.3 Hz, 2H), 3.16 (s, 6H), 3.76 (s, 6H), 4.11 (d, J=7.7 Hz, 1H), 5.09 (s, 2H), 5.14 (s, 2H), 5.48 (s, 1H), 5.96 (s, 1H), 6.49 (d, J=8.9 Hz, 1H), 6.99 (d, J=8.0 Hz, 2H), 7.26 (m, 1H), 7.44 (d, J=8.0 Hz, 2H), 7.52 (d, J=7.4 Hz, 2H), 7.68 (d, J=7.4 Hz, 2H), 7.87 (d, J=8.9 Hz, 1H); HRMS. Calc'd for $C_{40}H_{56}N_3O_4S$: 674.3992. Found: 674.4005.

Step 3: Preparation of Amino Diacid

A solution of 0.863 g (1.15 mmol) of dibenzyl ester (obtained from Step 2) and 0.232 g (5.52 mmol) of LiOH in 30 mL of THF and 30 mL of water was stirred at 40° C. under N₂ for 4 hours. The reaction mixture was diluted with ether and washed with 1% HCl. The aqueous layer was extracted twice with ether, and the combined extracts were washed with brine, dried over MgSO₄, and concentrated in vacuo to give the desired title compound as a solid: mp 175° C.; $^1$H NMR (THF-d8) 0.95 (q, 6H), 1.05–1.65 (m, 11H), 2.22 (t, 1H), 2.8 (s, 6H), 3.0 (t, 2H), 3.5 (s, 4H), 3.9 (s, 2H), 4.1 (d, 1H), 5.1 (s, 2H), 5.4 (s, 1H), 6.05 (s, 1H), 6.5 (d, 1H), 7.0 (d, 2H), 7.4 (m, 6H), 7.78 (d, 1H). HRMS. Calc'd for $C_{38}H_{50}N_2O_9S$: 695.3366. Found: 695.3359. Anal. Calc'd for $C_{38}H_{50}N_2O_8S$: C, 65.68; H, 7.25; N, 4.03; S, 4.61. Found: C, 64.95; H, 7.32; N, 3.94; S, 4.62.

Example 1427

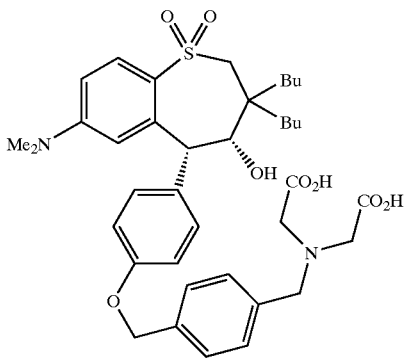

4R-cis)-N-(Carboxymethyl)-N-[[4-[[4-[3,3-dibutyl-7-(dimethylamino)-2,3,4,5-tetrahydro-4-hydroxy-1,1-dioxido-1-benzothiepin-5-yl]phenoxy]methyl]phenyl]methyl]glycine Step 1: Preparation of Chlorobenzyl Intermediate To a stirred solution of 144 mg (3.59 mmol, 60% disp) of NaH in 29 mL of DMF was added 1.5 g (3.26 mmol) of 5-(4'-hydroxyphenyl)-7-(dimethylamino)tetra-hydrobenzothiepine-1,1-dioxide (obtained from Example 1402, Step 10), and the resulting solution was stirred at ambient temperature for 45 min. To the solution was added 7.13 g (40.75 mmol) of dichloro p-xylene, and the mixture was stirred overnight. DMF was removed in vacuo, and the residue was extracted with ethyl acetate and washed with brine. The extract was dried over MgSO₄, and the concentrated residue was purified by column chromatography to give the chlorobenzyl intermediate: $^1$H NMR (CDCl₃) δ 0.90 (q, 6H), 1.05–1.65 (m, 11H), 2.2 (t, 1H), 2.8 (s, 6H), 3.0 (q, 2H), 4.1 (d, 1H), 4.6 (s, 2H), 5.1 (s, 2H), 5.5 (s, 1H), 6.0 (s, 1H), 6.6 (d, 1H), 7.0 (d, 2H), 7.4 (m, 6H), 7.8 (d, 1H).

Step 2: Preparation of Amino Diester

A mixture of 1.03 g (1.72 mmol) of chlorobenzyl intermediate (obtained from Step 1), 1.63 g (8.6 mmol) of diethyl amino diacetate, and 0.72 g (8.6 mmol) of NaHCO₃ in 30 mL of DMF was stirred at 100° C. for 6 hours. DMF was removed in vacuo and the residue was extracted with ether and washed with brine. The extract was dried over MgSO₄, and the concentrated residue was purified by column chromatography to give amino diester intermediate: $^1$H NMR (CDCl₃) δ 0.90 (q, 6H), 1.05–1.65 (m, 17H), 2.2 (t, 1H), 2.8 (s, 6H), 3.0 (q, 2H), 3.55 (s, 4H), 3.95 (s, 2H), 4.1–4.2 (m, 5H), 5.05 (s, 2H), 5.42 (s, 1H), 5.95 (s, 1H), 6.5 (d, 1H), 7.0 (d, 2H), 7.4 (s, 6H), 7.8 (d, 1H).

Example 1428

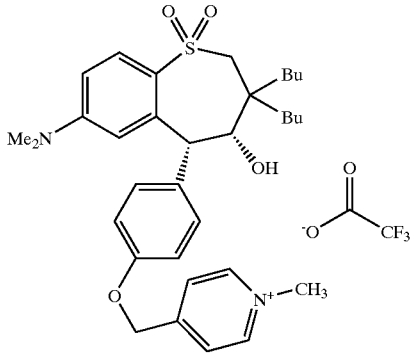

(4R-cis)-4-[[4-[3,3-Dibutyl-7-(dimethylamino)-2,3,4,5-tetrahydro-4-hydroxy-1,1-dioxido-1,1-dioxido-1-benzothiepin-5-yl]phenoxy]methyl]-1-methylpyridinium Salt With Trifluoroacetic Acid (1:1)

Step 1: Preparation of Picolyl Intermediate

To a stirred solution of 12.0 g (26.1 mmol) of 5-(4'-hydroxyphenyl)-7-(dimethylamino)tetra-hydrobenzothiepine-1,1-dioxide (obtained from Example 1402, Step 10) in 200 mL of DMF was added 1.4 g (60% oil dispersion, 35 mmol) of sodium hydride and the reaction stirred at ambient temperature for one hour. 5.99 g (36.5 mmol) of 4-picolyl chloride hydrochloride was treated with cold saturated NaHCO₃ solution and extracted with diethyl ether. The ethereal extracts were washed with brine, dried over MgSO₄, and filtered. The reaction was cooled in an ice bath and the solution of 4-picolyl chloride in diethyl ether was added. The reaction was stirred at ambient temperature for 17 hours. The reaction was quenched with 25 mL of saturated NH₄Cl, diluted with 600 mL ethyl acetate washed with 4×250 mL water, brine, dried over MgSO₄, filtered and concentrated in vacuo. Purification by silica gel chromatography (Waters-prep 500) using 60% ethyl acetate/hexanes afforded 11.05 g (77%) of the picolinyl intermediate as a colorless solid: mp 95–98° C.; $^1$H NMR (CDCl₃) δ 0.86–0.96 (m, 6H), 1.02–1.52 (m, 10H), 1.58–1.70 (m, 1H), 2.16–2.29 (m, 1H), 2.81 (s, 6H), 3.07 (AB$_q$, $J_{AB}$=15.3, 49.6 Hz, 2H), 4.10 (d, J=7.5 Hz, 1H), 5.15 (s, 2H), 5.50 (s, 1H), 5.94 (d, J=2.7 Hz, 1H), 6.51 (dd, J=2.4, 8.7 Hz, 1H), 7.00 (d, J=9.0 Hz, 2H), 7.39 (d, 6.0 Hz, 2H), 7.44 (s, J=8.7 Hz, 2H), 7.89 (d, J=9.0 Hz, 2H), 8.63 (dd, J=1.6, 4.8 Hz, 2H).

Step 2: Preparation of Quaternary Salt

To a stirred solution of 0.41 g (0.74 mmol) of picolinyl intermediate (obtained from Step 1) in 10 mL of acetonitrile and 3 mL of dichloromethane was added 137 mg (0.97 mmol) of iodomethane. The reaction was stirred at ambient temperature for 16 hours, then concentrated under a nitrogen stream. Purification by reversed phase chromatography (Waters-Delta prep) using 60–55% water/acetonitrile afforded 0.304 g (60%) of the desired title compound as a colorless solid: mp 96–99° C.; $^1$H NMR (CDCl$_3$) δ 0.85–0.95 (m, 6H), 1.03–1.52 (m, 10H), 1.57–1.70 (m, 1H), 2.12–2.27 (m, 1H), 2.84 (s, 6H), 3.09 (AB$_q$, J$_{AB}$=15.0, 27.9 Hz, 2H), 4.11 (s, 1H), 4.46 (s, 3H), 5.37 (s, 2H), 5.50 (s, 1H), 6.07 (d, J=2.4 Hz, 1H), 6.61 (dd, J=2.5, 8.7 Hz, 1H), 7.02 (d, J=8.7 Hz, 2H), 7.48 (d, J=7.2 Hz, 2H), 7.90 (d, J=8.7 Hz, 1H), 8.14 (d, J=6.3 Hz, 2H), 8.80 (d, J=6.6 Hz, 2H). HRMS Calc'd for C$_{33}$H$_{45}$N$_2$O$_4$S: 565.3100. Found: 565.3125.

Example 1429

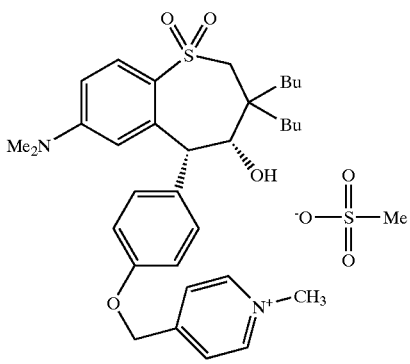

(4R-cis)-4-[[4-[3,3-Dibutyl-7-(dimethylamino)-2,3, 4,5-tetrahydro-4-hydroxy-1,1-dioxido-1,1-dioxido-1-benzothiepin-5-yl]phenoxy]methyl]-1-methylpyridinium, Methanesulfonate (Salt)

To a stirred solution of 6.5 g (11.8 mmol) of picolyl intermediate (obtained from Example 1428, Step 1) in 140 mL of acetonitrile heated at 70° C. was added 1.56 g (14.6 mmol) methanesulfonic acid methyl ester. Heating was continued at 70° C. for 15 hours. The reaction was cooled and diluted with 50 mL of ethyl acetate. The solid was collected by vacuum filtration to give 6.14 g (79%). The filtrate was concentrated in vacuo and the residue crystallized from hot acetonitrile to give 1.09 g (14%). A total of 7.23 g (93%) of the desired title compound was obtained as an off-white solid: mp 232–233.5° C.; $^1$H NMR (CDCl$_3$) δ 0.66–0.76 (m, 6H), 0.85–0.95 (m, 1H), 0.95–1.35 (m, 9H), 1.42–1.54 (m, 1H), 1.95–2.22 (m, 1H), 2.50 (s, 1H), 2.56 (s, 3H), 2.63 (s, 6H), 2.91 (AB$_q$, J=16.5, 24.0 Hz, 2H), 3.88 (s, 1H), 4.40 (s, 3H), 5.21 (s, 3H), 5.78 (d, J=2.4 Hz, 1H), 6.31 (dd, J=2.5, 8.7 Hz, 1H), 6.84 (d, J=8.7 Hz, 2H), 7.31 (d, J=8.4 Hz, 2H), 7.64 (d, J=8.7 Hz, 1H), 8.0 (d, J=6.6 Hz, 2H), 9.02 (d, J=6.6 Hz, 2H). HRMS Calc'd for C$_{33}$H$_{45}$N$_2$O$_4$S: 565.3100. Found: 656.3087. Anal. Calc'd for C$_{34}$H$_{48}$N$_2$O$_7$S$_2$: C, 61.79; H, 7.32; N, 4.24; S, 9.70. Found: C, 61.38, H, 7.47; N, 4.22; S, 9.95.

Example 1430

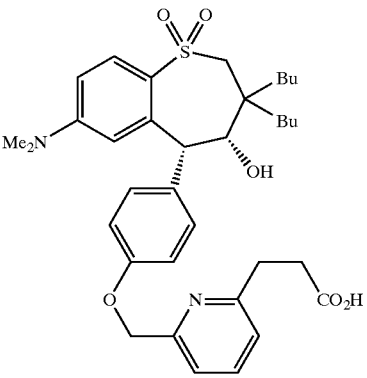

(4R-cis)-6-[[4-[3,3-Dibutyl-7-(dimethylamino)-2,3, 4,5-tetrahydro-4-hydroxy-1,1-dioxido-1-benzothiepin-5-yl]phenoxy]methyl]-2-pyridinepropanoic Acid Step 1: Preparation of Picolinyl Chloride Intermediate To a solution of 5-(4'-hydroxyphenyl)-7-(dimethylamino) tetrahydrobenzothiepine-1,1-dioxide (1 g, 2.1 mmol, obtained from Example 1402, Step 10) in acetone (50 mL) was added anhydrous K$_2$CO$_3$ (0.45 g, 3.2 mmol), tetrabutylammonium iodide (0.1 g, 0.2 mmol) and 2,6-bischloromethylpyridine (1.2 g, 10.8 mmol). The flask was equipped with nitrogen gas adapter and magnetic stirrer. The reaction was heated to reflux for overnight. After 18 hours, the reaction was diluted with ether and washed with water and brine (30 mL). The organic layers were dried over MgSO$_4$, filtered and concentrated in vacuo. Chromatographic purification through silica gel, eluting with 25% EtOAc/Hexane gave 0.75 g (55%) of the picolyl chloride intermediate as an oil (0.70 g, 55%): $^1$H NMR (CDCl$_3$) δ 0.84–0.95 (m, 6H), 1.02–1.5 (m, 10H), 1.56–1.66 (m, 1H), 2.14–2.24 (m, 1H), 2.80 (s, 6H) 3.05 (ABq, 2H), 4.10 (d, 2H), 4.65 (s, 2H), 5.20 (s, 2H), 5.45 (s, 1H), 5.95 (s, 1H), 6.50 (d, 1H), 7.0 (d, 2H), 7.35–7.50 (m, 4H), 7.70–7.85 (m, 2H).

Step 2: Preparation of Pyridinyl Malonate Intermediate

Dibenzyl malonate (1.42 g, 5.01 mmol) in DMF (20.0 mL) and sodium hydride (0.13 g, 3.3 mmol) were placed in a dry three-neck flask. The flask was equipped with nitrogen gas adapter and magnetic stirrer. The picolyl chloride intermediate (1 g, 1.67 mmol) was added and heated at 90° C. for overnight. The reaction was cooled and extracted with 5% HCl with methylene chloride and washed with water (25 mL), and brine (50 mL). The organic layers were dried over MgSO$_4$, filtered and concentrated. The residue was purified by C-18 reversed phase column eluting with 50% acetonitrile/water and gave pyridinyl malonate intermediate as a white foamy solid (1 g, 71%): $^1$H NMR (CDCl$_3$) δ 0.84–0.95 (m, 6H), 1.02–1.5 (m, 10H), 1.56–1.66 (m, 1H), 2.14–2.24 (m, 1H), 2.80 (s, 6H) 3.05 (ABq, 2H), 3.22 (d, 2H), 4.05 (d, 1H), 4.16 (t, 1H), 5.02 (s, 2H), 5.08 (s, 4H), 5.44 (s, 1H), 5.97 (s, 1H), 6.96–7.10 (m, 3H), 7.20–7.32 (m, 12H), 7.5 (t, 1H), 7.9 (d, 1H).

Step 3: Preparation of Pyridinyl Acid

The pyridinyl malonate intermediate (0.6 g, 0.7 mmol, obtained from Step 2), THF/water (25.0 mL, 1:1) and lithium hydroxide monohydrate (0.14 g, 3.4 mmol) were placed in a 100 mL round-bottom flask. The reaction was stirred at ambient temperature overnight. After 18 hours, the reaction was extracted with 1% HCl and ether and then washed with water (20 mL) and brine (30 mL). The organic layers were dried over MgSO$_4$, filtered and concentrated in vacuo gave the desired title compound as a white solid (0.44 g, 90%): mp 105–107° C.; $^1$H NMR (CDCl$_3$) δ 0.84–0.95 (m, 6H), 1.02–1.5 (m, 10H), 1.56–1.66 (m, 1H), 2.14–2.24 (m, 1H), 2.80 (s, 6H), 3.05 (m, 2H), 3.10 (ABq, 2H), 3.22 (m, 2H), 4.05 (s, 1H), 5.30 (s, 2H), 5.50 (s, 1H), 5.97 (s, 1H), 6.50 (d, 1H), 7.02 (d, 2H), 7.3 (d, 1H), 7.42 (d, 2H), 7.58 (d, 1H), 7.8–7.9 (m, 2H). HRMS. Calc'd for C$_{35}$H$_{46}$N$_2$O$_6$S: 623.3155. Found: 623.3188.

Example 1431

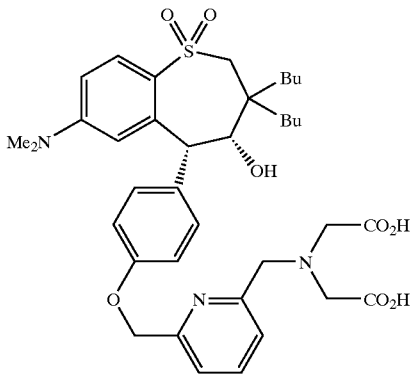

(4R-cis)-N-Carboxymethyl)-N-[[6-[[4-[3,3-dibutyl-7-(dimethylamino)-2,3,4,5-tetrahydro-4-hydroxy-1,1-dioxido-1-benzothiepin-5-yl]phenoxy]methyl]-2-pyridinyl]methyl]glycine Step 1: Preparation of Pyridinyl Diester Intermediate A mixture of diethyl aminodiacetate (8 g, 68 mmol) and sodium carbonate (0.63 g, 5.9 mmol) was treated with picolyl chloride intermediate (0.72 g, 1.2 mmol, obtained from Example 1430, Step 1), and stirred at 160° C. for three hours. The reaction was cooled and diluted with ether and washed with 1% HCl, water (25 mL), and brine (50 mL). The combined extracts were dried over MgSO$_4$, filtered and concentrated in vacuo. The residue was purified by distillation in the Kugelrohr to give pyridinyl diester intermediate as a yellowish foamy solid (0.72 g, 80%): $^1$H NMR (CDCl$_3$) δ 0.84–0.95 (m, 6H), 1.02–1.5 (m, 16H), 1.56–1.66 (m, 1H), 2.14–2.24 (m, 1H), 2.80 (s, 6H) 3.05 (ABq, 2H), 3.70 (s, 4H), 4.2–4.4 (m, 6H), 5.30 (s, 2H), 5.56 (s, 1H), 6.02 (s, 1H), 6.60 (d, 1H), 7.10 (d, 2H), 7.50 (m, 3H), 7.61 (d, 1H), 7.80 (t, 1H), 7.95 (d, 1H). HRMS. Calc'd for C$_{41}$H$_{57}$N$_3$O$_8$S: 752.3945. Found: 752.3948.

Step 2: Preparation of Pyridinyl Diacid

A mixture of pyridine-aminodiacetate intermediate (0.7 g, 0.93 mmol, obtained from Step 1), and lithium hydroxide monohydrate (0.18 g, 4.5 mmol) in THF/water (25.0 mL, 1:1) was stirred at 40° C. overnight (18 hours). The reaction mixture was diluted with ether and washed with 1% HCl, water (20 mL), and brine (30 mL). The organic layers were dried over MgSO$_4$, filtered and concentrated in vacuo to give the desired title compound as a white solid (0.44 g, 90%): mp 153–155° C.; $^1$H NMR (CDCl$_3$) δ 0.84–0.95 (m, 6H), 1.02–1.5 (m, 10H), 1.56–1.66 (m, 1H), 2.14–2.24 (m, 1H), 2.80 (s, 6H), 3.10 (ABq, 2H), 3.90 (m, 3H), 4.05 (s, 1H), 4.40 (s, 2H), 5.20 (s, 2H), 5.50 (s, 1H), 5.97 (s, 1H), 6.50 (d, 1H), 7.02 (d, 2H), 7.3 (d, 1H), 7.42 (d, 2H), 7.58 (d, 1H), 7.8–7.9 (m, 2H). HRMS. Calc'd for C$_{37}$H$_{49}$N$_3$O$_8$S: 696.3319. Found: 696.3331.

Example 1432

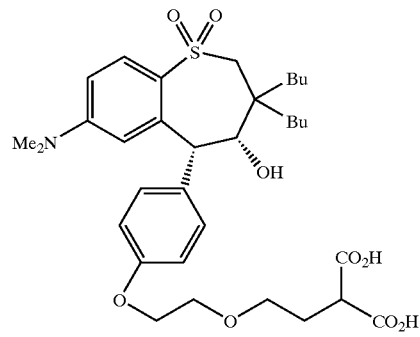

(4S-cis)-[2-[2-[4-[3,3-Dibutyl-7-(dimethylamino)-2,3,4,5-tetrahydro-4-hydroxy-1,1-dioxido-1-benzothiepin-5-yl]phenoxy]ethoxy]ethyl] propanedioic Acid Step 1: Preparation of Bromoethyl Ether Intermediate To a stirred solution of 0.192 g (4.785 mmol, 60% disp) of NaH in 28 mL of DMF was added 2.0 g (4.35 mmol) of 5-(4'-hydroxyphenyl)-7-(dimethylamino)tetrahydrobenzo-thiepine-1,1-dioxide (obtained from Example 1402, Step 10), and the resulting solution was stirred at ambient temperature for 30 min. To the solution was added 13.2 g (54.38 mmol) of bis(2-bromoethyl)ether, and stirring was continued at ambient temperature under N$_2$ overnight. DMF was removed in vacuo and the residue was extracted with ethyl acetate and washed with brine. The extract was dried over MgSO$_4$, and the concentrated residue was purified by column chromatography to give bromoethyl ether intermediate: $^1$H NMR (CDCl$_3$) δ 0.90 (q, 6h), 1.05–1.65 (m, 11H), 2.2 (t, 1H), 2.8 (s, 6H), 3.0 (q, 2H), 3.5 (t, 2H), 3.9 (m, 4H), 4.1 (d, 1H), 4.2 (d, 2H), 5.42 (s, 1H), 5.95 (s, 1H), 6.5 (d, 1H), 6.95 (d, 2H), 7.4 (d, 2H), 7.9 (d, 1H).

Step 2: Preparation of Diester Intermediate

To a mixture of 94 mg (2.34 mmol, 60% disp) of NaH in 45 mL of THF and 15 mL of DMF at 0° C. was added 1.33 g (4.68 mmol) of dibenzyl malonate (Aldrich), and the resulting solution was stirred at ambient temperature for 15 min, followed by the addition of 0.95 g (1.56 mmol) of bromoethyl ether intermediate (obtained from Step 1). The mixture was stirred under N$_2$ at 80° C. overnight. Solvent was removed in vacuo and the residue was extracted with methylene chloride and washed with brine. The extract was dried over MgSO$_4$, and the concentrated residue was purified by column chromatography to give the diester intermediate: $^1$H NMR (CDCl$_3$) δ 0.90 (q, 6H), 1.05–1.65 (m, 11H), 2.2–2.3 (m, 3H), 2.8 (s, 6H), 3.0 (q, 2H), 3.6 (t, 2H), 3.7 (m, 3H), 4.1 (m, 3H), 5.1 (s, 4H), 5.42 (s, 1H), 5.9 (s, 1H), 6.5 (d, 1H), 6.9 (d, 2H), 7.3 (m, 10H), 7.4 (d, 2H), 7.9 (d, 1H).

Step 3: Preparation of Diacid

A suspension of 0.761 g (0.935 mmol) of the diester intermediate (obtained from Step 2) and 35 mg of 10% Pd/C in 25 mL of ethanol and 5 mL of THF was agitated at ambient temperature under 20 psi of hydrogen gas for 2 hours. The catalyst was filtered off, and the filtrate was concentrated to give the desired title compound as a solid: mp 119.5° C.; $^1$H NMR (TBF-d8) 0.95 (q, 6H), 1.05–1.65 (m, 11H), 2.1 (q, 2H), 2.25 (t, 1H), 2.8 (s, 6H), 3.0 (t, 2H), 3.47 (q, 2H), 3.58 (s, 1H), 3.78 (t, 2H), 4.08 (d, 1H), 4.15 (t, 2H), 5.4 (s, 1H), 6.05 (s, 1H), 6.55 (d, 1H), 6.98 (d, 2H), 7.42 (d, 2H), 7.8 (d, 1H). HRMS. Calc'd for $C_{33}H_{47}NO_9S$: 632.2893. Found: 632.2882. Anal. Calc'd for $C_{33}H_{47}NO_9S$: C, 62.54; H, 7.47; N, 2.21; S, 5.06. Found: C, 61.75; H, 7.56; N, 2.13; S, 4.92.

Example 1433

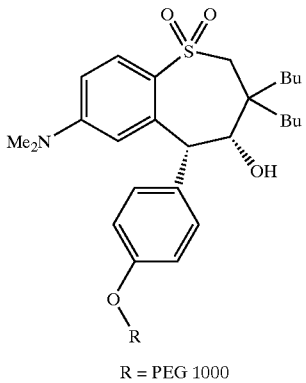

R = PEG 1000

(4R-cis)-a-[[4-[3,3-Dibutyl-7-(dimethylamino)-2,3,4,5-tetrahydro-4-hydroxy-1,1-dioxido-1-benzothiepin-5-yl]phenoxy]methyl]-w-methoxypoly(oxy-1,2-ethanediyl)

Step 1: Preparation of Monomethyl PEG Mesylate Intermediate

To a solution of 20 g of monomethyl ether PEG in 100 mL of methylene chloride was added 2.2 g (22 mmol) of triethyl amine, and to the resulting solution at 0° C. was added dropwise 2.5 g (22 mmol) of methanesulfonyl chloride. The resulting solution was stirred overnight at ambient temperature, and the triethyl amine hydrochloride was filtered off to give the monomethyl PEG mesylate intermediate which was used in the next Step without further purification and characterization.

Step 2: Preparation of Polyethylene-linked Benzothiepene

A mixture of 38 mg (1.52 mmol 95%) of NaH and 0.7 g (1.52 mmol) of 5-(4'-hydroxyphenyl)-7-(dimethylamino) tetrahydrobenzothiepine-1,1-dioxide (obtained from Example 1402, Step 10) in 5.5 mL of DMF was stirred at ambient temperature under $N_2$ for 30 min. To the solution was added 0.55 g (0.51 mmol) of the mesylate PEG intermediate (obtained from Step 1) in 5.5 mL of DMF, and the resulting solution was stirred overnight under $N_2$ at 50° C. DMF was removed in vacuo and the residue was extracted with methylene chloride and washed with brine. The extract was dried over $MgSO_4$, and the concentrated residue was purified by column chromatography to give the desired title compound as an oil: $^1$H NMR (CDCl$_3$) δ 0.9 (q, 6h), 1.05–1.65 (m, 11H), 2.2 (t, 1H), 2.8 (s, 6H), 3.0 (q, 2H), 3.4 (s, 4H), 3.5–3.85 (m, 95H), 4.1 (s, 1H), 4.15 (t, 2H), 5.5 (s, 1H), 6.05 (s, 1H), 6.6 (d, 1H), 6.9 (d, 2H), 7.4 (d, 2H), 7.9 (d, 1H).

Example 1434

Preparation of:

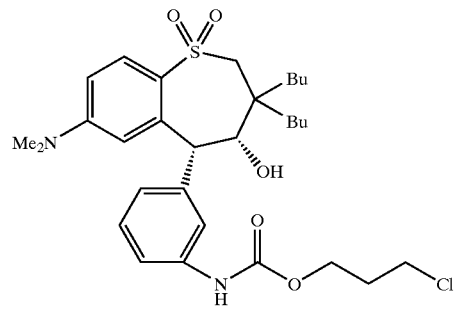

The 3-aminobenzothiepene prepared in Step 5 of Example 1398 (0.380 g, 0.828 mmol), sodium hydroxide (0.35 mL, 0.875 mmol, 10% in $H_2O$) and toluene (0.50 mL) were combined in a 10 mL round-bottom flask. The reaction flask was purged with $N_2$, equipped with magnetic stirrer, and cooled to 0° C. A solution of 3-chloropropyl chloroformate (1.440 g, 1.10 mmol 12% in $CH_2Cl_2$/THF) was added. After 3.5 hrs, toluene (3.0 mL) was added, and the mixture was washed with $H_2O$ (2×4 mL), dried (MgSO$_4$), filtered and concentrated in vacuo. Purification by flash chromatography on silica gel eluting with 20% EtOAc/hexane and concentrated in vacuo gave a white solid (0.269 g, 56%). $^1$H NMR (CDCl$_3$) δ 0.87–0.93 (m, 6H), 1.05–1.70 (m, 11H), 2.14 (t, J=6.3 Hz, 2H), 2.15–2.25 (m, 1H), 2.81 (s, 6H), 3.07 (ABq, 2H), 3.64 (t, J=6.3 Hz, 2H), 4.11 (d, J=7.5 Hz, 1H), 4.33 (t, J=6.0 Hz, 2H), 5.50 (s, 1H), 5.99 (d, J=2.4 Hz, 1H), 6.51 (dd, J=9.0, 2.7 Hz, 1H), 6.65 (s, 1H), 7.23 (d, J=7.8 Hz, 1H), 7.34–7.39 (m, 2H), 7.54 (d, J=7.2 Hz, 1H), 7.89 (d, 8.7 Hz, 1H). HRMS (M+H). Calc'd for $C_{30}H_{44}N_2O_5SCl$: 579.2659. Found: 579.2691.

Example 1435

Preparation of:

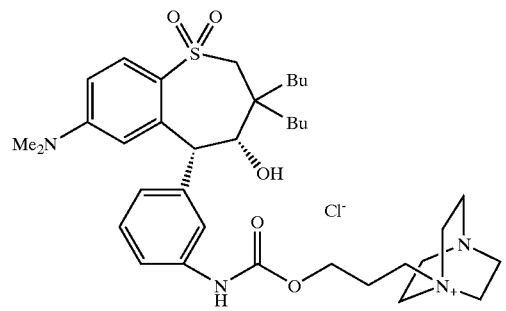

1,4-Diazabicyclo(2.2.2)octane (0.0785 g, 0.700 mmol) and acetonitrile (1.0 mL) were combined in a 10 mL round-bottom flask. The reaction flask was purged with $N_2$, equipped with magnetic stirrer, and heated to 37° C. A solution of the product of Example 1434 (0.250 g, 0.432 mmol) in acetonitrile (2.50 mL) was added. After 2.5 hrs, 1,4-diazabicyclo(2.2.2)octane (0.0200 g, 0.178 mmol) was added. After 64 hrs, 1,4-diazabicyclo(2.2.2)octane (0.0490 g, 0.437 mmol) was added. After 24 hrs, the reaction mixture was cooled to R.T. and concentrated in vacuo. The crude product was dissolved in acetonitrile (2.0 mL) and precipitated with ethyl ether (10.0 mL). The precipitate was filtered to yield a white solid. This trituration method was repeated, followed by concentrated in vacuo to give a white solid (0.185 g, 62%). mp 218.0–225.0° C.; $^1$H NMR (CD$_3$OD) δ 0.90 (m, 6H), 1.05–1.55 (m, 10H), 1.16 (t, J=6.6 Hz, 2H), 1.78 (m, 1H), 2.12 (m, 3H), 2.76 (s, 6H), 3.10 (m, 2H), 3.17 (t, J=7.2 Hz, 6H), 3.30–3.50 (m, 8H), 4.10 (s, 1H), 4.21 (t, J=5.4 Hz, 2H), 5.31 (s, 1H), 6.10 (s, 1H), 6.55 (d, J=7.2 Hz, 1H), 7.25 (d, J=6.9 Hz, 1H), 7.33–7.42 (m, 2H), 7.56 (s, 1H), 7.76 (d, J=9.0 Hz, 1H). HRMS. Calc'd for $C_{36}H_{55}N_4O_5SCl$: 655.3893. Found: 655.3880.

Example 1436

Preparation of:

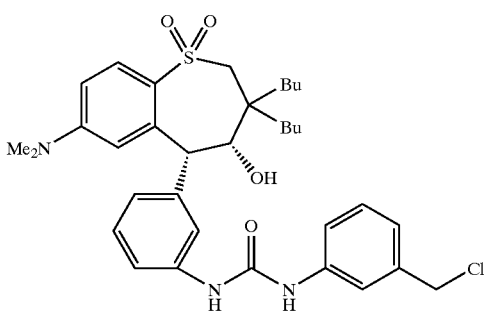

Step 1. Preparation of:

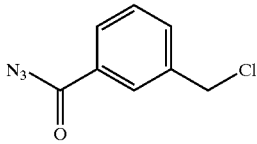

3-Chloromethylbenzoyl chloride (2.25 mL/5.8 mmol) and acetone (8.0 mL) were combined in a 25 mL round-bottom flask. The reaction flask was cooled to 0° C., and an aqueous solution of sodium azide (1.56 g in 5.50 mL, 24.0 mmol) was added. After 1.5 hrs, the reaction mixture was poured into ice water (80.0 mL), extracted with ethyl ether (2×25 mL), dried (MgSO$_4$), and concentrated in vacuo to give a colorless oil (2.660 g, 86%). $^1$H NMR (CDCl$_3$) δ 4.62 (s, 2H), 7.47 (t, J=7.8 Hz, 1H), 7.66 (d, J=7.8 Hz, 1H), 7.99 (d, J=7.8 Hz, 1H), 8.05 (s, 1H).

Step 2.

3-Chloromethylbenzoyl azide (0.142 g, 0.726 mmol) and toluene (2.0 mL) were combined in a 10 mL round-bottom flask. The reaction flask was purged with $N_2$, equipped with magnetic stirrer, and heated to 110° C. After 2 hrs, the reaction mixture was cooled to R.T, and the 3-aminobenzothiepene prepared in Step 5 of Example 1398 (0.365 g, 0.796 mmol) was added. After 2.25 hrs, the mixture was heated to 50° C. After 0.75 hrs, 3-chloromethylbenzoyl azide (0.025 g, 0.128 mmol) was added, and the reaction mixture was heated to reflux. After 0.5 hrs, the reaction mixture was cooled to R.T. and concentrated in vacuo. Purification by flash chromatography on silica gel eluting with 20–30% EtOAc/hexane and concentrated in vacuo gave a white foamy solid (0.309 g, 62%). $^1$H NMR (CDCl$_3$) δ 0.71 (t, J=5.4 Hz, 3H), 0.88 (t, J=6.3 Hz, 3H), 1.03–1.60 (m, 11H), 1.85 (d, 6.3 Hz, 1H), 2.27 (m, 1H), 2.76 (s, 6H), 3.15 (t, 2H), 4.17 (d, J=6.6 Hz, 1H), 4.48 (s, 2H), 5.42 (s, 1H), 6.07 (s, 1H), 6.99 (d, J=7.5 Hz), 7.18–7.26 (m, 2H), 7.30–7.41 (m, 3H), 7.63 (s, 1H), 7.86 (d, J=9.0 Hz, 2H), 7.96 (s, 1H), 8.17 (s, 1H). HRMS (M+Li). Calculated for $C_{34}H_{44}N_3O_4SClLi$: 632.2901. Found: 632.2889.

Example 1437

Preparation of:

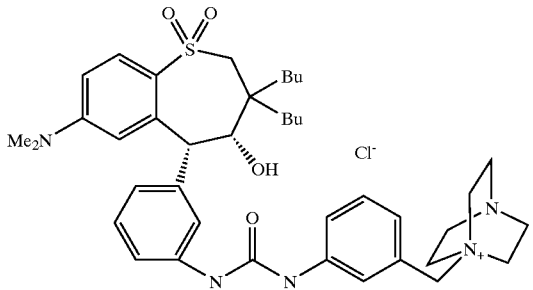

1,4-Diazabicyclo(2.2.2)octane (0.157 g, 1.40 mmol) and acetonitrile (1.00 mL) were combined in a 10 mL round-bottom flask. The reaction flask was purged with $N_2$ and equipped with magnetic stirrer. A solution of the product of Example 1436 (0.262 g, 0.418 mmol) in acetonitrile (2.70 mL) was added. After 2.5 hrs, a white precipitate had had formed. Ethyl ether (6.0 mL) was added, and the precipitate was filtered, washed with ethyl ether, and dried in vacuo to yield a white solid (0.250 g, 80%). mp 246.0–248.0° C.; $^1$H NMR (CD$_3$OD) δ 0.88 (m, 6H), 1.03–1.55 (m, 10H), 1.76 (m, 1H), 2.11 (m, 1H), 2.74 (s, 6H), 3.11 (m, 8H), 3.37 (m, 6H), 4.12 (s, 1H), 4.39 (s, 2H), 5.31 (s, 1H), 6.11 (s, 1H), 6.52 (dd, J=8.7, 1.8 Hz, 1H), 7.09 (d, J=7.2 Hz, 11H), 7.23 (d, J=6.9 Hz, 1H), 7.32–7.38 (m, 2H), 7.47 (m, 2H), 7.58 (s, 1H), 7.73 (d, J=8.7 Hz, 2H). HRMS. Calculated for $C_{40}H_{56}N_5O_4SCl$: 702.4053. Found: 702.4064. Anal. Calculated for $C_{40}H_{56}N_5O_4SCl$: C, 65.06; H, 7.64; N, Cl, 4.80. Found: C, 64.90; H, 7.77; N, 9.42; S, 4.16; Cl, 4.89.

Examples 1438–1454

The compounds of Examples 1438 through 1454 can be prepared in accordance with one or more of the synthetic schemes previously disclosed in this application or using methods known to those skilled in the art.

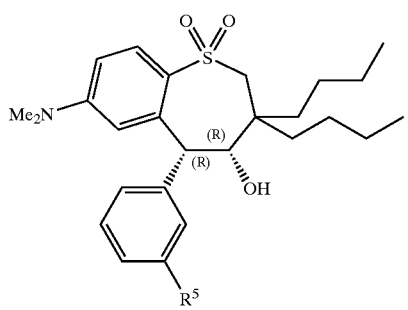
| | $R^5$ |
|---|---|
| 1438. | 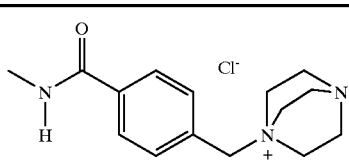 |
| 1439. | 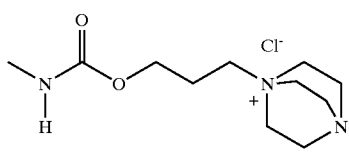 |
| 1440. | 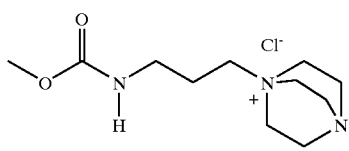 |
| 1441. | 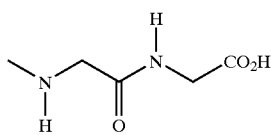 |
| 1442. | 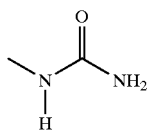 |
| 1443. | 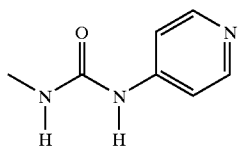 |
| 1444. | 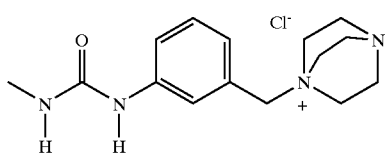 |
| 1445. | 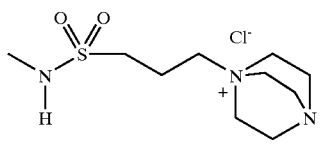 |

-continued

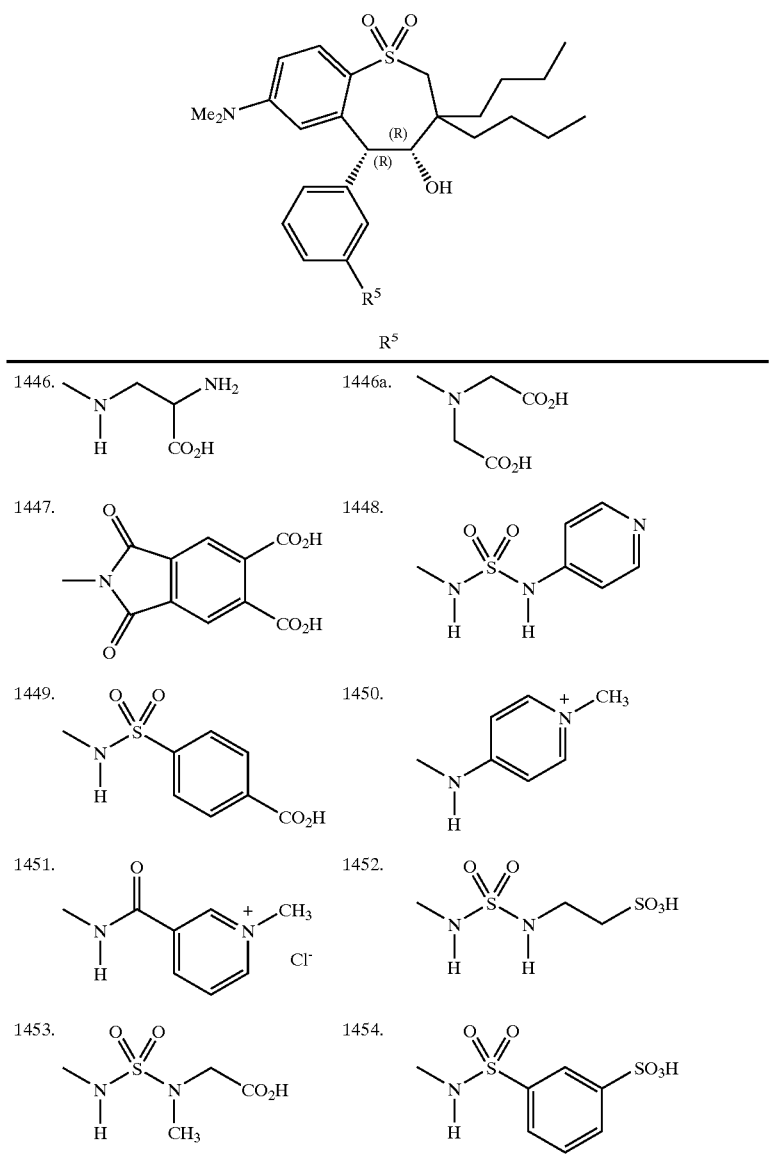

Example 1455

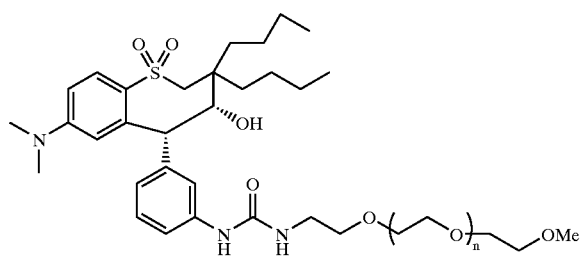

The 3-aminobenzothiepine of step 5 of Example 1398 (0.0165 g/0.0360 mmol), M-NCO-5000 (0.150 g/0.30 mmol) (Methoxy-PEG-NCO, MW 5000, purchased from Shearwater Polymers Inc., 2130 Memorial Parkway, SW, Huntsville, Ala. 35801), and $CDCl_3$ (0.7 mL) were combined in an 8 mm NMR tube. The tube was purged with $N_2$. After 72 hrs, the reaction mixture was heated to 50° C. After 24 hrs, an additional aliquot of the 3-aminobenzothiepine of step 5 of Example 1398 (0.0077 g/0.017 mmol) was added. After 24 hrs, the reaction mixture was transferred to a 2 mL vial and evaporated to dryness with a $N_2$ purge. The resulting white solid was dissolved in hot ethyl ether (2.0 mL) and ethyl acetate (0.057 mL/4 drops), cooled to precipitate and filtered. This precipitation procedure was repeated until no starting material was detected in the precipitate (TLC: $SiO_2$/80% EtOAc/hexanes). Concentrated in vacuo to give a white solid (0.0838 g/51%). $^1$H NMR ($CDCl_3$) d 0.82–0.90 (m, 6H), 1.05–1.49 (m, 14H), 1.18 (t, J=6.8 Hz, 2H), 1.59 (bt, 1H), 2.18 (bt, 1H), 2.34 (s, 2H), 2.78 (s, 6H), 3.04 (ABq, 2H), 3.35–3.80 (m, 625H), 4.09 (d, J=7.2 Hz, 2H), 5.42 (s, 1H), 5.78 (s, 1H), 6.04 (d, J=1.6 Hz, 1H), 6.47 (dd, J=6.4, 3.2 Hz, 1H), 7.07 (d, J=7.6 Hz, 1H), 7.31 (bs, 1H), 7.60 (d, J=7.6 Hz, 1H), 7.66 (s, 1H), 7.85 (d, J=8.8 Hz, 1H). Mass spectroscopy data also verified desired product.

Additional Examples
Additional schemes for forming compounds of the present invention are provided below.
Scheme 12
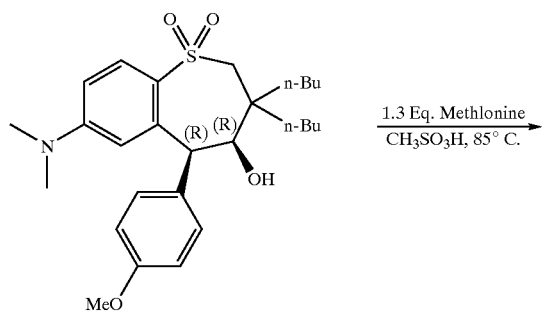
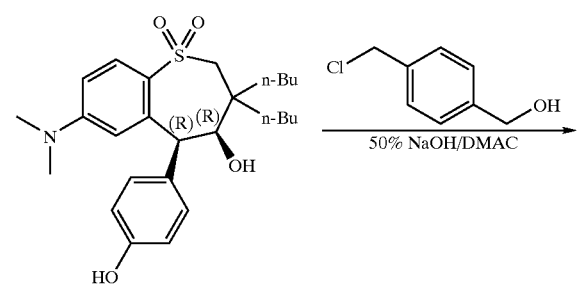
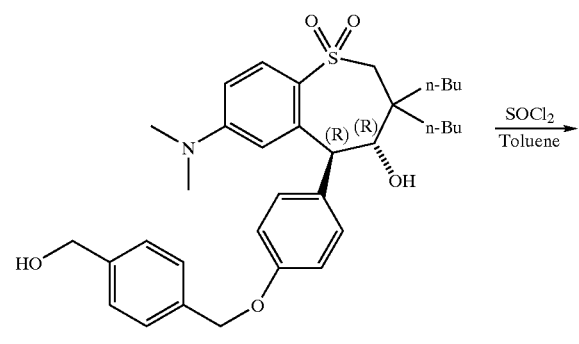
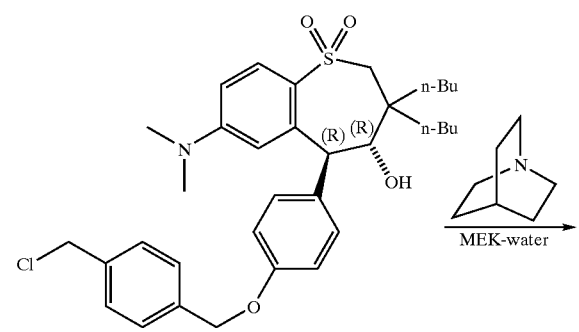
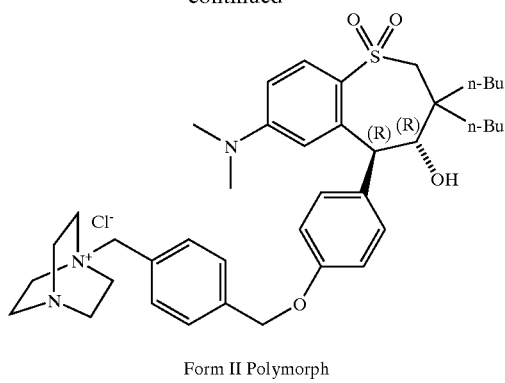
Form II Polymorph
Scheme 13
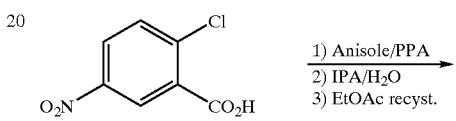
1) Anisole/PPA
2) IPA/H$_2$O
3) EtOAc recyst.
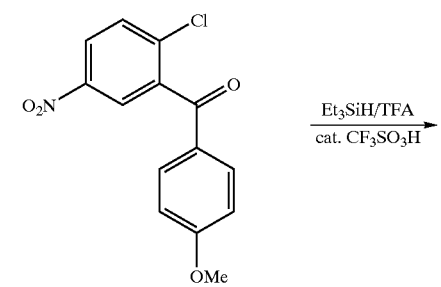
Et$_3$SiH/TFA
cat. CF$_3$SO$_3$H
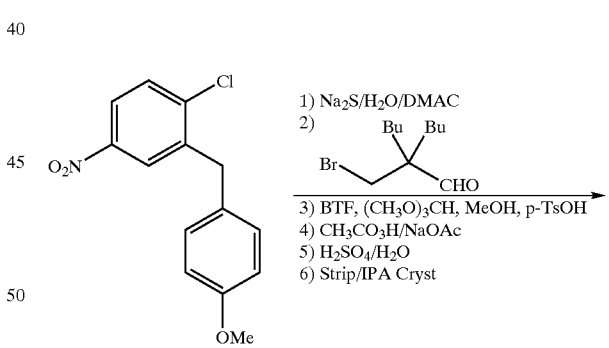
1) Na$_2$S/H$_2$O/DMAC
2)
3) BTF, (CH$_3$O)$_3$CH, MeOH, p-TsOH
4) CH$_3$CO$_3$H/NaOAc
5) H$_2$SO$_4$/H$_2$O
6) Strip/IPA Cryst
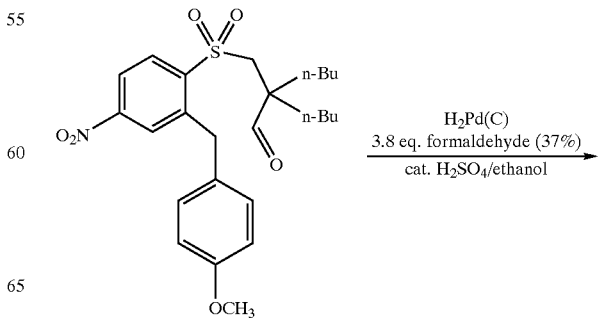
H$_2$Pd(C)
3.8 eq. formaldehyde (37%)
cat. H$_2$SO$_4$/ethanol

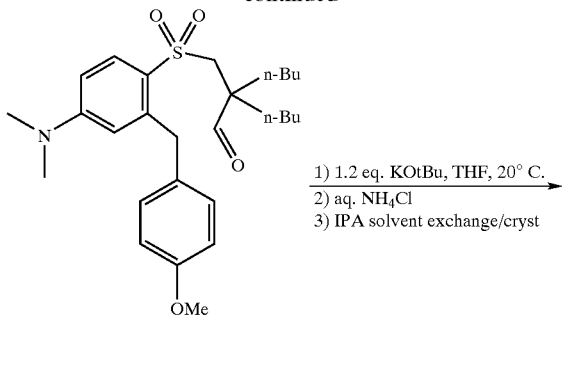

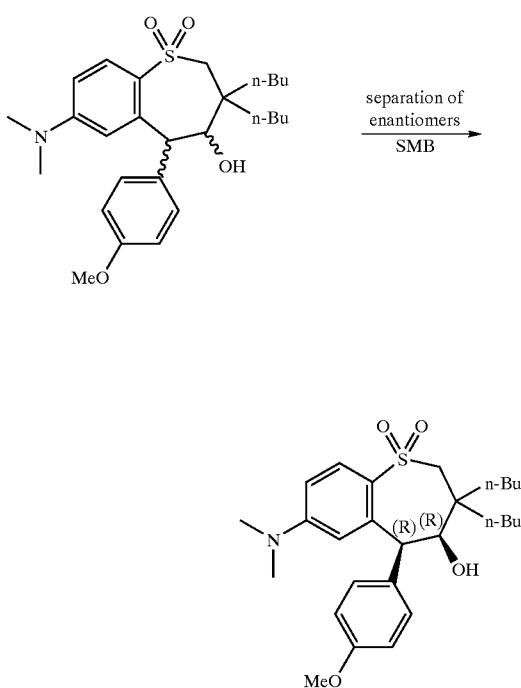

Generally, the process methods of the present invention can be performed as follows.

Example 1456

Preparation of 1-Chloro-2-(4-methoxyphenyl)methyl-4-nitrobenzene, 33x

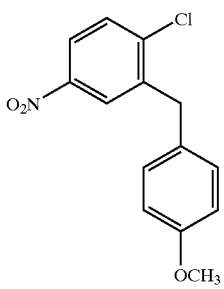

Step A. Preparation of 2-Chloro-5-nitrophenyl-4'-methoxyphenyl Ketone, 34x.

Method 1

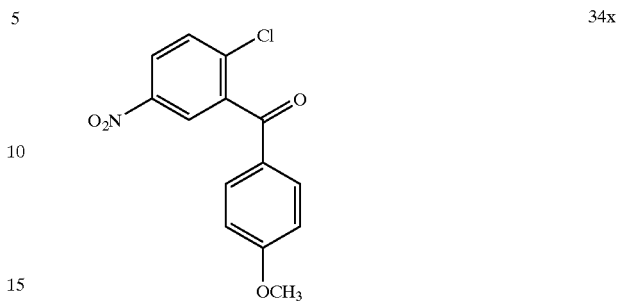

In an inert atmosphere, weigh out 68.3 g of phosphorus pentachloride (0.328 mole, Aldrich) into a 2-necked 500 mL round bottom flask. Fit the flask with a $N_2$ inlet adapter and suba seal. Remove from the inert atmosphere and begin $N_2$ purge. Add 50 mL of anhydrous chlorobenzene (Aldrich) to the $PCl_5$ via syringe and begin stirring with a magnetic stir bar.

Weigh out 60 g of 2-chloro-5-nitrobenzoic acid (0.298 mole, Aldrich). Slowly add the 2-chloro-5-nitrobenzoic acid to the chlorobenzene solution while under $N_2$ purge. Stir at room temperature overnight. After stirring at room temperature for about 20 hrs, place in an oil bath and heat at 50° C. for 1 hr. Remove chlorobenzene under high vacuum. Wash the residue with anhydrous hexane. Dry the acid chloride (wt=61.95 g). Store in inert and dry atmosphere.

In an inert atmosphere, dissolve the acid chloride in 105 mL of anhydrous anisole (0.97 mole, Aldrich). Place solution in a 2-neck 500 mL round bottom flask.

Weigh out 45.1 g of aluminum trichloride (0.34 moles, Aldrich) and place in a solid addition funnel. Fit the reaction flask with an addition funnel and a $N_2$ inlet adapter. Remove from inert atmosphere. Chill the reaction solution with an ice bath an begin the $N_2$ purge. Slowly add the $AlCl_3$ to the chilled solution. After addition is complete, allow to warm to room temperature. Stir overnight Quench the reaction by pouring into a solution of 300 mL 1N HCl and ice. Stir for 15 min. Extract twice with ether. Combine the organic layers and extract twice with 2% NaOH, then twice with deionized $H_2O$. Dry over $MgSO_4$, filter, and rotovap to dryness. Remove the anisole under high vacuum. Crystallize the product from 90% ethanol/10% ethyl acetate. Dry on a vacuum line. Wt=35.2 g. yield 41%. Mass spec (m/z=292).

Method 2

Change 230 kg of 2-chloro-5-nitrobenzoic acid (CNBA) to a clean dry reactor flushed with $N_2$. Seal the reactor and flush with $N_2$. To the reactor charge 460 kg of anisole. Start agitation and heat the mixture to 90° C., dissolving most of the CNBA. To the reactor charge 785 kg of polyphosphoric acid (PPA). PPA containers are warmed in a hot box (70° C.) prior to charging in order to lower viscosity. Two phases result. The upper phase contains the majority of the CNBA and anisole. The lower phase contains most of the PPA. The reaction conditions are maintained for 5 hr at which time sampling begins to determine residual CNBA. Analysis of samples is by gas chromatography. The reaction is quenched when 1.0% residual CNBA is achieved. The reaction is quenched into 796 kg $H_2O$. The temperature of the quenched mass is adjusted to 60° C. and maintained at this temperature until isolation. Agitation is stopped and the phases are split. The lower spent acid phase is sent to waste disposal. The upper product phase is washed with 18 kg of sodium bicarbonate in 203 kg of water, then washed with 114 kg of potable water. Agitation is stopped and the phases are split. The upper aqueous phase is sent to waste disposal. The lower product phase is cooled to about 0° C. and 312 kg of heptane is added. A mixture of ortho- and para-substituted product (total 10 kg) precipitates out of solution and is recovered by pressure filtration. To the product phase is added another 134 kg of heptane causing another 317 kg of a mixture of ortho- and para-substituted product to precipitate. The precipitate is recovered by pressure filtration. The wetcake is washed with heptane to remove residual anisole. The wetcake is dried in a rotary vacuum dryer at 60° C. Final yield of 34x is 65.1% (30.3% yield of the ortho-substituted product).

Step B. Preparation of 1-Chloro-2-(4-methoxyphenyl) methyl-4-nitrobenzene, 33x.

To a clean dry nitrogen purged 500 mL round bottom flask was charged 60.0 g (0.206 moles) of 34x. Trifluoroacetic acid (100 grams, ca 67 mL) was added to the reactor and the resulting suspension was heated to 30° C. to give a homogeneous wine colored solution. Next, 71.0 g (0.611 moles) of triethylsilane was placed in an addition funnel and 1.7 g (0.011 moles) of trifluoromethanesulfonic acid (triflic acid) was added to reactor. The color changed from burgundy to greenish brown. Triethylsilane was added dropwise to the solution at 30° C. The batch color changed to a grass green and an exothermic reaction ensued. The exotherm was allowed to raise the batch temperature to 45° C. with minimal cooling in a water bath. The reaction temperature was controlled between 45–50° C. for the duration of addition. Addition of triethylsilane was complete in 1 hour. The batch color became greenish brown at completion. The batch was stirred for three more hours at 40° C., then allowed to cool. When the batch temperature reached ca. 30° C., product started to crystallize. The batch was further cooled to 1–2° C. in a water/ice bath, and after stirring for another half hour at 1–2° C., the slurry was filtered. The crystalline solid was washed with two 60 mL portions of hexane, the first as a displacement wash and the second as a reslurry on the filter. The solids were vacuum filtered until dry on the filter under a stream of nitrogen and the solids were then transferred to a clean container. A total of 49.9 grams of material was isolated. Mp 87.5–90.5° C. and HNMR identical with known samples of 33x. GC (HP-5 25 meter colum, 1 mL $N_2$/min at 100° C., FID detection at 300° C., split 50:1) of the product showed homogeneous material. The isolated yield was 88% of 33x.

Example 1457

Preparation of 2,2-Dibutyl-1,3-propanediol, 54x

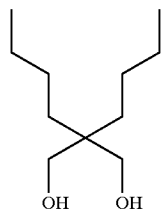

54x (This method is similar to that described in U.S. Pat. No. 5,994,391, Example Corresponding to Scheme XI, Step 1, column 264.) Lithium aluminum hydride (662 ml, 1.2 equivalents, 0.66 mol) in 662 mL of 1M THF was added dropwise to a stirred solution of dibutyl-diethylmalonate (150 g, 0.55 mol) (Aldrich) in dry THF (700 ml) while maintaining the temperature of the reaction mixture at between about −20° C. to about 0° C. using an acetone/dry ice bath. The reaction mixture was then stirred at room temperature overnight. The reaction was cooled to −20° C. and 40 ml of water, 80 ml of 10% NaOH and 80 ml of water were successively added dropwise. The resulting suspension was filtered. The filtrate was dried over sodium sulfate and concentrated under vacuum to give 98.4 g (yield 95%) of the diol as an oil. Proton NMR, carbon NMR and MS confirmed the product.

Alternate reducing agents that will be useful in this preparation of compound 54x include diisobutylaluminum hydride (DIBAL-H) or sodium bis(2-methoxyethyxy) aluminum hydride (for example, Red-Al supplied by Aldrich).

Example 1458

Preparation of 1-Bromo-2-butyl-2-(hydroxymethyl) hexane, 52x

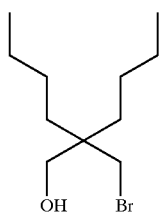

52x

A 250 mL 3-necked round-bottomed flask was fitted with a mechanical stirrer, a nitrogen inlet, an addition funnel or condenser or distilling head with receiver, a thermocouple connected to a J-Kem temperature controller and a thermocouple connected to analog data acquisition software, and a heating mantle. The flask was purged with nitrogen and charged with 20 grams of 54x. To this was added 57 grams of a 30 wt. % solution of HBr in acetic acid. The mixture was heated to 80° C. for 4 hrs. The solvents were distilled off to a pot temperature of 125° C. over 20 minutes. This removes most of the residual HBr. The mixture was cooled to 80° C. and 100 mL of Ethanol 2B (source: Aaper) was added at once. Next 1.0 mL of concentrated sulfuric acid was added. The solvent was distilled off (10 to 15 ml solvent at 79–80° C.). And the mixture was refluxed for 2 h. An additional 10 to 15 ml of solvent was distilled off and the mixture was again held at reflux temperature for 2 h. Further solvent was distilled off to a pot temperature of 125° C. and then the flask contents were cooled to 25.0° C. To the flask was added 100 mL of ethyl acetate and 100 mL of 2.5N sodium hydroxide. The mixture was agitated for 15 minutes and the aqueous layer was separated. Another 100 mL of water was added to the pot and the contents were agitated 15 minutes. The aqueous layer was separated and solvent was distilled off to a pot temperature of 125° C. During this process water is removed by azeotropic distillation with ethyl acetate. The product was concentrated under reduced pressure to afford 26.8 g of a brown oil containing the product 52x (96.81% by GC: HP1 column; initial temp. 50° C., hold for 2.5 min, Ramp 10° C./min to ending temp. 275° C., final time 15 min).

Example 1458a

Alternate Preparation of 1-Bromo-2-butyl-2-(hydroxymethyl)hexane, 52x

A 250 mL 3-necked round-bottomed flask is fitted with a mechanical stirrer, a nitrogen inlet, an addition funnel or condenser or distilling head with receiver, a thermocouple connected to a J-Kem temperature controller and a thermocouple connected to analog data acquisition software, and a heating mantle. The flask is purged with nitrogen and charged with 20 grams of 54x. To this is added 57 grams of a 30 wt. % solution of HBr in acetic acid. The mixture is heated to 80° C. for 4 hrs. The solvents are vacuum distilled off to a pot temperature of 90° C. over 20 minutes. This removes most of the residual HBr. The mixture is cooled to 80° C. and 100 mL of Ethanol 2B (source: Aaper) is added at once. Next 1.0 mL of concentrated sulfuric acid is added. The solvent is distilled off (10 to 15 ml solvent at 79–80° C. And the mixture is refluxed for 2 h. An additional 10 to 15 ml of solvent is distilled off and the mixture is again held at reflux temperature for 2 h. Further solvent is distilled off to a pot temperature of 85° C. and then the flask contents are cooled to 25.0° C. To the flask is added 100 mL of ethyl acetate and 100 mL of 2.5N sodium hydroxide. The mixture is agitated for 15 minutes and the aqueous layer is separated. Another 100 mL of water is added to the pot and the contents are agitated 15 minutes. The aqueous layer is separated and solvent is distilled off to a pot temperature of 85° C. During this process water is removed by azeotropic distillation with ethyl acetate. The material is concentrated under reduced pressure to afford the product 52x.

Example 1459

Preparation of 2-(Bromomethyl)-2-butylhexanal, 53x

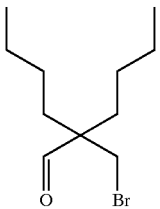

A 500 mL 3-necked round-bottom flask was fitted with a mechanical stirrer, a nitrogen inlet, an addition funnel or condenser or distilling head with receiver, a thermocouple connected to a J-Kem temperature controller and a thermocouple connected to analog data acquisition software, and a heating mantle. The flask was purged with nitrogen gas and charged with 26.0 grams of 52x and 15.6 grams of triethylamine. In a 250 ml flask was slurried 37.6 grams of sulfur trioxide-pyridine in 50 mL of DMSO. The DMSO slurry was added to the round-bottom flask by addition funnel over 15 min. The addition temperature started at 22° C. and reached a maximum of 41.0° C. (Addition of the slurry at temperatures below 18.0° C. will result in a very slow reaction, building up sulfur trioxide with will react rapidly when the temperature rises above 25° C.) The mixture was stirred for 15 minutes. To the mixture was added 100 mL of 2.5M HCl over 5 minutes. The temperature was maintained below 35° C. Next, 100 mL of ethyl acetate was added and the mixture was stirred 15 minutes. The mixture was then cooled to ambient and the aqueous layer was separated. To the pot was added 100 mL of water and the mixture was agitated for 15 minutes. The aqueous layer was separated. The solvent was distilled to a pot temperature of 115° C. and the remaining material was concentrated under reduce pressure to afford 21.8 g of a brown oil containing the product 53x (95.1% by GC: HP1 column; initial temp. 50° C., hold for 2.5 min; Ramp 10° C./min to ending temp. 275° C., final time 15 min).

Example 1459a

Alternate Preparation and Purification of 2-(Bromomethyl)-2-butylhexanal, 53x a. Preparation of Compound 52x To the reactor is charged 2,2-dibutyl-1,3-propanediol followed by 30 wt % HBr in acetic acid. The vessel is sealed and heated at an internal temperature of ca. 80° C. and held for a period of ca. 7 hours, pressure maintained below 25 psia A GC of the reaction mixture is taken to determine reaction completion (i.e., conversion of 2,2-dibutyl-1,3-propanediol into 3-acetoxy-2,2dibutyl-1-propanol). If the reaction is not complete at this point, the mixture may be heated for an additional period of time to complete the conversion. Acetic acid/HBr is then removed using house vacuum (ca. 25 mmHg) up to a maximum internal temperature of ca. 90° C. Ethanol is then added followed by sulfuric acid. A portion of the ethanol is removed (ca. one-quarter of the ethanol added) via atmospheric distillation. Ethanol is then added back (ca. the amount removed during the distillation) to the reactor containing the 3-acetoxy-2,2-dibutyl-1-propanol and the contents are heated to reflux (ca. 80° C. with a jacket temperature of 95° C.) and then held at reflux for ca. 8 hours. Ethanol is then removed via atmospheric distillation up to a maximum internal temperature of 85° C., using a jacket temperature of 95° C. A GC is taken to determine reaction completion (i.e., conversion of 3-acetoxy-2,2-dibutyl-1-propanol to compound 52x). If the reaction is not complete, ethanol is added back to the reactor and the contents are heated to reflux and then held at reflux for an additional 4 hours (ca. 80° C., with a jacket of 95° C.). Ethanol is then removed via atmospheric distillation up to a maximum internal temperature of 85° C., using a jacket temperature of 95° C. A GC is taken to determine reaction completion (i.e., conversion of 3-acetoxy-2,2-dibutyl-1-propanol to compound 52x). Once the reaction is deemed to be complete, the remaining ethanol is removed via atmospheric distillation up to a maximum internal temperature of 125° C. Methyl t-butyl ether is then added followed by a 5% sodium bicarbonate solution. The layers are separated, the aqueous layer is extracted once with MTBE, the organic extracts are combined, washed once with water, dried over MgSO$_4$, and concentrated under house vacuum (ca. 25 mmHg) to a maximum internal temperature of 60° C. The resultant oil is stored in the cooler until it is needed for further processing.

b. Preparation of Compound 53x.

Methyl sulfoxide is charged to the reactor followed by compound 52x and triethylamine. Pyridine-sulfur trioxide complex is then added portion-wise to the reactor while maintaining an internal temperature of <35° C. Once the pyridine-sulfur trioxide complex addition is complete, a GC of the reaction mixture is taken to determine reaction completion (i.e., conversion of 52x into 53x). If the reaction is not complete at this point, the mixture may be stirred for an additional period of time to complete the conversion. The reaction is quenched with an 11 wt % aqueous HCl solution. Ethyl acetate is added and the layers are separated, the aqueous layer is extracted once with ethyl acetate, the organic extracts are combined, washed once with water, dried over MgSO$_4$, and concentrated under house vacuum (ca. 25 mm/Hg) to a maximum internal temperature of 30° C. The resultant oil is stored in the cooler until it is needed for further processing.

c. Alternate Preparation of Compound 53x.

Compound 52x and methylene chloride are charged to the reactor followed by TEMPO. The solution is cooled to ca. 0–5° C. Potassium bromide and sodium bicarbonate are dissolved in a separate reactor and added to the solution of 52x and TEMPO at 0–5° C. The biphasic mixture is cooled to 0–5° C. and sodium hypochlorite is added at such a rate to maintain an internal temperature of 0–5° C. When the add is complete a GC of the reaction mixture is performed to determine reaction completion. If the reaction is not complete (>1% 52x remaining), additional sodium hypochlorite may be added to drive the reaction to completion. Immediately after the reaction is determined to be complete, an aqueous solution of sodium sulfite is added to quench the remaining sodium hypochlorite. The layers are separated, the aqueous layer is back-extracted with methylene chloride, the combined organic fractions are washed and dried over sodium sulfate. Compound 53x is then concentrated via a vacuum distillation, up to a maximum internal temperature of ca. 30° C. The crude aldehyde is stored in the cooler until it is required for further processing d. Purification of Compound 53x.

A Wiped Film Evaporated (WFE) apparatus is set up with the following conditions: evaporator temperature of 90° C., vacuum of ca. 0.2 mmHg and a wiper speed of 800 rpm's. The crude compound 53x is fed at a rate of 1.0–1.5 kilograms of crude per hour. The approximate ratio of product to residue during distillation is 90:10.

Example 1460

Preparation of 1-(2,2-Dibutyl-S,S-dioxido-3-oxopropylthio)-2-(( 4-methoxyphenyl)methyl)-4-nitrobenzene, 30x

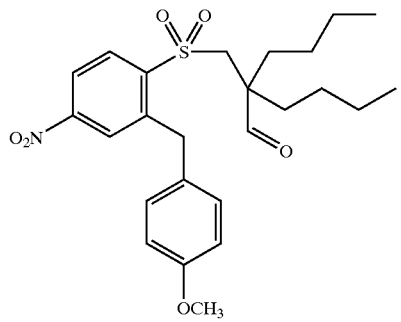

30x

A 1000 mL 4 neck jacketed Ace flask was fitted with a mechanical stirrer, a nitrogen inlet, an addition funnel or condenser or distilling head with receiver, a thermocouple, four internal baffles and a 28 mm Teflon turbine agitator. The flask was purged with nitrogen and charged with 75.0 grams of 33x. Next, the flask was charged with 315.0 grams of dimethylacetamide (DMAC), agitation was started and the mixture was heated to 30° C. Sodium sulfide (39.2 grams) was dissolved in 90 ml water in a separate flask. The aqueous sodium sulfide solution was charged into the flask over a 25 minute period. Temperature reached 37° C. at completion of addition. The solution turned dark red immediately and appeared to form a small amount of foam-like globules that adhered to the wall of the reactor. The temperature was held for two hrs at 40° C. To the flask was charged 77.9 grams of 53x all at once. The reaction mixture was heated to 65° C. and held for 2 hrs. Next 270 ml water was added at 65° C. The mixture was agitated 15 minutes. To the flask was then charge 315 ml of benzotrifluoride and the mixture was agitated 15 minutes. The aqueous layer was separated at 50° C. The organic layer was washed with 315 ml of 3% sodium chloride solution. The aqueous layer was separated at 50° C. The solvent was distilled to a pot temperature of 63° C. at 195 to 200 mmHg. The flask contents were cooled to 60° C. and to it was charged 87.7 grams of trimethyl orthoformate, and 5.2 grams of p-toluenesulfonic acid dissolved in 164.1 mL of methanol. The mixture was heated to reflux, 60 to 65° C. for 2 hours. The solvent was distilled to a pot temperature of 63° C. at 195 to 200 mmHg to remove methanol and methylformate. The flask was then charged with 252 ml benzotrifluoride and then cooled to 15° C. Next 22.2 grams sodium acetate as a slurry in 30 ml water was added to the flask. The flask was then charged with 256.7 grams of commercial peracetic acid (nominally 30–35% assay) over 20 minutes, starting at 15° C. and allowing the exotherm to reach 30 to 35° C. The addition was slow at first to control initial exotherm. After the first equivalent was charged the exotherm subsided. The mixture was heated to 30° C. and held for 3 hours. The aqueous layer was separated at 30° C. The organic layer was washed with 315 ml 6% sodium sulfite. The aqueous layer was separated. The flask was then charged with 40% by wt. sulfuric acid and heated to 75° C. for 2 hrs. The aqueous layer was separated from the bottom at 40 to 50° C. To the flask was added 315 ml saturated sodium bicarbonate and the contents were stirred for 15 minutes. The aqueous layer was separated. The solvent was distilled to a reactor temperature of 63° C. at 195 to 200 mmHg. Next, 600 ml isopropyl alcohol was charged over 10 minutes and the temperature was maintained at 50° C. The reactor was cooled to 38° C. and held for 1 hour. (The product may oil slightly at first then crystallize during the hold period. If product oils out at 38° C. or does not crystallize it should be seeded to promote crystallization before cooling.) The reactor was cooled to 15° C. over 30 minutes then held for 60 minutes. The solids were filtered and dried to yield 102.1 grams of a crystalline yellow solid. Wash with 150 ml 10° C. IPA. Analysis by HPLC (Zorbax RX-C8 colum, 0.1% aq. TFA/acetonitrile gradient mobile phase, UV detection at 225 nm) showed 97.7% by weight of 30x 79.4% isolated molar corrected yield.

Example 1460a

Alternate Preparation of 1-(2,2-Dibutyl-S,S-dioxido-3-oxopropylthio)-2-((4-methoxyphenyl)methyl)-4-nitrobenzene, 30x Step 1. Preparation of Sulfide Aldehyde Compound 69x.

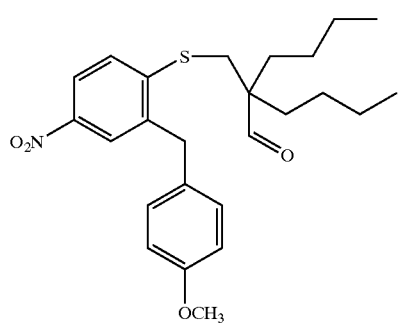

69x

A 1000 mL 4 neck jacketed Ace reator is fitted with a mechanical stirrer, nitrogen inlet, additional funnel, a thermocouple, four internal baffles, and a 28 mm Teflon turbine agitator. The flask is purged with nitrogen gas and charged with 145 g of compound 331 and 609 mL of N,N-dimethylacetamide (DMAC). Agitation is started and the mixture is heated to 30° C. In a separate flask 72.3 g of Na₂S (Spectrum) is dissolved in 166.3 mL of water. The aqueous Na₂S is charged to the flask over a period of about 90 minutes. Addition rate should be adjusted to maintain the reaction temperature below 35° C. The mixture is stirred at 35° C. for 2 hours and then 150.7 g of compound 53x is added all at once. The mixture is heated to 70° C. and held for 2 hours. To the mixture is adjusted to 50° C., to it is added 442.7 mL water and the mixture is agitated for 15 minutes. To the reactor is then charged 609 mL of benzotrifluoride followed by 15 minutes of agitation. The aqueous layer is separated at 50° C. The organic layer is washed with 3% aq. NaCl. The aqueous layer is separated at 50° C. The organic layer contains compound 69x. The organic layer is stable and can be held indefinitely.

Step 2. Preparation of Compound 70x.

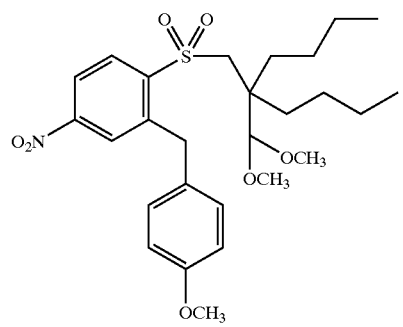

The solvent is distilled at about 63° C. to 66° C. and 195 to 200 mmHg from the organic layer resulting from Step 1 until a third to a half of the benzotrifluoride volume is distilled. The mixture is cooled to about 60° C. and charged with 169.6 g of trimethylorthoformate and about 10 g of p-toluenesulfonic acid dissolved in 317.2 mL of methanol. (Note: alternate orthoformates, for example triethylorthoformate, can be used in place of trimethylorthoformate to obtain other acetals.) The reactor is fitted with a condenser and a distillation head. The mixture is heated to boiling and from it is distilled 5 mL of methanol to remove residual water from the condenser and the mixture is held at reflux at 60° C. to 65° C. for about 2 hours. Solvent is then distilled to a pot temperature of 60° C. to 66° C. at 195 to 200 mm Hg to remove methanol and methylformate. To the mixture is added 355.4 mL benzotrifluoride and the mixture is cooled to 15° C. To the reactor is charged 32.1 g sodium acetate slurried in 77.2 mL water. The reaction is held for 72 hours. To the reactor is then charged 340.4 g of peracetic acid over a 2 hour period starting at 15° C. Addition was adjusted to keep the temperature at or below 20° C. The mixture was then heated to 25° C. for 4 hours. The aqueous (top) layer was separated at 25° C. and the organic layer was washed with 190 mL of 10% sodium sulfite. The organic layer contains compound 70x and can be stored indefinitely.

Step 3. Preparation of Compound 30x.

To the organic layer of Step 2 is added 383.8 g of concentrated sulfuric acid. The mixture is heated at 75° C. for 2 hours and the aqueous (bottom) layer is separated at 40 to 50° C. To the reactor is charged 609 mL of 10% sodium bicarbonate and the mixture is stirred for 15 minutes. The aqueous (top) layer is separated. Solvent is distilled from the organic layer at 63 to 66° C. at 195 to 200 mm Hg. To the reactor is charged 1160 mL of isopropyl alcohol over 10 minutes at 50° C. The reactor is cooled to 38° C. and held for 1 hour. Some crystallization occurs. The reactor is cooled to 15° C. over 30 minutes and held for 120 minutes, causing further crystallization of 30x. The crystals are filtered and dried to yield 200.0 g of a crystalline yellow solid. The crystals of 30x are washed with 290 mL of 10° C. isopropyl alcohol.

Example 1461

Preparation of 1-(2,2-Dibutyl-S,S-dioxido-3-oxopropylthio)-2-((4-methoxyphenyl)methyl)-4-dimethylaminobenzene, 29x

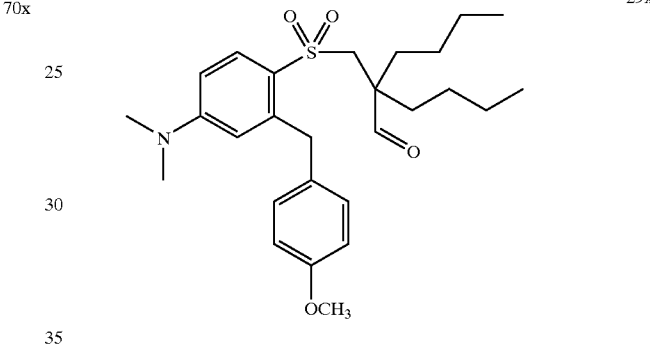

A 300 ml autoclave was fitted with a Stirmix hollow shaft gas mixing agitator, an automatic cooling and heating temperature control, and an in-reactor sampling line with sintered metal filter. At 20° C. the autoclave was charged with 15.0 grams of 30x. 2.5 grams of Pd/C catalyst, 60 grams of ethanol, 10.0 grams of formaldehyde (36% aqueous solution), and 0.55 grams of concentrated sulfuric acid. The reactor was closed and pressurized the reactor to 60 psig (515 kPa) with nitrogen to check for leakage. The pressure was then reduced to 1–2 psig (108–115 kPa). The purge was repeated three times. The autoclave was then pressurized with H₂ to 60 psig (515 kPa) while the reactor temperature was held at 22° C. The agitator was started and set to 800–1000 rpm and the reactor temperature control is set at 30–40° C. When the cooling capacity was not enough to control the temperature, the agitator rpm or the reactor pressure was reduced to maintain the set temperature. After about 45 minutes when the heat release was slowing down (about 70% of hydrogen usage was reacted), the temperature was raised to 60° C. Hydrogen was then released and the autoclave was purged with nitrogen three times. The content of the reactor was pressure filtered through a sintered metal filter at 60° C. The filtrate was stirred to cool to the room temperature over 1–2 hours and 50 grams of water was added over 1 hour. The mixture was stirred slowly at 4° C. overnight and filtered through a Buche type filter. The cake was air dried to give 13.0 grams of 29x with 99+% assay. The isolated yield was 89%.

Example 1462

Preparation of syn-3,3-Dibutyl-7-dimethylamino)-1,1-dioxido-4-hydroxy-5-(4-methoxyphenyl)-2,3,4,5-tetrahydrobenzothiepine, syn-24x

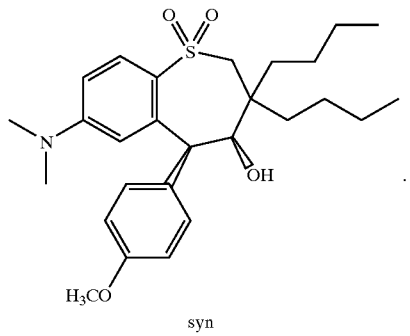

syn

A 250 ml round bottom glass reactor fitted with mechanical agitator and a heating/cooling bath was purged with nitrogen. Forty-five grams of potassium t-butoxide/THF solution were charged to the reactor and agitation was started. In a separate container 18 grams of 29x was dissolved in 25 grams of THF. The 29x/THF solution was charged into the reactor through a addition funnel over about 2.0 hours. The reactor temperature was controlled between about 16–20° C. Salt precipitated after about half of 29x was added. The slurry was stirred at 16–20° C. for an hour. The reaction was quenched with 54 grams of 7.4% ammonium chloride aqueous solution over a period of about 30 minutes while keeping the reactor temperature at 16–24° C. The mixture was gently stirred until all salt is dissolved (about 10 minutes). Agitation was stopped and the phases were allowed to separate. The aqueous layer was drained. The organic layer was charged with 50 ml water and 25 grams of isopropyl alcohol. The agitator was started and crystallization was allowed to take place. The THF was distilled under the ambient pressure, with b.p. from 60 to 65° C. and pot temperature from 70 to 77° C. The crystals dissolved as the pot gets heated and reappeared when the THF started to distill. After distillation was complete, the slurry was slowly cooled to 49° C. over 2–3 hours and stirred slowly for several hours. The slurry was filtered with a 150 ml Buche filter and the cake was washed with 10 grams of cold 2:1 water/isopropyl alcohol solution. Filtration was complete in about 5 minutes. The cake was air dried to give 16.7 grams of syn-24x with 99+% assay and a 50/50 mixture of R,R and S,S isomers.

Example 1463a

Conditions for Optical Resolution of Compound (4R,5R)-24x

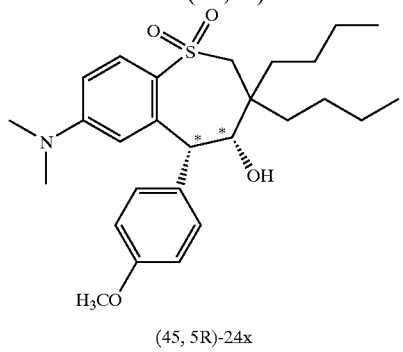

(4S, 5R)-24x

The following simulated moving bed chromatography (SMB) conditions are used to separate the (4R,5R) and (4S,5S) enantiomers of compound syn-24x.

| | |
|---|---|
| Column (CSP): | Daicel Chiralpak AS |
| Mobile Phase: | acetonitrile (100%) |
| Column Length: | 11 cm (9 cm for column 6) |
| Column I.D.: | 20.2 cm |
| Number of Columns: | 6 columns |
| Feed Concentration: | 39 grams/liter |
| Eluent Flowrate: | 182 L/hour |
| Feed Flowrate: | 55 L/hour |
| Extract Flowrate: | 129.4 L/hour |
| Raffinate Flowrate: | 107.8 L/hour |
| Recycling Flowrate: | 480.3 L/hour |
| Period: | 0.6 minute |
| Temperature: | Ambient |

SMB performance:

Less retained enantiomer purity (%): 92.8%

Less retained enantiomer concentration: 10 g/L

More retained enantiomer recovery yield (%): 99.3%

More retained enantiomer concentration: 7 g/L

Example 1463b

Alternate Conditions for Optical Resolution of Compound (4R,5R)-24x

The following simulated moving bed chromatography (SMB) conditions are used to separate the (4R,5R) and (4S,5S) enantiomers of compound syn-24x.

| | |
|---|---|
| Column (CSP): | di-methyl phenyl derivative of tartaric acid (Kromasil DMB) |
| Mobile Phase: | toluene/methyl tert-butyl ether (70/30) |
| Column Length: | 6.5 cm |
| Column I.D.: | 2.12 cm |
| Number of Columns: | 8 columns |
| Zones: | 2-3-2-1 |
| Feed Concentration: | 6.4 weight percent |
| Eluent Flowrate: | 20.3 g/minute |
| Feed Flowrate: | 0.7 g/minute |
| Extract Flowrate: | 5.0 g/minute |
| Raffinate Flowrate: | 16.0 g/minute |
| Period: | 8 minute |
| Temperature: | Ambient |

SMB performance:

Less retained enantiomer purity (%): >98%

Less retained enantiomer recovery yield (%): >95%

Example 1463c

Alternate Conditions for Optical Resolution of Compound (4R,5R)-24x

The following simulated moving bed chromatography (SMB) conditions are used to separate the (4R,5R) and (4S,5S) enantiomers of compound syn-24x.

| | |
|---|---|
| Column (CSP): | di-methyl phenyl derivative of tartaric acid (Kromasil DMB) |
| Mobile Phase: | toluene (100%) |
| Column Length: | 6.5 cm |

537

-continued

| Column I.D.: | 2.12 cm |
| --- | --- |
| Number of Columns: | 8 Columns |
| Zones: | 2-3-2-1 |
| Feed Concentration: | 64 weight percent |
| Eluent Flowrate: | 20.3 g/minute |
| Feed Flowrate: | 0.5 g/minute |
| Extract Flowrate: | 4.9 g/minute |
| Raffinate Flowrate: | 15.9 g/minute |
| Period: | 8 minute |
| Temperature: | Ambient |

SMB performance:

Less retained enantiomer purity (%): >98%

Less retained enantiomer recovery yield (%): >95%

Example 1463d

Racemization of Compound (4S,5S)-24x

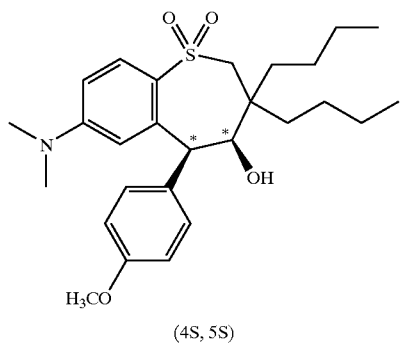

(4S, 5S)

A 250 mL round bottom glass reactor with mechanical agitator and a heating/cooling bath is purged with nitrogen gas. In a flask, 18 g of (4S,5S)-24x (obtained as the more retained enantiomer in Examples 8a–8c) is dissolved in 50 g of dry THF. This solution is charged into the reactor and brought to about 23–25° C. with agitation. To the reactor is charged 45 g of potassium t-butoxide/THF solution. (1 M, Aldrich) through an addition funnel over about 0.5 hour. A slurry forms. Stir the slurry at about 24–26° C. for about 1–1.5 hours. The reaction is quenched with 54 g of 7.5% aqueous ammonium chloride while keeping the reactor temperature at about 23–26° C. The first ca. 20% of the ammonium chloride solution is charged slowly until the slurry turns thin and the rest of the ammonium chloride solution is charged over about 0.5 hour. The mixture is stirred gently until all the salt is dissolved. The agitation is stopped and the phases are allowed to separate. The aqueous layer is removed. To the organic layer is charged 50 mL of water and 25 g of isopropyl alcohol. The agitator is started and crystallization is allowed to take place. THF is removed by distillation at ambient pressure. The crystals dissolve as the pot warms and then reappear when the THF starts to distill. The resulting slurry is cooled slowly to 4° C. within 2–3 hours and slowly stirred for 1–2 hours. The slurry is filtered with a 150 mL Buche filter and washed with 20 g of 04° C. isopropyl alcohol. The cake is air dried at about 50–60° C. under vacuum to give 16.7 g of racemic 24x.

538

Example 1464

Preparation of (4R,5R)-3,3-Dibutyl-7-(dimethylamino)-1,1-dioxido-4-hydroxy-5-(4-hydroxyphenyl)-2,3,4,5-tetrahydrobenzothiepine, (4R,5R)-28x

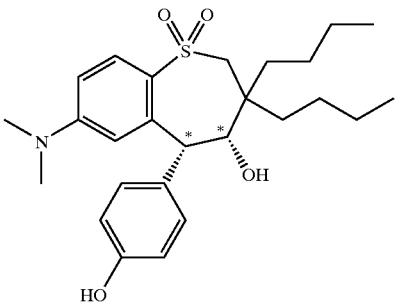

(4R, 5R)

A 1000 mL 4 neck Reliance jacketed reactor flask was fitted with a mechanical stirrer, a nitrogen inlet, an addition funnel, condenser or distillation head with receiver, a thermocouple, and a Teflon paddle agitator. The flask was purged with nitrogen gas and was charged with 41.3 grams of (4R,5R)-24x and 18.7 grams of methionine followed by 240 grams of methanesulfonic acid. The mixture was heated to 75° C. and stirred for 8 hrs. The mixture was then cooled to 25° C. and charged with 480 mL of 3-pentanone. The solution was homogeneous. Next, the flask was charged with 320 mL of dilution water and was stirred for 15 minutes. The aqueous layer was separated and to the organic layer was added 250 mL of saturated sodium bicarbonate. The mixture was stirred for 15 minutes and the aqueous layer was separated. Solvent was distilled to approximately one-half volume under vacuum at 50° C. The flask was charged with 480 mL of toluene, forming a clear solution. Approximately half the volume of solvent was removed at 100 mmHg. The mixture was cooled to 10° C. and stirred overnight. Crystals were filtered and washed with 150 mL cold toluene and allowed to dry under vacuum. Yielded 29.9 g with a 96.4 wt % assay. The filtrate was concentrated and toluene was added to give a second crop of 2.5 grams of crystals. A total of 32.1 g of dry off white crystalline (4R,5R)-28x was obtained.

Example 1464a

Alternate Preparation of (4R,5R)-3,3-Dibutyl-7-dimethylamino)-1,1-dioxido-4-hydroxy-5-(4-hydroxyphenyl)-2,3,4,5-tetrahydrobenzothiepine, (4R,5R)-28x A 1000 mL 4 neck Ace jacketed reactor flask is fitted with a mechanical stirrer, a nitrogen inlet, an addition funnel, condenser or distillation head with receiver, a thermocouple, and a Teflon paddle agitator. The flask is purged with nitrogen gas and is charged with 40.0 grams of (4R,5R)-24x and 17.8 grams of methionine followed by 178.6 grams of methanesulfonic acid. The mixture is heated to 80° C. and stirred for 12 hrs. The mixture is then cooled to 15° C. and charged with 241.1 mL of water over 30 minutes. The reactor is then charged with 361.7 mL of 3-pentanone. Next, the flask is stirred for 15 minutes. The aqueous layer is separated and to the organic layer is added 361.7 mL of saturated sodium bicarbonate. The mixture is stirred for 15 minutes and the aqueous layer was separated. Solvent is distilled to approximately one-half volume under vacuum at 50° C. Crystals start to form at this time. The flask is charged with 361.7 mL of toluene and the mixture is cooled to 0° C. Crystals are allowed to form. Crystals are filtered and washed with 150 mL cold toluene and allowed to dry under vacuum at 50° C. Yield 34.1 g of off-white crystalline (4R,5R)-28x.

Example 1464b

Alternate preparation of (4R,5R)-3,3-Dibutyl-7-(dimethylamino)-1,1-dioxido-4-hydroxy-5-(4-hydroxyphenyl)-2,3,4,5-tetrahydrobenzothiepine, (4R,5R)-28x A first 45 L reactor is purged with nitrogen gas. To it is charged 2.5 kg of (4R,5R)-24x followed by 1.1 kg of methionine and 11.1 kg of methanesulfonic acid. The reaction mixture is heated to 85° C. with agitation for 7 hours. The reaction mixture is then cooled to 5° C. and 17.5 L of water is slowly charged to the first reactor. The reaction temperature will reach about 57° C. Next, 17.5 L of methyl isobutyl ketone (MIBK) are charged to the first reactor and the reaction mixture is stirred for 30 minutes. The mixture is allowed to stand for 30 minutes and the layers are separated. The aqueous phase is transferred to a second 45 L reactor and 10 L of MIBK is charged to the second reactor. The second reactor and its contents are stirred for 30 minutes and then allowed to stand for 30 minutes while the layers separate. The organic phase is separated from the second reactor and the two organic phases are combined in the first reactor. To the first reactor is carefully charged 1.4 kg of aqueous sodium bicarbonate. The mixture is stirred for 30 minutes and then allowed to stand for 30 minutes. The phases are separated. If the pH of the aqueous phase is less than 6 then a second bicarbonate wash is performed. After the bicarbonate wash, 15 L of water is charged to the first reactor and the mixture is heated to 40° C. The mixture is stirred for 30 minutes and then allowed to stand for 30 minutes. The phases are separated. The organic phase is concentrated by vacuum distillation so that approximately 5 L of MIBK remain in the concentrate. The distillation starts when the batch temperature is at 35° C. at 1 psia The distillation is complete when the batch temperature reaches about 47.8° C. The batch temperature is then adjusted to 45° C. and 20 L of heptane is charged to the product mixture over 20 minutes. The resulting slurry is cooled to 20° C. The product slurry is filtered (10 micron cloth filter) and washed with 8 L of 20% MIBK/heptane solution. The product is dried on the filter at 80° C. for 21 hours under vacuum. A total of 2.16 kg of white crystalline (4R,5R)-28x is isolated.

Example 1464c

Batch Isolation of Compound (4R,5R)-28x (or Compound (4S,5S)-28x) From Acetonitrile Solution A 1 L reactor is equipped with baffles and a 4-blade radial flow turbine. The reactor is purged with 1 L of nigrogen gas and charged with 300 mL of water. The water is stirred at a minimum rate of 300 rpm at 5° C. The reactor is charged with 125–185 mL of (4R,5R)-28x in acetonitrile solution (20% w/w) at a rate of 1.4 mL/min. Upon addition, crystals start to form. After addition of the acetonitrile solution, crystals are filtered through a Buchner funnel. The cake is washed with 3 volumes of water and/or followed by 1–2 volumes of ice cold isopropyl alcohol before drying. Alternatively, this procedure can be used on an acetonitrile solution of (4S,5S)-28x to isolate (4S,5S)-28x.

Example 1464d

Continuous Isolation of Compound (4R,5R)-28x (or Compound (4S,5S)-28x) From Acetonitrile Solution A 1 L reactor is equipped with baffles and a 4-blade radial flow turbine. The reactor is purged with 1 L of nigrogen gas and charged with 60 grams of water and 30 grams of acetonitrile. The mixture is stirred at 300 rpm and 5° C. Into the reactor are fed 300 mL of water and 125 mL of 20% (w/w) (4R,5R)-28x in acetonitrile solution at rates of 1.7 mL/min and 1 mL/min, respectively. When the contents of the reactor reach 70–80% of the volume of the reactor, the slurry can be drained to a filter down to aminimum stirring level in the reactor and followed by more feeding. Alternatively, the reactor can be drained continuously as the feeds continue. The water/acetonitrile ratio can be in the range of about 2:1 to about 3:1. Filtered cake can be handled as described in Example 9c. Alternatively, this procedure can be used on an acetonitrile solution of (4S,5S)-28x to isolate (4S,5S)-28x.

Example 1465

Preparation of 1-(Chloromethyl)-4-(hydroxymethyl) benzene, 55x

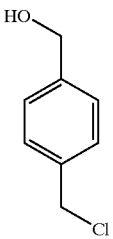

55x

A reaction flask fitted with a nitrogen inlet and outlet, a reflux condenser, and a magnetic stirrer was purged with nitrogen. The flask was charged with 25 g of 4-(chloromethyl)-benzoic acid. The flask was charged with 75 mL of THF at ambient temperature. Stirring caused a suspension to form. An endothermic reaction ensued in which the temperature of the reaction mixture dropped 22° C. to 14° C. To the reaction mixture 175mL of borane-THF adduct was added via a dropping funnel over about 30 minutes. During this exothermic addition, an ice-bath was used for external cooling to keep the temperature below 30° C. The reaction mixture was stirred at 20° C. for 1 h and it was then cooled to 0° C. The reaction mixture was quenched by slow addition of 1M sulfuric acid. The resulting reaction mixture was diluted with 150 mL of t-butyl methyl ether (TBME) and stirred for at least 20 min to destroy boric acid esters. The layers were separated and the aqueous layer was washed with another portion of 50 mL of TBME. The combined organic layers were washed twice with 100 mL of saturated sodium bicarbonate solution. The organic layer was dried over 11 g of anhydrous sodium sulfate and filtered. The solvents were evaporated on a rotary evaporator at 45° C. (bath temperature) and <350 mbar yielding a colorless oil. The oil was seeded with crystals and the resulting solid 55x was dried under vacuum. Yield: 19.7 g (86%). Assay by GC (HP-5 25 meter colum, 1 mL N$_2$/min at 100° C., FID detection at 300° C., split 50:1).

Example 1466

Preparation of (4R,5R)-1-((4-(4-(3,3-Dibutyl-7-(dimethylamino)-2,3,4,5-tetrahydro-4-hydroxy-1,1-dioxido-1-benzithiepin-5-yl)phenoxy)methyl)phenyl)methyl-4-aza-1-azoniabicyclo[2.2.2]octane Chloride, 41x

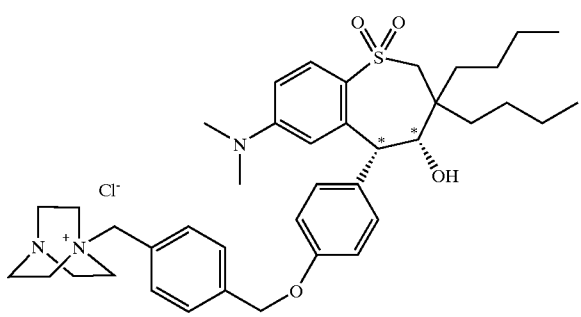

Step 1. Preparation of (4R,5R)-26x.

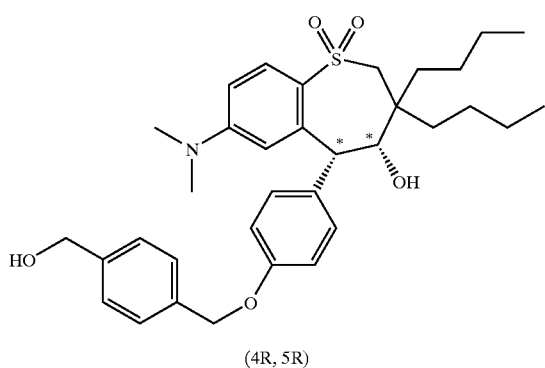

A 1000 mL 4 neck jacketed Ace reactor flask was fitted with a mechanical stirrer, a nitrogen inlet, an addition funnel or condenser or distilling head with receiver, a thermocouple, four internal baffles and a 28 mm Teflon turbine agitator. The flask was purged with nitrogen gas and charged with 25.0 grams of (4R,5R)-28x and 125 mL of N,N-dimethylacetamide (DMAC). To this was added 4.2 grams of 50% sodium hydroxide. The mixture was heated to 50° C. and stirred for 15 minutes. To the flask was added 8.3 grams of 55x dissolved in 10 mL of DMAC, all at once. The temperature was held at 50° C. for 24 hrs. To the flask was added 250 mL of toluene followed by 125 mL of dilution water. The mixture was stirred for 15 minutes and the layers were then allowed to separate at 50° C. The flask was then charged with 125 mL of saturated sodium chloride solution and stirred 15 minutes. Layers separated cleanly in 30 seconds at 50° C. Approximately half of the solvent was distilled off under vacuum at 50° C. The residual reaction mixture contained (4R,5R)-26x.

Step 2. Preparation of (4R,5R)-27x.

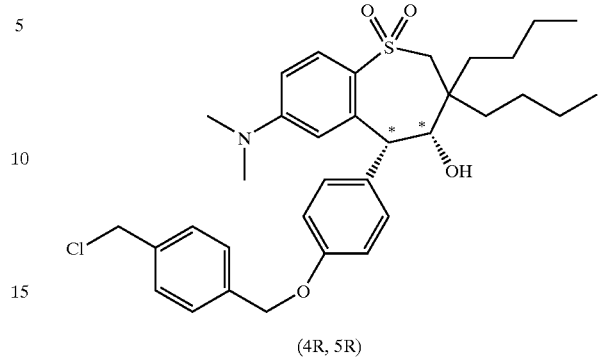

Toluene was charged back to the reaction mixture of Step 1 and the mixture was cooled to 35° C. To the mixture was then added 7.0 grams of thionyl chloride over 5 minutes. The reaction was exothermic and reached 39° C. The reaction turned cloudy on first addition of thionyl chloride, partially cleared then finally remained cloudy. The mixture was stirred for 0.5 hr and was then washed with 0.25N NaOH. The mixture appeared to form a small amount of solids that diminished on stirring, and the layers cleanly separated. The solvent was distilled to a minimum stir volume under vacuum at 50° C. The residual reaction mixture contained (4R,5R)-27x.

Step 3. Preparation of 41x

To the reaction mixture of Step 2 was charged with 350 mL of methyl ethyl ketone (MEK) followed by 10.5 mL water and 6.4 grams of diazabicyclo[2.2.2]octane (DABCO) dissolved in 10 mL of MEK. The mixture was heated to reflux, and HPLC showed <0.5% of (4R,5R)-27x. The reaction remained homogenous initially then crystallized at the completion of the reaction. An additional 5.3 mL of water was charged to the flask to redissolve product. Approximately 160 mL of solvent was then distilled off at atmospheric pressure. The mixture started to form crystals after 70 mL of solvent was distilled. Water separated out of distillate indicating a ternary azeotrope between toluene, water and methyl ethyl ketone (MEK). The mixture was then cooled to 25° C. The solids were filtered and washed with 150 mL MEK, and let dry under vacuum at 60° C. Isolated 29.8.0 g of off-white crystalline 41x.

Example 1466a

Alternate Preparation of (4R,5R)-1-((4-(4-(3,3-Dibutyl-7-(dimethylamino-2,3,4,5-tetrahydro-4-hydroxy-1,1-dioxido-1-benzithiepin-5-yl)phenoxy)methyl)phenyl)methyl-4-aza-1-azoniabicyclo[2.2.2]octane Chloride, Form II of 41x A 1000 mL 4 neck jacketed Ace reactor flask is fitted with a mechanical stirrer, a nitrogen inlet, an addition funnel or condenser or distilling head with receiver, a thermocouple, four internal baffles and a 28 mm Teflon turbine agitator. The flask is purged with nitrogen gas and charged with 25.0 grams of (4R,5R)-28x and 100 mL of N,N-dimethylacetamide (DMAC). The mixture is heated to 50° C. and to it is added 4.02 grams of 50% sodium hydroxide. The mixture is stirred for 30 minutes. To the flask is added 8.7 grams of 55x dissolved in 12.5 mL of DMAC, all at once. The charge vessel is washed with 12.5 mL DMAC and the wash is added to the reactor. The reactor is stirred for 3 hours. To the reactor is added 0.19 mL of 49.4% aq. NaOH and the mixture is stirred for 2 hours. To the mixture is added 0.9 g DABCO dissolved in 12.5 mL DMAC. The mixture is stirred 30 to 60 minutes at 50° C. To the flask is added 225 mL of toluene followed by 125 mL of dilution water. The mixture is stirred for 15 minutes and the layers are then allowed to separate at 50° C. The bottom aqueous layer is removed but any rag layer is retained. The flask is then charged with 175 mL of 5% hydrochloric acid solution and stirred 15 minutes. Layers are separated at 50° C. to remove the bottom aqueous layer, discarding any rag layer with the aqueous layer. Approximately half of the solvent is distilled off under vacuum at a maximum pot temperature of 80° C. The residual reaction mixture contains (4R,5R)-26x.
Step 2. Preparation of (4R,5R)-27x.

Toluene (225 mL) is charged back to the reaction mixture of Step 1 and the mixture is cooled to 30° C. To the mixture is then added 6.7 grams of thionyl chloride over 30 to 45 minutes. The temperature is maintained below 35° C. The reaction turns cloudy on first addition of thionyl chloride, then at about 30 minutes the layers go back together and form a clear mixture. The mixture is stirred for 0.5 hr and is then charged with 156.6 mL of 4% NaOH wash over a 30 minute period. The addition of the wash is stopped when the pH of the mixture reaches 8.0 to 10.0. The bottom aqueous layer is removed at 30° C. and any rag layer is retained with the organic layer. To the mixture is charged 175 mL of saturated NaCl wash with agitation. The layers are separated at 30° C. and the bottom aqueous layer is removed, discarding any rag layer with the aqueous layer. The solvent is distilled to a minimum stir volume under vacuum at 80° C. The residual reaction mixture contains (4R,5R)-27x.
Step 3. Preparation of 41x To the reaction mixture of Step 2 is charged 325 mL of methyl ethyl ketone (MEK) and 13 mL water. Next, the reactor is charged 6.2 grams of diazabicyclo[2.2.2]octane (DABCO) dissolved in 25 mL of MEK, The mixture is heated to reflux and held for 30 minutes. Approximately 10% of solvent volume is then distilled off. The mixture starts to form crystals during distillation. The mixture is then cooled to 20° C. for 1 hour. The off-white crystalline 41x (Form II) is filtered and washed with 50 mL MEK, and let dry under vacuum at 100° C.

Example 1466b

Alternate Preparation of (4R,5R)-1-((4-(4-(3,3-Dibutyl-7-(dimethylamino)-2,3,4,5-tetrahydro-4-hydroxy-1,1-dioxido-1-benzithiepin-5-yl)phenoxy)methyl)phenyl)methyl-4-aza-1-azoniabicyclo[2.2.2]octane Chloride, Form II of 41x A 1000 mL 4 neck jacketed Ace reactor flask is fitted with a mechanical stirrer, a nitrogen inlet, an addition funnel or condenser or distilling head with receiver, a thermocouple, four internal baffles and a Teflon turbine agitator. The flask is purged with nitrogen gas and charged with 25.0 grams of (4R,5R)-28x and 125 mL of N,N-dimethylacetamide (DMAC). The mixture is heated to 50° C. and to it is added 7.11 grams of 30% sodium hydroxide over a period of 15 to 30 minutes with agitation. The mixture is stirred for 30 minutes. To the flask is added 9.5 grams of solid 55x. The reactor is stirred for 3 hours. To the mixture is added 1.2 g of solid DABCO. The mixture is stirred 30 to 60 minutes at 50° C. To the flask is added 225 mL of toluene followed by 125 mL of water. The mixture is stirred for 15 minutes and the layers are then allowed to separate at 50° C. The bottom aqueous layer is removed but any rag layer is retained with the organic layer. The flask is then charged with 175 mL of 5% hydrochloric acid solution and stirred 15 minutes. Layers are separated at 50° C. to remove the bottom aqueous layer, discarding any rag layer with the aqueous layer. The flask is then charged with 225 mL of water and stirred 15 minutes. The layers are allowed to separate at 50° C. The bottom aqueous layer is removed, discarding any rag layer with the aqueous layer. Approximately half of the solvent is distilled off under vacuum at a maximum pot temperature of 80° C. The residual reaction mixture contains (4R,5R)-26x.
Step 2. Preparation of (4R,5R)-27x.

Toluene (112.5 mL) is charged back to the reaction mixture of Step 1 and the mixture is cooled to 25° C. To the mixture is then added 7.3 grams of thionyl chloride over 15 to 45 minutes. The temperature of the mixture is maintained above 20° C. and below 40° C. The reaction turns cloudy on first addition of thionyl chloride, then at about 30 minutes the layers go back together and form a clear mixture. The mixture is then charged with 179.5 mL of 4% NaOH wash over a 30 minute period. The mixture is maintained above 20° C. and below 40° C. during this time. The addition of the wash is stopped when the pH of the mixture reaches 8.0 to 10.0. The mixture is then allowed to separate at 40° C. for at least one hour. The bottom aqueous layer is removed and any rag layer is retained with the organic layer. To the mixture is charged 200 mL of dilution water. The mixture is stirred for 15 minutes and then allowed to separate at 40° C. for at least one hour. The bottom aqueous layer is removed, discarding any rag layer with the aqueous layer. The solvent is distilled to a minimum stir volume under vacuum at 80° C. The residual reaction mixture contains (4R,5R)-27x.
Step 3. Preparation of 41x.

To the reaction mixture of Step 2 is charged 350 mL of methyl ethyl ketone (MEK) and 7 mL water. The mixture is stirred for 15 minutes and the temperature of the mixture is adjusted to 25° C. Next, the reactor is charged with 6.7 grams of solid diazabicyclo[2.2.2]octane (DABCO). The mixture is maintained at 25° C. for three to four hours. It is then heated to 65° C. and maintained at that temperature for 30 minutes. The mixture is then cooled to 25° C. for 1 hour. The off-white crystalline 41x (Form II) is filtered and washed with 50 mL MEK, and let dry under vacuum at 100° C.

Example 1467

Alternate Preparation of (4R,5R)-1-((4-(4-(3,3-Dibutyl-7-(dimethylamino)-2,3,4,5-tetrahydro-4-hydroxy-1,1-dioxido-1-benzithiepin-5-yl)phenoxy)methyl)phenyl)methyl-4-aza-1-azoniabicyclo[2.2.2]octane Chloride, Form I of 41x (4R,5R)-27x (2.82 kg dry basis, 4.7 mol) was dissolved in MTBE (9.4 L). The solution of (4R,5R)-27x was passed through a 0.2 mm filter cartridge into the feeding vessel. The flask and was rinsed with MTBE (2×2.5 L). The obtained solution as passed through the cartridge filter and added to the solution of (4R,5R)-27x in the feeding vessel. DABCO (diazabicyclo[2.2.2]octane, 0.784 kg, 7.0 mol) was dissolved in MeOH (14.2 L). The DABCO solution was passed through the filter cartridge into the 100 L nitrogen-flushed reactor. The Pyrex bottle and the cartridge filter were rinsed with MeOH (7.5 L) and the solution was added to the reactor. The (4R,5R)-27x solution was added from the feeding vessel into the reactor at 37° C. over a period of 10 min, while stirring. Methanol (6.5 L) was added to the Pyrex bottle and via the cartridge filter added to the feeding vessel to rinse the remaining (4R,5R)-27x into the reactor. The reaction mixture was brought to 50–60° C. over 10–20 min and stirred at that temperature for about 1 h. The mixture was cooled to 20–25° C. over a period of 1 h. To the reaction mixture, methyl t-butyl ether (MTBE) (42 L) was added over a period of 1 h and stirred for a minimum of 1 h at 20–25° C. The suspension was filtered through a Buchner funnel. The reactor and the filter cake were washed with MTBE (2×14 L). The solids were dried on a rotary evaporator in a 20 L flask at 400–12 mbar, 40° C., for 22 h. A white crystalline solid was obtained. The yield of 41x (Form I) was 3.08 kg (2.97 kg dry, 93.8%) and the purity 99.7 area % (HPLC; Kromasil C 4, 250×4.6 mm column; 0.05% TFA in H$_2$O/0.05% TFA in ACN gradient, UV detection at 215 nm).

Example 1467a

Conversion of Form I of Compound 41x Into Form II of Compound 41x

To 10.0 grams of Form I of 41x in a 400 mL jacketed reactor is added 140 mL of MEK. The reactor is stirred (358 rpm) for 10 minutes at 23° C. for 10 minutes and the stirring rate is then changed to 178 rpm. The suspension is heated to reflux over 1 hour using a programmed temperature ramp (0.95° C./minute) using batch temperature control (cascade mode). The delta $T_{max}$ is set to 5° C. The mixture is held at reflux for 1 hour. The mixture is cooled to 25° C. After 3 hours at 25° C., a sample of the mixture is collected by filtration. Filtration is rapid (seconds) and the filtrate is clear and colorless. The white solid is dried in a vacuum oven (80° C., 25 in. Hg) to give a white solid. The remainder of the suspension is stirred at 25° C. for 18 hours. The mixture is filtered and the cake starts to shrink as the mother liquor reaches the top of the cake. The filtration is stopped and the reactor is rinsed with 14 mL of MEK. The reactor stirrer speed is increased from 100 to 300 rpm to rinse the reactor. The rinse is added to the filter and the solid is dried with a rapid air flow for 5 minutes. The solid is dried in a vacuum oven at 25 in. Hg for 84 hours to give Form II of 41x.

All patents, publications, textbooks, articles and any other publications referenced in this application are incorporated herein by reference in their entirety for all purposes.

What is claimed is:

1. A compound comprising a benzothiepene of Formula I-1 or I-2:

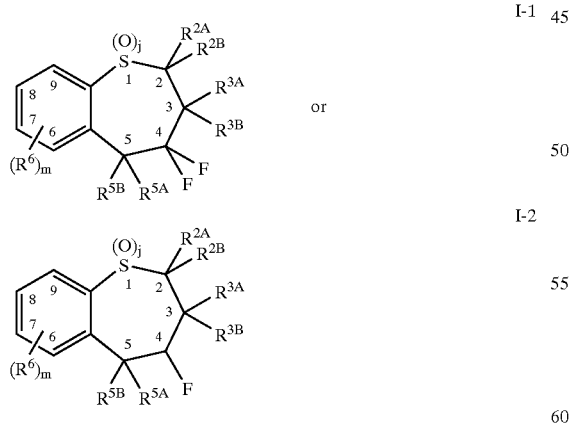

or a pharmaceutically acceptable salt, solvate, or prodrug thereof wherein j is 0, 1 or 2;
wherein m is 0, 1, 2, 3 or 4;
wherein $R^{2A}$ and $R^{2B}$ are independently selected from the group consisting of hydrogen and hydrocarbyl;
wherein $R^{3A}$, $R^{3B}$, $R^{5A}$, and $R^{5B}$ are independently selected from the group consisting of hydrogen, alkyl; cycloalkyl; alkenyl; alkynyl; heterocyclyl; quaternary heterocyclyl, oxo; aryl-$R^5$; —$OR^9$; —$NR^9R^{10}$; —$SR^9$; —$S(O)R^9$; —$SO_2R^9$; and —$SO_3R^9$;
wherein $R^9$ and $R^{10}$ are independently selected from the group consisting of hydrogen; hydrocarbyl; amino; and hydrocarbylamino;
wherein $R^5$ is selected from the group consisting of hydrogen; hydrocarbyl, heterocyclyl, outeraryloc; —$OR^9$; —$SR^9$; —$S(O)R^9$; —$SO_2R^9$; and —$SO_3R^9$;
wherein when $R^5$ is said cycloalkyl, aryl or heterocyclyl, said cycloalkyl, aryl or heterocyclyl are optionally substituted with —NH—X—R or —O—X—R;
wherein X is selected from the group consisting of —(C=O)$_s$-alkyl-; —(C=O)$_s$-alkyl-NH—; —(C=O)$_s$-alkyl-O—; —(C=O)$_s$-alkyl-(C=O)$_t$; and a covalent bond, wherein s and t are independently 0 or 1;
wherein R is selected from the group consisting of monosaccharides, disaccharides, and polysaccharides, wherein said monosaccharides, disaccharides, and polysaccharides are optionally protected with one or more sugar protecting groups;
wherein $R^9$ and $R^{10}$ are as previously defined;
wherein, when $R^5 \approx H$, $R^5$ is optionally substituted with one or more radicals independently selected from the group consisting of halogen; —$NO_2$; —CN; oxo; hydrocarbyl; —$OR^{13}$; —$NR^{13}R^{14}$; —$SR^{13}$; —$S(O)R_{13}$; —$SO_2R^{13}$—$SO_3R^{13}$; —$NR^{13}OR^{14}$; —$NR^{13}NR^{14}R^{15}$; —$CO_2R^{13}$; —OM; —$SO_2OM$; —$SO_2NR^{13}R^{14}$; —$C(O)NR^{13}R^{14}$; —C(O)OM; —$COR^{13}$; —$NR^{13}C(O)R^{14}$; —$NR^{13}C(O)NR^{14}R^{15}$; —$NR^{13}CO_2^{14}$; —$OC(O)R^{13}$; —$OC(O)NR^{13}R^{14}$; —$NR^{13}SOR^{14}$; —$NR^{13}SO_2R^{14}$; —$NR^{13}SONR^{14}R^{15}$; —$NR^{13}SO_2NR^{14}R^{15}$; —$PR^{13}R^{14}$; —$P(O)R^{13}R^{14}$; —$P^+R^{13}R^{14}R^{15}A^-$; —$P(OR^{13})OR^{14}$; —$S^+R^{13}R^{14}A^-$; and —$N^+R^{13}R^{14}R^{15}A^-$;
wherein $R^{13}$, $R^{14}$, and $R^{15}$ are independently selected from the group consisting of hydrogen and hydrocarbyl;
wherein $A^-$ is a pharmaceutically acceptable anion;
wherein M is a pharmaceutically acceptable cation;
wherein one or more $R^6$ radicals are independently selected from the group consisting of hydrogen; halogen; —CN; —$NO_2$; hydrocarbyl; —$R^5$; —$OR^{13}$; —$NR^{13}R^{14}$; —$SR^{13}$; —$S(O)R^{13}$; —$S(O)_2R^{13}$; —$SO_3R^{13}$; —$S^+R^{13}R^{14}A^-$; —$NR^{13}OR^{14}$; —$NR^{13}NR^{14}R^{15}$; —OM; —$SO_2OM$; —$SO_2NR^{13}R^{14}$; —$NR^{14}C(O)R^{13}$; —C(O)OM; —$S(O)NR^{13}R^{14}$; $N^+R^{13}R^{14}R^{15}A^-$; —$PR^{13}R^{14}$; —$P(O)R^{13}R^{14}$; —$P^+R^{13}R^{14}R^{15}A^-$; amino acid residue; peptide residue; polypeptide residue; and carbohydrate residue;
wherein $R^{13}$, $R^{14}$, $R^{15}$, $A^-$, and M are as defined above; and
wherein, in each instance, said hydrocarbyl may be optionally substituted with one or more groups comprising one or more heteroatoms, and wherein, in each instance, said hydrocarbyl optionally may have one or more carbon atoms replaced by one or more heteroatoms independently selected from the group consisting of oxygen, nitrogen, sulfur, phosphorus and combinations thereof.

2. The compound of claim 1 or a pharmaceutically acceptable salt, solvate or prodrug thereof, wherein $R^{2A}$ and $R^{2B}$ are independently selected from the group consisting of hydrogen and alkyl, $R^{3A}$ and $R^{3B}$ are independently selected from the group consisting of hydrogen, alkyl, alkenyl, alkynyl, cycloalkyl, cycloalkylalkyl, aryl and arakyl and $R^5$ is selected from the group consisting of alkyl, cycloalkyl, alkenyl, alkynyl and aryl.

3. The compound of claim 1 or a pharmaceutically acceptable salt, solvate or prodrug thereof, wherein $R^{5A}$ is aryl optionally substituted with said radical $R^5$ selected from the group consisting of (1)–(69) and (70):

(1)
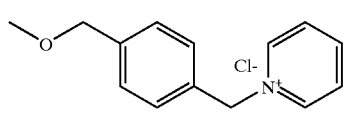

(2)
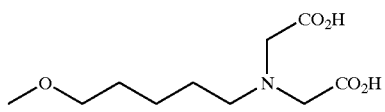

(3)
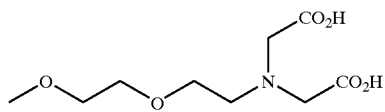

(4)
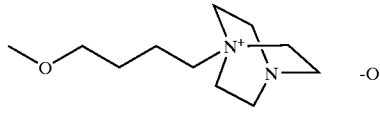

(5)
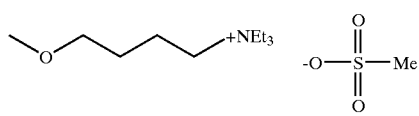

(6)
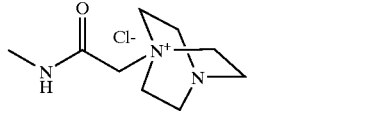

(7)
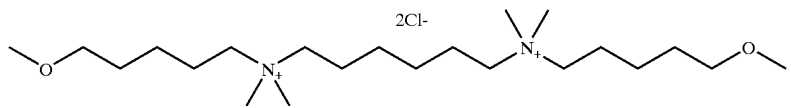

(8)
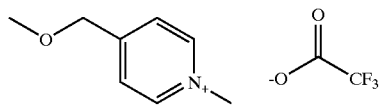

(9)
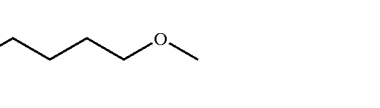

(10)
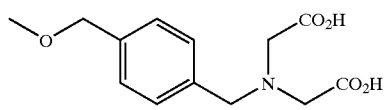

(11)
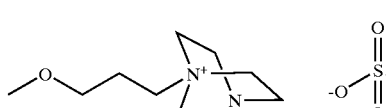

(12)
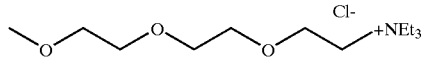

(13)
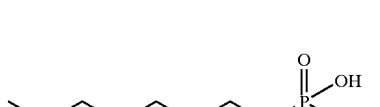

(14)
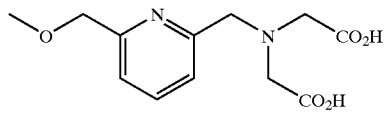

(15)
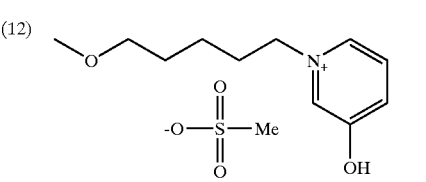

(15a)
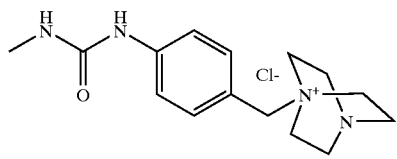

(16)
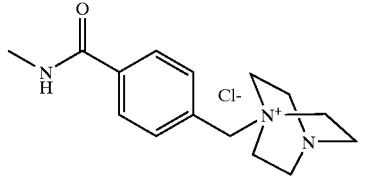

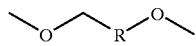
R = 1000 MW PEG

(17)
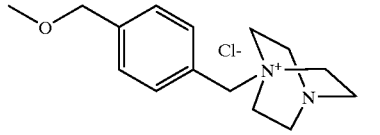

(18)
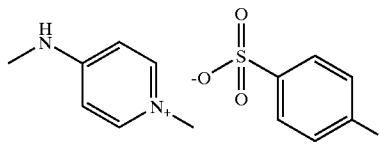

-continued
(19) 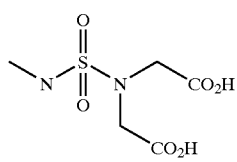
(20) 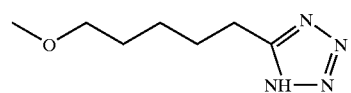
(21) 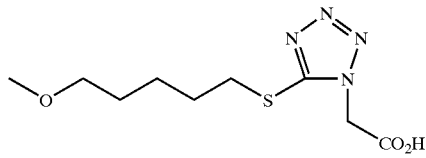
(22) 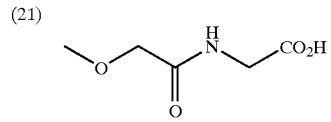
(23) 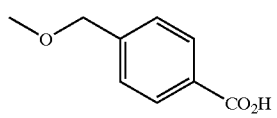
(24) 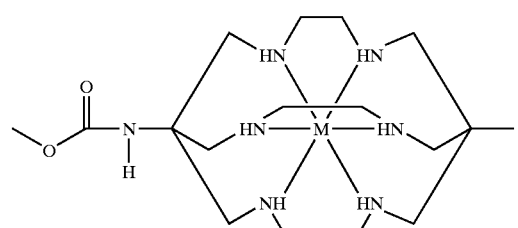
M = Co$^{II, III}$, Mn$^{II, III}$, Fe$^{II, III}$, Ni$^{II, III}$, Cr$^{III}$, Cu$^{II}$, Zn$^{II}$, Cd$^{II}$, Ga$^{III}$, In$^{III}$, V$^{IV}$, Ru$^{II}$, Pr$^{IV}$, Rh$^{III}$ or Ir$^{III}$
(25) 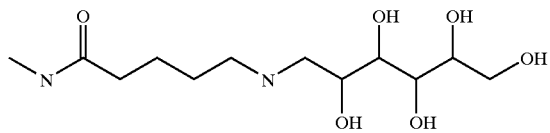
(26) 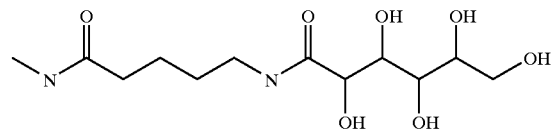
(27) 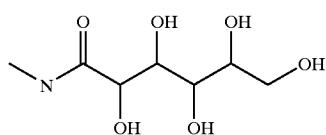
(28) 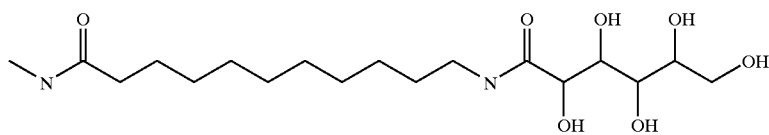
(29) 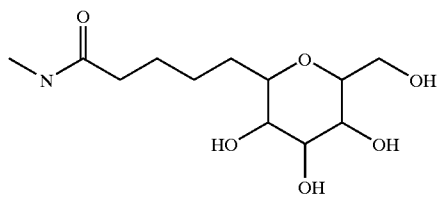
(30) 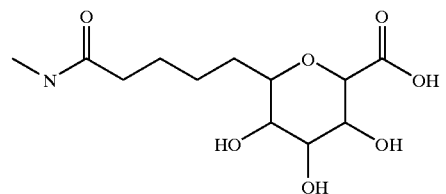
(31) 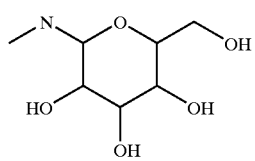
(32) 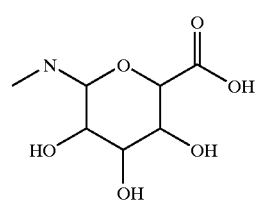

-continued
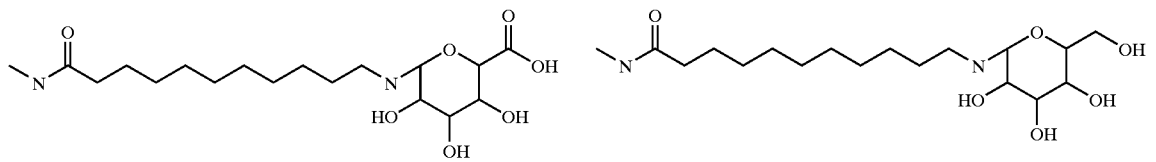
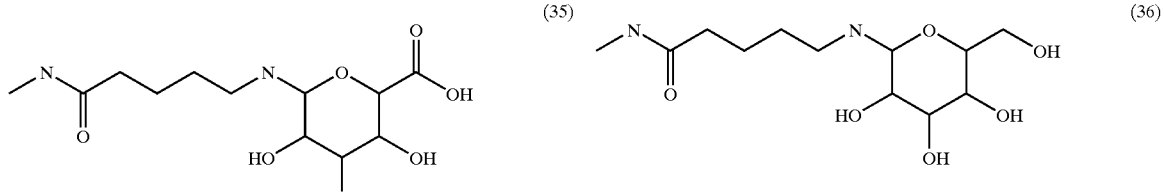
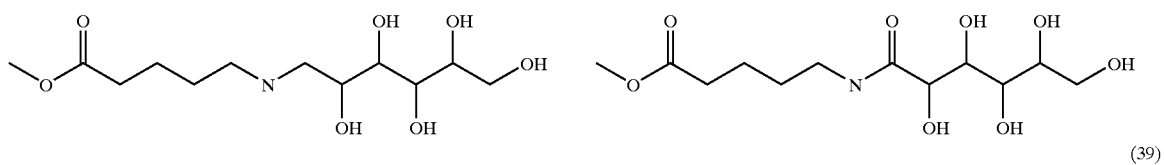
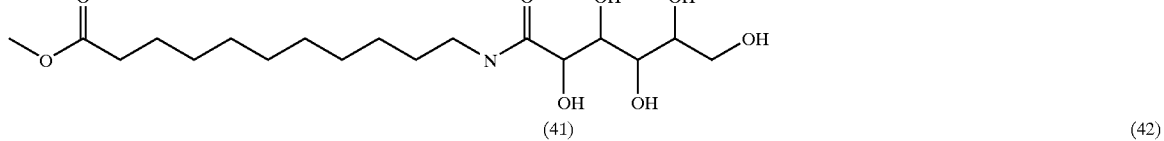
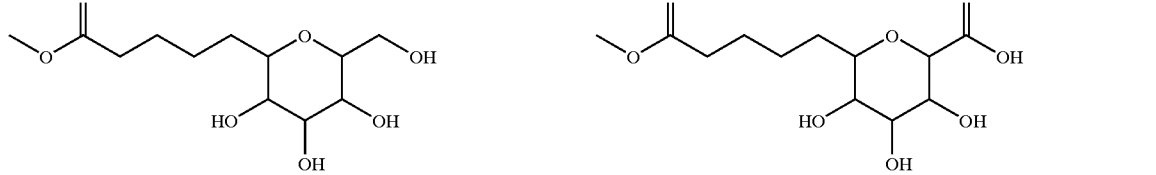
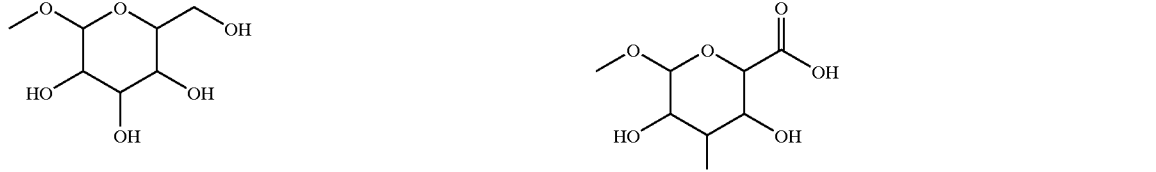
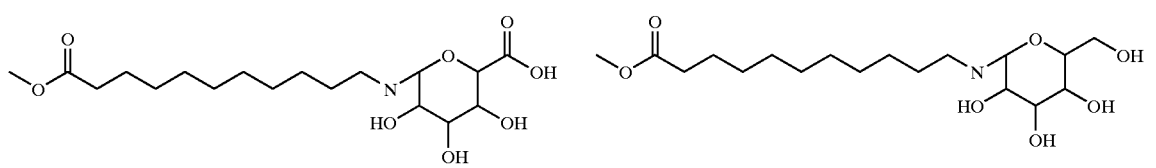
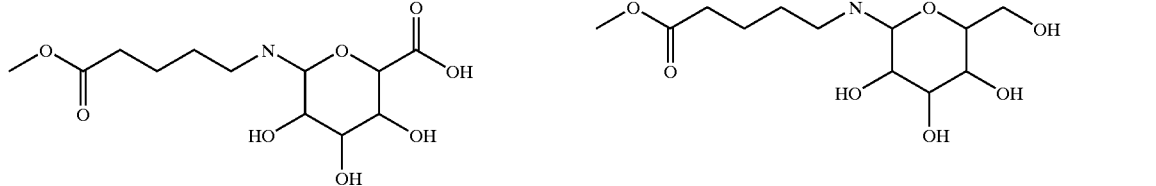

-continued
(49) 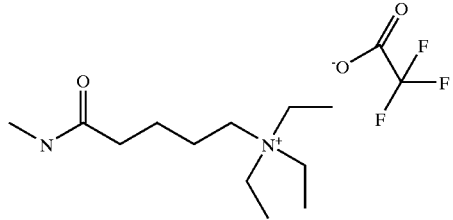
(50) 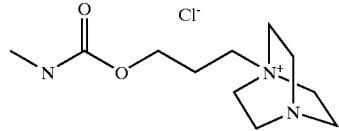
(51) 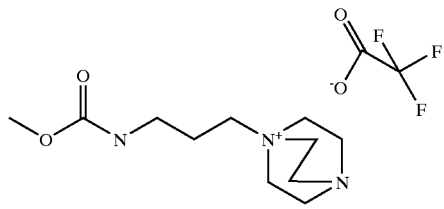
(52) 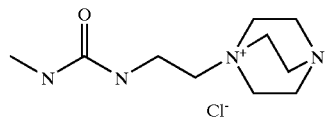
(53) 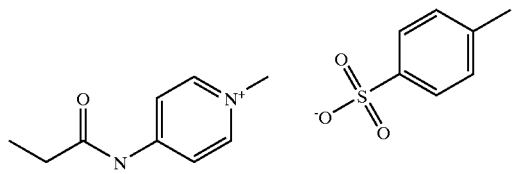
(54) 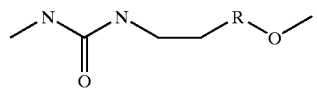
(55) 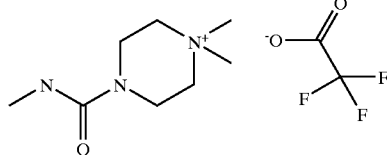
(56) 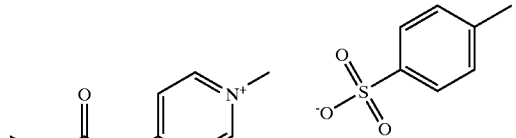
(57) 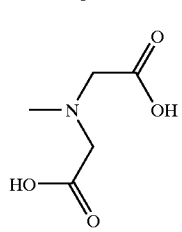
(58) 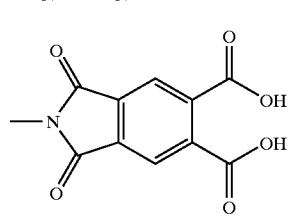
(59) 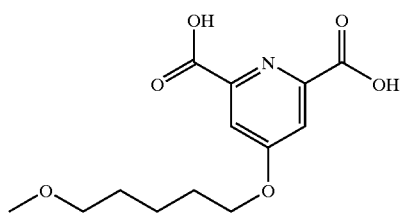
(60) 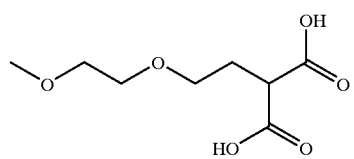
(61) 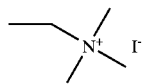
(62) 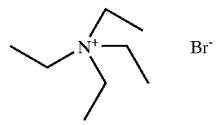
(63) 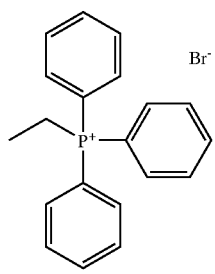
(64) 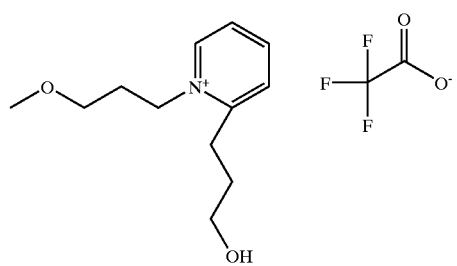

-continued

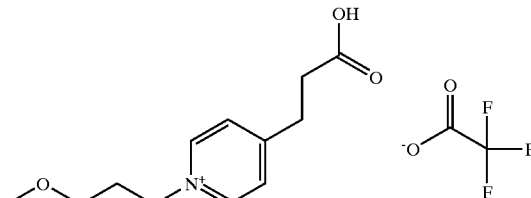
(65)

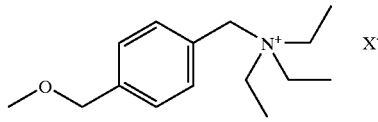
(66)

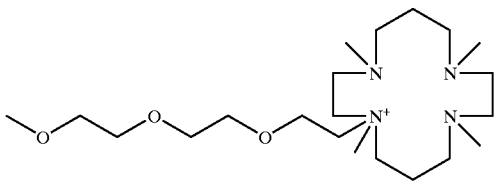
(67)

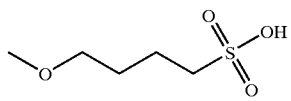
(68)

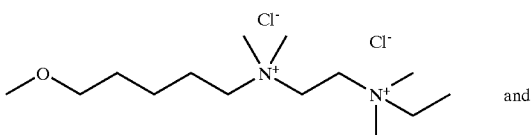
(69)

and

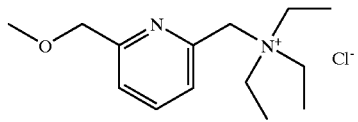
(70)

provided that when said $R^5$ is (7), (17) or (24), then said $R^{5A}$ is a left end of said $R^5$ and $R^{5B}$ is a right end of said $R^5$ or vice versa.

4. The compound of claim 3 or a pharmaceutically acceptable salt, solvate or prodrug thereof, wherein $R^{5A}$ is phenyl optionally substituted at least at either a para position or a meta position of said phenyl with said radical $R^5$.

5. The compound of claim 1 or a pharmaceutically acceptable salt, solvate or prodrug thereof, wherein j=2, $R^{2A}$ and $R^{2B}$ are independently selected from the group consisting of hydrogen and alkyl, and $R^{3A}$ and $R^{3B}$ are independently selected from the group consisting of hydrogen and alkyl.

6. The compound of claim 1 or a pharmaceutically acceptable salt, solvate or prodrug thereof, wherein j=2, at least one of $R^{2A}$ and $R^{2B}$ is hydrogen, and $R^{3A}$ and $R^{3B}$ each are alkyl.

7. The compound of claim 6 or a pharmaceutically acceptable salt, solvate or prodrug thereof, wherein $R^{2A}=R^{2B}=H$ and $R^{3A}$ and $R^{3B}$ are independently selected from the group consisting of ethyl, propyl and butyl.

8. The compound of claim 1 or a pharmaceutically acceptable salt, solvate or prodrug thereof, wherein $R^{2A}$ and $R^{2B}$ are independently selected from the group consisting of hydrogen and $C_{1-10}$ alkyl, $R^{3A}$ and $R^{3B}$ are independently selected from the group consisting of hydrogen and $C_{1-10}$ alkyl.

9. The compound of claim 1 or a pharmaceutically acceptable salt, solvate or prodrug thereof, wherein $R^{2A}$ and $R^{2B}$ are independently selected from the group consisting of hydrogen and $C_{1-6}$ alkyl, and $R^{3A}$ and $R^{3B}$ are independently selected from the group consisting of hydrogen and $C_{1-6}$ alkyl.

10. The compound of claim 1 or a pharmaceutically acceptable salt, solvate or prodrug thereof, wherein $R^{2A}$ and $R^{2B}$ are the same radical.

11. The compound of claim 10 or a pharmaceutically acceptable salt, solvate or prodrug thereof, wherein $R^{2A}$ and $R^{2B}$ are the same alkyl radical.

12. The compound of claim 10, or a pharmaceutically acceptable salt, solvate or prodrug thereof, wherein $R^{2A}$ and $R^{2B}$ are the same radical selected from the group consisting of hydrogen, $C_{1-10}$ alkyl, $C_{1-10}$ alkenyl and $C_{1-10}$ alkynyl.

13. The compound of claim 10 or a pharmaceutically acceptable salt, solvate or prodrug thereof, wherein $R^{3A}$ and $R^{3B}$ are the same radical.

14. The compound of claim 11 or a pharmaceutically acceptable salt, solvate or prodrug thereof, wherein $R^{3A}$ and $R^{3B}$ are the same alkyl radical.

15. The compound of claim 12 or a pharmaceutically acceptable salt, solvate or prodrug thereof, wherein $R^{3A}$ and $R^{3B}$ are the same radical selected from the group consisting of hydrogen, $C_{1-10}$ alkyl, $C_{1-10}$ alkenyl and $C_{1-10}$ alkynyl.

16. The compound of claim 1 or a pharmaceutically acceptable salt, solvate or prodrug thereof, wherein $R^{3A}$ and $R^{3B}$ are the same radical.

17. The compound of claim 16 or a pharmaceutically acceptable salt, solvate or prodrug thereof, wherein $R^{3A}$ and $R^{3B}$ are the same alkyl radical.

18. The compound of claim 16 or a pharmaceutically acceptable salt, solvate or prodrug thereof, wherein $R^{3A}$ and $R^{3B}$ are the same radical selected from the group consisting of hydrogen, $C_{1-10}$ alkyl, $C_{1-10}$ alkenyl and $C_{1-10}$ alkynyl.

19. The compound of claim 1 or a pharmaceutically acceptable salt, solvate or prodrug thereof, wherein $R^{2A}$ and $R^{2B}$ are the same $C_{1-20}$ hydrocarbyl radical.

20. The compound of claim 19 or a pharmaceutically acceptable salt, solvate or prodrug thereof, wherein $R^{2A}$ and $R^{2B}$ are the same $C_{1-10}$ hydrocarbyl radical.

21. The compound of claim 20 or a pharmaceutically acceptable salt, solvate or prodrug thereof, wherein $R^{2A}$ and $R^{2B}$ are the same $C_{1-10}$ hydrocarbyl radical.

22. The compound of claim 1 or a pharmaceutically acceptable salt, solvate or prodrug thereof, wherein $R^{3A}$ and $R^{3B}$ are the same $C_{1-20}$ hydrocarbyl radical.

23. The compound of claim 22 or a pharmaceutically acceptable salt, solvate or prodrug thereof, wherein $R^{3A}$ and $R^{3B}$ are the same $C_{1-10}$ hydrocarbyl radical.

24. The compound of claim 23 or a pharmaceutically acceptable salt, solvate or prodrug thereof, wherein $R^{3A}$ and $R^{3B}$ are the same $C_{1-6}$ hydrocarbyl radical.

25. The compound of claim 11 or a pharmaceutically acceptable salt, solvate or prodrug thereof, wherein $R^{2A}$ and $R^{2B}$ are each n-butyl.

26. The compound of claim 10 or a pharmaceutically acceptable salt, solvate or prodrug thereof, wherein $R^{2A}$ and $R^{2B}$ are each H.

27. The compound of claim 13 or a pharmaceutically acceptable salt, solvate or prodrug thereof, wherein $R^{3A}$ and $R^{3B}$ are each H or n-butyl.

28. The compound of claim 1 or a pharmaceutically acceptable salt, solvate or prodrug thereof, wherein one or more radicals $R^6$ are selected from the group consisting of hydrogen, halogen, hydroxy, alkoxy, amino, alkylamino and dialkylamino.

29. The compound of claim 28 or a pharmaceutically acceptable salt, solvate or prodrug thereof, wherein one or more radicals $R^6$ are selected from the group consisting of methoxy, ethoxy and dimethylamino.

30. The compound of claim 1 or a pharmaceutically acceptable salt, solvate or prodrug thereof, wherein j=2, m=1, one of $R^{5A}$ and $R^{5B}$ is hydrogen and the other of $R^{5A}$ and $R^{5B}$ is a phenyl radical optionally substituted at a para position of said phenyl radical with said radical $R^5$ selected from the group consisting of (1)–(69) and (70):

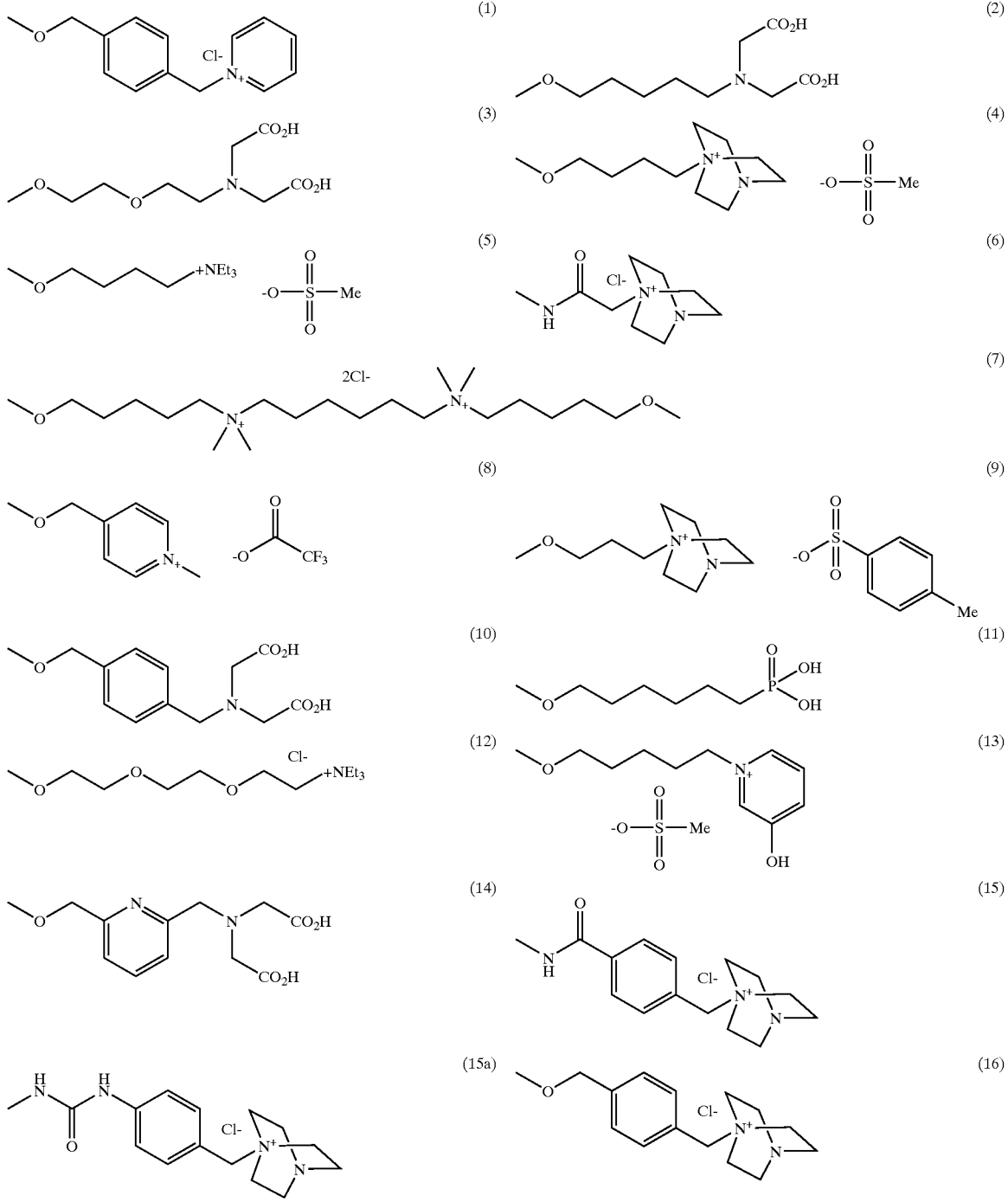

-continued
(17)
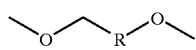
R = 1000 MW PEG
(18)
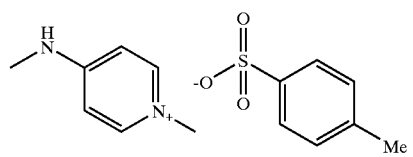
(19)
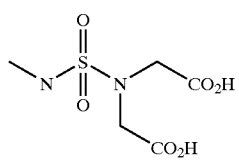
(20)
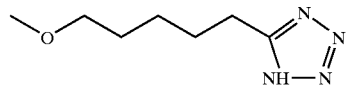
(21)
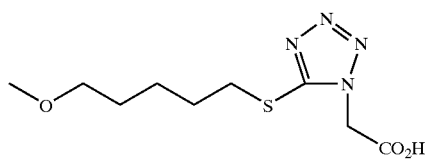
(22)
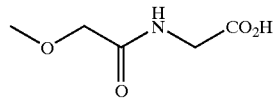
(23)
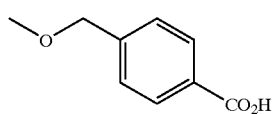
(24)
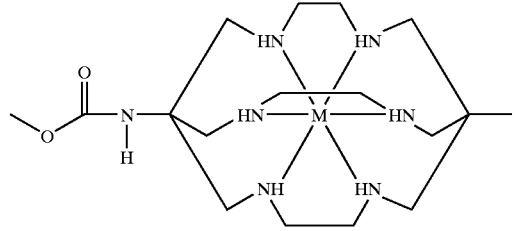
M = $Co^{II, III}$, $Mn^{II, III}$, $Fe^{II, III}$, $Ni^{II, III}$, $Cr^{III}$, $Cu^{II}$, $Zn^{II}$, $Cd^{II}$, $Ga^{III}$, $In^{III}$, $V^{IV}$, $Ru^{II}$, $Pr^{IV}$, $Rh^{III}$ or $Ir^{III}$
(25)
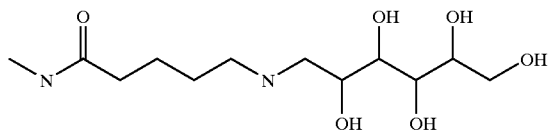
(26)
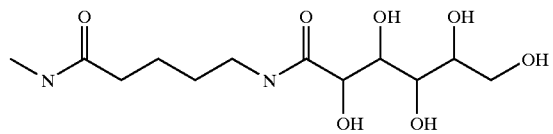
(27)
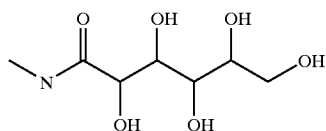
(28)
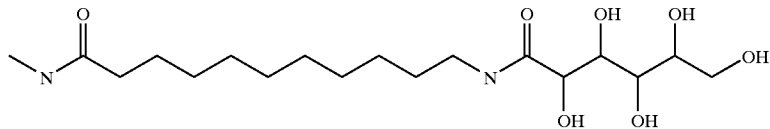
(29)
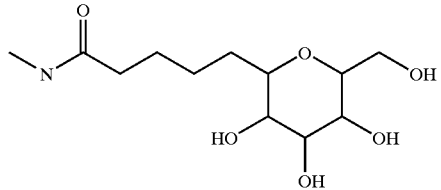
(30)
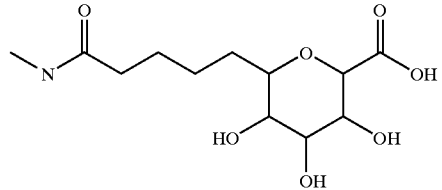

-continued
(31) 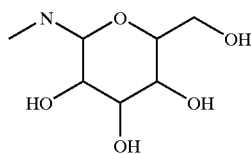
(32) 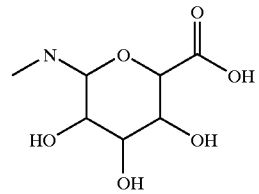
(33) 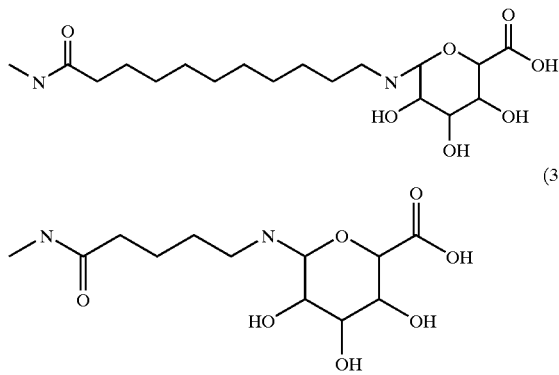
(34) 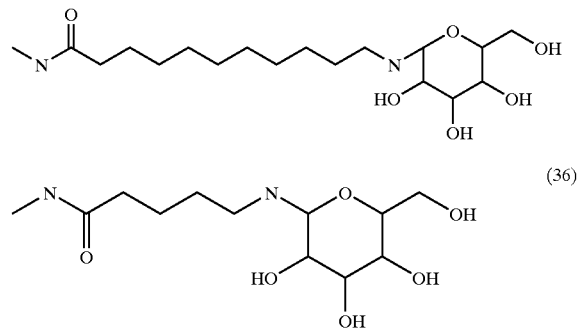
(35) 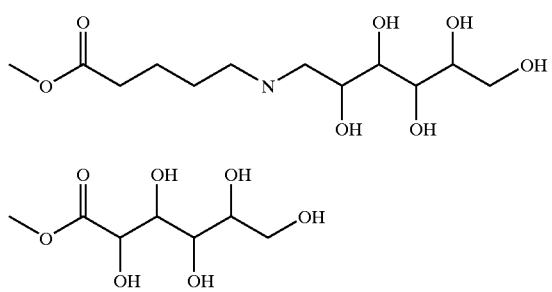
(36) 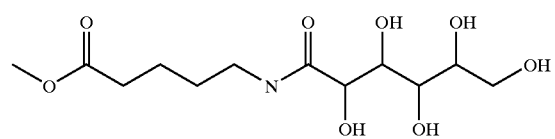
(37) 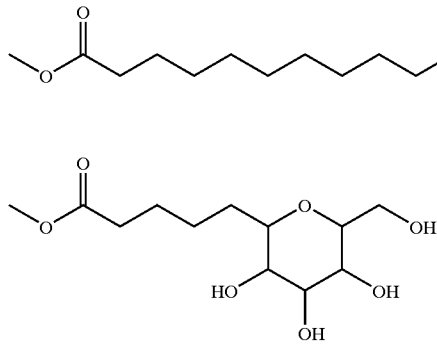
(38) 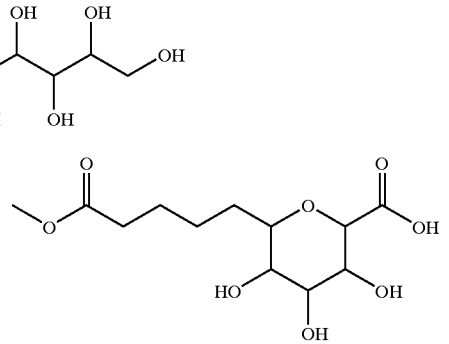
(39) 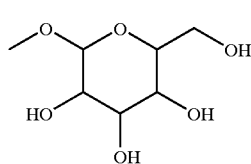
(40) 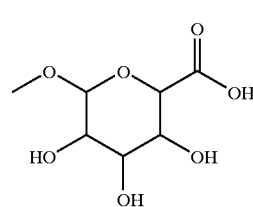
(41) 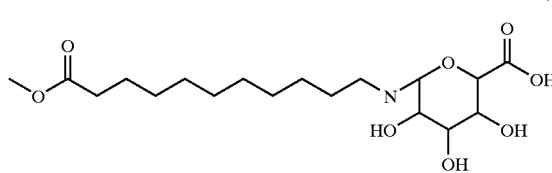
(42) 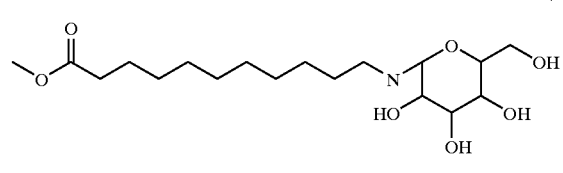
(43) 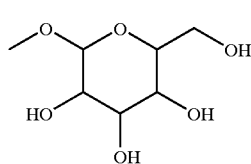
(44) 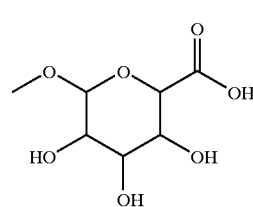
(45) 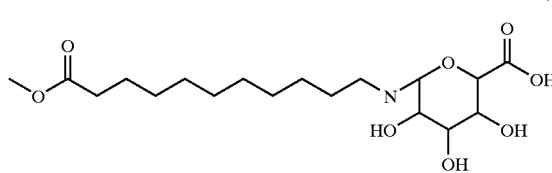
(46) 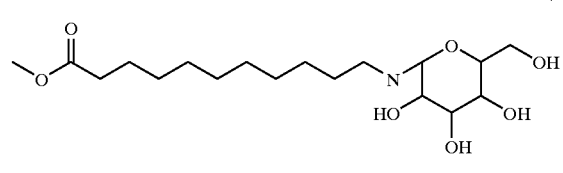

-continued
(47) 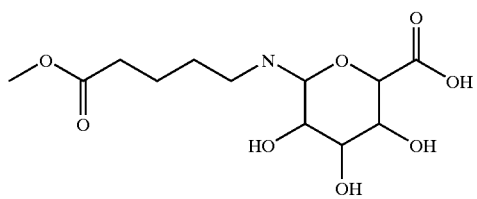
(48) 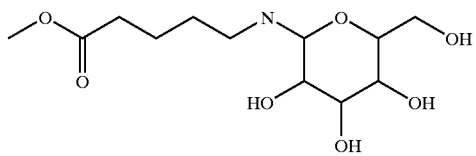
(49) 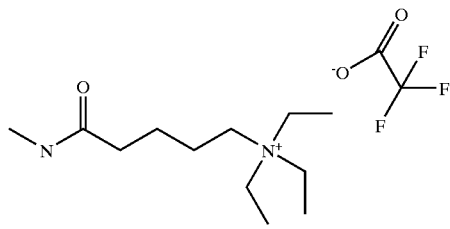
(50) 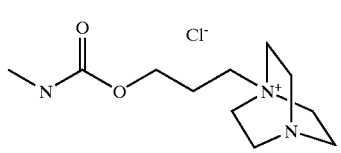
(51) 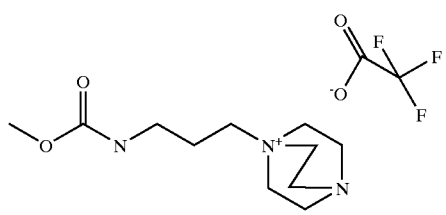
(52) 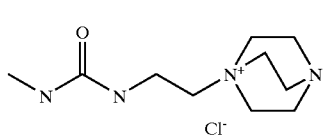
(53) 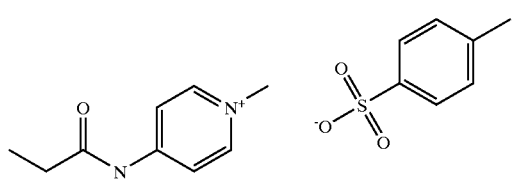
(54) 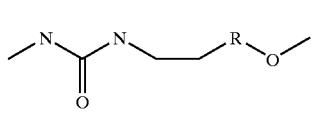
(55) 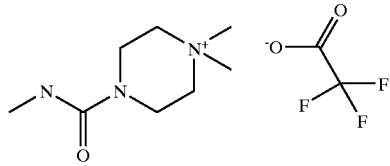
(56) 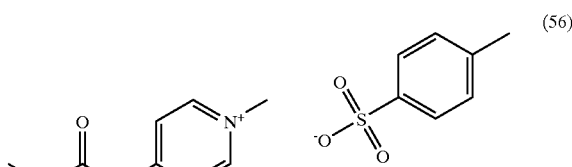
(57) 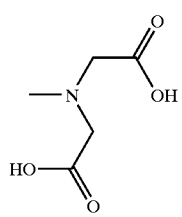
(58) 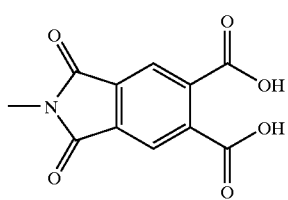
(59) 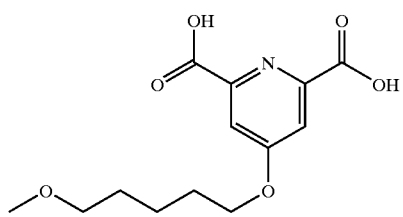
(60) 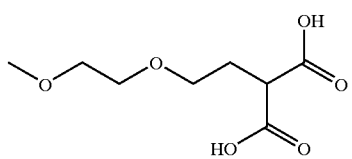
(61) 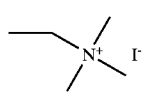
(62) 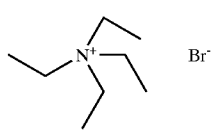

-continued

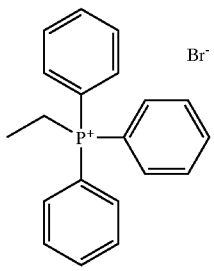 (63)

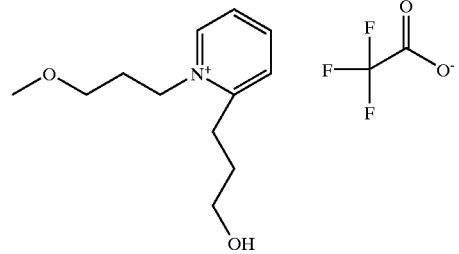 (64)

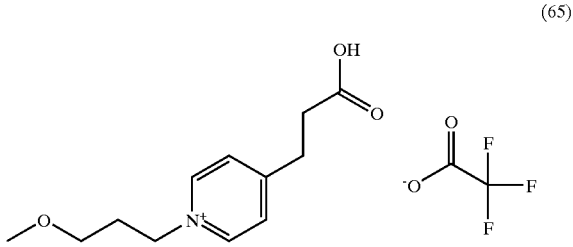 (65)

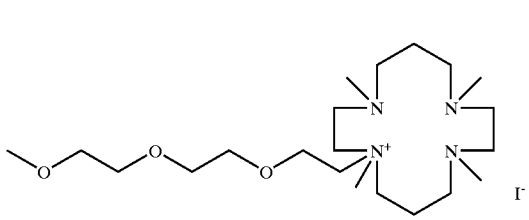 (66)

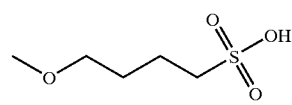 (68)

(67)

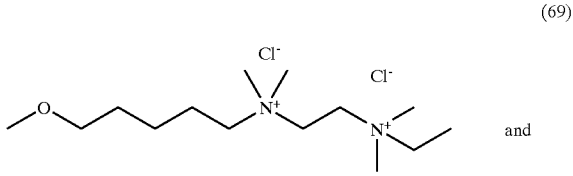 (68)

(69)

(70)

provided that when said $R^5$ is (7), (17) or (24), then said $R^{5A}$ is a left end of said $R^5$ and $R^{5B}$ is a right end of said $R^5$ or vice versa.

31. The compound of claim 1 wherein said benzothiepene comprises the compound of Formula I-17 or I-18:

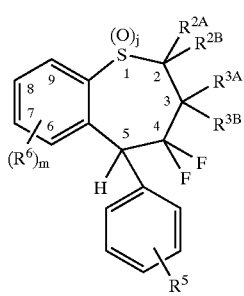

I-17

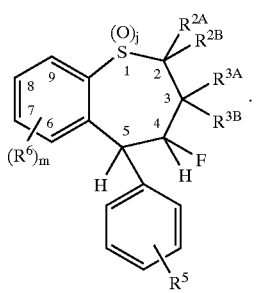

I-18

32. The compound of claim 31 wherein said $R^5$ is attached to either a para-position or a meta-position on said phenyl ring attached to the 5-position ring carbon of said benzothiepene compound of said Formulas I-17 or I-18.

33. The compound of claim 31 wherein said benzothiepene of said Formula I-17 comprises a member selected from the group consisting of Formulas I-21 and I-22:

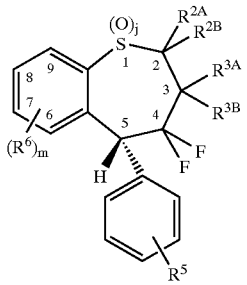

I-21

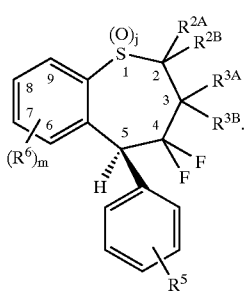

I-22

34. The compound of claim 32 wherein said benzothiepene of said Formulas I-21 and I-22 comprise Formulas I-9 and I-10, respectively, represented by:

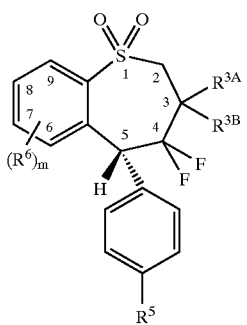

I-9

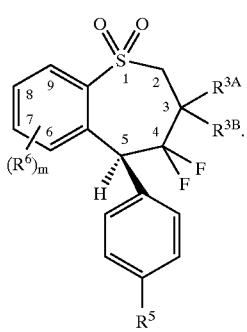

I-10

35. The compound of claim 31 wherein said benzothiepene of said Formula I-18 comprises a member selected from the group consisting of Formulas I-23, and I-24:

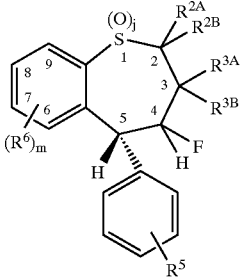

I-23

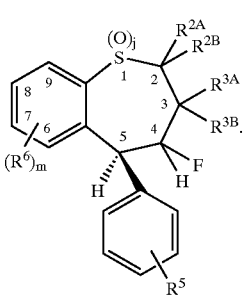

I-24

36. The compound of claim 35 wherein said benzothiepene of said Formulas I-23 and I-24 comprise Formulas I-19 and I-20, respectively, represented by:

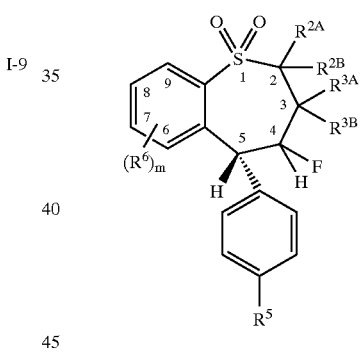

I-19

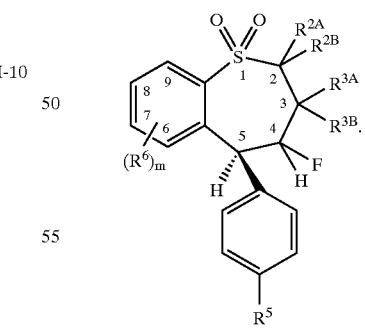

I-20

37. The compound of claim 35 wherein said $R^5$ is attached to either a meta-position or a para-position on said phenyl ring attached to said 5-position carbon ring of said benzothiepenes of said Formulas I-23 and I-24.

38. The compound of claim 31 wherein said $R^5$ is selected from the group consisting of (1)–(69) and (70):

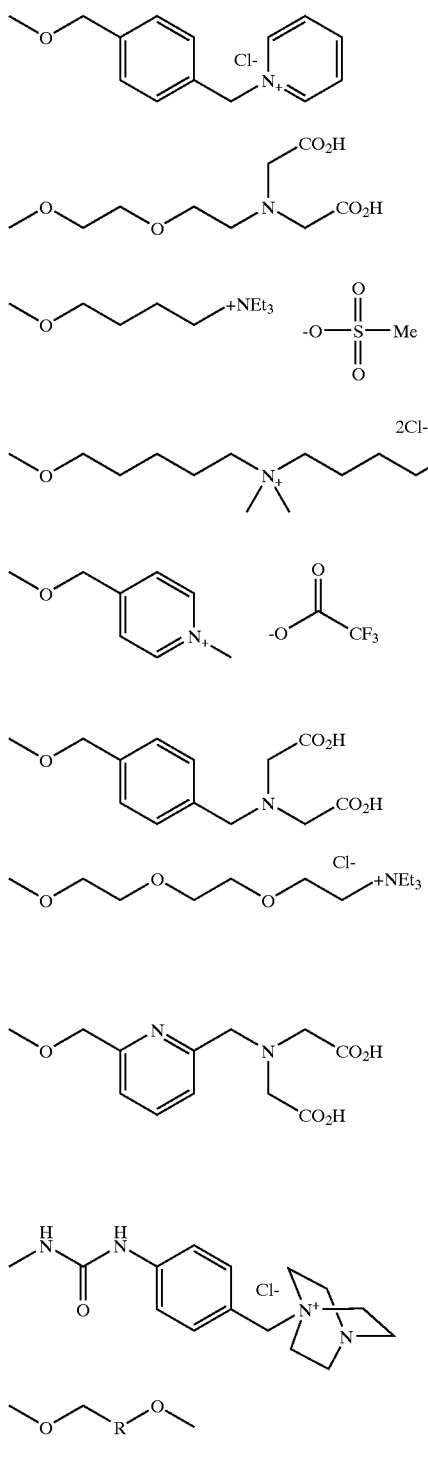
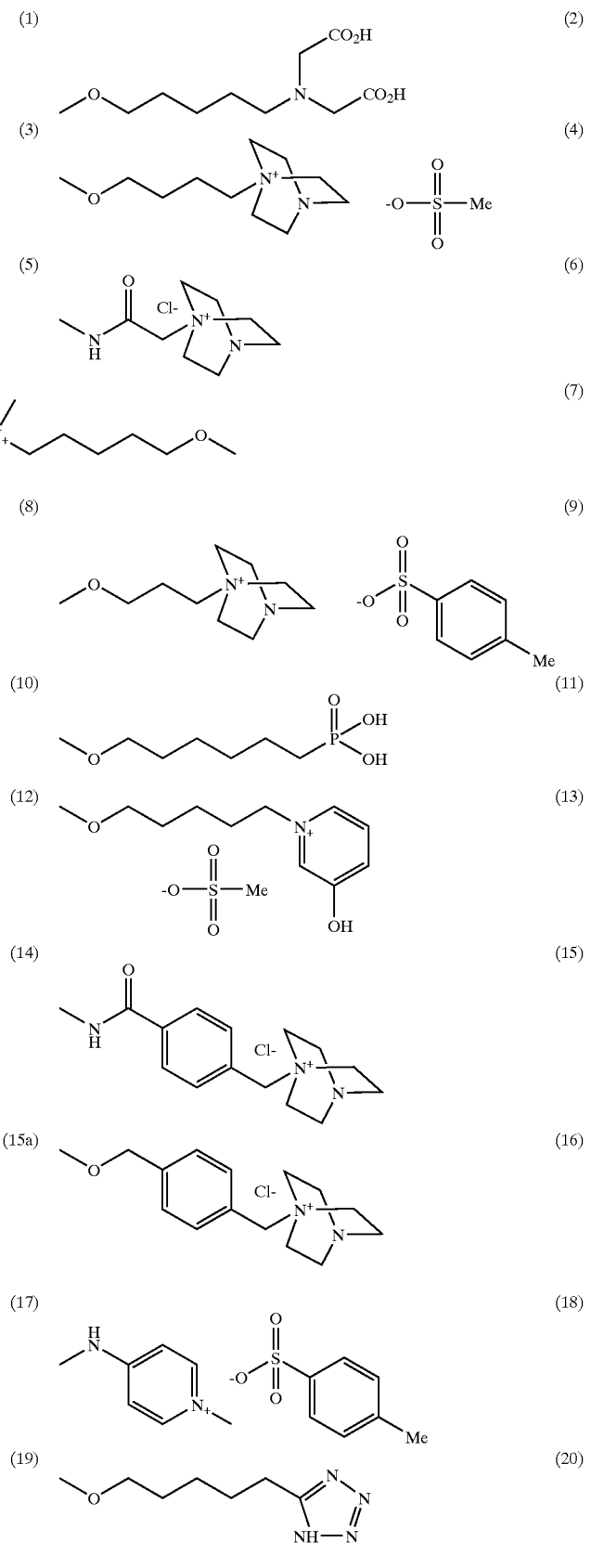
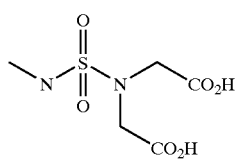

-continued
(21)
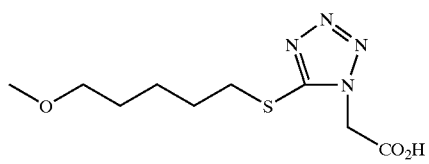
(22)
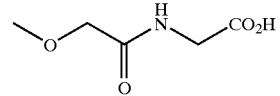
(23)
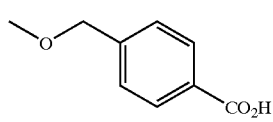
(24)
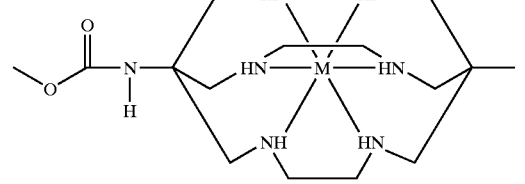
$M = Co^{II, III}, Mn^{II, III}, Fe^{II, III}, Ni^{II, III},$
$Cr^{III}, Cu^{II}, Zn^{II}, Cd^{II}, Ga^{III}, In^{III}, V^{IV},$
$Ru^{II}, Pr^{IV}, Rh^{III}$ or $Ir^{III}$
(25)
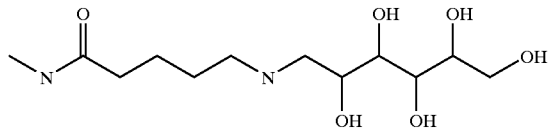
(26)
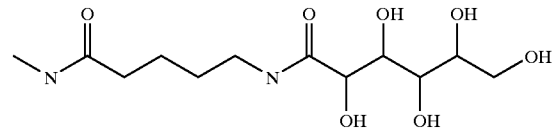
(27)
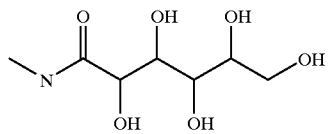
(28)
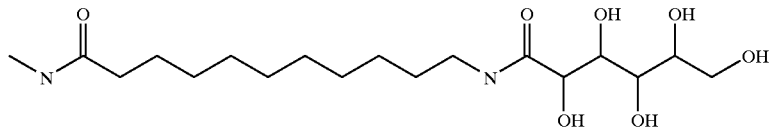
(29)
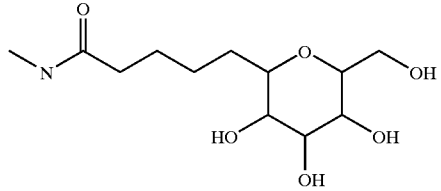
(30)
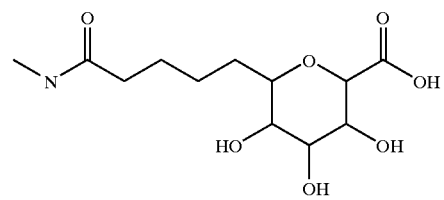
(31)
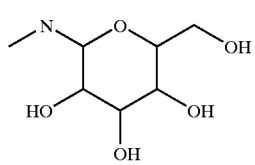
(32)
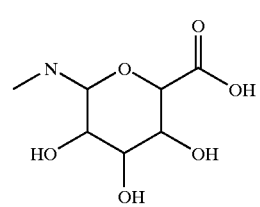
(33)
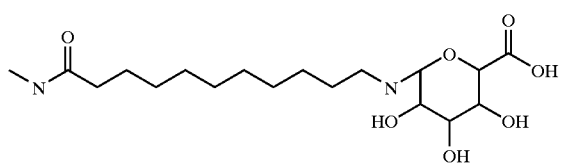
(34)
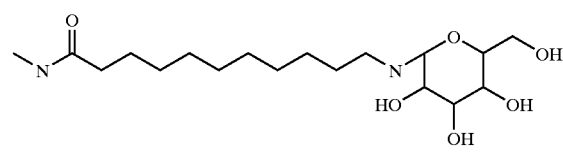

-continued
(35) 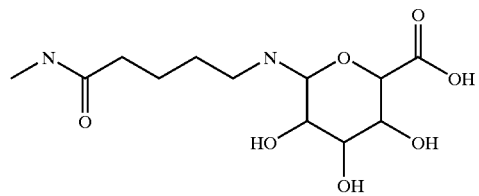
(36) 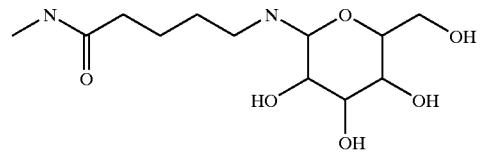
(37) 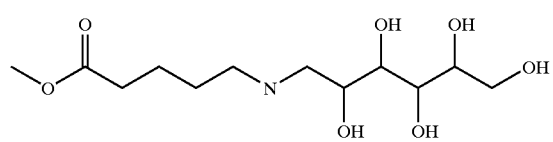
(38) 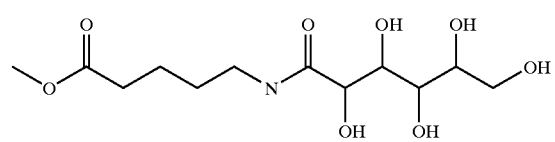
(39) 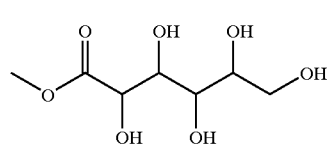
(40) 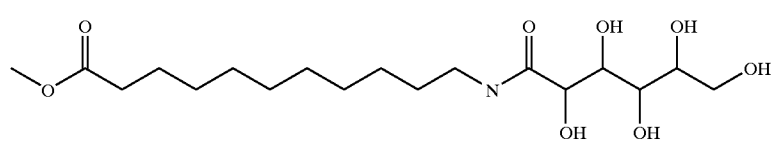
(41) 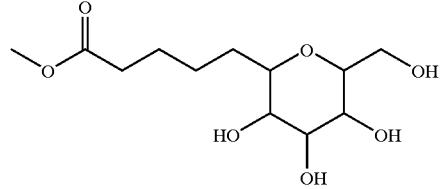
(42) 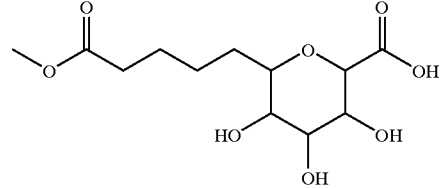
(43) 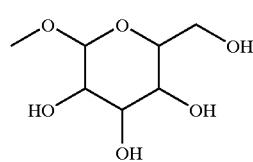
(44) 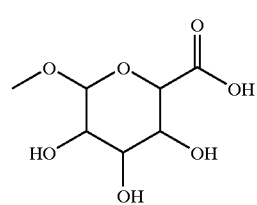
(45) 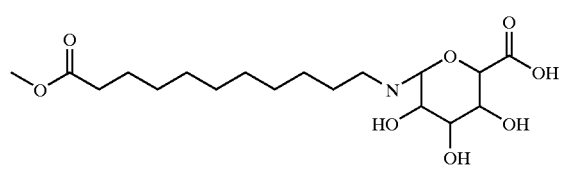
(46) 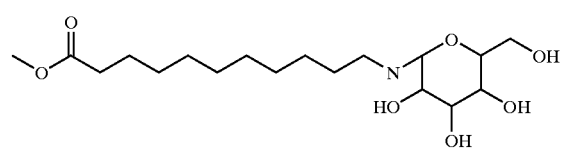
(47) 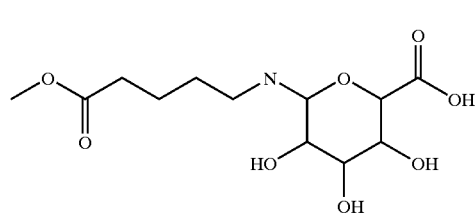
(48) 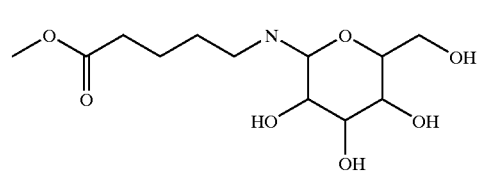

(49) 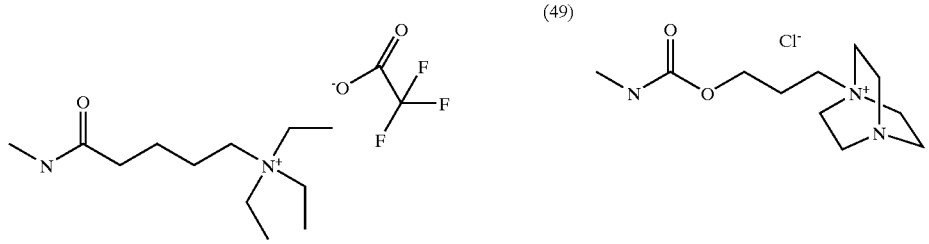
(50) 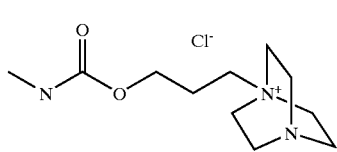
(51) 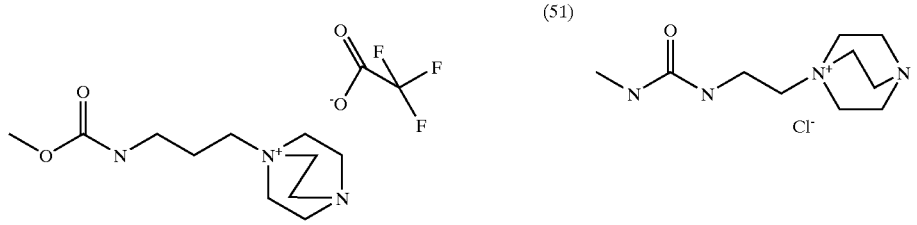
(52) 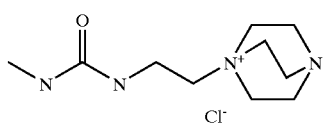
(53) 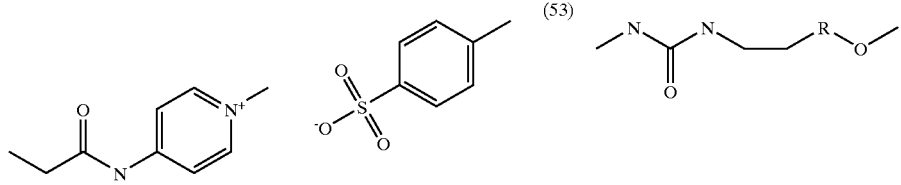
(54) 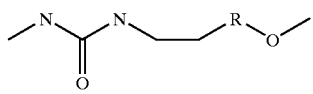
(55) 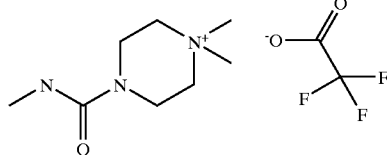
(56) 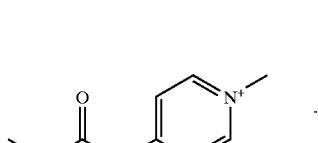
(57) 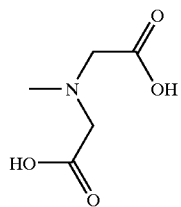
(58) 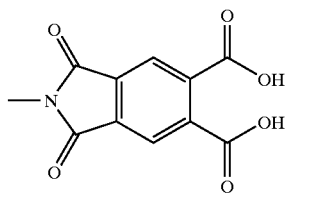
(59) 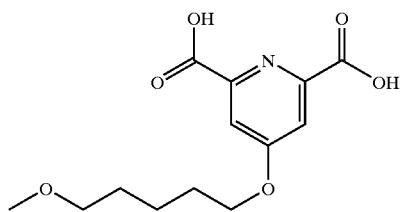
(60) 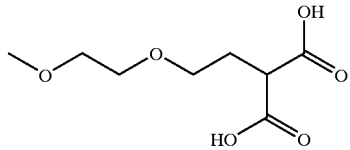
(61) 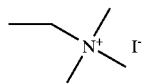
(62) 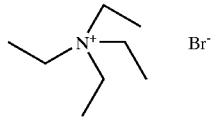
(63) 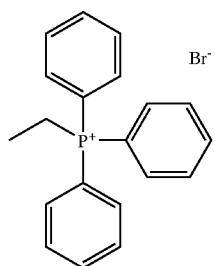
(64) 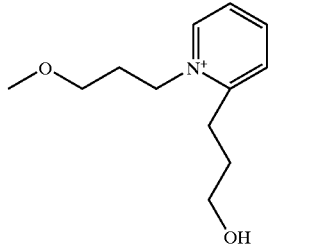 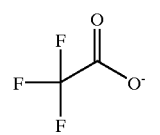

-continued

(65)
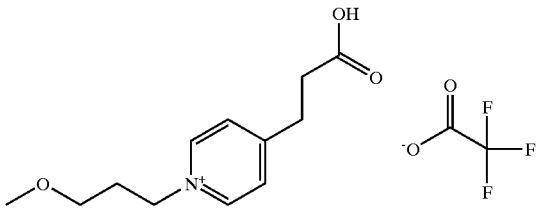

(66)
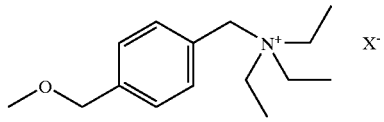

(67)
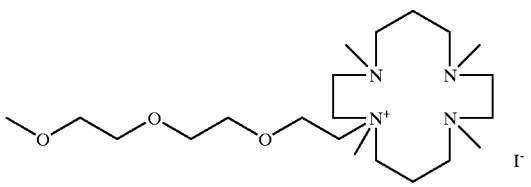

(68)
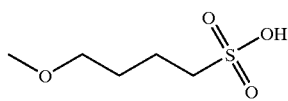

(69)
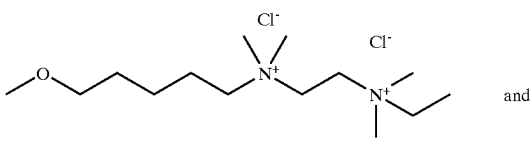 and

(70)
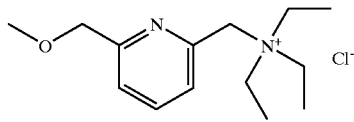

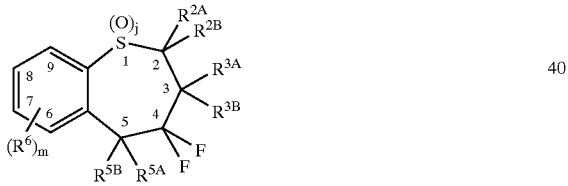

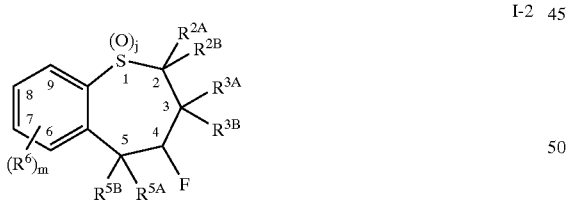

wherein when said $R^5$ is said (7), said (17) or said (24), then said $R^{5A}$ represents a left-end of said $R^5$ and said $R^{5B}$ represents a right end of said $R^5$ or vice versa.

39. A method for treating a hyprelipidemic condition in a subject comprising administering to said subject in need thereof a therapeutically effective amount of a compound of Formulas I-1 or I-2, wherein said Formulas I-1 and I-2 are represented by:

I-1

I-2 or a pharmaceutically acceptable salt, solvate, or prodrug thereof
wherein j is 0, 1 or 2;
wherein m is 0, 1, 2, 3 or 4;
wherein $R^{2A}$ and $R^{2B}$ are independently selected from the group consisting of hydrogen and hydrocarbyl;
wherein $R^{3A}$, $R^{3B}$, $R^{5A}$, and $R^{5B}$ are independently selected from the group consisting of hydrogen, alkyl; cycloalkyl; alkenyl; alkynyl; heterocyclyl; quaternary heterocyclyl, oxo; aryl-$R^5$; —$OR^9$; —$NR^9R^{10}$; —$SR^9$; —$S(O)R^9$; —$SO_2R^9$; and —$SO_3R^9$;
wherein $R^9$ and $R^{10}$ are independently selected from the group consisting of hydrogen; hydrocarbyl; amino; and hydrocarbylamino;

wherein $R^5$ is selected from the group consisting of hydrogen; hydrocarbyl, heterocyclyl; quaternary heterocyclyl; —$OR^9$; —$SR^9$; —$S(O)R^9$; —$SO_2R^9$; and —$SO_3R^9$;
wherein when $R^5$ is said cycloalkyl, aryl or heterocyclyl, said cycloalkyl, aryl or heterocyclyl are optionally substituted with —NH—X—R or —O—X—R;
wherein X is selected from the group consisting of —(C=O)$_s$-alkyl-; —(C=O)$_s$-alkyl-NH—; —(C=O)$_s$-alkyl-O—; —(C=O)$_s$-alkyl-(C=O)$_t$; and a covalent bond, wherein s and t are independently 0 or 1;
wherein R is selected from the group consisting of monosaccharides, disaccharides, and polysaccharides, wherein said monosaccharides, disaccharides, and polysaccharides are optionally protected with one or more sugar protecting groups;
wherein $R^9$ and $R^{10}$ are as previously defined;
wherein, when $R^5 \approx H$, $R^5$ is optionally substituted with one or more radicals independently selected from the group consisting of halogen; —$NO_2$; —CN; oxo; hydrocarbyl; —$OR^{13}$; —$NR^{13}R^{14}$; —$SR^{13}$; —$S(O)R^{13}$; —$SO_2R^{13}$; —$SO_3R^{13}$; —$NR^{13}OR^{14}$; —$NR^{13}NR^{14}R^{15}$; —$CO_2R^{13}$; —OM; —$SO_2OM$; —$SO_2NR^{13}R^{14}$; —$C(O)NR^{13}R^{14}$; —C(O)OM; —$COR^{13}$; —$NR^{13}C(O)R^{14}$; —$NR^{13}C(O)NR^{14}R^{15}$; —$NR^{13}CO_2R^{14}$; —$OC(O)R^{13}$; —$OC(O)NR^{13}R^{14}$; —$NR^{13}SOR^{14}$; —$NR^{13}SO_2R^{14}$; —$NR^{13}SONR^{14}R^{15}$; —$NR^{13}SO_2NR^{14}R^{15}$; —$PR^{13}R^{14}$; —$P(O)R^{13}R^{14}$; —$P^+R^{13}R^{14}R^{15}A^-$; —$P(OR^{13})OR^{14}$; —$S^+R^{13}R^{14}A^-$; and —$N^+R^{13}R^{14}R^{15}A^-$;
wherein $R^{13}$, $R^{14}$, and $R^{15}$ are independently selected from the group consisting of hydrogen and hydrocarbyl;
wherein $A^-$ is a pharmaceutically acceptable anion;
wherein M is a pharmaceutically acceptable cation;
wherein one or more $R^6$ radicals are independently selected from the group consisting of hydrogen; halogen; —CN; —$NO_2$; hydrocarbyl; —$R^5$; —$OR^{13}$;

—NR$^{13}$R$^{14}$; —SR$^{13}$; —S(O)R$^{13}$; —S(O)$_2$R$^{13}$; —SO$_3$R$^{13}$; —S$^+$R$^{13}$R$^{14}$A$^-$; —NR$^{13}$OR$^{14}$; —NR$^{13}$NR$^{14}$R$^{15}$; —OM; —SO$_2$OM; —SO$_2$NR$^{13}$R$^{14}$; —NR$^{14}$C(O)R$^{13}$; —C(O)OM; —S(O)NR$^{13}$R$^{14}$; —N$^+$R$^{13}$R$^{14}$R$^{15}$A—; —PR$^{13}$R$^{14}$; —P(O)R$^{13}$R$^{14}$; —P$^+$R$^{13}$R$^{14}$R$^{15}$A$^-$; amino acid residue; peptide residue; polypeptide residue; and carbohydrate residue;

wherein R$^{13}$, R$^{14}$, R$^{15}$, A$^-$, and M are as defined above; and wherein, in each instance, said hydrocarbyl may be optionally substituted with one or more groups comprising one or more heteroatoms, and wherein, in each instance, said hydrocarbyl optionally may have one or more carbon atoms replaced by one or more heteroatoms independently selected from the group consisting of oxygen, nitrogen, sulfur, phosphorus and combinations thereof.

40. A method of treating gallstones or a condition associated therewith in a subject comprising administering to said subject in need thereof a therapeutically effective amount of a compound of Formulas I-1 or I-2 represented by:

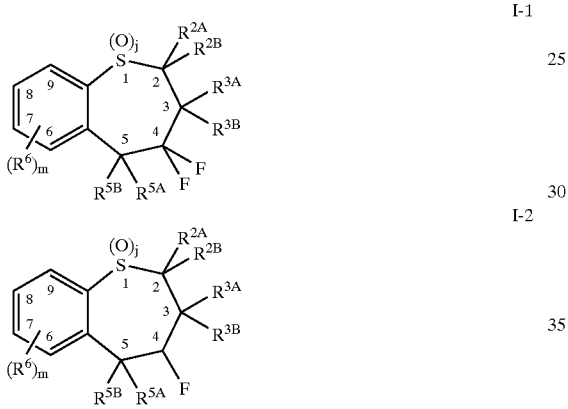

or a pharmaceutically acceptable salt, solvate, or prodrug thereof wherein j is 0, 1 or 2;

wherein m is 0, 1, 2, 3 or 4;

wherein R$^{2A}$ and R$^{2B}$ are independently selected from the group consisting of hydrogen and hydrocarbyl;

wherein R$^{3A}$, R$^{3B}$, R$^{5A}$, and R$^{5B}$ are independently selected from the group consisting of hydrogen, alkyl; cycloalkyl; alkenyl; alkynyl; heterocyclyl; quaternary heterocyclyl, oxo; aryl-R$^5$; —OR$^9$; —NR$^9$R$^{10}$; —SR$^9$; —S(O)R$^9$; —SO$_2$R$^9$; and —SO$_3$R$^9$;

wherein R$^9$ and R$^{10}$ are independently selected from the group consisting of hydrogen; hydrocarbyl; amino; and hydrocarbylamino;

wherein R$^5$ is selected from the group consisting of hydrogen; hydrocarbyl, heterocyclyl; quaternary heterocyclyl; —OR$^9$; —SR$^9$; —S(O)R$^9$; —SO$_2$R$^9$; and —SO$_3$R$^9$;

wherein when R$^5$ is said cycloalkyl, aryl or heterocyclyl, said cycloalkyl, aryl or heterocyclyl are optionally substituted with —NH—X—R or —O—X—R;

wherein X is selected from the group consisting of —(C=O)$_s$-alkyl-; —(C=O)$_s$-alkyl-NH—; —(C=O)$_s$-alkyl-O—; —(C=O)$_s$-alkyl-(C=O)$_t$; and a covalent bond, wherein s and t are independently 0 or 1;

wherein R is selected from the group consisting of monosaccharides, disaccharides, and polysaccharides, wherein said monosaccharides, disaccharides, and polysaccharides are optionally protected with one or more sugar protecting groups;

wherein R$^9$ and R$^{10}$ are as previously defined;

wherein, when R$^5$≈H, R$^5$ is optionally substituted with one or more radicals independently selected from the group consisting of halogen; —NO$_2$; —CN; oxo; hydrocarbyl; —OR$^{13}$; —NR$^{13}$R$^{14}$; —SR$^{13}$; —S(O)R$^{13}$; —SO$_2$R$^{13}$; —SO$_3$R$^{13}$; —NR$^{13}$OR$^{14}$; —NR$^{13}$NR$^{14}$R$^{15}$; —CO$_2$R$^{13}$; —OM; —SO$_2$OM; —SO$_2$NR$^{13}$R$^{14}$; —C(O)NR$^{13}$R$^{14}$; —C(O)OM; —COR$^{13}$; —NR$^{13}$C(O)R$^{14}$; —NR$^{13}$C(O)NR$^{14}$R$^{15}$; —NR$^{13}$CO$_2$R$^{14}$; —OC(O)R$^{13}$; —OC(O)NR$^{13}$R$^{14}$; —NR$^{13}$SOR$^{14}$; —NR$^{13}$SO$_2$R$^{14}$; —NR$^{13}$SONR$^{14}$R$^{15}$; —NR$^{13}$SO$_2$NR$^{14}$R$^{15}$; —PR$^{13}$R$^{14}$; —P(O)R$^{13}$R$^{14}$; —P$^+$R$^{13}$R$^{14}$R$^{15}$A$^-$; —P(OR$^{13}$)OR$^{14}$; —S$^+$R$^{13}$R$^{14}$A$^{31}$; and —N$^+$R$^{13}$R$^{14}$R$^{15}$A$^-$;

wherein R$^{13}$, R$^{14}$, and R$^{15}$ are independently selected from the group consisting of hydrogen and hydrocarbyl;

wherein A$^-$ is a pharmaceutically acceptable anion;

wherein M is a pharmaceutically acceptable cation;

wherein one or more R$^6$ radicals are independently selected from the group consisting of hydrogen; halogen; —CN; —NO$_2$; hydrocarbyl; —R$^5$; —OR$^{13}$; —NR$^{13}$R$^{14}$; —SR$^{13}$; —S(O)R$^{13}$; —S(O)$_2$R$^{13}$; —SO$_3$R$^{13}$; —S$^+$R$^{13}$R$^{14}$A$^-$; —NR$^{13}$OR$^{14}$; —NR$^{13}$NR$^{14}$R$^{15}$; —OM; —SO$_2$OM; —SO$_2$NR$^{13}$R$^{14}$; —NR$^{14}$C(O)R$^{13}$; —C(O)OM; —S(O)NR$^{13}$R$^{14}$; —N$^+$R$^{13}$R$^{14}$R$^{15}$A$^-$; —PR$^{13}$R$^{14}$; —P(O)R$^{13}$R$^{14}$; —P$^+$R$^{13}$R$^{14}$R$^{15}$A$^-$; amino acid residue; peptide residue; polypeptide residue; and carbohydrate residue;

wherein R$^{13}$, R$^{14}$, R$^{15}$, A$^-$, and M are as defined above; and wherein, in each instance, said hydrocarbyl may be optionally substituted with one or more groups comprising one or more heteroatoms, and wherein, in each instance, said hydrocarbyl optionally may have one or more carbon atoms replaced by one or more heteroatoms independently selected from the group consisting of oxygen, nitrogen, sulfur, phosphorus and combinations thereof.

41. The method of claim 39, wherein said subject is a mammal.

42. The method of claim 41, wherein said subject is a human.

43. The method of claim 40 wherein said subject is a mammal.

44. The method of claim 43, wherein said mammal is a human.

45. The method of claim 39, wherein said therapeutically effective amount is administered in a single dose or in multiple divided doses.

46. The method of claim 40 wherein said therapeutically effective amount is administered in a single dose or in multiple divided doses.

47. A method for treating a hyperlipidemic condition in a subject comprising administering to said subject in need thereof a therapeutically effective amount of a compound of Formulas I-17 or I-18 represented by:

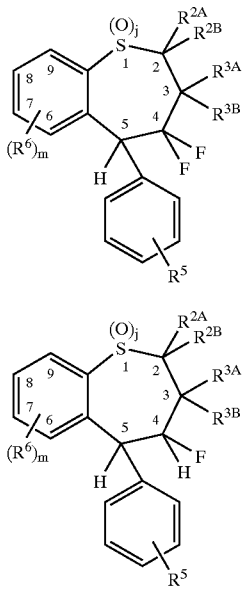

I-17

I-18 or a pharmaceutically acceptable salt, solvate, or prodrug thereof wherein j is 0, 1 or 2;

wherein m is 0, 1, 2, 3 or 4;

wherein $R^{2A}$ and $R^{2B}$ are independently selected from the group consisting of hydrogen and hydrocarbyl;

wherein $R^{3A}$, $R^{3B}$, $R^{5A}$, and $R^{5B}$ are independently selected from the group consisting of hydrogen, alkyl; cycloalkyl; alkenyl; alkynyl; heterocyclyl; quaternary heterocyclyl, oxo; aryl-$R^5$; —$OR^9$; —$NR^9R^{10}$; —$SR^9$; —$S(O)R^9$; —$SO_2R^9$; and —$SO_3R^9$;

wherein $R^9$ and $R^{10}$ are independently selected from the group consisting of hydrogen; hydrocarbyl; amino; and hydrocarbylamino;

wherein $R^5$ is selected from the group consisting of hydrogen; hydrocarbyl, heterocyclyl; quaternary heterocyclyl; —$OR^9$; —$SR^9$; —$S(O)R^9$; —$SO_2R^9$; and —$SO_3R^9$;

wherein when $R^5$ is said cycloalkyl, aryl or heterocyclyl, said cycloalkyl, aryl or heterocyclyl are optionally substituted with —NH—X—R or —O—X—R;

wherein X is selected from the group consisting of —(C=O)$_s$-alkyl-; —(C=O)$_s$-alkyl-NH—; —(C=O)$_s$-alkyl-O—; —(C=O)$_s$-alkyl-(C=O)$_t$; and a covalent bond, wherein s and t are independently 0 or 1;

wherein R is selected from the group consisting of monosaccharides, disaccharides, and polysaccharides, wherein said monosaccharides, disaccharides, and polysaccharides are optionally protected with one or more sugar protecting groups;

wherein $R^9$ and $R^{10}$ are as previously defined;

wherein, when $R^5 \approx H$, $R^5$ is optionally substituted with one or more radicals independently selected from the group consisting of halogen; —$NO_2$; —CN; oxo; hydrocarbyl; —$OR^{13}$; —$NR^{13}R^{14}$; —$SR^{13}$; —$S(O)R^{13}$; —$SO_2R^{13}$; —$SO_3R^{13}$; —$NR^{13}OR^{14}$; —$NR^{13}NR^{14}R^{15}$; —$CO_2R^{13}$; —OM; —$SO_2OM$; —$SO_2NR^{13}R^{14}$; —$C(O)NR^{13}R^{14}$; —$C(O)OM$; —$COR^{13}$; —$NR^{13}C(O)R^{14}$; —$NR^{13}C(O)NR^{14}R^{15}$; —$NR^{13}CO_2R^{14}$; —$OC(O)R^{13}$; —$OC(O)NR^{13}R^{14}$;

—$NR^{13}SOR^{14}$; —$NR^{13}SO_2R^{14}$; —$NR^{13}SONR^{14}R^{15}$; —$NR^{13}SO_2NR^{14}R^{15}$; —$PR^{13}R^{14}$; —$P(O)R^{13}R^{14}$; —$P^+R^{13}R^{14}R^{15}A^-$; —$P(OR^{13})OR^{14}$; —$S^+R^{13}R^{14}A^-$; and —$N^+R^{13}R^{14}R^{15}A^-$;

wherein $R^{13}$, $R^{14}$, and $R^{15}$ are independently selected from the group consisting of hydrogen and hydrocarbyl;

wherein $A^-$ is a pharmaceutically acceptable anion;

wherein M is a pharmaceutically acceptable cation;

wherein one or more $R^6$ radicals are independently selected from the group consisting of hydrogen; halogen; —CN; —$NO_2$; hydrocarbyl; —$R^5$; —$OR^{13}$; —$NR^{13}R^{14}$; —$SR^{13}$; —$S(O)R^{13}$; —$S(O)_2R^{13}$; —$SO_3R^{13}$; —$S^+R^{13}R^{14}A^-$; —$NR^{13}OR^{14}$; —$NR^{13}NR^{14}R^{15}$; —OM; —$SO_2OM$; —$SO_2NR^{13}R^{14}$; —$NR^{14}C(O)R^{13}$; —$C(O)OM$; —$S(O)NR^{13}R^{14}$; —$N^+R^{13}R^{14}R^{15}A-$; —$PR^{13}R^{14}$; —$P(O)R^{13}R^{14}$; —$P^+R^{13}R^{14}R^{15}A^-$; amino acid residue; peptide residue; polypeptide residue; and carbohydrate residue;

wherein $R^{13}$, $R^{14}$, $R^{15}$, $A^-$, and M are as defined above; and wherein, in each instance, said hydrocarbyl may be optionally substituted with one or more groups comprising one or more heteroatoms, and wherein, in each instance, said hydrocarbyl optionally may have one or more carbon atoms replaced by one or more heteroatoms independently selected from the group consisting of oxygen, nitrogen, sulfur, phosphorus and combinations thereof.

48. The method of claim 47 wherein said Formula I-17 comprises a member selected from the group consisting of I-21 and I-22 represented by:

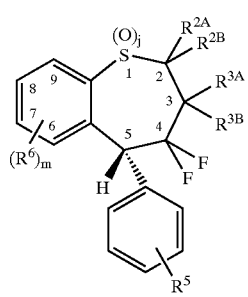

I-21

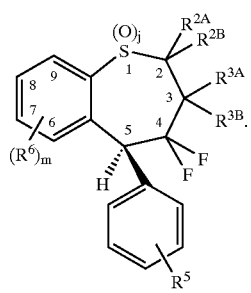

I-22

49. The method of claim 18 wherein said Formulas I-21 and I-22 comprise Formulas I-9 and I-10, respectively, represented by:

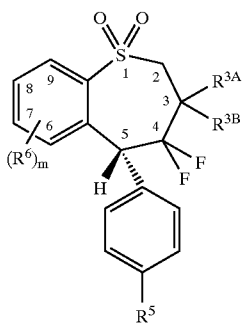

I-9

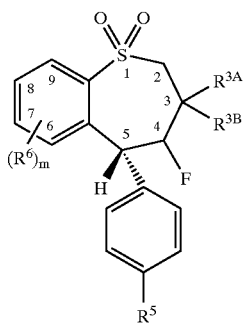

I-11

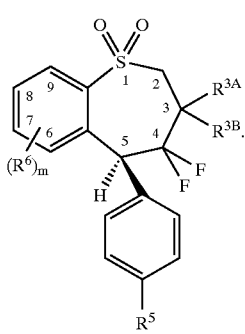

I-10

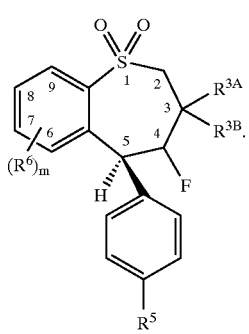

I-12

50. The method of claim 47 wherein said Formula I-18 comprises a member selected from the group consisting of I-19 and I-20 represented by:

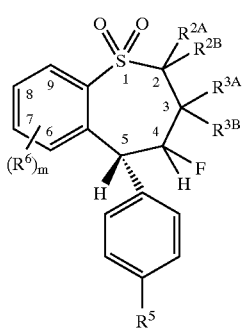

I-19

52. The method of claim 51 where said Formula I-11 comprises a member selected from the group consisting of Formulas I-13 and I-16 represented by:

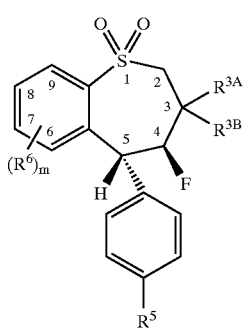

I-13

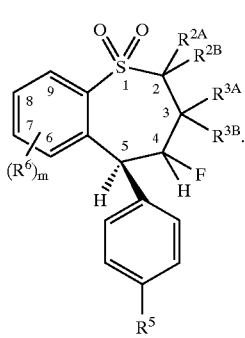

I-20

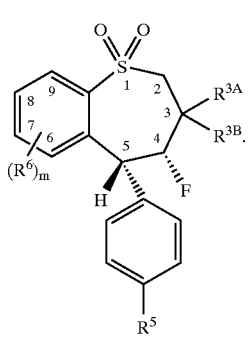

I-16

51. The method of claim 50 wherein said Formulas I-19 and I-20 comprise Formulas I-11 and I-12, respectively, represented by:

53. The method of claim 51 wherein said Formula I-12 comprises a member selected from the group consisting of Formulas I-14 and I-15 represented by:

I-14
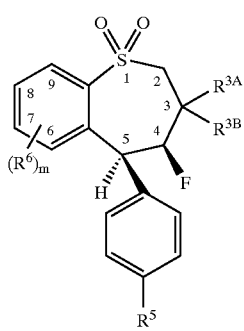
I-15
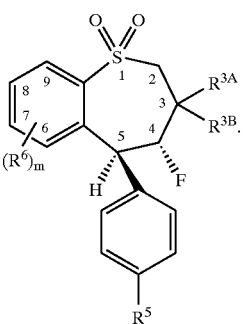
54. The method of claim 47 wherein said $R^5$ is a member selected from the group consisting of (1)–(69) and (70):
(1)
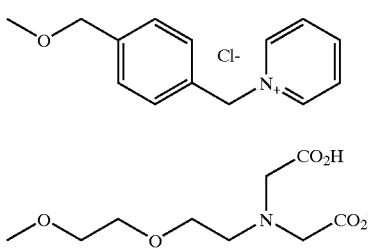
(2)
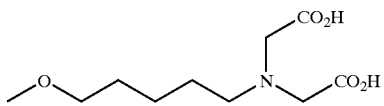
(3)
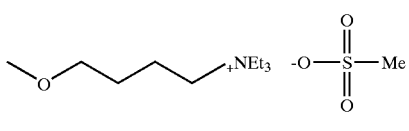
(4)
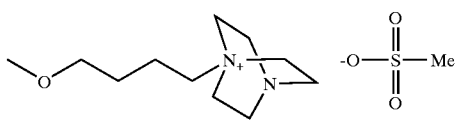
(5)
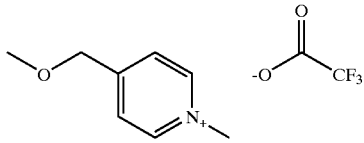
(6)
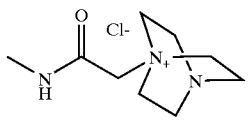
(7)
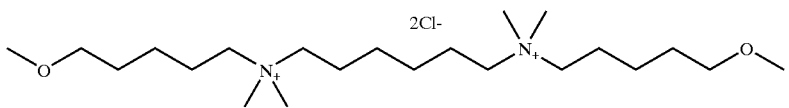
(8)
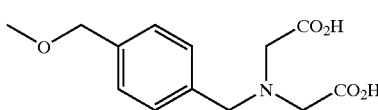
(9)
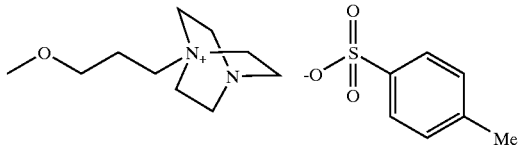
(10)
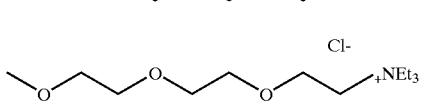
(11)
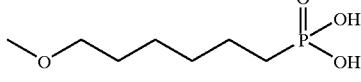
(12)
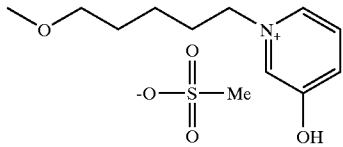
(13)
(14)
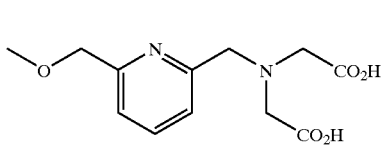
(15)
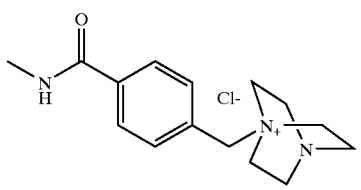

-continued
(15a)
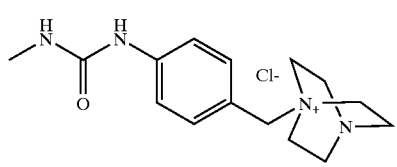
(16)
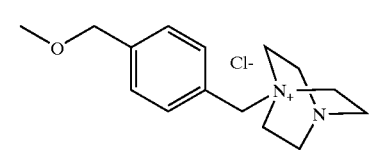
(17)
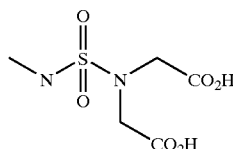
R = 1000 MW PEG
(18)
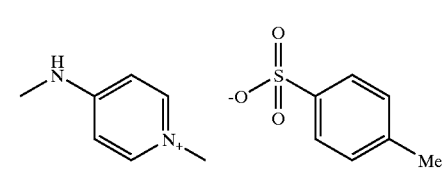
(19)
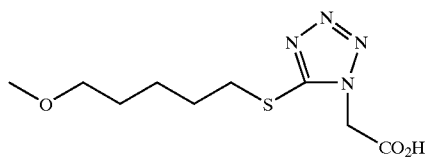
(20)
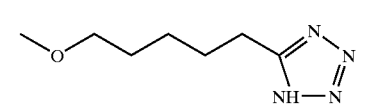
(21)
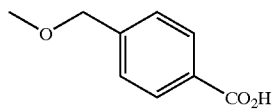
(22)
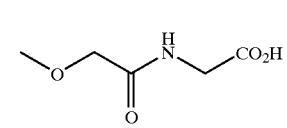
(23)
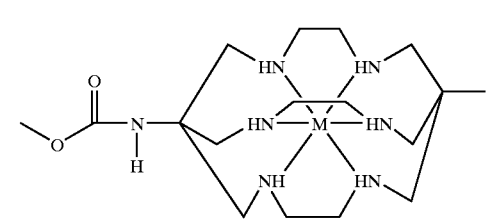
(24)
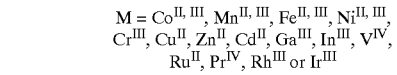
M = $Co^{II, III}$, $Mn^{II, III}$, $Fe^{II, III}$, $Ni^{II, III}$, $Cr^{III}$, $Cu^{II}$, $Zn^{II}$, $Cd^{II}$, $Ga^{III}$, $In^{III}$, $V^{IV}$, $Ru^{II}$, $Pr^{IV}$, $Rh^{III}$ or $Ir^{III}$
(25)
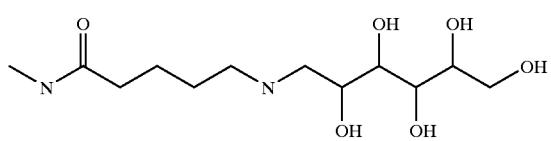
(26)
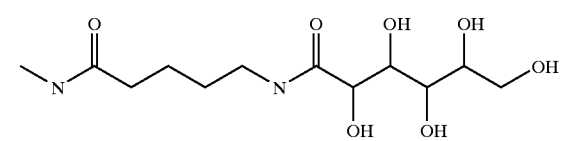
(27)
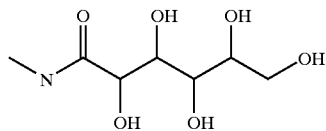
(28)
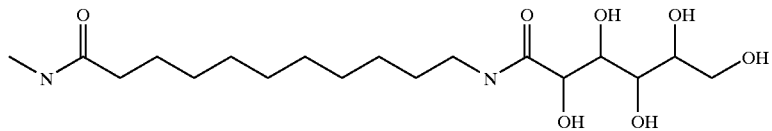
(29)
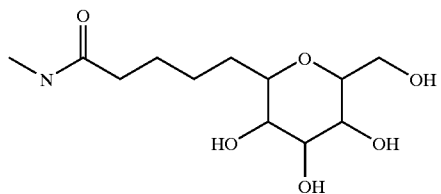
(30)
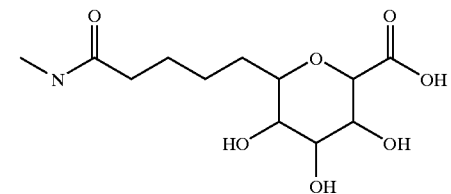

-continued
(31)
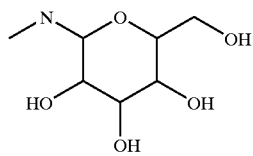
(32)
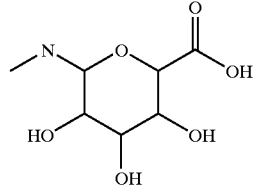
(33)
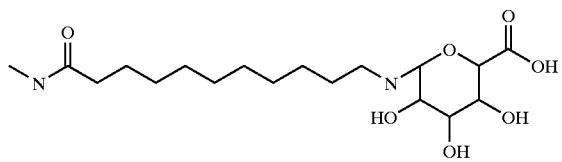
(34)
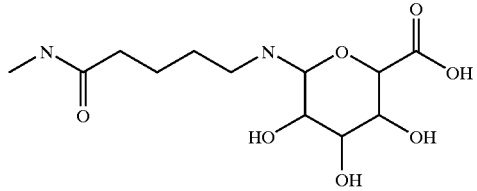
(35)
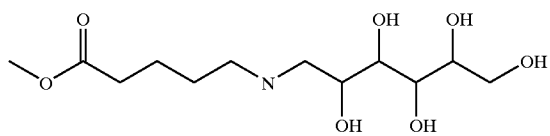
(36)
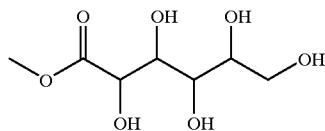
(37)
(38)
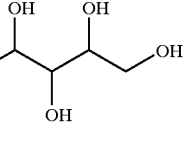
(39)
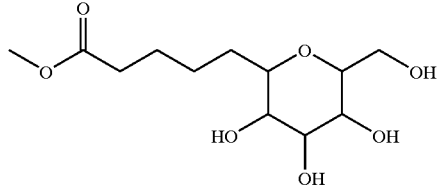
(40)
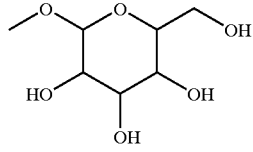
(41)
(42)
(43)
(44)
(45)
(46)
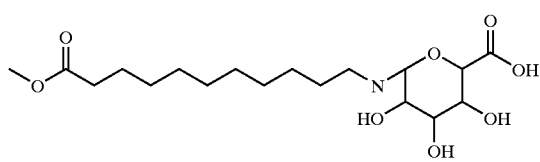

-continued
(47) 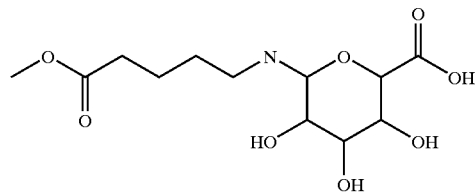
(48) 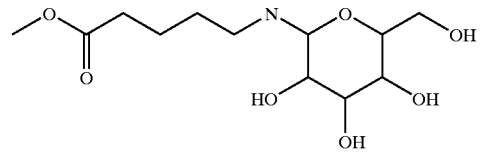
(49) 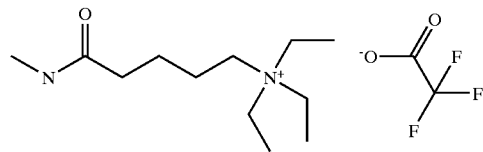
(50)
(51) 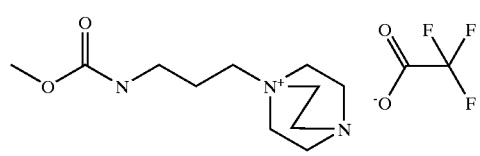
(52)
(53) 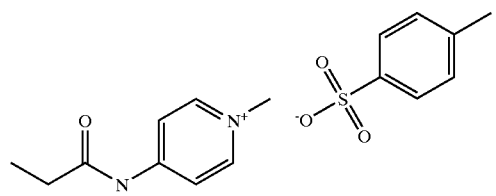
(54)
(55) 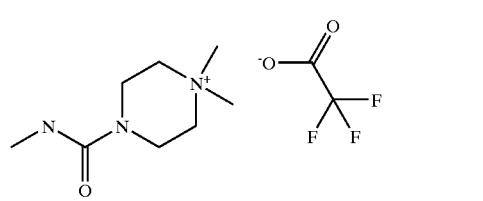
(56)
(57) 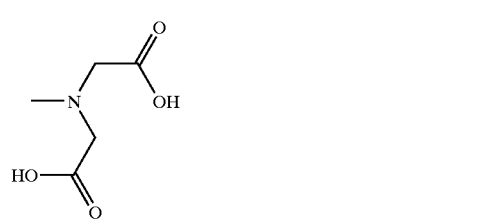
(58)
(59) 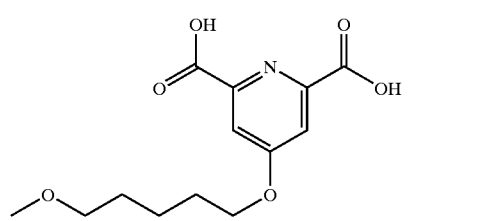
(60)
(61) 
(62) 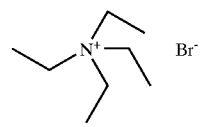

(63) 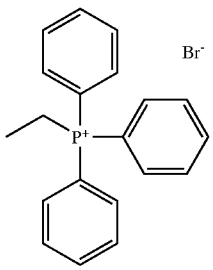

(64) 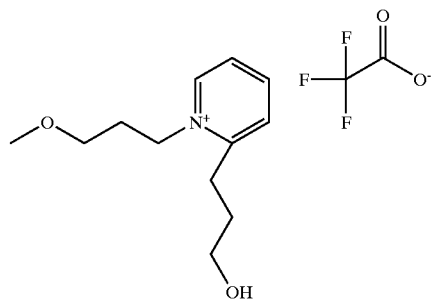

(65) 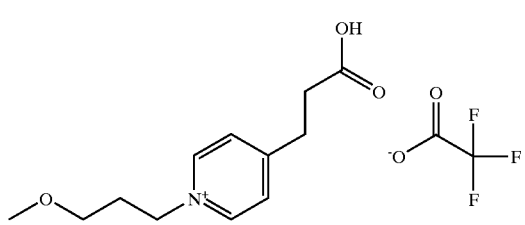

(66) 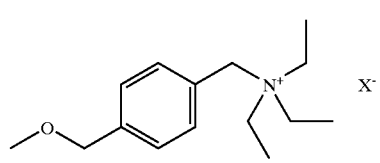

(67) 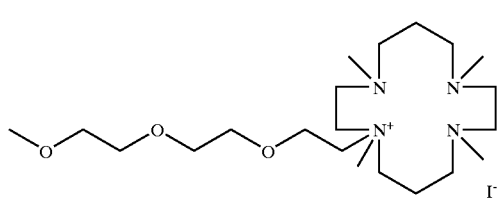

(68) 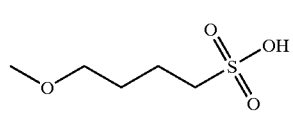

(69) 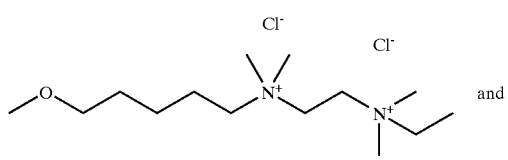

(70) 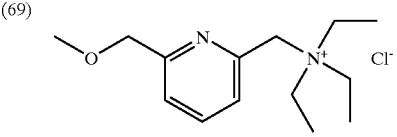

provided that when said $R^5$ is (7), (17) or (24), then said $R^{5A}$ is a left end of said $R^5$ and said $R^{5B}$ is a right end of said $R^5$ or vice versa.

55. A method for treating gallstones or a condition associated therewith in a subject in need thereof, said method comprising administering a therapeutically effective amount of a compound of Formulas I-17 or I-18 represented by:

I-17

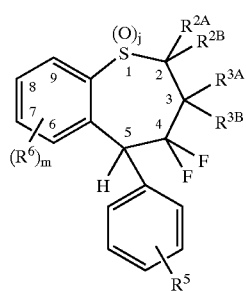

I-18

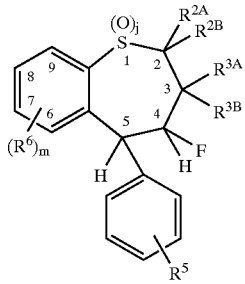

or a pharmaceutically acceptable salt, solvate, or prodrug thereof wherein j is 0, 1 or 2;
wherein m is 0, 1, 2, 3 or 4;
wherein $R^{2A}$ and $R^{2B}$ are independently selected from the group consisting of hydrogen and hydrocarbyl;
wherein $R^{3A}$, $R^{3B}$, $R^{5A}$, and $R^{5B}$ are independently selected from the group consisting of hydrogen, alkyl; cycloalkyl; alkenyl; alkynyl; heterocyclyl; quaternary heterocyclyl, oxo; aryl-R⁵; —OR⁹; —NR⁹R¹⁰ ; —SR⁹;
—S(O)R⁹; —SO₂R⁹; and —SO₃R⁹;

wherein R⁹ and R¹⁰ are independently selected from the group consisting of hydrogen; hydrocarbyl; amino; and hydrocarbylamino;

wherein R⁵ is selected from the group consisting of hydrogen; hydrocarbyl, heterocyclyl; quaternary heterocyclyl; —OR⁹; —SR⁹; —S(O)R⁹; —SO₂R⁹; and —SO₃R⁹;

wherein when R⁵ is said cycloalkyl, aryl or heterocyclyl, said cycloalkyl, aryl or heterocyclyl are optionally substituted with —NH—X—R or X—R;

wherein X is selected from the group consisting of —(C═O)$_s$-alkyl-; —(C═O)$_s$-alkyl-NH—; —(C═O)$_s$-alkyl-O—; —(C═O)$_s$-alkyl-(C═O)$_t$; and a covalent bond, wherein s and t are independently 0 or 1;

wherein R is selected from the group consisting of monosaccharides, disaccharides, and polysaccharides, wherein said monosaccharides, disaccharides, and polysaccharides are optionally protected with one or more sugar protecting groups;

wherein R⁹ and R¹⁰ are as previously defined;

wherein, when R⁵≠H, R⁵ is optionally substituted with one or more radicals independently selected from the group consisting of halogen; —NO₂; —CN; oxo; hydrocarbyl; —OR¹³; —NR¹³R¹⁴; —SR¹³; —S(O)R¹³; —SO₂R¹³; —SO₃R¹³; —NR¹³OR¹⁴; —NR¹³NR¹⁴R¹⁵; —CO₂R¹³; —OM; —SO₂OM; —SO₂NR¹³R¹⁴; —C(O)NR¹³R¹⁴; —C(O)OM; —COR¹³; —NR¹³C(O)R¹⁴; —NR¹³C(O)NR¹⁴R¹⁵; —NR¹³CO₂R¹⁴; —OC(O)R¹³; —OC(O)NR¹³R¹⁴; —NR¹³SOR¹⁴; —NR¹³SO₂R¹⁴; —NR¹³SONR¹⁴R¹⁵; —NR¹³SO₂NR¹⁴R¹⁵; —PR¹³R¹⁴; —P(O)R¹³R¹⁴; —P⁺R¹³R¹⁴R¹⁵A³¹; —P(OR¹³)OR¹⁴; —S⁺R¹³R¹⁴A⁻; and —N⁺R¹³R¹⁴R¹⁵A⁻;

wherein R¹³, R¹⁴, and R¹⁵ are independently selected from the group consisting of hydrogen and hydrocarbyl;

wherein A⁻ is a pharmaceutically acceptable anion;

wherein M is a pharmaceutically acceptable cation;

wherein one or more R⁶ radicals are independently selected from the group consisting of hydrogen; halogen; —CN; —NO₂; hydrocarbyl; —R⁵; —OR¹³; —NR¹³R¹⁴; —SR¹³; —S(O)R¹³; —S(O)₂R¹³; —SO₃R¹³; —S⁺R¹³R¹⁴A⁻; —NR¹³OR¹⁴; —NR¹³NR¹⁴R¹⁵; —OM; —SO₂OM; —SO₂NR¹³R¹⁴; —NR¹⁴C(O)R¹³; —C(O)OM; —S(O)N¹³R¹⁴; —N⁺R¹³R¹⁴R¹⁵A—; —PR¹³R¹⁴; —P(O)R¹³R¹⁴; —P⁺R¹³R¹⁴R¹⁵A⁻; amino acid residue; peptide residue; polypeptide residue; and carbohydrate residue;

wherein R¹³, R¹⁴, R¹⁵, A⁻, and M are as defined above; and wherein, in each instance, said hydrocarbyl may be optionally substituted with one or more groups comprising one or more heteroatoms, and wherein, in each instance, said hydrocarbyl optionally may have one or more carbon atoms replaced by one or more heteroatoms independently selected from the group consisting of oxygen, nitrogen, sulfur, phosphorus and combinations thereof.

56. The method of claim 55 wherein said Formula I-17 comprises a member selected from the group consisting of I-21 and I-22 represented by:

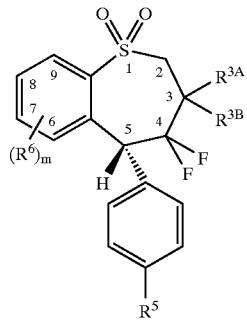

I-9

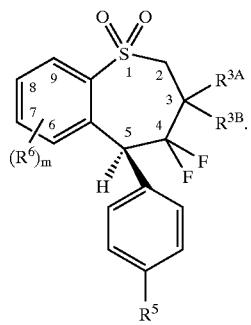

I-10

57. The method of claim 56 wherein said Formulas I-21 and I-22 comprise Formulas I-9 and I-10, respectively, represented by:

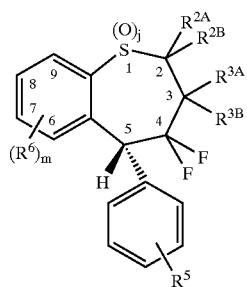

I-21

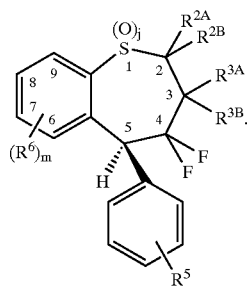

I-22

58. The method of claim 57 wherein said Formula I-18 comprises a member selected from the group consisting of I-19 and I-20 represented by:

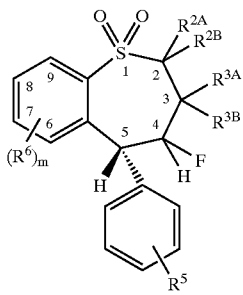

I-19

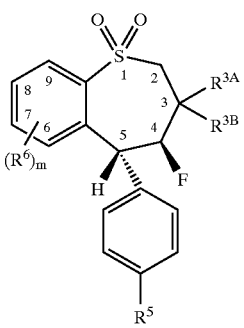

I-13

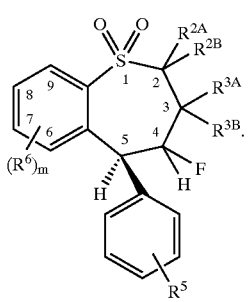

I-20

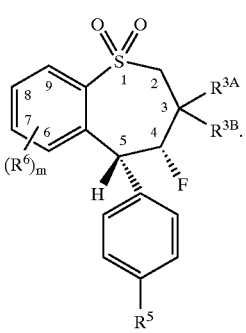

I-16

59. The method of claim 58 wherein said Formulas I-19 and I-20 comprise Formulas I-11 and I-12, respectively, represented by:

61. The method of claim 59 wherein said Formula I-12 comprises a member selected from the group consisting of Formulas I-14 and I-15 represented by:

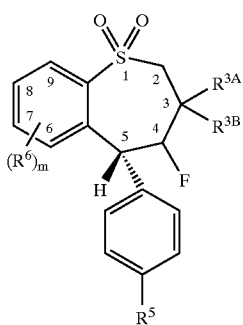

I-11

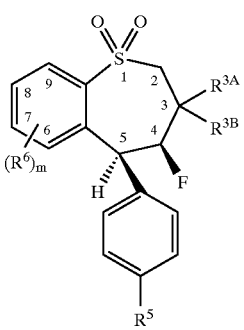

I-14

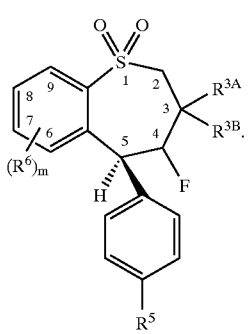

I-12

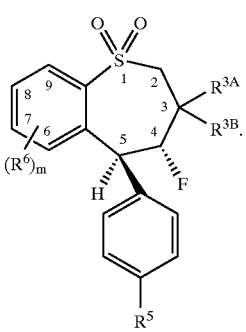

I-15

60. The method of claim 59 wherein said Formula I-11 comprises a member selected from the group consisting of Formulas I-13 and I-16 represented by:

62. The method of claim 55 wherein said $R^5$ is a member selected from the group consisting of (1)–(69) and (70):

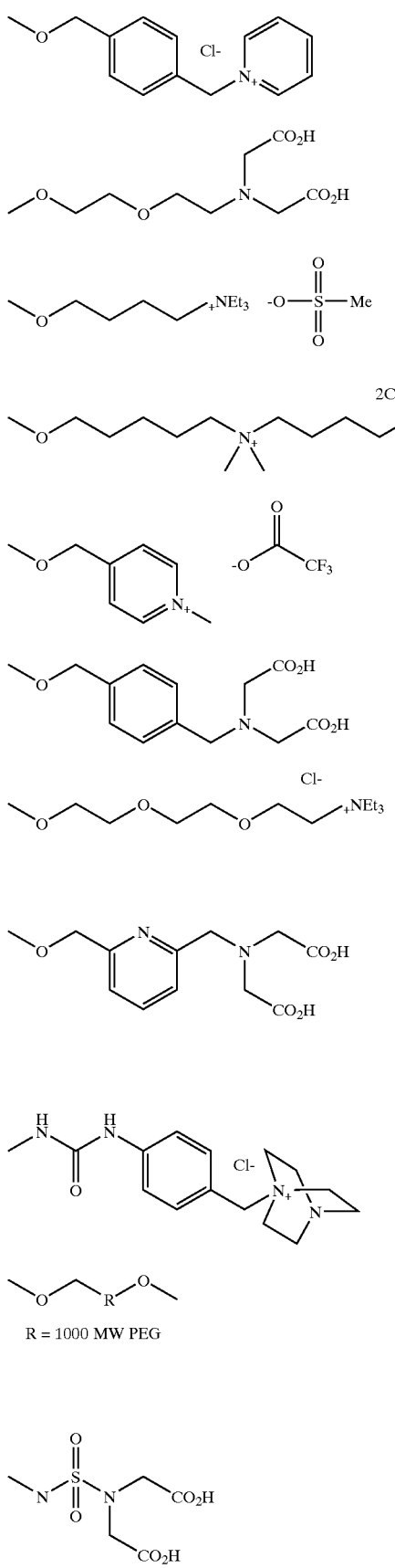

-continued
(21)
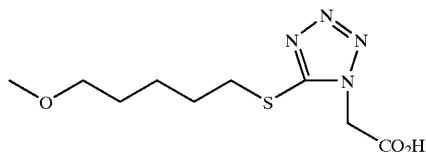
(22)
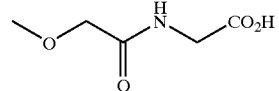
(23)
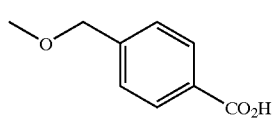
(24)
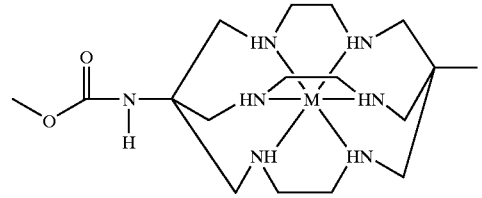
$M = Co^{II, III}, Mn^{II, III}, Fe^{II, III}, Ni^{II, III},$
$Cr^{III}, Cu^{II}, Zn^{II}, Cd^{II}, Ga^{III}, In^{III}, V^{IV},$
$Ru^{II}, Pr^{IV}, Rh^{III}$ or $Ir^{III}$
(25)
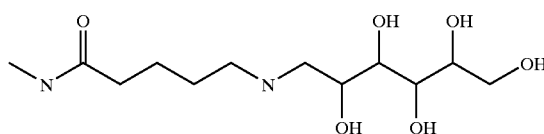
(26)
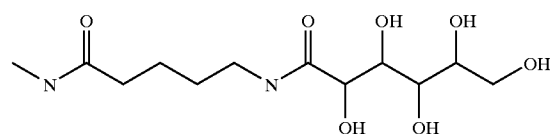
(27)
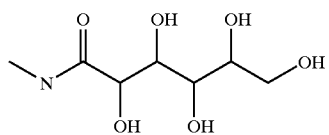
(28)
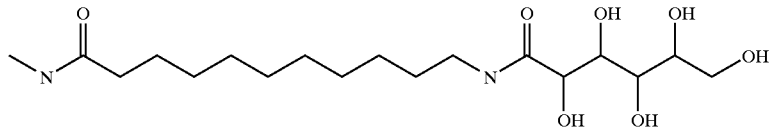
(29)
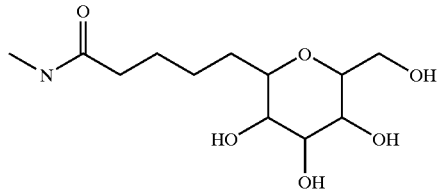
(30)
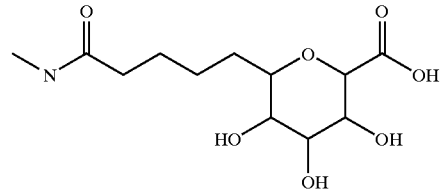
(31)
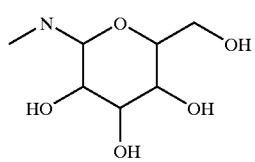
(32)
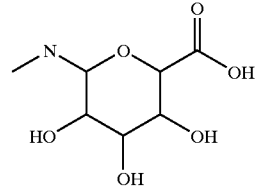
(33)
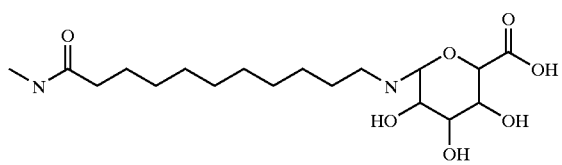
(34)
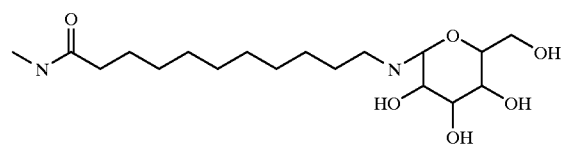

-continued
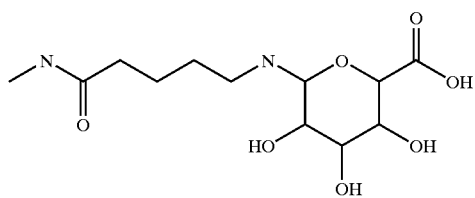(35)
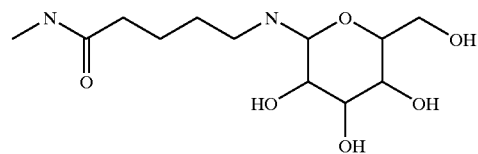(36)
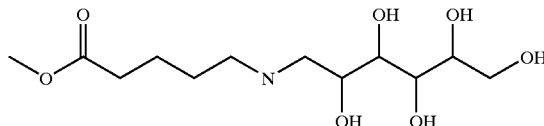(37)
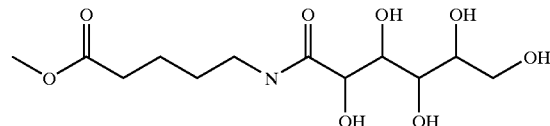(38)
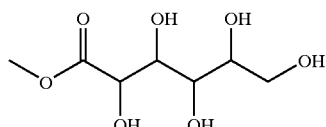(39)
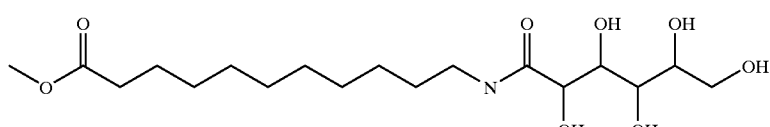(40)
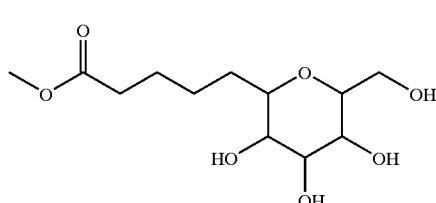(41)
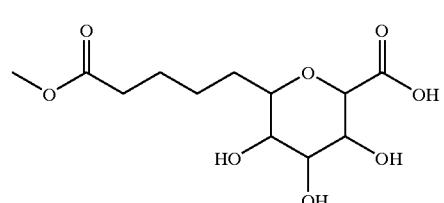(42)
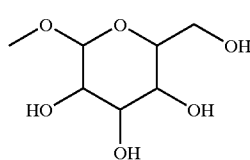(43)
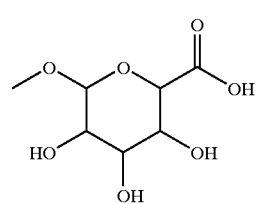(44)
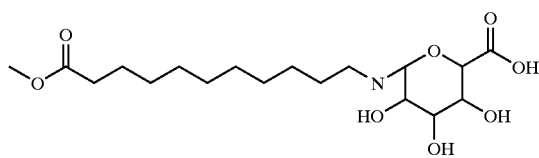(45)
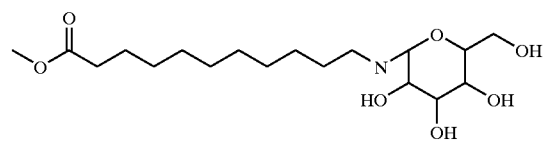(46)
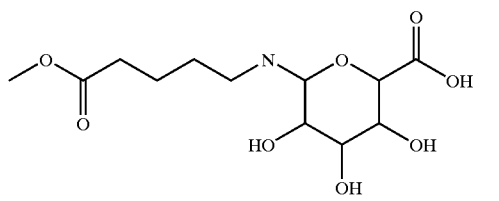(47)
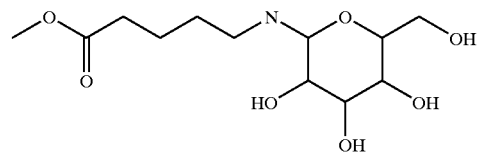(48)
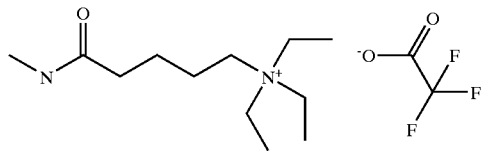(49)
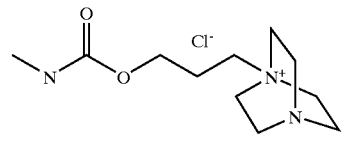(50)

-continued
(51) 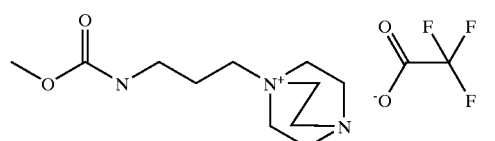
(52) 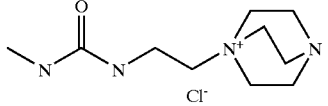
(53) 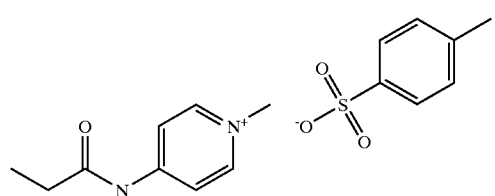
(54) 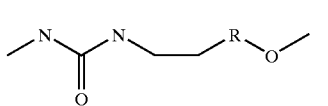
(55) 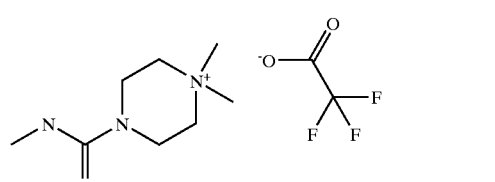
(56) 
(57) 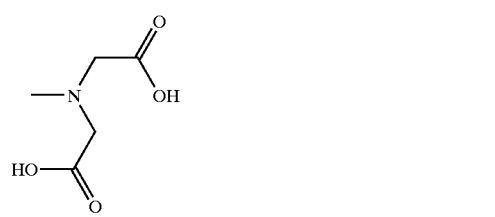
(58) 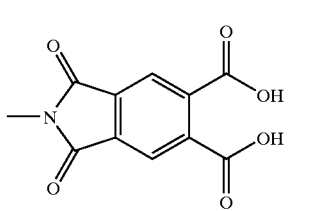
(59) 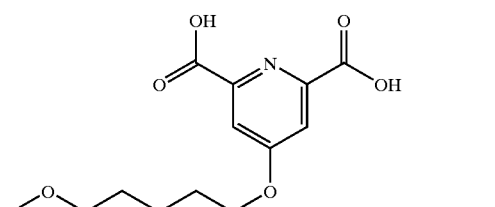
(60) 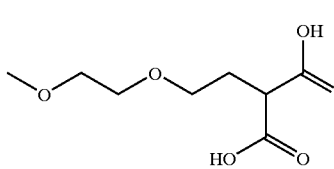
(61) 
(62) 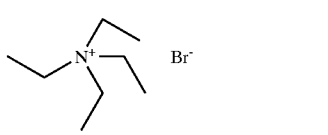
(63) 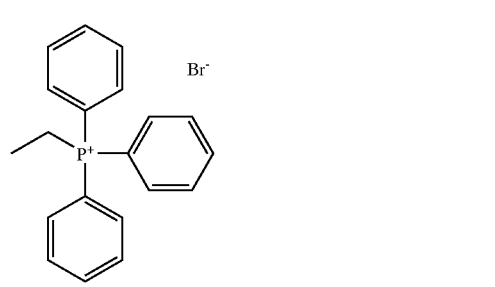
(64) 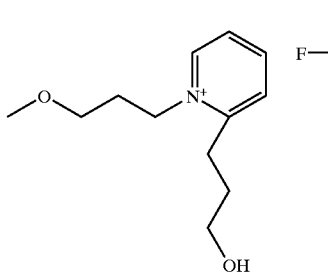
(65) 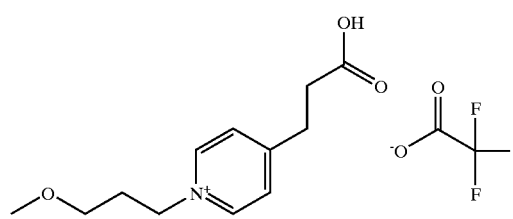
(66) 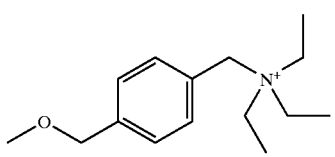

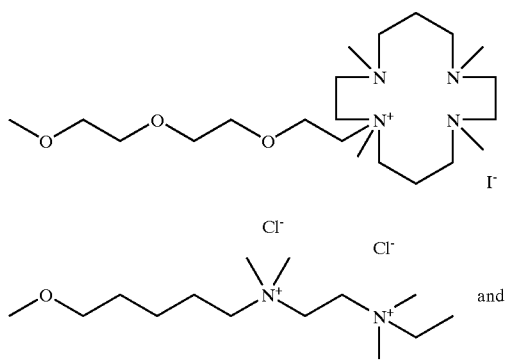 (67)

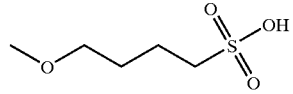 (68)

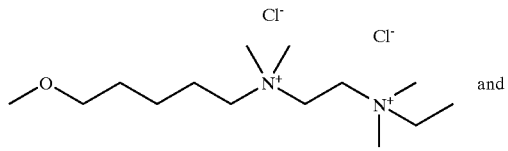 (69)

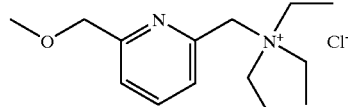 (70)

and provided that when said $R^5$ is (7), (17) or (24), then said $R^{5A}$ is a left end of said $R^5$ and said $R^{5B}$ is a right end of said $R^5$ or vice versa.

63. A method of forming a compound of the Formula I-1:

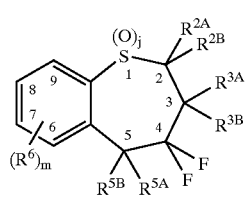

I-1 or a pharmaceutically acceptable salt, solvate, or prodrug thereof
wherein j is 0, 1 or 2;
wherein m is 0, 1, 2, 3 or 4;
wherein $R^{2A}$ and $R^{2B}$ are independently selected from the group consisting of hydrogen and hydrocarbyl;
wherein $R^{3A}$, $R^{3B}$, $R^{5A}$, and $R^{5B}$ are independently selected from the group consisting of hydrogen, alkyl; cycloalkyl; alkenyl; alkynyl; heterocyclyl; quaternary heterocyclyl, oxo; aryl-$R^5$; —$OR^9$; —$NR^9R^{10}$; —$SR^9$; —$S(O)R^9$; —$SO_2R^9$; and —$SO_3R^9$;
wherein $R^9$ and $R^{10}$ are independently selected from the group consisting of hydrogen; hydrocarbyl; amino; and hydrocarbylamino;
wherein $R^5$ is selected from the group consisting of hydrogen; hydrocarbyl; heterocyclyl; quaternary heterocyclyl; —$OR^9$; —$SR^9$; —$S(O)R^9$; —$SO_2R^9$; and —$SO_3R^9$;
wherein when $R^5$ is said cycloalkyl, aryl or heterocyclyl, said cycloalkyl, aryl or heterocyclyl are optionally substituted with —NH—X—R or —O—X—R;
wherein X is selected from the group consisting of —(C=O)$_s$-alkyl-; —(C=O)$_s$-alkyl-NH—; —(C=O)$_s$-alkyl-O—; —(C=O)$_s$-alkyl-(C=O)$_t$; and a covalent bond, wherein s and t are independently 0 or 1;
wherein R is selected from the group consisting of monosaccharides, disaccharides, and polysaccharides, wherein said monosaccharides, disaccharides, and polysaccharides are optionally protected with one or more sugar protecting groups;
wherein $R^9$ and $R^{10}$ are as previously defined;
wherein, when $R^5 \approx H$, $R^5$ is optionally substituted with one or more radicals independently selected from the group consisting of halogen; —$NO_2$; —CN; oxo; hydrocarbyl; —$OR^{13}$; —$NR^{13}R^{14}$; —$SR^{13}$; —$S(O)R^{13}$; —$SO_2R^{13}$; —$SO_3R^{13}$; —$NR^{13}OR^{14}$; —$NR^{13}NR^{14}R^{15}$; —$CO_2R^{13}$; —OM; —$SO_2OM$; —$SO_2NR^{13}R^{14}$; —$C(O)NR^{13}R^{14}$; —C(O)OM; —$COR^{13}$; —$NR^{13}C(O)R^{14}$; —$NR^{13}C(O)NR^{14}R^{15}$; —$NR^{13}CO_2R^{14}$; —$OC(O)R^{13}$; —$OC(O)NR^{13}R^{14}$; —$NR^{13}SOR^{14}$; —$NR^{13}SO_2R^{14}$; —$NR^{13}SONR^{14}R^{15}$; —$NR^{13}SO_2NR^{14}R^{15}$; —$PR^{13}R^{14}$; —$P(O)R^{13}R^{14}$; —$P^+R^{13}R^{14}R^{15}A^-$; —$P(OR^{13})OR^{14}$; —$S^+R^{13}R^{14}A^-$; and —$N^+R^{13}R^{14}R^{15}A^-$;
wherein $R^{13}$, $R^{14}$, and $R^{15}$ are independently selected from the group consisting of hydrogen and hydrocarbyl;
wherein $A^-$ is a pharmaceutically acceptable anion;
wherein M is a pharmaceutically acceptable cation;
wherein one or more $R^6$ radicals are independently selected from the group consisting of hydrogen; halogen; —CN; —$NO_2$; hydrocarbyl; —$R^5$; —$OR^{13}$; —$NR^{13}R^{14}$; —$SR^{13}$; —$S(O)R^{13}$; —$S(O)_2R^{13}$; —$SO_3R^{13}$; —$S^+R^{13}R^{14}A^-$; —$NR^{13}OR^{14}$; —$NR^{13}NR^{14}R^{15}$; —OM; —$SO_2OM$; —$SO_2NR^{13}R^{14}$; —$NR^{14}C(O)R^{13}$; —C(O)OM; —$S(O)NR^{13}R^{14}$; —$N^+R^{13}R^{14}R^{15}A—$; —$PR^{13}R^{14}$; —$P(O)R^{13}R^{14}$; —$P^+R^{13}R^{14}R^{15}A^-$; amino acid residue; peptide residue; polypeptide residue; and carbohydrate residue;
wherein $R^{13}$, $R^{14}$, $R^{15}$, $A^-$, and M are as defined above; and
wherein, in each instance, said hydrocarbyl may be optionally substituted with one or more groups comprising one or more heteroatoms, and wherein, in each instance, said hydrocarbyl optionally may have one or more carbon atoms replaced by one or more heteroatoms independently selected from the group consisting of oxygen, nitrogen, sulfur, phosphorus and combinations thereof,
said method comprising the steps of:
(a) forming a compound of Formula S1-78c:

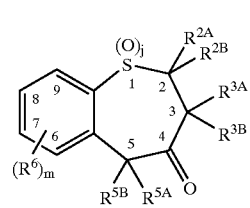

S1-78c wherein $R^{2A}$, $R^{2B}$, $R^{3A}$, $R^{3B}$, $R^{5A}$, $R^{5B}$, $R^6$, m and j are as previously defined; and (b) treating said compound of Formula S1-78c with diethylaminosulfur trifluoride to form said compound of Formula I-1.

64. The method of claim 63 wherein said treating step (b) is carried out in an inert solvent.

65. The method of claim 64 wherein said treating step (b) is carried out in said inert solvent cooled to from about −50° C. to about −78° C.

66. A method of forming a compound of Formula I-2:

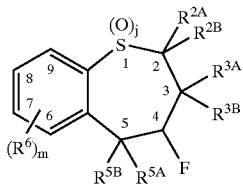

I-2 or a pharmaceutically acceptable salt, solvate, or prodrug thereof wherein j is 0, 1 or 2;

wherein m is 0, 1, 2, 3 or 4;

wherein $R^{2A}$ and $R^{2B}$ are independently selected from the group consisting of hydrogen and hydrocarbyl;

wherein $R^{3A}$, $R^{3B}$, $R^{5A}$, and $R^{5B}$ are independently selected from the group consisting of hydrogen, alkyl; cycloalkyl; alkenyl; alkynyl; heterocyclyl; quaternary heterocyclyl, oxo; aryl-$R^5$; —$OR^9$; —$NR^9R^{10}$; —$SR^9$; —$S(O)R^9$; —$SO_2R^9$; and —$SO_3R^9$;

wherein $R^9$ and $R^{10}$ are independently selected from the group consisting of hydrogen; hydrocarbyl; amino; and hydrocarbylamino;

wherein $R^5$ is selected from the group consisting of hydrogen; hydrocarbyl; heterocyclyl; quaternary heterocyclyl; —$OR^9$; —$SR^9$; —$S(O)R^9$; —$SO_2R^9$; and —$SO_3R^9$;

wherein when $R^5$ is said cycloalkyl, aryl or heterocyclyl, said cycloalkyl, aryl or heterocyclyl are optionally substituted with —NH—X—R or —O—X—R;

wherein X is selected from the group consisting of —(C=O)$_s$-alkyl-; —(C=O)$_s$-alkyl-NH—; —(C=O)$_s$-alkyl—O—; —(C=O)$_s$-alkyl-(C=O)$_t$; and a covalent bond, wherein s and t are independently 0 or 1;

wherein R is selected from the group consisting of monosaccharides, disaccharides, and polysaccharides, wherein said monosaccharides, disaccharides, and polysaccharides are optionally protected with one or more sugar protecting groups;

wherein $R^9$ and $R^{10}$ are as previously defined;

wherein, when $R^5 \approx H$, $R^5$ is optionally substituted with one or more radicals independently selected from the group consisting of halogen; —$NO_2$; —CN; oxo; hydrocarbyl; —$OR^{13}$; —$NR^{13}R^{14}$; —$SR^{13}$; —$S(O)R^{13}$; —$SO_2R^{13}$; —$SO_3R^{13}$; —$NR^{13}OR^{14}$; —$NR^{13}NR^{14}R^{15}$; —$CO_2R^{13}$; —OM; —$SO_2OM$; —$SO_2NR^{13}R^{14}$; —C(O)$NR^{13}R^{14}$; —C(O)OM; —$COR^{13}$; —$NR^{13}C(O)R^{14}$; —$NR^{13}C(O)NR^{14}R^{15}$; —$NR^{13}CO_2R^{14}$; —OC(O)$R^{13}$; —OC(O)$NR^{13}R^{14}$; —$NR^{13}SOR^{14}$; —$NR^{13}SO_2R^{14}$; —$NR^{13}SONR^{14}R^{15}$; —$NR^{13}SO_2NR^{14}R^{15}$; —$PR^{13}R^{14}$; —$P(O)R^{13}R^{14}$; —$P^+R^{13}R^{14}R^{15}A^-$; —$P(OR^{13})OR^{14}$; —$S^+R^{13}R^{14}A^-$; and —$N^+R^{13}R^{14}R^{15}A^-$;

wherein $R^{13}$, $R^{14}$, and $R^{15}$ are independently selected from the group consisting of hydrogen and hydrocarbyl;

wherein $A^-$ is a pharmaceutically acceptable anion;

wherein M is a pharmaceutically acceptable cation;

wherein one or more $R^6$ radicals are independently selected from the group consisting of hydrogen; halogen; —CN; —$NO_2$; hydrocarbyl; —$R^5$; —$OR^{13}$; —$NR^{13}R^{14}$; —$SR^{13}$; —$S(O)R^{13}$; —$S(O)_2R^{13}$; —$SO_3R^{13}$; —$S^+R^{13}R^{14}A^-$; —$NR^{13}OR^{14}$; —$NR^{13}NR^{13}R^{15}$; —OM; —$SO_2OM$; —$SO_2NR^{13}R^{14}$; —$NR^{14}C(O)R^{14}$; —C(O)OM; —$S(O)NR^{13}R^{14}$; —$N^+R^{13}R^{14}R^{15}A^-$; —$PR^{13}R^{14}$; —$P(O)R^{13}R^{14}$; —$P^+R^{13}R^{14}R^{15}A^-$; amino acid residue; peptide residue; polypeptide residue; and carbohydrate residue;

wherein $R^{13}$, $R^{14}$, $R^{15}$, $A^-$, and M are as defined above; and wherein, in each instance, said hydrocarbyl may be optionally substituted with one or more groups comprising one or more heteroatoms, and wherein, in each instance, said hydrocarbyl optionally may have one or more carbon atoms replaced by one or more heteroatoms independently selected from the group consisting of oxygen, nitrogen, sulfur, phosphorus and combinations thereof, said method comprising the steps of:
  (a) forming a compound of Formula S1-78a:

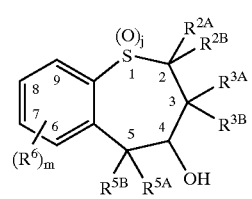

S1-78a wherein $R^{2A}$, $R^{2B}$, $R^{3A}$, $R^{3B}$, $R^{5A}$, $R^{5B}$, $R^6$, m and j are as previously defined; and (b) treating said compound of Formula S1-78a with diethylaminosulfur trifluoride to form said compound of Formula I-2.

67. The method of claim 66 wherein said treating step (b) is carried out in an inert solvent.

68. The method of claim 67 wherein said treating step (b) is carried out in solvent cooled to from about −50° C. to about −78° C.

69. The method of claim 63 wherein said compound of Formula I-1 comprises Formula I-17 represented by:

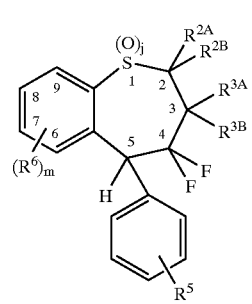

I-17 wherein $R^{2A}$, $R^{2B}$, $R^{3A}$, $R^{3B}$, $R^{5A}$, $R^{5B}$, $R^6$, m and j are as previously defined and $R^5$ is selected from the group consisting of (1)–(69) and (70):

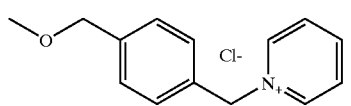 (1)
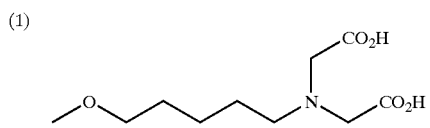 (2)
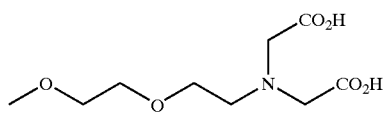 (3)
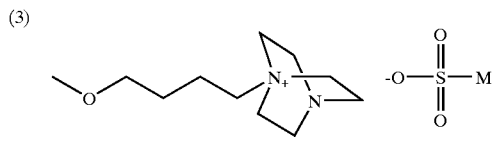 (4)
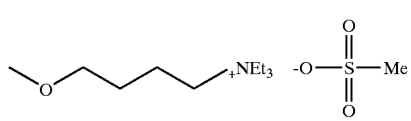 (5)
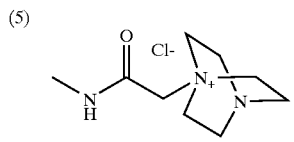 (6)
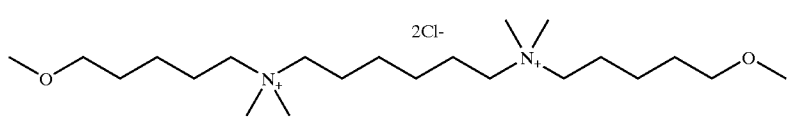 (7)
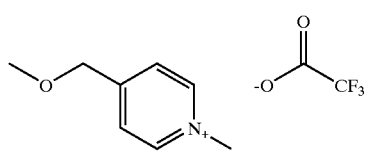 (8)
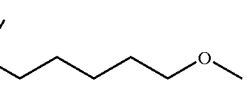 (9)
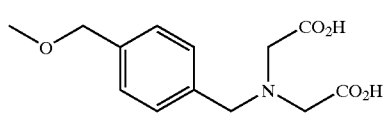 (10)
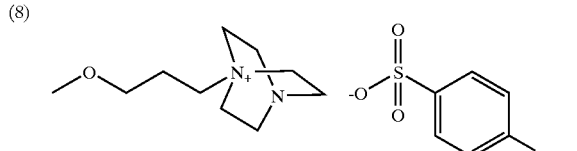 (11)
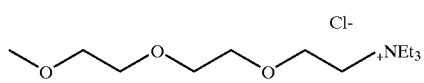 (12)
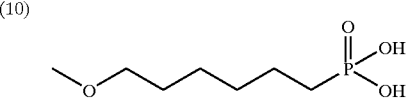 (13)
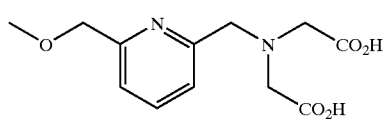 (14)
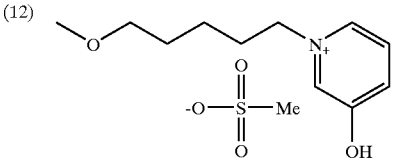 (15)
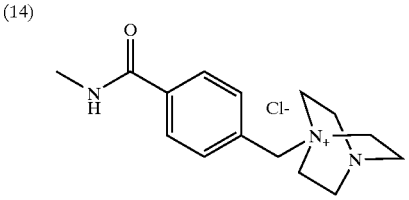 (15a)
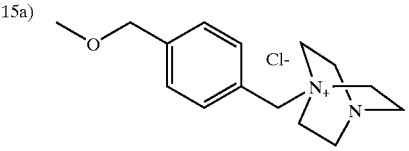 (16)
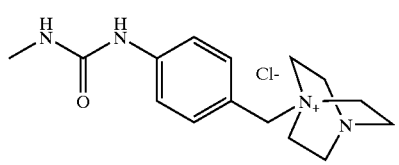 (17)
R = 1000 MW PEG
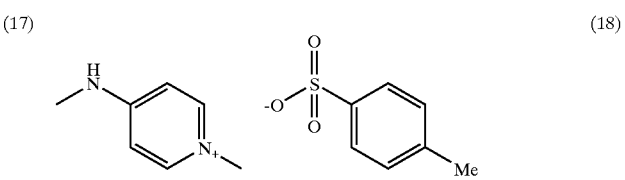 (18)
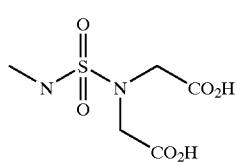 (19)
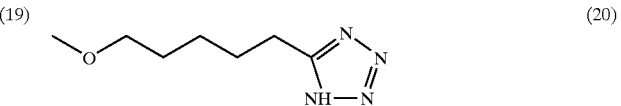 (20)

-continued
(21)
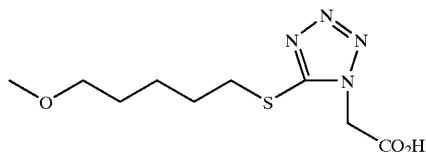
(22)
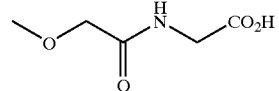
(23)
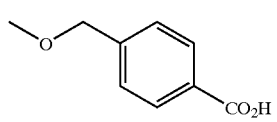
(24)
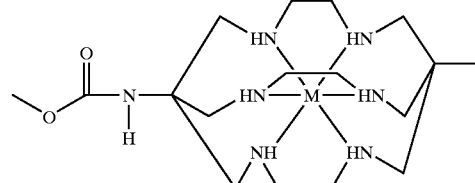
M = Co$^{II, III}$, Mn$^{II, III}$, Fe$^{II, III}$, Ni$^{II, III}$, Cr$^{III}$, Cu$^{II}$, Zn$^{II}$, Cd$^{II}$, Ga$^{III}$, In$^{III}$, V$^{IV}$, Ru$^{II}$, Pr$^{IV}$, Rh$^{III}$ or Ir$^{III}$
(25)
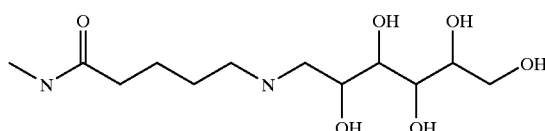
(26)
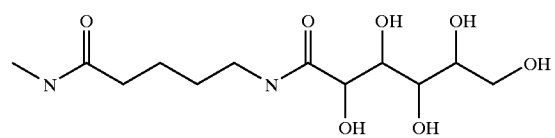
(27)
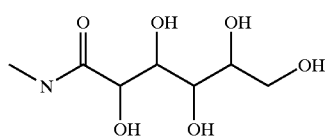
(28)
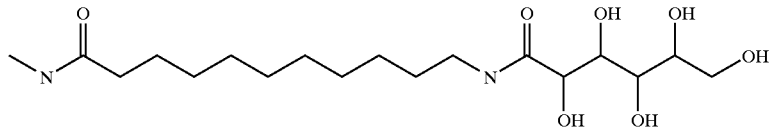
(29)
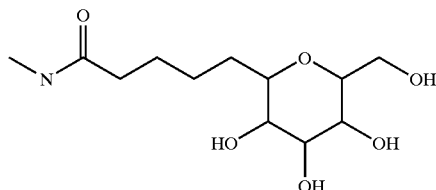
(30)
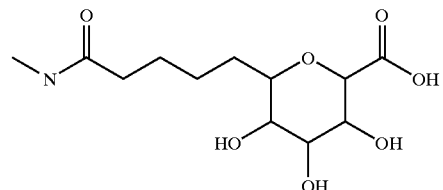
(31)
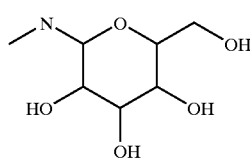
(32)
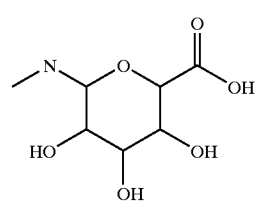
(33)
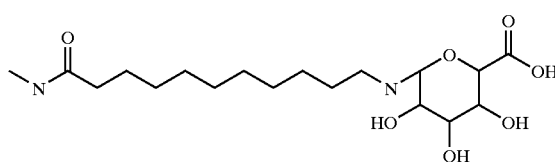
(34)
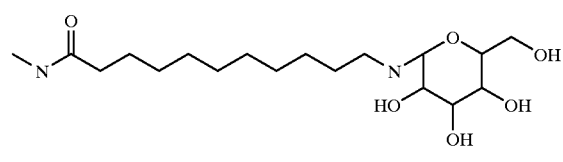

-continued
| (35) | (36) |
|---|---|
| 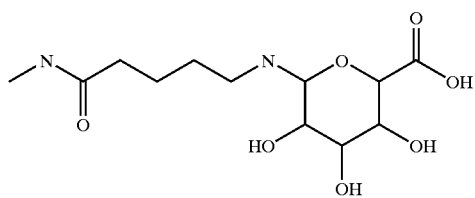 | 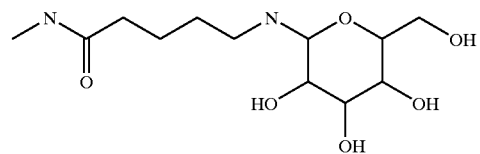 |
| (37) | (38) |
| 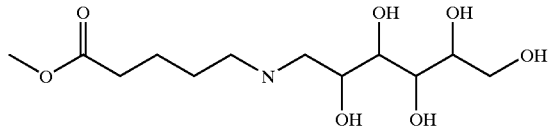 | 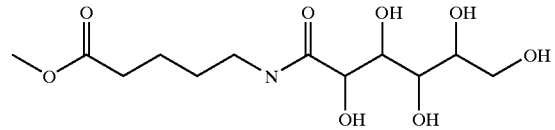 |
| (39) | |
| 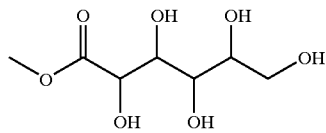 | |
| (40) | |
| 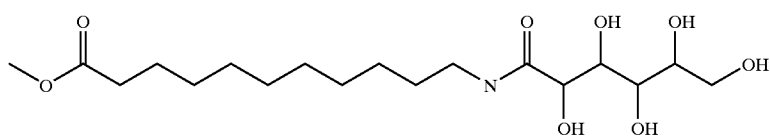 | |
| (41) | (42) |
| 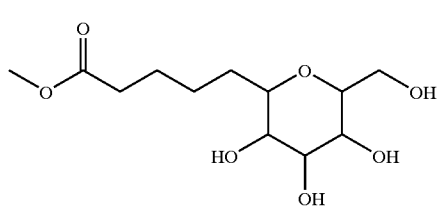 | 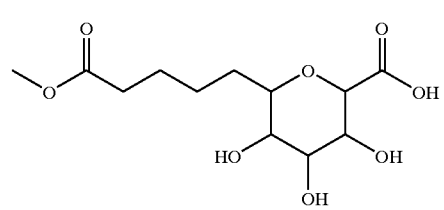 |
| (43) | (44) |
| 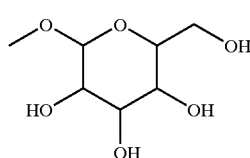 | 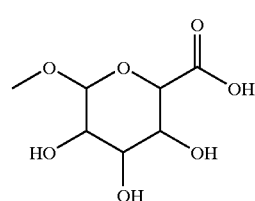 |
| (45) | (46) |
| 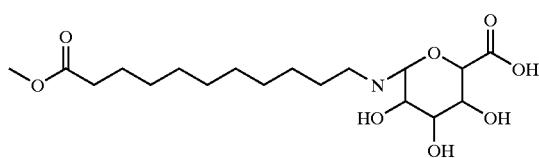 | 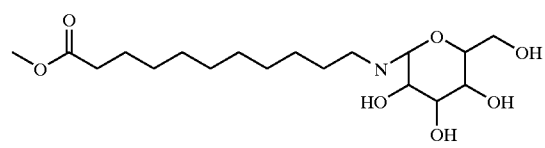 |
| (47) | (48) |
| 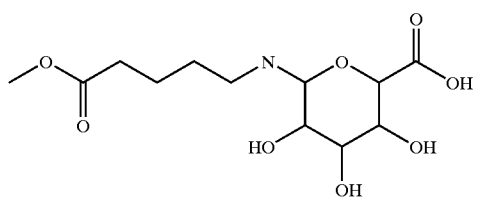 | 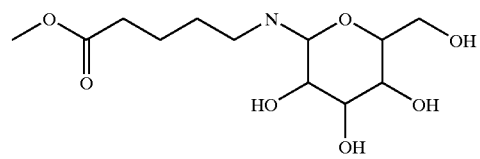 |
| (49) | (50) |
| 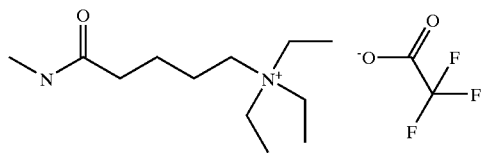 | 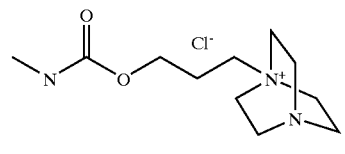 |

-continued
(51)
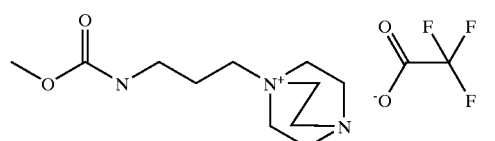
(52)
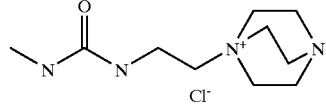
(53)
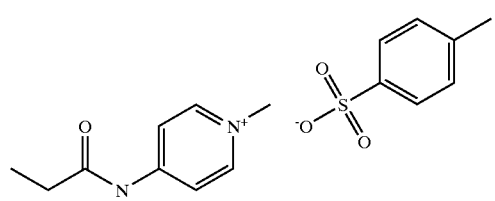
(54)
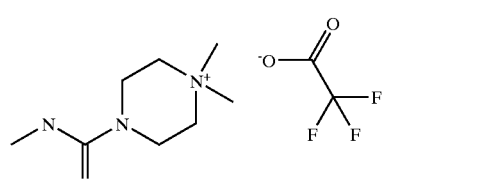
(55)
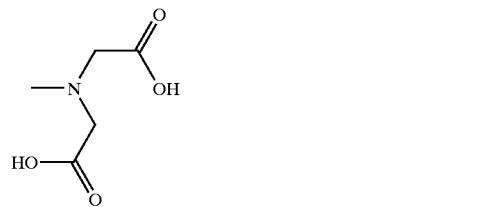
(56)
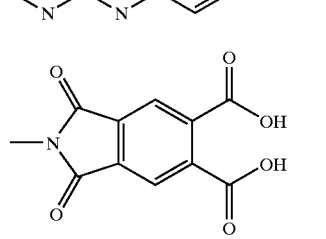
(57)
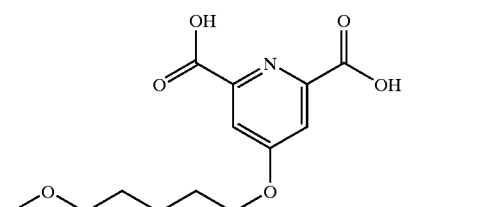
(58)
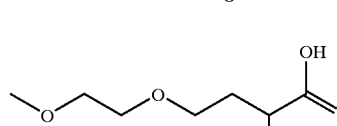
(59)
(60)
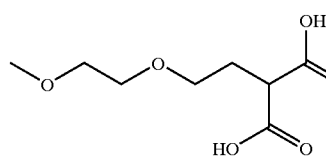
(61)
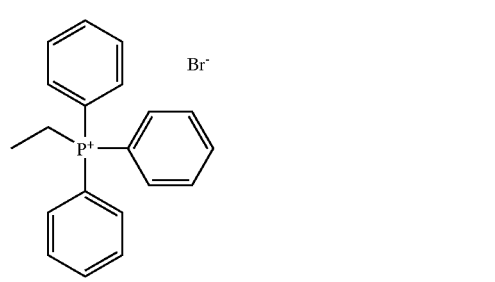
(62)
(63)
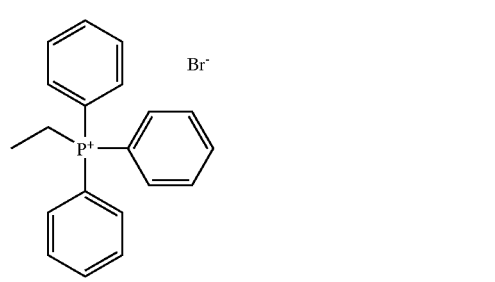
(64)
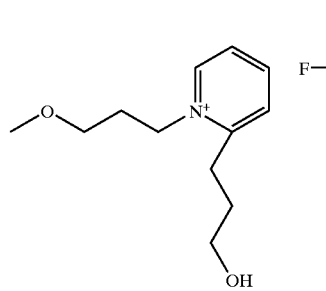
(65)
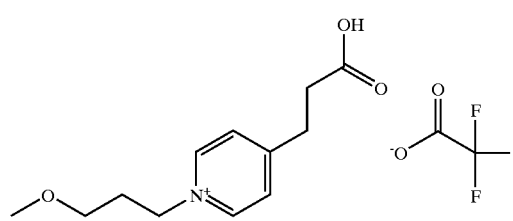
(66)
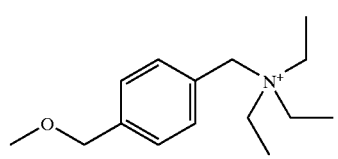

-continued

(67)
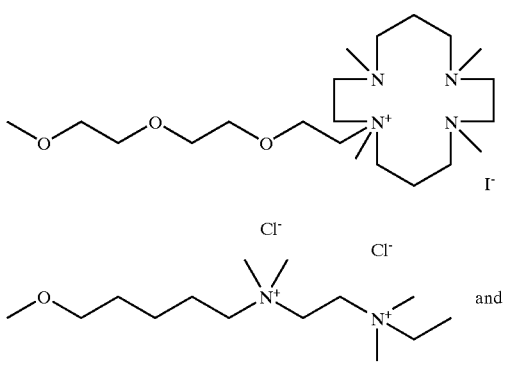

(68)
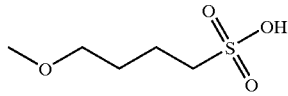

(69)
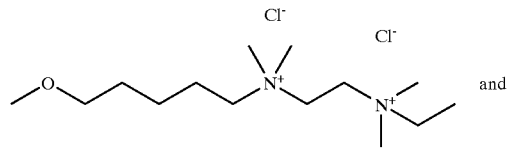
and

(70)
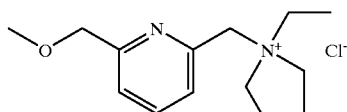

provided that when said $R^5$ is (7), (17) or (24), then said $R^{5A}$ is a left end of said $R^5$ and said $R^{5B}$ is a right end of said $R^5$ or vice versa.

70. The method of claim 69 wherein said Formula I-17 comprises Formulas I-21 or I-22 represented by:

I-21
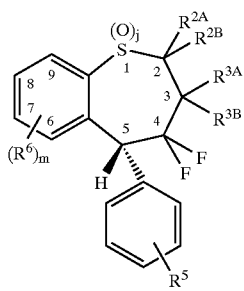

I-22
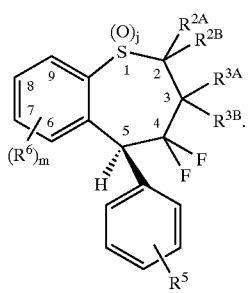

71. The method of claim 70 wherein said Formulas I-21 and I-22 comprise Formulas I-9 and I-10, respectively, represented by:

I-9
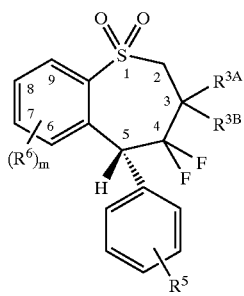

I-10
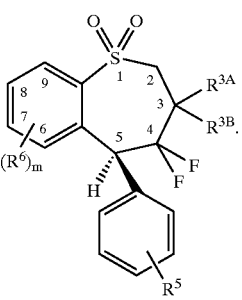

72. The method of claim 70 wherein said $R^5$ group is attached at least either at a meta position or at a para position of said phenyl ring attached to said 5-carbon position of said benzothiepene of said Formulas I-21 or I-22.

73. The method of claim 66 wherein said compound of Formula I-2 is selected from the group consisting of Formulas I-3 and I-4 represented by:

I-3
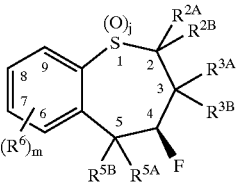

I-4
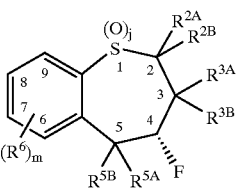

wherein $R^{2A}$, $R^{2B}$, $R^{3A}$, $R^{3B}$, $R^{5A}$, $R^{5B}$, $R^6$, m and j are as previously defined and said $R^5$ is selected from the group consisting of (1)–(69) and (70):

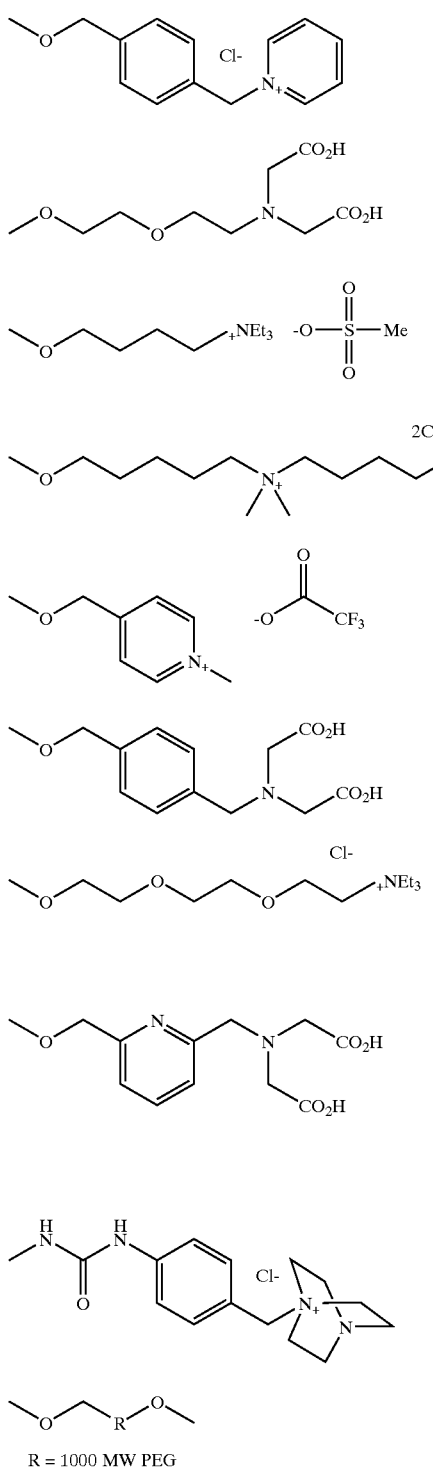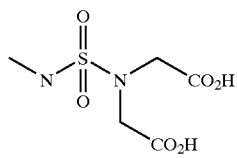

-continued
(21) 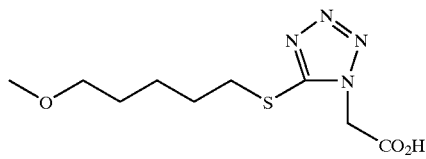
(22) 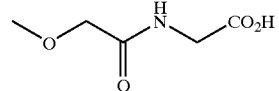
(23) 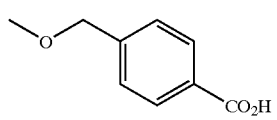
(24) 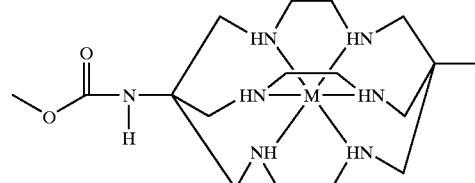
M = Co$^{II, III}$, Mn$^{II, III}$, Fe$^{II, III}$, Ni$^{II, III}$, Cr$^{III}$, Cu$^{II}$, Zn$^{II}$, Cd$^{II}$, Ga$^{III}$, In$^{III}$, V$^{IV}$, Ru$^{II}$, Pr$^{IV}$, Rh$^{III}$ or Ir$^{III}$
(25) 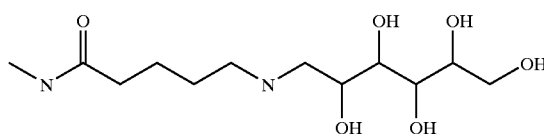
(26) 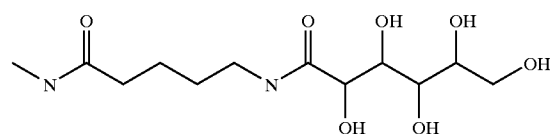
(27) 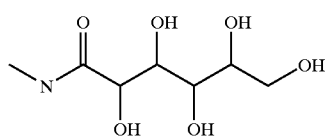
(28) 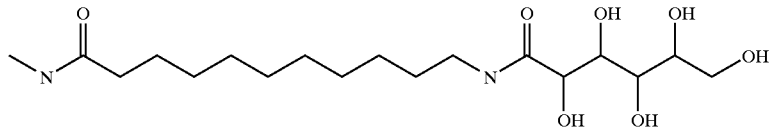
(29) 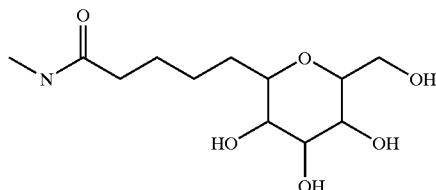
(30) 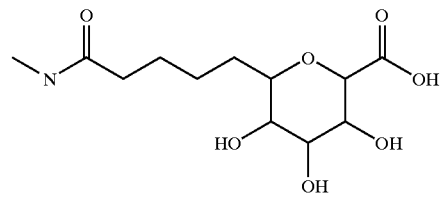
(31) 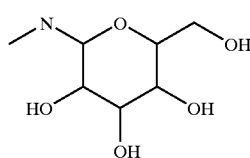
(32) 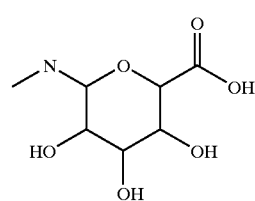
(33) 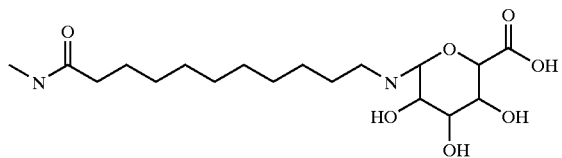
(34) 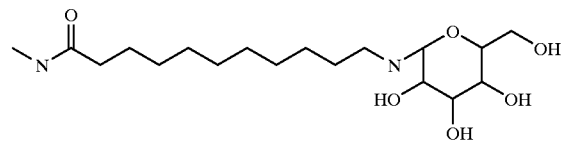

-continued
(35)
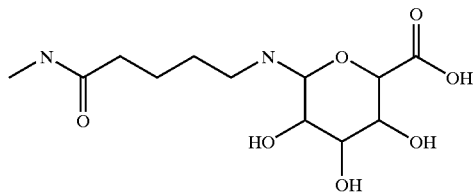
(36)
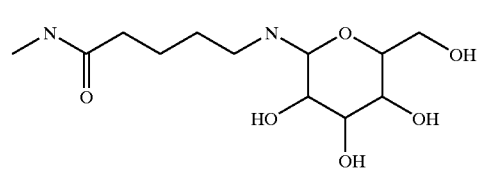
(37)
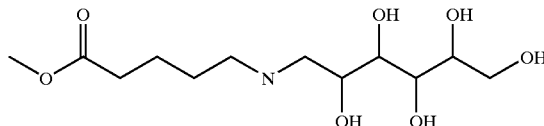
(38)
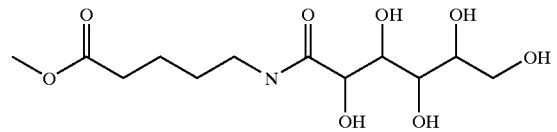
(39)
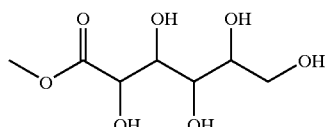
(40)
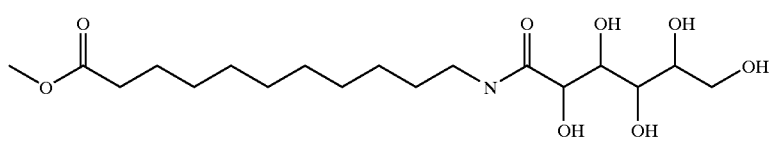
(41)
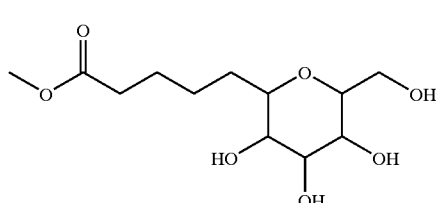
(42)
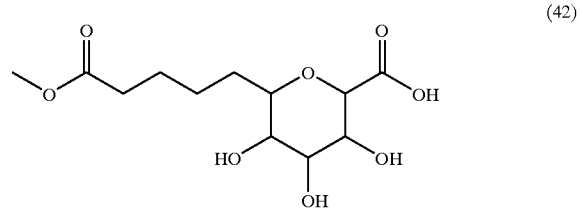
(43)
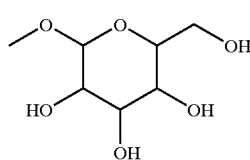
(44)
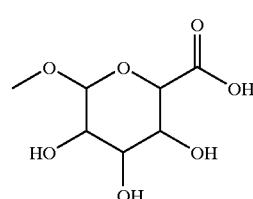
(45)
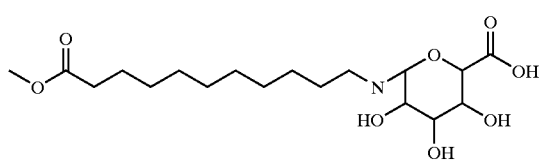
(46)
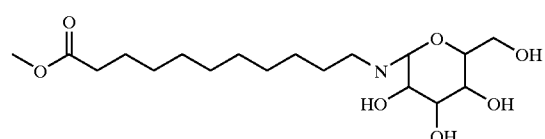
(47)
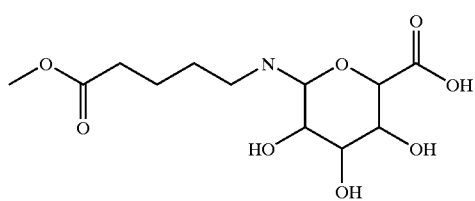
(48)
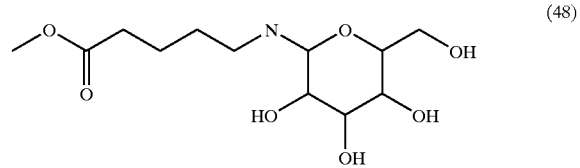
(49)
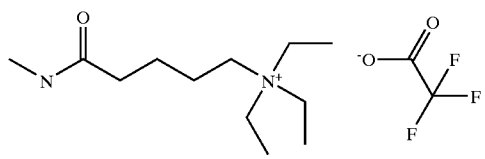
(50)
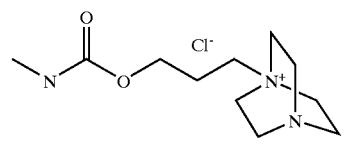

-continued
(51) 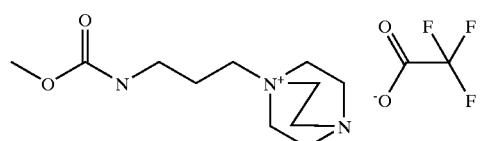
(52) 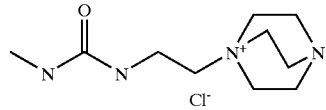
(53) 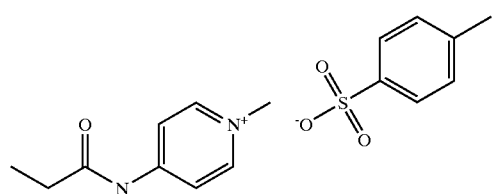
(54) 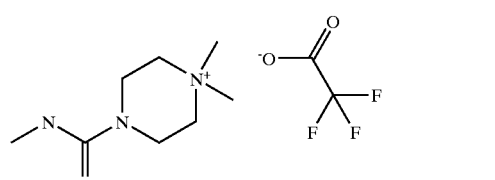
(55) 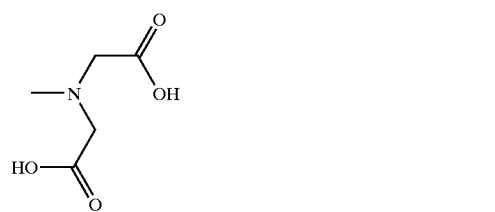
(56) 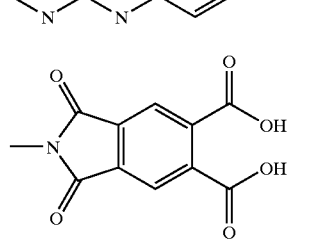
(57) 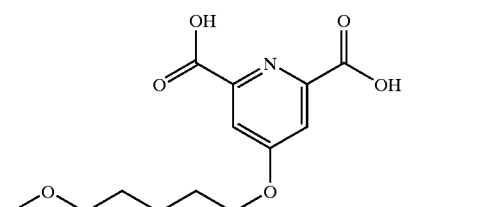
(58) 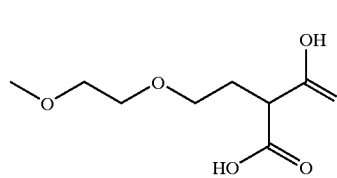
(59) 
(60) 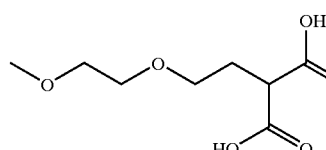
(61) 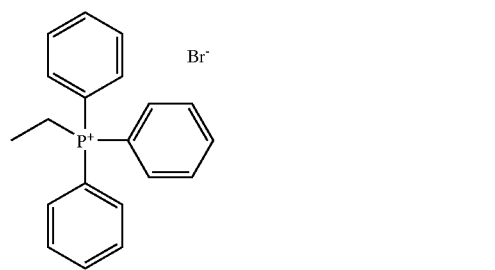
(62) 
(63) 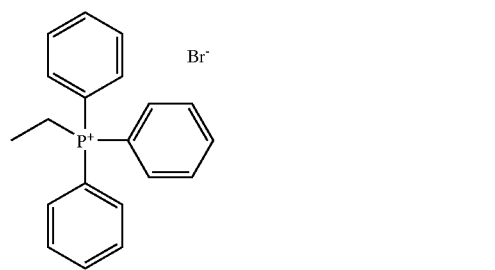
(64) 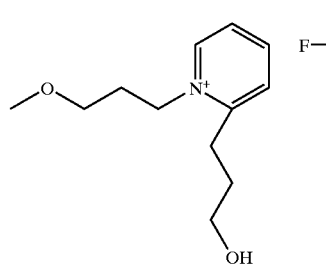
(65) 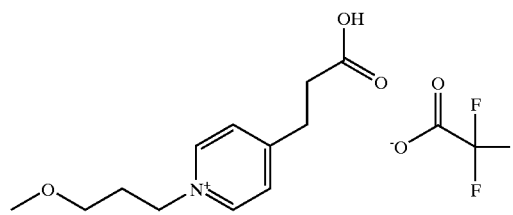
(66) 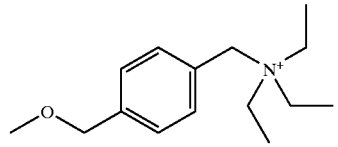

-continued

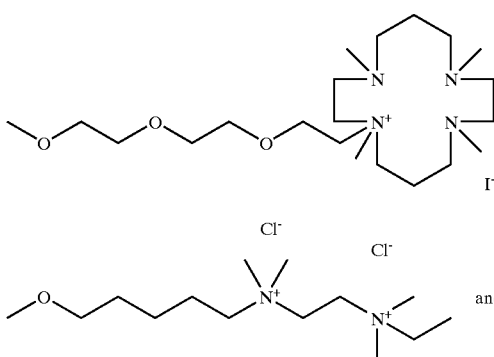
(67)

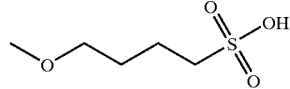
(68)

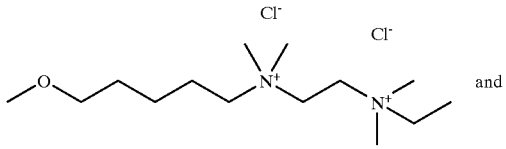
(69) and

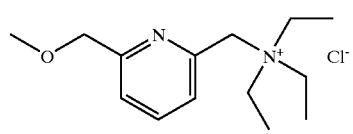
(70)

provided that when said $R^5$ is (7), (17) or (24), then said $R^{5A}$ is a left end of said $R^5$ and said $R^{5B}$ is a right end of said $R^5$ or vice versa.

74. The method of claim 73 wherein said Formula I-3 comprises a member selected from the group consisting of Formulas I-5 and I-6 represented by:

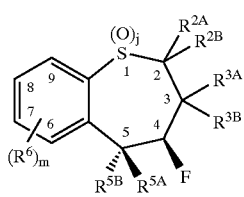
I-5

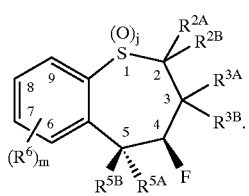
I-6

75. The method of claim 73 wherein said Formula I-4 comprises a member selected from the group consisting of Formulas I-7 and I-8 represented by:

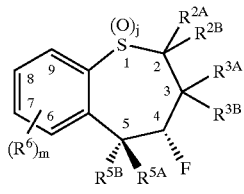
I-7

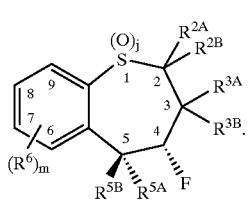
I-8

76. The method of claim 74 wherein said compounds of Formulas I-6 and I-5 comprise Formulas I-13 and I-14, respectively, represented by:

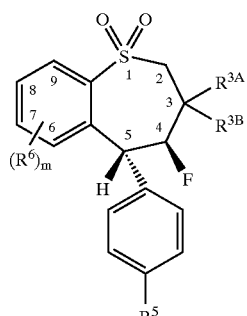
I-13

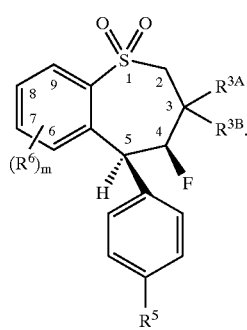
I-14

77. The method of claim 75 wherein said Formulas I-7 and I-8 comprise Formulas I-15 and I-16, respectively, represented by:

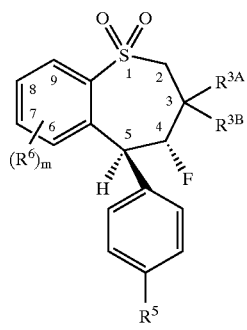
I-15

-continued

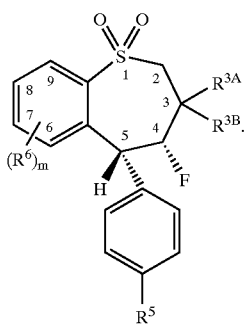
I-16

78. The method of claim 66 wherein said compound of Formula I-2 comprises a compound of Formulas I-18 represented by:

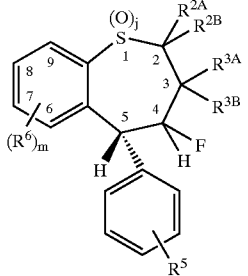
I-18

79. The method of claim 78 wherein said compound of Formula I-18 comprises a member selected from the group consisting of Formulas I-23 and I-24 represented by:

I-23

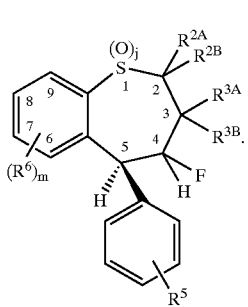

I-24

80. The method of claim 79 wherein said compounds of Formulas I-23 and I-24 comprises Formulas I-19 and I-20, respectively, represented by:

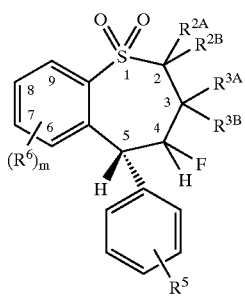
I-19

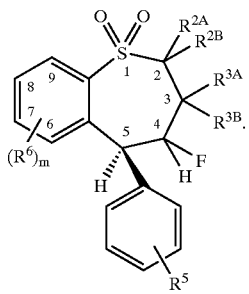
I-20

81. The method of claim 66 wherein said compound of Formula I-2 is selected from the group consisting of Formulas I-11 and I-12, respectively, represented by:

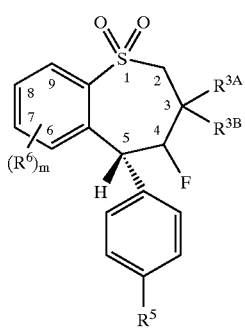
I-11

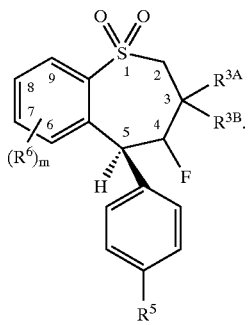
I-12

82. The compound of claim 1 wherein said compound of Formula I-1 comprises Formula I-17 represented by:

I-17 wherein $R^{2A}$, $R^{2B}$, $R^{3A}$, $R^{3B}$, $R^{5A}$, $R^{5B}$, $R^6$, m and j are as previously defined and said $R^5$ is selected from the group consisting of (1)–(69) and (70):

-continued
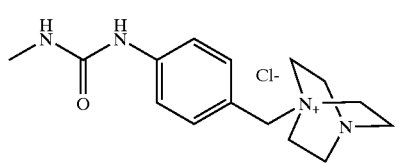(15a)
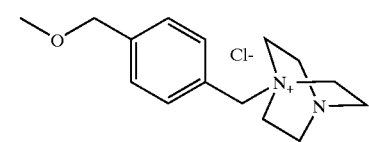(16)
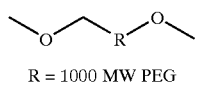
R = 1000 MW PEG
(17)
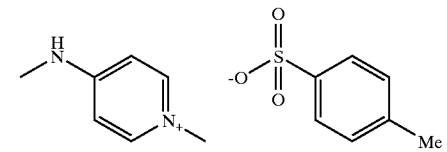(18)
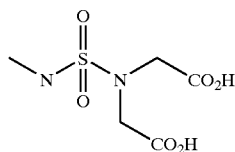(19)
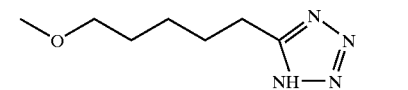(20)
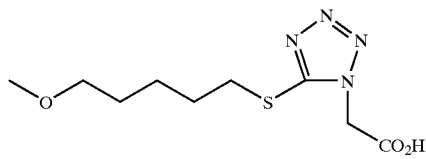(21)
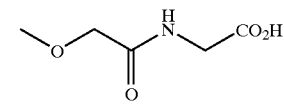(22)
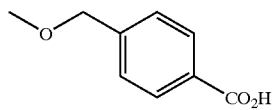(23)
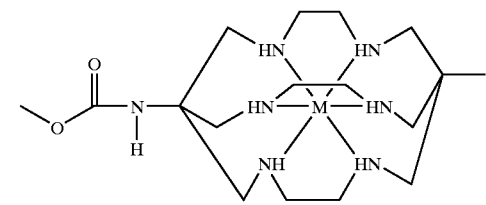
M = Co$^{II, III}$, Mn$^{II, III}$, Fe$^{II, III}$, Ni$^{II, III}$, Cr$^{III}$, Cu$^{II}$, Zn$^{II}$, Cd$^{II}$, Ga$^{III}$, In$^{III}$, V$^{IV}$, Ru$^{II}$, Pr$^{IV}$, Rh$^{III}$ or Ir$^{III}$
(24)
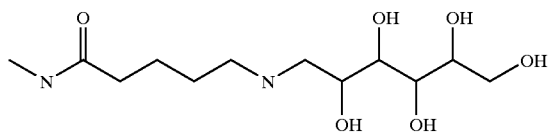(25)
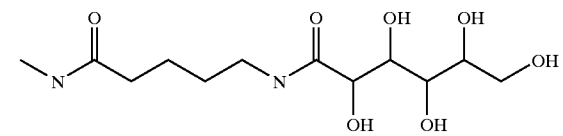(26)
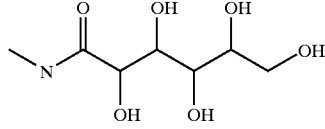(27)
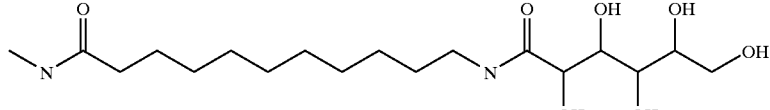(28)
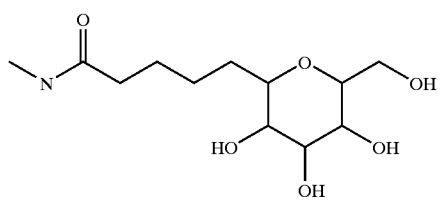(29)
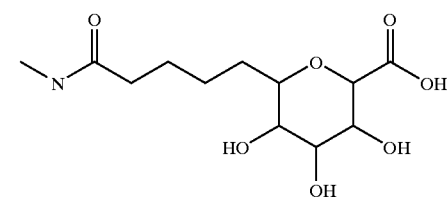(30)

-continued
(31) 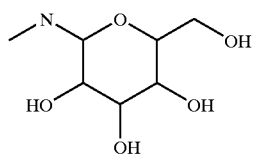
(32) 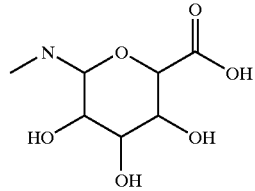
(33) 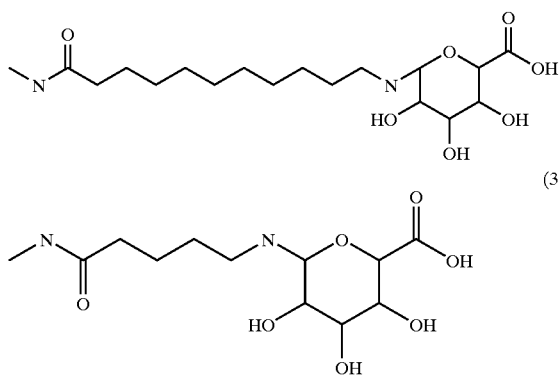
(34) 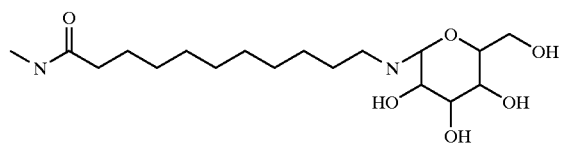
(35) 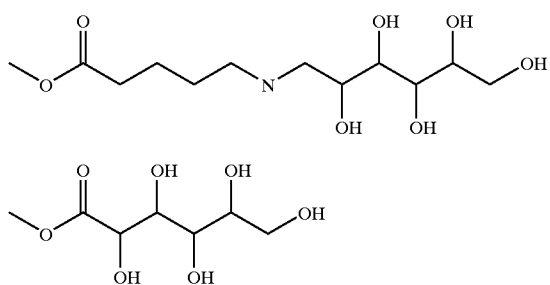
(36) 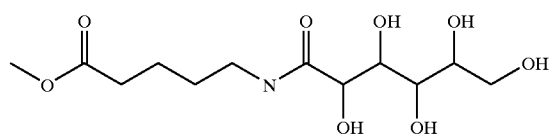
(37) 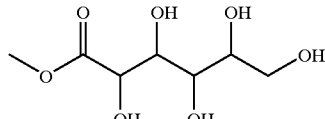
(38) 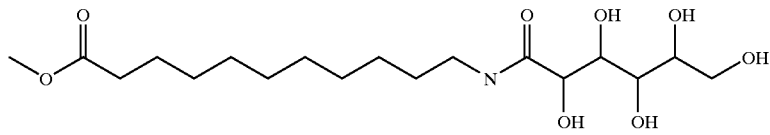
(39) 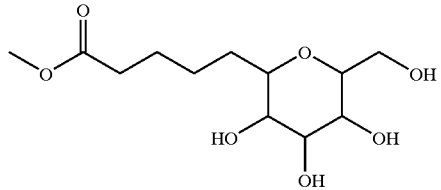
(40) 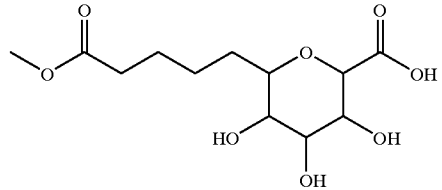
(41) 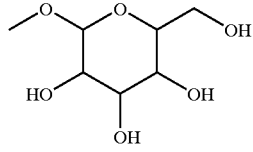
(42) 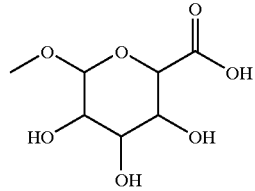
(43) 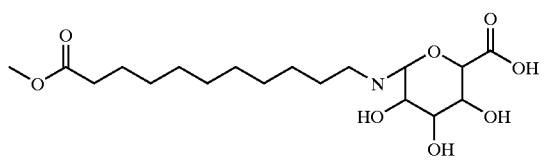
(44) 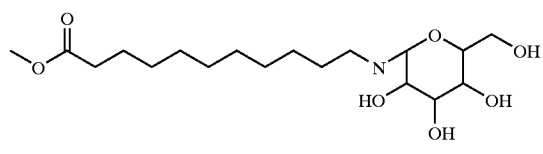
(45)
(46)

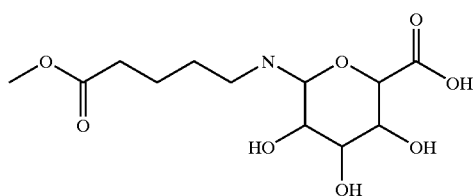(47)
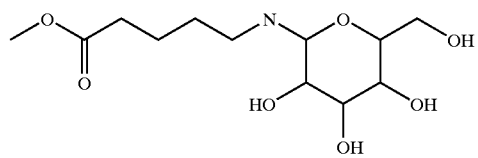(48)
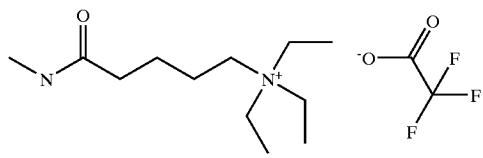(49)
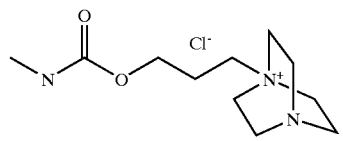(50)
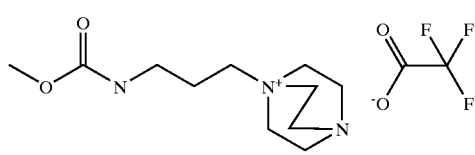(51)
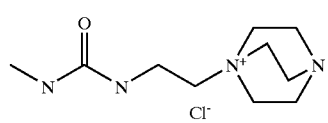(52)
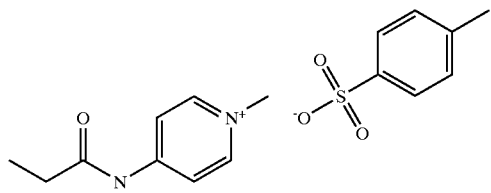(53)
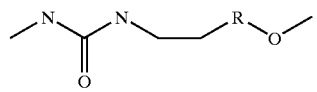(54)
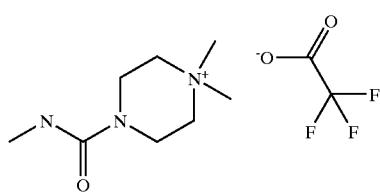(55)
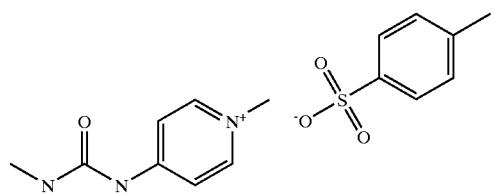(56)
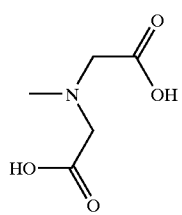(57)
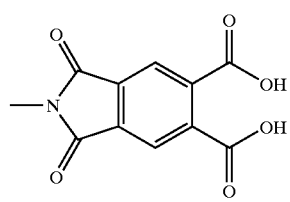(58)
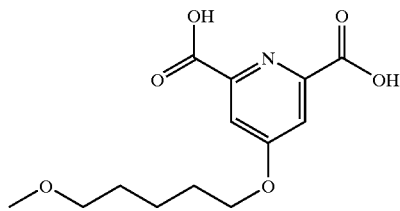(59)
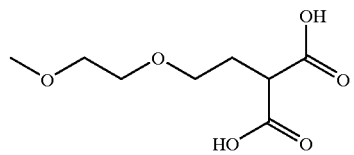(60)
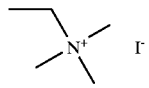(61)
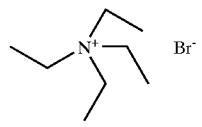(62)

-continued

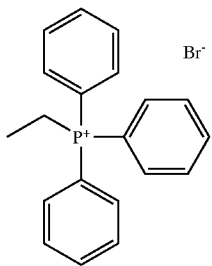 (63)

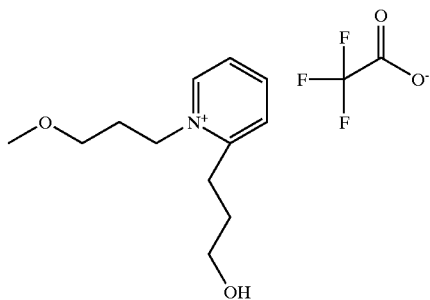 (64)

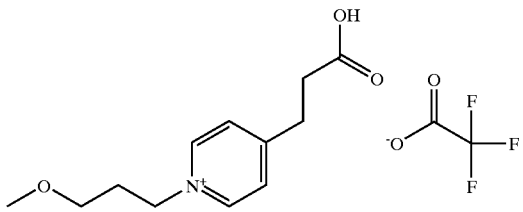 (65)

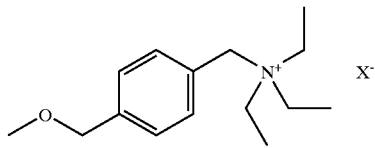 (66)

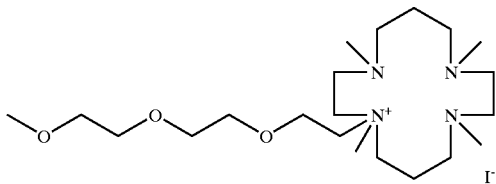 (67)

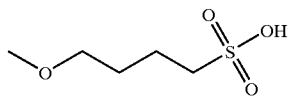 (68)

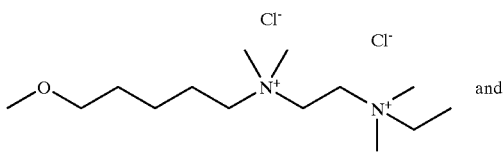 (69) and

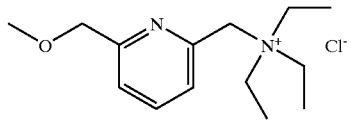 (70)

provided that when said $R^5$ is (7), (17) or (24), then said $R^{5A}$ is a left end of $R^5$ and said $R^{5B}$ is a right end of said $R^5$ or vice versa.

83. The compound of claim 82 wherein said compound of Formula 17 comprises a member selected from the group consisting of Formulas I-21 and I-22 represented by:

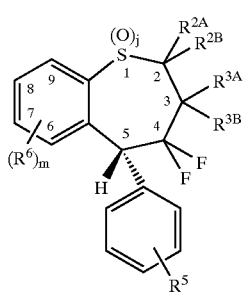 I-21

-continued

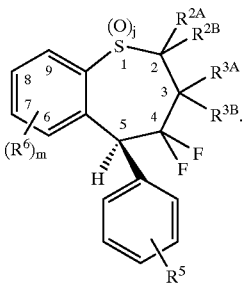 I-22

84. The method of claim 83 wherein said compounds of Formulas I-21 and I-22 comprise Formulas I-9 and I-10, respectively, represented by:

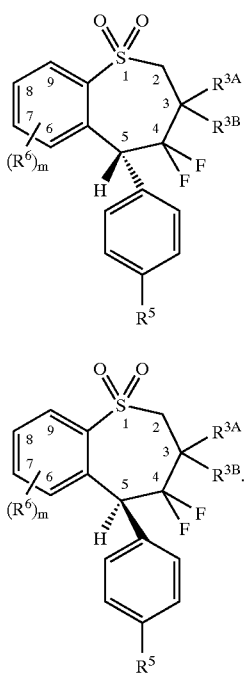
I-9
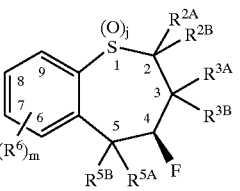
I-10
85. The compound of claim 1 wherein said compound of Formula I-2 is selected from the group consisting of Formulas I-3 and I-4 represented by:
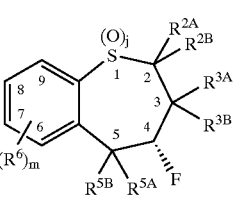
I-3
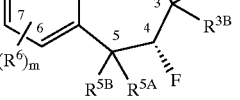
I-4
wherein $R^{2A}$, $R^{2B}$, $R^{3A}$, $R^{3B}$, $R^{5A}$, $R^{5B}$, $R^6$, m and j are as previously defined and said $R^5$ is selected from the group consisting of (1)–(69) and (70):
(1)
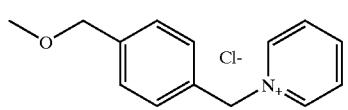
(2)
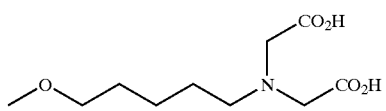
(3)
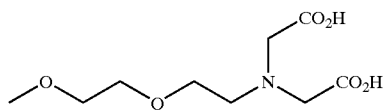
(4)
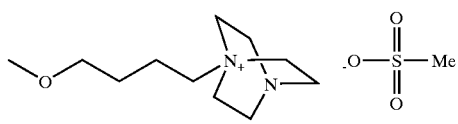
(5)
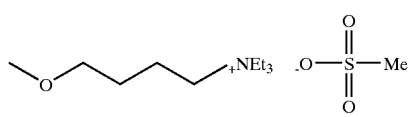
(6)
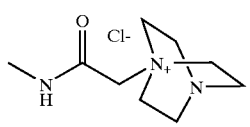
(7)
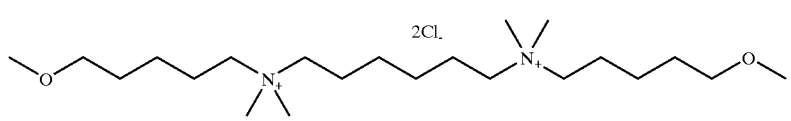
(8)
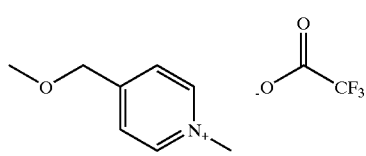
(9)
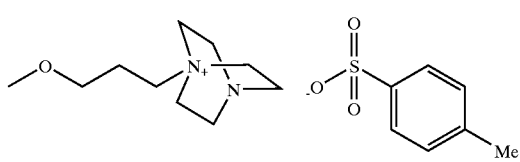
(10)
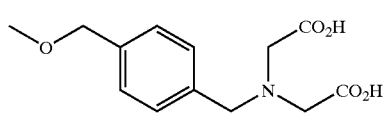
(11)
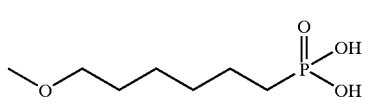

-continued
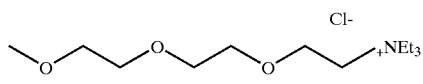 (12)
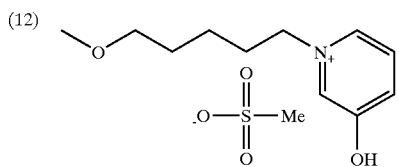 (13)
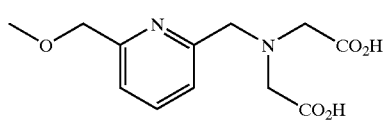 (14)
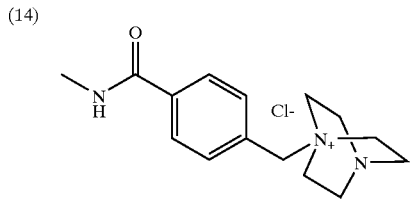 (15)
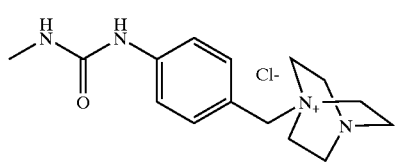 (15a)
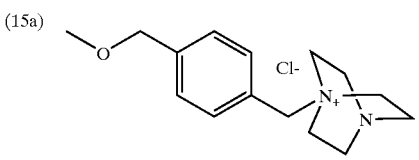 (16)
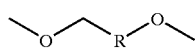
R = 1000 MW PEG
(17)
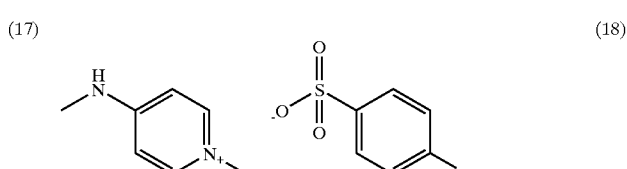 (18)
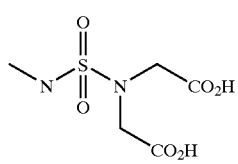 (19)
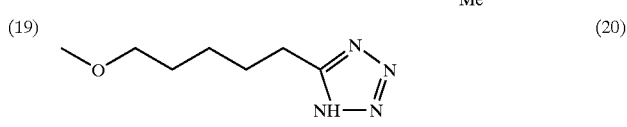 (20)
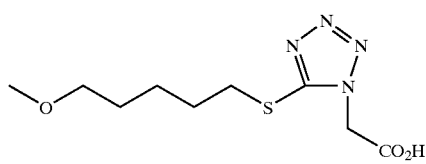 (21)
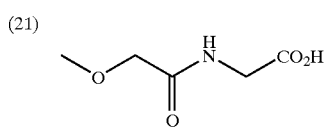 (22)
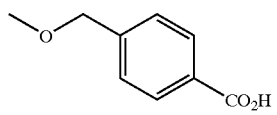 (23)
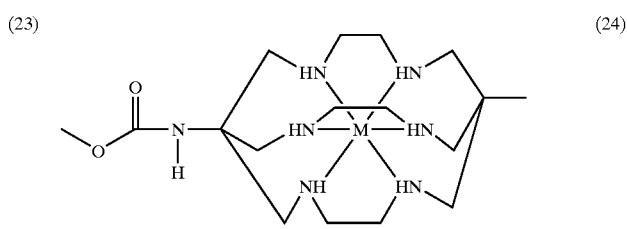 (24)
M = $Co^{II, III}$, $Mn^{II, III}$, $Fe^{II, III}$, $Ni^{II, III}$, $Cr^{III}$, $Cu^{II}$, $Zn^{II}$, $Cd^{II}$, $Ga^{III}$, $In^{III}$, $V^{IV}$, $Ru^{II}$, $Pr^{IV}$, $Rh^{III}$ or $Ir^{III}$
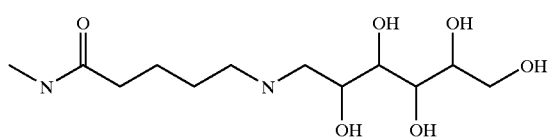 (25)
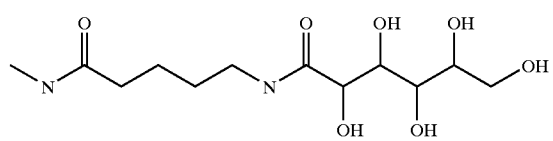 (26)
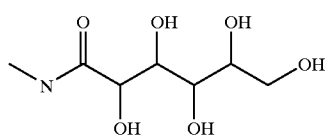 (27)

-continued
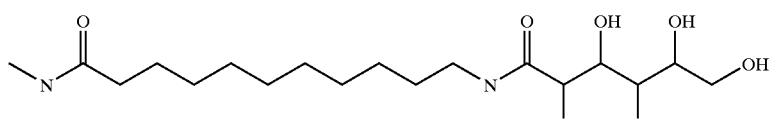
(28)
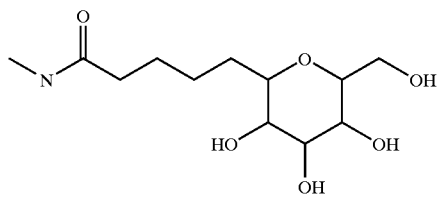
(29)
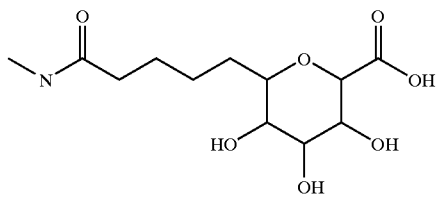
(30)
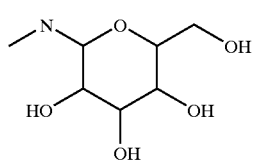
(31)
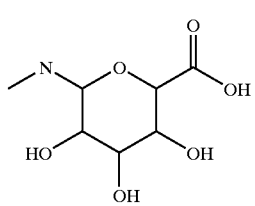
(32)
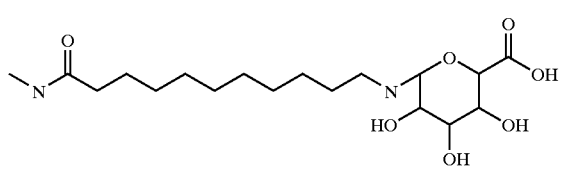
(33)
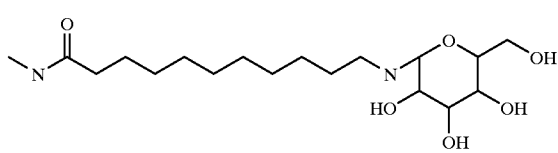
(34)
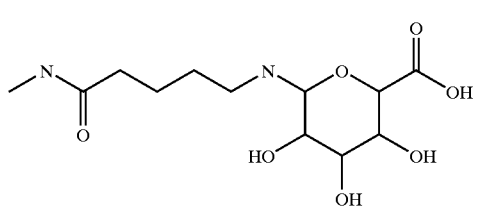
(35)
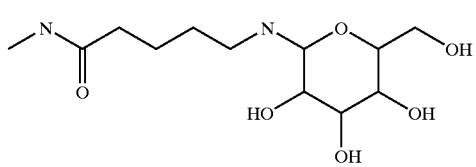
(36)
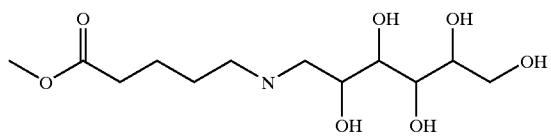
(37)
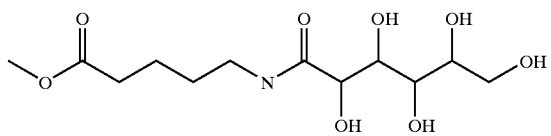
(38)
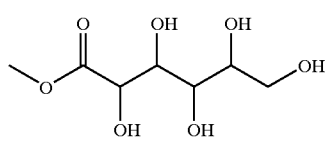
(39)
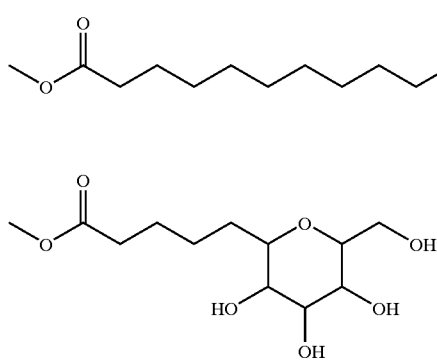
(40)
(41)
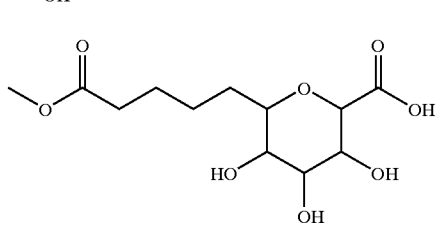
(42)

-continued
(43) 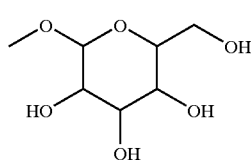
(44) 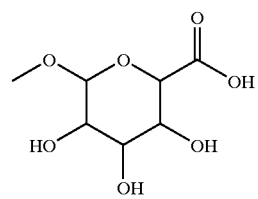
(45) 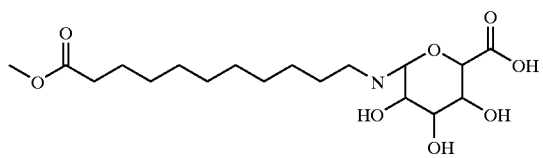
(46) 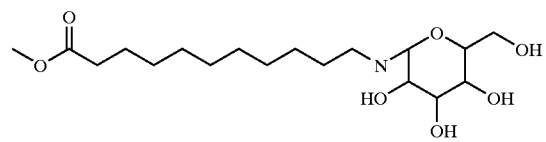
(47) 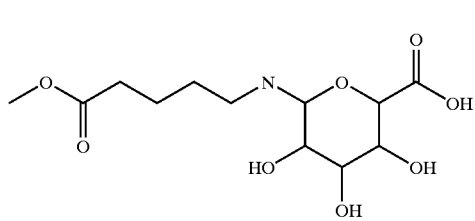
(48) 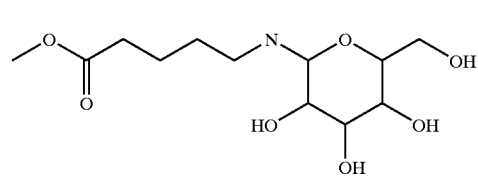
(49) 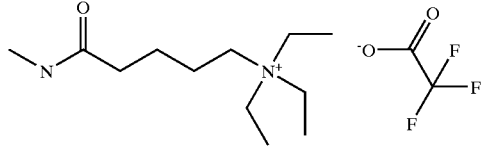
(50) 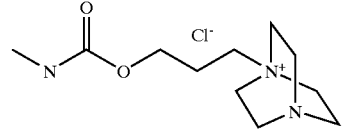
(51) 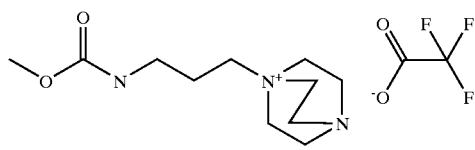
(52) 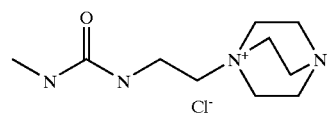
(53) 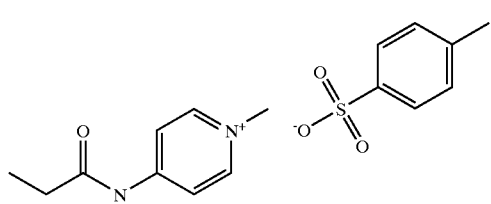
(54) 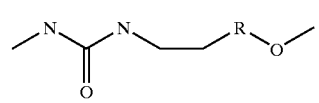
(55) 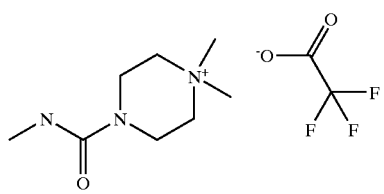
(56) 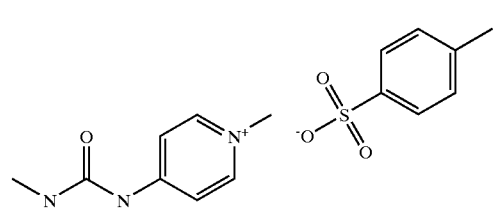
(57) 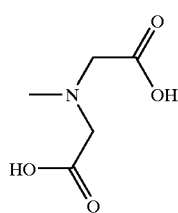
(58) 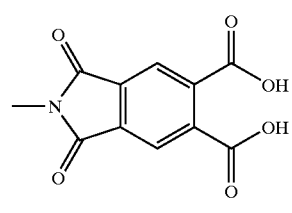

-continued
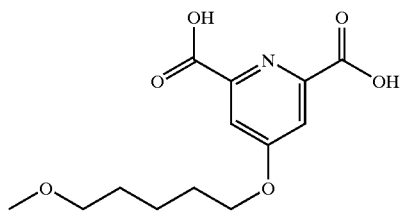 (59)
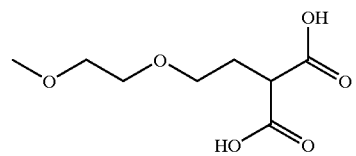 (60)
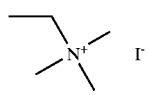 (61)
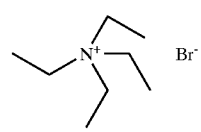 (62)
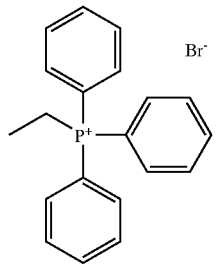 (63)
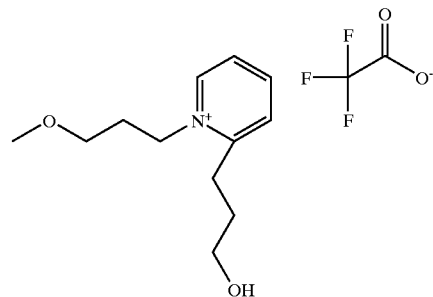 (64)
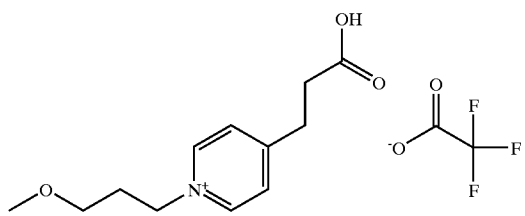 (65)
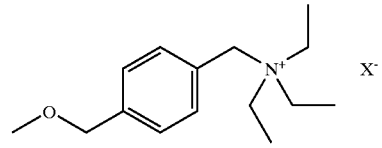 (66)
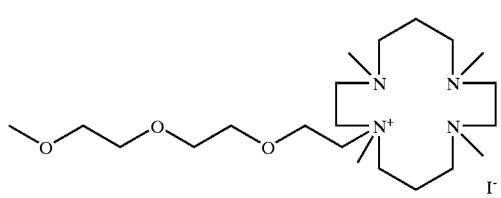 (67)
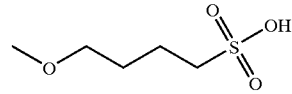 (68)
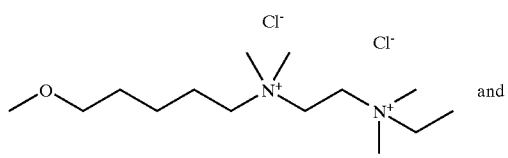 (69)
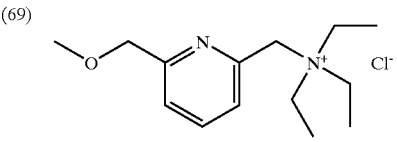 (70)
provided that when said $R^5$ is (7), (17) or (24), then said $R^{5A}$ is a left end of said $R^5$ and said $R^{5B}$ is a right end of said $R^5$ or vice versa.
86. The compound of claim 85 wherein said Formula I-3 comprises a member selected from the group consisting of Formulas I-5 and I-6 represented by:
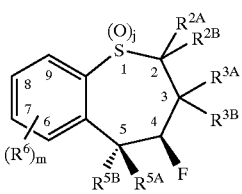
I-5

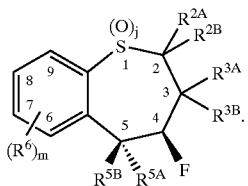

I-6

87. The compound of claim 85 wherein said Formula I-4 comprises a member selected from the group consisting of Formulas I-7 and I-8 represented by:

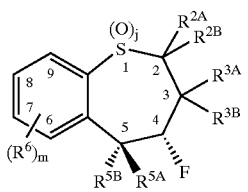

I-7

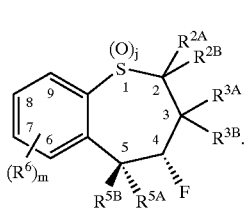

I-8

88. The compound of claim 86 wherein said compounds of Formulas I-6 and I-5 comprise Formulas I-13 and I-14, respectively, represented by:

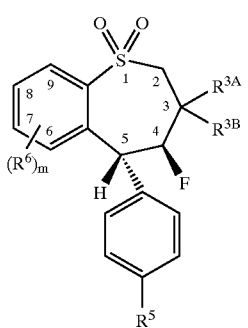

I-13

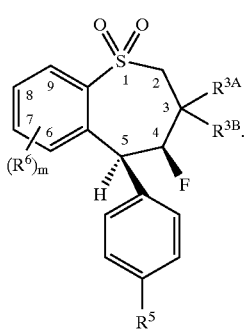

I-14

89. The compound of claim 87 wherein said compounds of Formulas I-7 and I-8 comprise Formulas I-15 and I-16, respectively, represented by:

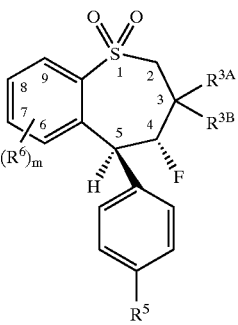

I-15

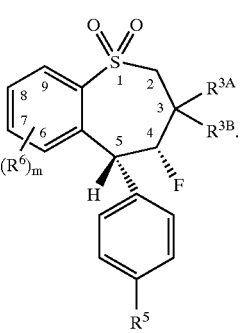

I-16

90. The compound of claim 1 wherein said compound of Formula I-2 comprises a compound of Formula I-18 represented by:

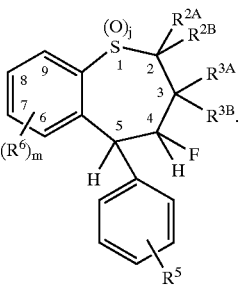

I-18 wherein $R^{2A}$, $R^{2B}$, $R^{3A}$, $R^{3B}$, $R^{5A}$, $R^{5B}$, $R^6$, m and j are as previously defined and said $R^5$ is selected from the group consisting of (1)–(69) and (70):

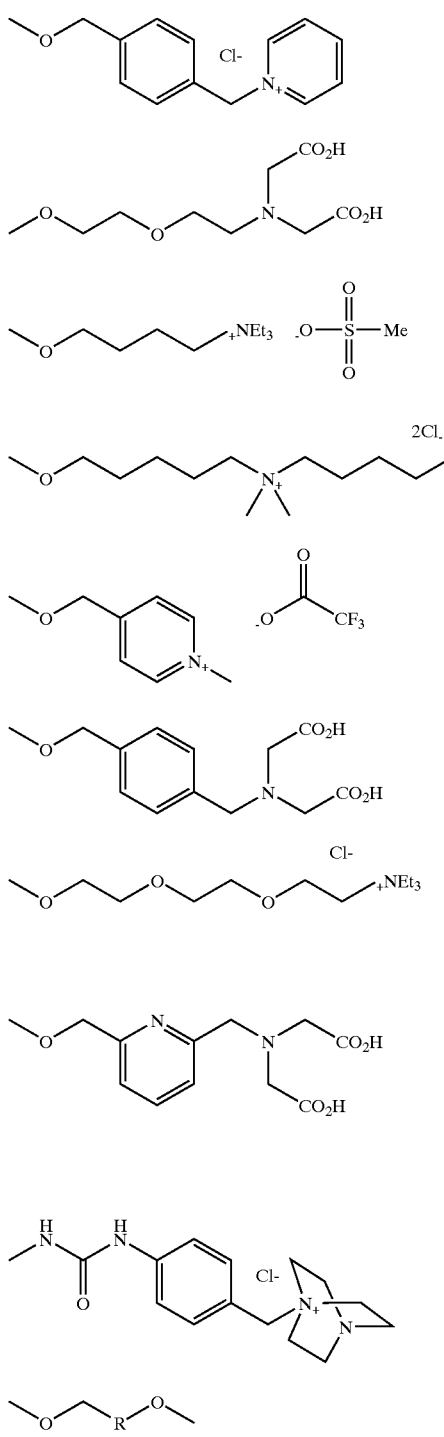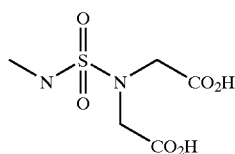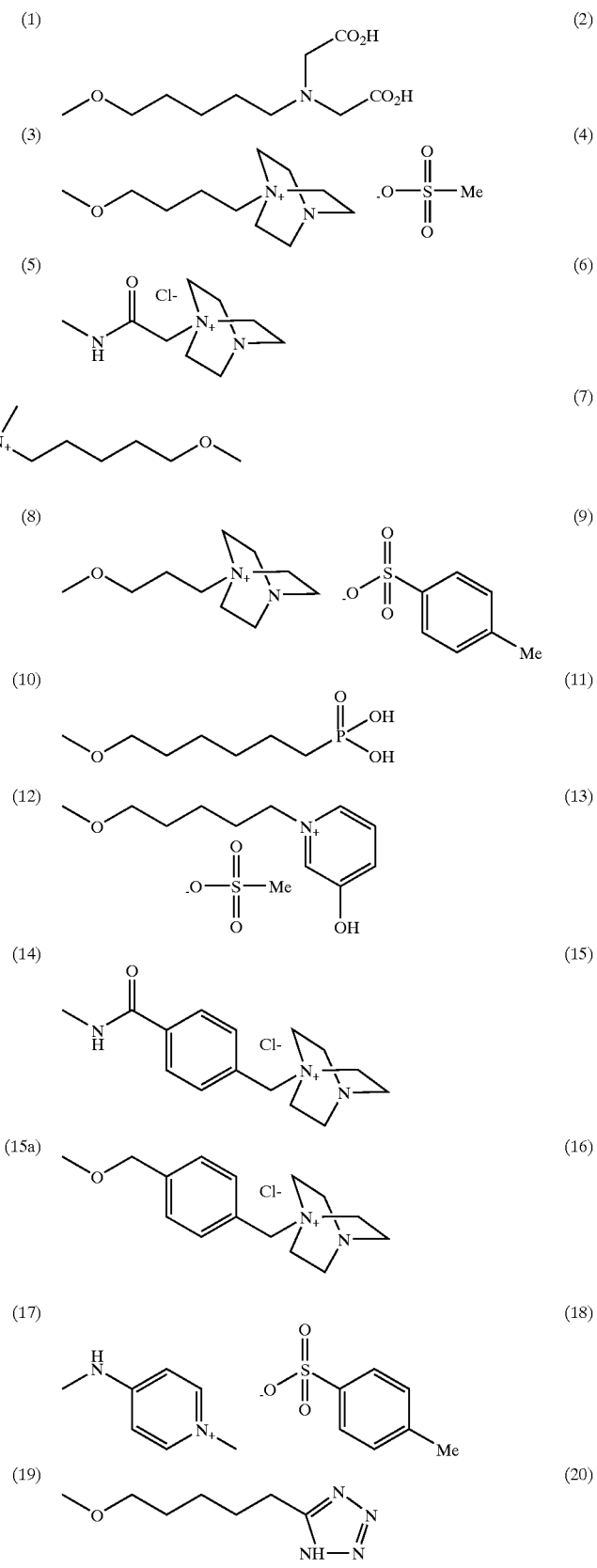

-continued
(21) 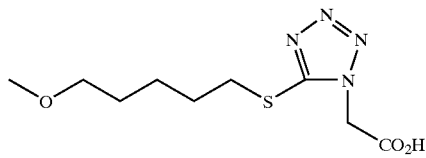
(22) 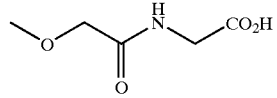
(23) 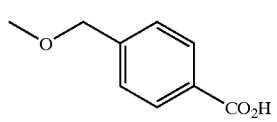
(24) 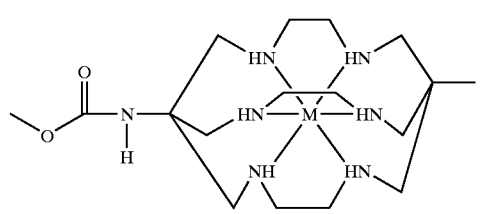
M = $Co^{II, III}$, $Mn^{II, III}$, $Fe^{II, III}$, $Ni^{II, III}$, $Cr^{III}$, $Cu^{II}$, $Zn^{II}$, $Cd^{II}$, $Ga^{III}$, $In^{III}$, $V^{IV}$, $Ru^{II}$, $Pr^{IV}$, $Rh^{III}$ or $Ir^{III}$
(25) 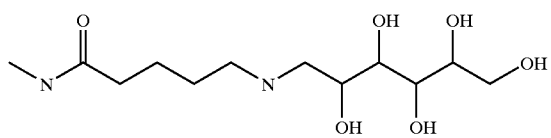
(26) 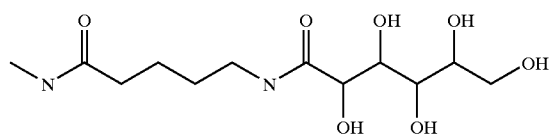
(27) 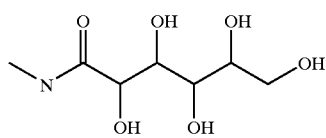
(28) 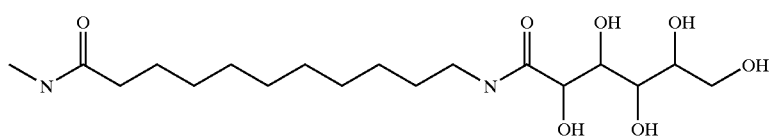
(29) 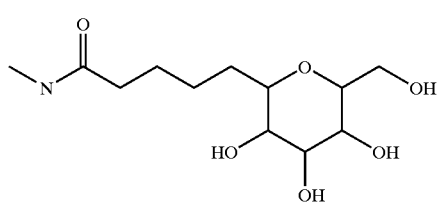
(30) 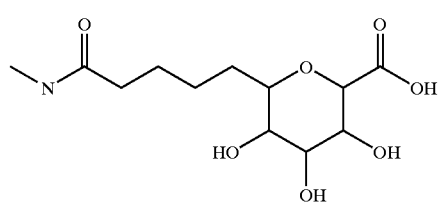
(31) 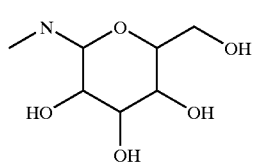
(32) 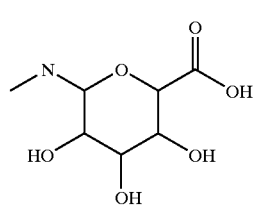
(33) 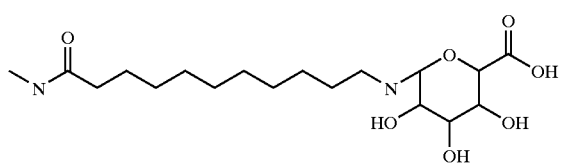
(34) 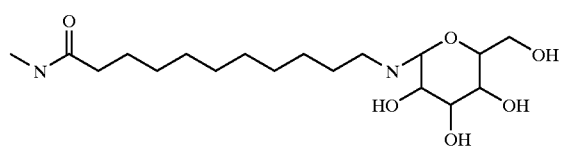

-continued
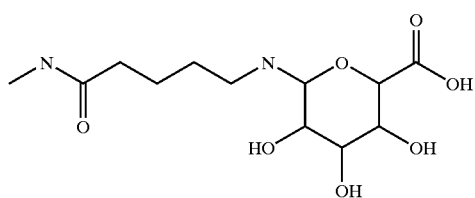
(35)
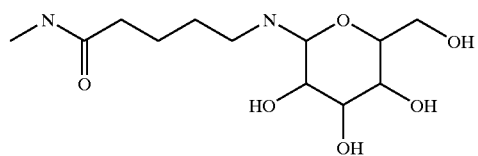
(36)
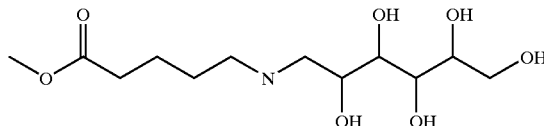
(37)
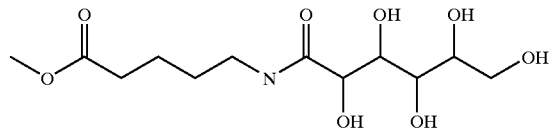
(38)
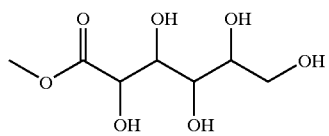
(39)
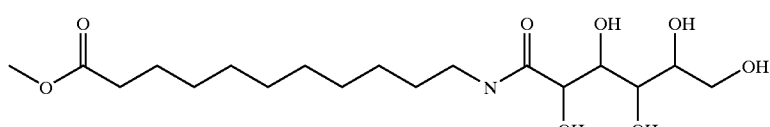
(40)
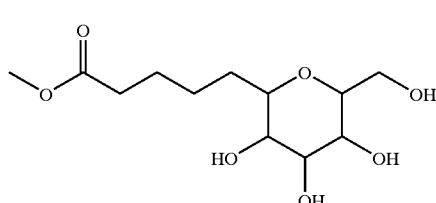
(41)
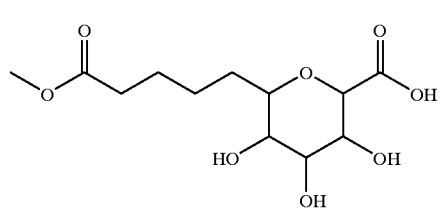
(42)
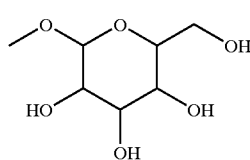
(43)
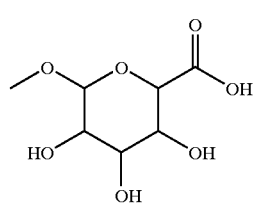
(44)
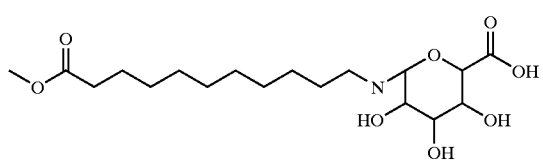
(45)
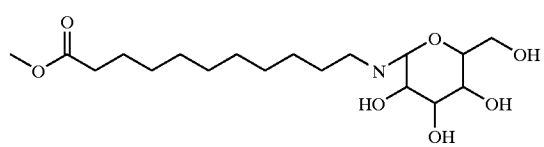
(46)
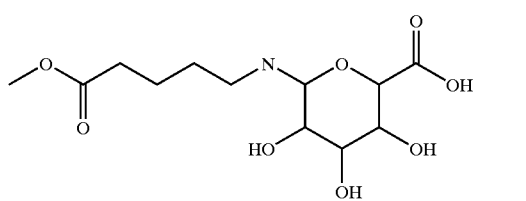
(47)
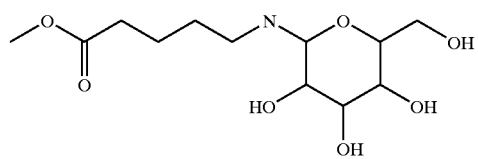
(48)
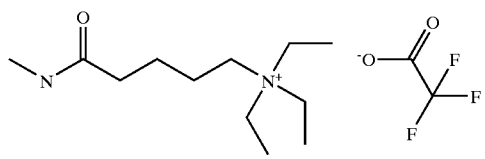
(49)
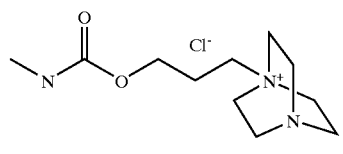
(50)

-continued
(51) 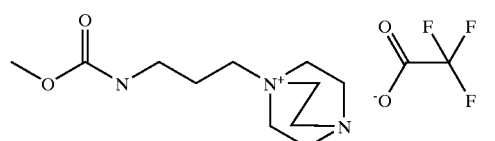
(52) 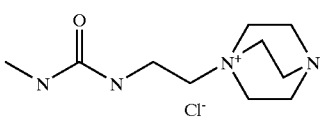
(53) 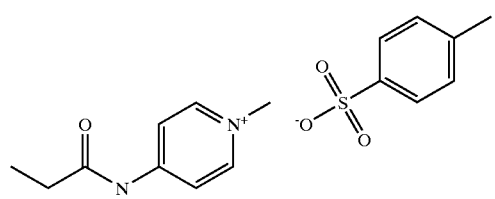
(54) 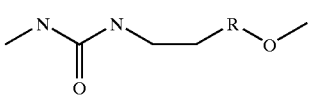
(55) 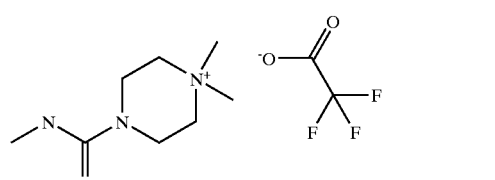
(56) 
(57) 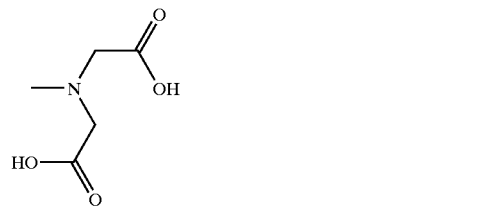
(58) 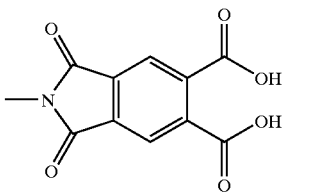
(59) 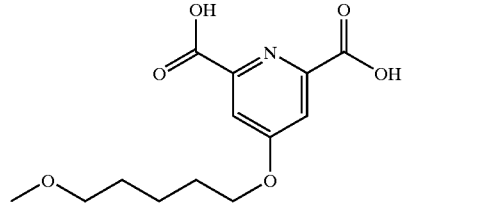
(60) 
(61) 
(62) 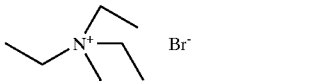
(63) 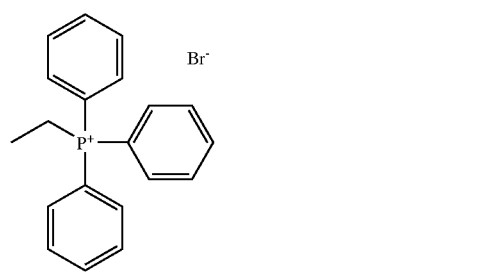
(64) 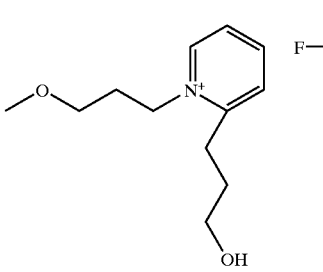
(65) 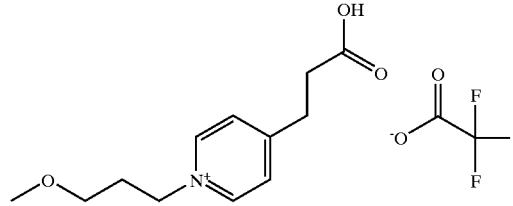
(66) 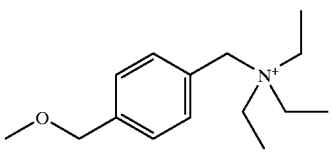

-continued

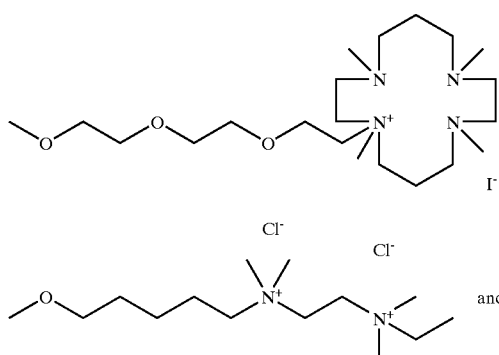
(67)

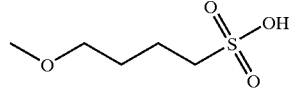
(68)

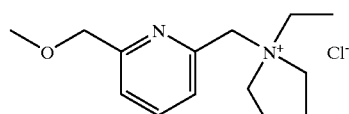
(69)

(70)

provided that when said $R^5$ is (7), (17) or (24), then said $R^{5A}$ is a left end of said $R^5$ and said $R^{5B}$ is a right end of said $R^5$ or vice versa.

91. The compound of claim 90 wherein said compound of Formula I-18 comprises a member selected from the group consisting of I-23 and I-24 represented by:

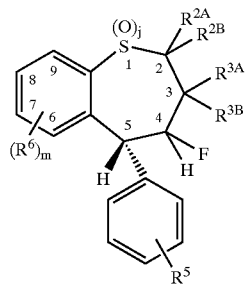
I-23

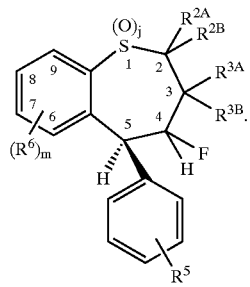
I-24

92. The compound of claim 91 wherein said compounds of Formulas I-23 and I-24 comprise compounds of Formulas I-19 and I-20, respectively, represented by:

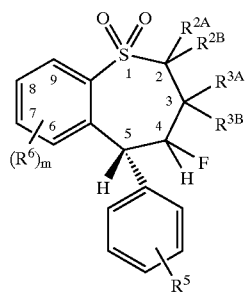
I-19

-continued

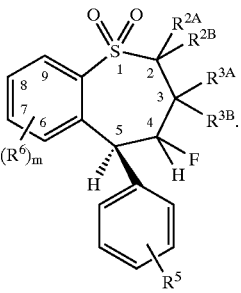
I-20

93. The compound of claim 1 wherein said compound of Formula I-2 is selected from the group consisting of Formulas I-11 and I-12 represented by:

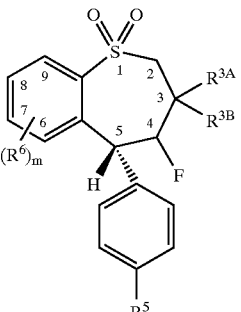
I-11

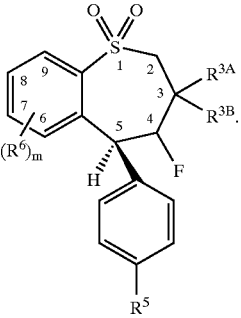
I-12

94. The method of claim 39 wherein said hyperlipidemic condition is hypercholesteremia.

95. The method of claim 94 wherein said therapeutically effective amount is a daily dose from about 0.001 mg to about 10,000 mg.

96. The method of claim 95 wherein said daily dose is from about 0.005 mg to about 1,000 mg.

97. The method of claim 96 wherein said daily dose is from about 0.008 to about 100 mg.

98. The method of claim 97 wherein said daily dose is from about 0.05 mg to about 50 mg.

99. The method of claim 95 wherein said daily dose is administered as a single dose or in multiple divided doses.

100. The method of claim 40 wherein said therapeutically effective amount is a daily dose from about 0.001 mg to about 10,000 mg.

101. The method of claim 100 wherein said daily dose is from about 0.005 mg to about 1,000 mg.

102. The method of claim 101 wherein said daily dose is from about 0.008 to about 100 mg.

103. The method of claim 101 wherein said daily dose is from about 0.05 mg to about 50 mg.

104. The method of claim 106 wherein said daily dose is administered as a single dose or in multiple divided doses.

105. The method of claim 95 wherein said daily dose is administered orally.

106. The method of claim 95 wherein said daily dose is administered parenterally.

107. The method of claim 95 wherein said daily dose is administered rectally.

108. The method of claim 107 wherein said daily dose is administered as a rectal dosage form comprising a suppository.

109. The method of claim 94 wherein said therapeutically effective amount is administered as a slow release dosage form.

110. The method of claim 109 wherein said slow release dosage form comprises an implant.

111. The method of claim 105 wherein said daily dose is administered in the form of an oral dosage form selected from the group consisting of a tablet, a capsule, a powder, a solution, a suspension, an emulsion, and a syrup.

112. The method of claim 111 wherein said solution comprises a syrup.

113. The method of claim 111 wherein said oral dosage form comprises a sublingual tablet, an effervescent tablet, or a slow release tablet.

114. The method of claim 106 wherein said parenteral dosage form is selected from the group consisting of an intramuscular injection, an intravenous injection, and a subcutaneous injection.

115. The method of claim 95 wherein said daily dose is administered topically.

116. The method of claim 100 wherein said daily dose is administered parenterally.

117. The method of claim 100 wherein said daily dose is administered rectally or vaginally.

118. The method of claim 117 wherein said daily dose is administered as a rectal dosage form or a vaginal dosage form comprising a suppository.

119. The method of claim 100 wherein said daily dose is administered as a slow release dosage form.

120. The method of claim 119 wherein said slow release dosage from comprises an implant.

121. The method of claim 100 wherein said daily dose is administered in the form of an oral dosage form selected from the group consisting of a tablet, a capsule, a powder, a solution, a suspension, and an emulsion.

122. The method of claim 121 wherein said solution comprises a syrup.

123. The method of claim 121 wherein said tablet comprises a sublingual tablet, an effervescent tablet, or a slow release tablet.

124. The method of claim 116 wherein said parenteral dosage form is selected from the group consisting of an intramuscular injection, an intravenous injection, and a subcutaneous injection.

125. The method of claim 100 wherein said daily dose is administered topically.

126. The method of claim 125 wherein said daily dose is administered in the form of a topical dosage form selected from the group consisting of a lotion, a cream, a suspension, an emulsion, a paste, and a solution.

127. The method of claim 115 wherein said daily dose is administered in the form of a topical dosage form selected from the group consisting of a lotion, a cream, a suspension, an emulsion, a paste, and a solution.

128. A pharmaceutical composition comprising a compound of Formula I-1 or I-2 of claim 1 and a pharmaceutically acceptable carrier.

129. The pharmaceutical composition of claim 128 wherein said compound of Formula I-1 comprises Formula I-17 represented by:

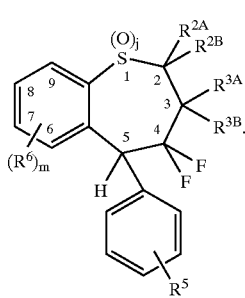

I-17 wherein $R^{2A}$, $R^{2B}$, $R^{3A}$, $R^{3B}$, $R^{5A}$, $R^{5B}$, $R^6$, m and j are as previously defined and said $R^5$ is selected from the group consisting of (1)–(69) and (70):

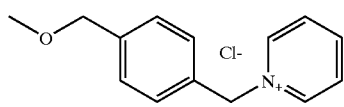

(1)

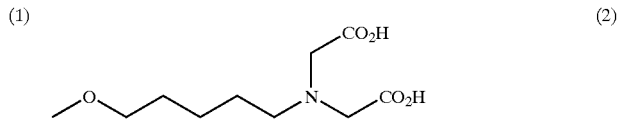

(2)

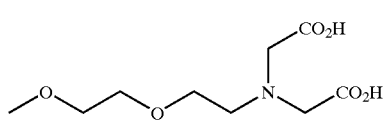

(3)

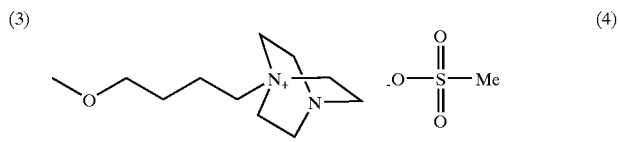

(4)

-continued

-continued
(23)
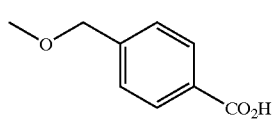
(24)
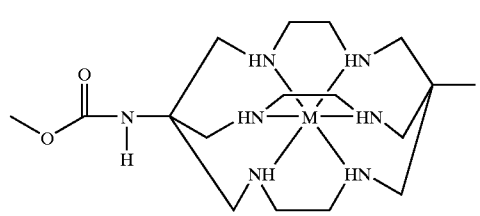
M = $Co^{II, III}$, $Mn^{II, III}$, $Fe^{II, III}$, $Ni^{II, III}$, $Cr^{III}$, $Cu^{II}$, $Zn^{II}$, $Cd^{II}$, $Ga^{III}$, $In^{III}$, $V^{IV}$, $Ru^{II}$, $Pr^{IV}$, $Rh^{III}$ or $Ir^{III}$
(25)
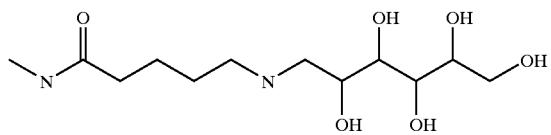
(26)
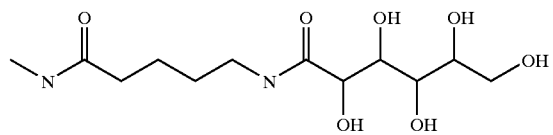
(27)
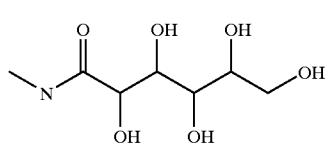
(28)
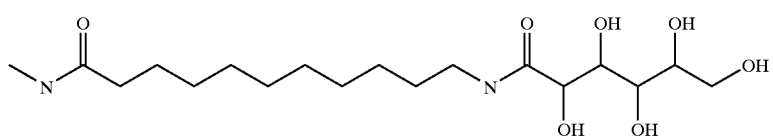
(29)
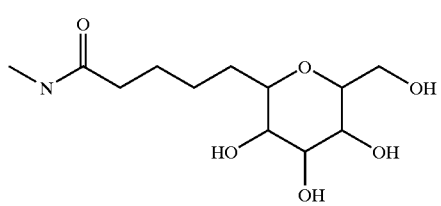
(30)
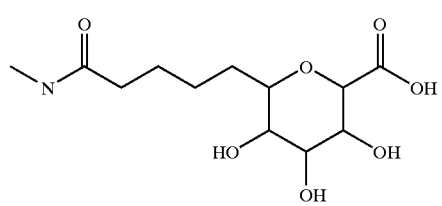
(31)
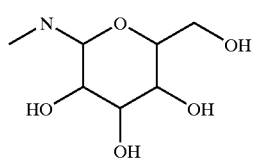
(32)
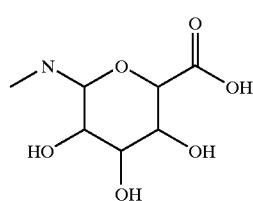
(33)
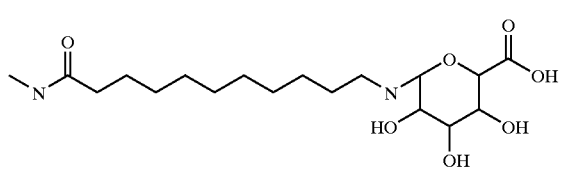
(34)
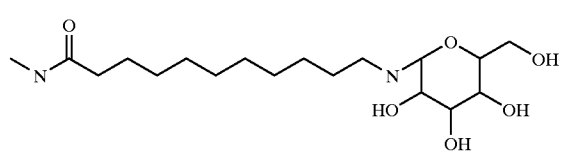
(35)
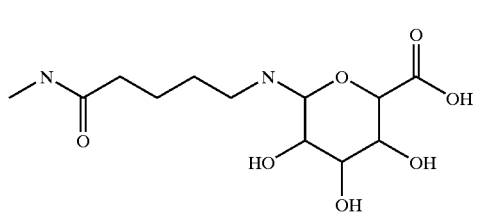
(36)
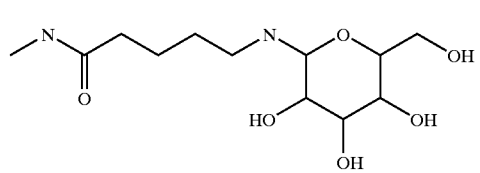

-continued
(37) 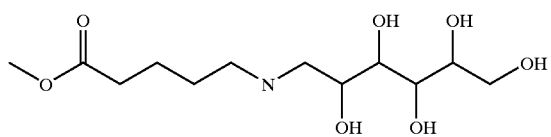
(38) 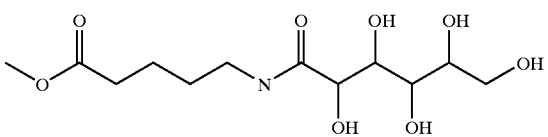
(39) 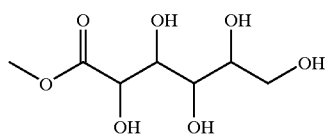
(40) 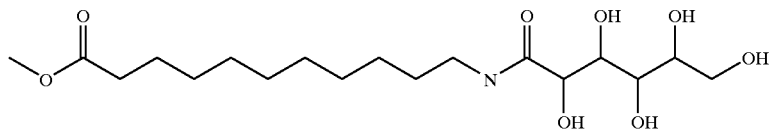
(41) 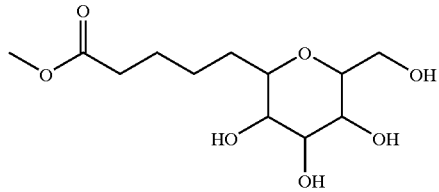
(42) 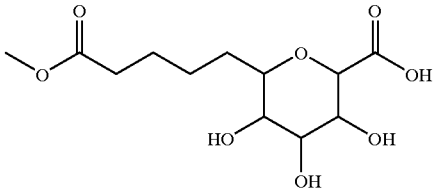
(43) 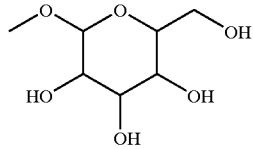
(44) 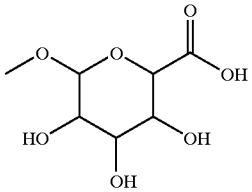
(45) 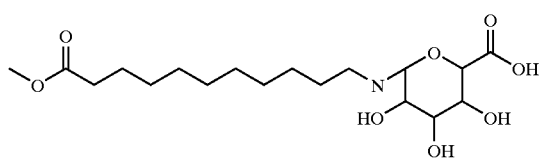
(46) 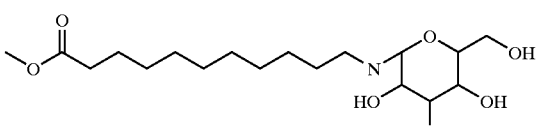
(47) 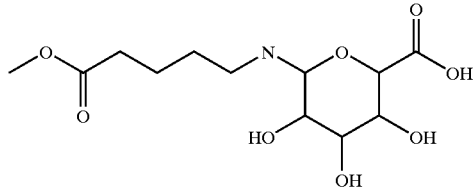
(48) 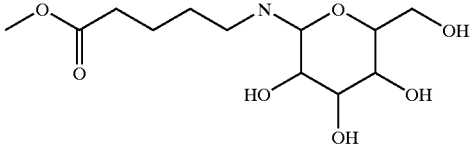
(49) 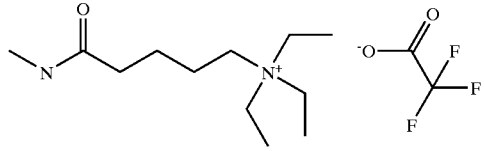
(50) 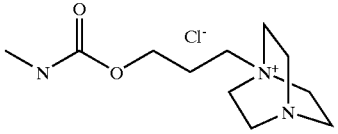
(51) 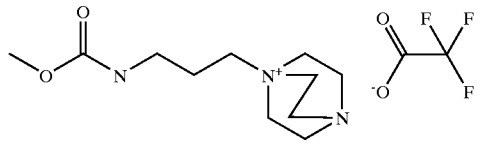
(52) 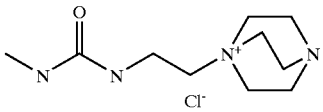

-continued
(53) 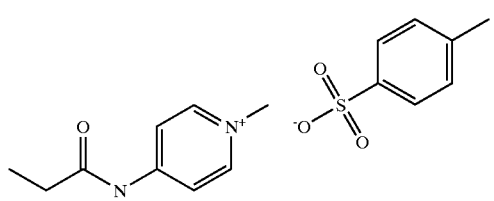
(54) 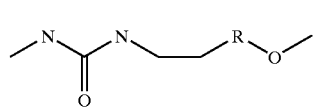
(55) 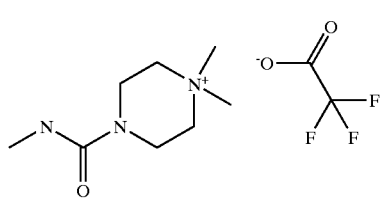
(56) 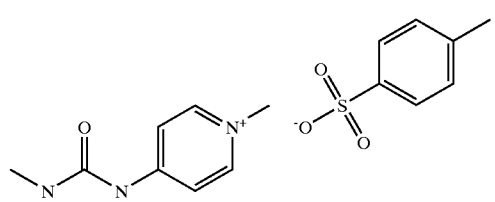
(57) 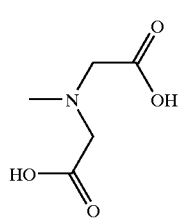
(58) 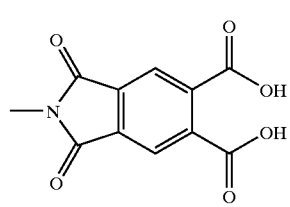
(59) 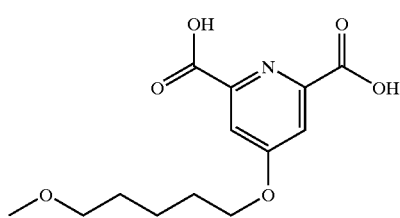
(60) 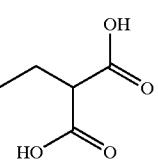
(61) 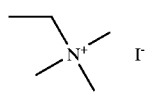
(62) 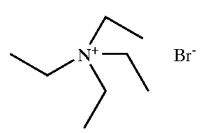
(63) 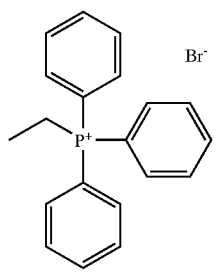
(64) 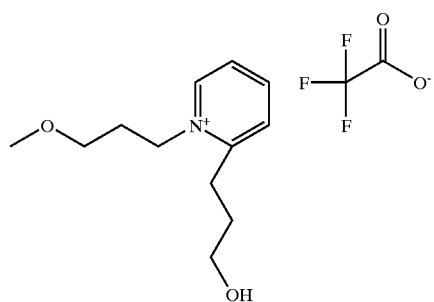
(65) 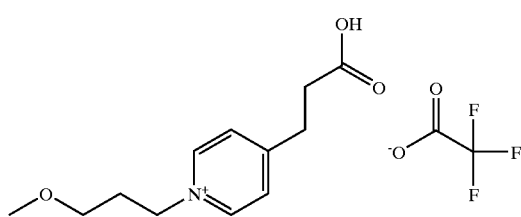
(66) 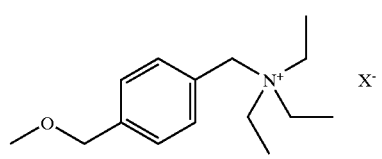

-continued

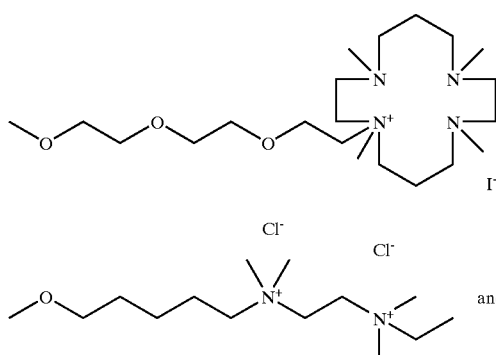

(67)

(68)

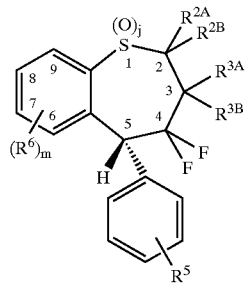

(69) and (70)

provided that when said R⁵ is (7), (17) or (24), then said $R^{5A}$ is a left end of said $R^5$ and $R^{5B}$ is a right end of said $R^5$ or vice versa.

130. The pharmaceutical composition of claim 129 wherein said compound of Formula I-17 comprises a member selected from the group consisting of Formulas I-21 and I-22 represented by:

I-21

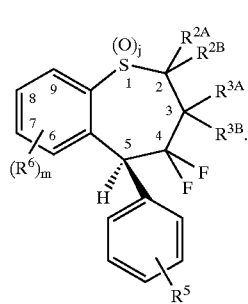

I-22

131. The pharmaceutical composition of claim 130 wherein said compounds of Formulas I-21 and I-22 comprise Formulas I-9 and I-10, respectively, represented by:

I-9

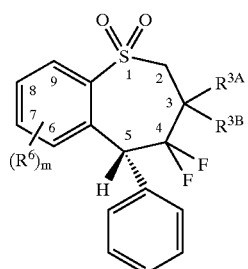

I-10

132. The pharmaceutical composition of claim 128 wherein said compound of Formula I-2 selected from the group consisting of Formulas I-3 and I-4 represented by:

I-3

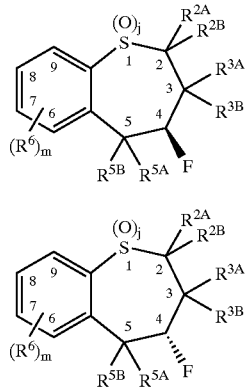

I-4 wherein $R^{2A}$, $R^{2B}$, $R^{3A}$, $R^{3B}$, $R^{5A}$, $R^{5B}$, $R^6$, m and j are as previously defined and said $R^5$ is selected from the group consisting of (1)–(69) and (70):

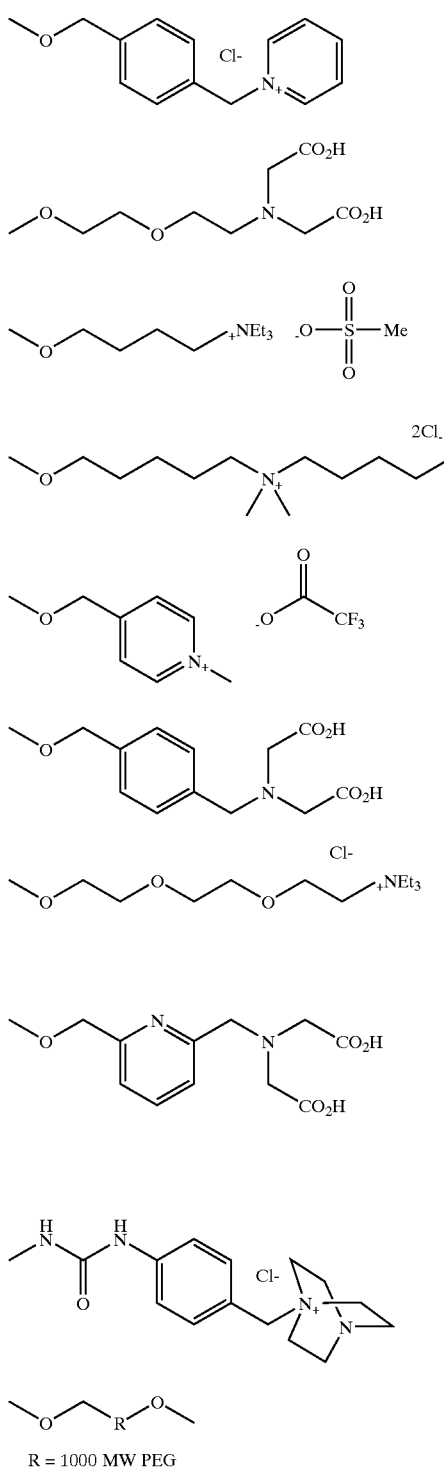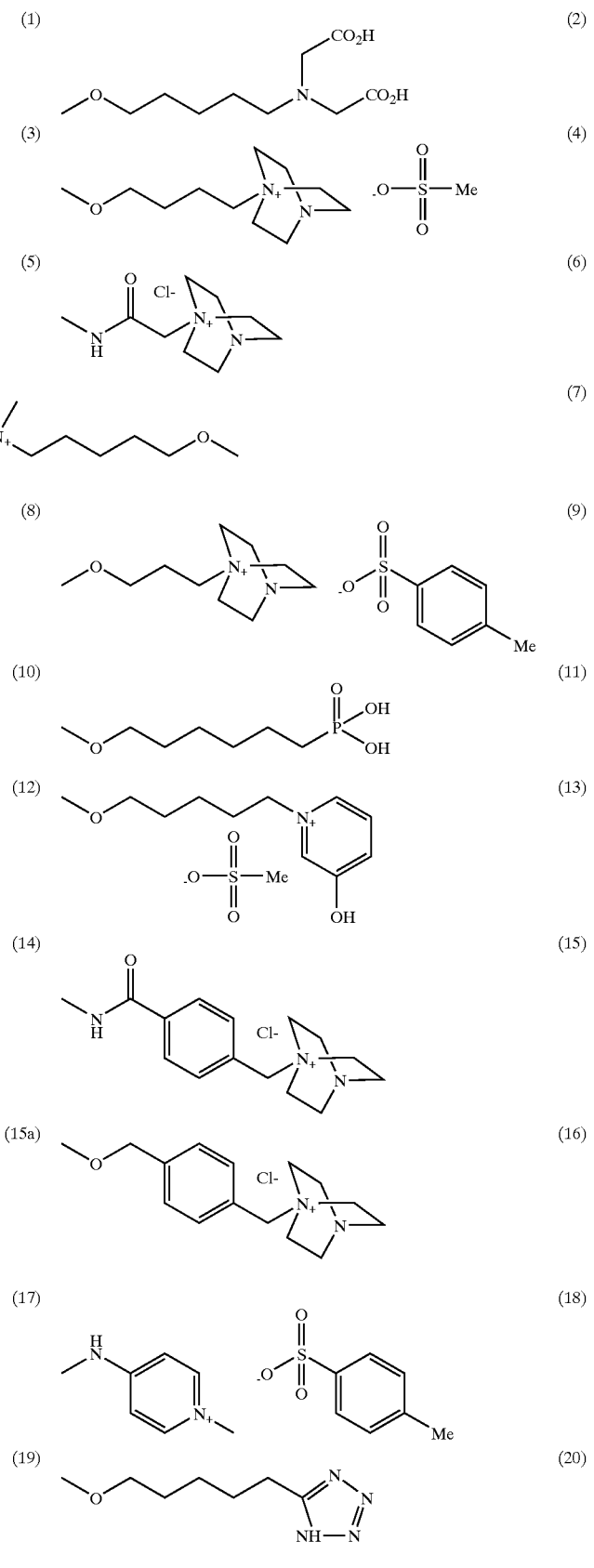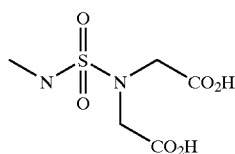

-continued
(21)
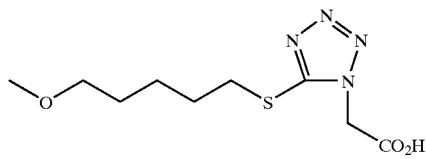
(22)
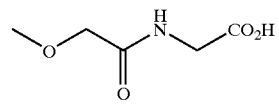
(23)
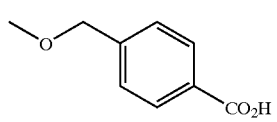
(24)
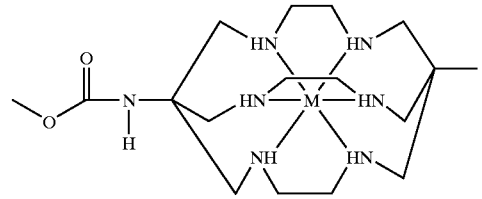
M = Co$^{II, III}$, Mn$^{II, III}$, Fe$^{II, III}$, Ni$^{II, III}$, Cr$^{III}$, Cu$^{II}$, Zn$^{II}$, Cd$^{II}$, Ga$^{III}$, In$^{III}$, V$^{IV}$, Ru$^{II}$, Pr$^{IV}$, Rh$^{III}$ or Ir$^{III}$
(25)
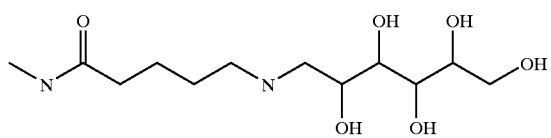
(26)
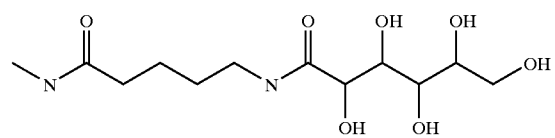
(27)
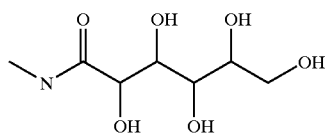
(28)
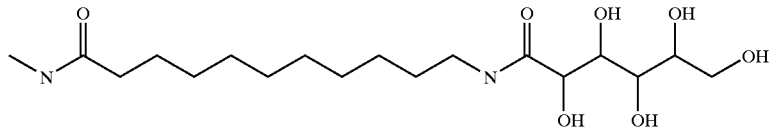
(29)
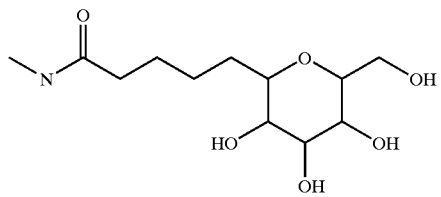
(30)
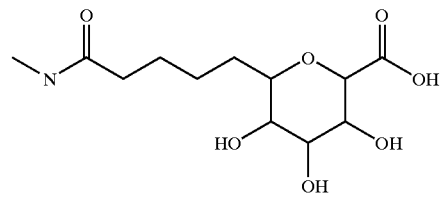
(31)
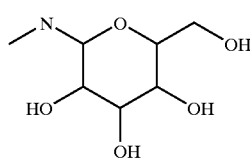
(32)
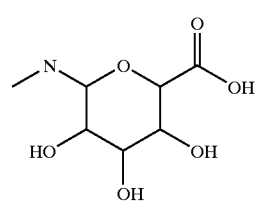
(33)
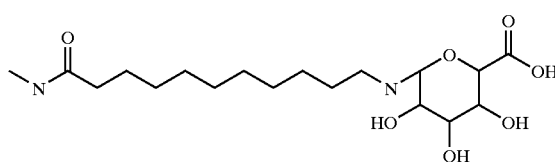
(34)
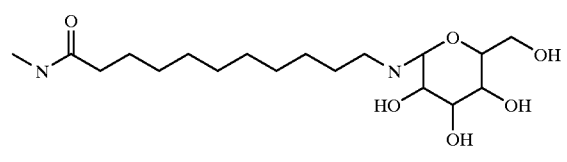

-continued
(35) 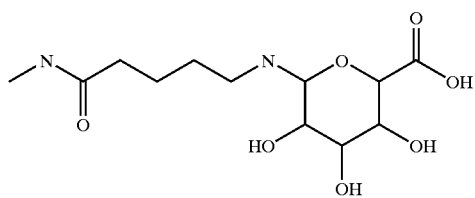
(36) 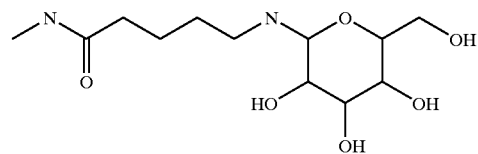
(37) 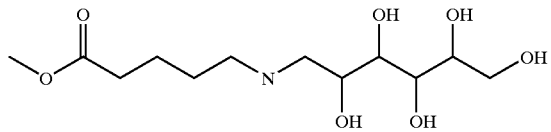
(38) 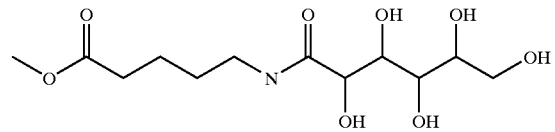
(39) 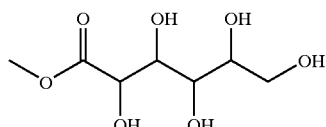
(40) 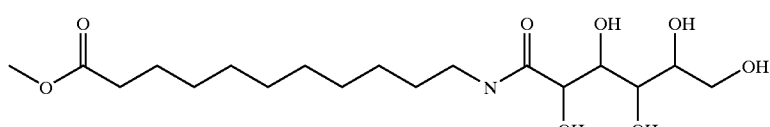
(41) 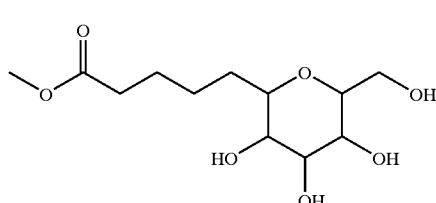
(42) 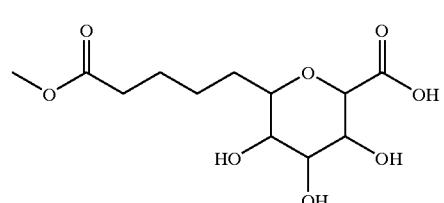
(43) 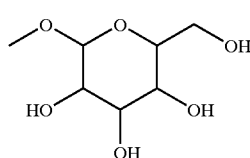
(44) 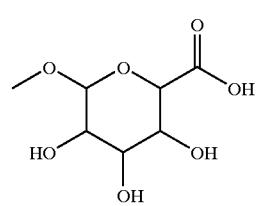
(45) 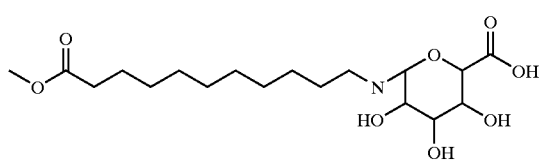
(46) 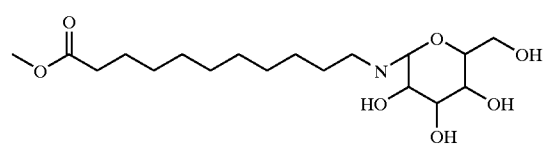
(47) 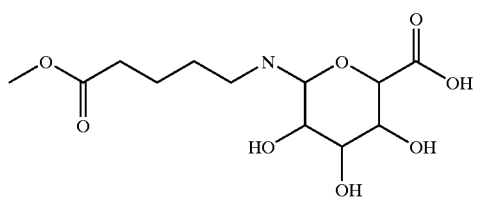
(48) 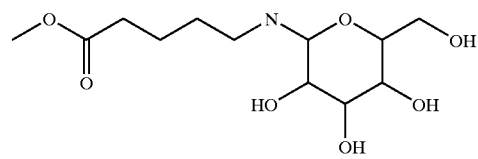
(49) 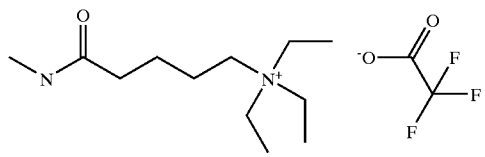
(50) 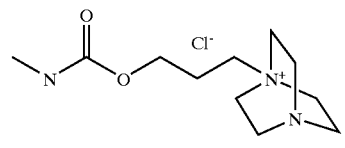

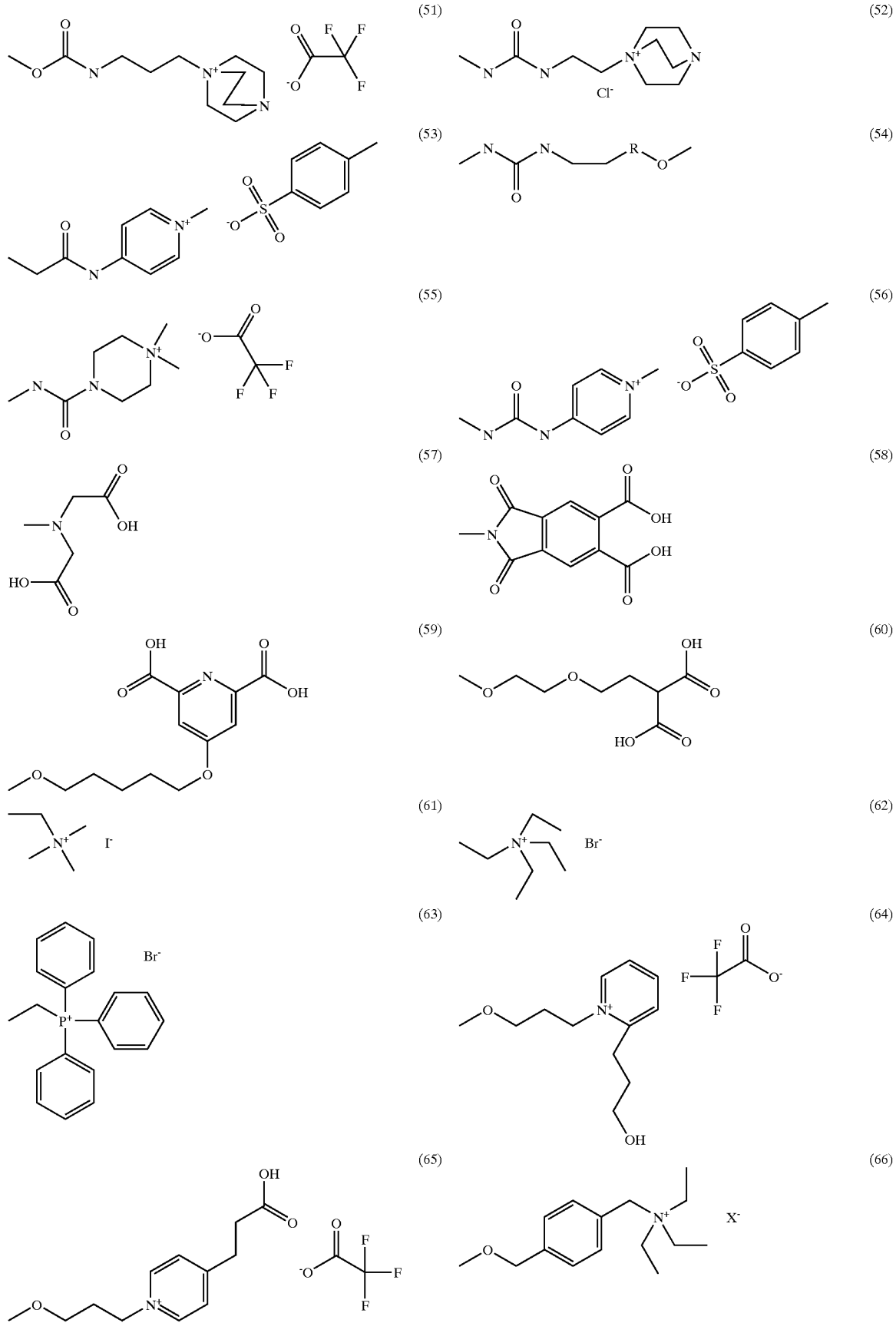

-continued

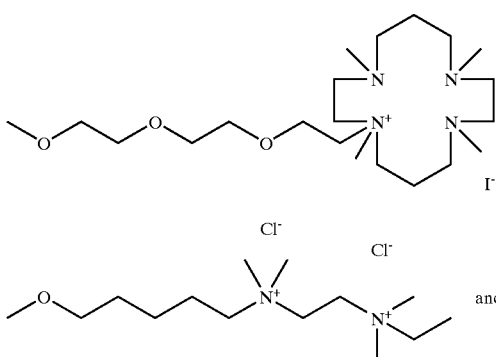

(67)

(68)

(69)

(70)

provided that when said $R^5$ is (7), (17) or (24), then said $R^{5A}$ is a left end of said $R^5$ and said $R^{5B}$ is a right end of said $R^5$ or vice versa.

133. The pharmaceutical composition of claim 132 wherein said Formula I-3 comprises a member selected from the group consisting of Formulas I-5 and I-6 represented by:

I-5

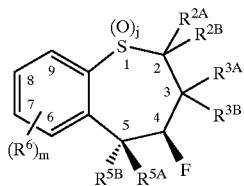

I-6

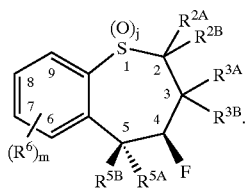

134. The pharmaceutical composition of claim 132 wherein said Formula I-4 comprises a member selected from the group consisting of Formulas I-7 and I-8 represented by:

I-7

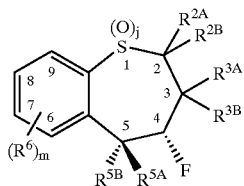

I-8

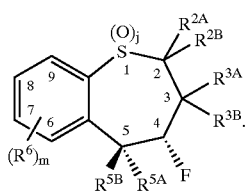

135. The pharmaceutical composition of claim 133 wherein said compounds of Formulas I-6 and I-5 comprise Formulas I-13 and I-14, respectively, represented by:

I-13

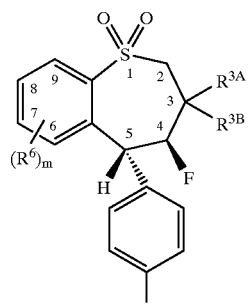

I-14

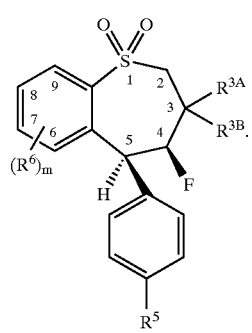

136. The pharmaceutical composition of claim 134 wherein said compounds of Formulas I-7 and I-8 comprise Formulas I-15 and I-16, respectively, represented by:

I-15

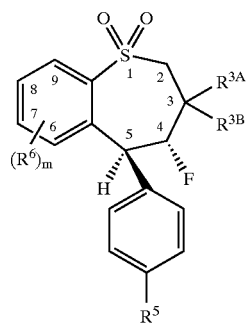

I-16

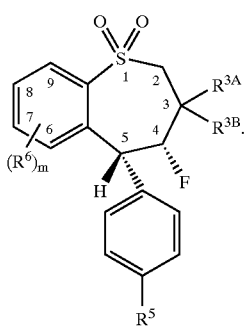

137. The pharmaceutical composition of claim 128 wherein said compound of Formula I-2 comprises a compound of Formula I-18 represented by:

I-18

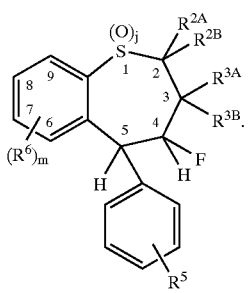

138. The pharmaceutical composition of claim 137 wherein said compound of Formula I-18 comprises a member selected from the group consisting of I-23 and I-24 represented by:

I-23

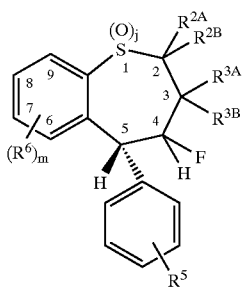

I-24

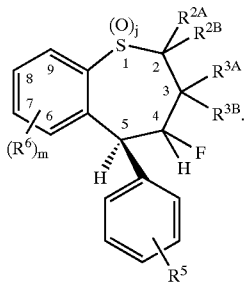

139. The pharmaceutical composition of claim 138 wherein said compounds of Formula I-23 and I-24 comprise compounds of Formulas I-19 and I-20, respectively, represented by:

I-19

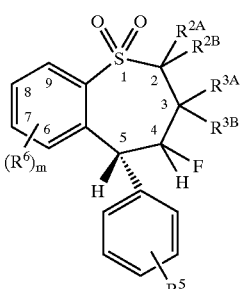

I-20

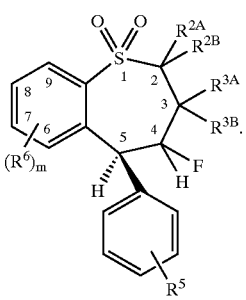

140. The pharmaceutical composition of claim 128 wherein said compound of Formula I-2 is selected from the group consisting of Formulas I-11 and I-12 represented by:

I-11

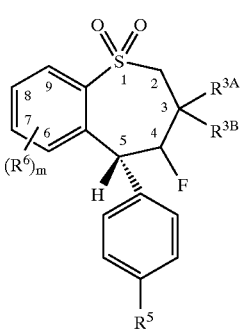

I-12

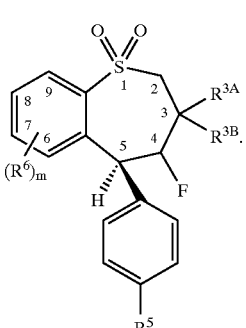

141. The pharmaceutical composition of claim 128 provided in a coated dosage form, said coated dosage form having a coating of cellulose acetate phthalate, polyvinylacetate phthalate, hydroxypropylmethyl cellulose phthalate, or an anionic polymer of methacrylic acid and methacrylic acid methyl ester.

142. The compound of claim 1 provided in a coated dosage form, said coated dosage form having a coating of cellulose acetate phthalate, polyvinylacetate phthalate, hydroxypropylmethyl cellulose phthalate, or an anionic polymer of methacrylic acid and methacrylic acid methyl ester.

143. The pharmaceutical composition of claim 128 provided in a dosage form selected from the group consisting of a tablet, a capsule, a suspension, an emulsion, a solution, a cream, a paste, a lotion, a suppository, or a powder.

144. The pharmaceutical composition of claim 128 in a dosage form selected from the group consisting of a sublingual tablet, an effervescent tablet, and a coated tablet.

145. The pharmaceutical composition of claim 128 provided in a dosage form comprising a slow release dosage form.

146. The pharmaceutical composition of claim 145 wherein said slow release dosage form is selected from the group consisting of an implant or a coated tablet.

147. The pharmaceutical composition of claim 146 wherein said solution, said suspension or said emulsion are suitable for parenteral administration to said subject.

148. The pharmaceutical composition of claim 143 wherein said solution comprises a syrup.

149. The pharmaceutical composition of claim 128 provided in a dosage form comprising a dispersion.

150. The compound of claim 1 provided in a dosage form selected from the group consisting of a tablet, a capsule, a suspension, an emulsion, a solution, a cream, a paste, a lotion, a suppository, and a powder.

* * * * *